US010508265B2

(12) United States Patent
Jo

(10) Patent No.: US 10,508,265 B2
(45) **Date of Patent: *Dec. 17, 2019**

(54) CELL-PERMEABLE REPROGRAMMING FACTOR (ICP-RF) RECOMBINANT PROTEIN AND USE THEREOF

(71) Applicant: CELLIVERY THERAPEUTICS, INC., Seoul (KR)

(72) Inventor: Daewoong Jo, Brentwood, TN (US)

(73) Assignee: CELLIVERY THERAPEUTICS, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,651

(22) Filed: Jan. 31, 2018

(65) Prior Publication Data

US 2018/0195047 A1 Jul. 12, 2018

Related U.S. Application Data

(63) Continuation of application No. PCT/KR2016/008757, filed on Aug. 9, 2016.

(60) Provisional application No. 62/202,987, filed on Aug. 10, 2015.

(51) Int. Cl.

| | |
|---|---|
| ***C12N 5/04*** | (2006.01) |
| ***C12N 5/074*** | (2010.01) |
| ***C07K 14/47*** | (2006.01) |
| ***C07K 14/435*** | (2006.01) |
| ***G01N 33/50*** | (2006.01) |
| *C12N 5/00* | (2006.01) |

(52) U.S. Cl.

CPC .......... *C12N 5/0696* (2013.01); *C07K 14/435* (2013.01); *C07K 14/4702* (2013.01); *G01N 33/5073* (2013.01); *C07K 2319/10* (2013.01); *C07K 2319/21* (2013.01); *C12N 5/0018* (2013.01)

(58) Field of Classification Search

None

See application file for complete search history.

(56) References Cited

U.S. PATENT DOCUMENTS

| | | | | |
|---|---|---|---|---|
| 2003/0104622 A1 | 6/2003 | Robbins et al. | | |
| 2010/0197598 A1* | 8/2010 | Jo | C07K 7/06 | 514/1.1 |
| 2010/0209447 A1 | 8/2010 | Kumar-Singh et al. | | |
| 2012/0196328 A1* | 8/2012 | Liu | C07K 14/4702 | 435/69.7 |
| 2014/0141452 A1 | 5/2014 | Watt et al. | | |
| 2014/0186379 A1 | 7/2014 | Jo et al. | | |
| 2016/0060310 A1* | 3/2016 | Jo | C07K 7/08 | 530/350 |
| 2016/0060312 A1* | 3/2016 | Jo | C07K 7/08 | 530/327 |
| 2016/0060313 A1* | 3/2016 | Jo | C07K 7/08 | 530/327 |
| 2016/0060314 A1* | 3/2016 | Jo | C07K 7/08 | 530/327 |
| 2016/0068825 A1* | 3/2016 | Jo | C12N 9/0065 | 424/94.3 |
| 2016/0083441 A1* | 3/2016 | Jo | C07K 14/47 | 514/19.3 |
| 2017/0137482 A1* | 5/2017 | Jo | C07K 7/08 | |
| 2017/0190754 A1* | 7/2017 | Jo | C07K 7/08 | |
| 2017/0198019 A1* | 7/2017 | Jo | C07K 14/47 | |
| 2017/0226168 A1* | 8/2017 | Jo | C07K 14/4703 | |
| 2017/0240598 A1* | 8/2017 | Jo | C07K 7/08 | |
| 2018/0051060 A1* | 2/2018 | Jo | C07K 14/4703 | |
| 2018/0171322 A1* | 6/2018 | Jo | C12N 9/93 | |
| 2018/0230444 A1* | 8/2018 | Jo | C12N 9/00 | |
| 2018/0237485 A1* | 8/2018 | Jo | C07K 7/08 | |
| 2018/0291073 A1* | 10/2018 | Jo | C07K 7/08 | |

FOREIGN PATENT DOCUMENTS

| | | | |
|---|---|---|---|
| EP | 1 362 917 | A3 | 11/2003 |
| EP | 2 407 488 | A2 | 1/2012 |
| JP | 2010-516758 | A | 5/2010 |
| KR | 10-2009-0123768 | A | 12/2009 |
| KR | 10-1258279 | B1 | 4/2013 |
| WO | 01/27154 | A3 | 4/2001 |
| WO | 03/097671 | A1 | 11/2003 |
| WO | 2008/093982 | A1 | 8/2008 |
| WO | 2009/139599 | A2 | 11/2009 |
| WO | 2012/050402 | A2 | 4/2012 |
| WO | 2012/072088 | A1 | 6/2012 |
| WO | 2016/028036 | A1 | 2/2016 |

OTHER PUBLICATIONS

Xia Li et al., "Generation of pluripotent stem cells via protein transduction", International Journal of Developmental Biology, 2014, pp. 21-27, vol. 58.

Junghee Lim et al., "Partial Somatic to Stem Cell Transformations Induced by Cell-Permeable Reprogramming Factors", Scientific Reports, 2014, pp. 1-10, vol. 4, No. 4361.

International Search Report for PCT/KR2016/008757 dated Oct. 21, 2016.

International Searching Authority, Communication dated Nov. 16, 2015 in PCT/KR2015/008544.

Australian Patent Office, Communication dated Oct. 13, 2017 by the Australian Patent Office in Application No. 2015304194.

European Patent Office, communication dated Nov. 27, 2017 by the European Patent Office in Application No. 15 833 496.1.

Japanese Patent Office; Communication dated Feb. 20, 2018 in Japanese application No. 2017-510405.

European Patent Office; Communication dated Feb. 9, 2018 in European application No. 15833496.1.

ChemPages. Hydrophobic Amino Acids. Datasheet [online], ChemPages Netorials. [retrieved on Jun. 15, 2018], Retrieved from the internet: URL:https://www.chem.wisc.edu/deptfiles/genchem/neotorial/modules/biomolecules/modules/protein1//prot13.htm, 1 page.

(Continued)

*Primary Examiner* — Fred H Reynolds

(74) *Attorney, Agent, or Firm* — Sughrue Mion, PLLC

(57) ABSTRACT

The iCP-RF recombinant protein of present invention could mediate generation of the induced pluripotent stem cells (iPSCs) from terminally differentiated somatic cells.

14 Claims, 79 Drawing Sheets

Specification includes a Sequence Listing.

(56) References Cited

OTHER PUBLICATIONS

Medical Physiology/Basic Biochemistry/Amino Acids. Classification of Amino Acids, [retrieved on Jun. 15, 2018], Retrieved from the internet: https://en.wikibooks.org/w/index.php?title=MedicaLPhysiology/Basic_Biochemistry/Amino_Acids_and_Proteins_&_oldid=3436225. Last edited on Jun. 15, 2018, 4 pages total.
ExPASy. ProtParam.Gasteiger, E et al. Protein identification and analysis tools on the ExPASy server. In: The Proteomics Protocols Handbook; Ed.: John M. Walker. Copyright 2005 Humana Press, [retrieved on Jun. 15, 2018],Retrieved from the internet <https://web.expasy.org/cgi-bin/protparam/protparam, 6 pages.
Junghee Lim et al., "Antitumor Activity of Cell-Permeable p18$^{INK4c}$ With Enhanced Membrane and Tissue Penetration", Molecular Therapy: The Journal of the American Society of Gene Therapy, vol. 20, No. 8, Aug. 1, 2012, pp. 1540-1549, XP055468096 (10 pages total).
European Patent Office; Communication dated Jul. 6, 2018 issued in counterpart European application No. 16835416.5.

* cited by examiner

【Figure 1】
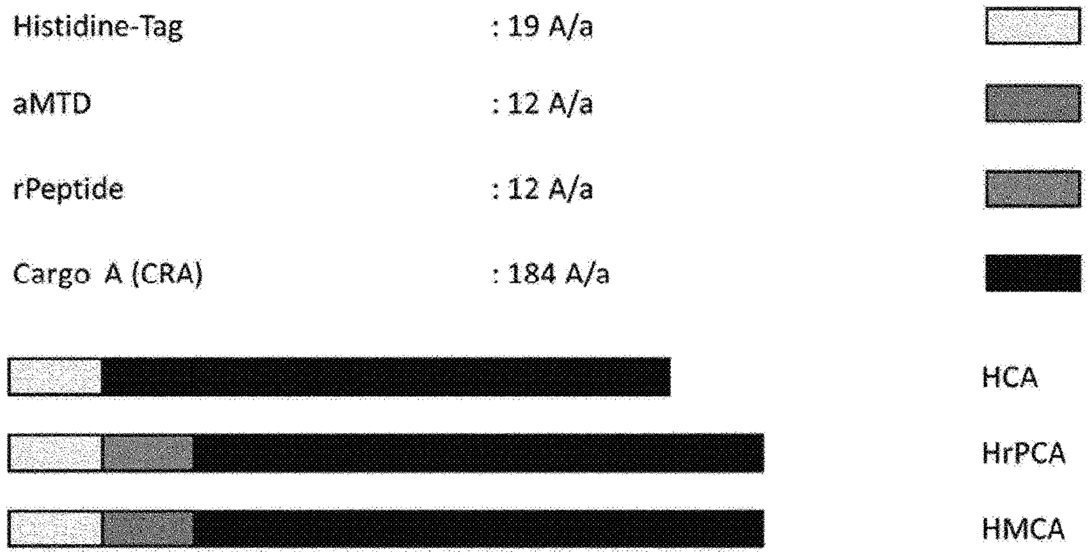
【Figure 2a】
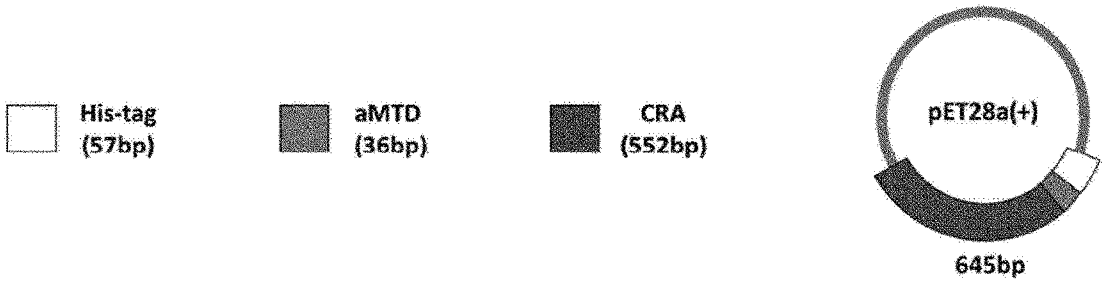

【Figure 2b】
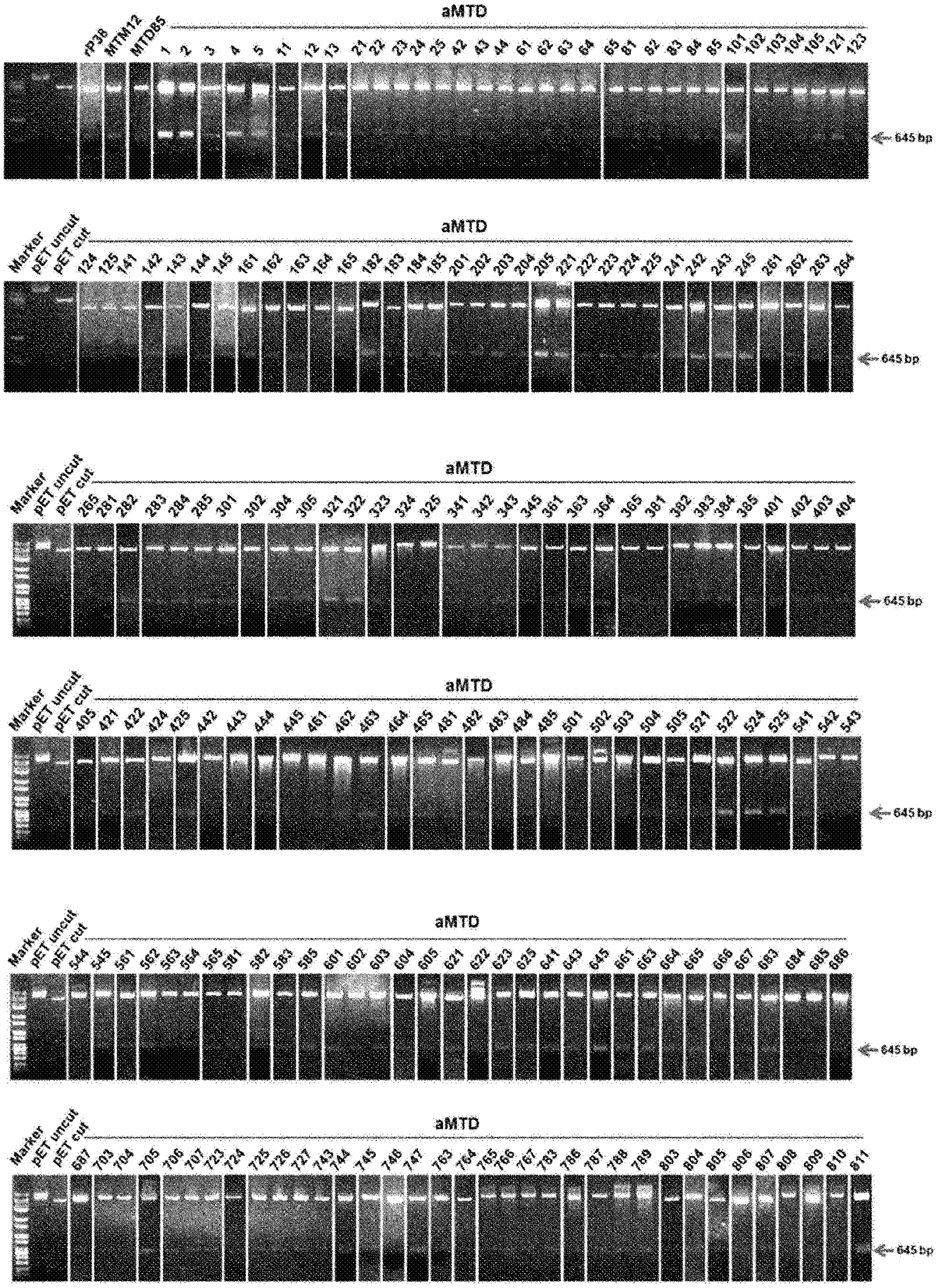

【Figure 2c】
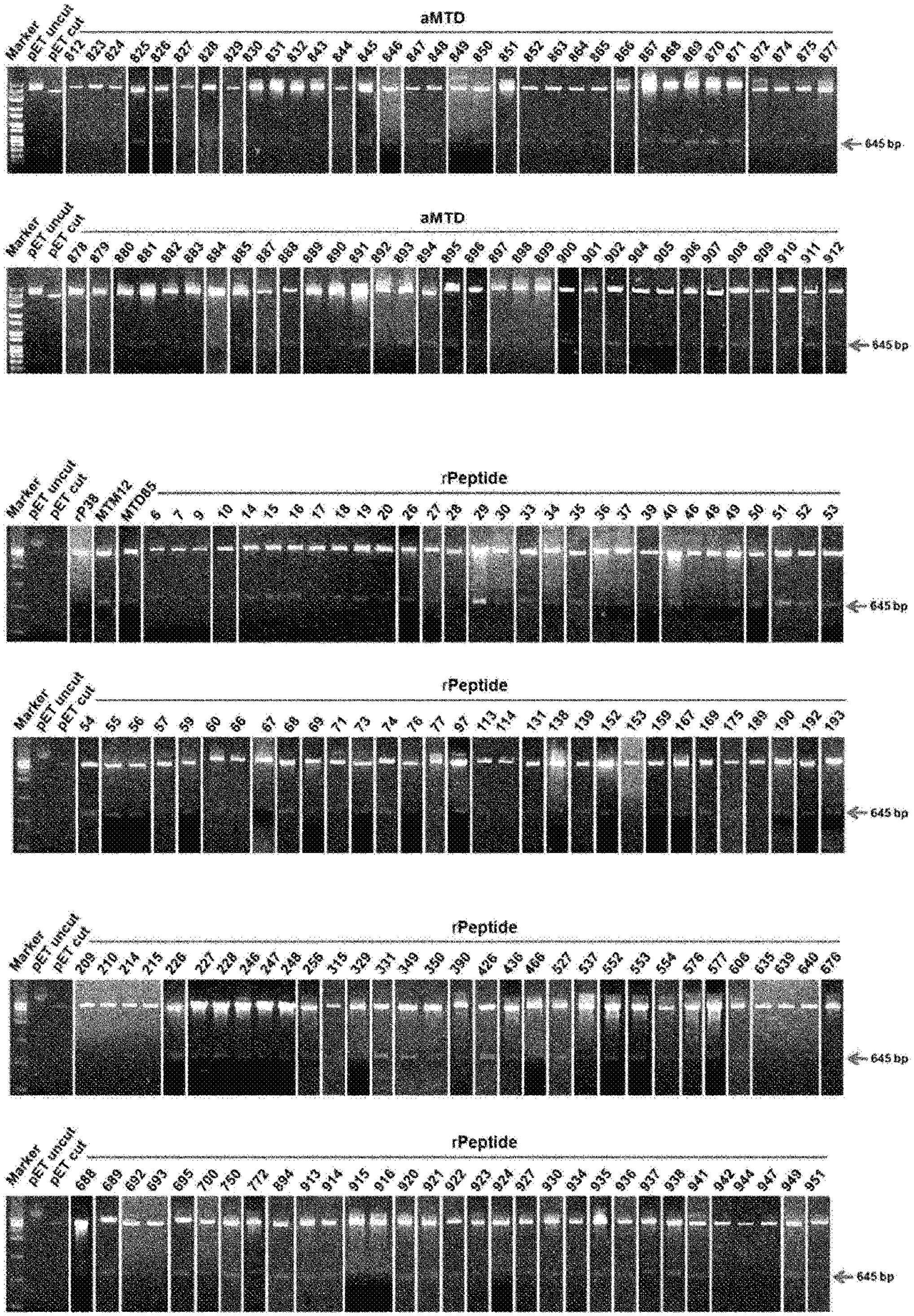

【Figure 3a】
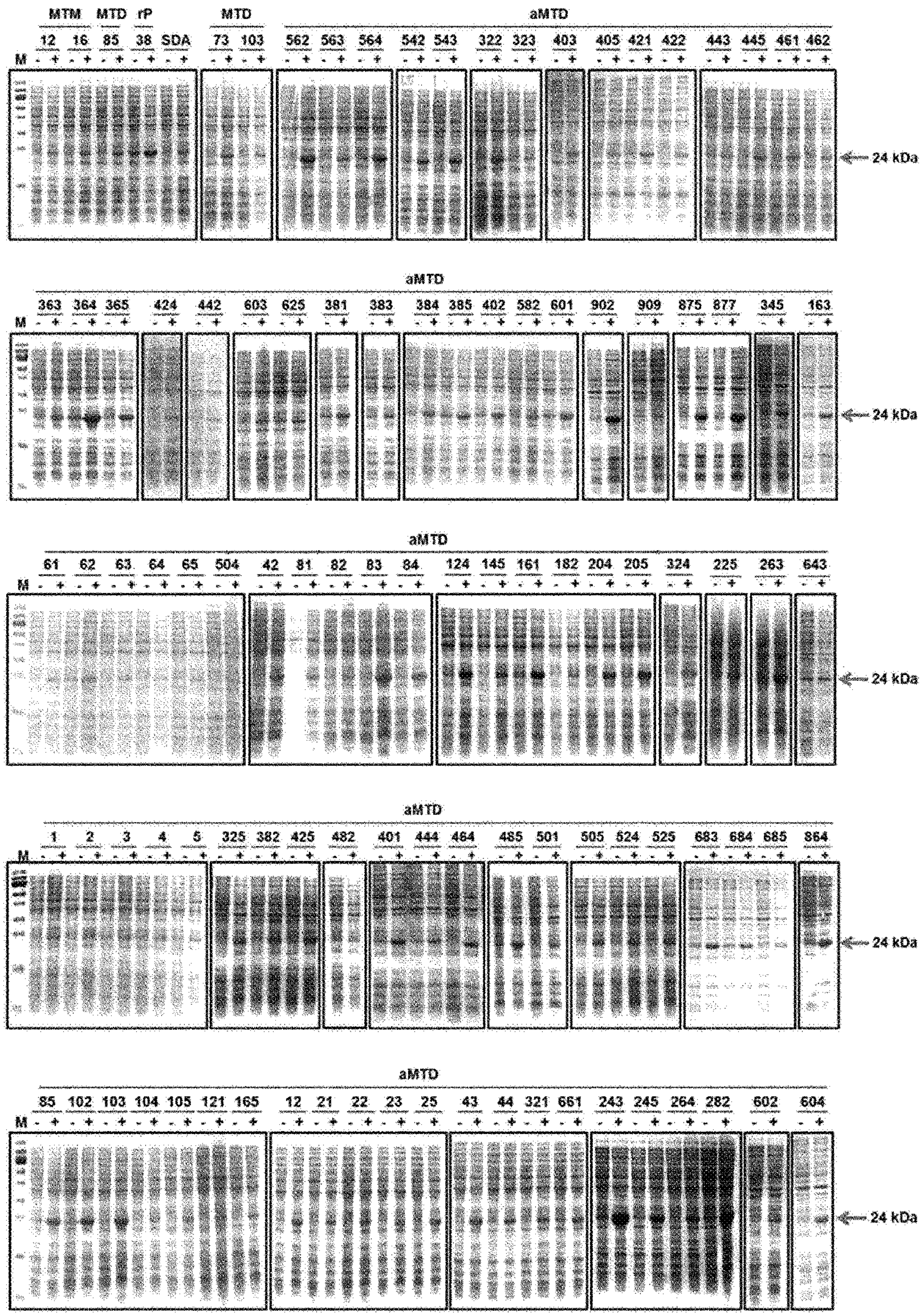

【Figure 3b】
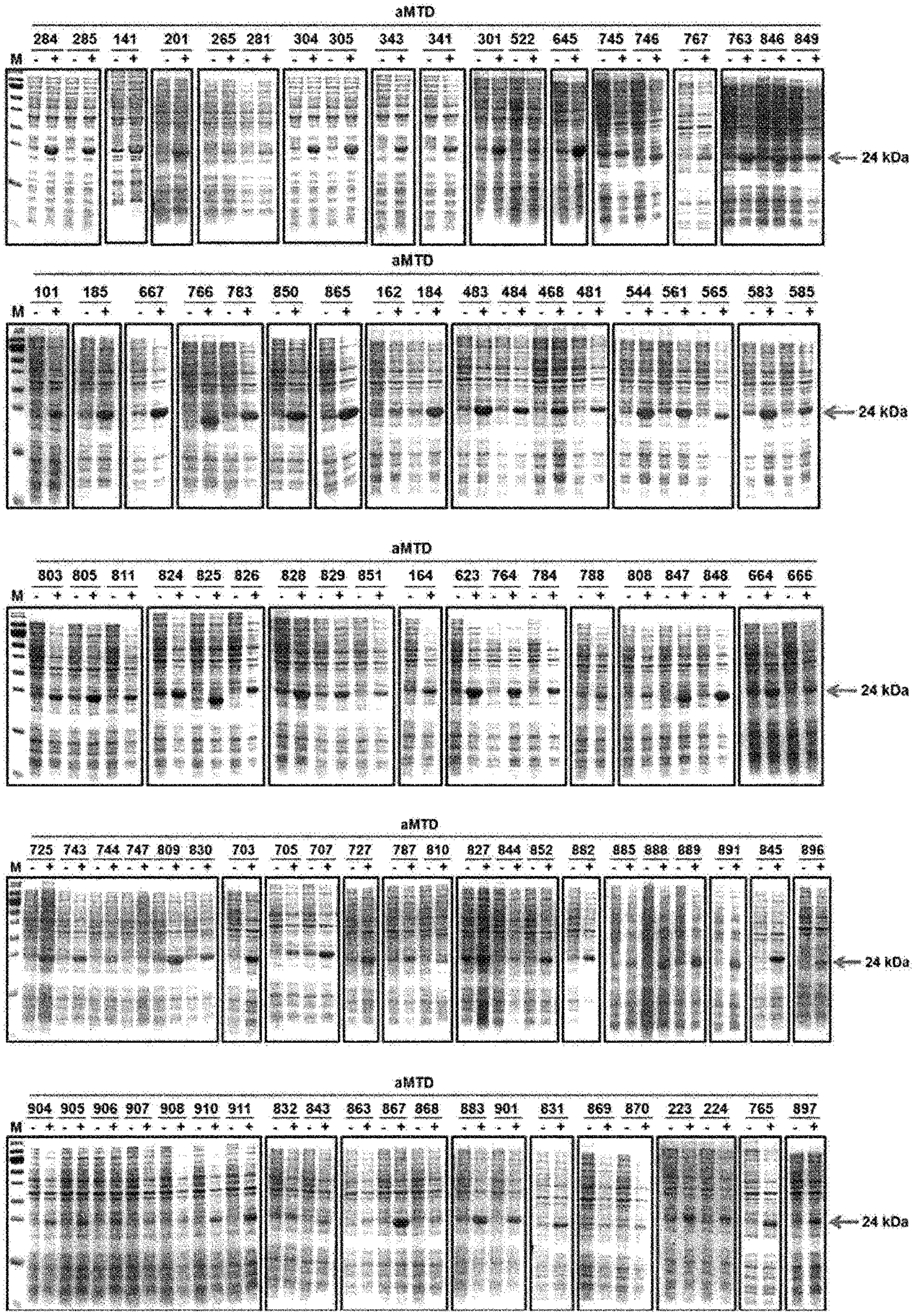

【Figure 3c】
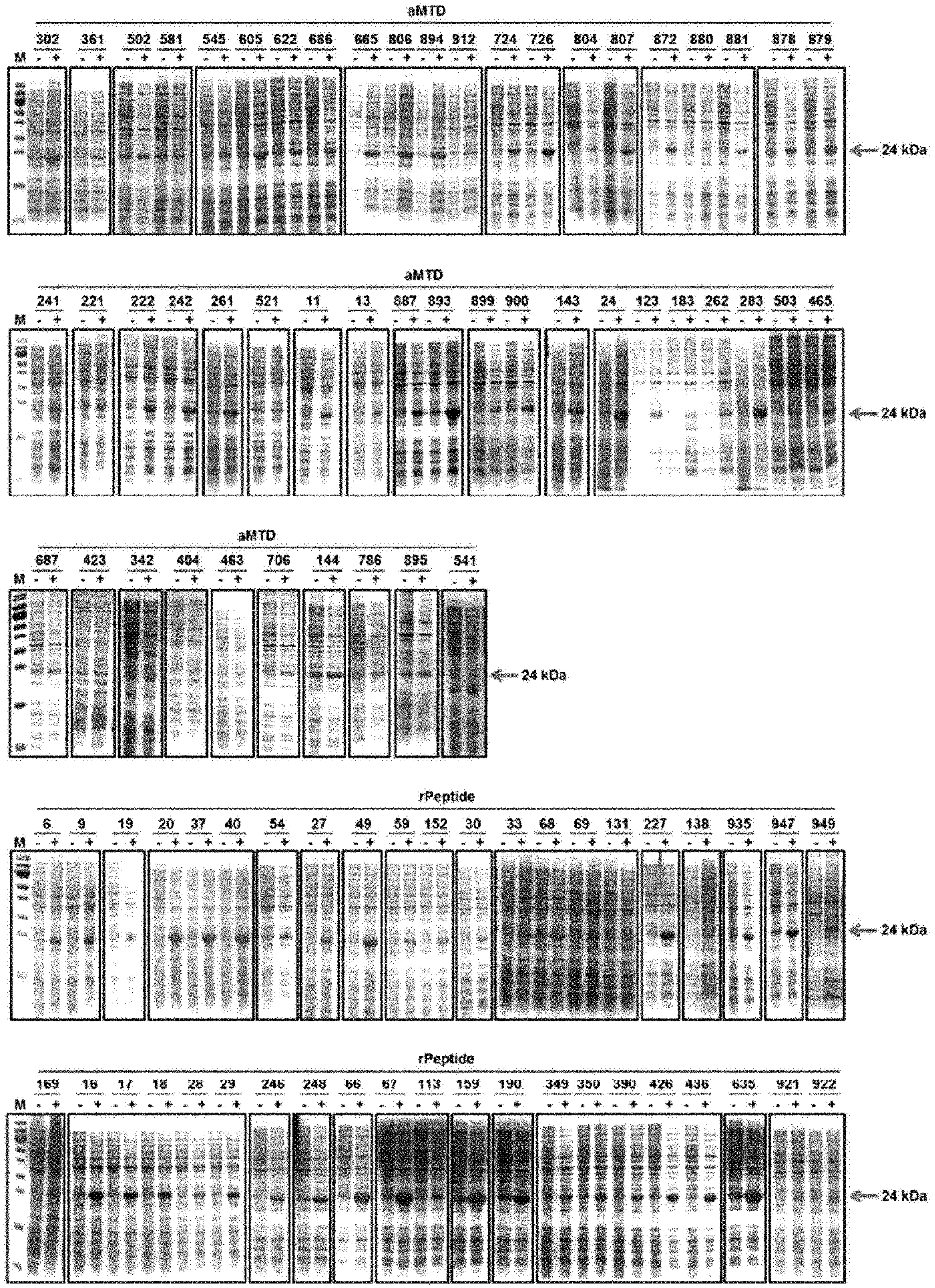

【Figure 3d】
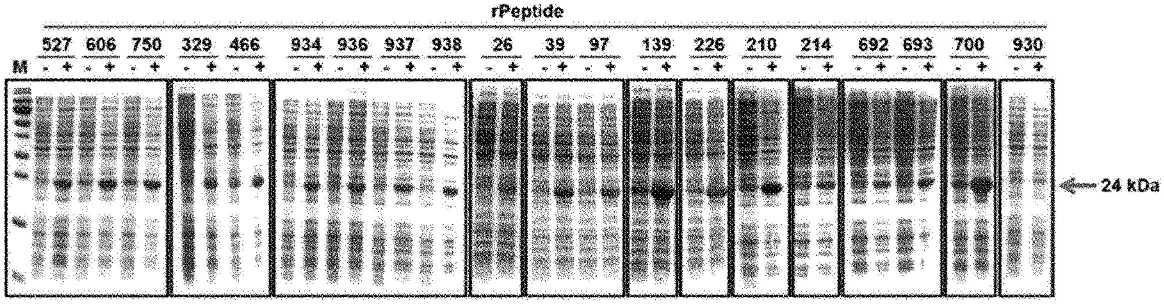
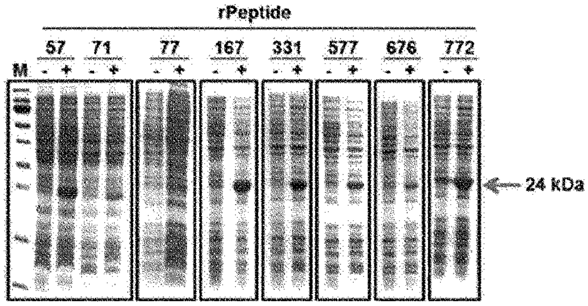

【Figure 4a】
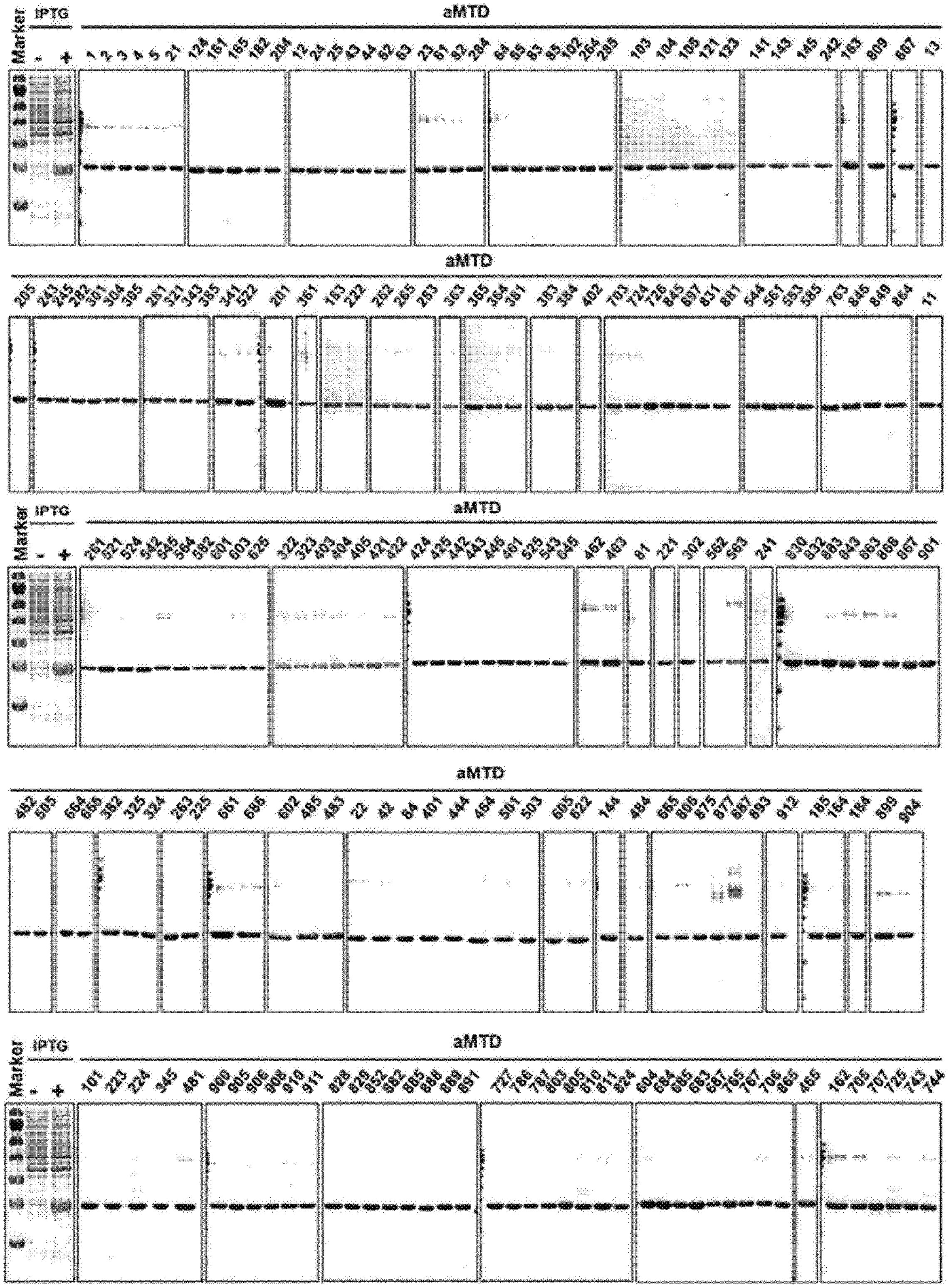

【Figure 4b】
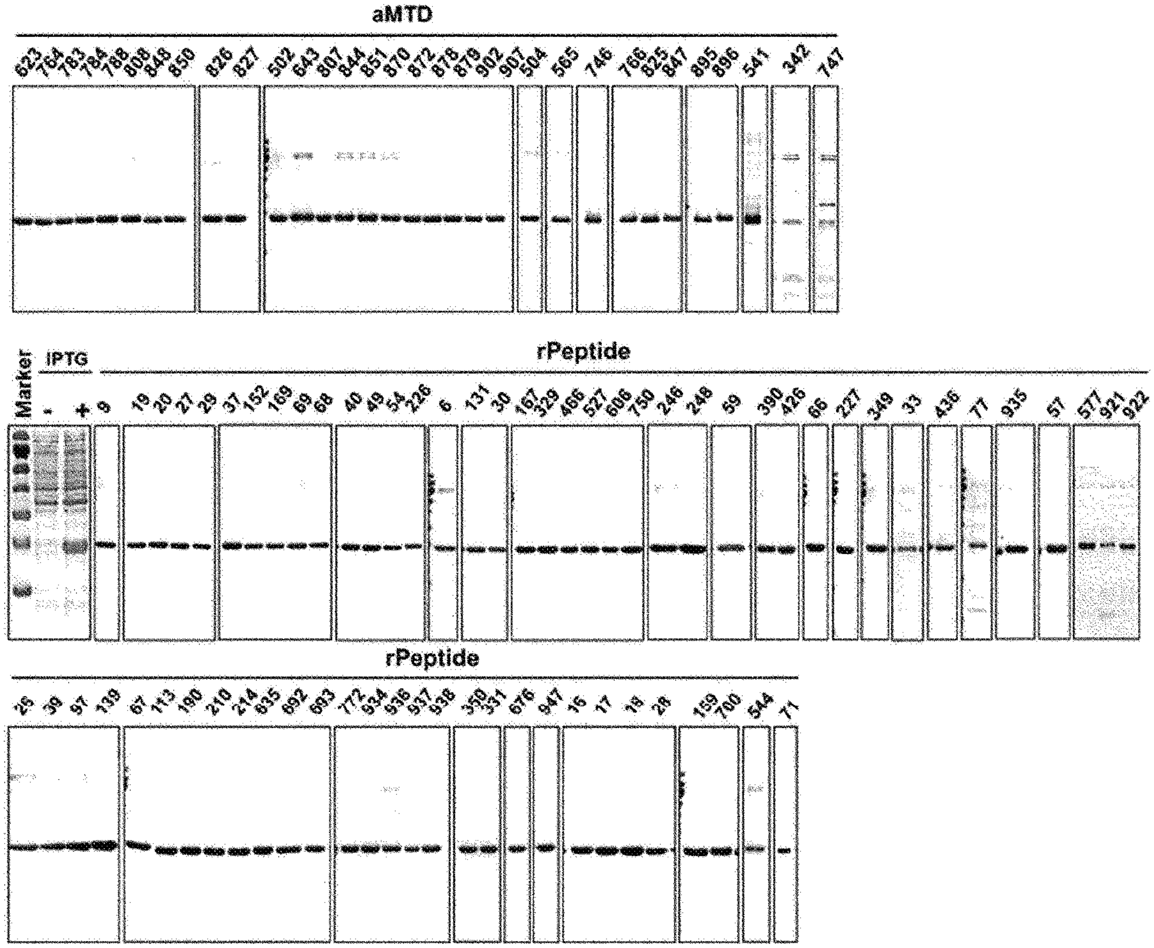

【Figure 5a】
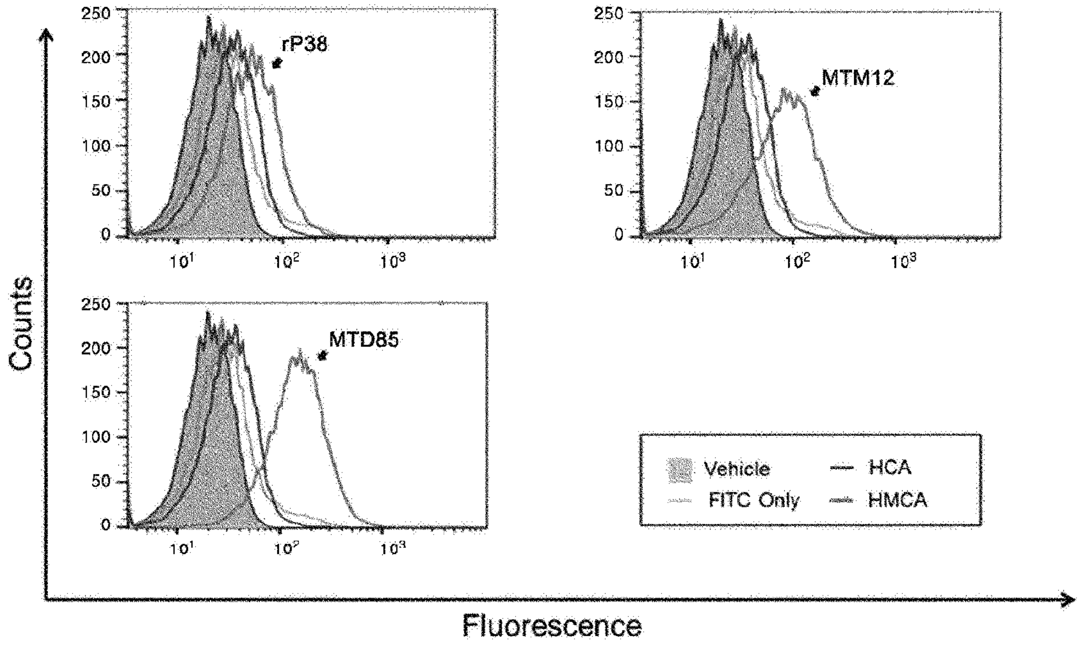
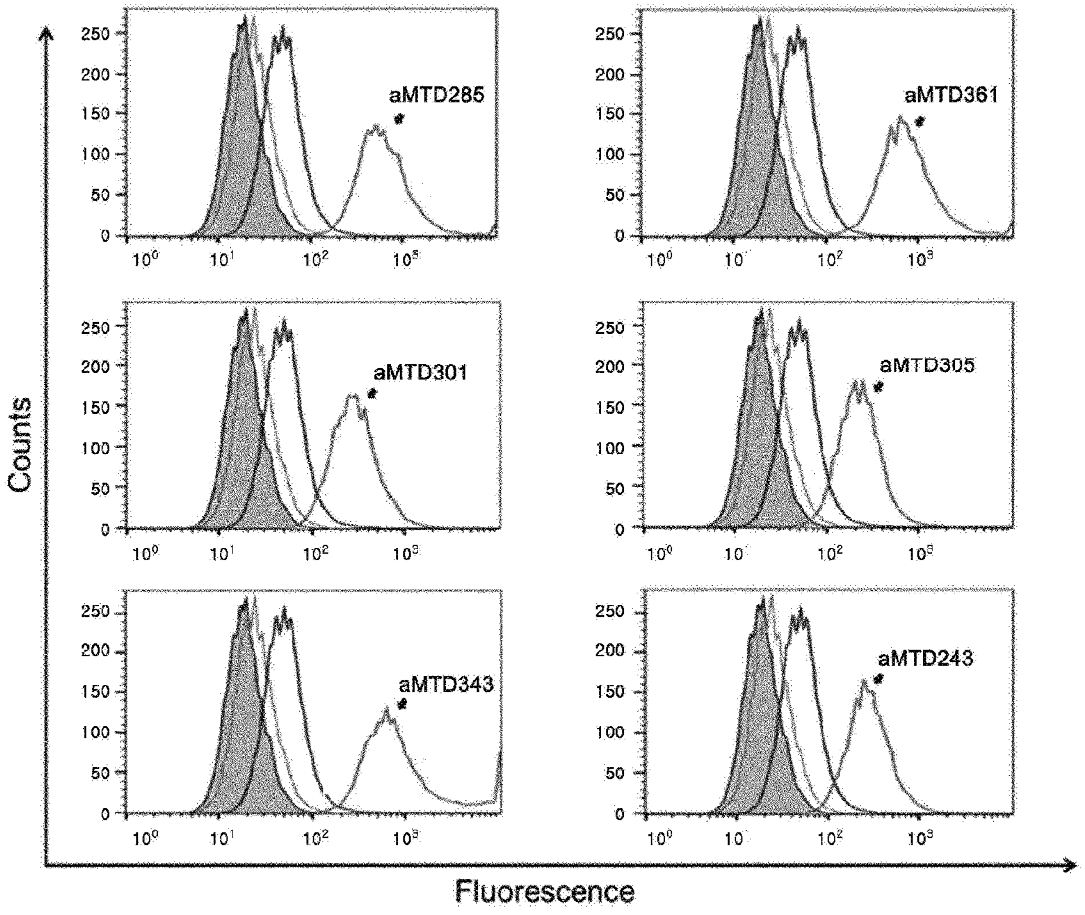

【Figure 5b】
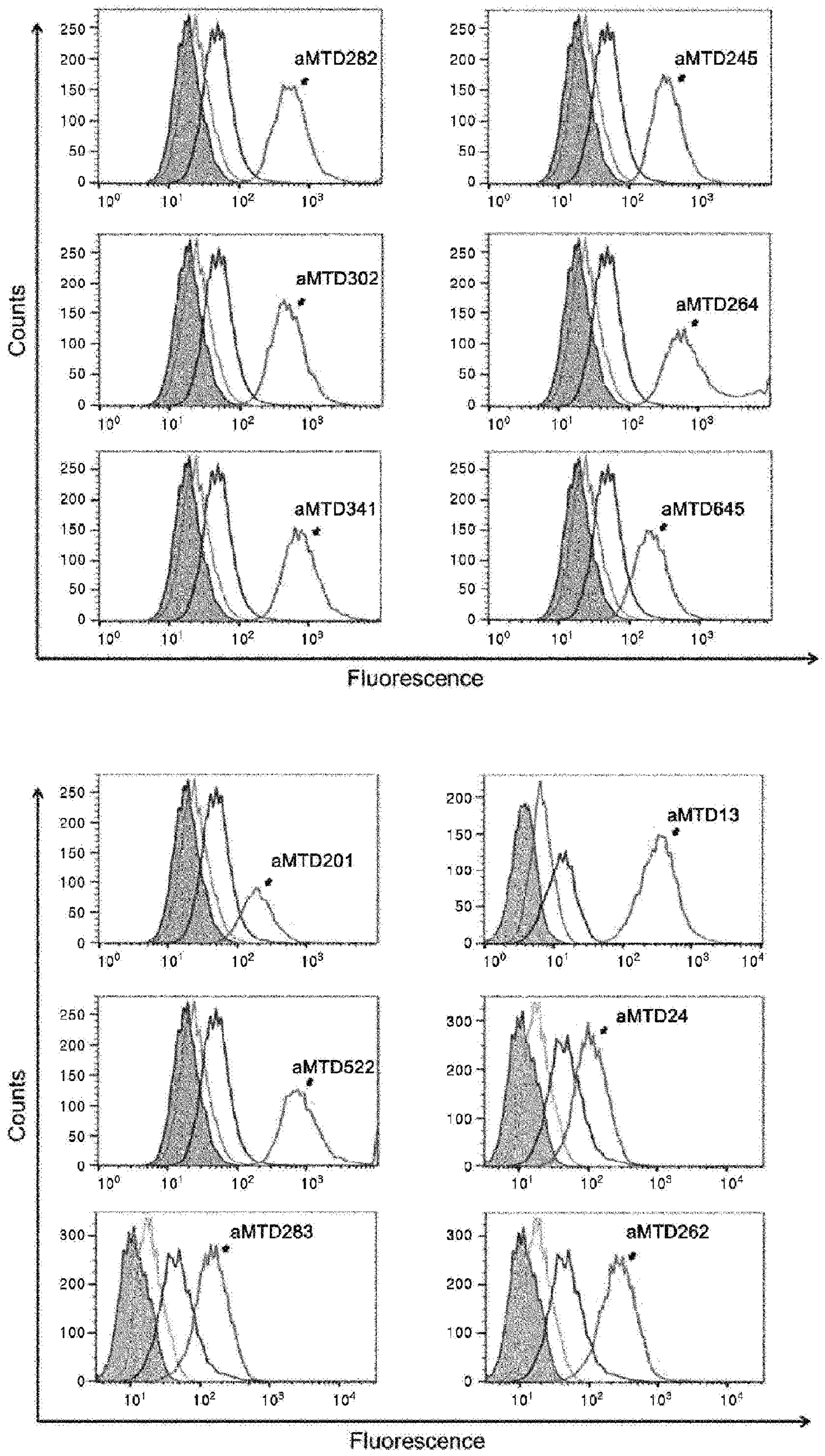

【Figure 5c】
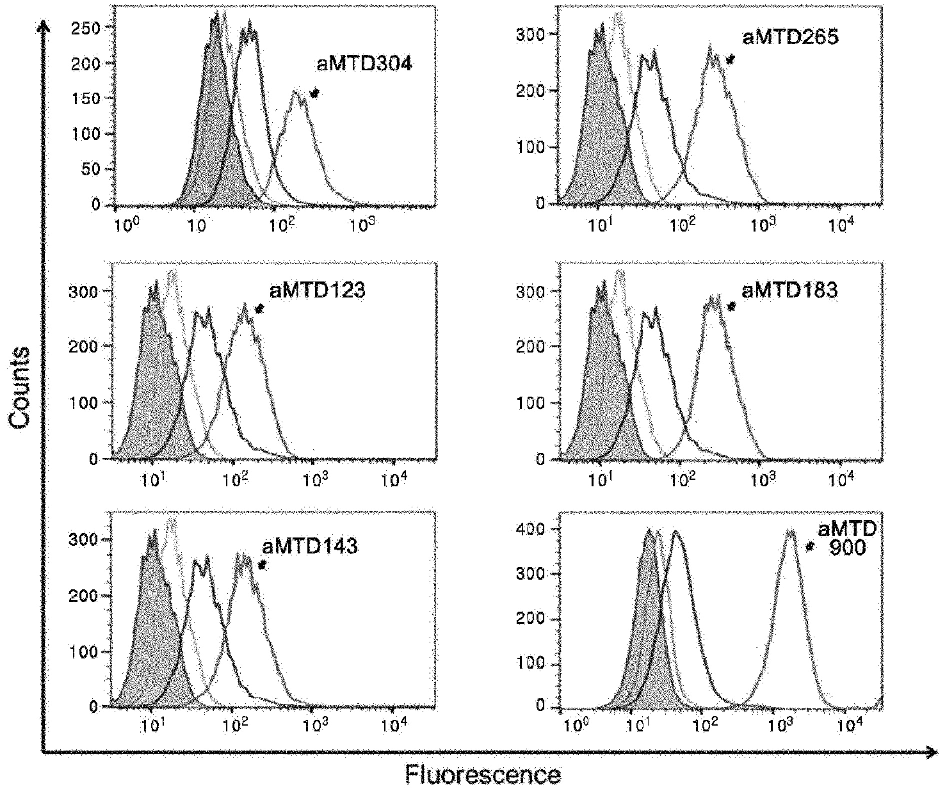
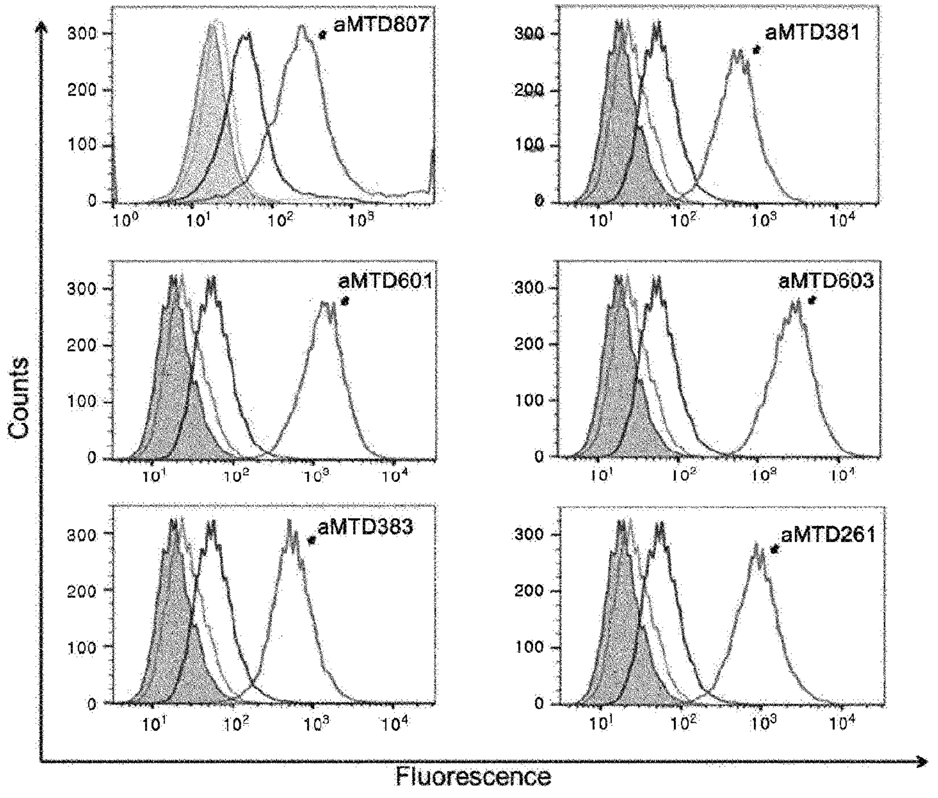

【Figure 5d】
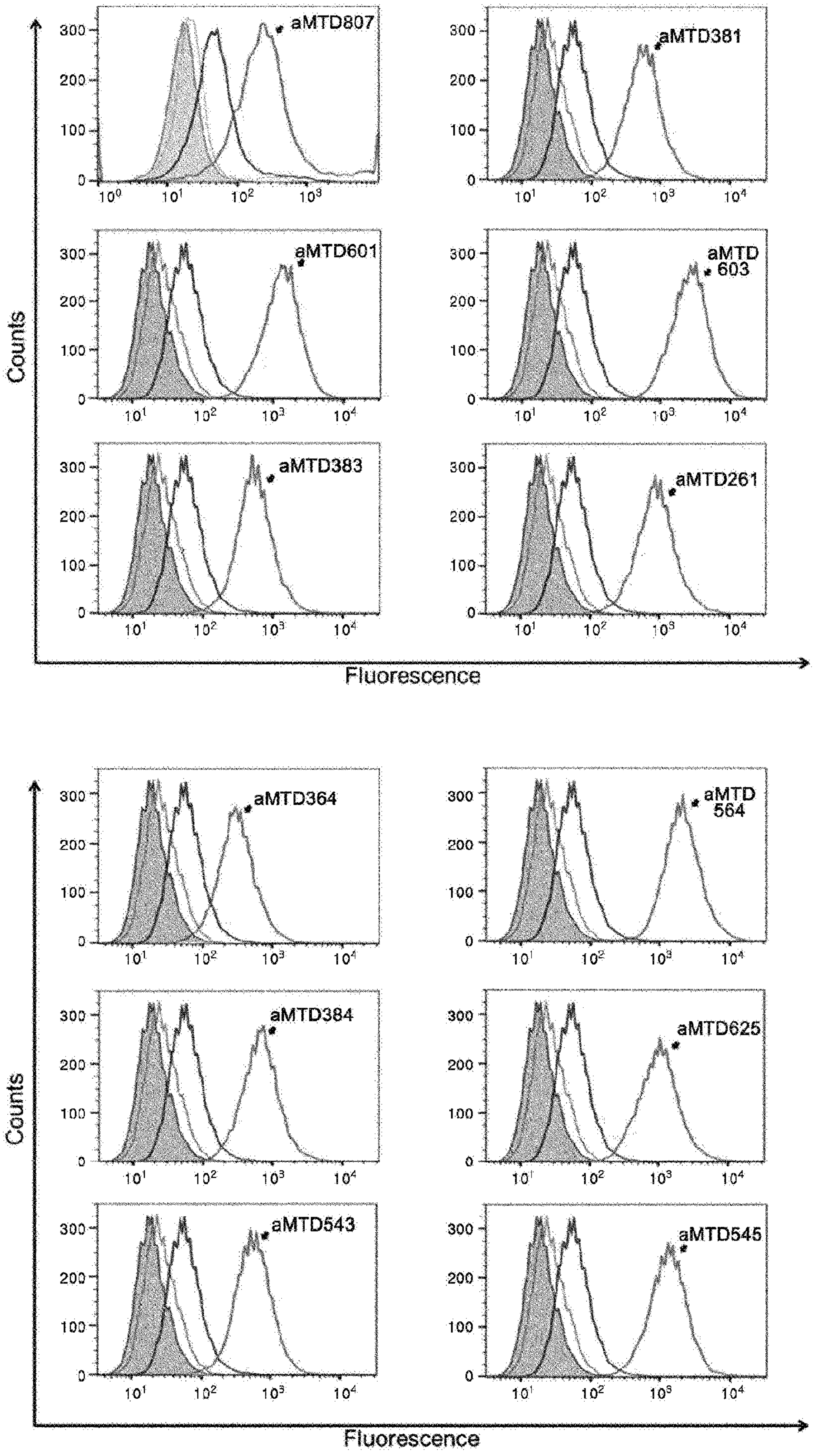

【Figure 5e】
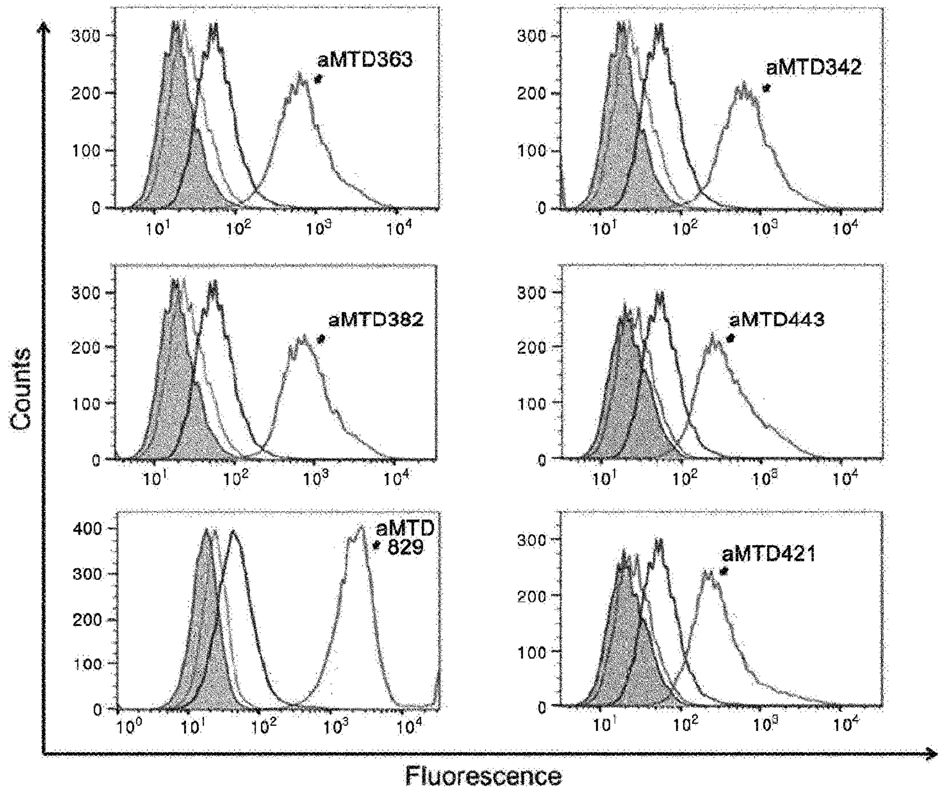
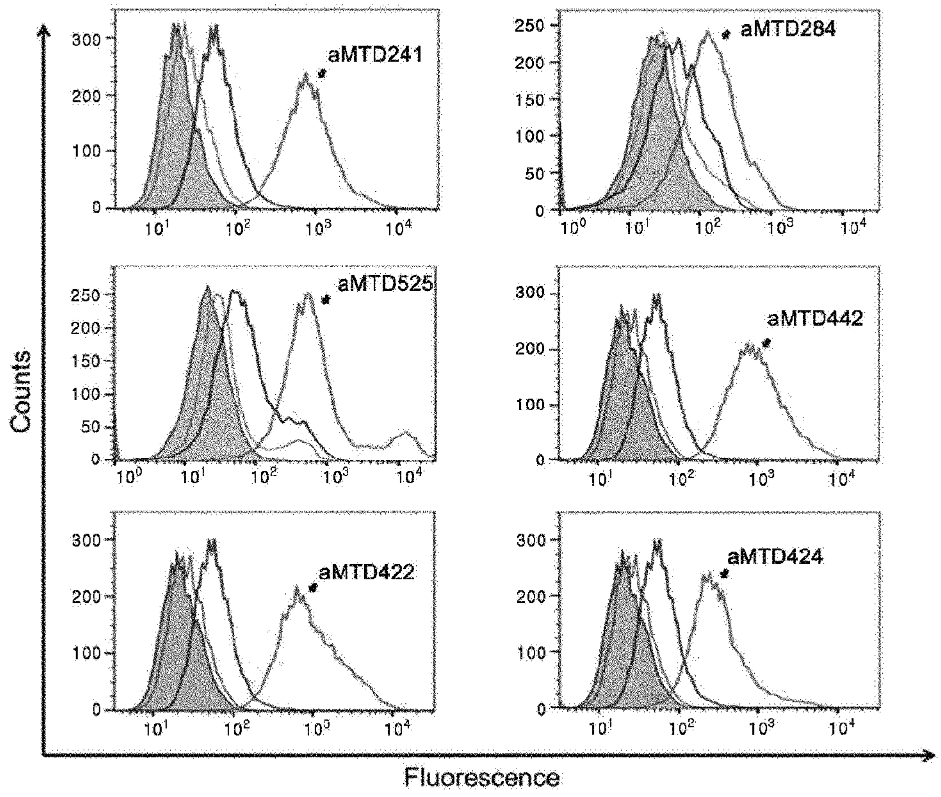

【Figure 5f】
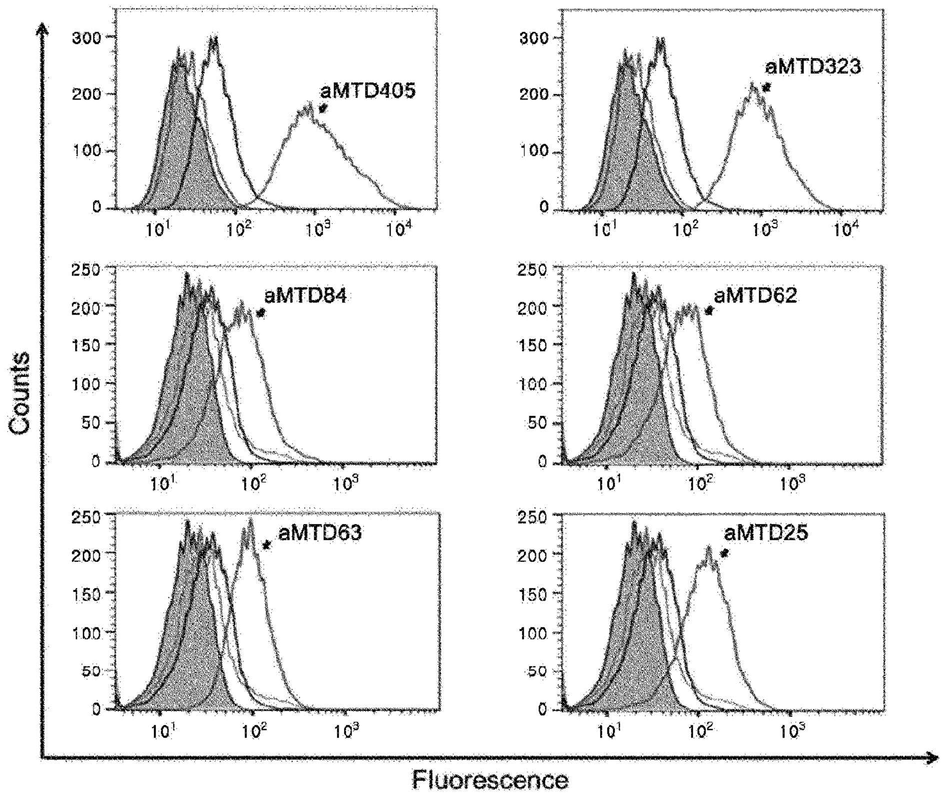
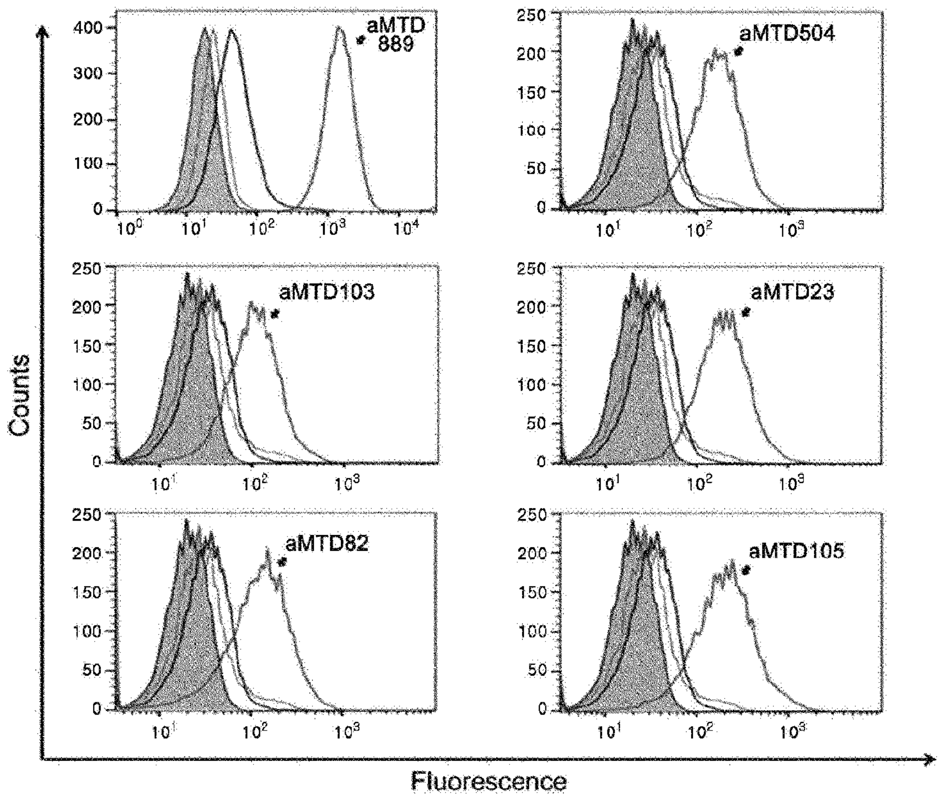

【Figure 5g】
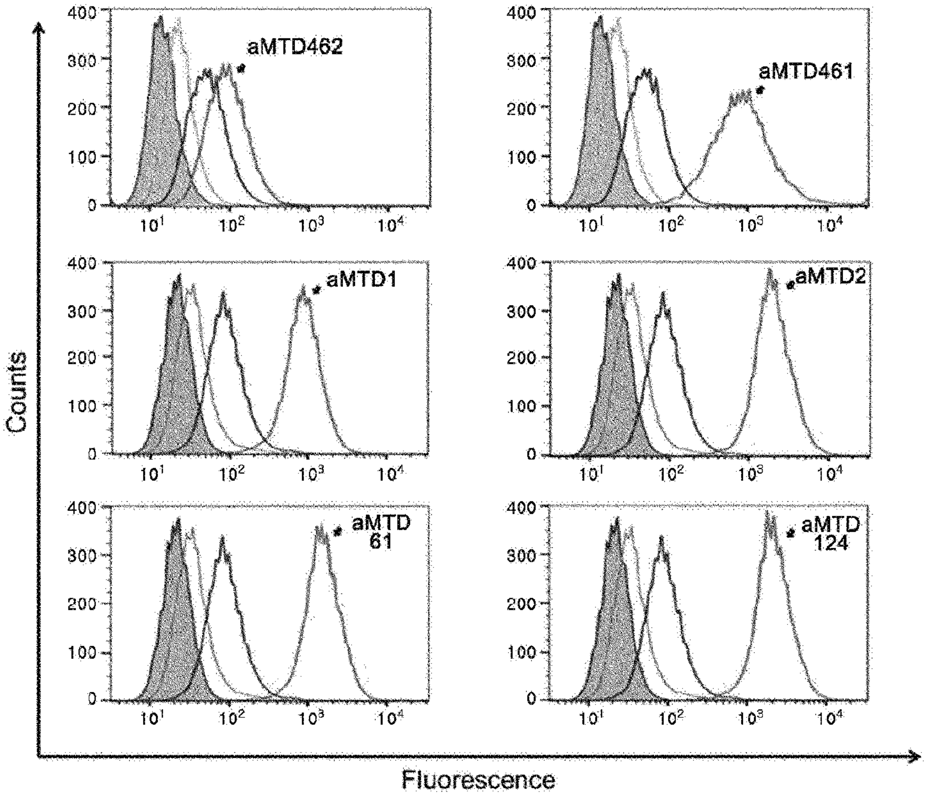
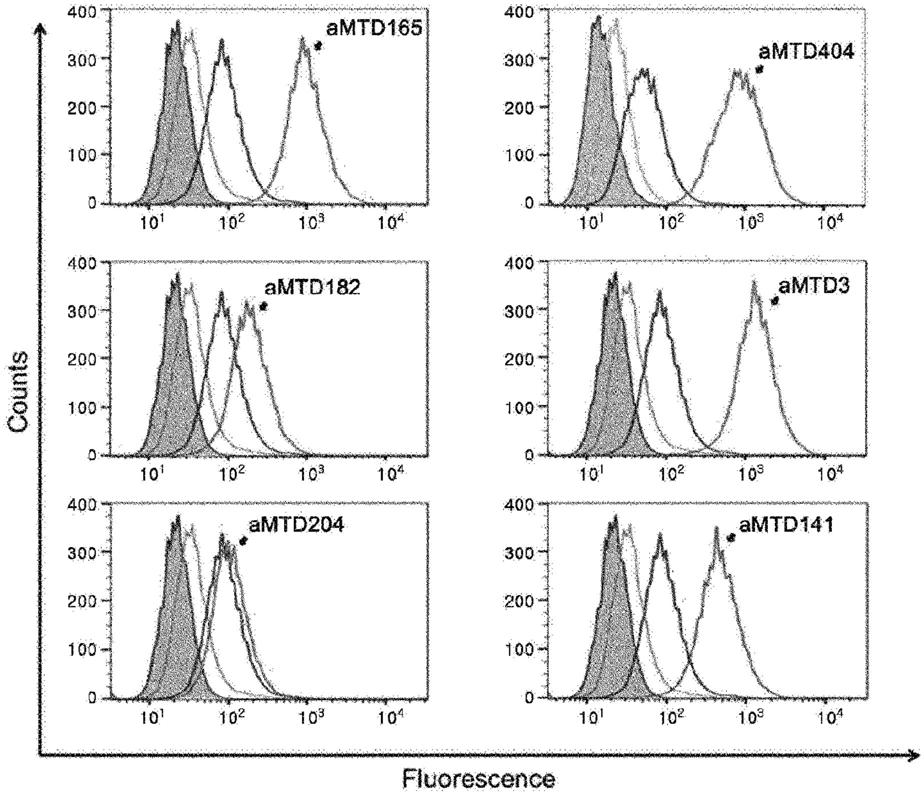

【Figure 5h】
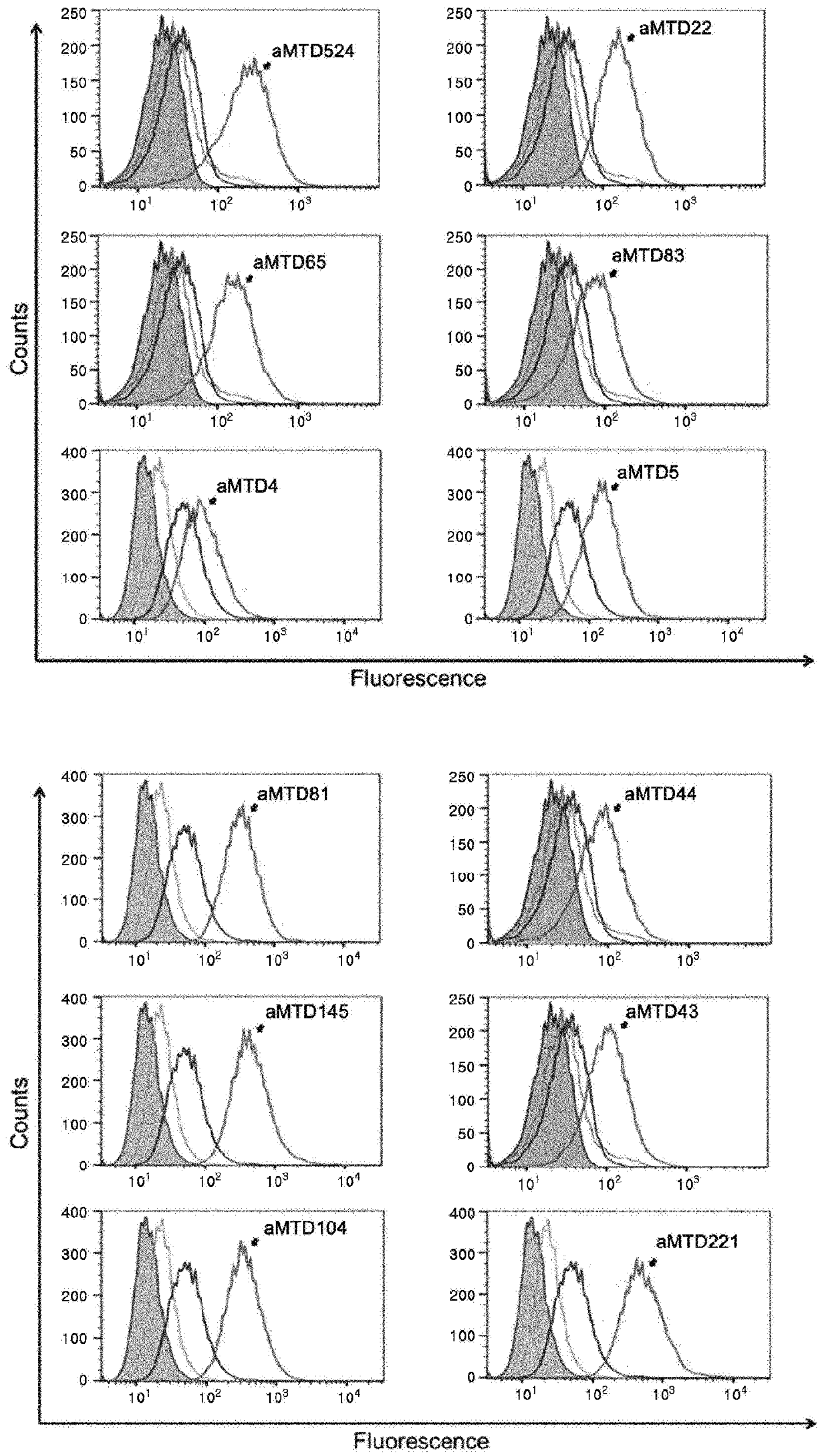

【Figure 5i】
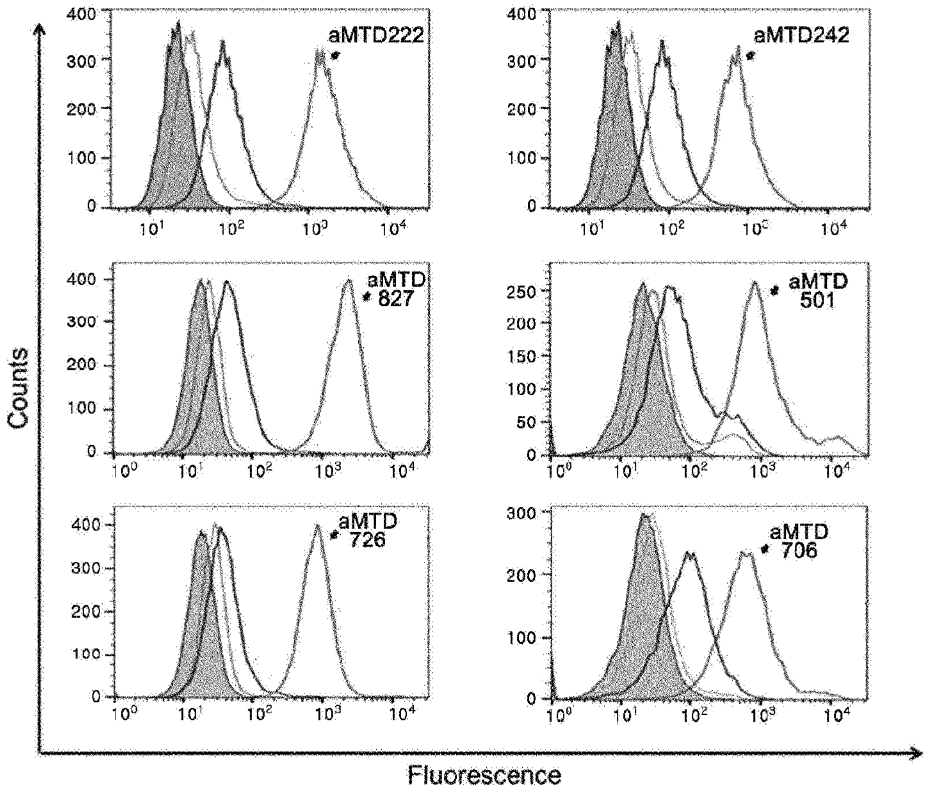
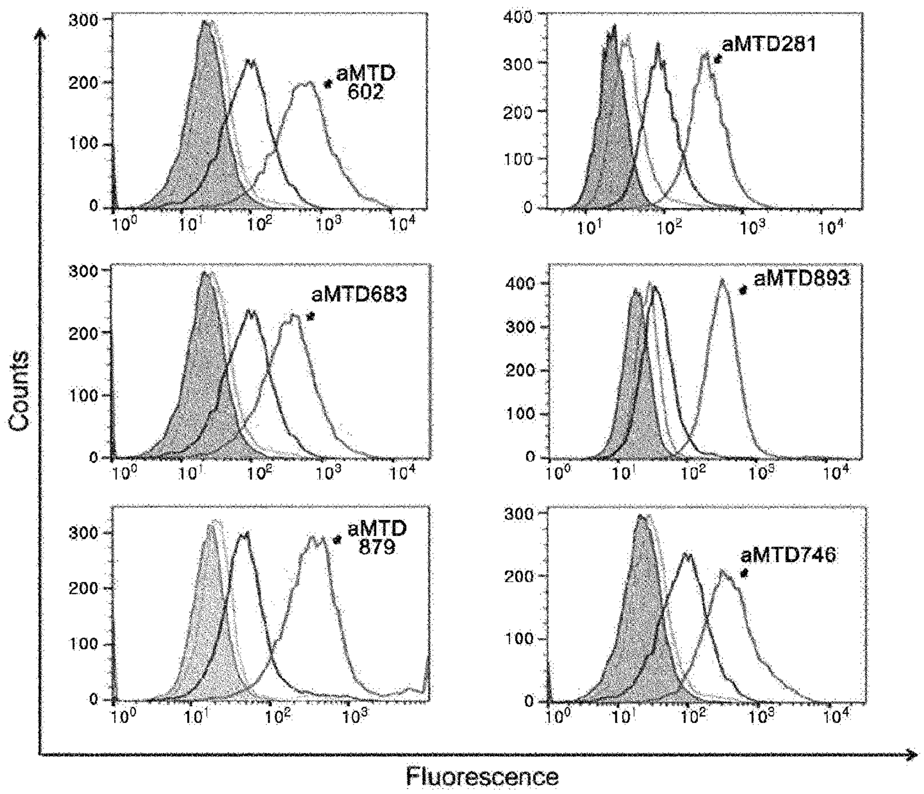

【Figure 5j】
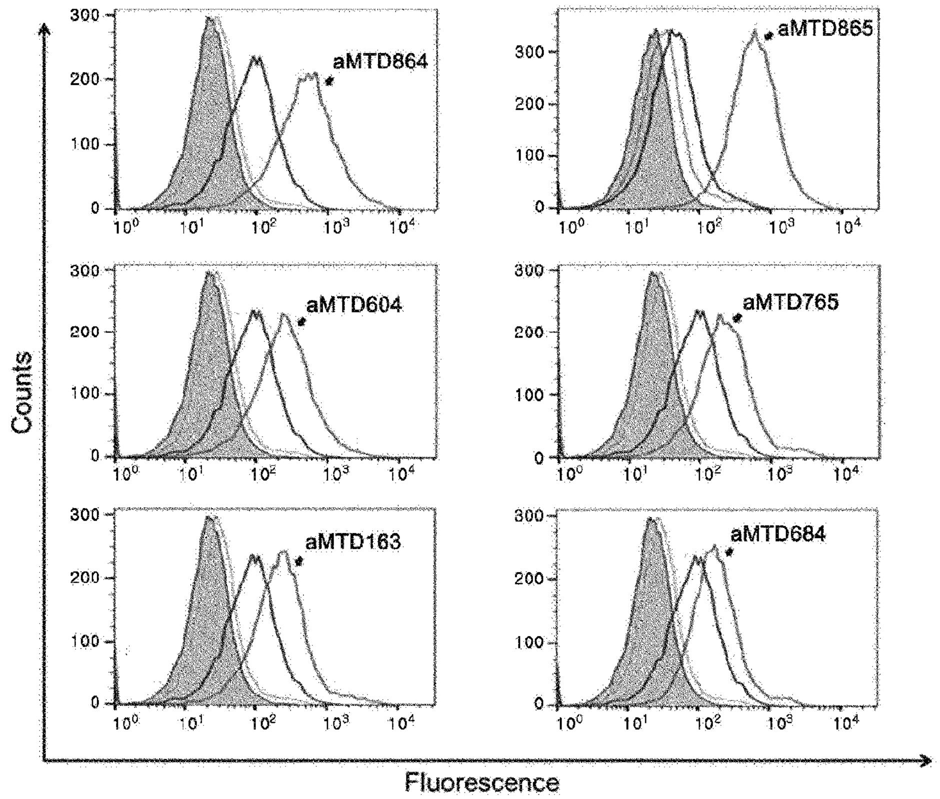
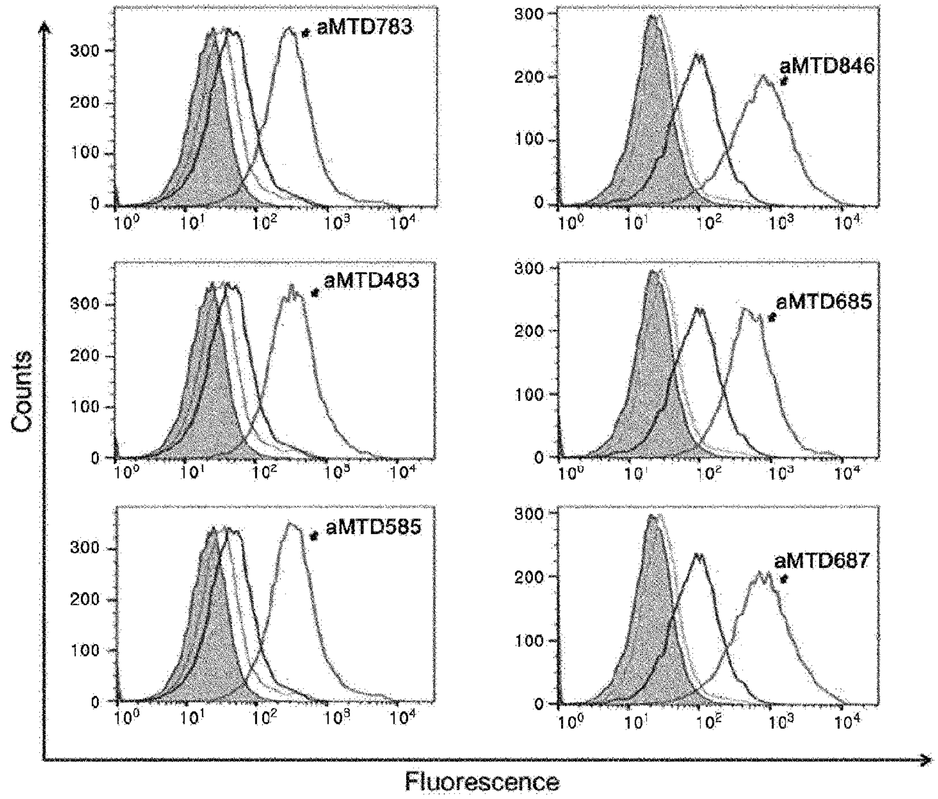

【Figure 5k】
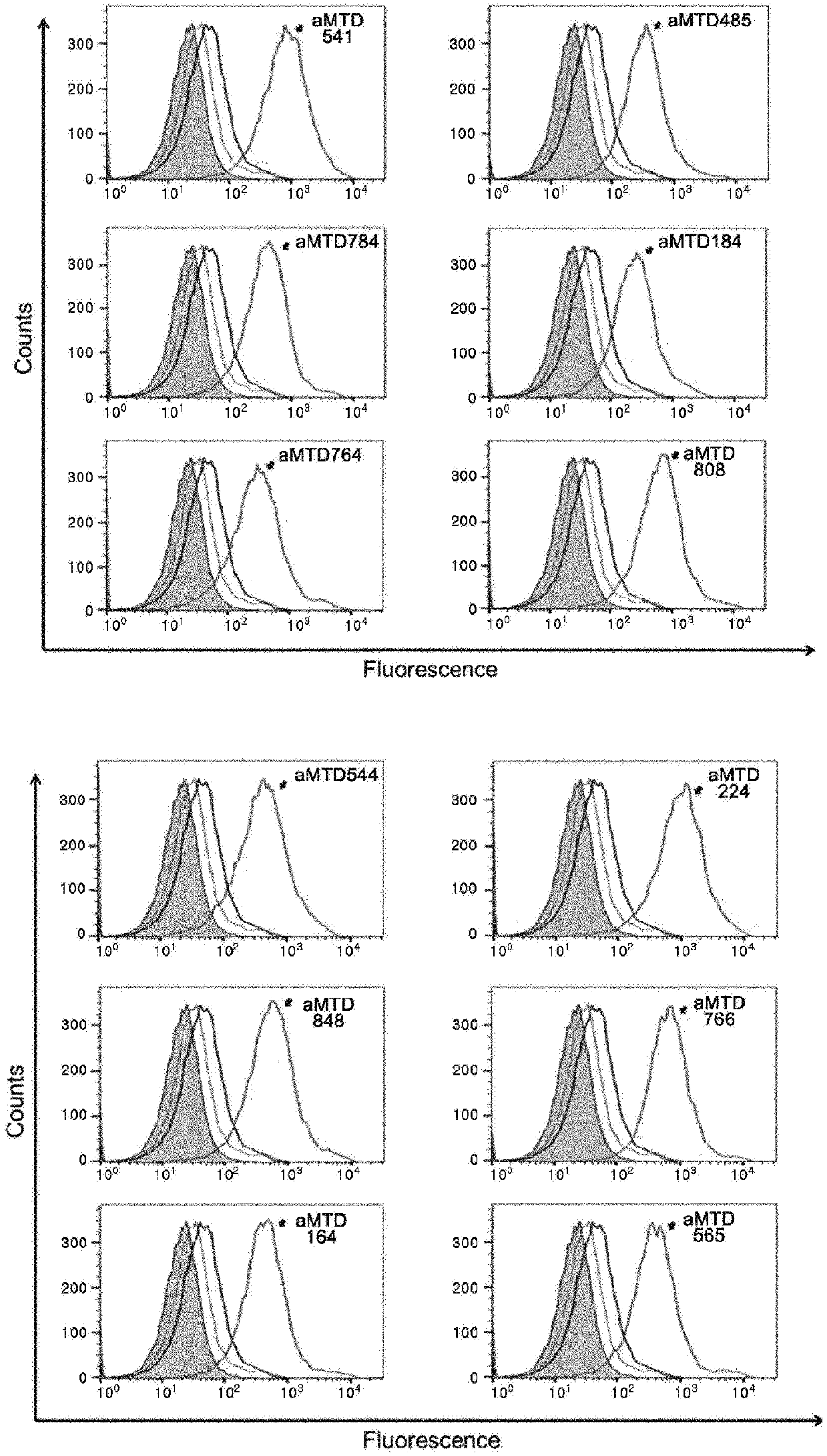

【Figure 51】
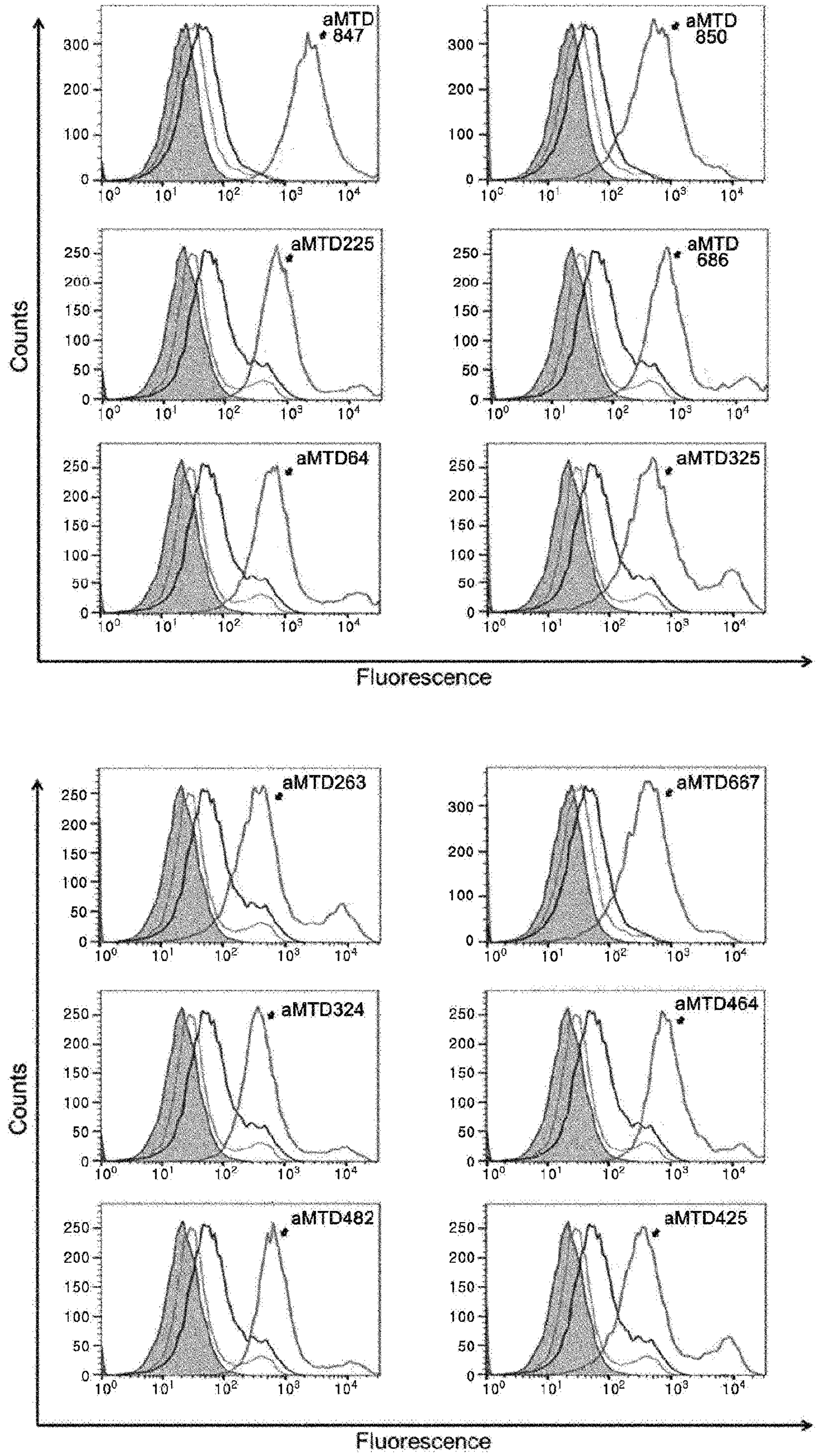

【Figure 5m】
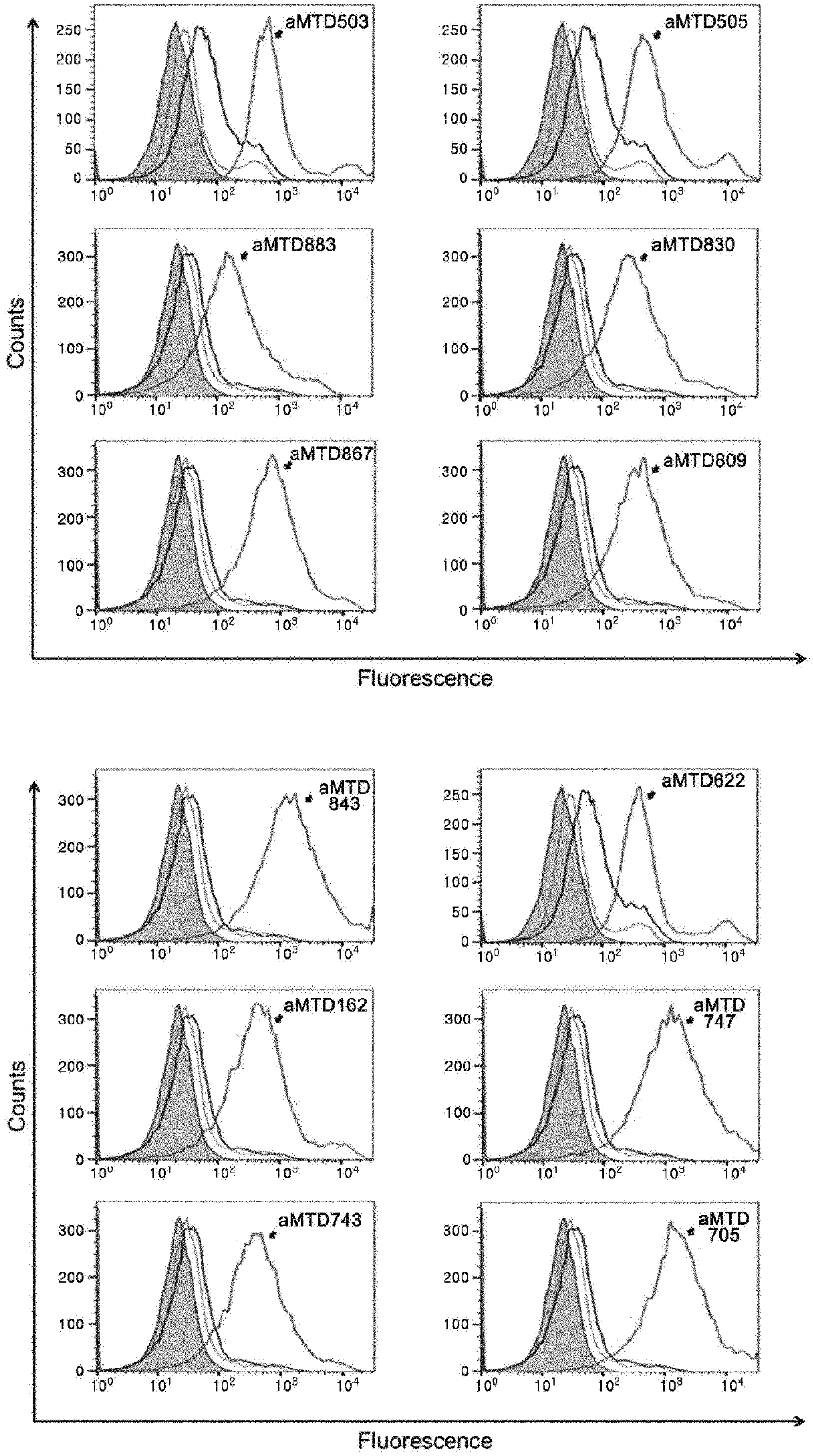

【Figure 5n】
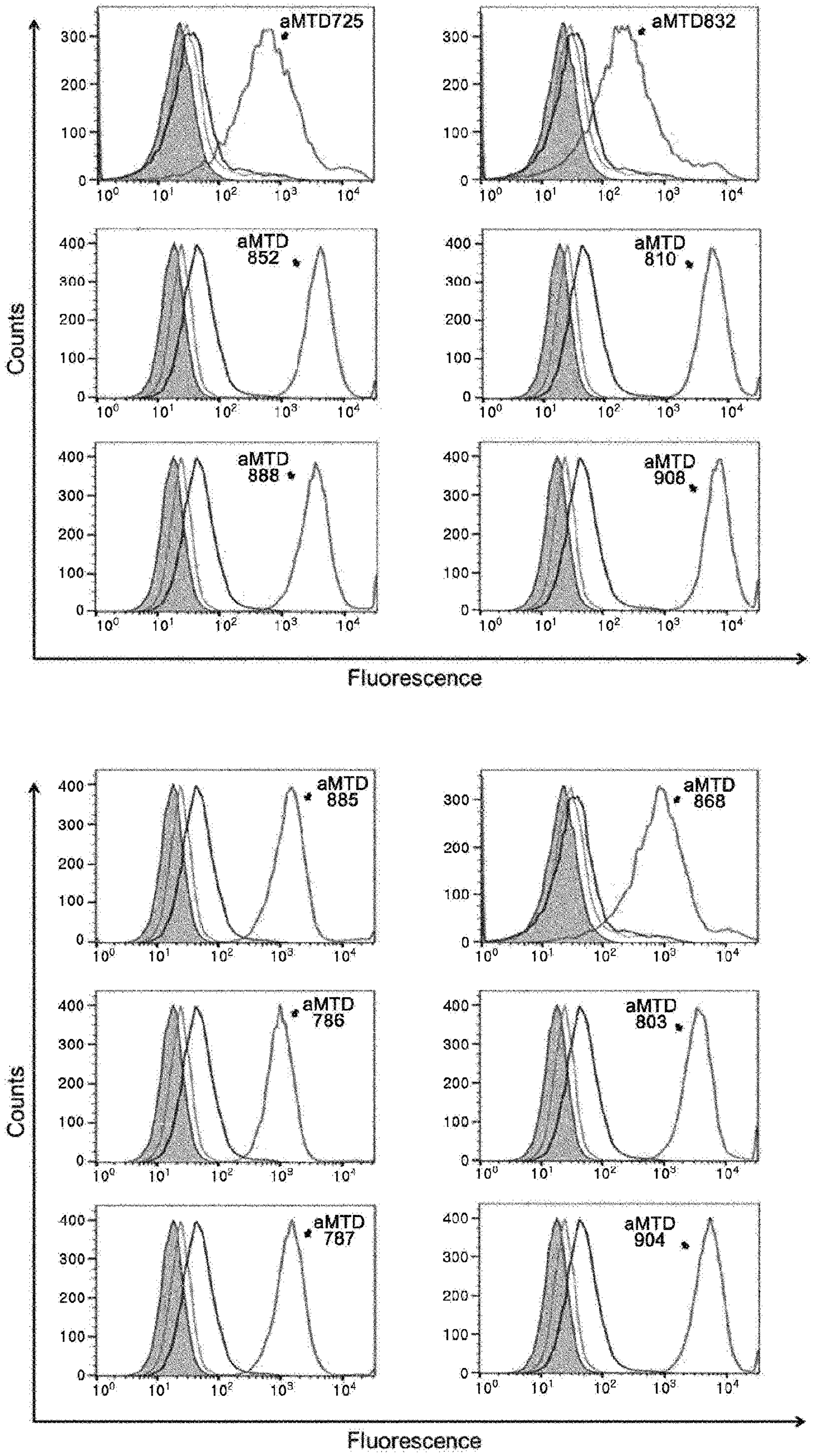

【Figure 5o】
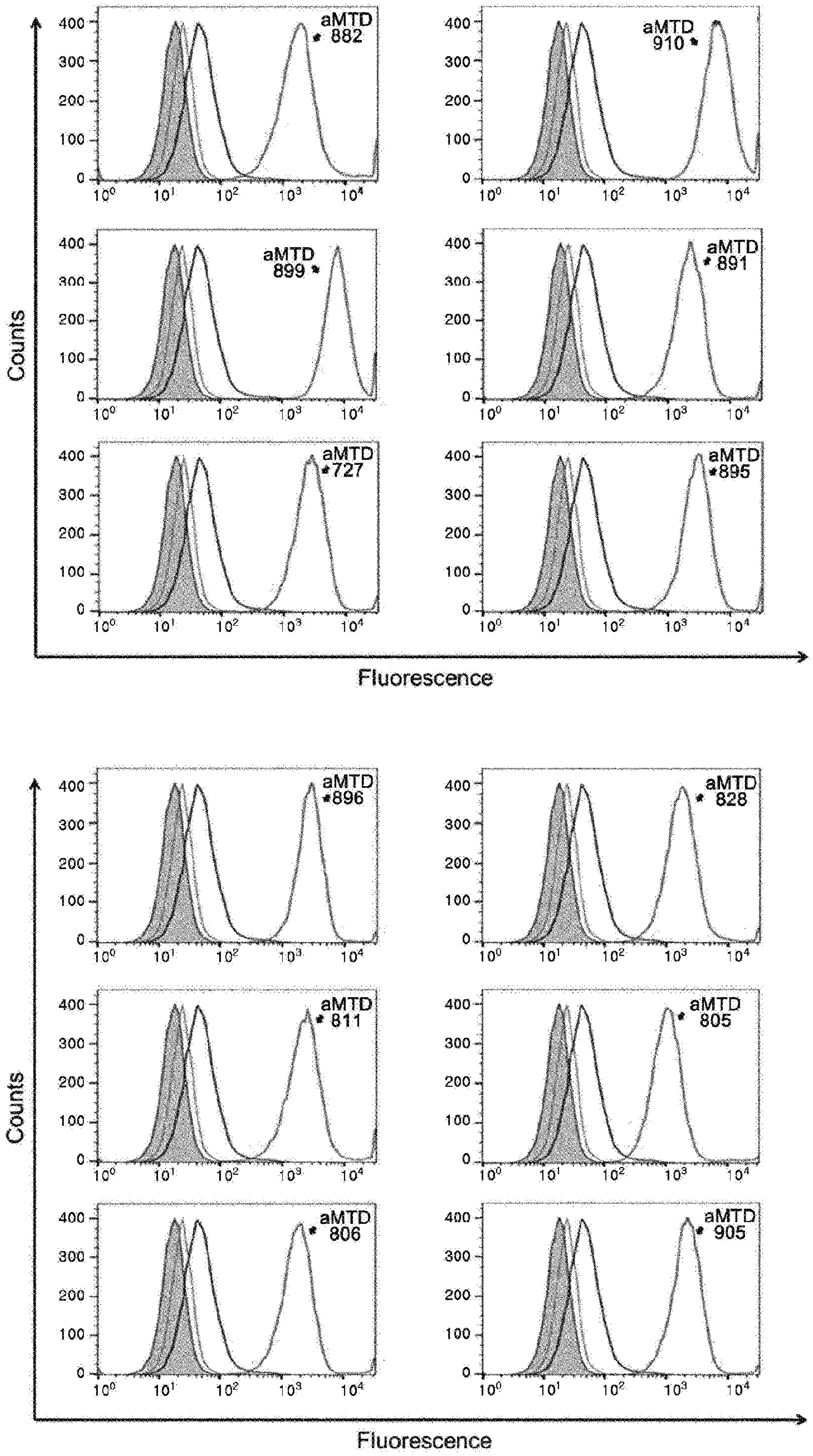

【Figure 5p】
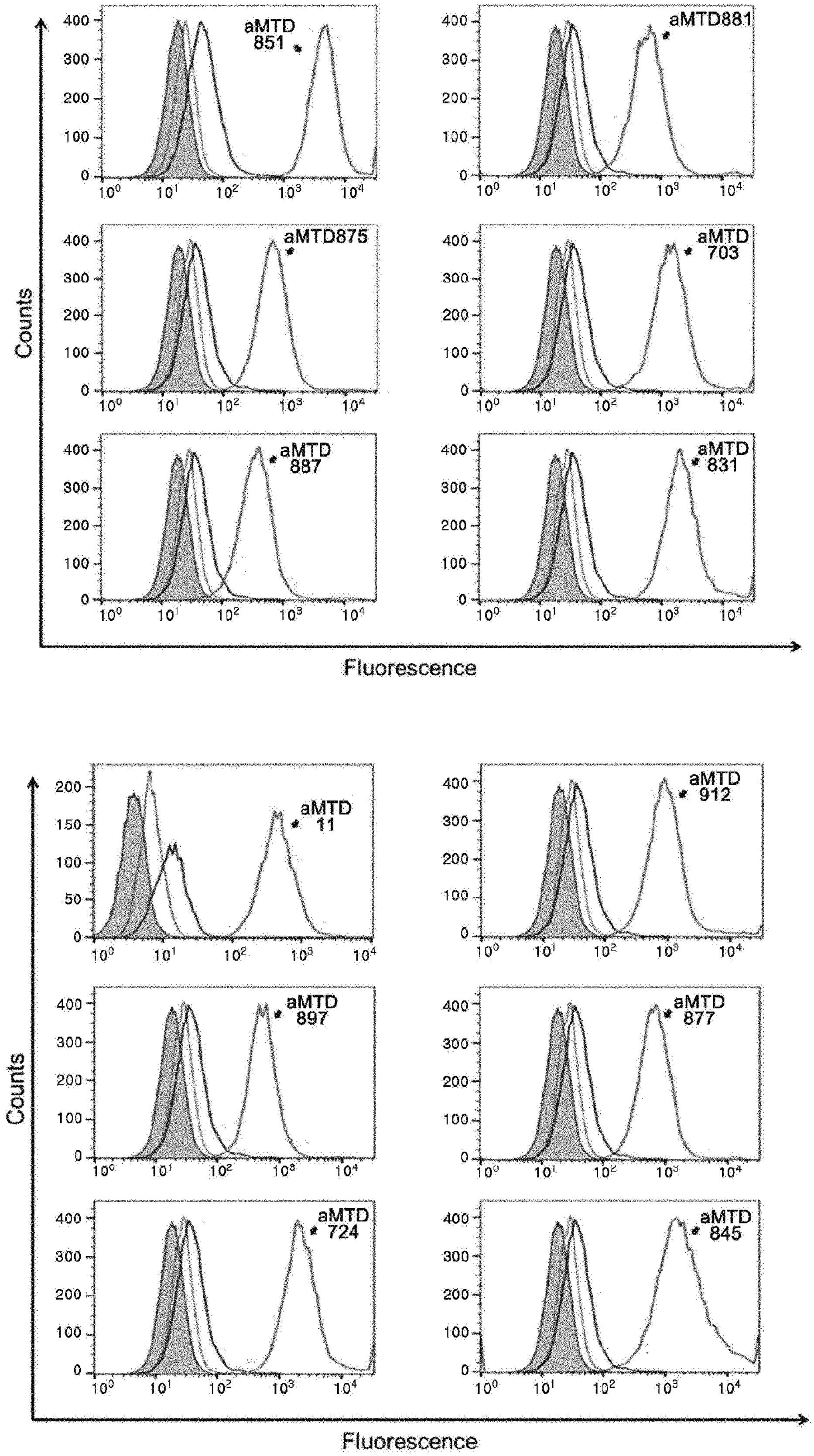

【Figure 5q】
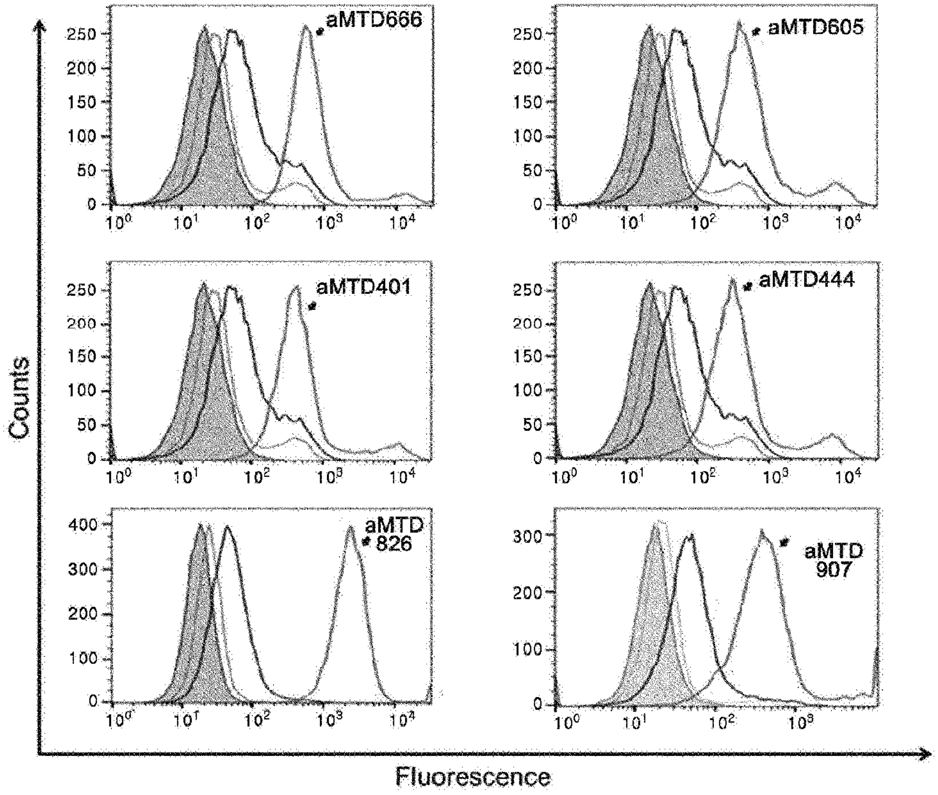
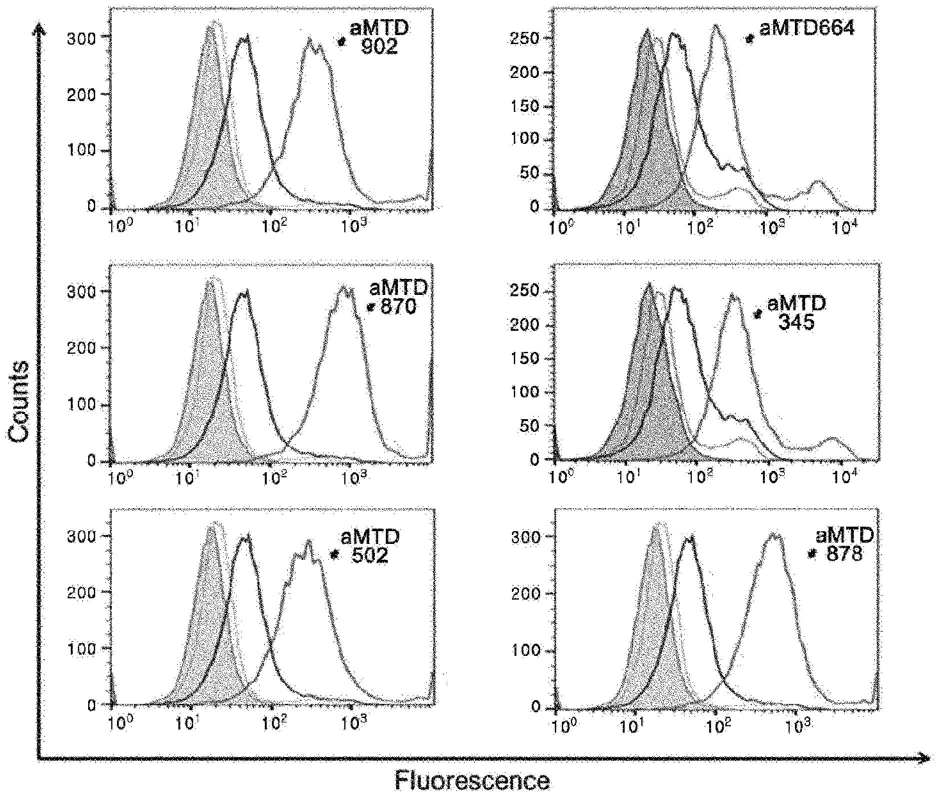

【Figure 5r】
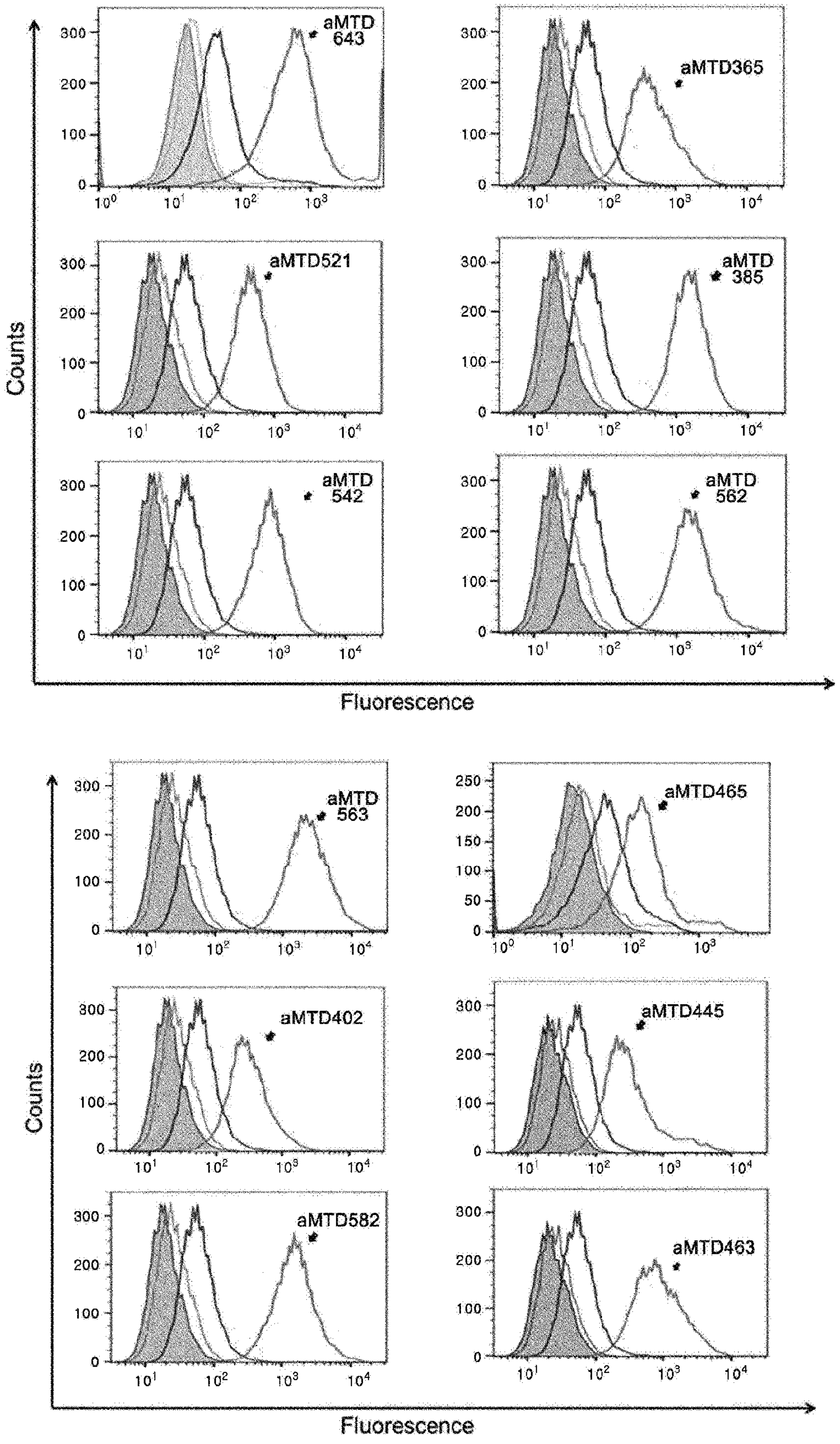

【Figure 5s】
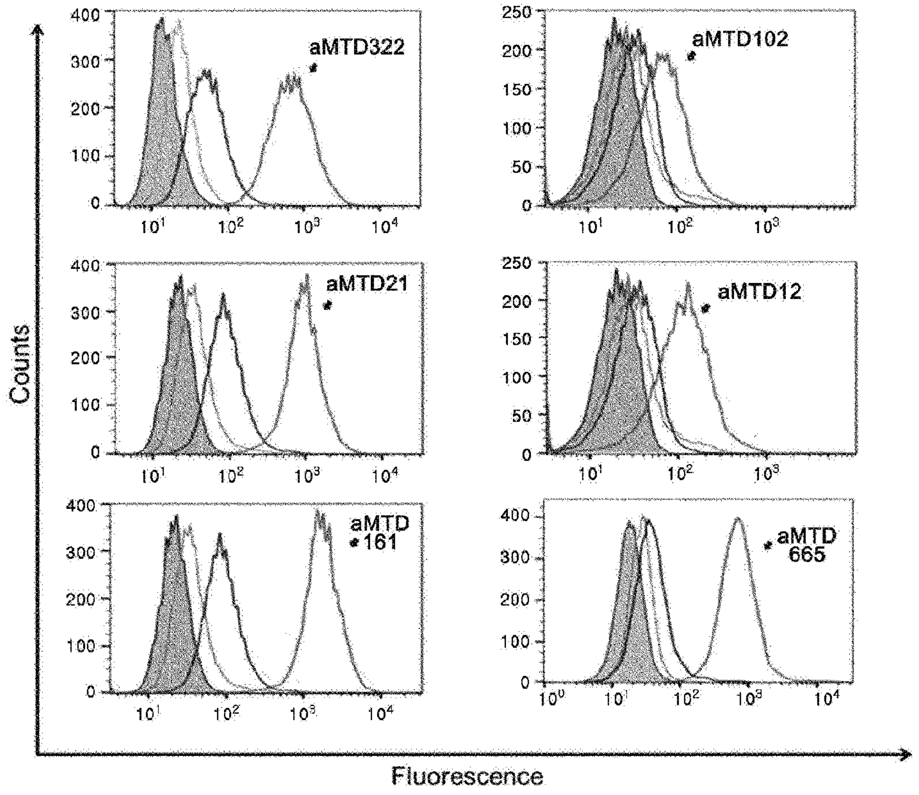
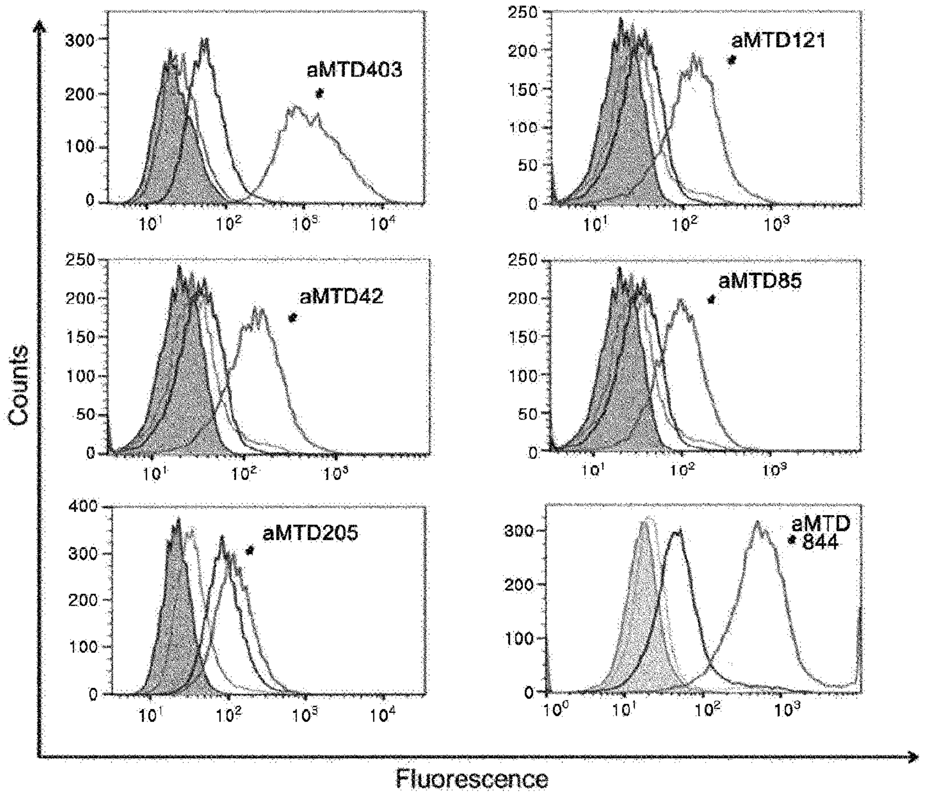

【Figure 5t】
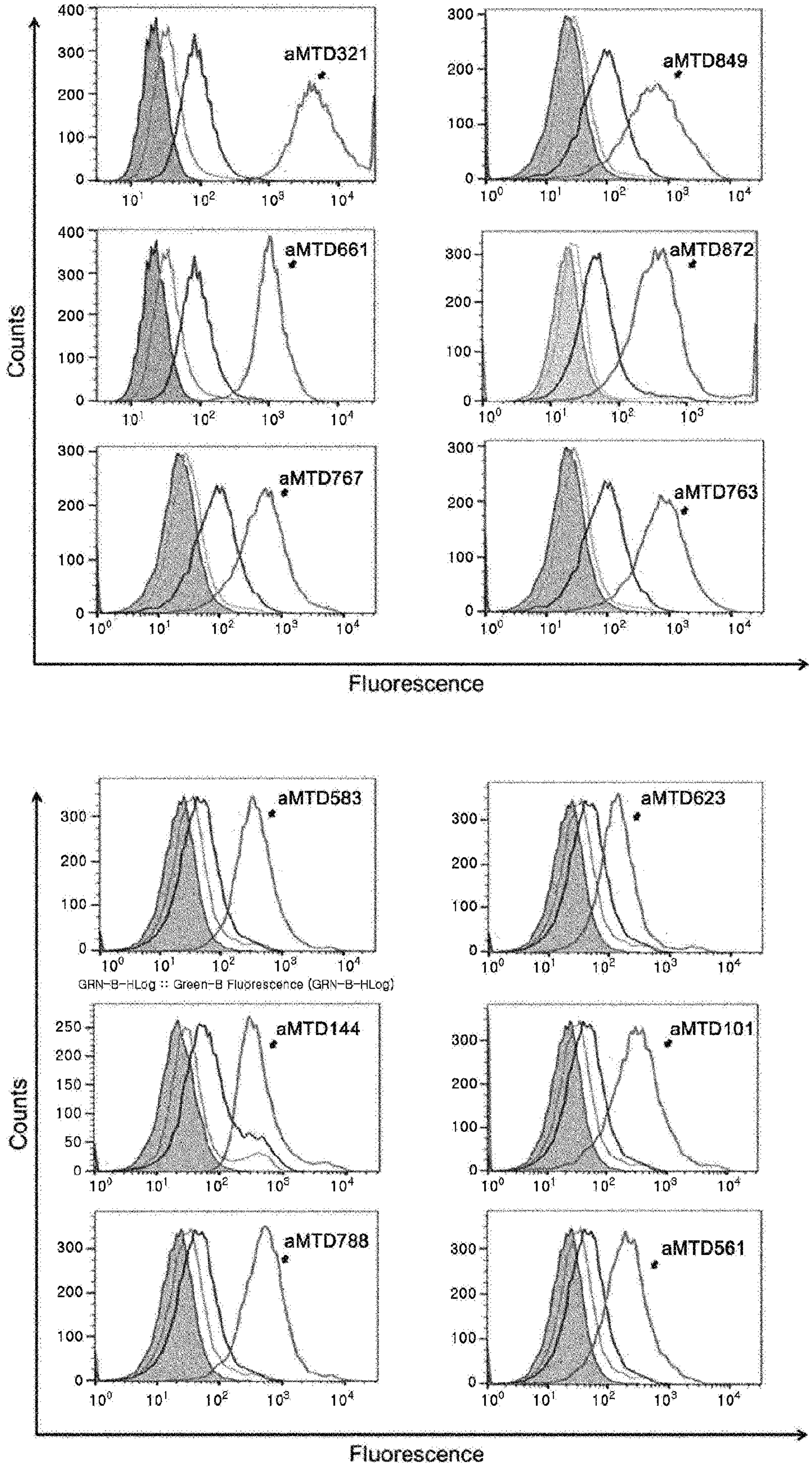

【Figure 5u】
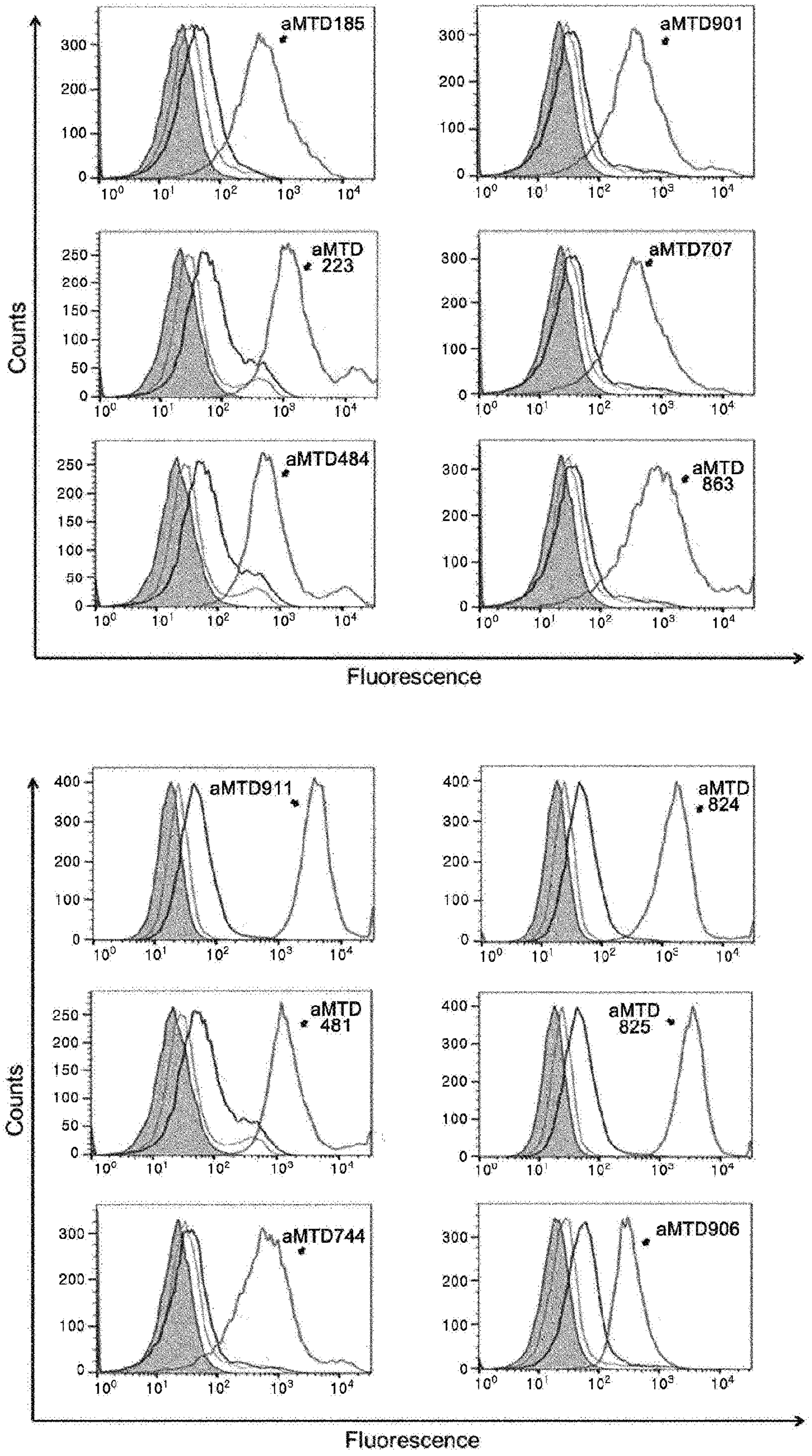

【Figure 6a】
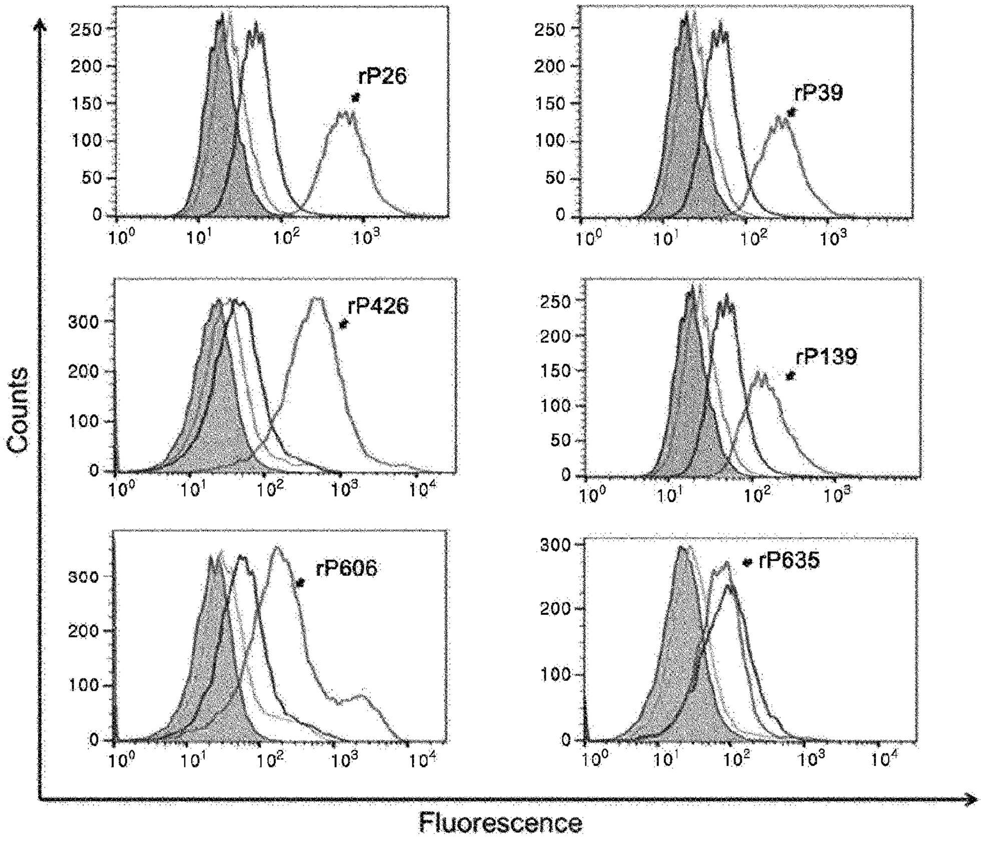

【Figure 6b】
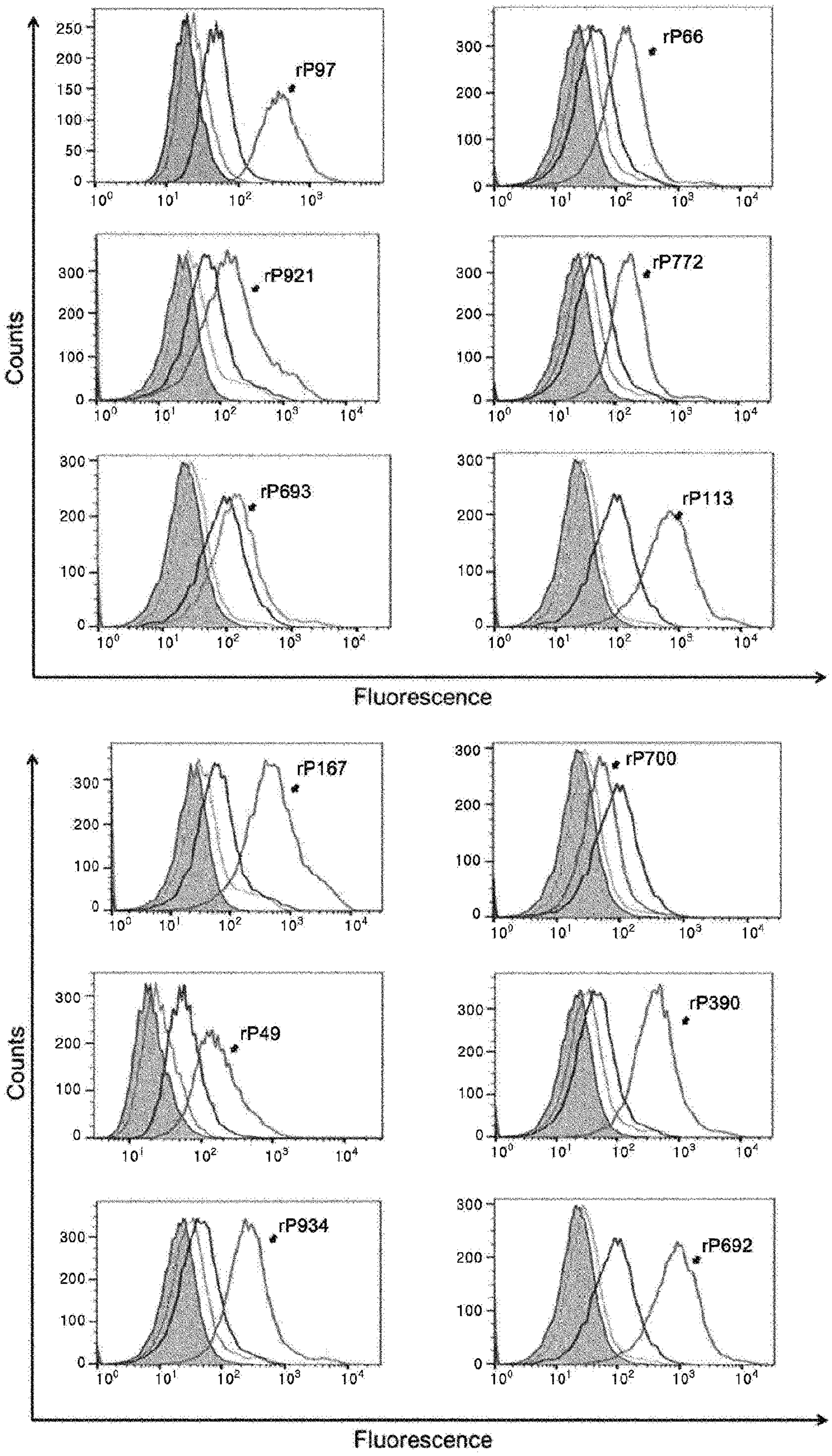

【Figure 6c】
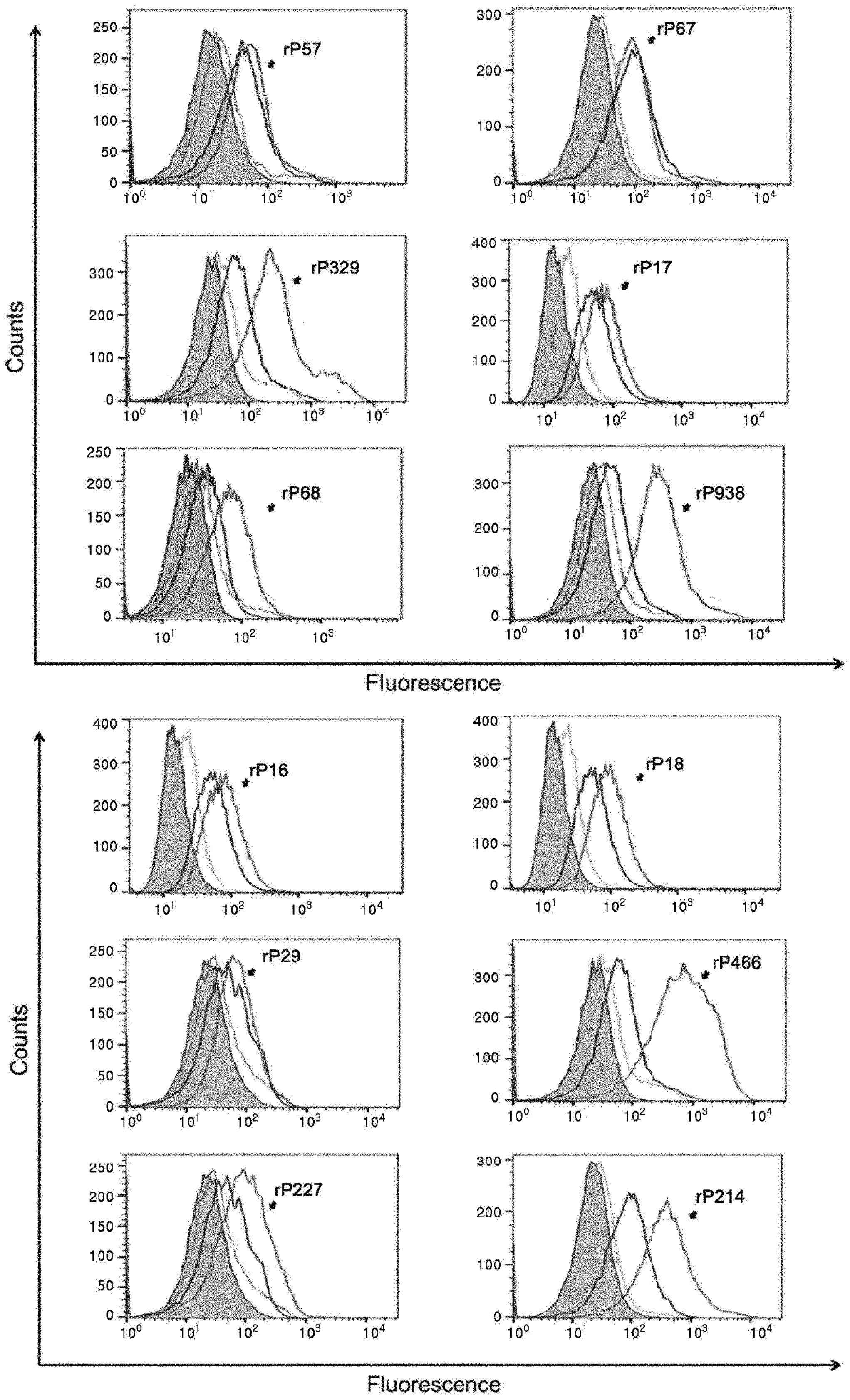

【Figure 7a】
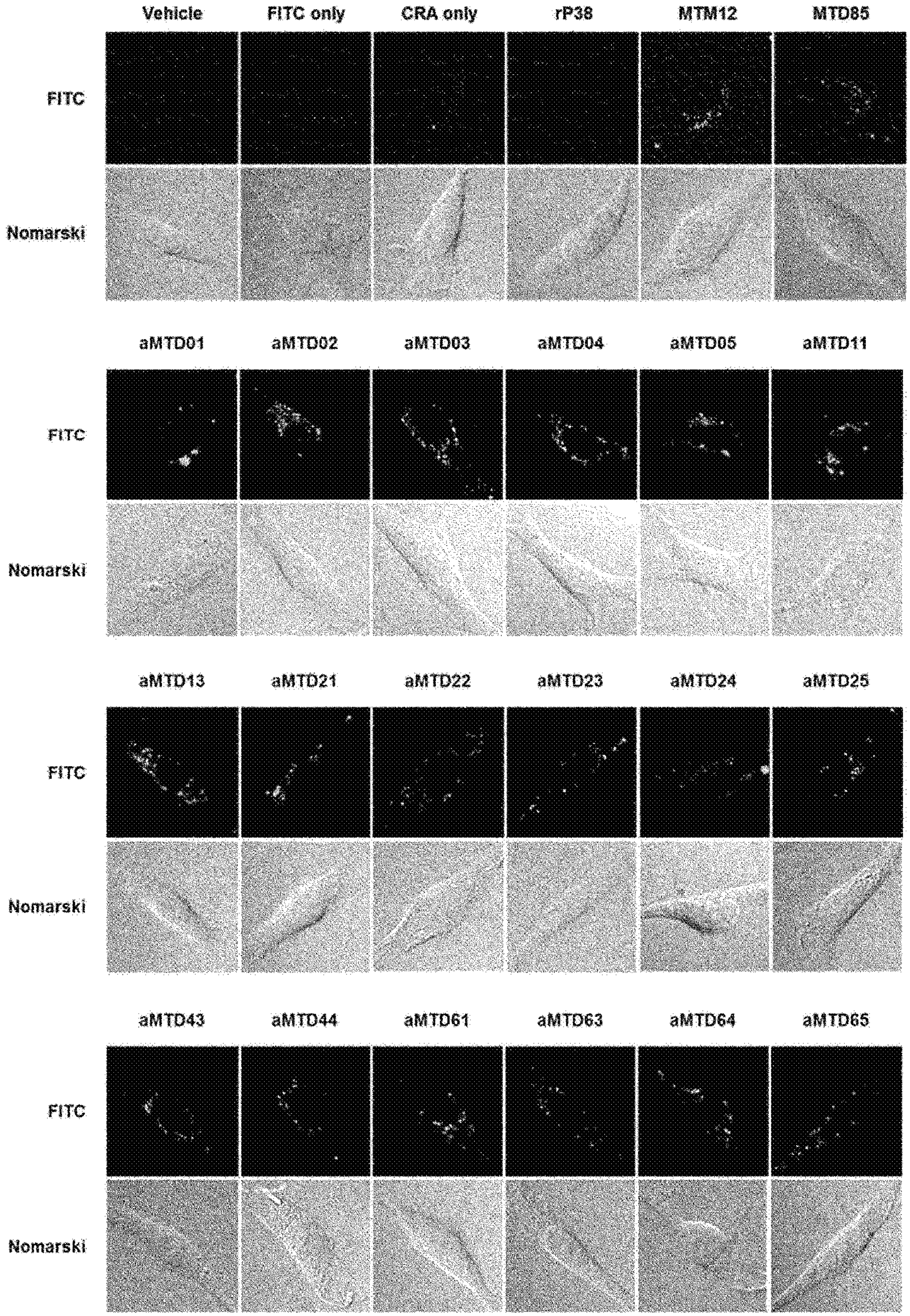

【Figure 7b】
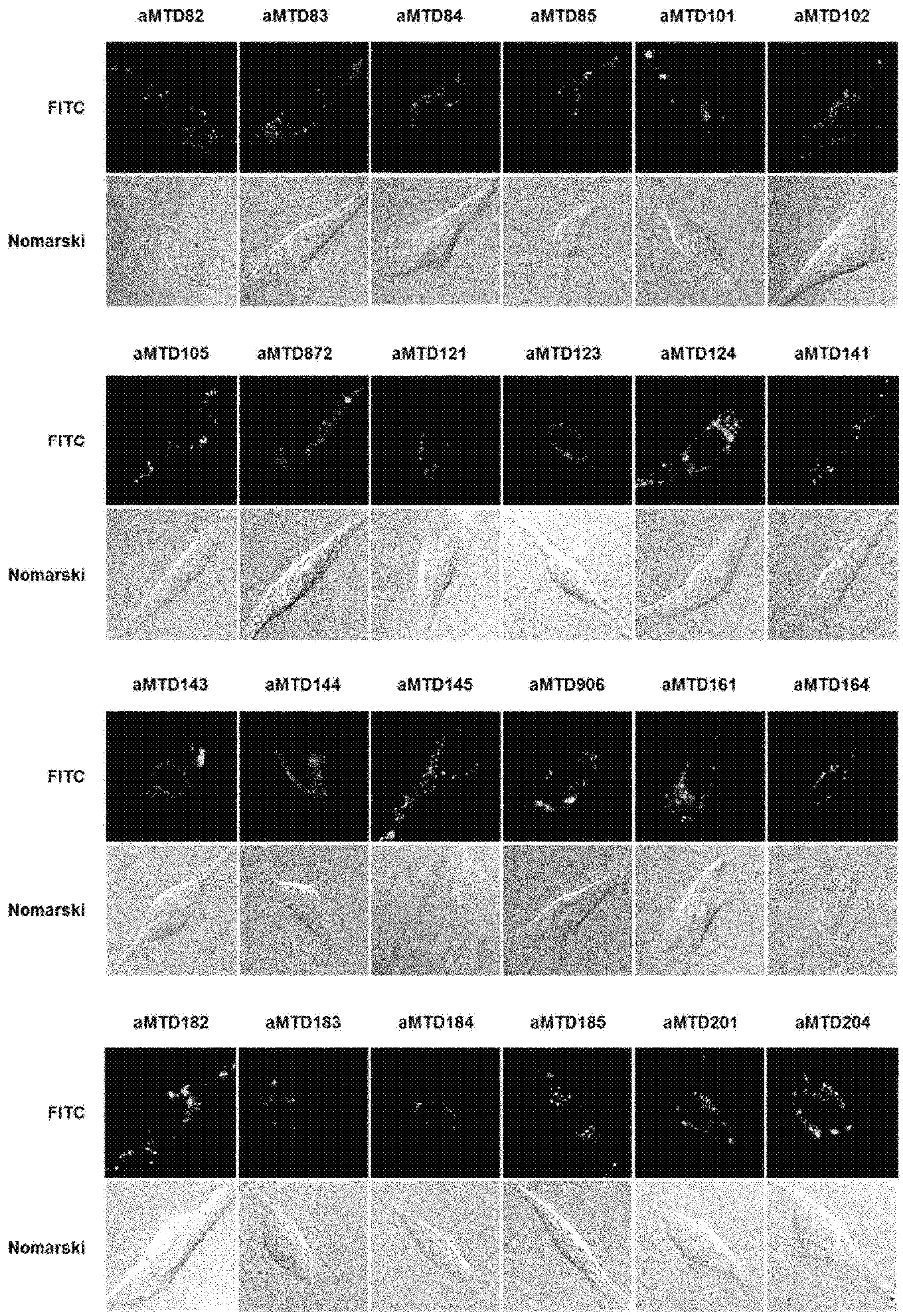

【Figure 7c】
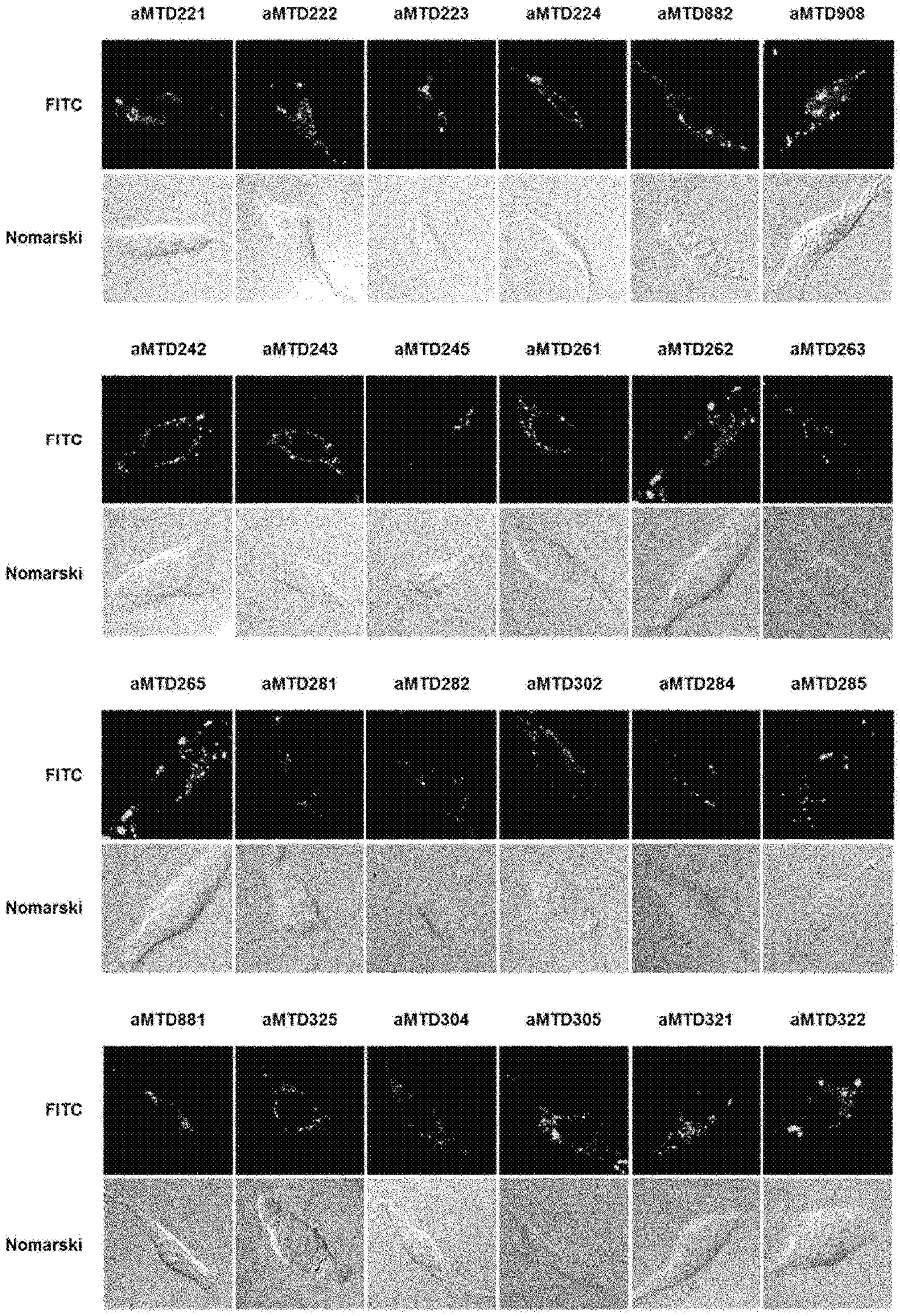

【Figure 7d】
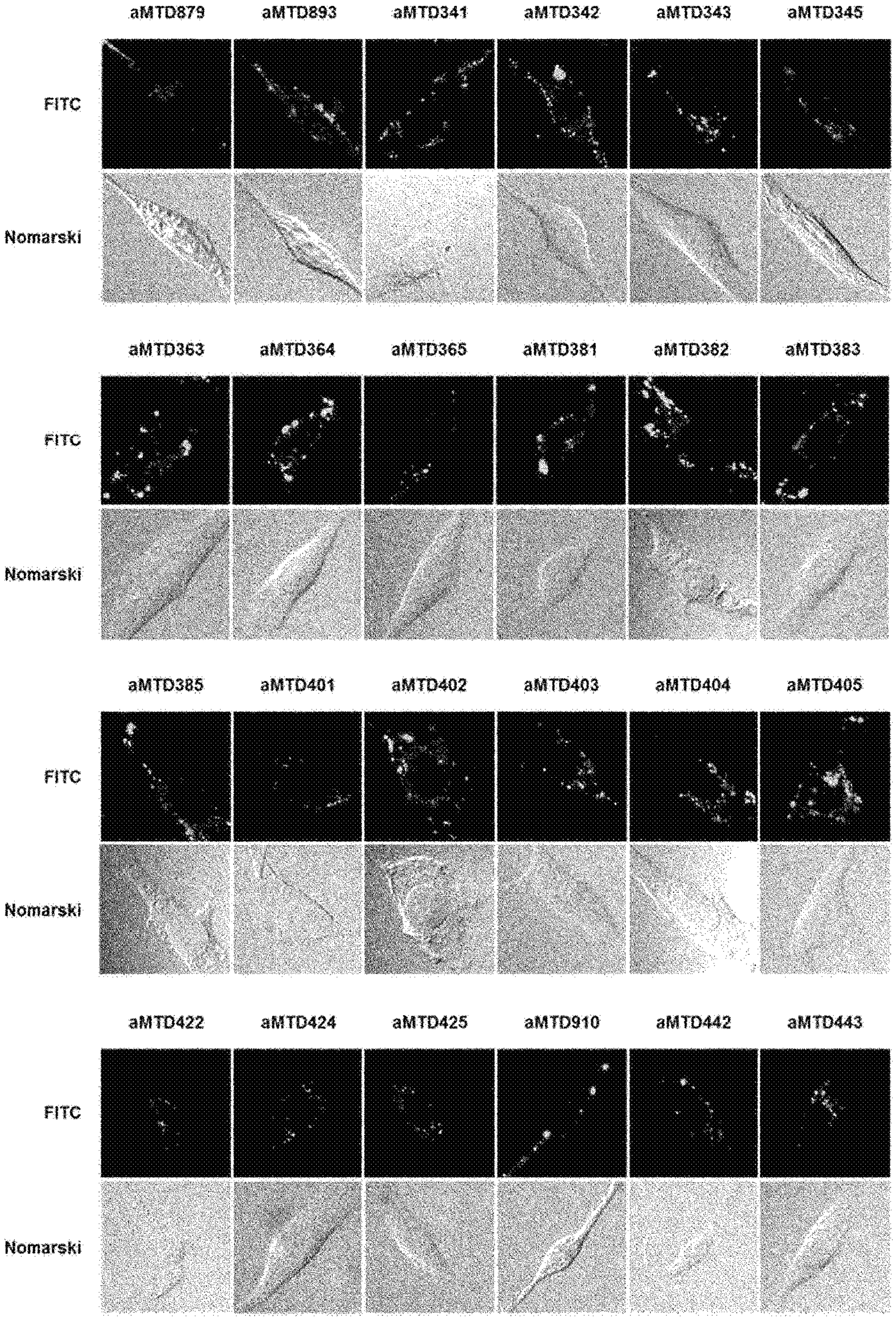

【Figure 7e】
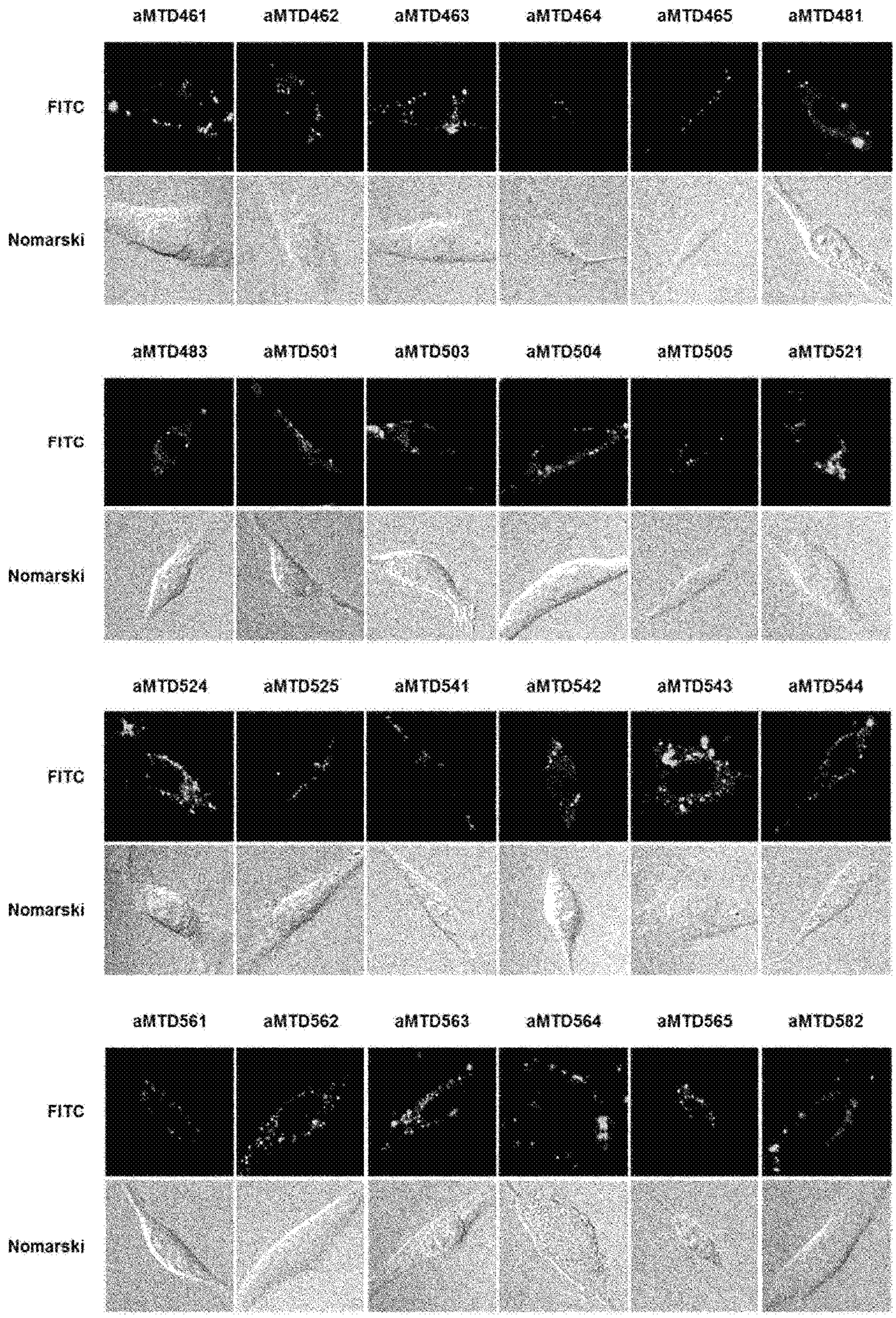

【Figure 7f】
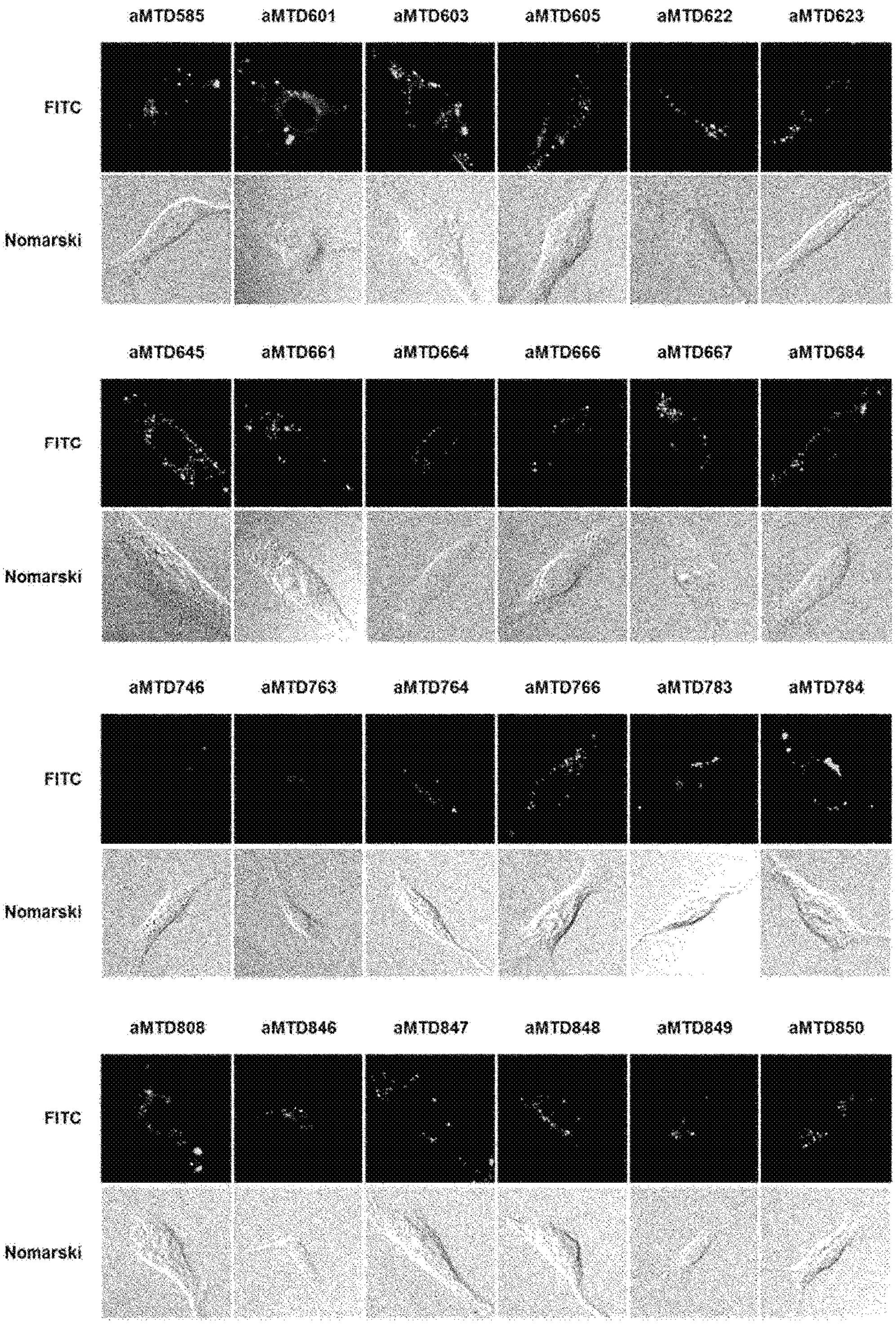

【Figure 7g】
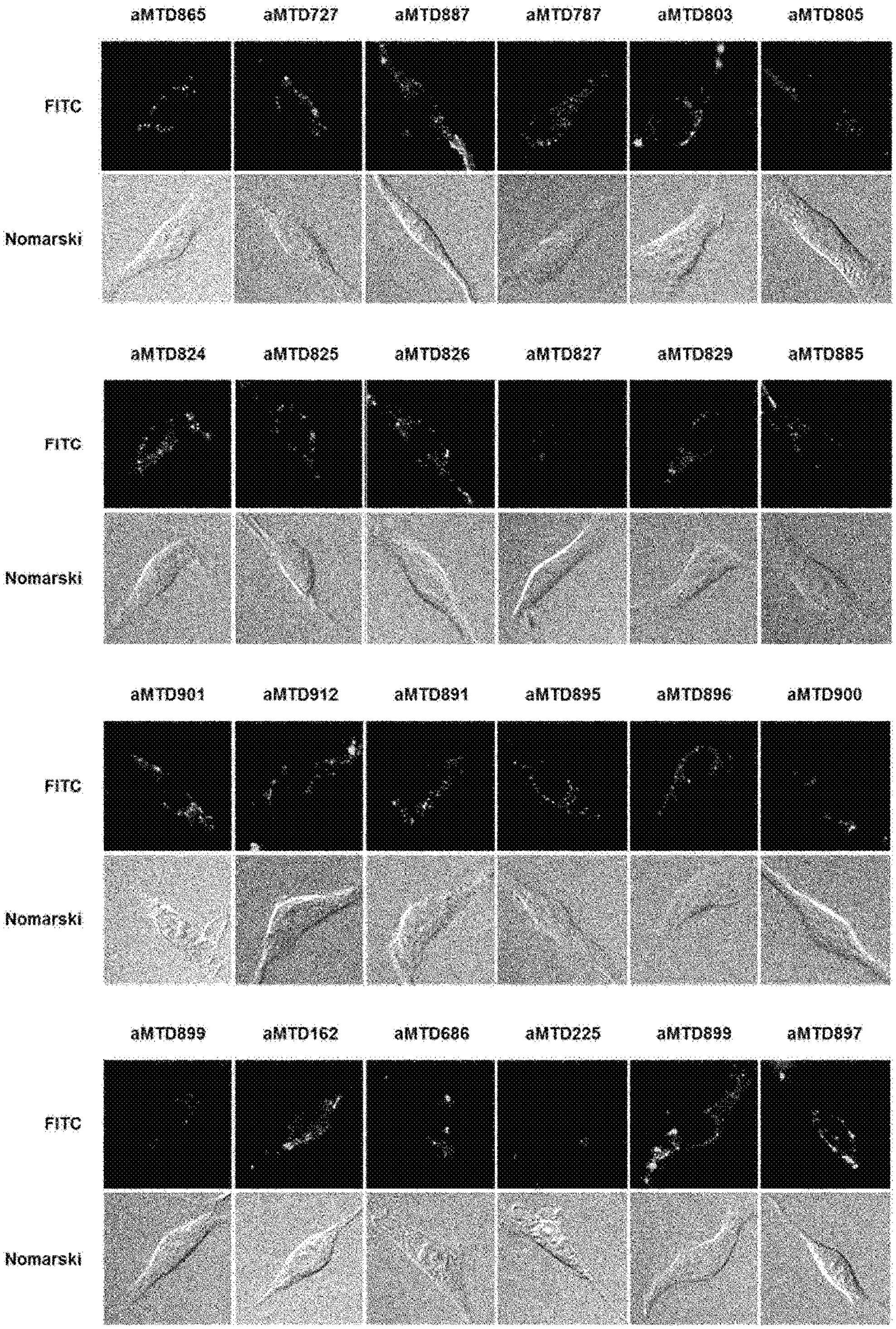

【Figure 7h】
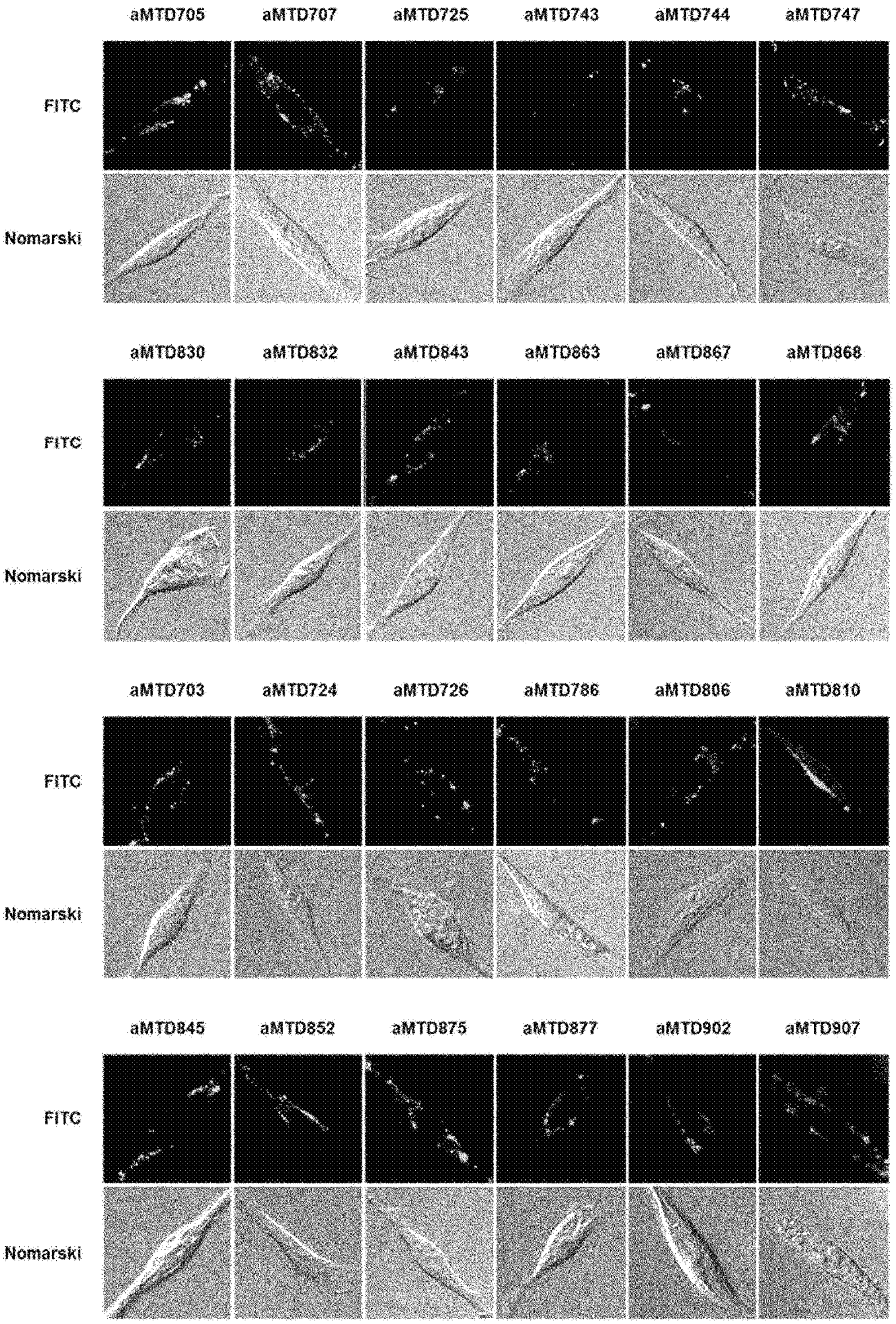

【Figure 7i】
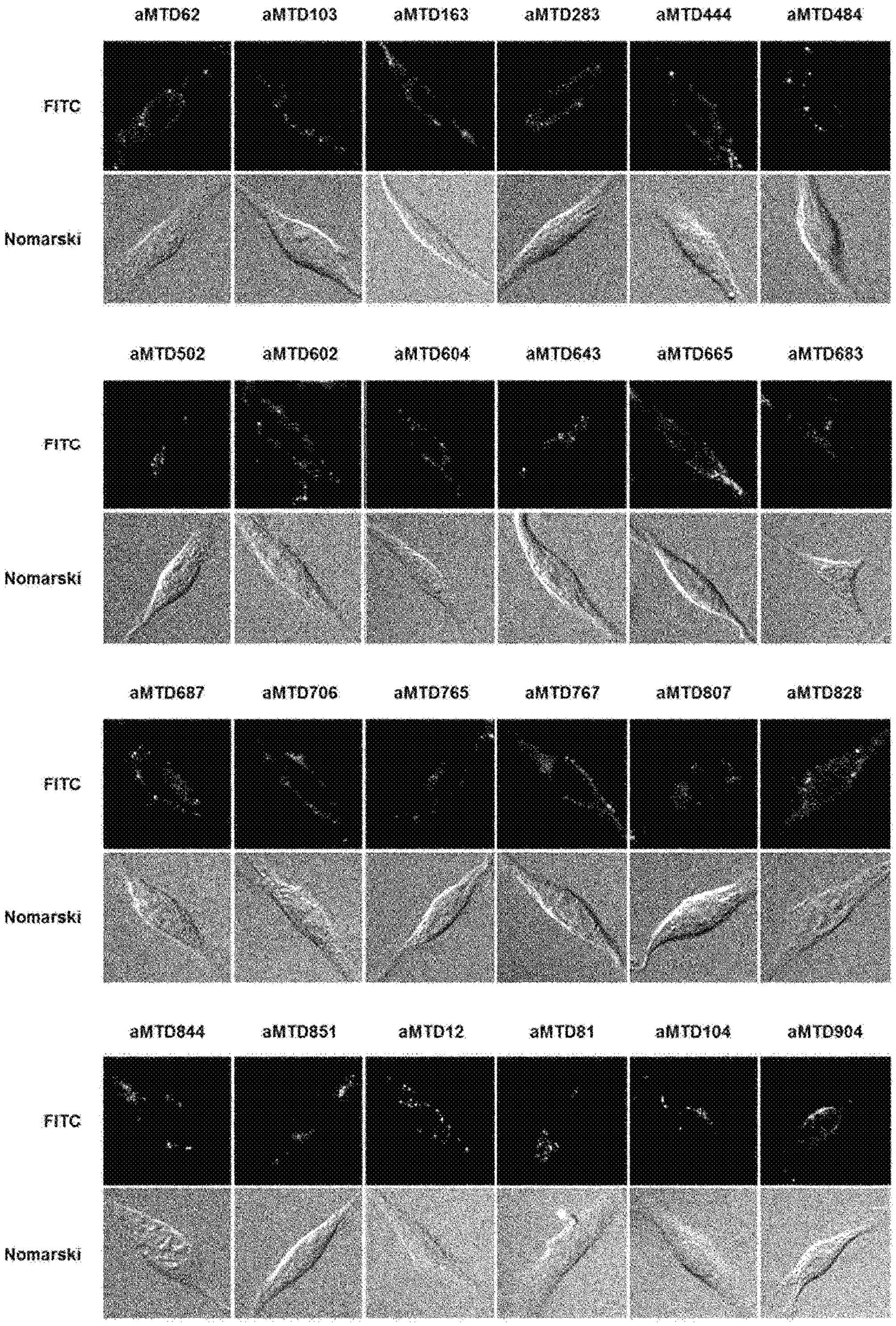

【Figure 7j】
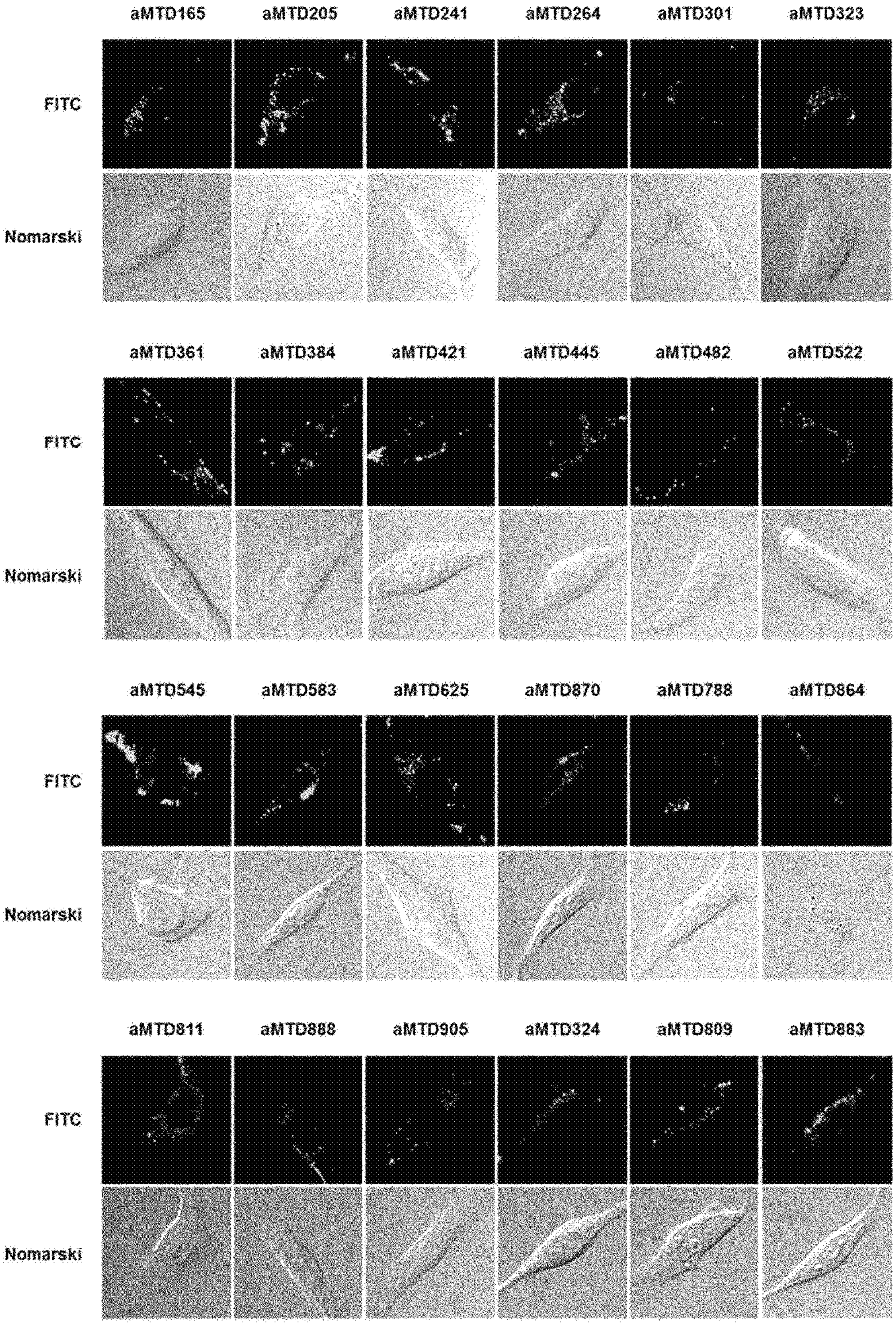

【Figure 7k】
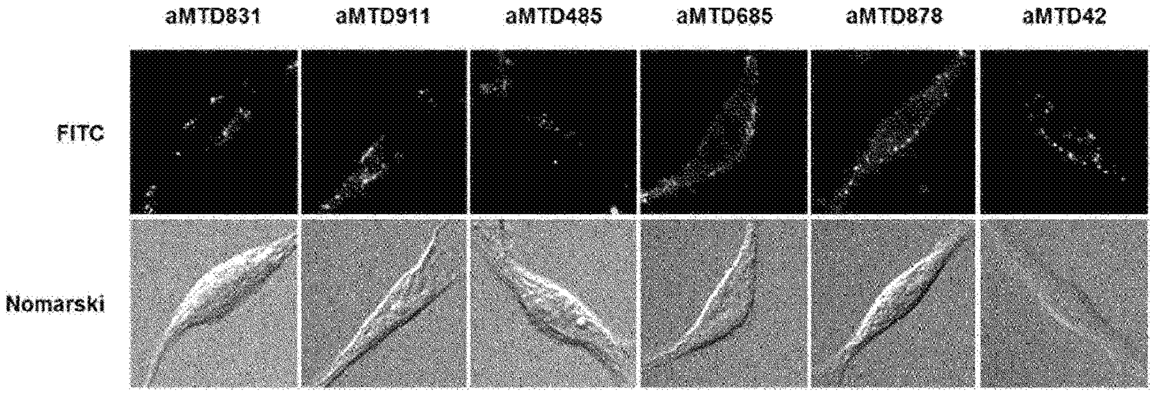

【Figure 8】
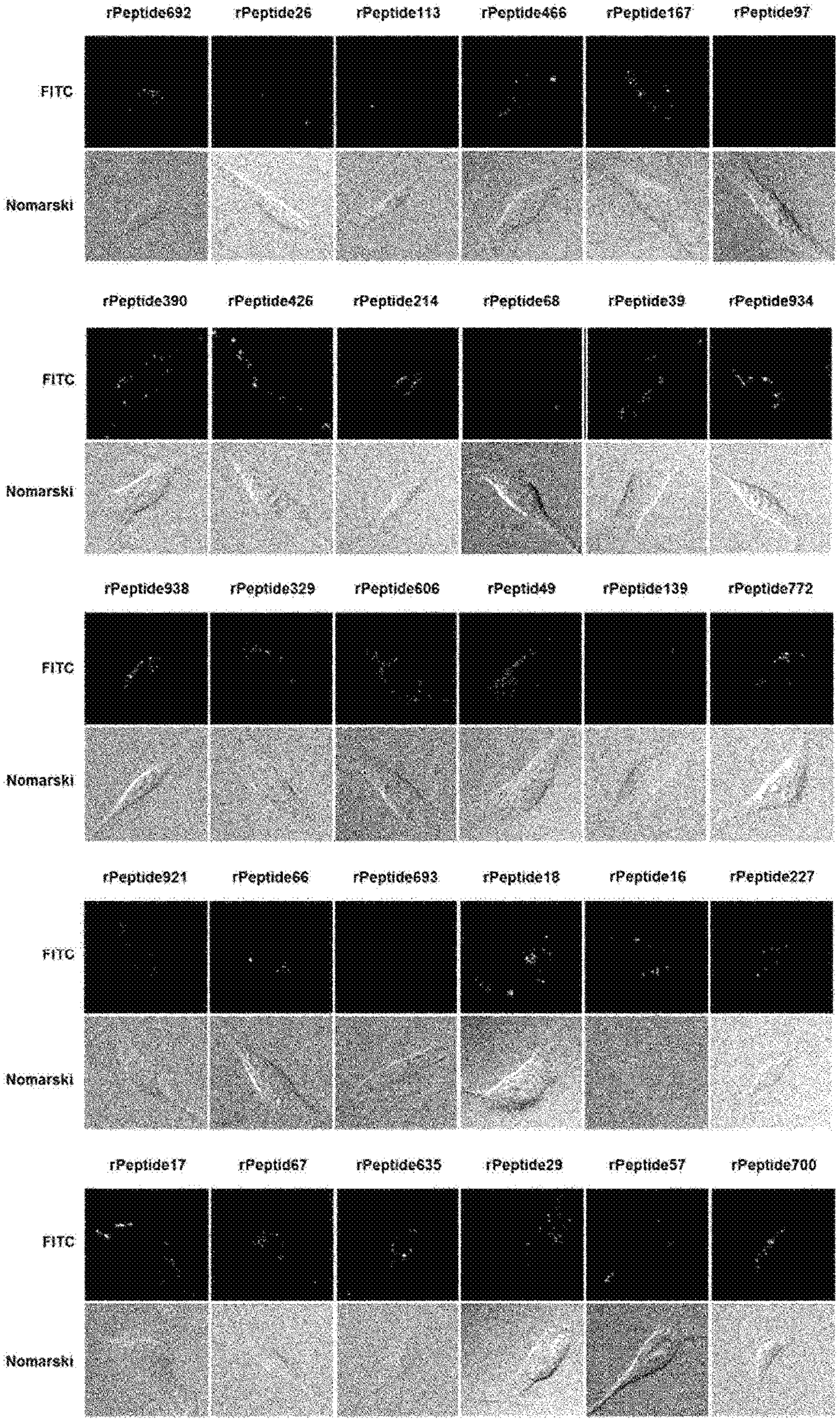

【Figure 9a】
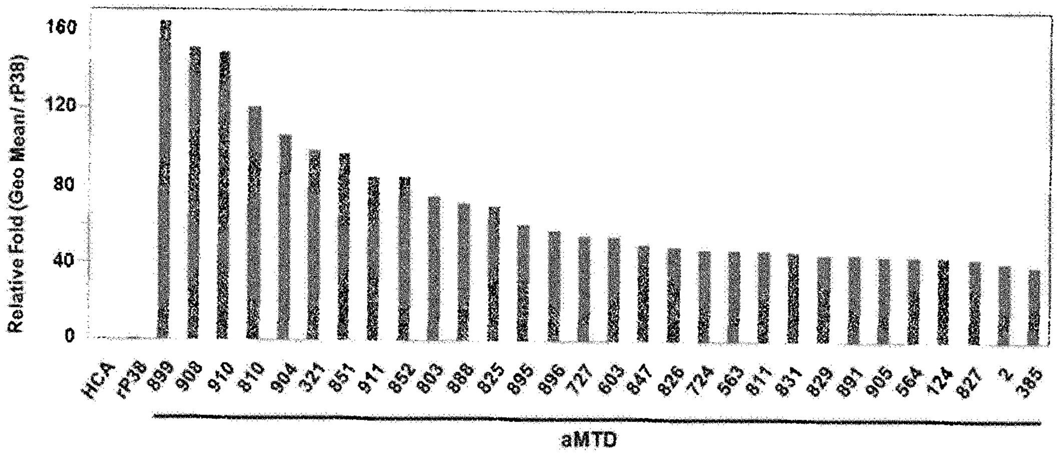
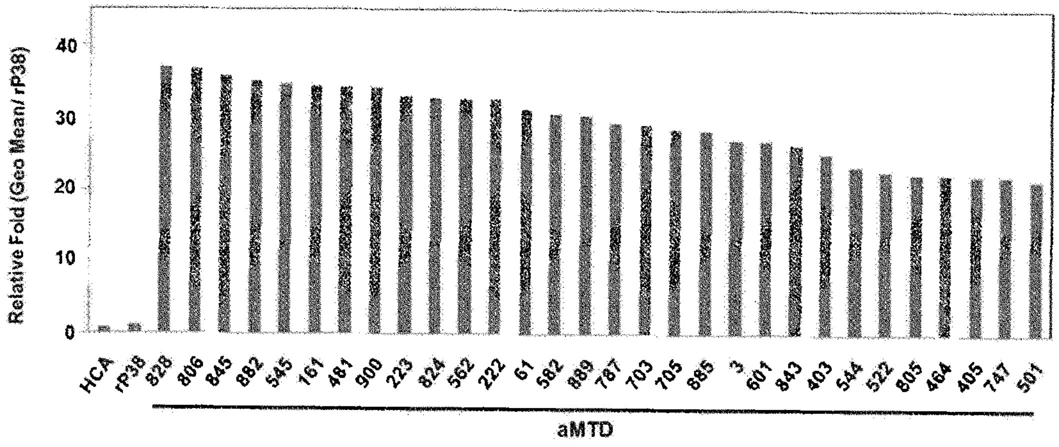
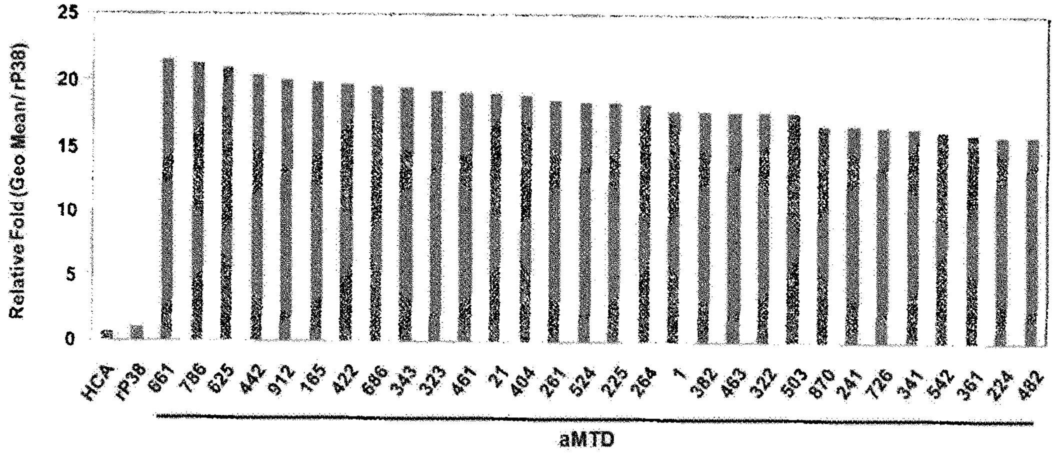

【Figure 9b】
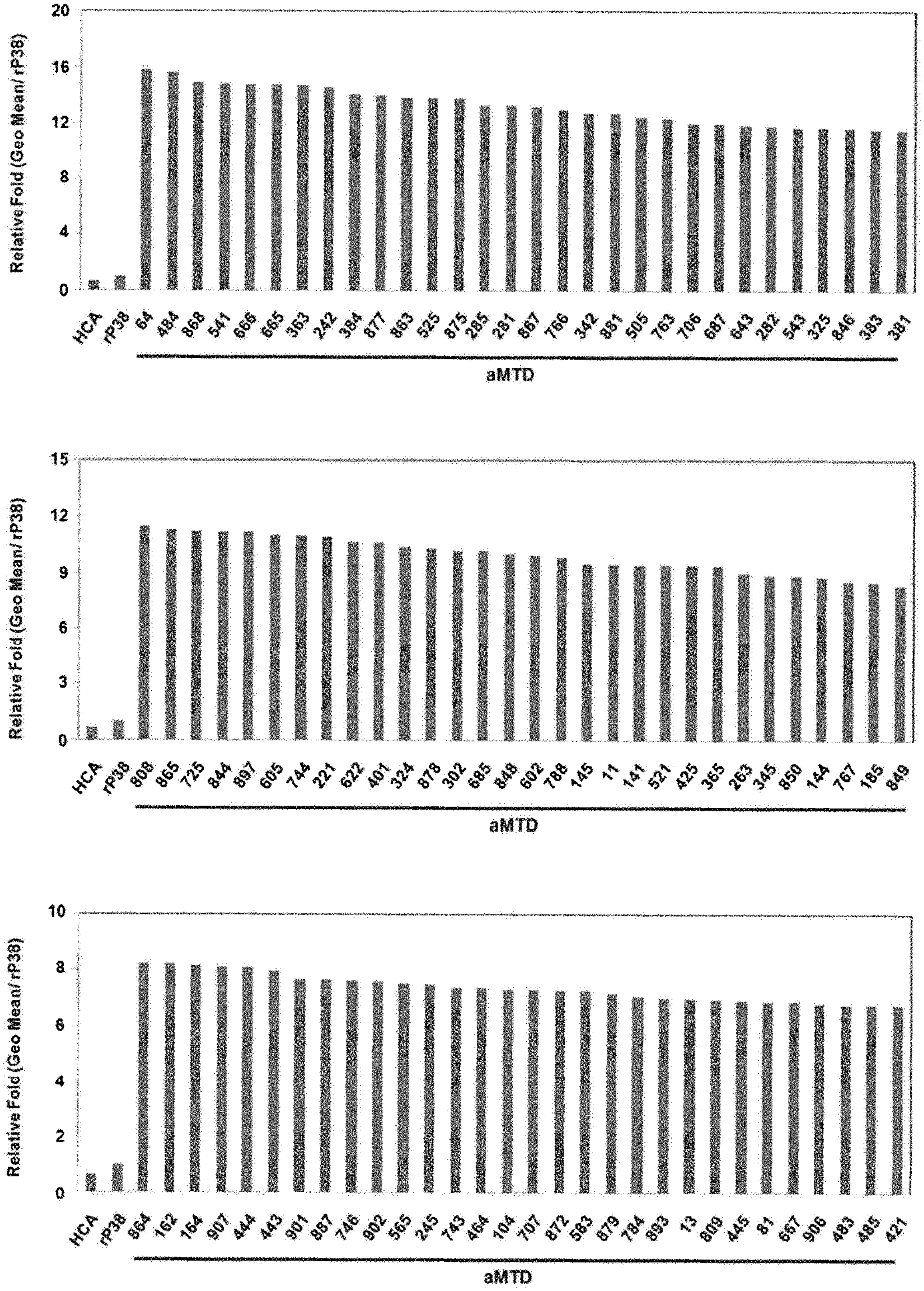

【Figure 9c】
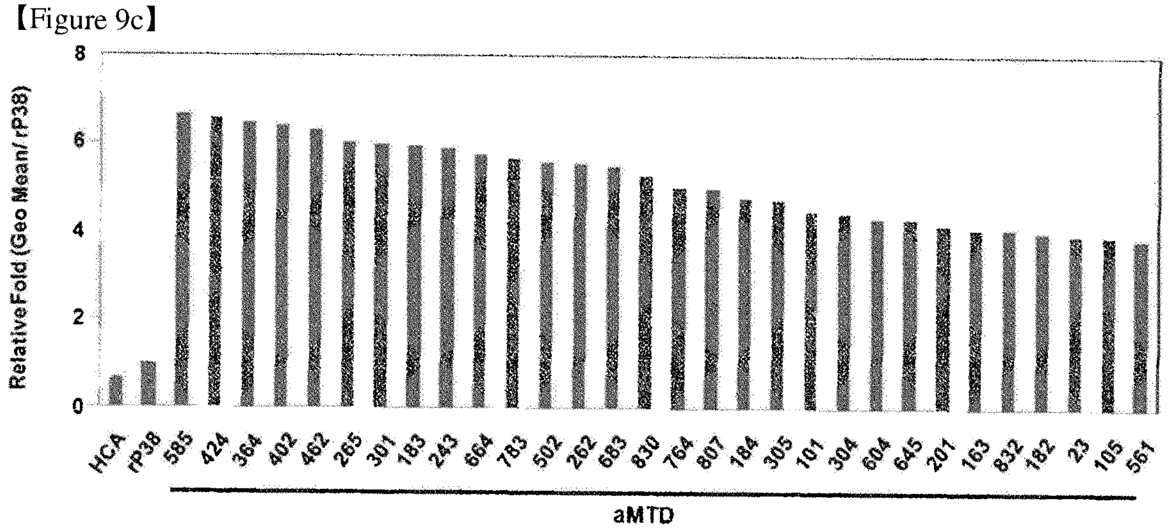
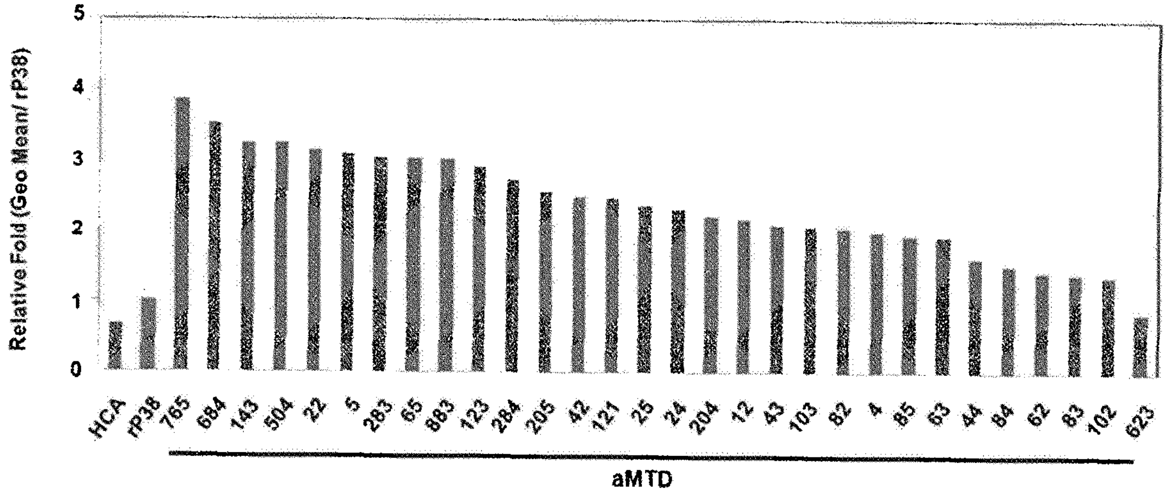

【Figure 10a】
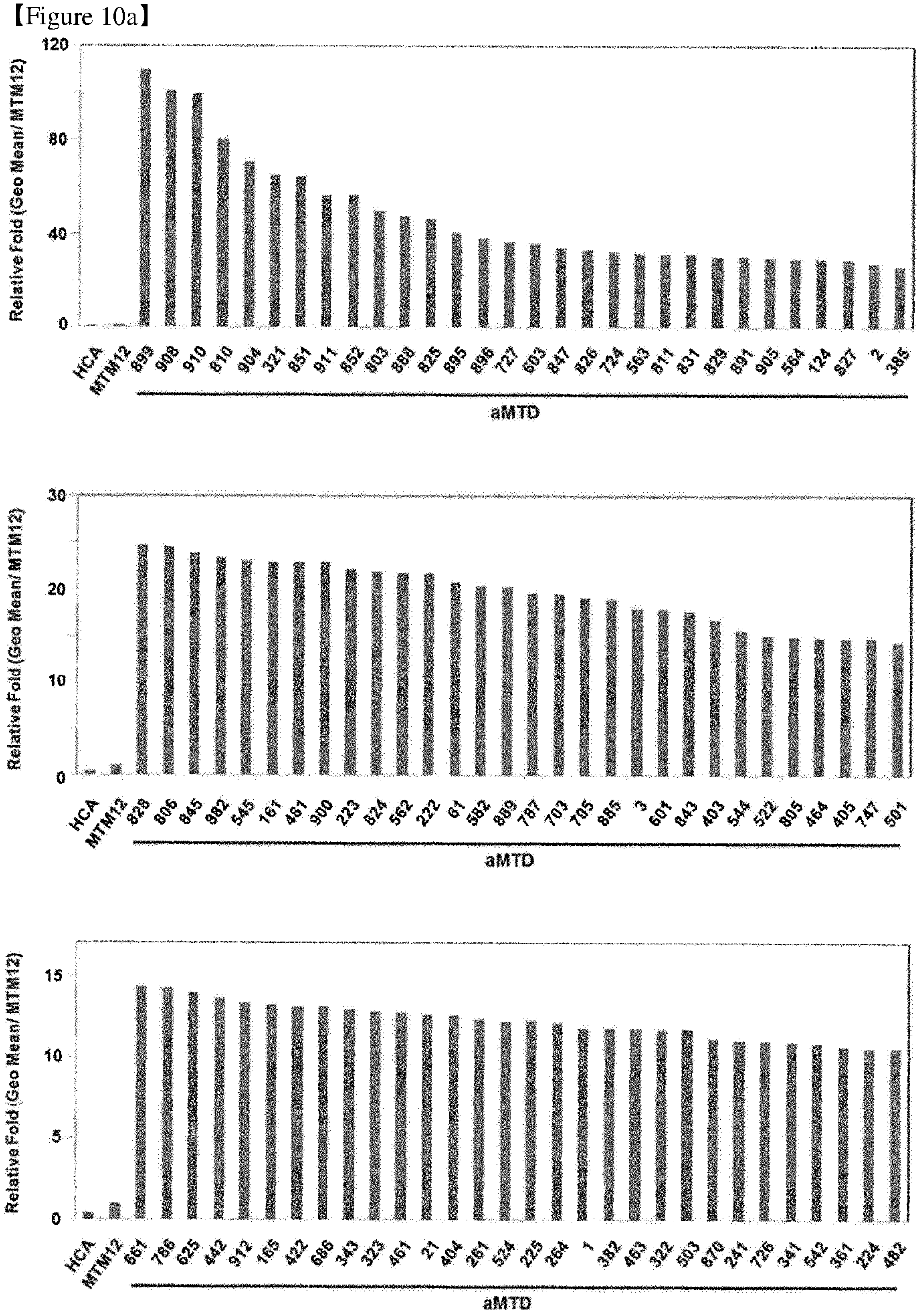

【Figure 10b】
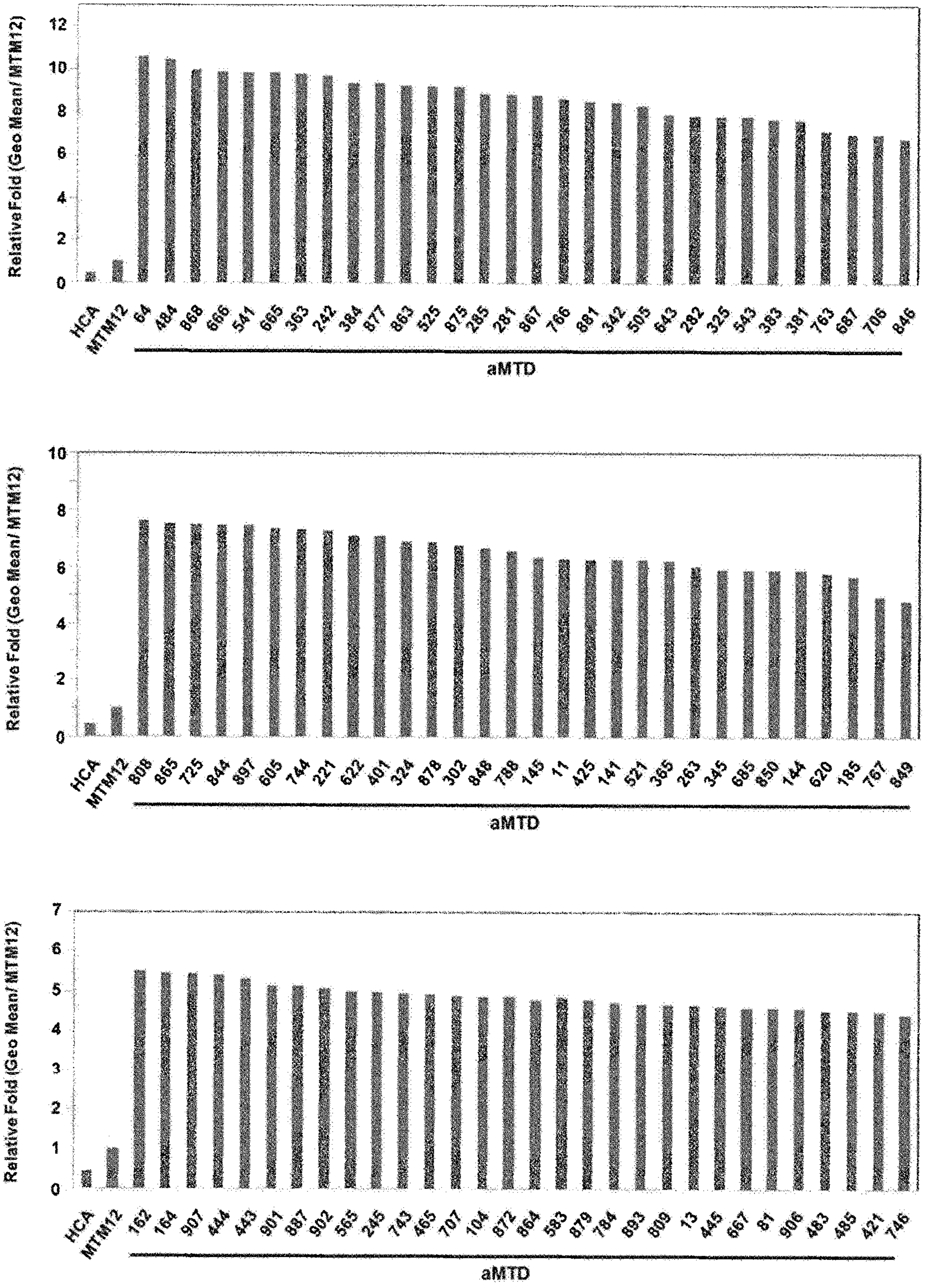

【Figure 10c】
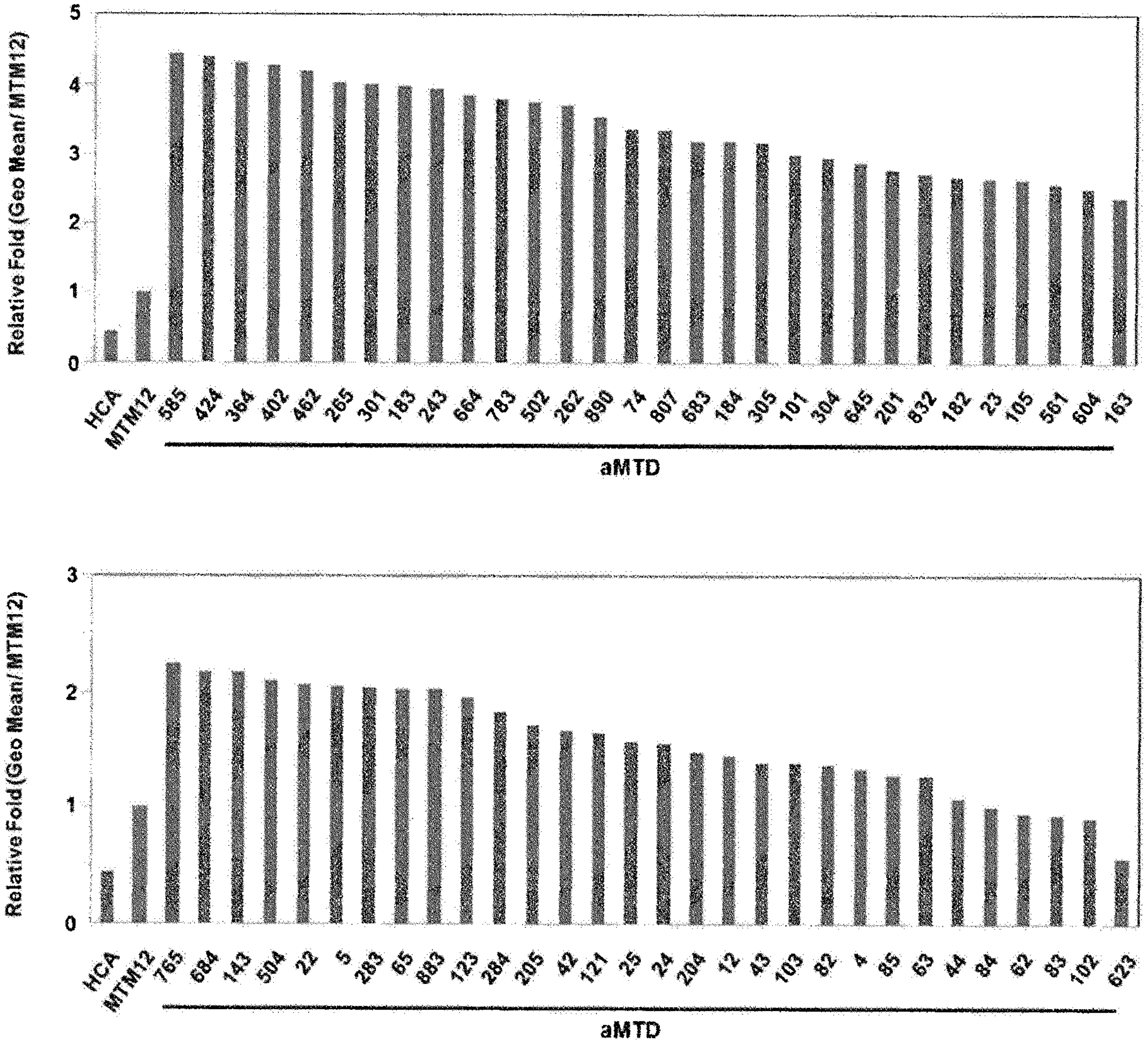

【Figure 11a】
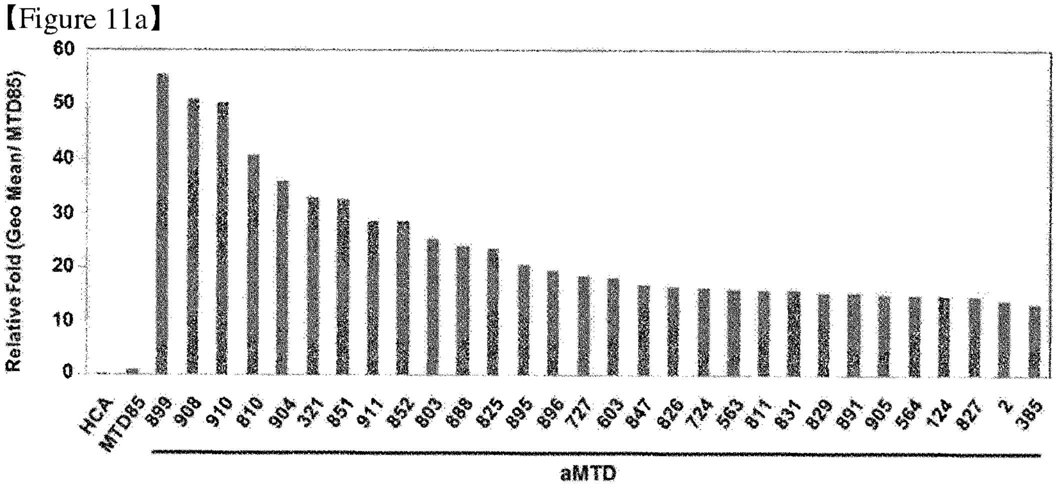
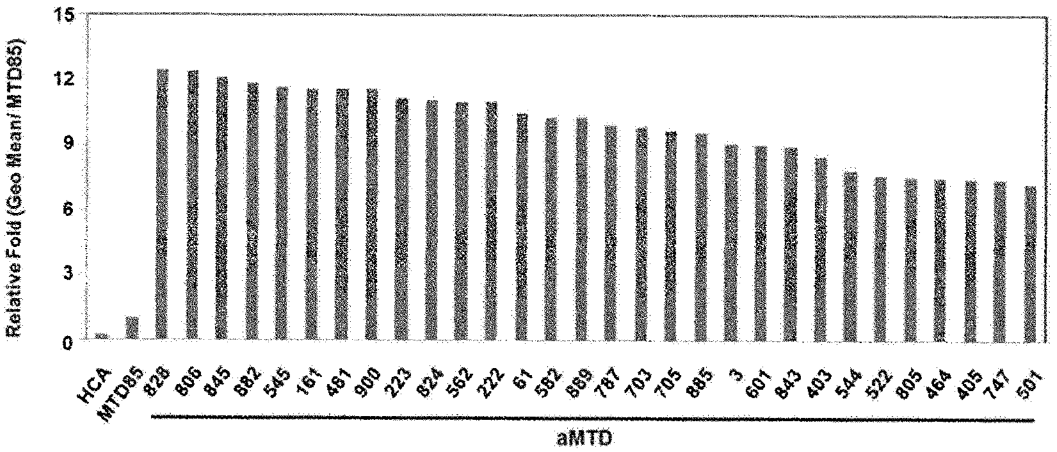
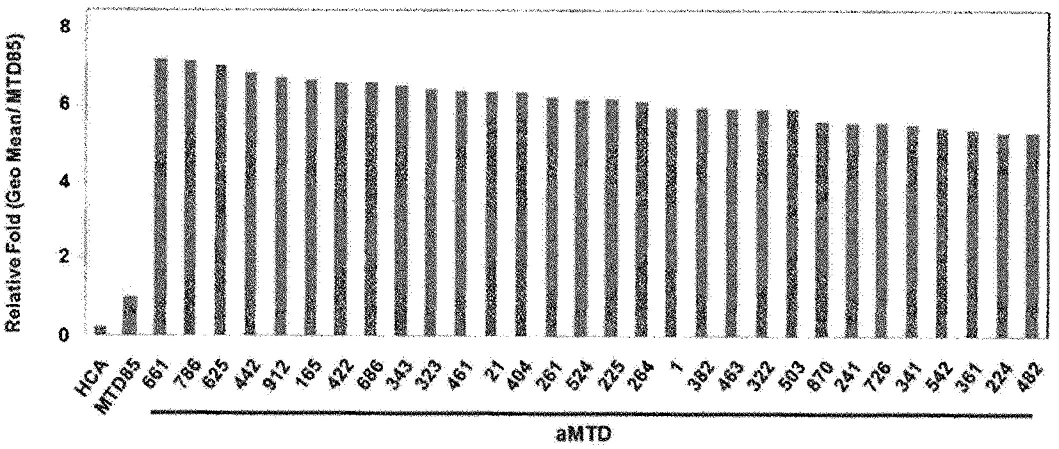

【Figure 11b】
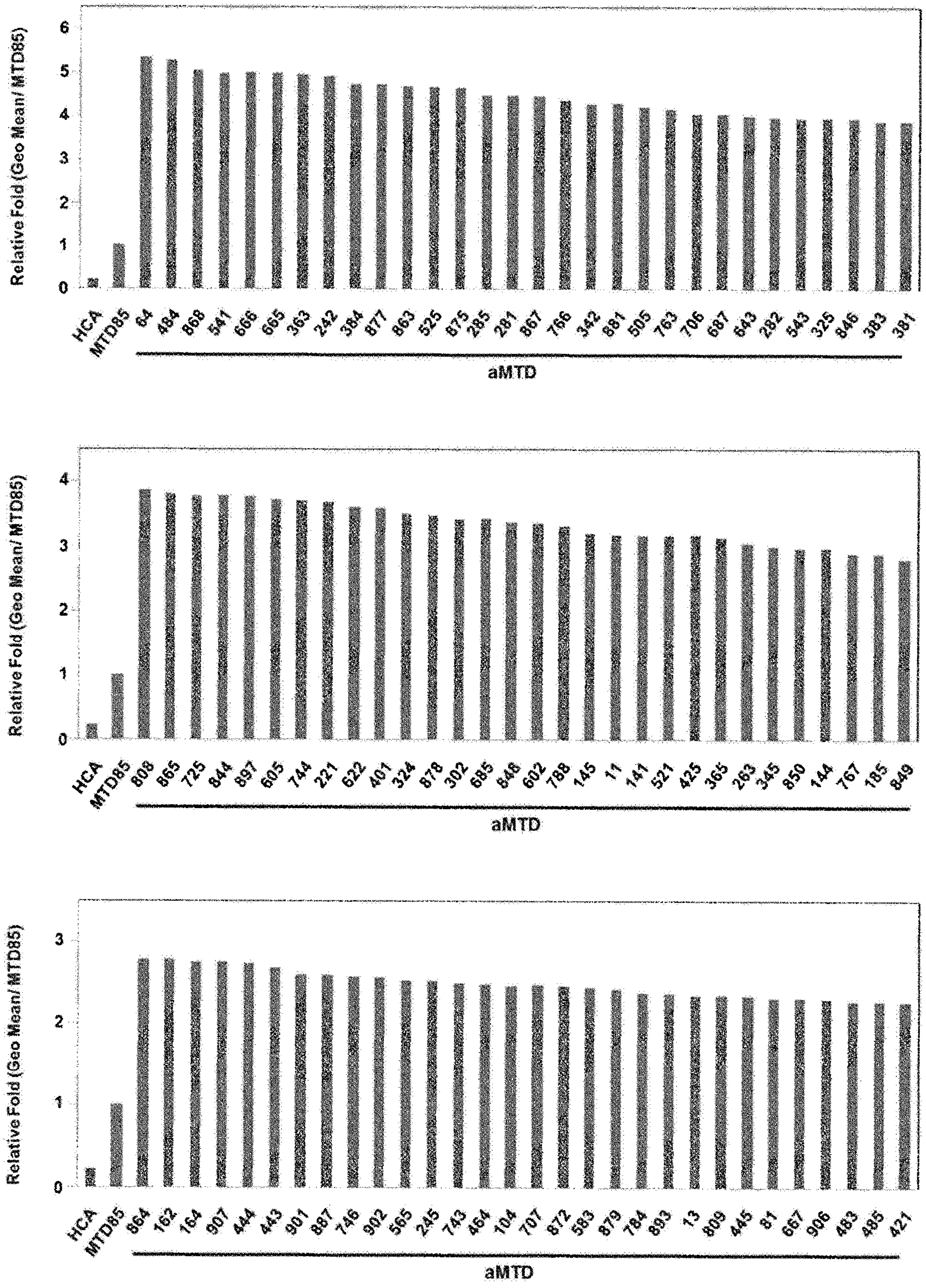

【Figure 11c】
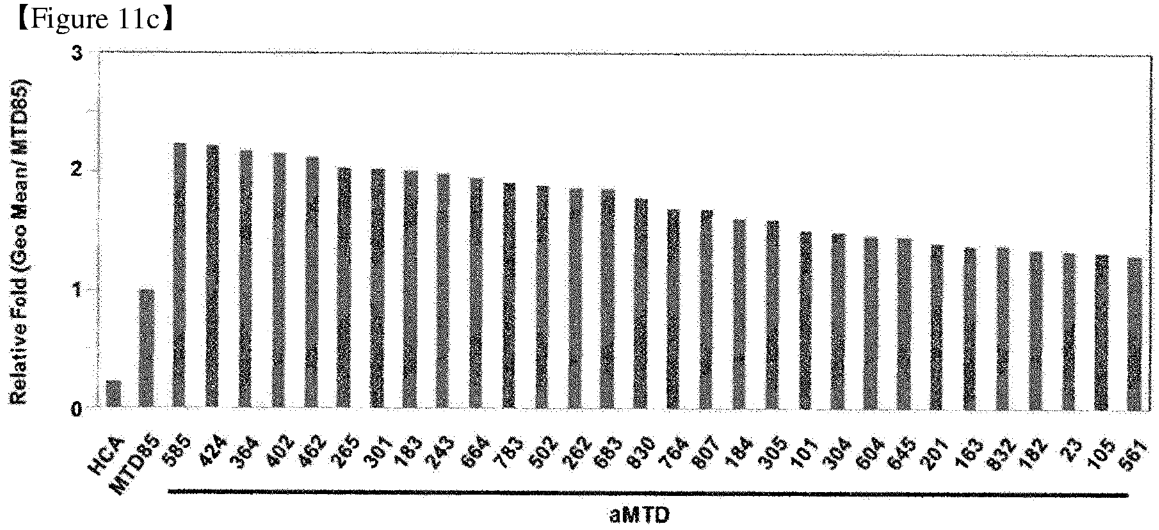
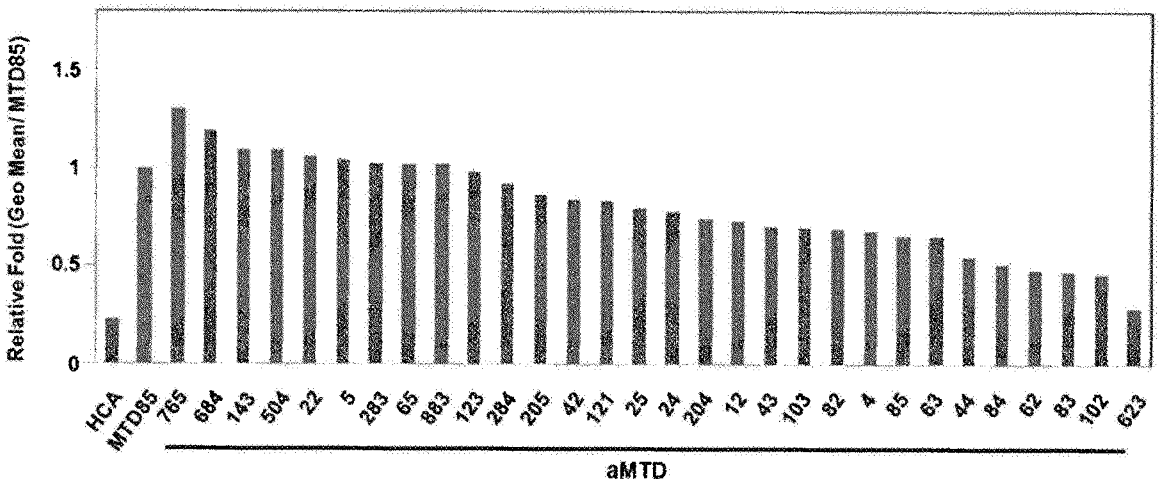
【Figure 12】
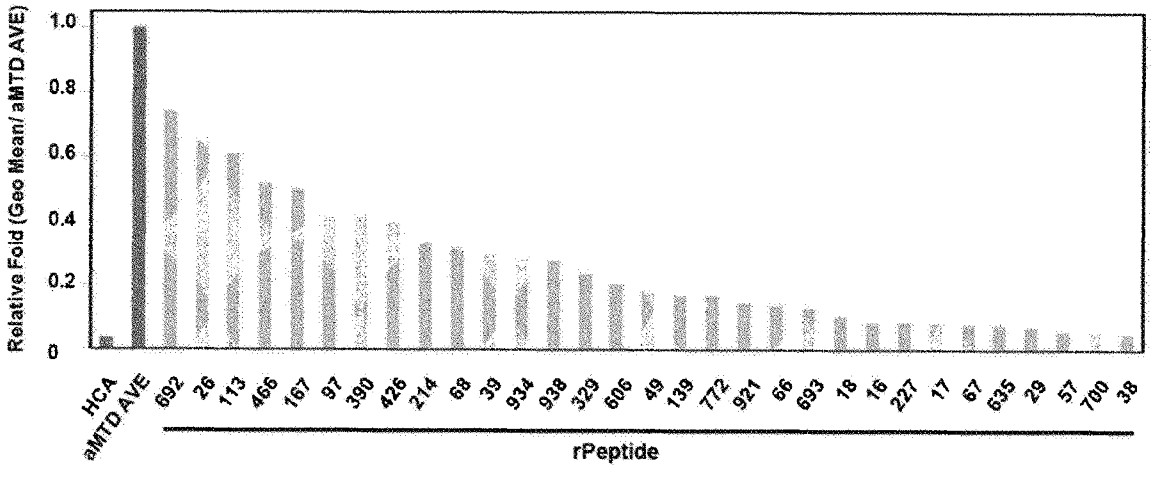

[Figure 13a]
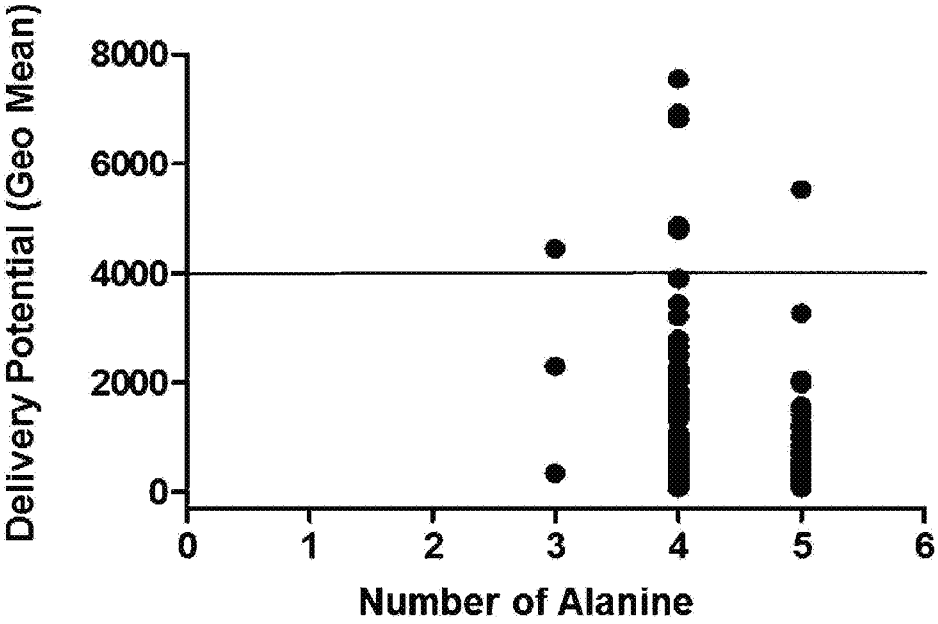
[Figure 13b]
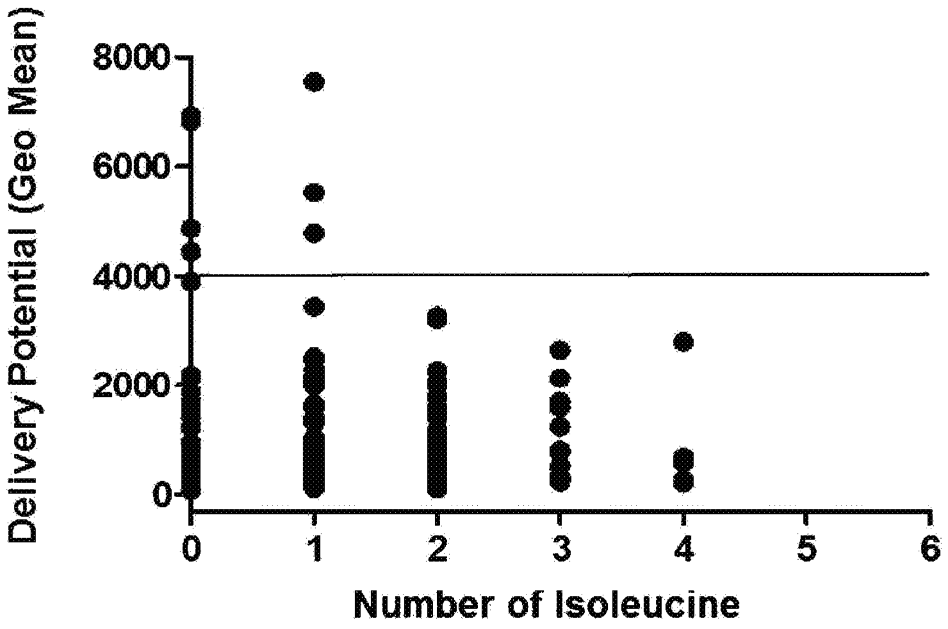

[Figure 13c]
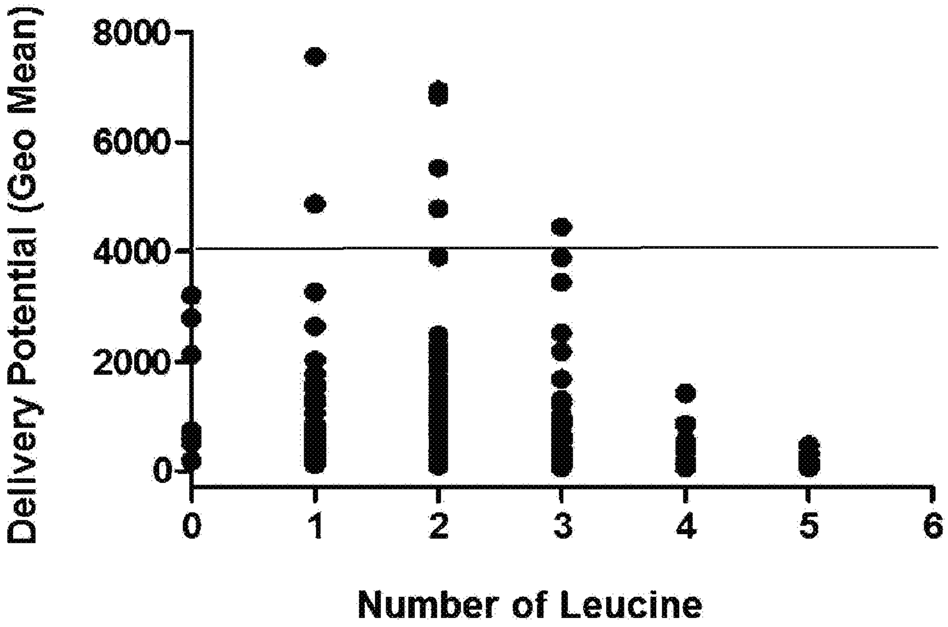
[Figure 13d]
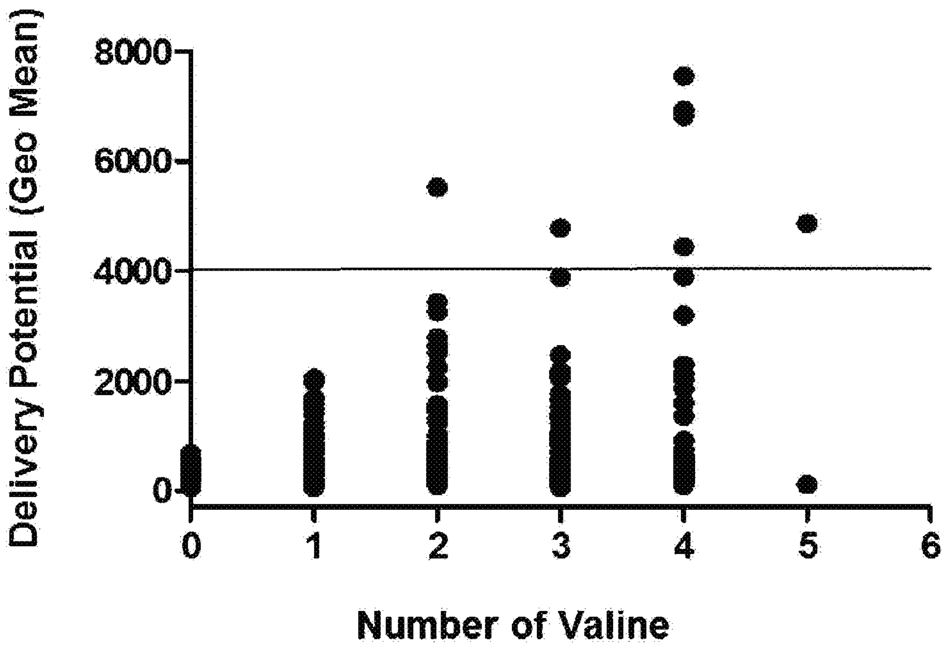

[Figure 14a]
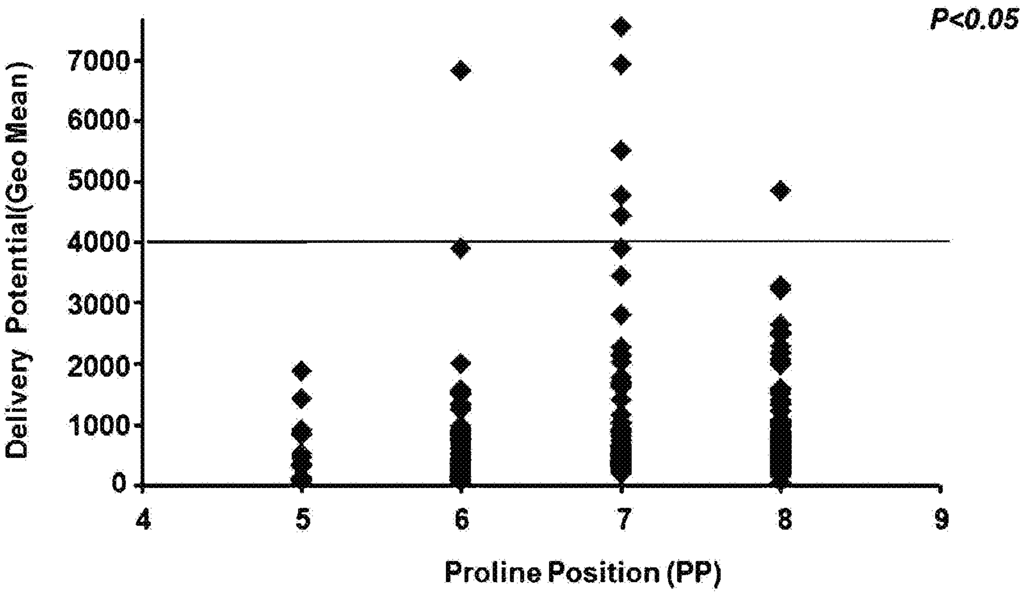
[Figure 14b]
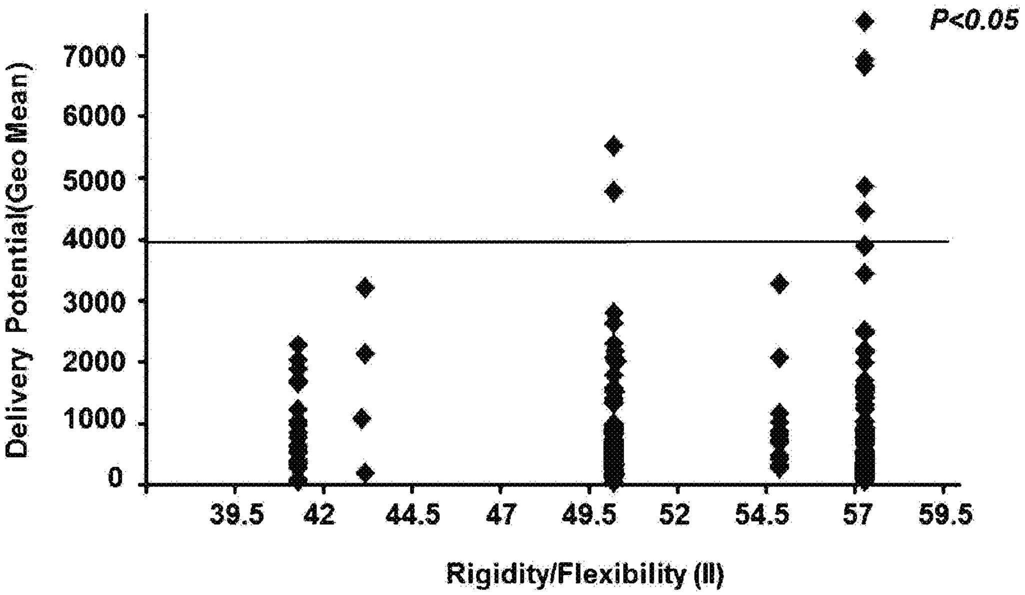

[Figure 14c]
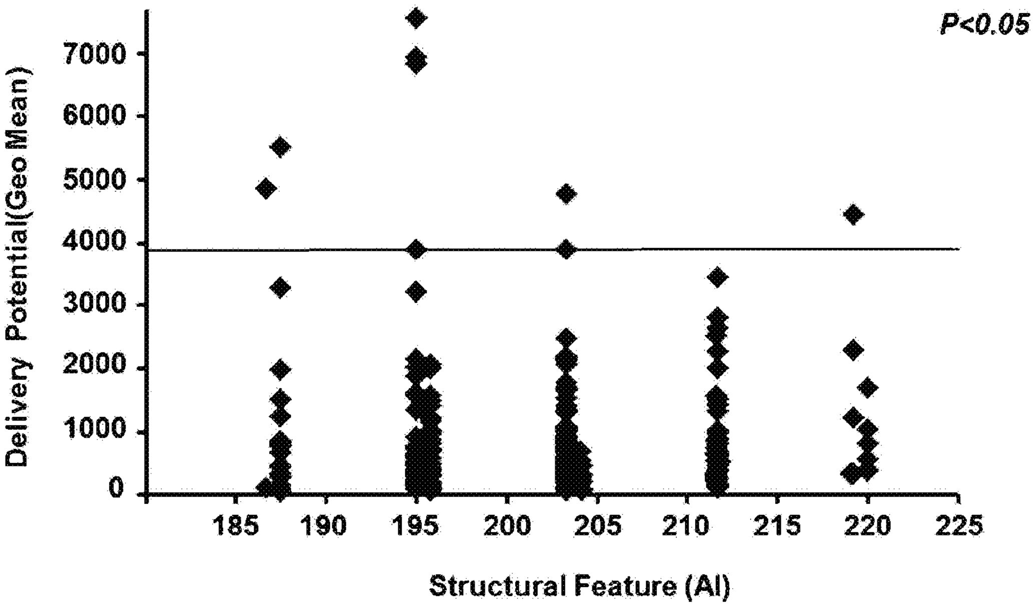
[Figure 14d]
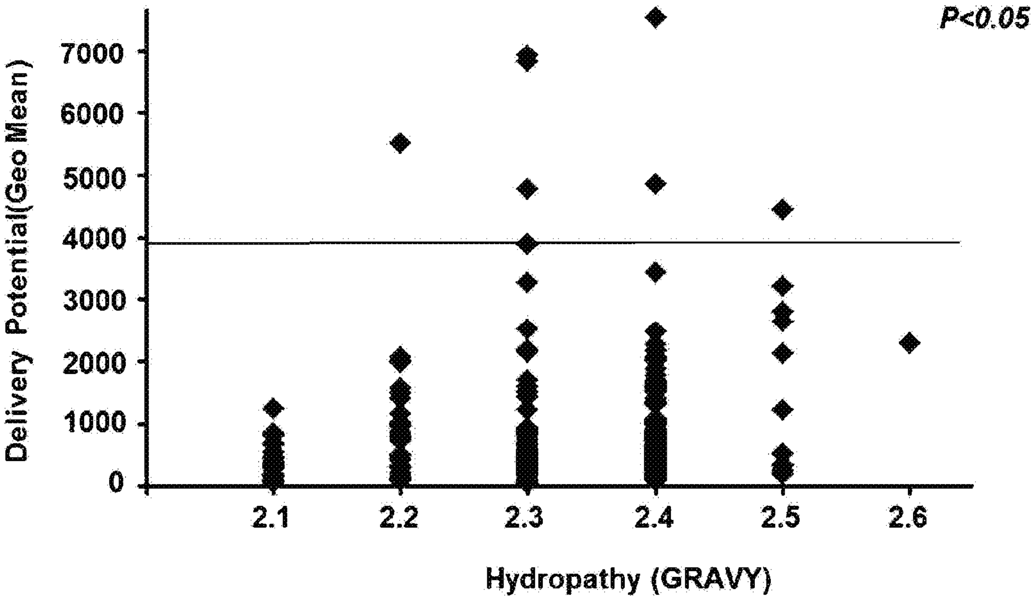

[Figure 15a]
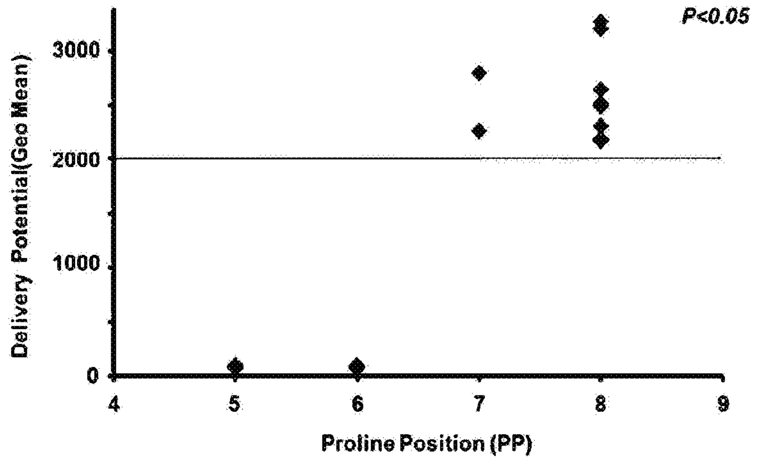
| ID | Proline Position (PP) | Delivery Potential (DP) |
|---|---|---|
| 888 | 8 | 3266 |
| 825 | 8 | 3204 |
| 895 | 7 | 2795 |
| 896 | 8 | 2645 |
| 727 | 8 | 2518 |
| 603 | 8 | 2491 |
| 847 | 8 | 2307 |
| 826 | 7 | 2262 |
| 724 | 8 | 2186 |
| 563 | 8 | 2167 |
| 43 | 5 | 97 |
| 103 | 6 | 97 |
| 4 | 6 | 93 |
| 85 | 5 | 89 |
| 63 | 6 | 89 |
| 44 | 5 | 75 |
| 84 | 6 | 70 |
| 62 | 6 | 65 |
| 83 | 6 | 64 |
| 102 | 5 | 63 |
[Figure 15b]
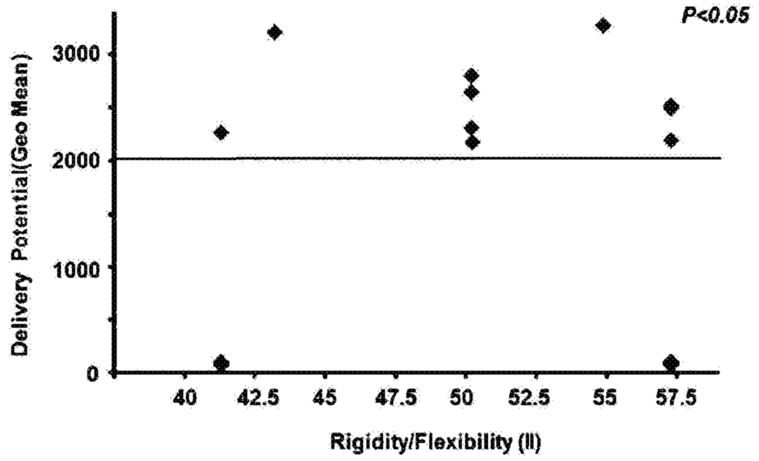
| ID | Rigidity/ Flexibility (II) | Delivery Potential (DP) |
|---|---|---|
| 888 | 54.9 | 3266 |
| 825 | 43.2 | 3204 |
| 895 | 50.2 | 2795 |
| 896 | 50.2 | 2645 |
| 727 | 57.3 | 2518 |
| 603 | 57.3 | 2491 |
| 847 | 50.2 | 2307 |
| 826 | 41.3 | 2262 |
| 724 | 57.3 | 2186 |
| 563 | 50.2 | 2167 |
| 43 | 41.3 | 97 |
| 103 | 57.3 | 97 |
| 4 | 57.3 | 93 |
| 85 | 57.3 | 89 |
| 63 | 57.3 | 89 |
| 44 | 57.3 | 75 |
| 84 | 41.3 | 70 |
| 62 | 57.3 | 65 |
| 83 | 41.3 | 64 |
| 102 | 57.3 | 63 |

[Figure 15c]
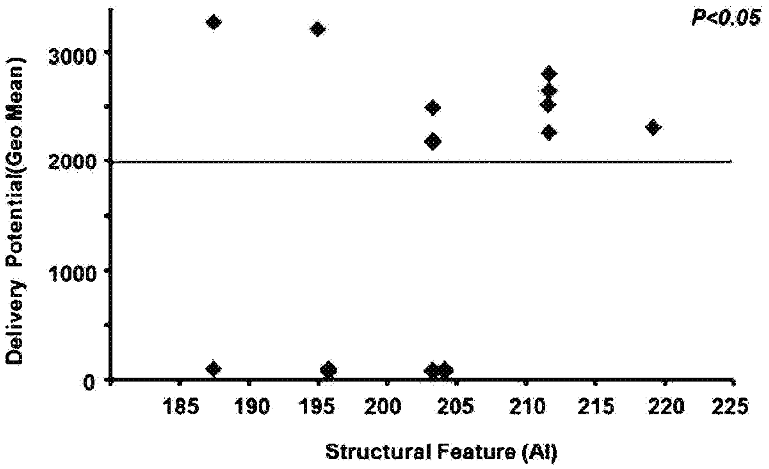
| ID | Structural Feature (AI) | Delivery Potential (DP) |
|---|---|---|
| 888 | 187.5 | 3266 |
| 825 | 195.0 | 3204 |
| 895 | 211.7 | 2795 |
| 896 | 211.7 | 2645 |
| 727 | 211.6 | 2518 |
| 603 | 203.3 | 2491 |
| 847 | 219.2 | 2307 |
| 826 | 211.7 | 2262 |
| 724 | 203.3 | 2186 |
| 563 | 203.3 | 2167 |
| 43 | 187.5 | 97 |
| 103 | 204.2 | 97 |
| 4 | 195.8 | 93 |
| 85 | 195.8 | 89 |
| 63 | 203.3 | 89 |
| 44 | 203.3 | 75 |
| 84 | 195.8 | 70 |
| 62 | 203.3 | 65 |
| 83 | 195.8 | 64 |
| 102 | 204.2 | 63 |
[Figure 15d]
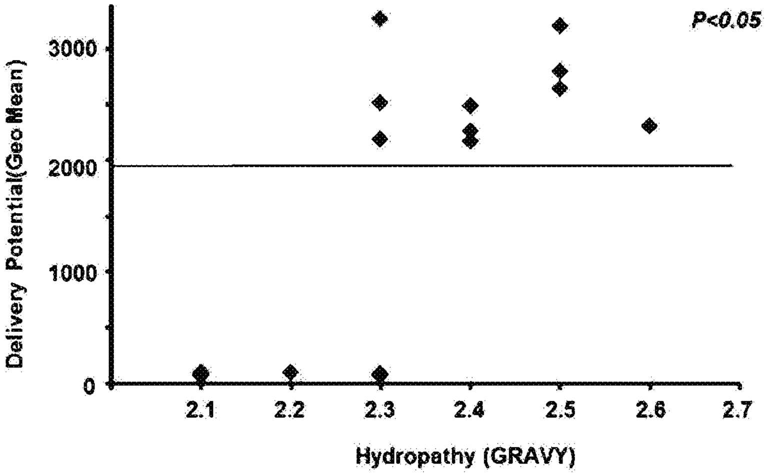
| ID | Hydropathy (GRAVY) | Delivery Potential (DP) |
|---|---|---|
| 888 | 2.3 | 3266 |
| 825 | 2.5 | 3204 |
| 895 | 2.5 | 2795 |
| 896 | 2.5 | 2645 |
| 727 | 2.3 | 2518 |
| 603 | 2.4 | 2491 |
| 847 | 2.6 | 2307 |
| 826 | 2.4 | 2262 |
| 724 | 2.3 | 2186 |
| 563 | 2.4 | 2167 |
| 43 | 2.1 | 97 |
| 103 | 2.2 | 97 |
| 4 | 2.1 | 93 |
| 85 | 2.1 | 89 |
| 63 | 2.3 | 89 |
| 44 | 2.3 | 75 |
| 84 | 2.1 | 70 |
| 62 | 2.3 | 65 |
| 83 | 2.1 | 64 |
| 102 | 2.1 | 63 |

【Figure 16】
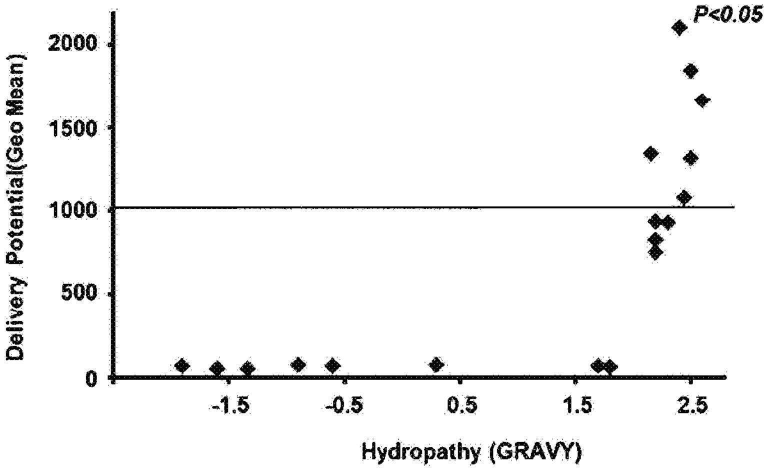
| ID | Hydropathy (GRAVY) | Delivery Potential (DP) |
|---|---|---|
| 33 | 2.4 | 2100 |
| 931 | 2.5 | 1843 |
| 436 | 2.6 | 1661 |
| 138 | 2.2 | 1339 |
| 77 | 2.5 | 1311 |
| 936 | 2.4 | 1077 |
| 226 | 2.2 | 935 |
| 30 | 2.3 | 931 |
| 6 | 2.2 | 824 |
| 750 | 2.2 | 750 |
| 67 | 0.3 | 71 |
| 20 | -0.9 | 70 |
| 635 | -1.9 | 67 |
| 29 | 1.7 | 63 |
| 40 | -0.6 | 63 |
| 190 | 1.8 | 59 |
| 57 | -1.6 | 51 |
| 159 | -1.3 | 51 |
| 700 | -1.6 | 47 |
【Figure 17a】
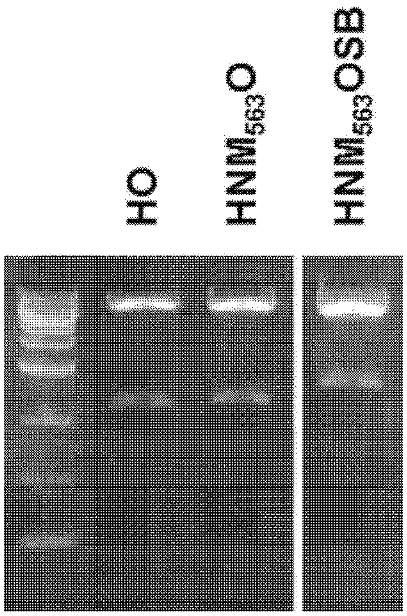

【Figure 17b】
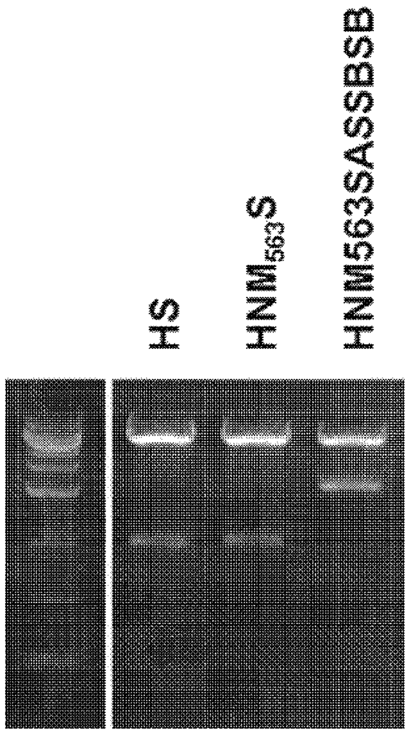
【Figure 17c】
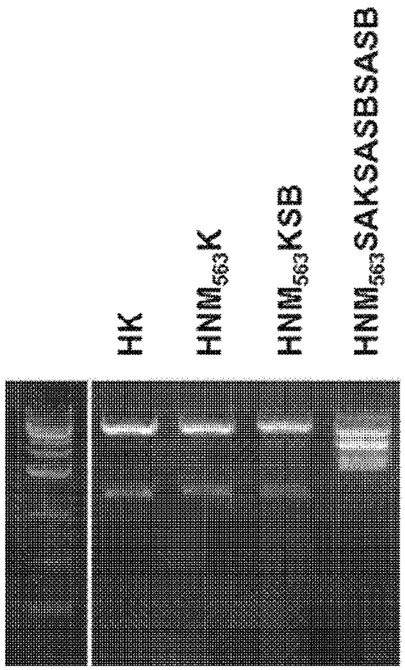

【Figure 17d】
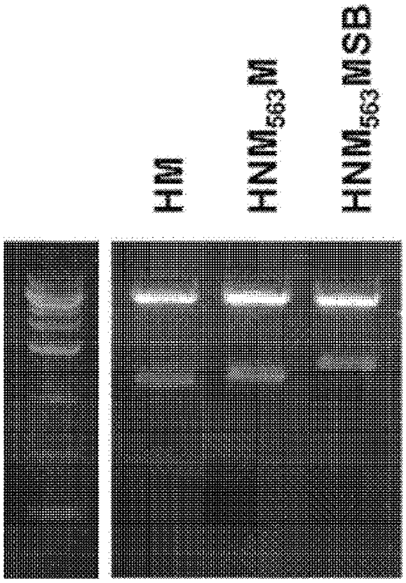
【Figure 17e】
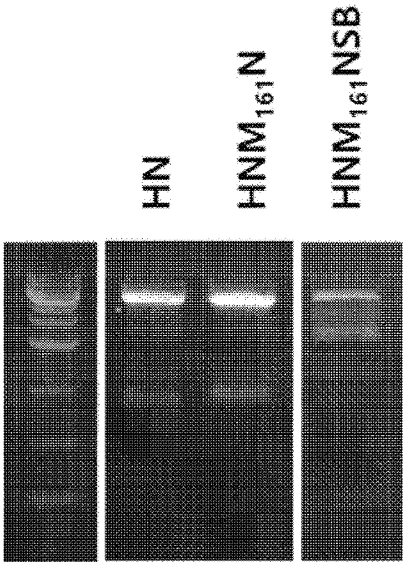

【Figure 17f】
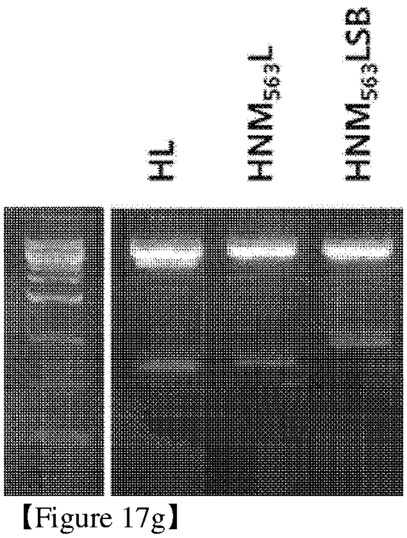
【Figure 17g】
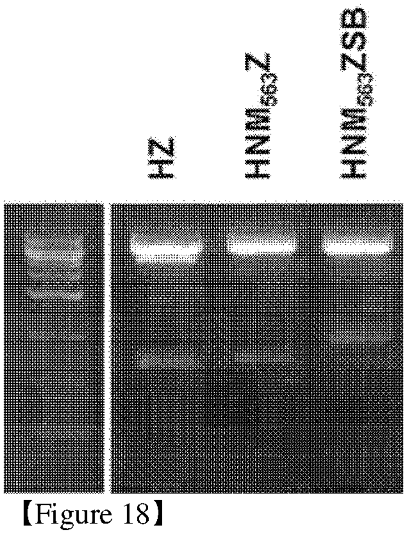
【Figure 18】
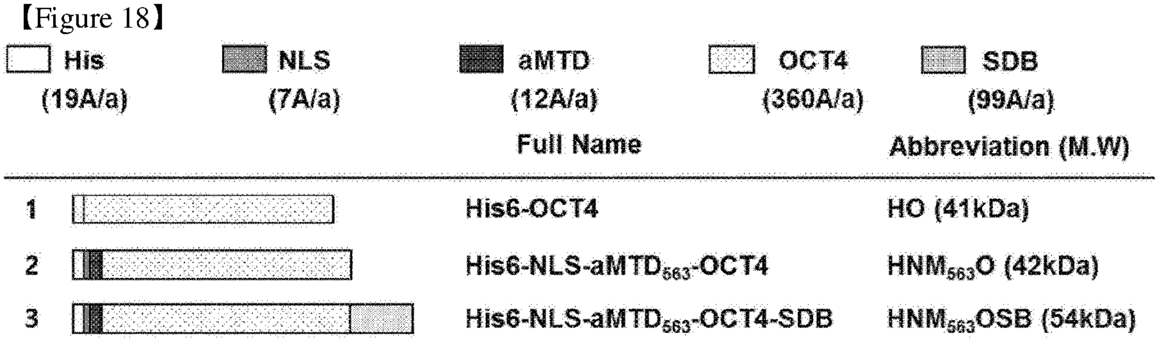

【Figure 19】

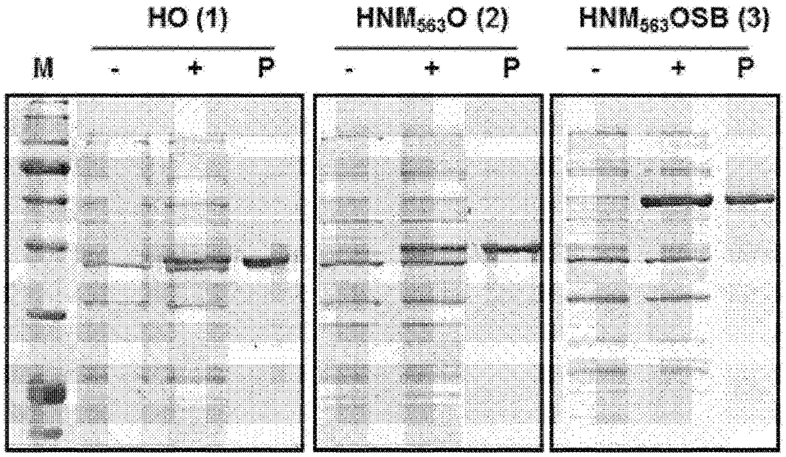

| | HO (1) | $HNM_{563}O$ (2) | $HNM_{563}OSB$ (3) |
|---|---|---|---|
| Solubility | +++++ | +++++ | +++++ |
| Yield(mg/L) | 5 | 5 | 33 |

【Figure 20】

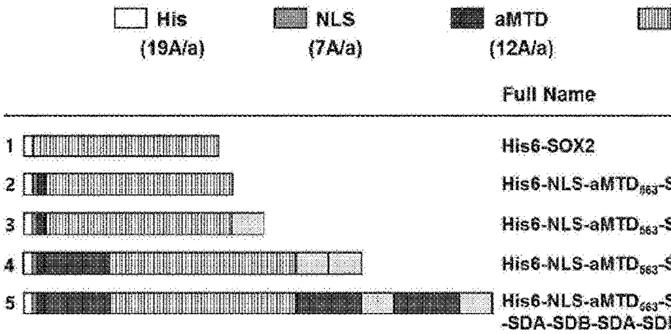

| | Full Name | Abbreviation (M.W) |
|---|---|---|
| 1 | His6-SOX2 | HS (37kDa) |
| 2 | His6-NLS-$aMTD_{563}$-SOX2 | $HNM_{563}S$ (38kDa) |
| 3 | His6-NLS-$aMTD_{563}$-SOX2-SDB | $HNM_{563}SSB$ (49kDa) |
| 4 | His6-NLS-$aMTD_{563}$-SDA-SOX2-SDB-SDB | $HNM_{563}SASSBSB$ (81kDa) |
| 5 | His6-NLS-$aMTD_{563}$-SDA-SOX2-SDA-SDB-SDA-SDB | $HNM_{563}SASSASBSASB$ (130kDa) |

【Figure 21】

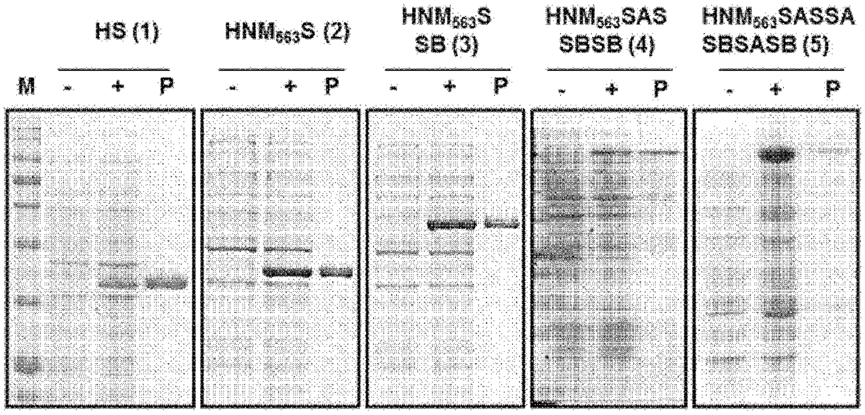

| | HS (1) | $HNM_{563}S$ (2) | $HNM_{563}SSB$ (3) | $HNM_{563}SAS$ SBSB (4) | $HNM_{563}SASSA$ SBSASB (6-5) |
|---|---|---|---|---|---|
| Solubility | + | + | + | ++++ | +++++ |
| Yield(mg/L) | 0.3 | 1 | 1 | 141.5 | 62 |

【Figure 22】
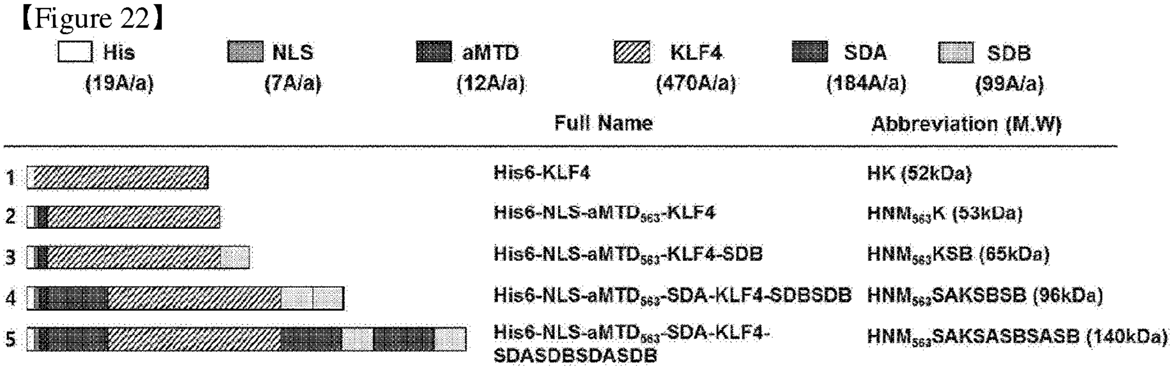
【Figure 23】
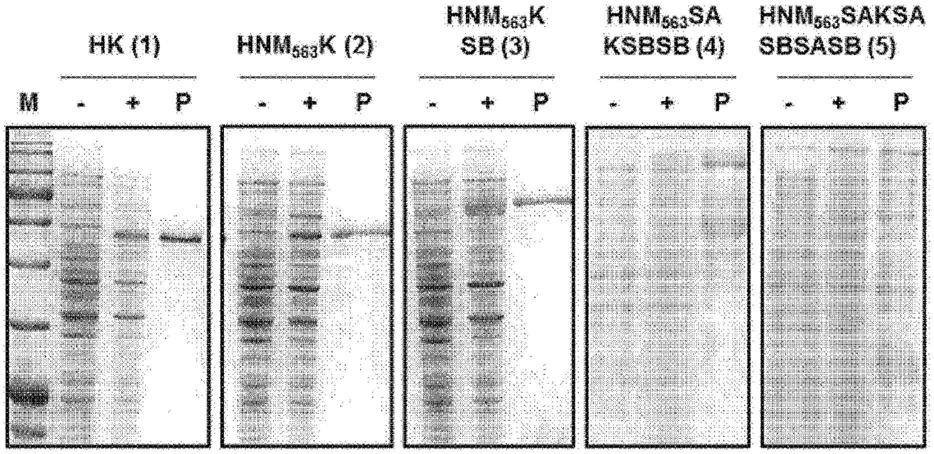
| | HK (1) | HNM$_{563}$K (2) | HNM$_{563}$KSB (3) | HNM$_{563}$SAKSBS B (4) | HNM$_{563}$SAKSA SBSASB (6-5) |
|---|---|---|---|---|---|
| Solubility | + | ++ | +++ | +++++ | +++++ |
| Yield(mg/L) | 3 | 4 | 16 | 11 | 14.6 |
【Figure 24】
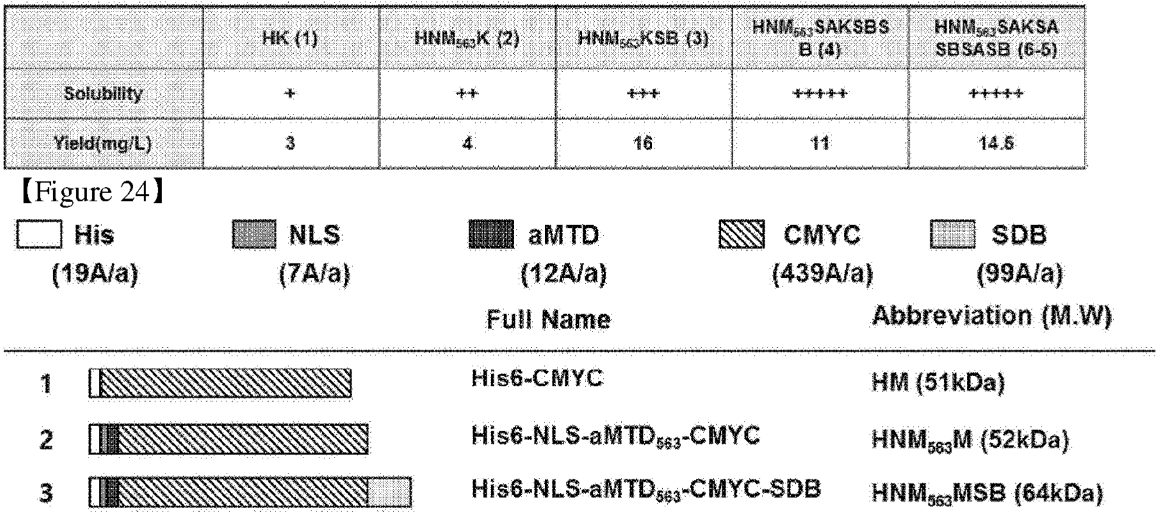

【Figure 25】
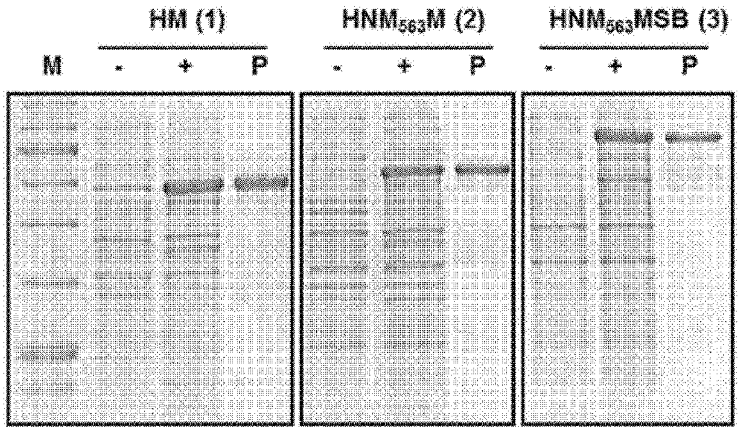
| | HM (1) | HNM$_{563}$M (2) | HNM$_{563}$MSB (3) |
|---|---|---|---|
| Solubility | +++++ | +++++ | +++++ |
| Yield(mg/L) | 107 | 79 | 75 |
【Figure 26】
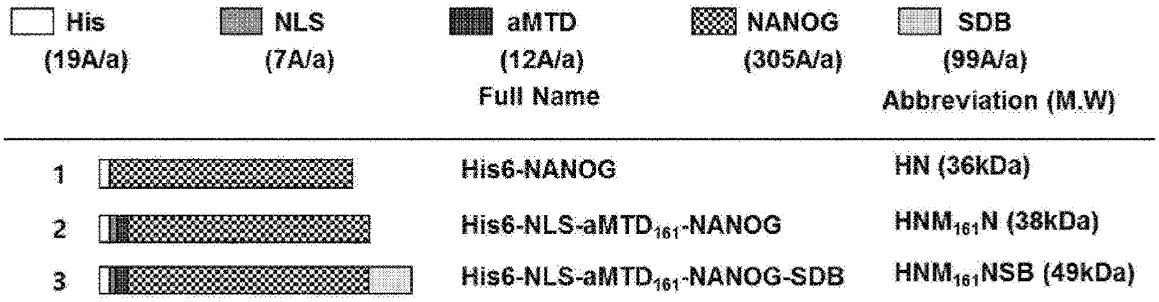
【Figure 27】
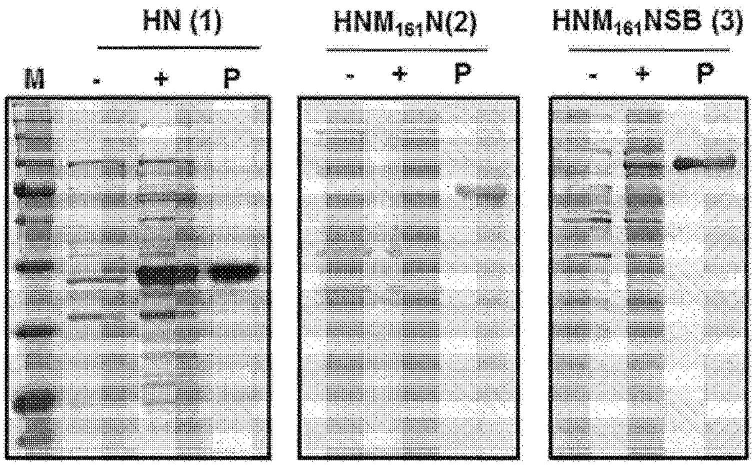
| | HK (1) | HNM$_{161}$N (2) | HNM$_{161}$NSB (3) |
|---|---|---|---|
| Solubility | +++++ | ++++ | +++++ |
| Yield(mg/L) | 5 | 2 | 1 |

【Figure 28】
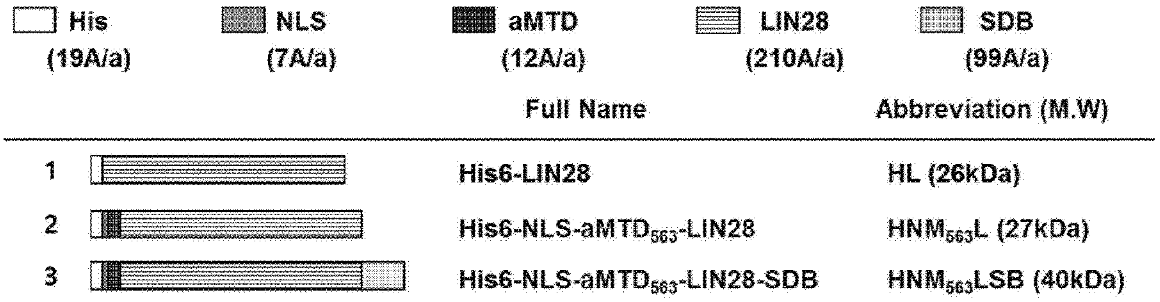
【Figure 29】
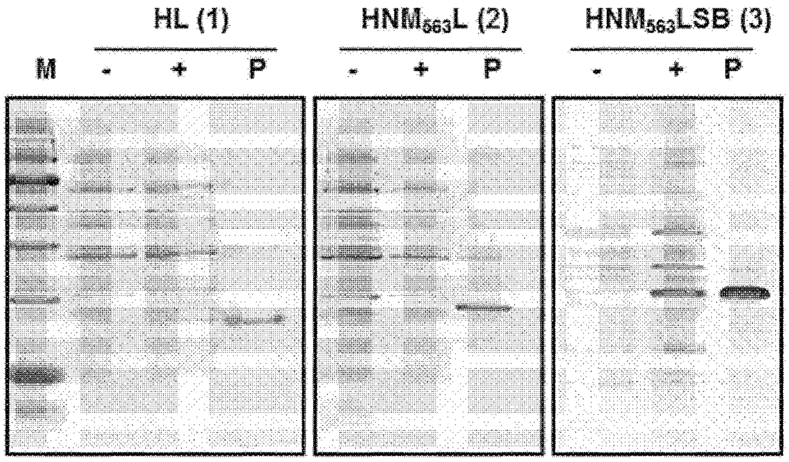
| | HL (#1) | $HNM_{563}L$ (#2) | $HNM_{563}LSB$ (#3) |
|---|---|---|---|
| Solubility | +++++ | +++++ | +++++ |
| Yield(mg/L) | 10 | 9 | 11 |
【Figure 30】
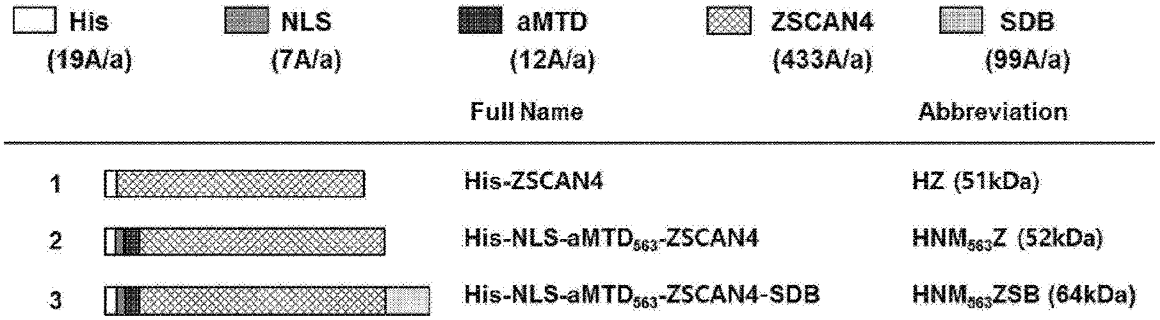

【Figure 31】
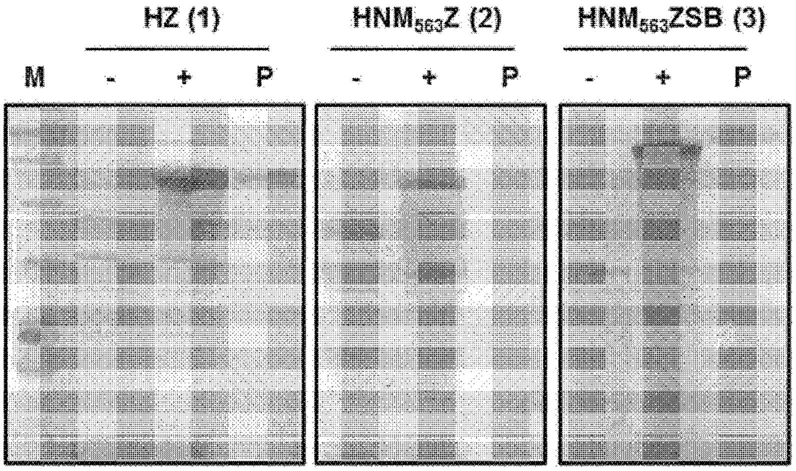
| | HZ (1) | HNM$_{563}$Z (2) | HNM$_{563}$ZSB (3) |
|---|---|---|---|
| Solubility | +++++ | +++ | +++++ |
| Yield(mg/L) | 49 | 6 | 55 |
【Figure 32】
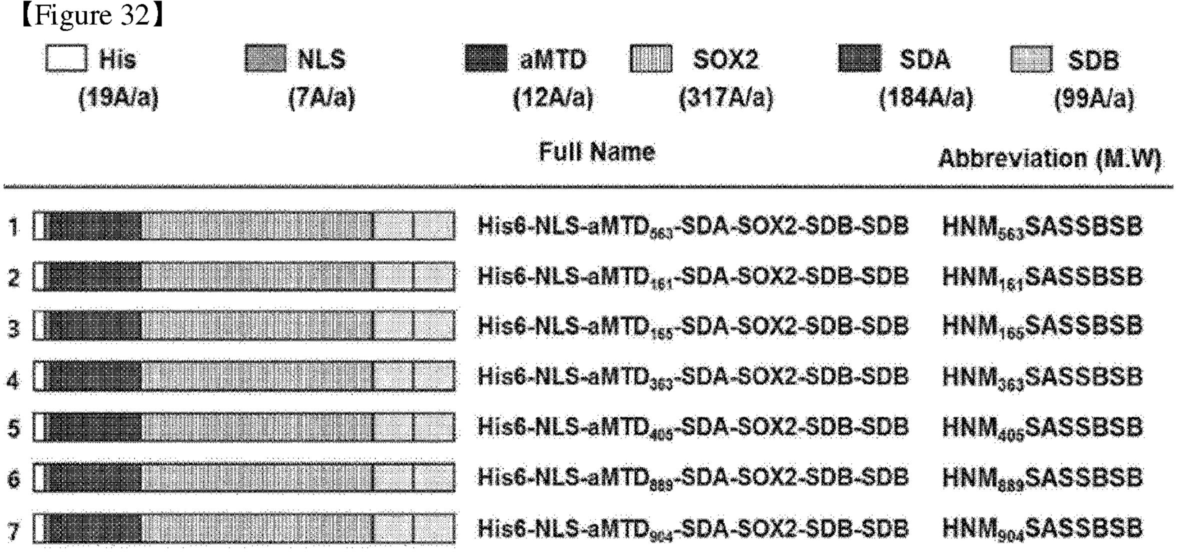

[Figure 33]
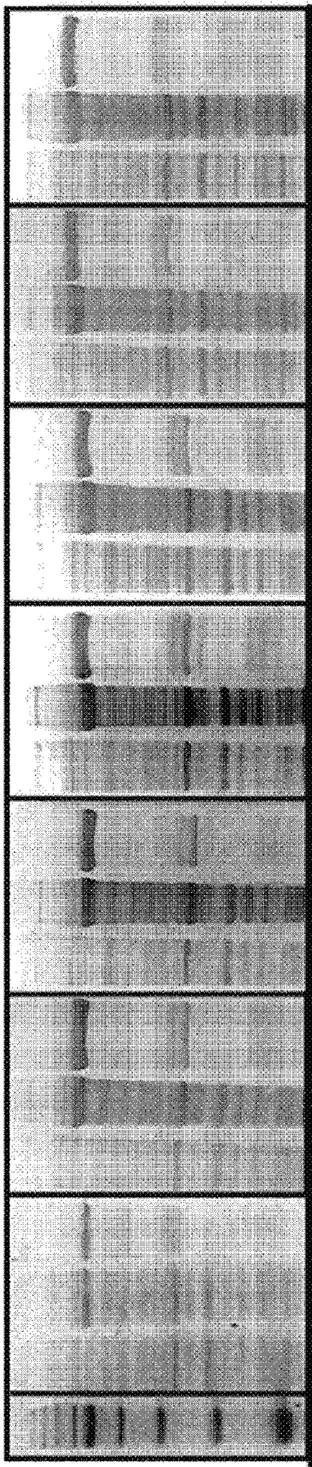
| | aMTD563 | aMTD161 | aMTD165 | aMTD363 | aMTD405 | aMTD889 | aMTD904 |
|---|---|---|---|---|---|---|---|
| Size (kDa) | 81 | 81 | 81 | 81 | 81 | 81 | 81 |
| Yield (mg/L) | 142 | 3 | 7 | 3 | 3 | 6 | 4 |
| Solubility | ++++ | +++ | +++ | +++ | +++ | +++ | +++ |
| Recovery (%) | 69 | 30 | 66 | 31 | 26 | 57 | 36 |
| Concentration (μg/μl) | 0.8 | 0.2 | 0.3 | 0.2 | 0.2 | 0.3 | 0.2 |

【Figure 34】
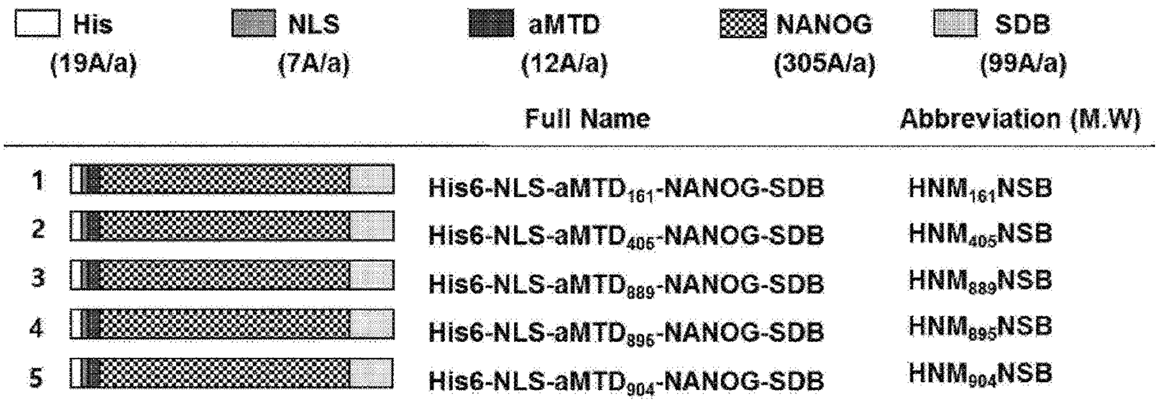
【Figure 35】
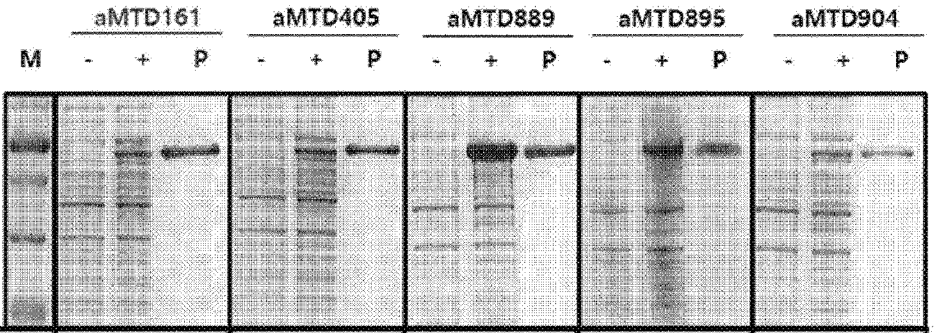
| | aMTD161 | aMTD405 | aMTD889 | aMTD895 | aMTD904 |
|---|---|---|---|---|---|
| Size (kDa) | 49 | 49 | 49 | 49 | 49 |
| Yield (mg/L) | 1 | 1 | 10 | 13 | 0.2 |
| Solubility | +++++ | ++++ | ++++ | ++++ | ++++ |
| Recovery (%) | 98 | 53 | 65 | 87 | 30 |
| Concentration (μg/μl) | 0.3 | 0.3 | 0.6 | 0.3 | 0.07 |
【Figure 36】
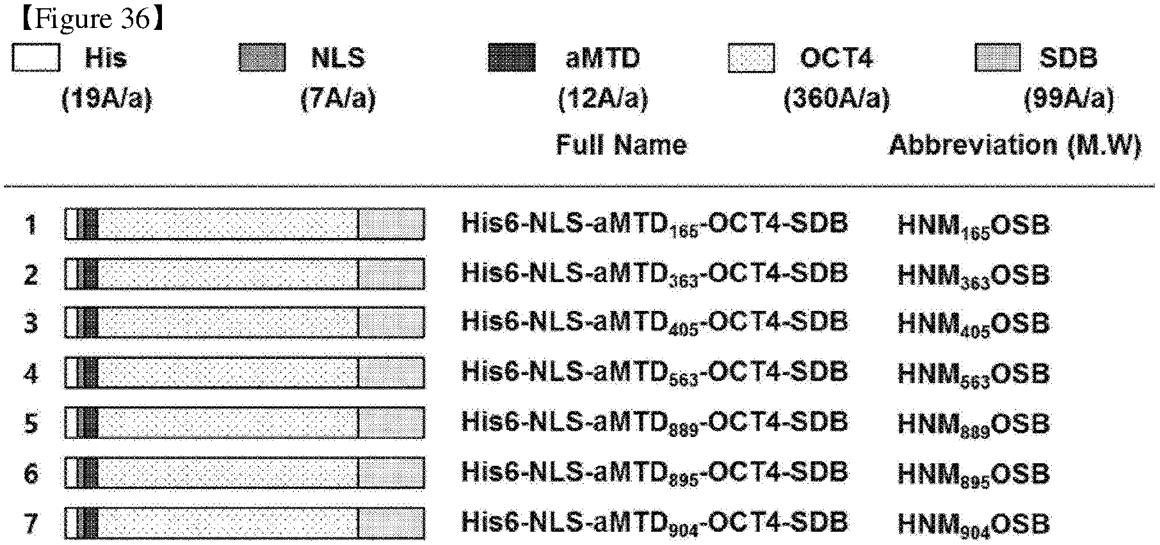

【Figure 37】
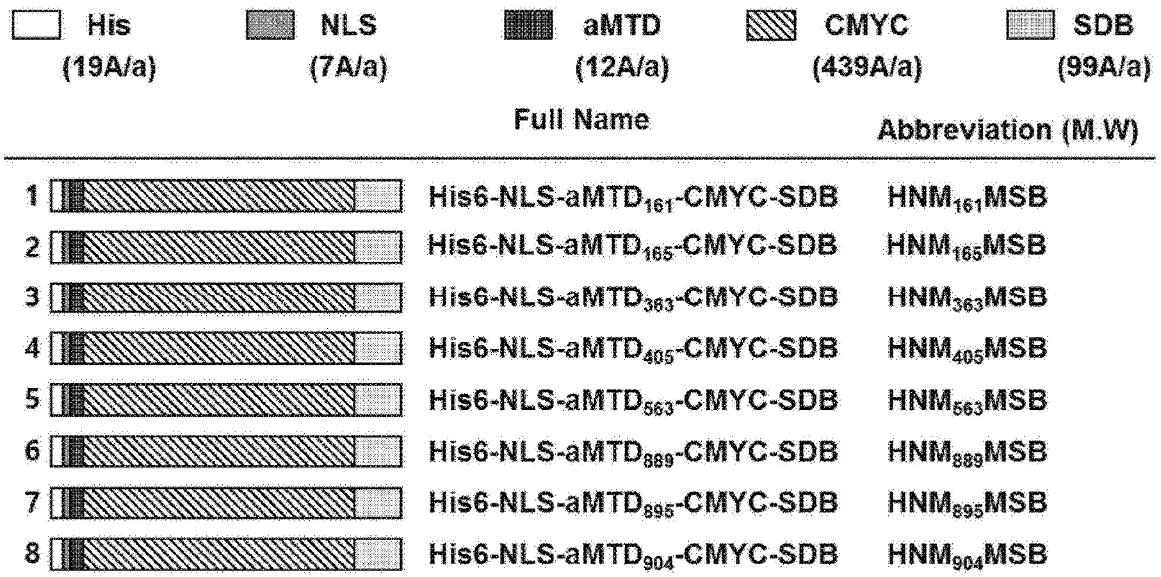
【Figure 38】
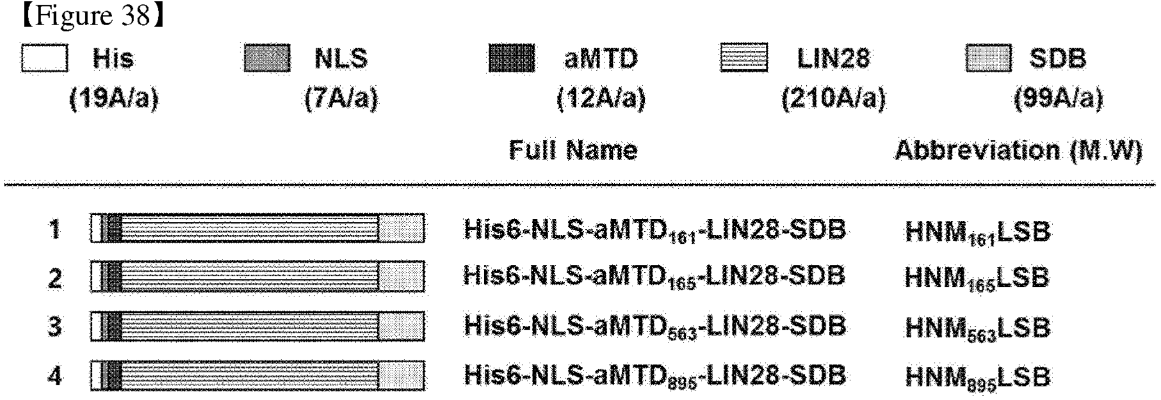

【Figure 39】
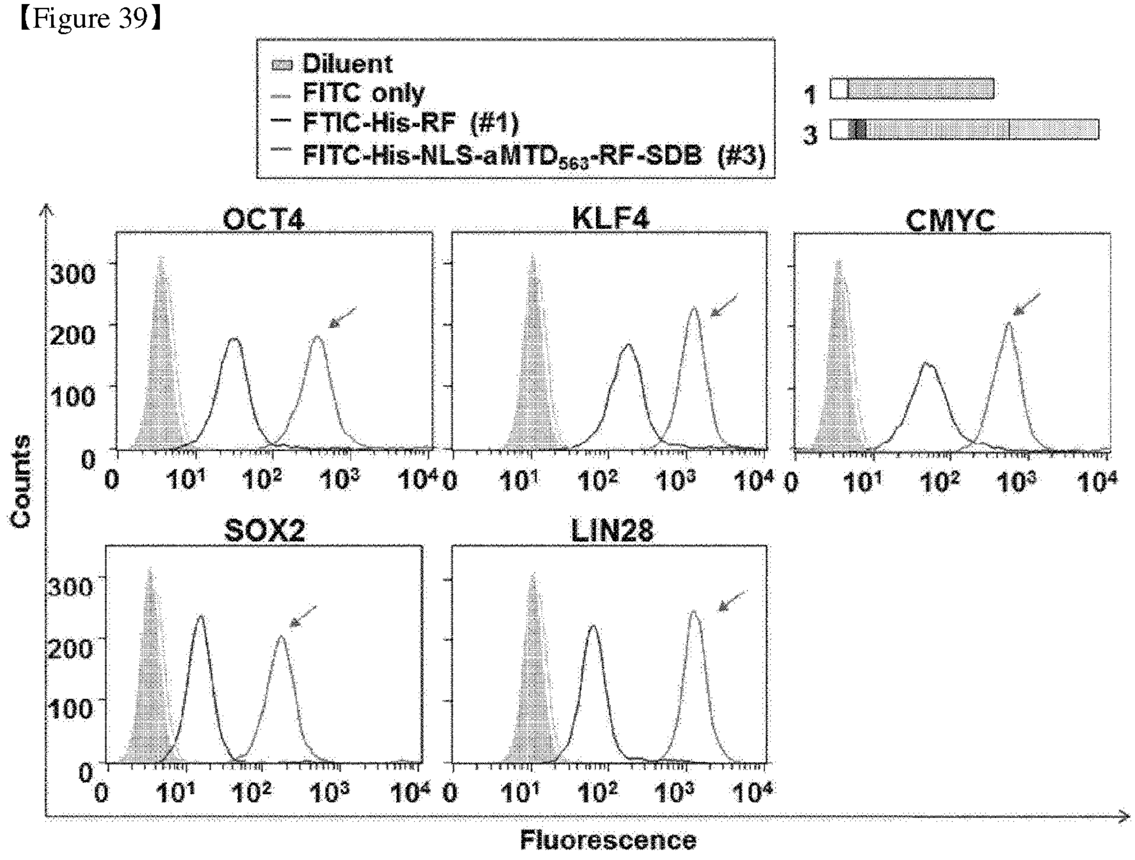
【Figure 40】
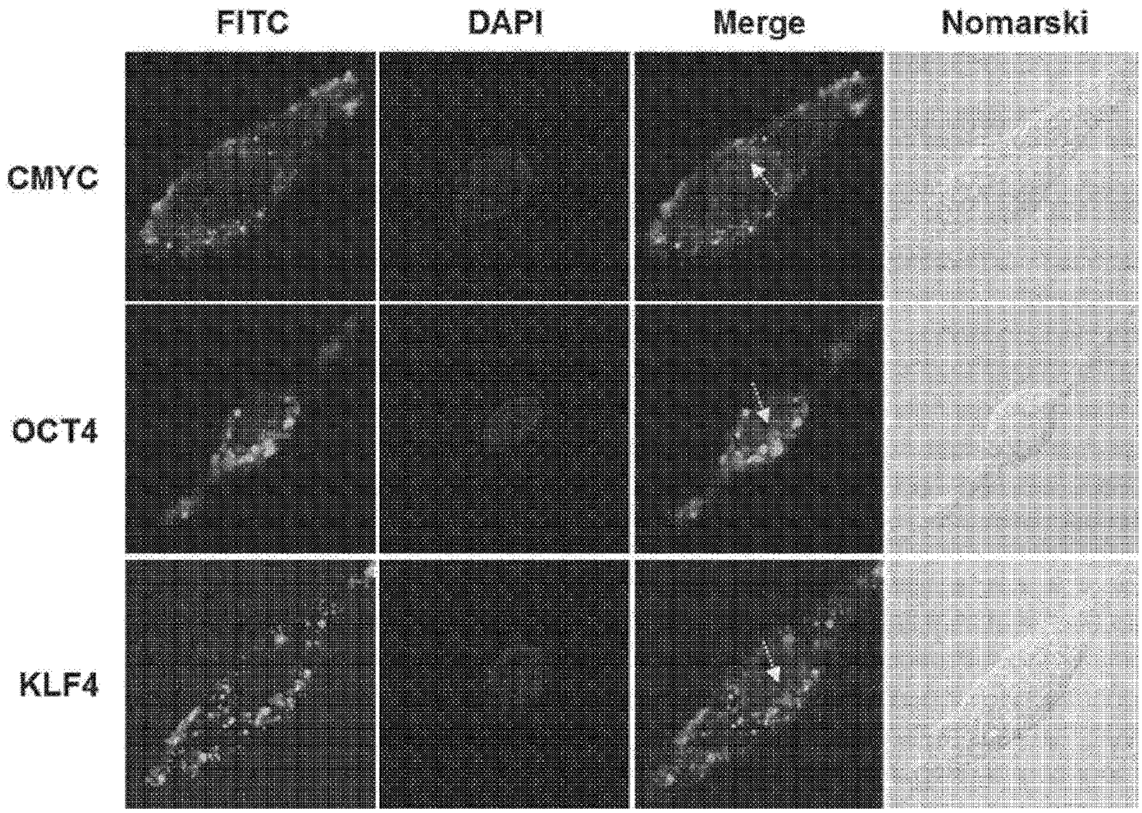

【Figure 41a】
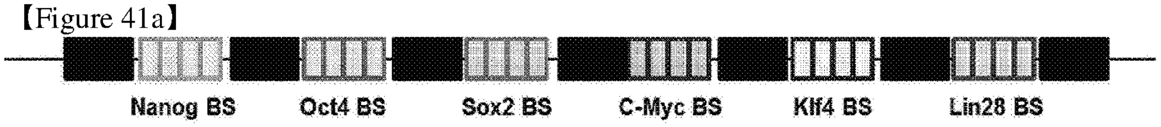
【Figure 41b】
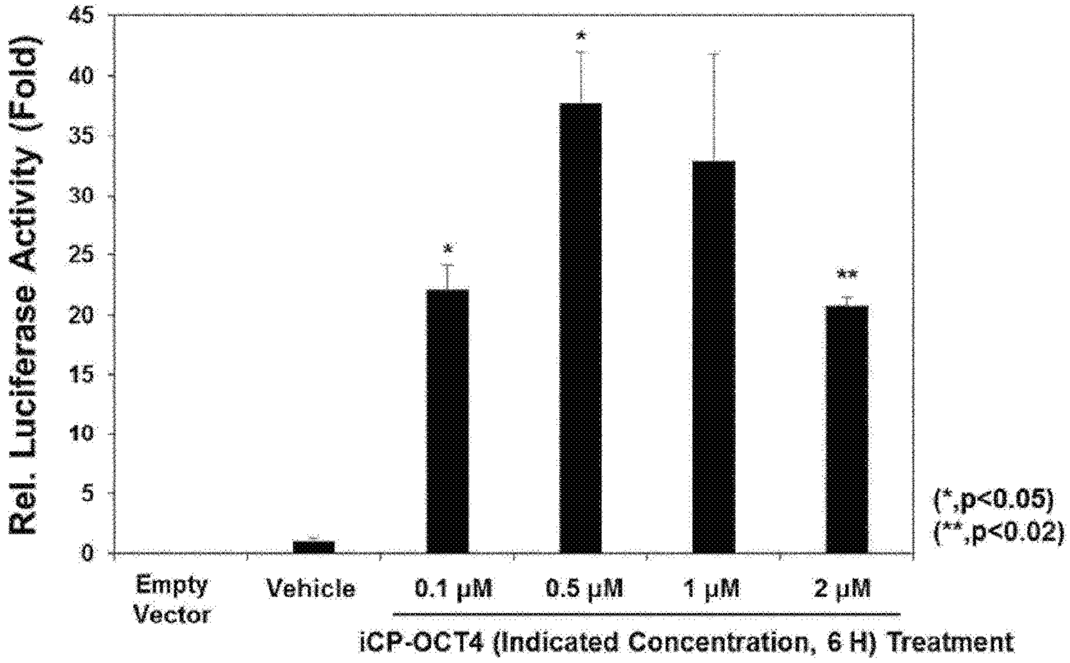
【Figure 42】
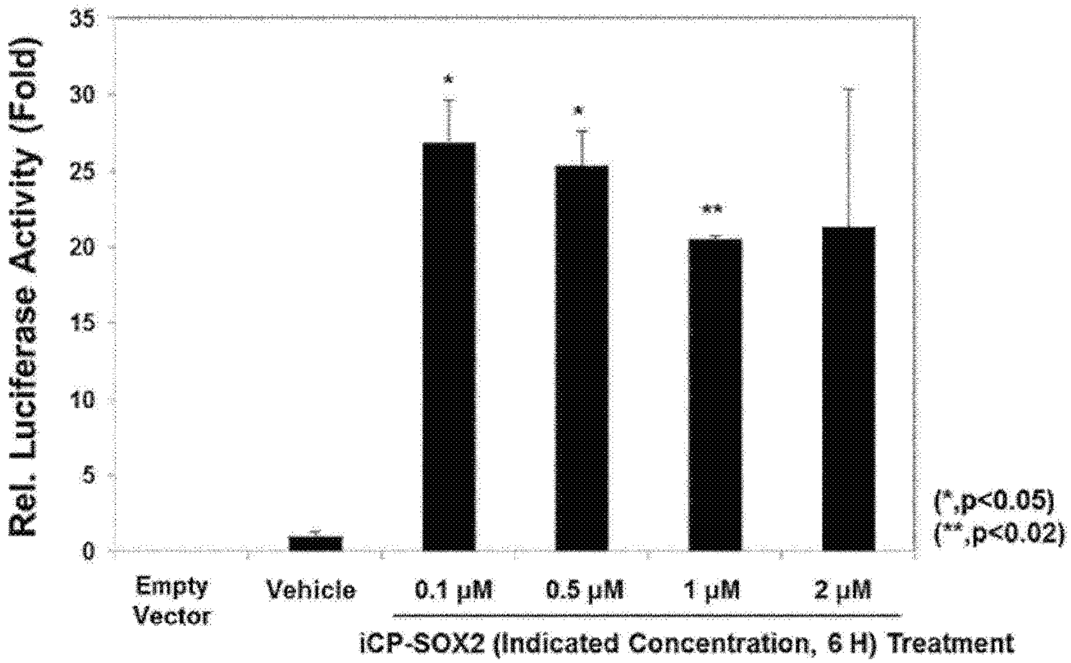

【Figure 43】
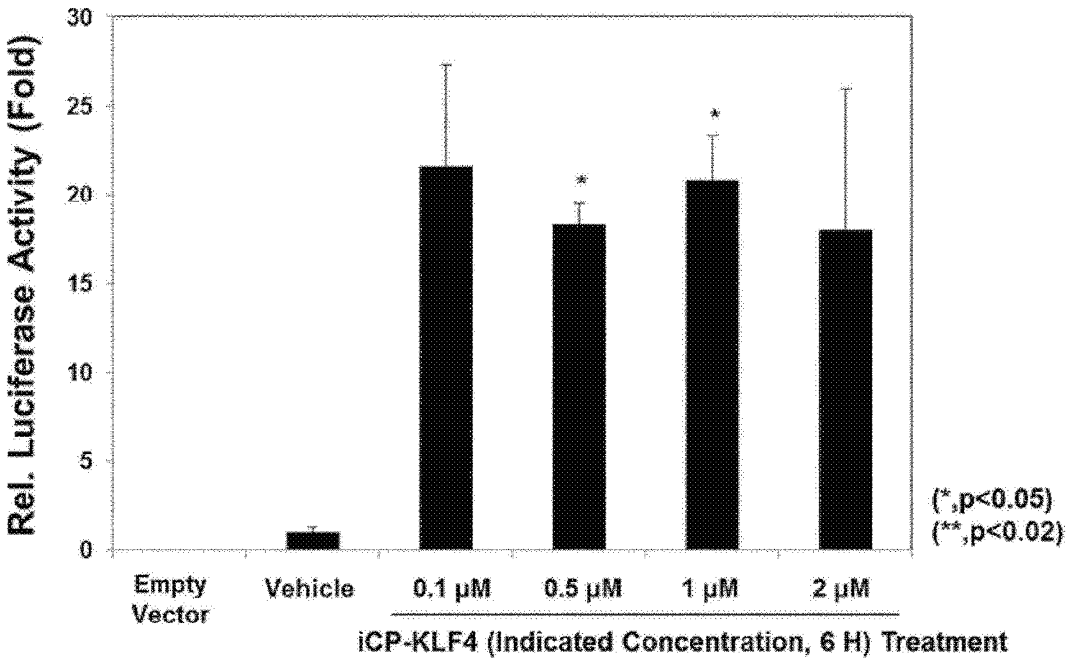
【Figure 44】
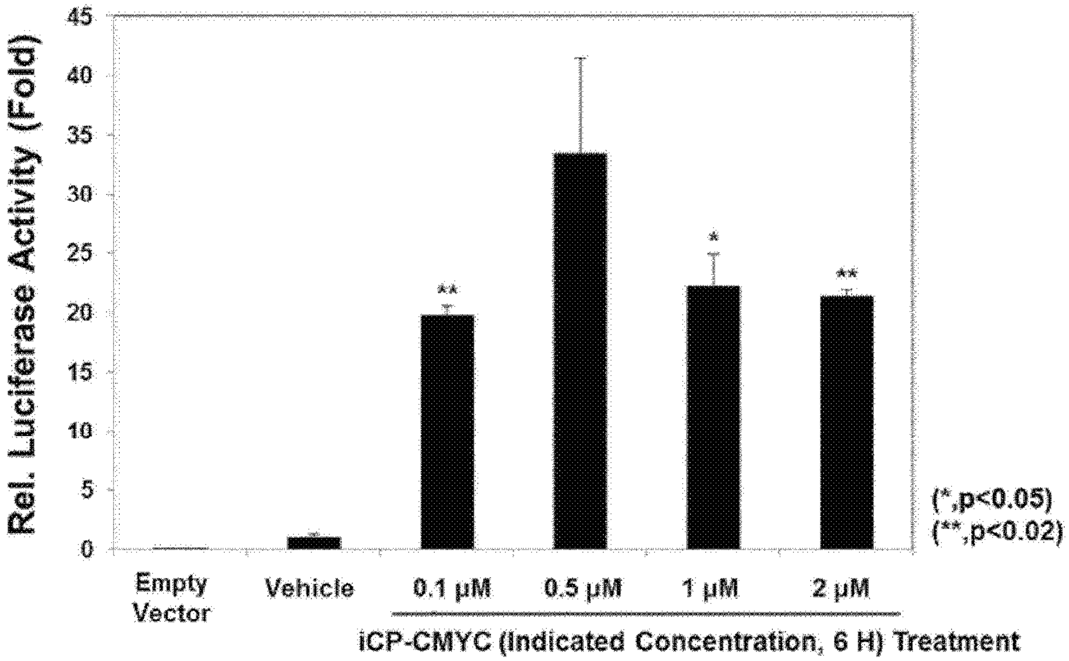

【Figure 45】
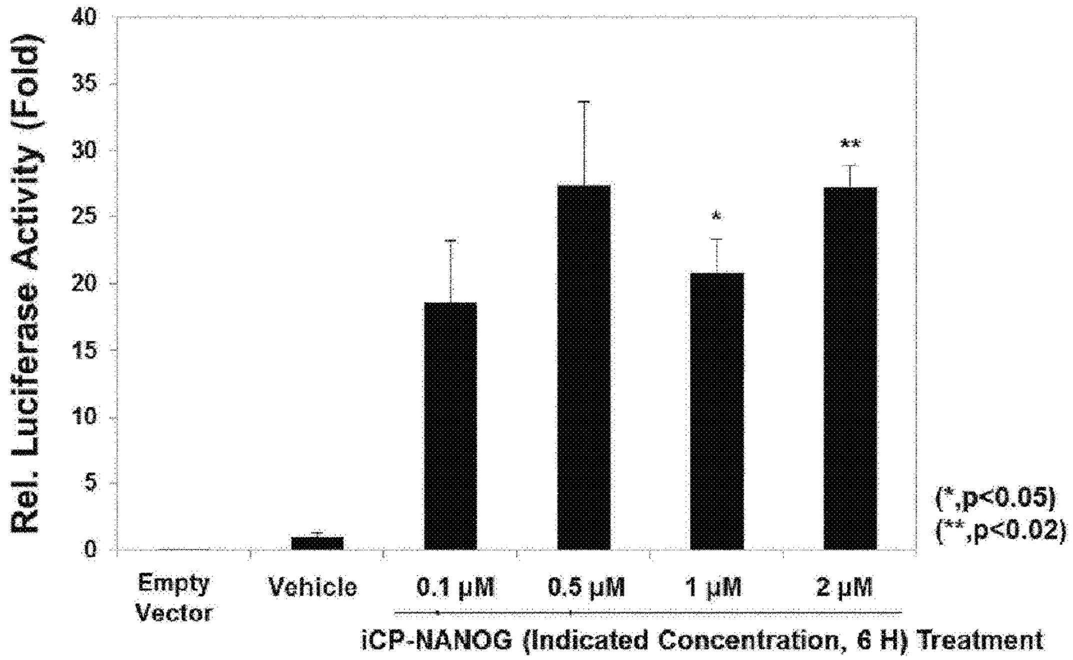
【Figure 46】
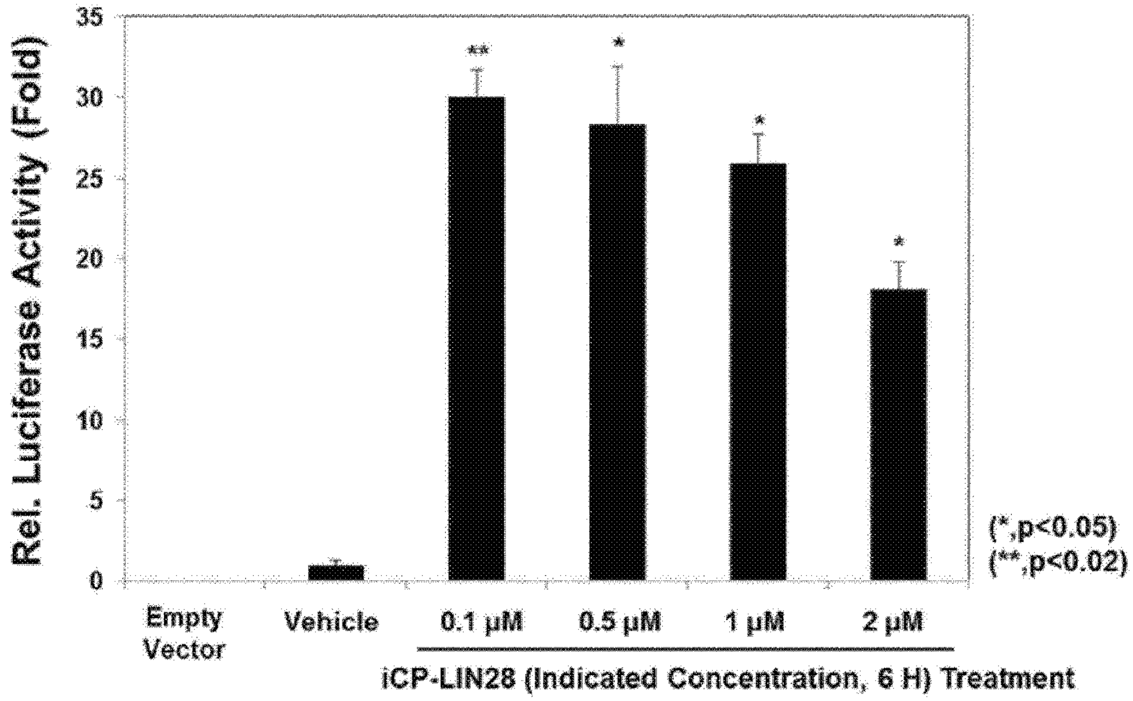

【Figure 47】
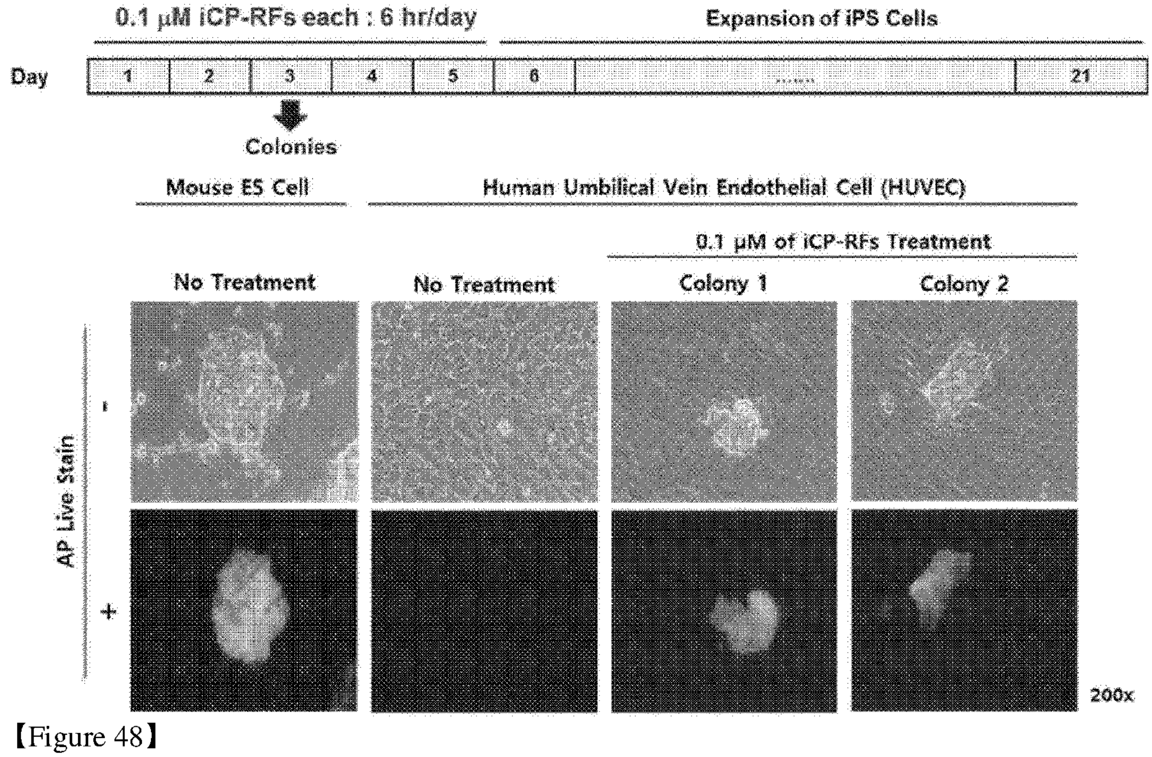
【Figure 48】
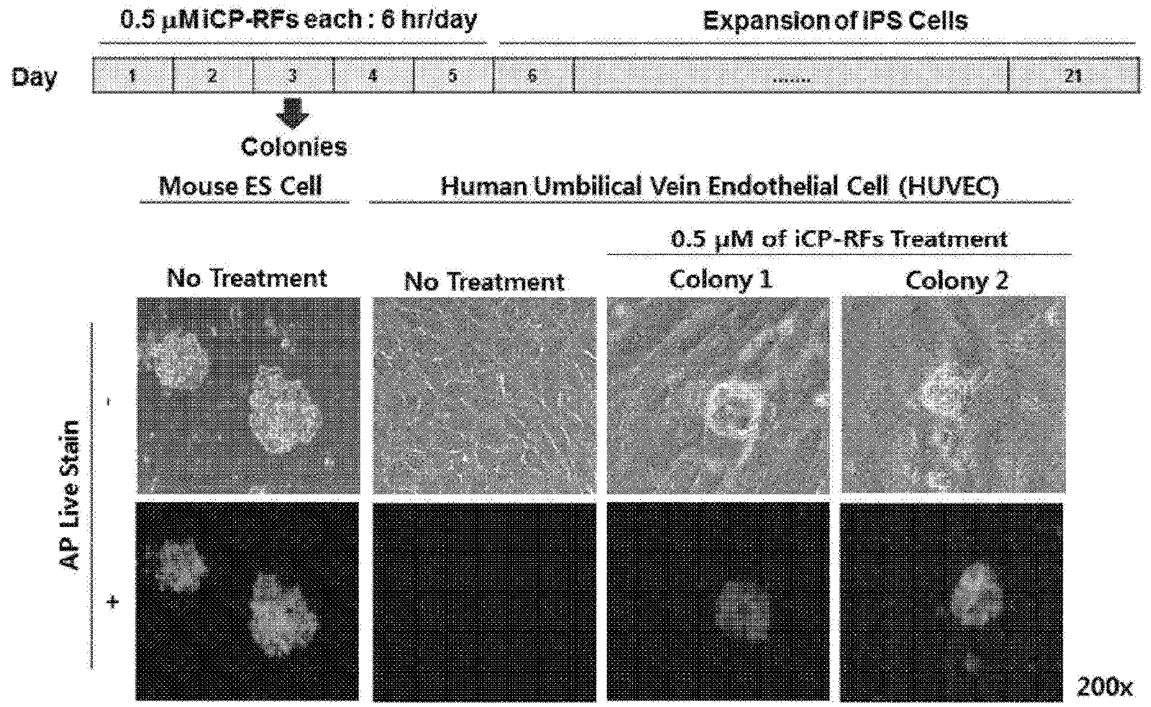

【Figure 49】
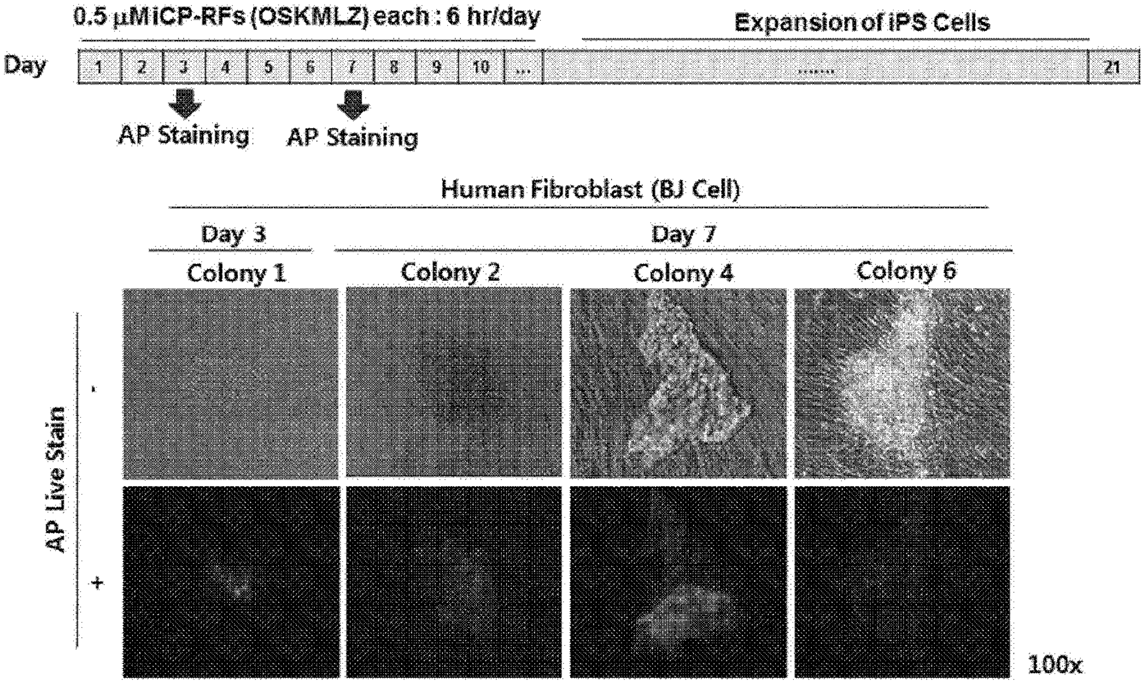
【Figure 50】
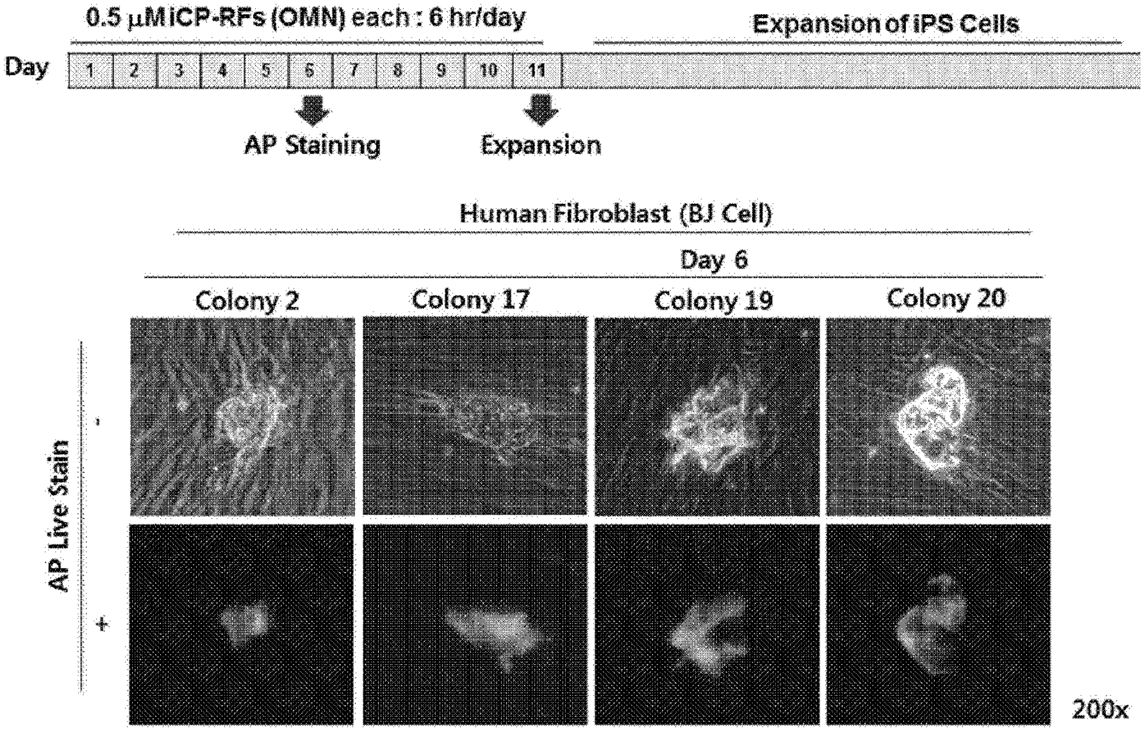

【Figure 51】
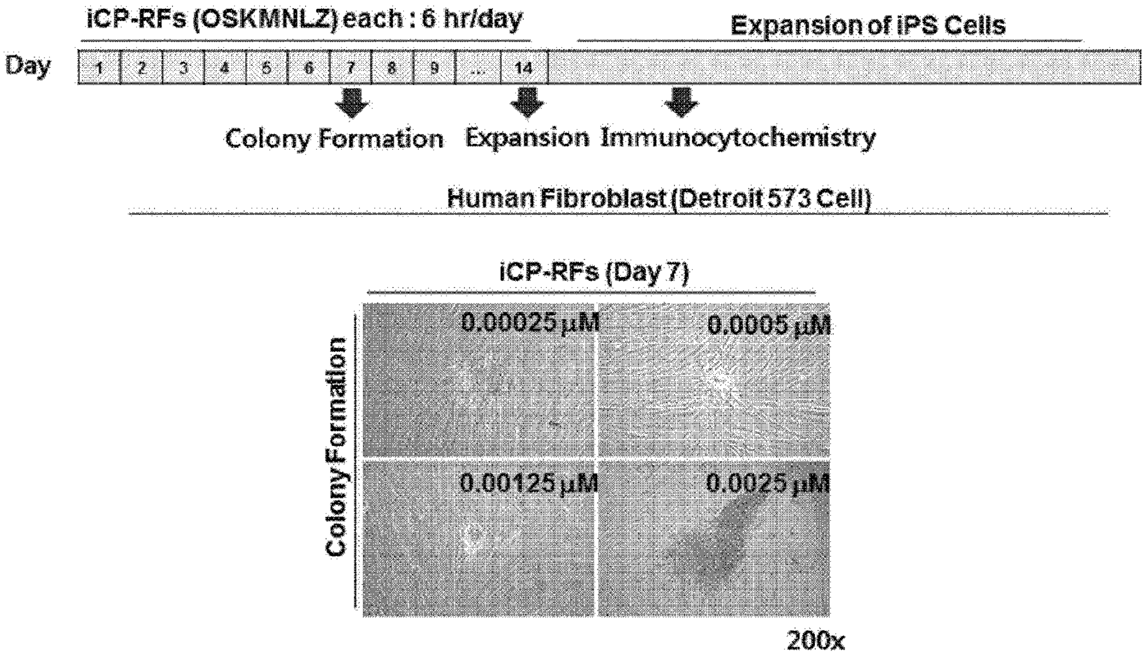
【Figure 52】
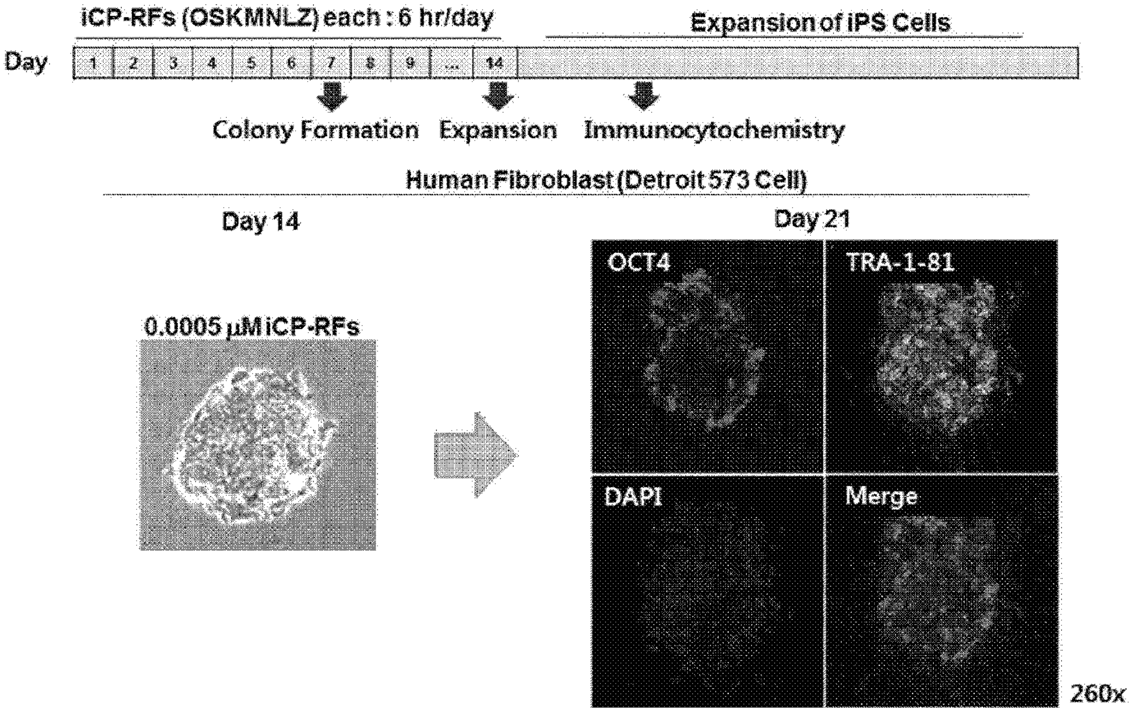

SEQUENCE LISTING

<160> NUMBER OF SEQ ID NOS: 873

<210> SEQ ID NO 1
<211> LENGTH: 12
<212> TYPE: PRT
<213> ORGANISM: Artificial Sequence
<220> FEATURE:
<223> OTHER INFORMATION: Amino acid Sequence of aMTD1

<400> SEQUENCE: 1

Ala Ala Ala Leu Ala Pro Val Val Leu Ala Leu Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Amino acid Sequence of aMTD2

<400> SEQUENCE: 2

Ala Ala Ala Val Pro Leu Leu Ala Val Val Val Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Amino acid Sequence of aMTD3

<400> SEQUENCE: 3

Ala Ala Leu Leu Val Pro Ala Ala Val Leu Ala Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Amino acid Sequence of aMTD4

<400> SEQUENCE: 4

Ala Leu Ala Leu Leu Pro Val Ala Ala Leu Ala Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Amino acid Sequence of aMTD5

<400> SEQUENCE: 5

Ala Ala Ala Leu Leu Pro Val Ala Leu Val Ala Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Amino acid Sequence of aMTD11

<400> SEQUENCE: 6

Val Val Ala Leu Ala Pro Ala Leu Ala Ala Leu Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Amino acid Sequence of aMTD12

<400> SEQUENCE: 7

Leu Leu Ala Ala Val Pro Ala Val Leu Leu Ala Pro
1 5 10

<210> SEQ ID NO 8
<211> LENGTH: 12
<212> TYPE: PRT
<213> ORGANISM: Artificial Sequence
<220> FEATURE:
<223> OTHER INFORMATION: Amino acid Sequence of aMTD13

<400> SEQUENCE: 8

Ala Ala Ala Leu Val Pro Val Val Ala Leu Leu Pro
1 5 10

<210> SEQ ID NO 9
<211> LENGTH: 12
<212> TYPE: PRT
<213> ORGANISM: Artificial Sequence
<220> FEATURE:
<223> OTHER INFORMATION: Amino acid Sequence of aMTD21

<400> SEQUENCE: 9

Ala Val Ala Leu Leu Pro Ala Leu Leu Ala Val Pro
1 5 10

<210> SEQ ID NO 10
<211> LENGTH: 12
<212> TYPE: PRT
<213> ORGANISM: Artificial Sequence
<220> FEATURE:
<223> OTHER INFORMATION: Amino acid Sequence of aMTD22

<400> SEQUENCE: 10

Ala Val Val Leu Val Pro Val Leu Ala Ala Ala Pro
1 5 10

<210> SEQ ID NO 11
<211> LENGTH: 12
<212> TYPE: PRT
<213> ORGANISM: Artificial Sequence
<220> FEATURE:
<223> OTHER INFORMATION: Amino acid Sequence of aMTD23

<400> SEQUENCE: 11

Val Val Leu Val Leu Pro Ala Ala Ala Ala Val Pro
1 5 10

<210> SEQ ID NO 12
<211> LENGTH: 12
<212> TYPE: PRT
<213> ORGANISM: Artificial Sequence
<220> FEATURE:
<223> OTHER INFORMATION: Amino acid Sequence of aMTD24

<400> SEQUENCE: 12

Ile Ala Leu Ala Ala Pro Ala Leu Ile Val Ala Pro
1 5 10

<210> SEQ ID NO 13
<211> LENGTH: 12
<212> TYPE: PRT
<213> ORGANISM: Artificial Sequence
<220> FEATURE:
<223> OTHER INFORMATION: Amino acid Sequence of aMTD25

<400> SEQUENCE: 13

Ile Val Ala Val Ala Pro Ala Leu Val Ala Leu Pro
1 5 10

<210> SEQ ID NO 14
<211> LENGTH: 12
<212> TYPE: PRT
<213> ORGANISM: Artificial Sequence
<220> FEATURE:
<223> OTHER INFORMATION: Amino acid Sequence of aMTD42

<400> SEQUENCE: 14

Val Ala Ala Leu Pro Val Val Ala Val Val Ala Pro
1 5 10

<210> SEQ ID NO 15
<211> LENGTH: 12
<212> TYPE: PRT
<213> ORGANISM: Artificial Sequence
<220> FEATURE:
<223> OTHER INFORMATION: Amino acid Sequence of aMTD43

<400> SEQUENCE: 15

Leu Leu Ala Ala Pro Leu Val Val Ala Ala Val Pro
1 5 10

<210> SEQ ID NO 16
<211> LENGTH: 12
<212> TYPE: PRT
<213> ORGANISM: Artificial Sequence
<220> FEATURE:
<223> OTHER INFORMATION: Amino acid Sequence of aMTD44

<400> SEQUENCE: 16

Ala Leu Ala Val Pro Val Ala Leu Leu Val Ala Pro
1 5 10

<210> SEQ ID NO 17
<211> LENGTH: 12
<212> TYPE: PRT
<213> ORGANISM: Artificial Sequence
<220> FEATURE:
<223> OTHER INFORMATION: Amino acid Sequence of aMTD61

<400> SEQUENCE: 17

Val Ala Ala Leu Pro Val Leu Leu Ala Ala Leu Pro
1 5 10

<210> SEQ ID NO 18
<211> LENGTH: 12
<212> TYPE: PRT
<213> ORGANISM: Artificial Sequence
<220> FEATURE:
<223> OTHER INFORMATION: Amino acid Sequence of aMTD62

<400> SEQUENCE: 18

Val Ala Leu Leu Ala Pro Val Ala Leu Ala Val Pro
1 5 10

<210> SEQ ID NO 19
<211> LENGTH: 12
<212> TYPE: PRT
<213> ORGANISM: Artificial Sequence
<220> FEATURE:
<223> OTHER INFORMATION: Amino acid Sequence of aMTD63

<400> SEQUENCE: 19

Ala Ala Leu Leu Val Pro Ala Leu Val Ala Val Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Amino acid Sequence of aMTD64

<400> SEQUENCE: 20

Ala Ile Val Ala Leu Pro Val Ala Val Leu Ala Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Amino acid Sequence of aMTD65

<400> SEQUENCE: 21

Ile Ala Ile Val Ala Pro Val Val Ala Leu Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Amino acid Sequence of aMTD81

<400> SEQUENCE: 22

Ala Ala Leu Leu Pro Ala Leu Ala Ala Leu Leu Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Amino acid Sequence of aMTD82

<400> SEQUENCE: 23

Ala Val Val Leu Ala Pro Val Ala Ala Val Leu Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Amino acid Sequence of aMTD83

<400> SEQUENCE: 24

Leu Ala Val Ala Ala Pro Leu Ala Leu Ala Leu Pro
1               5                   10

<210> SEQ ID NO 25

<211> LENGTH: 12
<212> TYPE: PRT
<213> ORGANISM: Artificial Sequence
<220> FEATURE:
<223> OTHER INFORMATION: Amino acid Sequence of aMTD84

<400> SEQUENCE: 25

Ala Ala Val Ala Ala Pro Leu Leu Leu Ala Leu Pro
1 5 10

<210> SEQ ID NO 26
<211> LENGTH: 12
<212> TYPE: PRT
<213> ORGANISM: Artificial Sequence
<220> FEATURE:
<223> OTHER INFORMATION: Amino acid Sequence of aMTD85

<400> SEQUENCE: 26

Leu Leu Val Leu Pro Ala Ala Ala Leu Ala Ala Pro
1 5 10

<210> SEQ ID NO 27
<211> LENGTH: 12
<212> TYPE: PRT
<213> ORGANISM: Artificial Sequence
<220> FEATURE:
<223> OTHER INFORMATION: Amino acid Sequence of aMTD101

<400> SEQUENCE: 27

Leu Val Ala Leu Ala Pro Val Ala Ala Val Leu Pro
1 5 10

<210> SEQ ID NO 28
<211> LENGTH: 12
<212> TYPE: PRT
<213> ORGANISM: Artificial Sequence
<220> FEATURE:
<223> OTHER INFORMATION: Amino acid Sequence of aMTD102

<400> SEQUENCE: 28

Leu Ala Leu Ala Pro Ala Ala Leu Ala Leu Leu Pro
1 5 10

<210> SEQ ID NO 29
<211> LENGTH: 12
<212> TYPE: PRT
<213> ORGANISM: Artificial Sequence
<220> FEATURE:
<223> OTHER INFORMATION: Amino acid Sequence of aMTD103

<400> SEQUENCE: 29

Ala Leu Ile Ala Ala Pro Ile Leu Ala Leu Ala Pro
1 5 10

<210> SEQ ID NO 30
<211> LENGTH: 12
<212> TYPE: PRT
<213> ORGANISM: Artificial Sequence
<220> FEATURE:
<223> OTHER INFORMATION: Amino acid Sequence of aMTD104

<400> SEQUENCE: 30

Ala Val Val Ala Ala Pro Leu Val Leu Ala Leu Pro
1 5 10

<210> SEQ ID NO 31
<211> LENGTH: 12

<212> TYPE: PRT
<213> ORGANISM: Artificial Sequence
<220> FEATURE:
<223> OTHER INFORMATION: Amino acid Sequence of aMTD105

<400> SEQUENCE: 31

Leu Leu Ala Leu Ala Pro Ala Ala Leu Leu Ala Pro
1 5 10

<210> SEQ ID NO 32
<211> LENGTH: 12
<212> TYPE: PRT
<213> ORGANISM: Artificial Sequence
<220> FEATURE:
<223> OTHER INFORMATION: Amino acid Sequence of aMTD121

<400> SEQUENCE: 32

Ala Ile Val Ala Leu Pro Ala Leu Ala Leu Ala Pro
1 5 10

<210> SEQ ID NO 33
<211> LENGTH: 12
<212> TYPE: PRT
<213> ORGANISM: Artificial Sequence
<220> FEATURE:
<223> OTHER INFORMATION: Amino acid Sequence of aMTD123

<400> SEQUENCE: 33

Ala Ala Ile Ile Val Pro Ala Ala Leu Leu Ala Pro
1 5 10

<210> SEQ ID NO 34
<211> LENGTH: 12
<212> TYPE: PRT
<213> ORGANISM: Artificial Sequence
<220> FEATURE:
<223> OTHER INFORMATION: Amino acid Sequence of aMTD124

<400> SEQUENCE: 34

Ile Ala Val Ala Leu Pro Ala Leu Ile Ala Ala Pro
1 5 10

<210> SEQ ID NO 35
<211> LENGTH: 12
<212> TYPE: PRT
<213> ORGANISM: Artificial Sequence
<220> FEATURE:
<223> OTHER INFORMATION: Amino acid Sequence of aMTD141

<400> SEQUENCE: 35

Ala Val Ile Val Leu Pro Ala Leu Ala Val Ala Pro
1 5 10

<210> SEQ ID NO 36
<211> LENGTH: 12
<212> TYPE: PRT
<213> ORGANISM: Artificial Sequence
<220> FEATURE:
<223> OTHER INFORMATION: Amino acid Sequence of aMTD143

<400> SEQUENCE: 36

Ala Val Leu Ala Val Pro Ala Val Leu Val Ala Pro
1 5 10

<210> SEQ ID NO 37
<211> LENGTH: 12
<212> TYPE: PRT

<213> ORGANISM: Artificial Sequence
<220> FEATURE:
<223> OTHER INFORMATION: Amino acid Sequence of aMTD144

<400> SEQUENCE: 37

Val Leu Ala Ile Val Pro Ala Val Ala Leu Ala Pro
1 5 10

<210> SEQ ID NO 38
<211> LENGTH: 12
<212> TYPE: PRT
<213> ORGANISM: Artificial Sequence
<220> FEATURE:
<223> OTHER INFORMATION: Amino acid Sequence of aMTD145

<400> SEQUENCE: 38

Leu Leu Ala Val Val Pro Ala Val Ala Leu Ala Pro
1 5 10

<210> SEQ ID NO 39
<211> LENGTH: 12
<212> TYPE: PRT
<213> ORGANISM: Artificial Sequence
<220> FEATURE:
<223> OTHER INFORMATION: Amino acid Sequence of aMTD161

<400> SEQUENCE: 39

Ala Val Ile Ala Leu Pro Ala Leu Ile Ala Ala Pro
1 5 10

<210> SEQ ID NO 40
<211> LENGTH: 12
<212> TYPE: PRT
<213> ORGANISM: Artificial Sequence
<220> FEATURE:
<223> OTHER INFORMATION: Amino acid Sequence of aMTD162

<400> SEQUENCE: 40

Ala Val Val Ala Leu Pro Ala Ala Leu Ile Val Pro
1 5 10

<210> SEQ ID NO 41
<211> LENGTH: 12
<212> TYPE: PRT
<213> ORGANISM: Artificial Sequence
<220> FEATURE:
<223> OTHER INFORMATION: Amino acid Sequence of aMTD163

<400> SEQUENCE: 41

Leu Ala Leu Val Leu Pro Ala Ala Leu Ala Ala Pro
1 5 10

<210> SEQ ID NO 42
<211> LENGTH: 12
<212> TYPE: PRT
<213> ORGANISM: Artificial Sequence
<220> FEATURE:
<223> OTHER INFORMATION: Amino acid Sequence of aMTD164

<400> SEQUENCE: 42

Leu Ala Ala Val Leu Pro Ala Leu Leu Ala Ala Pro
1 5 10

<210> SEQ ID NO 43
<211> LENGTH: 12
<212> TYPE: PRT
<213> ORGANISM: Artificial Sequence
<220> FEATURE:
<223> OTHER INFORMATION: Amino acid Sequence of aMTD165

<400> SEQUENCE: 43

Ala Leu Ala Val Pro Val Ala Leu Ala Ile Val Pro
1 5 10

<210> SEQ ID NO 44
<211> LENGTH: 12
<212> TYPE: PRT
<213> ORGANISM: Artificial Sequence
<220> FEATURE:
<223> OTHER INFORMATION: Amino acid Sequence of aMTD182

<400> SEQUENCE: 44

Ala Leu Ile Ala Pro Val Val Ala Leu Val Ala Pro
1 5 10

<210> SEQ ID NO 45
<211> LENGTH: 12
<212> TYPE: PRT
<213> ORGANISM: Artificial Sequence
<220> FEATURE:
<223> OTHER INFORMATION: Amino acid Sequence of aMTD183

<400> SEQUENCE: 45

Leu Leu Ala Ala Pro Val Val Ile Ala Leu Ala Pro
1 5 10

<210> SEQ ID NO 46
<211> LENGTH: 12
<212> TYPE: PRT
<213> ORGANISM: Artificial Sequence
<220> FEATURE:
<223> OTHER INFORMATION: Amino acid Sequence of aMTD184

<400> SEQUENCE: 46

Leu Ala Ala Ile Val Pro Ala Ile Ile Ala Val Pro
1 5 10

<210> SEQ ID NO 47
<211> LENGTH: 12
<212> TYPE: PRT
<213> ORGANISM: Artificial Sequence
<220> FEATURE:
<223> OTHER INFORMATION: Amino acid Sequence of aMTD185

<400> SEQUENCE: 47

Ala Ala Leu Val Leu Pro Leu Ile Ile Ala Ala Pro
1 5 10

<210> SEQ ID NO 48
<211> LENGTH: 12
<212> TYPE: PRT
<213> ORGANISM: Artificial Sequence
<220> FEATURE:
<223> OTHER INFORMATION: Amino acid Sequence of aMTD201

<400> SEQUENCE: 48

Leu Ala Leu Ala Val Pro Ala Leu Ala Ala Leu Pro
1 5 10

<210> SEQ ID NO 49
<211> LENGTH: 12
<212> TYPE: PRT
<213> ORGANISM: Artificial Sequence
<220> FEATURE:

<223> OTHER INFORMATION: Amino acid Sequence of aMTD204

<400> SEQUENCE: 49

Leu Ile Ala Ala Leu Pro Ala Val Ala Ala Leu Pro
1 5 10

<210> SEQ ID NO 50
<211> LENGTH: 12
<212> TYPE: PRT
<213> ORGANISM: Artificial Sequence
<220> FEATURE:
<223> OTHER INFORMATION: Amino acid Sequence of aMTD205

<400> SEQUENCE: 50

Ala Leu Ala Leu Val Pro Ala Ile Ala Ala Leu Pro
1 5 10

<210> SEQ ID NO 51
<211> LENGTH: 12
<212> TYPE: PRT
<213> ORGANISM: Artificial Sequence
<220> FEATURE:
<223> OTHER INFORMATION: Amino acid Sequence of aMTD221

<400> SEQUENCE: 51

Ala Ala Ile Leu Ala Pro Ile Val Ala Leu Ala Pro
1 5 10

<210> SEQ ID NO 52
<211> LENGTH: 12
<212> TYPE: PRT
<213> ORGANISM: Artificial Sequence
<220> FEATURE:
<223> OTHER INFORMATION: Amino acid Sequence of aMTD222

<400> SEQUENCE: 52

Ala Leu Leu Ile Ala Pro Ala Ala Val Ile Ala Pro
1 5 10

<210> SEQ ID NO 53
<211> LENGTH: 12
<212> TYPE: PRT
<213> ORGANISM: Artificial Sequence
<220> FEATURE:
<223> OTHER INFORMATION: Amino acid Sequence of aMTD223

<400> SEQUENCE: 53

Ala Ile Leu Ala Val Pro Ile Ala Val Val Ala Pro
1 5 10

<210> SEQ ID NO 54
<211> LENGTH: 12
<212> TYPE: PRT
<213> ORGANISM: Artificial Sequence
<220> FEATURE:
<223> OTHER INFORMATION: Amino acid Sequence of aMTD224

<400> SEQUENCE: 54

Ile Leu Ala Ala Val Pro Ile Ala Leu Ala Ala Pro
1 5 10

<210> SEQ ID NO 55
<211> LENGTH: 12
<212> TYPE: PRT
<213> ORGANISM: Artificial Sequence
<220> FEATURE:
<223> OTHER INFORMATION: Amino acid Sequence of aMTD225

<400> SEQUENCE: 55

Val Ala Ala Leu Leu Pro Ala Ala Ala Val Leu Pro
1 5 10

<210> SEQ ID NO 56
<211> LENGTH: 12
<212> TYPE: PRT
<213> ORGANISM: Artificial Sequence
<220> FEATURE:
<223> OTHER INFORMATION: Amino acid Sequence of aMTD241

<400> SEQUENCE: 56

Ala Ala Ala Val Val Pro Val Leu Leu Val Ala Pro
1 5 10

<210> SEQ ID NO 57
<211> LENGTH: 12
<212> TYPE: PRT
<213> ORGANISM: Artificial Sequence
<220> FEATURE:
<223> OTHER INFORMATION: Amino acid Sequence of aMTD242

<400> SEQUENCE: 57

Ala Ala Leu Leu Val Pro Ala Leu Val Ala Ala Pro
1 5 10

<210> SEQ ID NO 58
<211> LENGTH: 12
<212> TYPE: PRT
<213> ORGANISM: Artificial Sequence
<220> FEATURE:
<223> OTHER INFORMATION: Amino acid Sequence of aMTD243

<400> SEQUENCE: 58

Ala Ala Val Leu Leu Pro Val Ala Leu Ala Ala Pro
1 5 10

<210> SEQ ID NO 59
<211> LENGTH: 12
<212> TYPE: PRT
<213> ORGANISM: Artificial Sequence
<220> FEATURE:
<223> OTHER INFORMATION: Amino acid Sequence of aMTD245

<400> SEQUENCE: 59

Ala Ala Ala Leu Ala Pro Val Leu Ala Leu Val Pro
1 5 10

<210> SEQ ID NO 60
<211> LENGTH: 12
<212> TYPE: PRT
<213> ORGANISM: Artificial Sequence
<220> FEATURE:
<223> OTHER INFORMATION: Amino acid Sequence of aMTD261

<400> SEQUENCE: 60

Leu Val Leu Val Pro Leu Leu Ala Ala Ala Ala Pro
1 5 10

<210> SEQ ID NO 61
<211> LENGTH: 12
<212> TYPE: PRT
<213> ORGANISM: Artificial Sequence
<220> FEATURE:
<223> OTHER INFORMATION: Amino acid Sequence of aMTD262

<400> SEQUENCE: 61

Ala Leu Ile Ala Val Pro Ala Ile Ile Val Ala Pro
1 5 10

<210> SEQ ID NO 62
<211> LENGTH: 12
<212> TYPE: PRT
<213> ORGANISM: Artificial Sequence
<220> FEATURE:
<223> OTHER INFORMATION: Amino acid Sequence of aMTD263

<400> SEQUENCE: 62

Ala Leu Ala Val Ile Pro Ala Ala Ala Ile Leu Pro
1 5 10

<210> SEQ ID NO 63
<211> LENGTH: 12
<212> TYPE: PRT
<213> ORGANISM: Artificial Sequence
<220> FEATURE:
<223> OTHER INFORMATION: Amino acid Sequence of aMTD264

<400> SEQUENCE: 63

Leu Ala Ala Ala Pro Val Val Ile Val Ile Ala Pro
1 5 10

<210> SEQ ID NO 64
<211> LENGTH: 12
<212> TYPE: PRT
<213> ORGANISM: Artificial Sequence
<220> FEATURE:
<223> OTHER INFORMATION: Amino acid Sequence of aMTD265

<400> SEQUENCE: 64

Val Leu Ala Ile Ala Pro Leu Leu Ala Ala Val Pro
1 5 10

<210> SEQ ID NO 65
<211> LENGTH: 12
<212> TYPE: PRT
<213> ORGANISM: Artificial Sequence
<220> FEATURE:
<223> OTHER INFORMATION: Amino acid Sequence of aMTD281

<400> SEQUENCE: 65

Ala Leu Ile Val Leu Pro Ala Ala Val Ala Val Pro
1 5 10

<210> SEQ ID NO 66
<211> LENGTH: 12
<212> TYPE: PRT
<213> ORGANISM: Artificial Sequence
<220> FEATURE:
<223> OTHER INFORMATION: Amino acid Sequence of aMTD282

<400> SEQUENCE: 66

Val Leu Ala Val Ala Pro Ala Leu Ile Val Ala Pro
1 5 10

<210> SEQ ID NO 67
<211> LENGTH: 12
<212> TYPE: PRT
<213> ORGANISM: Artificial Sequence
<220> FEATURE:
<223> OTHER INFORMATION: Amino acid Sequence of aMTD283

<400> SEQUENCE: 67

```
Ala Ala Leu Leu Ala Pro Ala Leu Ile Val Ala Pro
1               5                   10


<210> SEQ ID NO 68
<211> LENGTH: 12
<212> TYPE: PRT
<213> ORGANISM: Artificial Sequence
<220> FEATURE:
<223> OTHER INFORMATION: Amino acid Sequence of aMTD284

<400> SEQUENCE: 68

Ala Leu Ile Ala Pro Ala Val Ala Leu Ile Val Pro
1               5                   10


<210> SEQ ID NO 69
<211> LENGTH: 12
<212> TYPE: PRT
<213> ORGANISM: Artificial Sequence
<220> FEATURE:
<223> OTHER INFORMATION: Amino acid Sequence of aMTD285

<400> SEQUENCE: 69

Ala Ile Val Leu Leu Pro Ala Ala Val Val Ala Pro
1               5                   10


<210> SEQ ID NO 70
<211> LENGTH: 12
<212> TYPE: PRT
<213> ORGANISM: Artificial Sequence
<220> FEATURE:
<223> OTHER INFORMATION: Amino acid Sequence of aMTD301

<400> SEQUENCE: 70

Val Ile Ala Ala Pro Val Leu Ala Val Leu Ala Pro
1               5                   10


<210> SEQ ID NO 71
<211> LENGTH: 12
<212> TYPE: PRT
<213> ORGANISM: Artificial Sequence
<220> FEATURE:
<223> OTHER INFORMATION: Amino acid Sequence of aMTD302

<400> SEQUENCE: 71

Leu Ala Leu Ala Pro Ala Leu Ala Leu Leu Ala Pro
1               5                   10


<210> SEQ ID NO 72
<211> LENGTH: 12
<212> TYPE: PRT
<213> ORGANISM: Artificial Sequence
<220> FEATURE:
<223> OTHER INFORMATION: Amino acid Sequence of aMTD304

<400> SEQUENCE: 72

Ala Ile Ile Leu Ala Pro Ile Ala Ala Ile Ala Pro
1               5                   10


<210> SEQ ID NO 73
<211> LENGTH: 12
<212> TYPE: PRT
<213> ORGANISM: Artificial Sequence
<220> FEATURE:
<223> OTHER INFORMATION: Amino acid Sequence of aMTD305

<400> SEQUENCE: 73
```

Ile Ala Leu Ala Ala Pro Ile Leu Leu Ala Ala Pro
1 5 10

<210> SEQ ID NO 74
<211> LENGTH: 12
<212> TYPE: PRT
<213> ORGANISM: Artificial Sequence
<220> FEATURE:
<223> OTHER INFORMATION: Amino acid Sequence of aMTD321

<400> SEQUENCE: 74

Ile Val Ala Val Ala Leu Pro Ala Leu Ala Val Pro
1 5 10

<210> SEQ ID NO 75
<211> LENGTH: 12
<212> TYPE: PRT
<213> ORGANISM: Artificial Sequence
<220> FEATURE:
<223> OTHER INFORMATION: Amino acid Sequence of aMTD322

<400> SEQUENCE: 75

Val Val Ala Ile Val Leu Pro Ala Leu Ala Ala Pro
1 5 10

<210> SEQ ID NO 76
<211> LENGTH: 12
<212> TYPE: PRT
<213> ORGANISM: Artificial Sequence
<220> FEATURE:
<223> OTHER INFORMATION: Amino acid Sequence of aMTD323

<400> SEQUENCE: 76

Ile Val Ala Val Ala Leu Pro Val Ala Leu Ala Pro
1 5 10

<210> SEQ ID NO 77
<211> LENGTH: 12
<212> TYPE: PRT
<213> ORGANISM: Artificial Sequence
<220> FEATURE:
<223> OTHER INFORMATION: Amino acid Sequence of aMTD324

<400> SEQUENCE: 77

Ile Val Ala Val Ala Leu Pro Ala Ala Leu Val Pro
1 5 10

<210> SEQ ID NO 78
<211> LENGTH: 12
<212> TYPE: PRT
<213> ORGANISM: Artificial Sequence
<220> FEATURE:
<223> OTHER INFORMATION: Amino acid Sequence of aMTD325

<400> SEQUENCE: 78

Ile Val Ala Val Ala Leu Pro Ala Val Ala Leu Pro
1 5 10

<210> SEQ ID NO 79
<211> LENGTH: 12
<212> TYPE: PRT
<213> ORGANISM: Artificial Sequence
<220> FEATURE:
<223> OTHER INFORMATION: Amino acid Sequence of aMTD341

<400> SEQUENCE: 79

Ile Val Ala Val Ala Leu Pro Ala Val Leu Ala Pro 1 5 10

<210> SEQ ID NO 80
<211> LENGTH: 12
<212> TYPE: PRT
<213> ORGANISM: Artificial Sequence
<220> FEATURE:
<223> OTHER INFORMATION: Amino acid Sequence of aMTD342

<400> SEQUENCE: 80

Val Ile Val Ala Leu Ala Pro Ala Val Leu Ala Pro
1 5 10

<210> SEQ ID NO 81
<211> LENGTH: 12
<212> TYPE: PRT
<213> ORGANISM: Artificial Sequence
<220> FEATURE:
<223> OTHER INFORMATION: Amino acid Sequence of aMTD343

<400> SEQUENCE: 81

Ile Val Ala Val Ala Leu Pro Ala Leu Val Ala Pro
1 5 10

<210> SEQ ID NO 82
<211> LENGTH: 12
<212> TYPE: PRT
<213> ORGANISM: Artificial Sequence
<220> FEATURE:
<223> OTHER INFORMATION: Amino acid Sequence of aMTD345

<400> SEQUENCE: 82

Ala Leu Leu Ile Val Ala Pro Val Ala Val Ala Pro
1 5 10

<210> SEQ ID NO 83
<211> LENGTH: 12
<212> TYPE: PRT
<213> ORGANISM: Artificial Sequence
<220> FEATURE:
<223> OTHER INFORMATION: Amino acid Sequence of aMTD361

<400> SEQUENCE: 83

Ala Val Val Ile Val Ala Pro Ala Val Ile Ala Pro
1 5 10

<210> SEQ ID NO 84
<211> LENGTH: 12
<212> TYPE: PRT
<213> ORGANISM: Artificial Sequence
<220> FEATURE:
<223> OTHER INFORMATION: Amino acid Sequence of aMTD363

<400> SEQUENCE: 84

Ala Val Leu Ala Val Ala Pro Ala Leu Ile Val Pro
1 5 10

<210> SEQ ID NO 85
<211> LENGTH: 12
<212> TYPE: PRT
<213> ORGANISM: Artificial Sequence
<220> FEATURE:
<223> OTHER INFORMATION: Amino acid Sequence of aMTD364

<400> SEQUENCE: 85

Leu Val Ala Ala Val Ala Pro Ala Leu Ile Val Pro
1 5 10

<210> SEQ ID NO 86
<211> LENGTH: 12
<212> TYPE: PRT
<213> ORGANISM: Artificial Sequence
<220> FEATURE:
<223> OTHER INFORMATION: Amino acid Sequence of aMTD365

<400> SEQUENCE: 86

Ala Val Ile Val Val Ala Pro Ala Leu Leu Ala Pro
1 5 10

<210> SEQ ID NO 87
<211> LENGTH: 12
<212> TYPE: PRT
<213> ORGANISM: Artificial Sequence
<220> FEATURE:
<223> OTHER INFORMATION: Amino acid Sequence of aMTD381

<400> SEQUENCE: 87

Val Val Ala Ile Val Leu Pro Ala Val Ala Ala Pro
1 5 10

<210> SEQ ID NO 88
<211> LENGTH: 12
<212> TYPE: PRT
<213> ORGANISM: Artificial Sequence
<220> FEATURE:
<223> OTHER INFORMATION: Amino acid Sequence of aMTD382

<400> SEQUENCE: 88

Ala Ala Ala Leu Val Ile Pro Ala Ile Leu Ala Pro
1 5 10

<210> SEQ ID NO 89
<211> LENGTH: 12
<212> TYPE: PRT
<213> ORGANISM: Artificial Sequence
<220> FEATURE:
<223> OTHER INFORMATION: Amino acid Sequence of aMTD383

<400> SEQUENCE: 89

Val Ile Val Ala Leu Ala Pro Ala Leu Leu Ala Pro
1 5 10

<210> SEQ ID NO 90
<211> LENGTH: 12
<212> TYPE: PRT
<213> ORGANISM: Artificial Sequence
<220> FEATURE:
<223> OTHER INFORMATION: Amino acid Sequence of aMTD384

<400> SEQUENCE: 90

Val Ile Val Ala Ile Ala Pro Ala Leu Leu Ala Pro
1 5 10

<210> SEQ ID NO 91
<211> LENGTH: 12
<212> TYPE: PRT
<213> ORGANISM: Artificial Sequence
<220> FEATURE:
<223> OTHER INFORMATION: Amino acid Sequence of aMTD385

<400> SEQUENCE: 91

Ile Val Ala Ile Ala Val Pro Ala Leu Val Ala Pro
1 5 10

<210> SEQ ID NO 92
<211> LENGTH: 12
<212> TYPE: PRT
<213> ORGANISM: Artificial Sequence
<220> FEATURE:
<223> OTHER INFORMATION: Amino acid Sequence of aMTD401

<400> SEQUENCE: 92

Ala Ala Leu Ala Val Ile Pro Ala Ala Ile Leu Pro
1 5 10

<210> SEQ ID NO 93
<211> LENGTH: 12
<212> TYPE: PRT
<213> ORGANISM: Artificial Sequence
<220> FEATURE:
<223> OTHER INFORMATION: Amino acid Sequence of aMTD402

<400> SEQUENCE: 93

Ala Leu Ala Ala Val Ile Pro Ala Ala Ile Leu Pro
1 5 10

<210> SEQ ID NO 94
<211> LENGTH: 12
<212> TYPE: PRT
<213> ORGANISM: Artificial Sequence
<220> FEATURE:
<223> OTHER INFORMATION: Amino acid Sequence of aMTD403

<400> SEQUENCE: 94

Ala Ala Ala Leu Val Ile Pro Ala Ala Ile Leu Pro
1 5 10

<210> SEQ ID NO 95
<211> LENGTH: 12
<212> TYPE: PRT
<213> ORGANISM: Artificial Sequence
<220> FEATURE:
<223> OTHER INFORMATION: Amino acid Sequence of aMTD404

<400> SEQUENCE: 95

Leu Ala Ala Ala Val Ile Pro Ala Ala Ile Leu Pro
1 5 10

<210> SEQ ID NO 96
<211> LENGTH: 12
<212> TYPE: PRT
<213> ORGANISM: Artificial Sequence
<220> FEATURE:
<223> OTHER INFORMATION: Amino acid Sequence of aMTD405

<400> SEQUENCE: 96

Leu Ala Ala Ala Val Ile Pro Val Ala Ile Leu Pro
1 5 10

<210> SEQ ID NO 97
<211> LENGTH: 12
<212> TYPE: PRT
<213> ORGANISM: Artificial Sequence
<220> FEATURE:
<223> OTHER INFORMATION: Amino acid Sequence of aMTD421

<400> SEQUENCE: 97

Ala Ala Ile Leu Ala Ala Pro Leu Ile Ala Val Pro
1 5 10

<210> SEQ ID NO 98
<211> LENGTH: 12
<212> TYPE: PRT
<213> ORGANISM: Artificial Sequence
<220> FEATURE:
<223> OTHER INFORMATION: Amino acid Sequence of aMTD422

<400> SEQUENCE: 98

Val Val Ala Ile Leu Ala Pro Leu Leu Ala Ala Pro
1 5 10

<210> SEQ ID NO 99
<211> LENGTH: 12
<212> TYPE: PRT
<213> ORGANISM: Artificial Sequence
<220> FEATURE:
<223> OTHER INFORMATION: Amino acid Sequence of aMTD424

<400> SEQUENCE: 99

Ala Val Val Val Ala Ala Pro Val Leu Ala Leu Pro
1 5 10

<210> SEQ ID NO 100
<211> LENGTH: 12
<212> TYPE: PRT
<213> ORGANISM: Artificial Sequence
<220> FEATURE:
<223> OTHER INFORMATION: Amino acid Sequence of aMTD425

<400> SEQUENCE: 100

Ala Val Val Ala Ile Ala Pro Val Leu Ala Leu Pro
1 5 10

<210> SEQ ID NO 101
<211> LENGTH: 12
<212> TYPE: PRT
<213> ORGANISM: Artificial Sequence
<220> FEATURE:
<223> OTHER INFORMATION: Amino acid Sequence of aMTD442

<400> SEQUENCE: 101

Ala Leu Ala Ala Leu Val Pro Ala Val Leu Val Pro
1 5 10

<210> SEQ ID NO 102
<211> LENGTH: 12
<212> TYPE: PRT
<213> ORGANISM: Artificial Sequence
<220> FEATURE:
<223> OTHER INFORMATION: Amino acid Sequence of aMTD443

<400> SEQUENCE: 102

Ala Leu Ala Ala Leu Val Pro Val Ala Leu Val Pro
1 5 10

<210> SEQ ID NO 103
<211> LENGTH: 12
<212> TYPE: PRT
<213> ORGANISM: Artificial Sequence
<220> FEATURE:
<223> OTHER INFORMATION: Amino acid Sequence of aMTD444

<400> SEQUENCE: 103

Leu Ala Ala Ala Leu Val Pro Val Ala Leu Val Pro
1 5 10

<210> SEQ ID NO 104

<211> LENGTH: 12
<212> TYPE: PRT
<213> ORGANISM: Artificial Sequence
<220> FEATURE:
<223> OTHER INFORMATION: Amino acid Sequence of aMTD445

<400> SEQUENCE: 104

Ala Leu Ala Ala Leu Val Pro Ala Leu Val Val Pro
1 5 10

<210> SEQ ID NO 105
<211> LENGTH: 12
<212> TYPE: PRT
<213> ORGANISM: Artificial Sequence
<220> FEATURE:
<223> OTHER INFORMATION: Amino acid Sequence of aMTD461

<400> SEQUENCE: 105

Ile Ala Ala Val Ile Val Pro Ala Val Ala Leu Pro
1 5 10

<210> SEQ ID NO 106
<211> LENGTH: 12
<212> TYPE: PRT
<213> ORGANISM: Artificial Sequence
<220> FEATURE:
<223> OTHER INFORMATION: Amino acid Sequence of aMTD462

<400> SEQUENCE: 106

Ile Ala Ala Val Leu Val Pro Ala Val Ala Leu Pro
1 5 10

<210> SEQ ID NO 107
<211> LENGTH: 12
<212> TYPE: PRT
<213> ORGANISM: Artificial Sequence
<220> FEATURE:
<223> OTHER INFORMATION: Amino acid Sequence of aMTD463

<400> SEQUENCE: 107

Ala Val Ala Ile Leu Val Pro Leu Leu Ala Ala Pro
1 5 10

<210> SEQ ID NO 108
<211> LENGTH: 12
<212> TYPE: PRT
<213> ORGANISM: Artificial Sequence
<220> FEATURE:
<223> OTHER INFORMATION: Amino acid Sequence of aMTD464

<400> SEQUENCE: 108

Ala Val Val Ile Leu Val Pro Leu Ala Ala Ala Pro
1 5 10

<210> SEQ ID NO 109
<211> LENGTH: 12
<212> TYPE: PRT
<213> ORGANISM: Artificial Sequence
<220> FEATURE:
<223> OTHER INFORMATION: Amino acid Sequence of aMTD465

<400> SEQUENCE: 109

Ile Ala Ala Val Ile Val Pro Val Ala Ala Leu Pro
1 5 10

<210> SEQ ID NO 110
<211> LENGTH: 12

<212> TYPE: PRT
<213> ORGANISM: Artificial Sequence
<220> FEATURE:
<223> OTHER INFORMATION: Amino acid Sequence of aMTD481

<400> SEQUENCE: 110

Ala Ile Ala Ile Ala Ile Val Pro Val Ala Leu Pro
1 5 10

<210> SEQ ID NO 111
<211> LENGTH: 12
<212> TYPE: PRT
<213> ORGANISM: Artificial Sequence
<220> FEATURE:
<223> OTHER INFORMATION: Amino acid Sequence of aMTD482

<400> SEQUENCE: 111

Ile Leu Ala Val Ala Ala Ile Pro Val Ala Val Pro
1 5 10

<210> SEQ ID NO 112
<211> LENGTH: 12
<212> TYPE: PRT
<213> ORGANISM: Artificial Sequence
<220> FEATURE:
<223> OTHER INFORMATION: Amino acid Sequence of aMTD483

<400> SEQUENCE: 112

Ile Leu Ala Ala Ala Ile Ile Pro Ala Ala Leu Pro
1 5 10

<210> SEQ ID NO 113
<211> LENGTH: 12
<212> TYPE: PRT
<213> ORGANISM: Artificial Sequence
<220> FEATURE:
<223> OTHER INFORMATION: Amino acid Sequence of aMTD484

<400> SEQUENCE: 113

Leu Ala Val Val Leu Ala Ala Pro Ala Ile Val Pro
1 5 10

<210> SEQ ID NO 114
<211> LENGTH: 12
<212> TYPE: PRT
<213> ORGANISM: Artificial Sequence
<220> FEATURE:
<223> OTHER INFORMATION: Amino acid Sequence of aMTD485

<400> SEQUENCE: 114

Ala Ile Leu Ala Ala Ile Val Pro Leu Ala Val Pro
1 5 10

<210> SEQ ID NO 115
<211> LENGTH: 12
<212> TYPE: PRT
<213> ORGANISM: Artificial Sequence
<220> FEATURE:
<223> OTHER INFORMATION: Amino acid Sequence of aMTD501

<400> SEQUENCE: 115

Val Ile Val Ala Leu Ala Val Pro Ala Leu Ala Pro
1 5 10

<210> SEQ ID NO 116
<211> LENGTH: 12
<212> TYPE: PRT

<213> ORGANISM: Artificial Sequence
<220> FEATURE:
<223> OTHER INFORMATION: Amino acid Sequence of aMTD502

<400> SEQUENCE: 116

Ala Ile Val Ala Leu Ala Val Pro Val Leu Ala Pro
1 5 10

<210> SEQ ID NO 117
<211> LENGTH: 12
<212> TYPE: PRT
<213> ORGANISM: Artificial Sequence
<220> FEATURE:
<223> OTHER INFORMATION: Amino acid Sequence of aMTD503

<400> SEQUENCE: 117

Ala Ala Ile Ile Ile Val Leu Pro Ala Ala Leu Pro
1 5 10

<210> SEQ ID NO 118
<211> LENGTH: 12
<212> TYPE: PRT
<213> ORGANISM: Artificial Sequence
<220> FEATURE:
<223> OTHER INFORMATION: Amino acid Sequence of aMTD504

<400> SEQUENCE: 118

Leu Ile Val Ala Leu Ala Val Pro Ala Leu Ala Pro
1 5 10

<210> SEQ ID NO 119
<211> LENGTH: 12
<212> TYPE: PRT
<213> ORGANISM: Artificial Sequence
<220> FEATURE:
<223> OTHER INFORMATION: Amino acid Sequence of aMTD505

<400> SEQUENCE: 119

Ala Ile Ile Ile Val Ile Ala Pro Ala Ala Ala Pro
1 5 10

<210> SEQ ID NO 120
<211> LENGTH: 12
<212> TYPE: PRT
<213> ORGANISM: Artificial Sequence
<220> FEATURE:
<223> OTHER INFORMATION: Amino acid Sequence of aMTD521

<400> SEQUENCE: 120

Leu Ala Ala Leu Ile Val Val Pro Ala Val Ala Pro
1 5 10

<210> SEQ ID NO 121
<211> LENGTH: 12
<212> TYPE: PRT
<213> ORGANISM: Artificial Sequence
<220> FEATURE:
<223> OTHER INFORMATION: Amino acid Sequence of aMTD522

<400> SEQUENCE: 121

Ala Leu Leu Val Ile Ala Val Pro Ala Val Ala Pro
1 5 10

<210> SEQ ID NO 122
<211> LENGTH: 12
<212> TYPE: PRT
<213> ORGANISM: Artificial Sequence
<220> FEATURE:
<223> OTHER INFORMATION: Amino acid Sequence of aMTD524

<400> SEQUENCE: 122

Ala Val Ala Leu Ile Val Val Pro Ala Leu Ala Pro
1 5 10

<210> SEQ ID NO 123
<211> LENGTH: 12
<212> TYPE: PRT
<213> ORGANISM: Artificial Sequence
<220> FEATURE:
<223> OTHER INFORMATION: Amino acid Sequence of aMTD525

<400> SEQUENCE: 123

Ala Leu Ala Ile Val Val Ala Pro Val Ala Val Pro
1 5 10

<210> SEQ ID NO 124
<211> LENGTH: 12
<212> TYPE: PRT
<213> ORGANISM: Artificial Sequence
<220> FEATURE:
<223> OTHER INFORMATION: Amino acid Sequence of aMTD541

<400> SEQUENCE: 124

Leu Leu Ala Leu Ile Ile Ala Pro Ala Ala Ala Pro
1 5 10

<210> SEQ ID NO 125
<211> LENGTH: 12
<212> TYPE: PRT
<213> ORGANISM: Artificial Sequence
<220> FEATURE:
<223> OTHER INFORMATION: Amino acid Sequence of aMTD542

<400> SEQUENCE: 125

Ala Leu Ala Leu Ile Ile Val Pro Ala Val Ala Pro
1 5 10

<210> SEQ ID NO 126
<211> LENGTH: 12
<212> TYPE: PRT
<213> ORGANISM: Artificial Sequence
<220> FEATURE:
<223> OTHER INFORMATION: Amino acid Sequence of aMTD543

<400> SEQUENCE: 126

Leu Leu Ala Ala Leu Ile Ala Pro Ala Ala Leu Pro
1 5 10

<210> SEQ ID NO 127
<211> LENGTH: 12
<212> TYPE: PRT
<213> ORGANISM: Artificial Sequence
<220> FEATURE:
<223> OTHER INFORMATION: Amino acid Sequence of aMTD544

<400> SEQUENCE: 127

Ile Val Ala Leu Ile Val Ala Pro Ala Ala Val Pro
1 5 10

<210> SEQ ID NO 128
<211> LENGTH: 12
<212> TYPE: PRT
<213> ORGANISM: Artificial Sequence
<220> FEATURE:

<223> OTHER INFORMATION: Amino acid Sequence of aMTD545

<400> SEQUENCE: 128

Val Val Leu Val Leu Ala Ala Pro Ala Ala Val Pro
1 5 10

<210> SEQ ID NO 129
<211> LENGTH: 12
<212> TYPE: PRT
<213> ORGANISM: Artificial Sequence
<220> FEATURE:
<223> OTHER INFORMATION: Amino acid Sequence of aMTD561

<400> SEQUENCE: 129

Ala Ala Val Ala Ile Val Leu Pro Ala Val Val Pro
1 5 10

<210> SEQ ID NO 130
<211> LENGTH: 12
<212> TYPE: PRT
<213> ORGANISM: Artificial Sequence
<220> FEATURE:
<223> OTHER INFORMATION: Amino acid Sequence of aMTD562

<400> SEQUENCE: 130

Ala Leu Ile Ala Ala Ile Val Pro Ala Leu Val Pro
1 5 10

<210> SEQ ID NO 131
<211> LENGTH: 12
<212> TYPE: PRT
<213> ORGANISM: Artificial Sequence
<220> FEATURE:
<223> OTHER INFORMATION: Amino acid Sequence of aMTD563

<400> SEQUENCE: 131

Ala Leu Ala Val Ile Val Val Pro Ala Leu Ala Pro
1 5 10

<210> SEQ ID NO 132
<211> LENGTH: 12
<212> TYPE: PRT
<213> ORGANISM: Artificial Sequence
<220> FEATURE:
<223> OTHER INFORMATION: Amino acid Sequence of aMTD564

<400> SEQUENCE: 132

Val Ala Ile Ala Leu Ile Val Pro Ala Leu Ala Pro
1 5 10

<210> SEQ ID NO 133
<211> LENGTH: 12
<212> TYPE: PRT
<213> ORGANISM: Artificial Sequence
<220> FEATURE:
<223> OTHER INFORMATION: Amino acid Sequence of aMTD565

<400> SEQUENCE: 133

Val Ala Ile Val Leu Val Ala Pro Ala Val Ala Pro
1 5 10

<210> SEQ ID NO 134
<211> LENGTH: 12
<212> TYPE: PRT
<213> ORGANISM: Artificial Sequence
<220> FEATURE:
<223> OTHER INFORMATION: Amino acid Sequence of aMTD582

<400> SEQUENCE: 134

Val Ala Val Ala Leu Ile Val Pro Ala Leu Ala Pro
1 5 10

<210> SEQ ID NO 135
<211> LENGTH: 12
<212> TYPE: PRT
<213> ORGANISM: Artificial Sequence
<220> FEATURE:
<223> OTHER INFORMATION: Amino acid Sequence of aMTD583

<400> SEQUENCE: 135

Ala Val Ile Leu Ala Leu Ala Pro Ile Val Ala Pro
1 5 10

<210> SEQ ID NO 136
<211> LENGTH: 12
<212> TYPE: PRT
<213> ORGANISM: Artificial Sequence
<220> FEATURE:
<223> OTHER INFORMATION: Amino acid Sequence of aMTD585

<400> SEQUENCE: 136

Ala Leu Ile Val Ala Ile Ala Pro Ala Leu Val Pro
1 5 10

<210> SEQ ID NO 137
<211> LENGTH: 12
<212> TYPE: PRT
<213> ORGANISM: Artificial Sequence
<220> FEATURE:
<223> OTHER INFORMATION: Amino acid Sequence of aMTD601

<400> SEQUENCE: 137

Ala Ala Ile Leu Ile Ala Val Pro Ile Ala Ala Pro
1 5 10

<210> SEQ ID NO 138
<211> LENGTH: 12
<212> TYPE: PRT
<213> ORGANISM: Artificial Sequence
<220> FEATURE:
<223> OTHER INFORMATION: Amino acid Sequence of aMTD602

<400> SEQUENCE: 138

Val Ile Val Ala Leu Ala Ala Pro Val Leu Ala Pro
1 5 10

<210> SEQ ID NO 139
<211> LENGTH: 12
<212> TYPE: PRT
<213> ORGANISM: Artificial Sequence
<220> FEATURE:
<223> OTHER INFORMATION: Amino acid Sequence of aMTD603

<400> SEQUENCE: 139

Val Leu Val Ala Leu Ala Ala Pro Val Ile Ala Pro
1 5 10

<210> SEQ ID NO 140
<211> LENGTH: 12
<212> TYPE: PRT
<213> ORGANISM: Artificial Sequence
<220> FEATURE:
<223> OTHER INFORMATION: Amino acid Sequence of aMTD604

<400> SEQUENCE: 140

Val Ala Leu Ile Ala Val Ala Pro Ala Val Val Pro
1 5 10

<210> SEQ ID NO 141
<211> LENGTH: 12
<212> TYPE: PRT
<213> ORGANISM: Artificial Sequence
<220> FEATURE:
<223> OTHER INFORMATION: Amino acid Sequence of aMTD605

<400> SEQUENCE: 141

Val Ile Ala Ala Val Leu Ala Pro Val Ala Val Pro
1 5 10

<210> SEQ ID NO 142
<211> LENGTH: 12
<212> TYPE: PRT
<213> ORGANISM: Artificial Sequence
<220> FEATURE:
<223> OTHER INFORMATION: Amino acid Sequence of aMTD622

<400> SEQUENCE: 142

Ala Leu Ile Val Leu Ala Ala Pro Val Ala Val Pro
1 5 10

<210> SEQ ID NO 143
<211> LENGTH: 12
<212> TYPE: PRT
<213> ORGANISM: Artificial Sequence
<220> FEATURE:
<223> OTHER INFORMATION: Amino acid Sequence of aMTD623

<400> SEQUENCE: 143

Val Ala Ala Ala Ile Ala Leu Pro Ala Ile Val Pro
1 5 10

<210> SEQ ID NO 144
<211> LENGTH: 12
<212> TYPE: PRT
<213> ORGANISM: Artificial Sequence
<220> FEATURE:
<223> OTHER INFORMATION: Amino acid Sequence of aMTD625

<400> SEQUENCE: 144

Ile Leu Ala Ala Ala Ala Ala Pro Leu Ile Val Pro
1 5 10

<210> SEQ ID NO 145
<211> LENGTH: 12
<212> TYPE: PRT
<213> ORGANISM: Artificial Sequence
<220> FEATURE:
<223> OTHER INFORMATION: Amino acid Sequence of aMTD643

<400> SEQUENCE: 145

Leu Ala Leu Val Leu Ala Ala Pro Ala Ile Val Pro
1 5 10

<210> SEQ ID NO 146
<211> LENGTH: 12
<212> TYPE: PRT
<213> ORGANISM: Artificial Sequence
<220> FEATURE:
<223> OTHER INFORMATION: Amino acid Sequence of aMTD645

<400> SEQUENCE: 146

```
Ala Leu Ala Val Val Ala Leu Pro Ala Ile Val Pro
1               5                   10


<210> SEQ ID NO 147
<211> LENGTH: 12
<212> TYPE: PRT
<213> ORGANISM: Artificial Sequence
<220> FEATURE:
<223> OTHER INFORMATION: Amino acid Sequence of aMTD661

<400> SEQUENCE: 147

Ala Ala Ile Leu Ala Pro Ile Val Ala Ala Leu Pro
1               5                   10


<210> SEQ ID NO 148
<211> LENGTH: 12
<212> TYPE: PRT
<213> ORGANISM: Artificial Sequence
<220> FEATURE:
<223> OTHER INFORMATION: Amino acid Sequence of aMTD664

<400> SEQUENCE: 148

Ile Leu Ile Ala Ile Ala Ile Pro Ala Ala Ala Pro
1               5                   10


<210> SEQ ID NO 149
<211> LENGTH: 12
<212> TYPE: PRT
<213> ORGANISM: Artificial Sequence
<220> FEATURE:
<223> OTHER INFORMATION: Amino acid Sequence of aMTD665

<400> SEQUENCE: 149

Leu Ala Ile Val Leu Ala Ala Pro Val Ala Val Pro
1               5                   10


<210> SEQ ID NO 150
<211> LENGTH: 12
<212> TYPE: PRT
<213> ORGANISM: Artificial Sequence
<220> FEATURE:
<223> OTHER INFORMATION: Amino acid Sequence of aMTD666

<400> SEQUENCE: 150

Ala Ala Ile Ala Ile Ile Ala Pro Ala Ile Val Pro
1               5                   10


<210> SEQ ID NO 151
<211> LENGTH: 12
<212> TYPE: PRT
<213> ORGANISM: Artificial Sequence
<220> FEATURE:
<223> OTHER INFORMATION: Amino acid Sequence of aMTD667

<400> SEQUENCE: 151

Leu Ala Val Ala Ile Val Ala Pro Ala Leu Val Pro
1               5                   10


<210> SEQ ID NO 152
<211> LENGTH: 12
<212> TYPE: PRT
<213> ORGANISM: Artificial Sequence
<220> FEATURE:
<223> OTHER INFORMATION: Amino acid Sequence of aMTD683

<400> SEQUENCE: 152
```

```
Leu Ala Ile Val Leu Ala Ala Pro Ala Val Leu Pro
1               5                   10


<210> SEQ ID NO 153
<211> LENGTH: 12
<212> TYPE: PRT
<213> ORGANISM: Artificial Sequence
<220> FEATURE:
<223> OTHER INFORMATION: Amino acid Sequence of aMTD684

<400> SEQUENCE: 153

Ala Ala Ile Val Leu Ala Leu Pro Ala Val Leu Pro
1               5                   10


<210> SEQ ID NO 154
<211> LENGTH: 12
<212> TYPE: PRT
<213> ORGANISM: Artificial Sequence
<220> FEATURE:
<223> OTHER INFORMATION: Amino acid Sequence of aMTD685

<400> SEQUENCE: 154

Ala Leu Leu Val Ala Val Leu Pro Ala Ala Leu Pro
1               5                   10


<210> SEQ ID NO 155
<211> LENGTH: 12
<212> TYPE: PRT
<213> ORGANISM: Artificial Sequence
<220> FEATURE:
<223> OTHER INFORMATION: Amino acid Sequence of aMTD686

<400> SEQUENCE: 155

Ala Ala Leu Val Ala Val Leu Pro Val Ala Leu Pro
1               5                   10


<210> SEQ ID NO 156
<211> LENGTH: 12
<212> TYPE: PRT
<213> ORGANISM: Artificial Sequence
<220> FEATURE:
<223> OTHER INFORMATION: Amino acid Sequence of aMTD687

<400> SEQUENCE: 156

Ala Ile Leu Ala Val Ala Leu Pro Leu Leu Ala Pro
1               5                   10


<210> SEQ ID NO 157
<211> LENGTH: 12
<212> TYPE: PRT
<213> ORGANISM: Artificial Sequence
<220> FEATURE:
<223> OTHER INFORMATION: Amino acid Sequence of aMTD703

<400> SEQUENCE: 157

Ile Val Ala Val Ala Leu Val Pro Ala Leu Ala Pro
1               5                   10


<210> SEQ ID NO 158
<211> LENGTH: 12
<212> TYPE: PRT
<213> ORGANISM: Artificial Sequence
<220> FEATURE:
<223> OTHER INFORMATION: Amino acid Sequence of aMTD705

<400> SEQUENCE: 158

Ile Val Ala Val Ala Leu Leu Pro Ala Leu Ala Pro
```

1 5 10

<210> SEQ ID NO 159
<211> LENGTH: 12
<212> TYPE: PRT
<213> ORGANISM: Artificial Sequence
<220> FEATURE:
<223> OTHER INFORMATION: Amino acid Sequence of aMTD706

<400> SEQUENCE: 159

Ile Val Ala Val Ala Leu Leu Pro Ala Val Ala Pro
1 5 10

<210> SEQ ID NO 160
<211> LENGTH: 12
<212> TYPE: PRT
<213> ORGANISM: Artificial Sequence
<220> FEATURE:
<223> OTHER INFORMATION: Amino acid Sequence of aMTD707

<400> SEQUENCE: 160

Ile Val Ala Leu Ala Val Leu Pro Ala Val Ala Pro
1 5 10

<210> SEQ ID NO 161
<211> LENGTH: 12
<212> TYPE: PRT
<213> ORGANISM: Artificial Sequence
<220> FEATURE:
<223> OTHER INFORMATION: Amino acid Sequence of aMTD724

<400> SEQUENCE: 161

Val Ala Val Leu Ala Val Leu Pro Ala Leu Ala Pro
1 5 10

<210> SEQ ID NO 162
<211> LENGTH: 12
<212> TYPE: PRT
<213> ORGANISM: Artificial Sequence
<220> FEATURE:
<223> OTHER INFORMATION: Amino acid Sequence of aMTD725

<400> SEQUENCE: 162

Ile Ala Val Leu Ala Val Ala Pro Ala Val Leu Pro
1 5 10

<210> SEQ ID NO 163
<211> LENGTH: 12
<212> TYPE: PRT
<213> ORGANISM: Artificial Sequence
<220> FEATURE:
<223> OTHER INFORMATION: Amino acid Sequence of aMTD726

<400> SEQUENCE: 163

Leu Ala Val Ala Ile Ile Ala Pro Ala Val Ala Pro
1 5 10

<210> SEQ ID NO 164
<211> LENGTH: 12
<212> TYPE: PRT
<213> ORGANISM: Artificial Sequence
<220> FEATURE:
<223> OTHER INFORMATION: Amino acid Sequence of aMTD727

<400> SEQUENCE: 164

Val Ala Leu Ala Ile Ala Leu Pro Ala Val Leu Pro
1 5 10

<210> SEQ ID NO 165
<211> LENGTH: 12
<212> TYPE: PRT
<213> ORGANISM: Artificial Sequence
<220> FEATURE:
<223> OTHER INFORMATION: Amino acid Sequence of aMTD743

<400> SEQUENCE: 165

Ala Ile Ala Ile Ala Leu Val Pro Val Ala Leu Pro
1 5 10

<210> SEQ ID NO 166
<211> LENGTH: 12
<212> TYPE: PRT
<213> ORGANISM: Artificial Sequence
<220> FEATURE:
<223> OTHER INFORMATION: Amino acid Sequence of aMTD744

<400> SEQUENCE: 166

Ala Ala Val Val Ile Val Ala Pro Val Ala Leu Pro
1 5 10

<210> SEQ ID NO 167
<211> LENGTH: 12
<212> TYPE: PRT
<213> ORGANISM: Artificial Sequence
<220> FEATURE:
<223> OTHER INFORMATION: Amino acid Sequence of aMTD746

<400> SEQUENCE: 167

Val Ala Ile Ile Val Val Ala Pro Ala Leu Ala Pro
1 5 10

<210> SEQ ID NO 168
<211> LENGTH: 12
<212> TYPE: PRT
<213> ORGANISM: Artificial Sequence
<220> FEATURE:
<223> OTHER INFORMATION: Amino acid Sequence of aMTD747

<400> SEQUENCE: 168

Val Ala Leu Leu Ala Ile Ala Pro Ala Leu Ala Pro
1 5 10

<210> SEQ ID NO 169
<211> LENGTH: 12
<212> TYPE: PRT
<213> ORGANISM: Artificial Sequence
<220> FEATURE:
<223> OTHER INFORMATION: Amino acid Sequence of aMTD763

<400> SEQUENCE: 169

Val Ala Val Leu Ile Ala Val Pro Ala Leu Ala Pro
1 5 10

<210> SEQ ID NO 170
<211> LENGTH: 12
<212> TYPE: PRT
<213> ORGANISM: Artificial Sequence
<220> FEATURE:
<223> OTHER INFORMATION: Amino acid Sequence of aMTD764

<400> SEQUENCE: 170

Ala Val Ala Leu Ala Val Leu Pro Ala Val Val Pro
1 5 10

<210> SEQ ID NO 171
<211> LENGTH: 12
<212> TYPE: PRT
<213> ORGANISM: Artificial Sequence
<220> FEATURE:
<223> OTHER INFORMATION: Amino acid Sequence of aMTD765

<400> SEQUENCE: 171

Ala Val Ala Leu Ala Val Val Pro Ala Val Leu Pro
1 5 10

<210> SEQ ID NO 172
<211> LENGTH: 12
<212> TYPE: PRT
<213> ORGANISM: Artificial Sequence
<220> FEATURE:
<223> OTHER INFORMATION: Amino acid Sequence of aMTD766

<400> SEQUENCE: 172

Ile Val Val Ile Ala Val Ala Pro Ala Val Ala Pro
1 5 10

<210> SEQ ID NO 173
<211> LENGTH: 12
<212> TYPE: PRT
<213> ORGANISM: Artificial Sequence
<220> FEATURE:
<223> OTHER INFORMATION: Amino acid Sequence of aMTD767

<400> SEQUENCE: 173

Ile Val Val Ala Ala Val Val Pro Ala Leu Ala Pro
1 5 10

<210> SEQ ID NO 174
<211> LENGTH: 12
<212> TYPE: PRT
<213> ORGANISM: Artificial Sequence
<220> FEATURE:
<223> OTHER INFORMATION: Amino acid Sequence of aMTD783

<400> SEQUENCE: 174

Ile Val Ala Leu Val Pro Ala Val Ala Ile Ala Pro
1 5 10

<210> SEQ ID NO 175
<211> LENGTH: 12
<212> TYPE: PRT
<213> ORGANISM: Artificial Sequence
<220> FEATURE:
<223> OTHER INFORMATION: Amino acid Sequence of aMTD784

<400> SEQUENCE: 175

Val Ala Ala Leu Pro Ala Val Ala Leu Val Val Pro
1 5 10

<210> SEQ ID NO 176
<211> LENGTH: 12
<212> TYPE: PRT
<213> ORGANISM: Artificial Sequence
<220> FEATURE:
<223> OTHER INFORMATION: Amino acid Sequence of aMTD786

<400> SEQUENCE: 176

Leu Val Ala Ile Ala Pro Leu Ala Val Leu Ala Pro
1 5 10

<210> SEQ ID NO 177
<211> LENGTH: 12
<212> TYPE: PRT
<213> ORGANISM: Artificial Sequence
<220> FEATURE:
<223> OTHER INFORMATION: Amino acid Sequence of aMTD787

<400> SEQUENCE: 177

Ala Val Ala Leu Val Pro Val Ile Val Ala Ala Pro
1 5 10

<210> SEQ ID NO 178
<211> LENGTH: 12
<212> TYPE: PRT
<213> ORGANISM: Artificial Sequence
<220> FEATURE:
<223> OTHER INFORMATION: Amino acid Sequence of aMTD788

<400> SEQUENCE: 178

Ala Ile Ala Val Ala Ile Ala Pro Val Ala Leu Pro
1 5 10

<210> SEQ ID NO 179
<211> LENGTH: 12
<212> TYPE: PRT
<213> ORGANISM: Artificial Sequence
<220> FEATURE:
<223> OTHER INFORMATION: Amino acid Sequence of aMTD803

<400> SEQUENCE: 179

Ala Ile Ala Leu Ala Val Pro Val Leu Ala Leu Pro
1 5 10

<210> SEQ ID NO 180
<211> LENGTH: 12
<212> TYPE: PRT
<213> ORGANISM: Artificial Sequence
<220> FEATURE:
<223> OTHER INFORMATION: Amino acid Sequence of aMTD805

<400> SEQUENCE: 180

Leu Val Leu Ile Ala Ala Ala Pro Ile Ala Leu Pro
1 5 10

<210> SEQ ID NO 181
<211> LENGTH: 12
<212> TYPE: PRT
<213> ORGANISM: Artificial Sequence
<220> FEATURE:
<223> OTHER INFORMATION: Amino acid Sequence of aMTD806

<400> SEQUENCE: 181

Leu Val Ala Leu Ala Val Pro Ala Ala Val Leu Pro
1 5 10

<210> SEQ ID NO 182
<211> LENGTH: 12
<212> TYPE: PRT
<213> ORGANISM: Artificial Sequence
<220> FEATURE:
<223> OTHER INFORMATION: Amino acid Sequence of aMTD807

<400> SEQUENCE: 182

Ala Val Ala Leu Ala Val Pro Ala Leu Val Leu Pro
1 5 10

<210> SEQ ID NO 183

<211> LENGTH: 12
<212> TYPE: PRT
<213> ORGANISM: Artificial Sequence
<220> FEATURE:
<223> OTHER INFORMATION: Amino acid Sequence of aMTD808

<400> SEQUENCE: 183

Leu Val Val Leu Ala Ala Ala Pro Leu Ala Val Pro
1 5 10

<210> SEQ ID NO 184
<211> LENGTH: 12
<212> TYPE: PRT
<213> ORGANISM: Artificial Sequence
<220> FEATURE:
<223> OTHER INFORMATION: Amino acid Sequence of aMTD809

<400> SEQUENCE: 184

Leu Ile Val Leu Ala Ala Pro Ala Leu Ala Ala Pro
1 5 10

<210> SEQ ID NO 185
<211> LENGTH: 12
<212> TYPE: PRT
<213> ORGANISM: Artificial Sequence
<220> FEATURE:
<223> OTHER INFORMATION: Amino acid Sequence of aMTD810

<400> SEQUENCE: 185

Val Ile Val Leu Ala Ala Pro Ala Leu Ala Ala Pro
1 5 10

<210> SEQ ID NO 186
<211> LENGTH: 12
<212> TYPE: PRT
<213> ORGANISM: Artificial Sequence
<220> FEATURE:
<223> OTHER INFORMATION: Amino acid Sequence of aMTD811

<400> SEQUENCE: 186

Ala Val Val Leu Ala Val Pro Ala Leu Ala Val Pro
1 5 10

<210> SEQ ID NO 187
<211> LENGTH: 12
<212> TYPE: PRT
<213> ORGANISM: Artificial Sequence
<220> FEATURE:
<223> OTHER INFORMATION: Amino acid Sequence of aMTD824

<400> SEQUENCE: 187

Leu Ile Ile Val Ala Ala Ala Pro Ala Val Ala Pro
1 5 10

<210> SEQ ID NO 188
<211> LENGTH: 12
<212> TYPE: PRT
<213> ORGANISM: Artificial Sequence
<220> FEATURE:
<223> OTHER INFORMATION: Amino acid Sequence of aMTD825

<400> SEQUENCE: 188

Ile Val Ala Val Ile Val Ala Pro Ala Val Ala Pro
1 5 10

<210> SEQ ID NO 189
<211> LENGTH: 12

<212> TYPE: PRT
<213> ORGANISM: Artificial Sequence
<220> FEATURE:
<223> OTHER INFORMATION: Amino acid Sequence of aMTD826

<400> SEQUENCE: 189

Leu Val Ala Leu Ala Ala Pro Ile Ile Ala Val Pro
1 5 10

<210> SEQ ID NO 190
<211> LENGTH: 12
<212> TYPE: PRT
<213> ORGANISM: Artificial Sequence
<220> FEATURE:
<223> OTHER INFORMATION: Amino acid Sequence of aMTD827

<400> SEQUENCE: 190

Ile Ala Ala Val Leu Ala Ala Pro Ala Leu Val Pro
1 5 10

<210> SEQ ID NO 191
<211> LENGTH: 12
<212> TYPE: PRT
<213> ORGANISM: Artificial Sequence
<220> FEATURE:
<223> OTHER INFORMATION: Amino acid Sequence of aMTD828

<400> SEQUENCE: 191

Ile Ala Leu Leu Ala Ala Pro Ile Ile Ala Val Pro
1 5 10

<210> SEQ ID NO 192
<211> LENGTH: 12
<212> TYPE: PRT
<213> ORGANISM: Artificial Sequence
<220> FEATURE:
<223> OTHER INFORMATION: Amino acid Sequence of aMTD829

<400> SEQUENCE: 192

Ala Ala Leu Ala Leu Val Ala Pro Val Ile Val Pro
1 5 10

<210> SEQ ID NO 193
<211> LENGTH: 12
<212> TYPE: PRT
<213> ORGANISM: Artificial Sequence
<220> FEATURE:
<223> OTHER INFORMATION: Amino acid Sequence of aMTD830

<400> SEQUENCE: 193

Ile Ala Leu Val Ala Ala Pro Val Ala Leu Val Pro
1 5 10

<210> SEQ ID NO 194
<211> LENGTH: 12
<212> TYPE: PRT
<213> ORGANISM: Artificial Sequence
<220> FEATURE:
<223> OTHER INFORMATION: Amino acid Sequence of aMTD831

<400> SEQUENCE: 194

Ile Ile Val Ala Val Ala Pro Ala Ala Ile Val Pro
1 5 10

<210> SEQ ID NO 195
<211> LENGTH: 12
<212> TYPE: PRT

<213> ORGANISM: Artificial Sequence
<220> FEATURE:
<223> OTHER INFORMATION: Amino acid Sequence of aMTD832

<400> SEQUENCE: 195

Ala Val Ala Ala Ile Val Pro Val Ile Val Ala Pro
1 5 10

<210> SEQ ID NO 196
<211> LENGTH: 12
<212> TYPE: PRT
<213> ORGANISM: Artificial Sequence
<220> FEATURE:
<223> OTHER INFORMATION: Amino acid Sequence of aMTD843

<400> SEQUENCE: 196

Ala Val Leu Val Leu Val Ala Pro Ala Ala Ala Pro
1 5 10

<210> SEQ ID NO 197
<211> LENGTH: 12
<212> TYPE: PRT
<213> ORGANISM: Artificial Sequence
<220> FEATURE:
<223> OTHER INFORMATION: Amino acid Sequence of aMTD844

<400> SEQUENCE: 197

Val Val Ala Leu Leu Ala Pro Leu Ile Ala Ala Pro
1 5 10

<210> SEQ ID NO 198
<211> LENGTH: 12
<212> TYPE: PRT
<213> ORGANISM: Artificial Sequence
<220> FEATURE:
<223> OTHER INFORMATION: Amino acid Sequence of aMTD845

<400> SEQUENCE: 198

Ala Ala Val Val Ile Ala Pro Leu Leu Ala Val Pro
1 5 10

<210> SEQ ID NO 199
<211> LENGTH: 12
<212> TYPE: PRT
<213> ORGANISM: Artificial Sequence
<220> FEATURE:
<223> OTHER INFORMATION: Amino acid Sequence of aMTD846

<400> SEQUENCE: 199

Ile Ala Val Ala Val Ala Ala Pro Leu Leu Val Pro
1 5 10

<210> SEQ ID NO 200
<211> LENGTH: 12
<212> TYPE: PRT
<213> ORGANISM: Artificial Sequence
<220> FEATURE:
<223> OTHER INFORMATION: Amino acid Sequence of aMTD847

<400> SEQUENCE: 200

Leu Val Ala Ile Val Val Leu Pro Ala Val Ala Pro
1 5 10

<210> SEQ ID NO 201
<211> LENGTH: 12
<212> TYPE: PRT
<213> ORGANISM: Artificial Sequence
<220> FEATURE:
<223> OTHER INFORMATION: Amino acid Sequence of aMTD848

<400> SEQUENCE: 201

Ala Val Ala Ile Val Val Leu Pro Ala Val Ala Pro
1 5 10

<210> SEQ ID NO 202
<211> LENGTH: 12
<212> TYPE: PRT
<213> ORGANISM: Artificial Sequence
<220> FEATURE:
<223> OTHER INFORMATION: Amino acid Sequence of aMTD849

<400> SEQUENCE: 202

Ala Val Ile Leu Leu Ala Pro Leu Ile Ala Ala Pro
1 5 10

<210> SEQ ID NO 203
<211> LENGTH: 12
<212> TYPE: PRT
<213> ORGANISM: Artificial Sequence
<220> FEATURE:
<223> OTHER INFORMATION: Amino acid Sequence of aMTD850

<400> SEQUENCE: 203

Leu Val Ile Ala Leu Ala Ala Pro Val Ala Leu Pro
1 5 10

<210> SEQ ID NO 204
<211> LENGTH: 12
<212> TYPE: PRT
<213> ORGANISM: Artificial Sequence
<220> FEATURE:
<223> OTHER INFORMATION: Amino acid Sequence of aMTD851

<400> SEQUENCE: 204

Val Leu Ala Val Val Leu Pro Ala Val Ala Leu Pro
1 5 10

<210> SEQ ID NO 205
<211> LENGTH: 12
<212> TYPE: PRT
<213> ORGANISM: Artificial Sequence
<220> FEATURE:
<223> OTHER INFORMATION: Amino acid Sequence of aMTD852

<400> SEQUENCE: 205

Val Leu Ala Val Ala Ala Pro Ala Val Leu Leu Pro
1 5 10

<210> SEQ ID NO 206
<211> LENGTH: 12
<212> TYPE: PRT
<213> ORGANISM: Artificial Sequence
<220> FEATURE:
<223> OTHER INFORMATION: Amino acid Sequence of aMTD863

<400> SEQUENCE: 206

Ala Ala Val Val Leu Leu Pro Ile Ile Ala Ala Pro
1 5 10

<210> SEQ ID NO 207
<211> LENGTH: 12
<212> TYPE: PRT
<213> ORGANISM: Artificial Sequence
<220> FEATURE:

<223> OTHER INFORMATION: Amino acid Sequence of aMTD864

<400> SEQUENCE: 207

Ala Leu Leu Val Ile Ala Pro Ala Ile Ala Val Pro
1 5 10

<210> SEQ ID NO 208
<211> LENGTH: 12
<212> TYPE: PRT
<213> ORGANISM: Artificial Sequence
<220> FEATURE:
<223> OTHER INFORMATION: Amino acid Sequence of aMTD865

<400> SEQUENCE: 208

Ala Val Leu Val Ile Ala Val Pro Ala Ile Ala Pro
1 5 10

<210> SEQ ID NO 209
<211> LENGTH: 12
<212> TYPE: PRT
<213> ORGANISM: Artificial Sequence
<220> FEATURE:
<223> OTHER INFORMATION: Amino acid Sequence of aMTD867

<400> SEQUENCE: 209

Ala Leu Leu Val Val Ile Ala Pro Leu Ala Ala Pro
1 5 10

<210> SEQ ID NO 210
<211> LENGTH: 12
<212> TYPE: PRT
<213> ORGANISM: Artificial Sequence
<220> FEATURE:
<223> OTHER INFORMATION: Amino acid Sequence of aMTD868

<400> SEQUENCE: 210

Val Leu Val Ala Ala Ile Leu Pro Ala Ala Ile Pro
1 5 10

<210> SEQ ID NO 211
<211> LENGTH: 12
<212> TYPE: PRT
<213> ORGANISM: Artificial Sequence
<220> FEATURE:
<223> OTHER INFORMATION: Amino acid Sequence of aMTD870

<400> SEQUENCE: 211

Val Leu Val Ala Ala Val Leu Pro Ile Ala Ala Pro
1 5 10

<210> SEQ ID NO 212
<211> LENGTH: 12
<212> TYPE: PRT
<213> ORGANISM: Artificial Sequence
<220> FEATURE:
<223> OTHER INFORMATION: Amino acid Sequence of aMTD872

<400> SEQUENCE: 212

Val Leu Ala Ala Ala Val Leu Pro Leu Val Val Pro
1 5 10

<210> SEQ ID NO 213
<211> LENGTH: 12
<212> TYPE: PRT
<213> ORGANISM: Artificial Sequence
<220> FEATURE:
<223> OTHER INFORMATION: Amino acid Sequence of aMTD875

<400> SEQUENCE: 213

Ala Ile Ala Ile Val Val Pro Ala Val Ala Val Pro
1 5 10

<210> SEQ ID NO 214
<211> LENGTH: 12
<212> TYPE: PRT
<213> ORGANISM: Artificial Sequence
<220> FEATURE:
<223> OTHER INFORMATION: Amino acid Sequence of aMTD877

<400> SEQUENCE: 214

Val Ala Ile Ile Ala Val Pro Ala Val Val Ala Pro
1 5 10

<210> SEQ ID NO 215
<211> LENGTH: 12
<212> TYPE: PRT
<213> ORGANISM: Artificial Sequence
<220> FEATURE:
<223> OTHER INFORMATION: Amino acid Sequence of aMTD878

<400> SEQUENCE: 215

Ile Val Ala Leu Val Ala Pro Ala Ala Val Val Pro
1 5 10

<210> SEQ ID NO 216
<211> LENGTH: 12
<212> TYPE: PRT
<213> ORGANISM: Artificial Sequence
<220> FEATURE:
<223> OTHER INFORMATION: Amino acid Sequence of aMTD879

<400> SEQUENCE: 216

Ala Ala Ile Val Leu Leu Pro Ala Val Val Val Pro
1 5 10

<210> SEQ ID NO 217
<211> LENGTH: 12
<212> TYPE: PRT
<213> ORGANISM: Artificial Sequence
<220> FEATURE:
<223> OTHER INFORMATION: Amino acid Sequence of aMTD881

<400> SEQUENCE: 217

Ala Ala Leu Ile Val Val Pro Ala Val Ala Val Pro
1 5 10

<210> SEQ ID NO 218
<211> LENGTH: 12
<212> TYPE: PRT
<213> ORGANISM: Artificial Sequence
<220> FEATURE:
<223> OTHER INFORMATION: Amino acid Sequence of aMTD882

<400> SEQUENCE: 218

Ala Ile Ala Leu Val Val Pro Ala Val Ala Val Pro
1 5 10

<210> SEQ ID NO 219
<211> LENGTH: 12
<212> TYPE: PRT
<213> ORGANISM: Artificial Sequence
<220> FEATURE:
<223> OTHER INFORMATION: Amino acid Sequence of aMTD883

<400> SEQUENCE: 219

Leu Ala Ile Val Pro Ala Ala Ile Ala Ala Leu Pro
1 5 10

<210> SEQ ID NO 220
<211> LENGTH: 12
<212> TYPE: PRT
<213> ORGANISM: Artificial Sequence
<220> FEATURE:
<223> OTHER INFORMATION: Amino acid Sequence of aMTD885

<400> SEQUENCE: 220

Leu Val Ala Ile Ala Pro Ala Val Ala Val Leu Pro
1 5 10

<210> SEQ ID NO 221
<211> LENGTH: 12
<212> TYPE: PRT
<213> ORGANISM: Artificial Sequence
<220> FEATURE:
<223> OTHER INFORMATION: Amino acid Sequence of aMTD887

<400> SEQUENCE: 221

Val Leu Ala Val Ala Pro Ala Val Ala Val Leu Pro
1 5 10

<210> SEQ ID NO 222
<211> LENGTH: 12
<212> TYPE: PRT
<213> ORGANISM: Artificial Sequence
<220> FEATURE:
<223> OTHER INFORMATION: Amino acid Sequence of aMTD888

<400> SEQUENCE: 222

Ile Leu Ala Val Val Ala Ile Pro Ala Ala Ala Pro
1 5 10

<210> SEQ ID NO 223
<211> LENGTH: 12
<212> TYPE: PRT
<213> ORGANISM: Artificial Sequence
<220> FEATURE:
<223> OTHER INFORMATION: Amino acid Sequence of aMTD889

<400> SEQUENCE: 223

Ile Leu Val Ala Ala Ala Pro Ile Ala Ala Leu Pro
1 5 10

<210> SEQ ID NO 224
<211> LENGTH: 12
<212> TYPE: PRT
<213> ORGANISM: Artificial Sequence
<220> FEATURE:
<223> OTHER INFORMATION: Amino acid Sequence of aMTD891

<400> SEQUENCE: 224

Ile Leu Ala Val Ala Ala Ile Pro Ala Ala Leu Pro
1 5 10

<210> SEQ ID NO 225
<211> LENGTH: 12
<212> TYPE: PRT
<213> ORGANISM: Artificial Sequence
<220> FEATURE:
<223> OTHER INFORMATION: Amino acid Sequence of aMTD893

<400> SEQUENCE: 225

Val Ile Ala Ile Pro Ala Ile Leu Ala Ala Ala Pro
1 5 10

<210> SEQ ID NO 226
<211> LENGTH: 12
<212> TYPE: PRT
<213> ORGANISM: Artificial Sequence
<220> FEATURE:
<223> OTHER INFORMATION: Amino acid Sequence of aMTD895

<400> SEQUENCE: 226

Ala Ile Ile Ile Val Val Pro Ala Ile Ala Ala Pro
1 5 10

<210> SEQ ID NO 227
<211> LENGTH: 12
<212> TYPE: PRT
<213> ORGANISM: Artificial Sequence
<220> FEATURE:
<223> OTHER INFORMATION: Amino acid Sequence of aMTD896

<400> SEQUENCE: 227

Ala Ile Leu Ile Val Val Ala Pro Ile Ala Ala Pro
1 5 10

<210> SEQ ID NO 228
<211> LENGTH: 12
<212> TYPE: PRT
<213> ORGANISM: Artificial Sequence
<220> FEATURE:
<223> OTHER INFORMATION: Amino acid Sequence of aMTD897

<400> SEQUENCE: 228

Ala Val Ile Val Pro Val Ala Ile Ile Ala Ala Pro
1 5 10

<210> SEQ ID NO 229
<211> LENGTH: 12
<212> TYPE: PRT
<213> ORGANISM: Artificial Sequence
<220> FEATURE:
<223> OTHER INFORMATION: Amino acid Sequence of aMTD899

<400> SEQUENCE: 229

Ala Val Val Ile Ala Leu Pro Ala Val Val Ala Pro
1 5 10

<210> SEQ ID NO 230
<211> LENGTH: 12
<212> TYPE: PRT
<213> ORGANISM: Artificial Sequence
<220> FEATURE:
<223> OTHER INFORMATION: Amino acid Sequence of aMTD900

<400> SEQUENCE: 230

Ala Leu Val Ala Val Ile Ala Pro Val Val Ala Pro
1 5 10

<210> SEQ ID NO 231
<211> LENGTH: 12
<212> TYPE: PRT
<213> ORGANISM: Artificial Sequence
<220> FEATURE:
<223> OTHER INFORMATION: Amino acid Sequence of aMTD901

<400> SEQUENCE: 231

Ala Leu Val Ala Val Leu Pro Ala Val Ala Val Pro
1 5 10

<210> SEQ ID NO 232
<211> LENGTH: 12
<212> TYPE: PRT
<213> ORGANISM: Artificial Sequence
<220> FEATURE:
<223> OTHER INFORMATION: Amino acid Sequence of aMTD902

<400> SEQUENCE: 232

Ala Leu Val Ala Pro Leu Leu Ala Val Ala Val Pro
1 5 10

<210> SEQ ID NO 233
<211> LENGTH: 12
<212> TYPE: PRT
<213> ORGANISM: Artificial Sequence
<220> FEATURE:
<223> OTHER INFORMATION: Amino acid Sequence of aMTD904

<400> SEQUENCE: 233

Ala Val Leu Ala Val Val Ala Pro Val Val Ala Pro
1 5 10

<210> SEQ ID NO 234
<211> LENGTH: 12
<212> TYPE: PRT
<213> ORGANISM: Artificial Sequence
<220> FEATURE:
<223> OTHER INFORMATION: Amino acid Sequence of aMTD905

<400> SEQUENCE: 234

Ala Val Ile Ala Val Ala Pro Leu Val Val Ala Pro
1 5 10

<210> SEQ ID NO 235
<211> LENGTH: 12
<212> TYPE: PRT
<213> ORGANISM: Artificial Sequence
<220> FEATURE:
<223> OTHER INFORMATION: Amino acid Sequence of aMTD906

<400> SEQUENCE: 235

Ala Val Ile Ala Leu Ala Pro Val Val Val Ala Pro
1 5 10

<210> SEQ ID NO 236
<211> LENGTH: 12
<212> TYPE: PRT
<213> ORGANISM: Artificial Sequence
<220> FEATURE:
<223> OTHER INFORMATION: Amino acid Sequence of aMTD907

<400> SEQUENCE: 236

Val Ala Ile Ala Leu Ala Pro Val Val Val Ala Pro
1 5 10

<210> SEQ ID NO 237
<211> LENGTH: 12
<212> TYPE: PRT
<213> ORGANISM: Artificial Sequence
<220> FEATURE:
<223> OTHER INFORMATION: Amino acid Sequence of aMTD908

<400> SEQUENCE: 237

Val Ala Leu Ala Leu Ala Pro Val Val Val Ala Pro 1 5 10

<210> SEQ ID NO 238
<211> LENGTH: 12
<212> TYPE: PRT
<213> ORGANISM: Artificial Sequence
<220> FEATURE:
<223> OTHER INFORMATION: Amino acid Sequence of aMTD910

<400> SEQUENCE: 238

Val Ala Ala Leu Leu Pro Ala Val Val Val Ala Pro
1 5 10

<210> SEQ ID NO 239
<211> LENGTH: 12
<212> TYPE: PRT
<213> ORGANISM: Artificial Sequence
<220> FEATURE:
<223> OTHER INFORMATION: Amino acid Sequence of aMTD911

<400> SEQUENCE: 239

Val Ala Leu Ala Leu Pro Ala Val Val Val Ala Pro
1 5 10

<210> SEQ ID NO 240
<211> LENGTH: 12
<212> TYPE: PRT
<213> ORGANISM: Artificial Sequence
<220> FEATURE:
<223> OTHER INFORMATION: Amino acid Sequence of aMTD912

<400> SEQUENCE: 240

Val Ala Leu Leu Ala Pro Ala Val Val Val Ala Pro
1 5 10

<210> SEQ ID NO 241
<211> LENGTH: 36
<212> TYPE: DNA
<213> ORGANISM: Artificial Sequence
<220> FEATURE:
<223> OTHER INFORMATION: cDNA Sequence of aMTD1

<400> SEQUENCE: 241
gcggcggcgc tggcgccggt ggtgctggcg ctgccg 36

<210> SEQ ID NO 242
<211> LENGTH: 36
<212> TYPE: DNA
<213> ORGANISM: Artificial Sequence
<220> FEATURE:
<223> OTHER INFORMATION: cDNA Sequence of aMTD2

<400> SEQUENCE: 242
gcggcggcgg tgccgctgct ggcggtggtg gtgccg 36

<210> SEQ ID NO 243
<211> LENGTH: 36
<212> TYPE: DNA
<213> ORGANISM: Artificial Sequence
<220> FEATURE:
<223> OTHER INFORMATION: cDNA Sequence of aMTD3

<400> SEQUENCE: 243
gcggcgctgc tggtgccggc ggcggtgctg gcgccg 36

<210> SEQ ID NO 244

<211> LENGTH: 36
<212> TYPE: DNA
<213> ORGANISM: Artificial Sequence
<220> FEATURE:
<223> OTHER INFORMATION: cDNA Sequence of aMTD4

<400> SEQUENCE: 244
gcgctggcgc tgctgccggt ggcggcgctg gcgccg 36

<210> SEQ ID NO 245
<211> LENGTH: 36
<212> TYPE: DNA
<213> ORGANISM: Artificial Sequence
<220> FEATURE:
<223> OTHER INFORMATION: cDNA Sequence of aMTD5

<400> SEQUENCE: 245
gcggcggcgc tgctgccggt ggcgctggtg gcgccg 36

<210> SEQ ID NO 246
<211> LENGTH: 36
<212> TYPE: DNA
<213> ORGANISM: Artificial Sequence
<220> FEATURE:
<223> OTHER INFORMATION: cDNA Sequence of aMTD11

<400> SEQUENCE: 246
gtggtggcgc tggcgccggc gctggcggcg ctgccg 36

<210> SEQ ID NO 247
<211> LENGTH: 36
<212> TYPE: DNA
<213> ORGANISM: Artificial Sequence
<220> FEATURE:
<223> OTHER INFORMATION: cDNA Sequence of aMTD12

<400> SEQUENCE: 247
ctgctggcgg cggtgccggc ggtgctgctg gcgccg 36

<210> SEQ ID NO 248
<211> LENGTH: 36
<212> TYPE: DNA
<213> ORGANISM: Artificial Sequence
<220> FEATURE:
<223> OTHER INFORMATION: cDNA Sequence of aMTD13

<400> SEQUENCE: 248
gcggcggcgc tggtgccggt ggtggcgctg ctgccg 36

<210> SEQ ID NO 249
<211> LENGTH: 36
<212> TYPE: DNA
<213> ORGANISM: Artificial Sequence
<220> FEATURE:
<223> OTHER INFORMATION: cDNA Sequence of aMTD21

<400> SEQUENCE: 249
gcggtggcgc tgctgccggc gctgctggcg gtgccg 36

<210> SEQ ID NO 250
<211> LENGTH: 36
<212> TYPE: DNA
<213> ORGANISM: Artificial Sequence
<220> FEATURE:
<223> OTHER INFORMATION: cDNA Sequence of aMTD22

<400> SEQUENCE: 250
gcggtggtgc tggtgccggt gctggcggcg gcgccg 36

<210> SEQ ID NO 251
<211> LENGTH: 36
<212> TYPE: DNA
<213> ORGANISM: Artificial Sequence
<220> FEATURE:
<223> OTHER INFORMATION: cDNA Sequence of aMTD23

<400> SEQUENCE: 251
gtggtgctgg tgctgccggc ggcggcggcg gtgccg 36

<210> SEQ ID NO 252
<211> LENGTH: 36
<212> TYPE: DNA
<213> ORGANISM: Artificial Sequence
<220> FEATURE:
<223> OTHER INFORMATION: cDNA Sequence of aMTD24

<400> SEQUENCE: 252
attgcgctgg cggcgccggc gctgattgtg gcgccg 36

<210> SEQ ID NO 253
<211> LENGTH: 36
<212> TYPE: DNA
<213> ORGANISM: Artificial Sequence
<220> FEATURE:
<223> OTHER INFORMATION: cDNA Sequence of aMTD25

<400> SEQUENCE: 253
attgtggcgg tggcgccggc gctggtggcg ctgccg 36

<210> SEQ ID NO 254
<211> LENGTH: 36
<212> TYPE: DNA
<213> ORGANISM: Artificial Sequence
<220> FEATURE:
<223> OTHER INFORMATION: Polynucleotide Sequence of aMTD42

<400> SEQUENCE: 254
gtggcggcgc tgccggtggt ggcggtggtg gcgccg 36

<210> SEQ ID NO 255
<211> LENGTH: 36
<212> TYPE: DNA
<213> ORGANISM: Artificial Sequence
<220> FEATURE:
<223> OTHER INFORMATION: cDNA Sequence of aMTD43

<400> SEQUENCE: 255
ctgctggcgg cgccgctggt ggtggcggcg gtgccg 36

<210> SEQ ID NO 256
<211> LENGTH: 36
<212> TYPE: DNA
<213> ORGANISM: Artificial Sequence
<220> FEATURE:
<223> OTHER INFORMATION: cDNA Sequence of aMTD44

<400> SEQUENCE: 256
gcgctggcgg tgccggtggc gctgctggtg gcgccg 36

<210> SEQ ID NO 257
<211> LENGTH: 36
<212> TYPE: DNA

<213> ORGANISM: Artificial Sequence
<220> FEATURE:
<223> OTHER INFORMATION: cDNA Sequence of aMTD61

<400> SEQUENCE: 257
gtggcggcgc tgccggtgct gctggcggcg ctgccg 36

<210> SEQ ID NO 258
<211> LENGTH: 36
<212> TYPE: DNA
<213> ORGANISM: Artificial Sequence
<220> FEATURE:
<223> OTHER INFORMATION: cDNA Sequence of aMTD62

<400> SEQUENCE: 258
gtggcgctgc tggcgccggt ggcgctggcg gtgccg 36

<210> SEQ ID NO 259
<211> LENGTH: 36
<212> TYPE: DNA
<213> ORGANISM: Artificial Sequence
<220> FEATURE:
<223> OTHER INFORMATION: cDNA Sequence of aMTD63

<400> SEQUENCE: 259
gcggcgctgc tggtgccggc gctggtggcg gtgccg 36

<210> SEQ ID NO 260
<211> LENGTH: 36
<212> TYPE: DNA
<213> ORGANISM: Artificial Sequence
<220> FEATURE:
<223> OTHER INFORMATION: cDNA Sequence of aMTD64

<400> SEQUENCE: 260
gcgattgtgg cgctgccggt ggcggtgctg gcgccg 36

<210> SEQ ID NO 261
<211> LENGTH: 36
<212> TYPE: DNA
<213> ORGANISM: Artificial Sequence
<220> FEATURE:
<223> OTHER INFORMATION: cDNA Sequence of aMTD65

<400> SEQUENCE: 261
attgcgattg tggcgccggt ggtggcgctg gcgccg 36

<210> SEQ ID NO 262
<211> LENGTH: 36
<212> TYPE: DNA
<213> ORGANISM: Artificial Sequence
<220> FEATURE:
<223> OTHER INFORMATION: cDNA Sequence of aMTD81

<400> SEQUENCE: 262
gcggcgctgc tgccggcgct ggcggcgctg ctgccg 36

<210> SEQ ID NO 263
<211> LENGTH: 36
<212> TYPE: DNA
<213> ORGANISM: Artificial Sequence
<220> FEATURE:
<223> OTHER INFORMATION: cDNA Sequence of aMTD82

<400> SEQUENCE: 263
gcggtggtgc tggcgccggt ggcggcggtg ctgccg 36

<210> SEQ ID NO 264
<211> LENGTH: 36
<212> TYPE: DNA
<213> ORGANISM: Artificial Sequence
<220> FEATURE:
<223> OTHER INFORMATION: cDNA Sequence of aMTD83

<400> SEQUENCE: 264
ctggcggtgg cggcgccgct ggcgctggcg ctgccg 36

<210> SEQ ID NO 265
<211> LENGTH: 36
<212> TYPE: DNA
<213> ORGANISM: Artificial Sequence
<220> FEATURE:
<223> OTHER INFORMATION: cDNA Sequence of aMTD84

<400> SEQUENCE: 265
gcggcggtgg cggcgccgct gctgctggcg ctgccg 36

<210> SEQ ID NO 266
<211> LENGTH: 36
<212> TYPE: DNA
<213> ORGANISM: Artificial Sequence
<220> FEATURE:
<223> OTHER INFORMATION: cDNA Sequence of aMTD85

<400> SEQUENCE: 266
ctgctggtgc tgccggcggc ggcgctggcg gcgccg 36

<210> SEQ ID NO 267
<211> LENGTH: 36
<212> TYPE: DNA
<213> ORGANISM: Artificial Sequence
<220> FEATURE:
<223> OTHER INFORMATION: cDNA Sequence of aMTD101

<400> SEQUENCE: 267
ctggtggcgg tggcgccggt ggcggcggtg ctgccg 36

<210> SEQ ID NO 268
<211> LENGTH: 36
<212> TYPE: DNA
<213> ORGANISM: Artificial Sequence
<220> FEATURE:
<223> OTHER INFORMATION: cDNA Sequence of aMTD102

<400> SEQUENCE: 268
ctggcgctgg cgccggcggc gctggcgctg ctgccg 36

<210> SEQ ID NO 269
<211> LENGTH: 36
<212> TYPE: DNA
<213> ORGANISM: Artificial Sequence
<220> FEATURE:
<223> OTHER INFORMATION: cDNA Sequence of aMTD103

<400> SEQUENCE: 269
gcgctgattg cggcgccgat tctggcgctg gcgccg 36

<210> SEQ ID NO 270
<211> LENGTH: 36
<212> TYPE: DNA
<213> ORGANISM: Artificial Sequence
<220> FEATURE:

<223> OTHER INFORMATION: cDNA Sequence of aMTD104

<400> SEQUENCE: 270
gcggtggtgg cggcgccgct ggtgctggcg ctgccg 36

<210> SEQ ID NO 271
<211> LENGTH: 36
<212> TYPE: DNA
<213> ORGANISM: Artificial Sequence
<220> FEATURE:
<223> OTHER INFORMATION: cDNA Sequence of aMTD105

<400> SEQUENCE: 271
ctgctggcgc tggcgccggc ggcgctgctg gcgccg 36

<210> SEQ ID NO 272
<211> LENGTH: 36
<212> TYPE: DNA
<213> ORGANISM: Artificial Sequence
<220> FEATURE:
<223> OTHER INFORMATION: cDNA Sequence of aMTD121

<400> SEQUENCE: 272
gcgattgtgg cgctgccggc gctggcgctg gcgccg 36

<210> SEQ ID NO 273
<211> LENGTH: 36
<212> TYPE: DNA
<213> ORGANISM: Artificial Sequence
<220> FEATURE:
<223> OTHER INFORMATION: cDNA Sequence of aMTD123

<400> SEQUENCE: 273
gcggcgatta ttgtgccggc ggcgctgctg gcgccg 36

<210> SEQ ID NO 274
<211> LENGTH: 36
<212> TYPE: DNA
<213> ORGANISM: Artificial Sequence
<220> FEATURE:
<223> OTHER INFORMATION: cDNA Sequence of aMTD124

<400> SEQUENCE: 274
attgcggtgg cgctgccggc gctgattgcg gcgccg 36

<210> SEQ ID NO 275
<211> LENGTH: 36
<212> TYPE: DNA
<213> ORGANISM: Artificial Sequence
<220> FEATURE:
<223> OTHER INFORMATION: Polynucleotide Sequence of aMTD141

<400> SEQUENCE: 275
gcggtgattg tgctgccggc gctggcggtg gcgccg 36

<210> SEQ ID NO 276
<211> LENGTH: 36
<212> TYPE: DNA
<213> ORGANISM: Artificial Sequence
<220> FEATURE:
<223> OTHER INFORMATION: Polynucleotide Sequence of aMTD143

<400> SEQUENCE: 276
gcggtgctgg cggtgccggc ggtgctggtg gcgccg 36

<210> SEQ ID NO 277
<211> LENGTH: 36
<212> TYPE: DNA
<213> ORGANISM: Artificial Sequence
<220> FEATURE:
<223> OTHER INFORMATION: Polynucleotide Sequence of aMTD144

<400> SEQUENCE: 277
gtgctggcga ttgtgccggc ggtggcgctg gcgccg 36

<210> SEQ ID NO 278
<211> LENGTH: 36
<212> TYPE: DNA
<213> ORGANISM: Artificial Sequence
<220> FEATURE:
<223> OTHER INFORMATION: Polynucleotide Sequence of aMTD145

<400> SEQUENCE: 278
ctgctggcgg tggtgccggc ggtggcgctg gcgccg 36

<210> SEQ ID NO 279
<211> LENGTH: 36
<212> TYPE: DNA
<213> ORGANISM: Artificial Sequence
<220> FEATURE:
<223> OTHER INFORMATION: cDNA Sequence of aMTD161

<400> SEQUENCE: 279
gcggtgattg cgctgccggc gctgattgcg gcgccg 36

<210> SEQ ID NO 280
<211> LENGTH: 36
<212> TYPE: DNA
<213> ORGANISM: Artificial Sequence
<220> FEATURE:
<223> OTHER INFORMATION: cDNA Sequence of aMTD162

<400> SEQUENCE: 280
gcggtggtgg cgctgccggc ggcgctgatt gtgccg 36

<210> SEQ ID NO 281
<211> LENGTH: 36
<212> TYPE: DNA
<213> ORGANISM: Artificial Sequence
<220> FEATURE:
<223> OTHER INFORMATION: cDNA Sequence of aMTD163

<400> SEQUENCE: 281
ctggcgctgg tgctgccggc ggcgctggcg gcgccg 36

<210> SEQ ID NO 282
<211> LENGTH: 36
<212> TYPE: DNA
<213> ORGANISM: Artificial Sequence
<220> FEATURE:
<223> OTHER INFORMATION: cDNA Sequence of aMTD164

<400> SEQUENCE: 282
ctggcggcgg tgctgccggc gctgctggcg gcgccg 36

<210> SEQ ID NO 283
<211> LENGTH: 36
<212> TYPE: DNA
<213> ORGANISM: Artificial Sequence
<220> FEATURE:
<223> OTHER INFORMATION: cDNA Sequence of aMTD165

<400> SEQUENCE: 283
gcgctggcgg tgccggtggc gctggcgatt gtgccg 36

<210> SEQ ID NO 284
<211> LENGTH: 36
<212> TYPE: DNA
<213> ORGANISM: Artificial Sequence
<220> FEATURE:
<223> OTHER INFORMATION: cDNA Sequence of aMTD182

<400> SEQUENCE: 284
gcgctgattg cgccggtggt ggcgctggtg gcgccg 36

<210> SEQ ID NO 285
<211> LENGTH: 36
<212> TYPE: DNA
<213> ORGANISM: Artificial Sequence
<220> FEATURE:
<223> OTHER INFORMATION: cDNA Sequence of aMTD183

<400> SEQUENCE: 285
ctgctggcgg cgccggtggt gattgcgctg gcgccg 36

<210> SEQ ID NO 286
<211> LENGTH: 36
<212> TYPE: DNA
<213> ORGANISM: Artificial Sequence
<220> FEATURE:
<223> OTHER INFORMATION: cDNA Sequence of aMTD184

<400> SEQUENCE: 286
ctggcggcga ttgtgccggc gattattgcg gtgccg 36

<210> SEQ ID NO 287
<211> LENGTH: 36
<212> TYPE: DNA
<213> ORGANISM: Artificial Sequence
<220> FEATURE:
<223> OTHER INFORMATION: cDNA Sequence of aMTD185

<400> SEQUENCE: 287
gcggcgctgg tgctgccgct gattattgcg gcgccg 36

<210> SEQ ID NO 288
<211> LENGTH: 36
<212> TYPE: DNA
<213> ORGANISM: Artificial Sequence
<220> FEATURE:
<223> OTHER INFORMATION: cDNA Sequence of aMTD201

<400> SEQUENCE: 288
ctggcgctgg cggtgccggc gctggcggcg ctgccg 36

<210> SEQ ID NO 289
<211> LENGTH: 36
<212> TYPE: DNA
<213> ORGANISM: Artificial Sequence
<220> FEATURE:
<223> OTHER INFORMATION: cDNA Sequence of aMTD204

<400> SEQUENCE: 289
ctgattgcgg cgctgccggc ggtggcggcg ctgccg 36

<210> SEQ ID NO 290
<211> LENGTH: 36

<212> TYPE: DNA
<213> ORGANISM: Artificial Sequence
<220> FEATURE:
<223> OTHER INFORMATION: cDNA Sequence of aMTD205

<400> SEQUENCE: 290
gcgctggcgc tggtgccggc gattgcggcg ctgccg 36

<210> SEQ ID NO 291
<211> LENGTH: 36
<212> TYPE: DNA
<213> ORGANISM: Artificial Sequence
<220> FEATURE:
<223> OTHER INFORMATION: cDNA Sequence of aMTD221

<400> SEQUENCE: 291
gcggcgattc tggcgccgat tgtggcgctg gcgccg 36

<210> SEQ ID NO 292
<211> LENGTH: 36
<212> TYPE: DNA
<213> ORGANISM: Artificial Sequence
<220> FEATURE:
<223> OTHER INFORMATION: cDNA Sequence of aMTD222

<400> SEQUENCE: 292
gcgctgctga ttgcgccggc ggcggtgatt gcgccg 36

<210> SEQ ID NO 293
<211> LENGTH: 36
<212> TYPE: DNA
<213> ORGANISM: Artificial Sequence
<220> FEATURE:
<223> OTHER INFORMATION: cDNA Sequence of aMTD223

<400> SEQUENCE: 293
gcgattctgg cggtgccgat tgcggtggtg gcgccg 36

<210> SEQ ID NO 294
<211> LENGTH: 36
<212> TYPE: DNA
<213> ORGANISM: Artificial Sequence
<220> FEATURE:
<223> OTHER INFORMATION: cDNA Sequence of aMTD224

<400> SEQUENCE: 294
attctggcgg cggtgccgat tgcgctggcg gcgccg 36

<210> SEQ ID NO 295
<211> LENGTH: 36
<212> TYPE: DNA
<213> ORGANISM: Artificial Sequence
<220> FEATURE:
<223> OTHER INFORMATION: cDNA Sequence of aMTD225

<400> SEQUENCE: 295
gtggcggcgc tgctgccggc ggcggcggtg ctgccg 36

<210> SEQ ID NO 296
<211> LENGTH: 36
<212> TYPE: DNA
<213> ORGANISM: Artificial Sequence
<220> FEATURE:
<223> OTHER INFORMATION: cDNA Sequence of aMTD241

<400> SEQUENCE: 296
gcggcggcgg tggtgccggt gctgctggtg gcgccg 36

<210> SEQ ID NO 297
<211> LENGTH: 36
<212> TYPE: DNA
<213> ORGANISM: Artificial Sequence
<220> FEATURE:
<223> OTHER INFORMATION: cDNA Sequence of aMTD242

<400> SEQUENCE: 297
gcggcgctgc tggtgccggc gctggtggcg gcgccg 36

<210> SEQ ID NO 298
<211> LENGTH: 36
<212> TYPE: DNA
<213> ORGANISM: Artificial Sequence
<220> FEATURE:
<223> OTHER INFORMATION: cDNA Sequence of aMTD243

<400> SEQUENCE: 298
gcggcggtgc tgctgccggt ggcgctggcg gcgccg 36

<210> SEQ ID NO 299
<211> LENGTH: 36
<212> TYPE: DNA
<213> ORGANISM: Artificial Sequence
<220> FEATURE:
<223> OTHER INFORMATION: cDNA Sequence of aMTD245

<400> SEQUENCE: 299
gcggcggcgc tggcgccggt gctggcgctg gtgccg 36

<210> SEQ ID NO 300
<211> LENGTH: 36
<212> TYPE: DNA
<213> ORGANISM: Artificial Sequence
<220> FEATURE:
<223> OTHER INFORMATION: cDNA Sequence of aMTD261

<400> SEQUENCE: 300
ctggtgctgg tgccgctgct ggcggcggcg gcgccg 36

<210> SEQ ID NO 301
<211> LENGTH: 36
<212> TYPE: DNA
<213> ORGANISM: Artificial Sequence
<220> FEATURE:
<223> OTHER INFORMATION: cDNA Sequence of aMTD262

<400> SEQUENCE: 301
gcgctgattg cggtgccggc gattattgtg gcgccg 36

<210> SEQ ID NO 302
<211> LENGTH: 36
<212> TYPE: DNA
<213> ORGANISM: Artificial Sequence
<220> FEATURE:
<223> OTHER INFORMATION: cDNA Sequence of aMTD263

<400> SEQUENCE: 302
gcgctggcgg tgattccggc ggcggcgatt ctgccg 36

<210> SEQ ID NO 303
<211> LENGTH: 36
<212> TYPE: DNA
<213> ORGANISM: Artificial Sequence
<220> FEATURE:
<223> OTHER INFORMATION: cDNA Sequence of aMTD264

<400> SEQUENCE: 303
ctggcggcgg cgccggtggt gattgtgatt gcgccg 36

<210> SEQ ID NO 304
<211> LENGTH: 36
<212> TYPE: DNA
<213> ORGANISM: Artificial Sequence
<220> FEATURE:
<223> OTHER INFORMATION: cDNA Sequence of aMTD265

<400> SEQUENCE: 304
gtgctggcga ttgcgccgct gctggcggcg gtgccg 36

<210> SEQ ID NO 305
<211> LENGTH: 36
<212> TYPE: DNA
<213> ORGANISM: Artificial Sequence
<220> FEATURE:
<223> OTHER INFORMATION: cDNA Sequence of aMTD281

<400> SEQUENCE: 305
gcgctgattg tgctgccggc ggcggtggcg gtgccg 36

<210> SEQ ID NO 306
<211> LENGTH: 36
<212> TYPE: DNA
<213> ORGANISM: Artificial Sequence
<220> FEATURE:
<223> OTHER INFORMATION: cDNA Sequence of aMTD282

<400> SEQUENCE: 306
gtgctggcgg tggcgccggc gctgattgtg gcgccg 36

<210> SEQ ID NO 307
<211> LENGTH: 36
<212> TYPE: DNA
<213> ORGANISM: Artificial Sequence
<220> FEATURE:
<223> OTHER INFORMATION: cDNA Sequence of aMTD283

<400> SEQUENCE: 307
gcggcgctgc tggcgccggc gctgattgtg gcgccg 36

<210> SEQ ID NO 308
<211> LENGTH: 36
<212> TYPE: DNA
<213> ORGANISM: Artificial Sequence
<220> FEATURE:
<223> OTHER INFORMATION: cDNA Sequence of aMTD284

<400> SEQUENCE: 308
gcgctgattg cgccggcggt ggcgctgatt gtgccg 36

<210> SEQ ID NO 309
<211> LENGTH: 36
<212> TYPE: DNA
<213> ORGANISM: Artificial Sequence
<220> FEATURE:
<223> OTHER INFORMATION: cDNA Sequence of aMTD285

<400> SEQUENCE: 309
gcgattgtgc tgctgccggc ggcggtggtg gcgccg 36

<210> SEQ ID NO 310
<211> LENGTH: 36
<212> TYPE: DNA
<213> ORGANISM: Artificial Sequence
<220> FEATURE:
<223> OTHER INFORMATION: cDNA Sequence of aMTD301

<400> SEQUENCE: 310
gtgattgcgg cgccggtgct ggcggtgctg gcgccg 36

<210> SEQ ID NO 311
<211> LENGTH: 36
<212> TYPE: DNA
<213> ORGANISM: Artificial Sequence
<220> FEATURE:
<223> OTHER INFORMATION: cDNA Sequence of aMTD302

<400> SEQUENCE: 311
ctggcgctgg cgccggcgct ggcgctgctg gcgccg 36

<210> SEQ ID NO 312
<211> LENGTH: 36
<212> TYPE: DNA
<213> ORGANISM: Artificial Sequence
<220> FEATURE:
<223> OTHER INFORMATION: cDNA Sequence of aMTD304

<400> SEQUENCE: 312
gcgattattc tggcgccgat tgcggcgatt gcgccg 36

<210> SEQ ID NO 313
<211> LENGTH: 36
<212> TYPE: DNA
<213> ORGANISM: Artificial Sequence
<220> FEATURE:
<223> OTHER INFORMATION: cDNA Sequence of aMTD305

<400> SEQUENCE: 313
attgcgctgg cggcgccgat tctgctggcg gcgccg 36

<210> SEQ ID NO 314
<211> LENGTH: 36
<212> TYPE: DNA
<213> ORGANISM: Artificial Sequence
<220> FEATURE:
<223> OTHER INFORMATION: cDNA Sequence of aMTD321

<400> SEQUENCE: 314
attgtggcgg tggcgctgcc ggcgctggcg gtgccg 36

<210> SEQ ID NO 315
<211> LENGTH: 36
<212> TYPE: DNA
<213> ORGANISM: Artificial Sequence
<220> FEATURE:
<223> OTHER INFORMATION: cDNA Sequence of aMTD322

<400> SEQUENCE: 315
gtggtggcga ttgtgctgcc ggcgctggcg gcgccg 36

<210> SEQ ID NO 316
<211> LENGTH: 36
<212> TYPE: DNA
<213> ORGANISM: Artificial Sequence
<220> FEATURE:
<223> OTHER INFORMATION: cDNA Sequence of aMTD323

<400> SEQUENCE: 316
attgtggcgg tggcgctgcc ggtggcgctg gcgccg 36

<210> SEQ ID NO 317
<211> LENGTH: 36
<212> TYPE: DNA
<213> ORGANISM: Artificial Sequence
<220> FEATURE:
<223> OTHER INFORMATION: cDNA Sequence of aMTD324

<400> SEQUENCE: 317
attgtggcgg tggcgctgcc ggcggcgctg gtgccg 36

<210> SEQ ID NO 318
<211> LENGTH: 36
<212> TYPE: DNA
<213> ORGANISM: Artificial Sequence
<220> FEATURE:
<223> OTHER INFORMATION: cDNA Sequence of aMTD325

<400> SEQUENCE: 318
attgtggcgg tggcgctgcc ggcggtggcg ctgccg 36

<210> SEQ ID NO 319
<211> LENGTH: 36
<212> TYPE: DNA
<213> ORGANISM: Artificial Sequence
<220> FEATURE:
<223> OTHER INFORMATION: cDNA Sequence of aMTD341

<400> SEQUENCE: 319
attgtggcgg tggcgctgcc ggcggtgctg gcgccg 36

<210> SEQ ID NO 320
<211> LENGTH: 36
<212> TYPE: DNA
<213> ORGANISM: Artificial Sequence
<220> FEATURE:
<223> OTHER INFORMATION: cDNA Sequence of aMTD342

<400> SEQUENCE: 320
gtgattgtgg cgctggcgcc ggcggtgctg gcgccg 36

<210> SEQ ID NO 321
<211> LENGTH: 36
<212> TYPE: DNA
<213> ORGANISM: Artificial Sequence
<220> FEATURE:
<223> OTHER INFORMATION: cDNA Sequence of aMTD343

<400> SEQUENCE: 321
attgtggcgg tggcgctgcc ggcgctggtg gcgccg 36

<210> SEQ ID NO 322
<211> LENGTH: 36
<212> TYPE: DNA
<213> ORGANISM: Artificial Sequence
<220> FEATURE:
<223> OTHER INFORMATION: cDNA Sequence of aMTD345

<400> SEQUENCE: 322
gcgctgctga ttgtggcgcc ggtggcggtg gcgccg 36

<210> SEQ ID NO 323

<211> LENGTH: 36
<212> TYPE: DNA
<213> ORGANISM: Artificial Sequence
<220> FEATURE:
<223> OTHER INFORMATION: cDNA Sequence of aMTD361

<400> SEQUENCE: 323
gcggtggtga ttgtggcgcc ggcggtgatt gcgccg 36

<210> SEQ ID NO 324
<211> LENGTH: 36
<212> TYPE: DNA
<213> ORGANISM: Artificial Sequence
<220> FEATURE:
<223> OTHER INFORMATION: cDNA Sequence of aMTD363

<400> SEQUENCE: 324
gcggtgctgg cggtggcgcc ggcgctgatt gtgccg 36

<210> SEQ ID NO 325
<211> LENGTH: 36
<212> TYPE: DNA
<213> ORGANISM: Artificial Sequence
<220> FEATURE:
<223> OTHER INFORMATION: cDNA Sequence of aMTD364

<400> SEQUENCE: 325
ctggtggcgg cggtggcgcc ggcgctgatt gtgccg 36

<210> SEQ ID NO 326
<211> LENGTH: 36
<212> TYPE: DNA
<213> ORGANISM: Artificial Sequence
<220> FEATURE:
<223> OTHER INFORMATION: cDNA Sequence of aMTD365

<400> SEQUENCE: 326
gcggtgattg tggtggcgcc ggcgctgctg gcgccg 36

<210> SEQ ID NO 327
<211> LENGTH: 36
<212> TYPE: DNA
<213> ORGANISM: Artificial Sequence
<220> FEATURE:
<223> OTHER INFORMATION: cDNA Sequence of aMTD381

<400> SEQUENCE: 327
gtggtggcga ttgtgctgcc ggcggtggcg gcgccg 36

<210> SEQ ID NO 328
<211> LENGTH: 36
<212> TYPE: DNA
<213> ORGANISM: Artificial Sequence
<220> FEATURE:
<223> OTHER INFORMATION: cDNA Sequence of aMTD382

<400> SEQUENCE: 328
gcggcggcgc tggtgattcc ggcgattctg gcgccg 36

<210> SEQ ID NO 329
<211> LENGTH: 36
<212> TYPE: DNA
<213> ORGANISM: Artificial Sequence
<220> FEATURE:
<223> OTHER INFORMATION: cDNA Sequence of aMTD383

<400> SEQUENCE: 329
gtgattgtgg cgctggcgcc ggcgctgctg gcgccg 36

<210> SEQ ID NO 330
<211> LENGTH: 36
<212> TYPE: DNA
<213> ORGANISM: Artificial Sequence
<220> FEATURE:
<223> OTHER INFORMATION: cDNA Sequence of aMTD384

<400> SEQUENCE: 330
gtgattgtgg cgattgcgcc ggcgctgctg gcgccg 36

<210> SEQ ID NO 331
<211> LENGTH: 36
<212> TYPE: DNA
<213> ORGANISM: Artificial Sequence
<220> FEATURE:
<223> OTHER INFORMATION: cDNA Sequence of aMTD385

<400> SEQUENCE: 331
attgtggcga ttgcggtgcc ggcgctggtg gcgccg 36

<210> SEQ ID NO 332
<211> LENGTH: 36
<212> TYPE: DNA
<213> ORGANISM: Artificial Sequence
<220> FEATURE:
<223> OTHER INFORMATION: cDNA Sequence of aMTD401

<400> SEQUENCE: 332
gcggcgctgg cggtgattcc ggcggcgatt ctgccg 36

<210> SEQ ID NO 333
<211> LENGTH: 36
<212> TYPE: DNA
<213> ORGANISM: Artificial Sequence
<220> FEATURE:
<223> OTHER INFORMATION: Polynucleotide of aMTD402

<400> SEQUENCE: 333
gcgctggcgg cggtgattcc ggcggcgatt ctgccg 36

<210> SEQ ID NO 334
<211> LENGTH: 36
<212> TYPE: DNA
<213> ORGANISM: Artificial Sequence
<220> FEATURE:
<223> OTHER INFORMATION: cDNA Sequence of aMTD403

<400> SEQUENCE: 334
gcggcggcgc tggtgattcc ggcggcgatt ctgccg 36

<210> SEQ ID NO 335
<211> LENGTH: 36
<212> TYPE: DNA
<213> ORGANISM: Artificial Sequence
<220> FEATURE:
<223> OTHER INFORMATION: cDNA Sequence of aMTD404

<400> SEQUENCE: 335
ctggcggcgg cggtgattcc ggcggcgatt ctgccg 36

<210> SEQ ID NO 336
<211> LENGTH: 36
<212> TYPE: DNA

<213> ORGANISM: Artificial Sequence
<220> FEATURE:
<223> OTHER INFORMATION: cDNA Sequence of aMTD405

<400> SEQUENCE: 336
ctggcggcgg cggtgattcc ggtggcgatt ctgccg 36

<210> SEQ ID NO 337
<211> LENGTH: 36
<212> TYPE: DNA
<213> ORGANISM: Artificial Sequence
<220> FEATURE:
<223> OTHER INFORMATION: cDNA Sequence of aMTD421

<400> SEQUENCE: 337
gcggcgattc tggcggcgcc gctgattgcg gtgccg 36

<210> SEQ ID NO 338
<211> LENGTH: 36
<212> TYPE: DNA
<213> ORGANISM: Artificial Sequence
<220> FEATURE:
<223> OTHER INFORMATION: cDNA Sequence of aMTD422

<400> SEQUENCE: 338
gtggtggcga ttctggcgcc gctgctggcg gcgccg 36

<210> SEQ ID NO 339
<211> LENGTH: 36
<212> TYPE: DNA
<213> ORGANISM: Artificial Sequence
<220> FEATURE:
<223> OTHER INFORMATION: cDNA Sequence of aMTD424

<400> SEQUENCE: 339
gcggtggtgg tggcggcgcc ggtgctggcg ctgccg 36

<210> SEQ ID NO 340
<211> LENGTH: 36
<212> TYPE: DNA
<213> ORGANISM: Artificial Sequence
<220> FEATURE:
<223> OTHER INFORMATION: cDNA Sequence of aMTD425

<400> SEQUENCE: 340
gcggtggtgg cgattgcgcc ggtgctggcg ctgccg 36

<210> SEQ ID NO 341
<211> LENGTH: 36
<212> TYPE: DNA
<213> ORGANISM: Artificial Sequence
<220> FEATURE:
<223> OTHER INFORMATION: cDNA Sequence of aMTD442

<400> SEQUENCE: 341
gcgctggcgg cgctggtgcc ggcggtgctg gtgccg 36

<210> SEQ ID NO 342
<211> LENGTH: 36
<212> TYPE: DNA
<213> ORGANISM: Artificial Sequence
<220> FEATURE:
<223> OTHER INFORMATION: cDNA Sequence of aMTD443

<400> SEQUENCE: 342
gcgctggcgg cgctggtgcc ggtggcgctg gtgccg 36

<210> SEQ ID NO 343
<211> LENGTH: 36
<212> TYPE: DNA
<213> ORGANISM: Artificial Sequence
<220> FEATURE:
<223> OTHER INFORMATION: cDNA Sequence of aMTD444

<400> SEQUENCE: 343
ctggcggcgg cgctggtgcc ggtggcgctg gtgccg 36

<210> SEQ ID NO 344
<211> LENGTH: 36
<212> TYPE: DNA
<213> ORGANISM: Artificial Sequence
<220> FEATURE:
<223> OTHER INFORMATION: cDNA Sequence of aMTD445

<400> SEQUENCE: 344
gcgctggcgg cgctggtgcc ggcgctggtg gtgccg 36

<210> SEQ ID NO 345
<211> LENGTH: 36
<212> TYPE: DNA
<213> ORGANISM: Artificial Sequence
<220> FEATURE:
<223> OTHER INFORMATION: cDNA Sequence of aMTD461

<400> SEQUENCE: 345
attgcggcgg tgattgtgcc ggcggtggcg ctgccg 36

<210> SEQ ID NO 346
<211> LENGTH: 36
<212> TYPE: DNA
<213> ORGANISM: Artificial Sequence
<220> FEATURE:
<223> OTHER INFORMATION: cDNA Sequence of aMTD462

<400> SEQUENCE: 346
attgcggcgg tgctggtgcc ggcggtggcg ctgccg 36

<210> SEQ ID NO 347
<211> LENGTH: 36
<212> TYPE: DNA
<213> ORGANISM: Artificial Sequence
<220> FEATURE:
<223> OTHER INFORMATION: cDNA Sequence of aMTD463

<400> SEQUENCE: 347
gcggtggcga ttctggtgcc gctgctggcg gcgccg 36

<210> SEQ ID NO 348
<211> LENGTH: 36
<212> TYPE: DNA
<213> ORGANISM: Artificial Sequence
<220> FEATURE:
<223> OTHER INFORMATION: cDNA Sequence of aMTD464

<400> SEQUENCE: 348
gcggtggtga ttctggtgcc gctggcggcg gcgccg 36

<210> SEQ ID NO 349
<211> LENGTH: 36
<212> TYPE: DNA
<213> ORGANISM: Artificial Sequence
<220> FEATURE:

<223> OTHER INFORMATION: cDNA Sequence of aMTD465

<400> SEQUENCE: 349
attgcggcgg tgattgtgcc ggtggcggcg ctgccg 36

<210> SEQ ID NO 350
<211> LENGTH: 36
<212> TYPE: DNA
<213> ORGANISM: Artificial Sequence
<220> FEATURE:
<223> OTHER INFORMATION: cDNA Sequence of aMTD481

<400> SEQUENCE: 350
gcgattgcga ttgcgattgt gccggtggcg ctgccg 36

<210> SEQ ID NO 351
<211> LENGTH: 36
<212> TYPE: DNA
<213> ORGANISM: Artificial Sequence
<220> FEATURE:
<223> OTHER INFORMATION: cDNA Sequence of aMTD482

<400> SEQUENCE: 351
attctggcgg tggcggcgat tccggtggcg gtgccg 36

<210> SEQ ID NO 352
<211> LENGTH: 36
<212> TYPE: DNA
<213> ORGANISM: Artificial Sequence
<220> FEATURE:
<223> OTHER INFORMATION: cDNA Sequence of aMTD483

<400> SEQUENCE: 352
attctggcgg cggcgattat tccggcggcg ctgccg 36

<210> SEQ ID NO 353
<211> LENGTH: 36
<212> TYPE: DNA
<213> ORGANISM: Artificial Sequence
<220> FEATURE:
<223> OTHER INFORMATION: cDNA Sequence of aMTD484

<400> SEQUENCE: 353
ctggcggtgg tgctggcggc gccggcgatt gtgccg 36

<210> SEQ ID NO 354
<211> LENGTH: 36
<212> TYPE: DNA
<213> ORGANISM: Artificial Sequence
<220> FEATURE:
<223> OTHER INFORMATION: cDNA Sequence of aMTD485

<400> SEQUENCE: 354
gcgattctgg cggcgattgt gccgctggcg gtgccg 36

<210> SEQ ID NO 355
<211> LENGTH: 36
<212> TYPE: DNA
<213> ORGANISM: Artificial Sequence
<220> FEATURE:
<223> OTHER INFORMATION: cDNA Sequence of aMTD501

<400> SEQUENCE: 355
gtgattgtgg cgctggcggt gccggcgctg gcgccg 36

<210> SEQ ID NO 356
<211> LENGTH: 36
<212> TYPE: DNA
<213> ORGANISM: Artificial Sequence
<220> FEATURE:
<223> OTHER INFORMATION: cDNA Sequence of aMTD502

<400> SEQUENCE: 356
gcgattgtgg cgctggcggt gccggtgctg gcgccg 36

<210> SEQ ID NO 357
<211> LENGTH: 36
<212> TYPE: DNA
<213> ORGANISM: Artificial Sequence
<220> FEATURE:
<223> OTHER INFORMATION: cDNA Sequence of aMTD503

<400> SEQUENCE: 357
gcggcgatta ttattgtgct gccggcggcg ctgccg 36

<210> SEQ ID NO 358
<211> LENGTH: 36
<212> TYPE: DNA
<213> ORGANISM: Artificial Sequence
<220> FEATURE:
<223> OTHER INFORMATION: cDNA Sequence of aMTD504

<400> SEQUENCE: 358
ctgattgtgg cgctggcggt gccggcgctg gcgccg 36

<210> SEQ ID NO 359
<211> LENGTH: 36
<212> TYPE: DNA
<213> ORGANISM: Artificial Sequence
<220> FEATURE:
<223> OTHER INFORMATION: cDNA Sequence of aMTD505

<400> SEQUENCE: 359
gcgattatta ttgtgattgc gccggcggcg gcgccg 36

<210> SEQ ID NO 360
<211> LENGTH: 36
<212> TYPE: DNA
<213> ORGANISM: Artificial Sequence
<220> FEATURE:
<223> OTHER INFORMATION: cDNA Sequence of aMTD521

<400> SEQUENCE: 360
ctggcggcgc tgattgtggt gccggcggtg gcgccg 36

<210> SEQ ID NO 361
<211> LENGTH: 36
<212> TYPE: DNA
<213> ORGANISM: Artificial Sequence
<220> FEATURE:
<223> OTHER INFORMATION: cDNA Sequence of aMTD522

<400> SEQUENCE: 361
gcgctgctgg tgattgcggt gccggcggtg gcgccg 36

<210> SEQ ID NO 362
<211> LENGTH: 36
<212> TYPE: DNA
<213> ORGANISM: Artificial Sequence
<220> FEATURE:
<223> OTHER INFORMATION: cDNA Sequence of aMTD524

<400> SEQUENCE: 362
gcggtggcgc tgattgtggt gccggcgctg gcgccg 36

<210> SEQ ID NO 363
<211> LENGTH: 36
<212> TYPE: DNA
<213> ORGANISM: Artificial Sequence
<220> FEATURE:
<223> OTHER INFORMATION: cDNA Sequence of aMTD525

<400> SEQUENCE: 363
gcgctggcga ttgtggtggc gccggtggcg gtgccg 36

<210> SEQ ID NO 364
<211> LENGTH: 36
<212> TYPE: DNA
<213> ORGANISM: Artificial Sequence
<220> FEATURE:
<223> OTHER INFORMATION: cDNA Sequence of aMTD541

<400> SEQUENCE: 364
ctgctggcgc tgattattgc gccggcggcg gcgccg 36

<210> SEQ ID NO 365
<211> LENGTH: 36
<212> TYPE: DNA
<213> ORGANISM: Artificial Sequence
<220> FEATURE:
<223> OTHER INFORMATION: cDNA Sequence of aMTD542

<400> SEQUENCE: 365
gcgctggcgc tgattattgt gccggcggtg gcgccg 36

<210> SEQ ID NO 366
<211> LENGTH: 36
<212> TYPE: DNA
<213> ORGANISM: Artificial Sequence
<220> FEATURE:
<223> OTHER INFORMATION: cDNA Sequence of aMTD543

<400> SEQUENCE: 366
ctgctggcgg cgctgattgc gccggcggcg ctgccg 36

<210> SEQ ID NO 367
<211> LENGTH: 36
<212> TYPE: DNA
<213> ORGANISM: Artificial Sequence
<220> FEATURE:
<223> OTHER INFORMATION: cDNA Sequence of aMTD544

<400> SEQUENCE: 367
attgtggcgc tgattgtggc gccggcggcg gtgccg 36

<210> SEQ ID NO 368
<211> LENGTH: 36
<212> TYPE: DNA
<213> ORGANISM: Artificial Sequence
<220> FEATURE:
<223> OTHER INFORMATION: cDNA Sequence of aMTD545

<400> SEQUENCE: 368
gtggtgctgg tgctggcggc gccggcggcg gtgccg 36

<210> SEQ ID NO 369
<211> LENGTH: 36

<212> TYPE: DNA
<213> ORGANISM: Artificial Sequence
<220> FEATURE:
<223> OTHER INFORMATION: cDNA Sequence of aMTD561

<400> SEQUENCE: 369
gcggcggtgg cgattgtgct gccggcggtg gtgccg 36

<210> SEQ ID NO 370
<211> LENGTH: 36
<212> TYPE: DNA
<213> ORGANISM: Artificial Sequence
<220> FEATURE:
<223> OTHER INFORMATION: cDNA Sequence of aMTD562

<400> SEQUENCE: 370
gcgctgattg cggcgattgt gccggcgctg gtgccg 36

<210> SEQ ID NO 371
<211> LENGTH: 36
<212> TYPE: DNA
<213> ORGANISM: Artificial Sequence
<220> FEATURE:
<223> OTHER INFORMATION: cDNA Sequence of aMTD563

<400> SEQUENCE: 371
gcgctggcgg tgattgtggt gccggcgctg gcgccg 36

<210> SEQ ID NO 372
<211> LENGTH: 36
<212> TYPE: DNA
<213> ORGANISM: Artificial Sequence
<220> FEATURE:
<223> OTHER INFORMATION: cDNA Sequence of aMTD564

<400> SEQUENCE: 372
gtggcgattg cgctgattgt gccggcgctg gcgccg 36

<210> SEQ ID NO 373
<211> LENGTH: 36
<212> TYPE: DNA
<213> ORGANISM: Artificial Sequence
<220> FEATURE:
<223> OTHER INFORMATION: cDNA Sequence of aMTD565

<400> SEQUENCE: 373
gtggcgattg tgctggtggc gccggcggtg gcgccg 36

<210> SEQ ID NO 374
<211> LENGTH: 36
<212> TYPE: DNA
<213> ORGANISM: Artificial Sequence
<220> FEATURE:
<223> OTHER INFORMATION: cDNA Sequence of aMTD582

<400> SEQUENCE: 374
gtggcggtgg cgctgattgt gccggcgctg gcgccg 36

<210> SEQ ID NO 375
<211> LENGTH: 36
<212> TYPE: DNA
<213> ORGANISM: Artificial Sequence
<220> FEATURE:
<223> OTHER INFORMATION: cDNA Sequence of aMTD583

<400> SEQUENCE: 375
gcggtgattc tggcgctggc gccgattgtg gcgccg 36

<210> SEQ ID NO 376
<211> LENGTH: 36
<212> TYPE: DNA
<213> ORGANISM: Artificial Sequence
<220> FEATURE:
<223> OTHER INFORMATION: cDNA Sequence of aMTD585

<400> SEQUENCE: 376
gcgctgattg tggcgattgc gccggcgctg gtgccg 36

<210> SEQ ID NO 377
<211> LENGTH: 36
<212> TYPE: DNA
<213> ORGANISM: Artificial Sequence
<220> FEATURE:
<223> OTHER INFORMATION: cDNA Sequence of aMTD601

<400> SEQUENCE: 377
gcggcgattc tgattgcggt gccgattgcg gcgccg 36

<210> SEQ ID NO 378
<211> LENGTH: 36
<212> TYPE: DNA
<213> ORGANISM: Artificial Sequence
<220> FEATURE:
<223> OTHER INFORMATION: cDNA Sequence of aMTD602

<400> SEQUENCE: 378
gtgattgtgg cgctggcggc gccggtgctg gcgccg 36

<210> SEQ ID NO 379
<211> LENGTH: 36
<212> TYPE: DNA
<213> ORGANISM: Artificial Sequence
<220> FEATURE:
<223> OTHER INFORMATION: cDNA Sequence of aMTD603

<400> SEQUENCE: 379
gtgctggtgg cgctggcggc gccggtgatt gcgccg 36

<210> SEQ ID NO 380
<211> LENGTH: 36
<212> TYPE: DNA
<213> ORGANISM: Artificial Sequence
<220> FEATURE:
<223> OTHER INFORMATION: cDNA Sequence of aMTD604

<400> SEQUENCE: 380
gtggcgctga ttgcggtggc gccggcggtg gtgccg 36

<210> SEQ ID NO 381
<211> LENGTH: 36
<212> TYPE: DNA
<213> ORGANISM: Artificial Sequence
<220> FEATURE:
<223> OTHER INFORMATION: cDNA Sequence of aMTD605

<400> SEQUENCE: 381
gtgattgcgg cggtgctggc gccggtggcg gtgccg 36

<210> SEQ ID NO 382
<211> LENGTH: 36
<212> TYPE: DNA
<213> ORGANISM: Artificial Sequence
<220> FEATURE:
<223> OTHER INFORMATION: cDNA Sequence of aMTD622

<400> SEQUENCE: 382
gcgctgattg tgctggcggc gccggtggcg gtgccg 36

<210> SEQ ID NO 383
<211> LENGTH: 36
<212> TYPE: DNA
<213> ORGANISM: Artificial Sequence
<220> FEATURE:
<223> OTHER INFORMATION: cDNA Sequence of aMTD623

<400> SEQUENCE: 383
gtggcggcgg cgattgcgct gccggcgatt gtgccg 36

<210> SEQ ID NO 384
<211> LENGTH: 36
<212> TYPE: DNA
<213> ORGANISM: Artificial Sequence
<220> FEATURE:
<223> OTHER INFORMATION: cDNA Sequence of aMTD625

<400> SEQUENCE: 384
attctggcgg cggcggcggc gccgctgatt gtgccg 36

<210> SEQ ID NO 385
<211> LENGTH: 36
<212> TYPE: DNA
<213> ORGANISM: Artificial Sequence
<220> FEATURE:
<223> OTHER INFORMATION: cDNA Sequence of aMTD643

<400> SEQUENCE: 385
ctggcgctgg tgctggcggc gccggcgatt gtgccg 36

<210> SEQ ID NO 386
<211> LENGTH: 36
<212> TYPE: DNA
<213> ORGANISM: Artificial Sequence
<220> FEATURE:
<223> OTHER INFORMATION: cDNA Sequence of aMTD645

<400> SEQUENCE: 386
gcgctggcgg tggtggcgct gccggcgatt gtgccg 36

<210> SEQ ID NO 387
<211> LENGTH: 36
<212> TYPE: DNA
<213> ORGANISM: Artificial Sequence
<220> FEATURE:
<223> OTHER INFORMATION: cDNA Sequence of aMTD661

<400> SEQUENCE: 387
gcggcgattc tggcgccgat tgtggcggcg ctgccg 36

<210> SEQ ID NO 388
<211> LENGTH: 36
<212> TYPE: DNA
<213> ORGANISM: Artificial Sequence
<220> FEATURE:
<223> OTHER INFORMATION: cDNA Sequence of aMTD664

<400> SEQUENCE: 388
attctgattg cgattgcgat tccggcggcg gcgccg 36

<210> SEQ ID NO 389
<211> LENGTH: 36
<212> TYPE: DNA
<213> ORGANISM: Artificial Sequence
<220> FEATURE:
<223> OTHER INFORMATION: cDNA Sequence of aMTD665

<400> SEQUENCE: 389
ctggcgattg tgctggcggc gccggtggcg gtgccg 36

<210> SEQ ID NO 390
<211> LENGTH: 36
<212> TYPE: DNA
<213> ORGANISM: Artificial Sequence
<220> FEATURE:
<223> OTHER INFORMATION: cDNA Sequence of aMTD666

<400> SEQUENCE: 390
gcggcgattg cgattattgc gccggcgatt gtgccg 36

<210> SEQ ID NO 391
<211> LENGTH: 36
<212> TYPE: DNA
<213> ORGANISM: Artificial Sequence
<220> FEATURE:
<223> OTHER INFORMATION: cDNA Sequence of aMTD667

<400> SEQUENCE: 391
ctggcggtgg cgattgtggc gccggcgctg gtgccg 36

<210> SEQ ID NO 392
<211> LENGTH: 36
<212> TYPE: DNA
<213> ORGANISM: Artificial Sequence
<220> FEATURE:
<223> OTHER INFORMATION: cDNA Sequence of aMTD683

<400> SEQUENCE: 392
ctggcgattg tgctggcggc gccggcggtg ctgccg 36

<210> SEQ ID NO 393
<211> LENGTH: 36
<212> TYPE: DNA
<213> ORGANISM: Artificial Sequence
<220> FEATURE:
<223> OTHER INFORMATION: cDNA Sequence of aMTD684

<400> SEQUENCE: 393
gcggcgattg tgctggcgct gccggcggtg ctgccg 36

<210> SEQ ID NO 394
<211> LENGTH: 36
<212> TYPE: DNA
<213> ORGANISM: Artificial Sequence
<220> FEATURE:
<223> OTHER INFORMATION: cDNA Sequence of aMTD685

<400> SEQUENCE: 394
gcgctgctgg tggcggtgct gccggcggcg ctgccg 36

<210> SEQ ID NO 395
<211> LENGTH: 36
<212> TYPE: DNA
<213> ORGANISM: Artificial Sequence
<220> FEATURE:
<223> OTHER INFORMATION: cDNA Sequence of aMTD686

<400> SEQUENCE: 395
gcggcgctgg tggcggtgct gccggtggcg ctgccg 36

<210> SEQ ID NO 396
<211> LENGTH: 36
<212> TYPE: DNA
<213> ORGANISM: Artificial Sequence
<220> FEATURE:
<223> OTHER INFORMATION: cDNA Sequence of aMTD687

<400> SEQUENCE: 396
attgtggcgg tggcgctggt gccggcgctg gcgccg 36

<210> SEQ ID NO 397
<211> LENGTH: 36
<212> TYPE: DNA
<213> ORGANISM: Artificial Sequence
<220> FEATURE:
<223> OTHER INFORMATION: cDNA Sequence of aMTD703

<400> SEQUENCE: 397
attgtggcgg tggcgctggt gccggcgctg gcgccg 36

<210> SEQ ID NO 398
<211> LENGTH: 36
<212> TYPE: DNA
<213> ORGANISM: Artificial Sequence
<220> FEATURE:
<223> OTHER INFORMATION: cDNA Sequence of aMTD705

<400> SEQUENCE: 398
attgtggcgg tggcgctgct gccggcgctg gcgccg 36

<210> SEQ ID NO 399
<211> LENGTH: 36
<212> TYPE: DNA
<213> ORGANISM: Artificial Sequence
<220> FEATURE:
<223> OTHER INFORMATION: cDNA Sequence of aMTD706

<400> SEQUENCE: 399
attgtggcgg tggcgctgct gccggcggtg gcgccg 36

<210> SEQ ID NO 400
<211> LENGTH: 36
<212> TYPE: DNA
<213> ORGANISM: Artificial Sequence
<220> FEATURE:
<223> OTHER INFORMATION: cDNA Sequence of aMTD707

<400> SEQUENCE: 400
attgtggcgc tggcggtgct gccggcggtg gcgccg 36

<210> SEQ ID NO 401
<211> LENGTH: 36
<212> TYPE: DNA
<213> ORGANISM: Artificial Sequence
<220> FEATURE:
<223> OTHER INFORMATION: cDNA Sequence of aMTD724

<400> SEQUENCE: 401
gtggcggtgc tggcggtgct gccggcgctg gcgccg 36

<210> SEQ ID NO 402

<211> LENGTH: 36
<212> TYPE: DNA
<213> ORGANISM: Artificial Sequence
<220> FEATURE:
<223> OTHER INFORMATION: cDNA Sequence of aMTD725

<400> SEQUENCE: 402
attgcggtgc tggcggtggc gccggcggtg ctgccg 36

<210> SEQ ID NO 403
<211> LENGTH: 36
<212> TYPE: DNA
<213> ORGANISM: Artificial Sequence
<220> FEATURE:
<223> OTHER INFORMATION: cDNA Sequence of aMTD726

<400> SEQUENCE: 403
ctggcggtgg cgattattgc gccggcggtg gcgccg 36

<210> SEQ ID NO 404
<211> LENGTH: 36
<212> TYPE: DNA
<213> ORGANISM: Artificial Sequence
<220> FEATURE:
<223> OTHER INFORMATION: cDNA Sequence of aMTD727

<400> SEQUENCE: 404
gtggcgctgg cgattgcgct gccggcggtg ctgccg 36

<210> SEQ ID NO 405
<211> LENGTH: 36
<212> TYPE: DNA
<213> ORGANISM: Artificial Sequence
<220> FEATURE:
<223> OTHER INFORMATION: cDNA Sequence of aMTD743

<400> SEQUENCE: 405
gcgattgcga ttgcgctggt gccggtggcg ctgccg 36

<210> SEQ ID NO 406
<211> LENGTH: 36
<212> TYPE: DNA
<213> ORGANISM: Artificial Sequence
<220> FEATURE:
<223> OTHER INFORMATION: cDNA Sequence of aMTD744

<400> SEQUENCE: 406
gcggcggtgg tgattgtggc gccggtggcg ctgccg 36

<210> SEQ ID NO 407
<211> LENGTH: 36
<212> TYPE: DNA
<213> ORGANISM: Artificial Sequence
<220> FEATURE:
<223> OTHER INFORMATION: cDNA Sequence of aMTD746

<400> SEQUENCE: 407
gcggcgattc tggcgattgt ggcgccgctg gcgccg 36

<210> SEQ ID NO 408
<211> LENGTH: 36
<212> TYPE: DNA
<213> ORGANISM: Artificial Sequence
<220> FEATURE:
<223> OTHER INFORMATION: cDNA Sequence of aMTD747

<400> SEQUENCE: 408
gtggcgctgc tggcgattgc gccggcgctg gcgccg 36

<210> SEQ ID NO 409
<211> LENGTH: 36
<212> TYPE: DNA
<213> ORGANISM: Artificial Sequence
<220> FEATURE:
<223> OTHER INFORMATION: cDNA Sequence of aMTD763

<400> SEQUENCE: 409
gtggcggtgc tgattgcggt gccggcgctg gcgccg 36

<210> SEQ ID NO 410
<211> LENGTH: 36
<212> TYPE: DNA
<213> ORGANISM: Artificial Sequence
<220> FEATURE:
<223> OTHER INFORMATION: cDNA Sequence of aMTD764

<400> SEQUENCE: 410
gcggtggcgc tggcggtgct gccggcggtg gtgccg 36

<210> SEQ ID NO 411
<211> LENGTH: 36
<212> TYPE: DNA
<213> ORGANISM: Artificial Sequence
<220> FEATURE:
<223> OTHER INFORMATION: cDNA Sequence of aMTD765

<400> SEQUENCE: 411
gcggtggcgc tggcggtggt gccggcggtg ctgccg 36

<210> SEQ ID NO 412
<211> LENGTH: 36
<212> TYPE: DNA
<213> ORGANISM: Artificial Sequence
<220> FEATURE:
<223> OTHER INFORMATION: cDNA Sequence of aMTD766

<400> SEQUENCE: 412
attgtggtga ttgcggtggc gccggcggtg gcgccg 36

<210> SEQ ID NO 413
<211> LENGTH: 36
<212> TYPE: DNA
<213> ORGANISM: Artificial Sequence
<220> FEATURE:
<223> OTHER INFORMATION: cDNA Sequence of aMTD767

<400> SEQUENCE: 413
attgtggtgg cggcggtggt gccggcgctg gcgccg 36

<210> SEQ ID NO 414
<211> LENGTH: 36
<212> TYPE: DNA
<213> ORGANISM: Artificial Sequence
<220> FEATURE:
<223> OTHER INFORMATION: cDNA Sequence of aMTD783

<400> SEQUENCE: 414
attgtggcgc tggtgccggc ggtggcgatt gcgccg 36

<210> SEQ ID NO 415
<211> LENGTH: 36
<212> TYPE: DNA

<213> ORGANISM: Artificial Sequence
<220> FEATURE:
<223> OTHER INFORMATION: cDNA Sequence of aMTD784

<400> SEQUENCE: 415
gtggcggcgc tgccggcggt ggcgctggtg gtgccg 36

<210> SEQ ID NO 416
<211> LENGTH: 36
<212> TYPE: DNA
<213> ORGANISM: Artificial Sequence
<220> FEATURE:
<223> OTHER INFORMATION: cDNA Sequence of aMTD786

<400> SEQUENCE: 416
ctggtggcga ttgcgccgct ggcggtgctg gcgccg 36

<210> SEQ ID NO 417
<211> LENGTH: 36
<212> TYPE: DNA
<213> ORGANISM: Artificial Sequence
<220> FEATURE:
<223> OTHER INFORMATION: cDNA Sequence of aMTD787

<400> SEQUENCE: 417
gcggtggcgc tggtgccggt gattgtggcg gcgccg 36

<210> SEQ ID NO 418
<211> LENGTH: 36
<212> TYPE: DNA
<213> ORGANISM: Artificial Sequence
<220> FEATURE:
<223> OTHER INFORMATION: cDNA Sequence of aMTD788

<400> SEQUENCE: 418
gcgattgcgg tggcgattgc gccggtggcg ctgccg 36

<210> SEQ ID NO 419
<211> LENGTH: 36
<212> TYPE: DNA
<213> ORGANISM: Artificial Sequence
<220> FEATURE:
<223> OTHER INFORMATION: cDNA Sequence of aMTD803

<400> SEQUENCE: 419
gcgattgcgc tggcggtgcc ggtgctggcg ctgccg 36

<210> SEQ ID NO 420
<211> LENGTH: 36
<212> TYPE: DNA
<213> ORGANISM: Artificial Sequence
<220> FEATURE:
<223> OTHER INFORMATION: cDNA Sequence of aMTD805

<400> SEQUENCE: 420
ctggtgctga ttgcggcggc gccgattgcg ctgccg 36

<210> SEQ ID NO 421
<211> LENGTH: 36
<212> TYPE: DNA
<213> ORGANISM: Artificial Sequence
<220> FEATURE:
<223> OTHER INFORMATION: cDNA Sequence of aMTD806

<400> SEQUENCE: 421
ctggtggcgc tggcggtgcc ggcggcggtg ctgccg 36

<210> SEQ ID NO 422
<211> LENGTH: 36
<212> TYPE: DNA
<213> ORGANISM: Artificial Sequence
<220> FEATURE:
<223> OTHER INFORMATION: cDNA Sequence of aMTD807

<400> SEQUENCE: 422
gcggtggcgc tggcggtgcc ggcgctggtg ctgccg 36

<210> SEQ ID NO 423
<211> LENGTH: 36
<212> TYPE: DNA
<213> ORGANISM: Artificial Sequence
<220> FEATURE:
<223> OTHER INFORMATION: cDNA Sequence of aMTD808

<400> SEQUENCE: 423
ctggtggtgc tggcggcggc gccgctggcg gtgccg 36

<210> SEQ ID NO 424
<211> LENGTH: 36
<212> TYPE: DNA
<213> ORGANISM: Artificial Sequence
<220> FEATURE:
<223> OTHER INFORMATION: cDNA Sequence of aMTD809

<400> SEQUENCE: 424
ctgattgtgc tggcggcgcc ggcgctggcg gcgccg 36

<210> SEQ ID NO 425
<211> LENGTH: 36
<212> TYPE: DNA
<213> ORGANISM: Artificial Sequence
<220> FEATURE:
<223> OTHER INFORMATION: cDNA Sequence of aMTD810

<400> SEQUENCE: 425
gtgattgtgc tggcggcgcc ggcgctggcg gcgccg 36

<210> SEQ ID NO 426
<211> LENGTH: 36
<212> TYPE: DNA
<213> ORGANISM: Artificial Sequence
<220> FEATURE:
<223> OTHER INFORMATION: cDNA Sequence of aMTD811

<400> SEQUENCE: 426
gcggtggtgc tggcggtgcc ggcgctggcg gtgccg 36

<210> SEQ ID NO 427
<211> LENGTH: 36
<212> TYPE: DNA
<213> ORGANISM: Artificial Sequence
<220> FEATURE:
<223> OTHER INFORMATION: cDNA Sequence of aMTD824

<400> SEQUENCE: 427
ctgattattg tggcggcggc gccggcggtg gcgccg 36

<210> SEQ ID NO 428
<211> LENGTH: 36
<212> TYPE: DNA
<213> ORGANISM: Artificial Sequence
<220> FEATURE:

<223> OTHER INFORMATION: cDNA Sequence of aMTD825

<400> SEQUENCE: 428
attgtggcgg tgattgtggc gccggcggtg gcgccg 36

<210> SEQ ID NO 429
<211> LENGTH: 36
<212> TYPE: DNA
<213> ORGANISM: Artificial Sequence
<220> FEATURE:
<223> OTHER INFORMATION: cDNA Sequence of aMTD826

<400> SEQUENCE: 429
ctggtggcgc tggcggcgcc gattattgcg gtgccg 36

<210> SEQ ID NO 430
<211> LENGTH: 36
<212> TYPE: DNA
<213> ORGANISM: Artificial Sequence
<220> FEATURE:
<223> OTHER INFORMATION: cDNA Sequence of aMTD827

<400> SEQUENCE: 430
attgcggcgg tgctggcggc gccggcgctg gtgccg 36

<210> SEQ ID NO 431
<211> LENGTH: 36
<212> TYPE: DNA
<213> ORGANISM: Artificial Sequence
<220> FEATURE:
<223> OTHER INFORMATION: cDNA Sequence of aMTD828

<400> SEQUENCE: 431
attgcgctgc tggcggcgcc gattattgcg gtgccg 36

<210> SEQ ID NO 432
<211> LENGTH: 36
<212> TYPE: DNA
<213> ORGANISM: Artificial Sequence
<220> FEATURE:
<223> OTHER INFORMATION: cDNA Sequence of aMTD829

<400> SEQUENCE: 432
gcggcgctgg cgctggtggc gccggtgatt gtgccg 36

<210> SEQ ID NO 433
<211> LENGTH: 36
<212> TYPE: DNA
<213> ORGANISM: Artificial Sequence
<220> FEATURE:
<223> OTHER INFORMATION: cDNA Sequence of aMTD830

<400> SEQUENCE: 433
attgcgctgg tggcggcgcc ggtggcgctg gtgccg 36

<210> SEQ ID NO 434
<211> LENGTH: 36
<212> TYPE: DNA
<213> ORGANISM: Artificial Sequence
<220> FEATURE:
<223> OTHER INFORMATION: cDNA Sequence of aMTD831

<400> SEQUENCE: 434
attattgtgg cggtggcgcc ggcggcgatt gtgccg 36

<210> SEQ ID NO 435
<211> LENGTH: 36
<212> TYPE: DNA
<213> ORGANISM: Artificial Sequence
<220> FEATURE:
<223> OTHER INFORMATION: cDNA Sequence of aMTD832

<400> SEQUENCE: 435
gcggtggcgg cgattgtgcc ggtgattgtg gcgccg 36

<210> SEQ ID NO 436
<211> LENGTH: 36
<212> TYPE: DNA
<213> ORGANISM: Artificial Sequence
<220> FEATURE:
<223> OTHER INFORMATION: cDNA Sequence of aMTD843

<400> SEQUENCE: 436
gcggtgctgg tgctggtggc gccggcggcg gcgccg 36

<210> SEQ ID NO 437
<211> LENGTH: 36
<212> TYPE: DNA
<213> ORGANISM: Artificial Sequence
<220> FEATURE:
<223> OTHER INFORMATION: cDNA Sequence of aMTD844

<400> SEQUENCE: 437
gtggtggcgc tgctggcgcc gctgattgcg gcgccg 36

<210> SEQ ID NO 438
<211> LENGTH: 36
<212> TYPE: DNA
<213> ORGANISM: Artificial Sequence
<220> FEATURE:
<223> OTHER INFORMATION: cDNA Sequence of aMTD845

<400> SEQUENCE: 438
gcggcggtgg tgattgcgcc gctgctggcg gtgccg 36

<210> SEQ ID NO 439
<211> LENGTH: 36
<212> TYPE: DNA
<213> ORGANISM: Artificial Sequence
<220> FEATURE:
<223> OTHER INFORMATION: cDNA Sequence of aMTD846

<400> SEQUENCE: 439
attgcggtgg cggtggcggc gccgctgctg gtgccg 36

<210> SEQ ID NO 440
<211> LENGTH: 36
<212> TYPE: DNA
<213> ORGANISM: Artificial Sequence
<220> FEATURE:
<223> OTHER INFORMATION: cDNA Sequence of aMTD847

<400> SEQUENCE: 440
ctggtggcga ttgtggtgct gccggcggtg gcgccg 36

<210> SEQ ID NO 441
<211> LENGTH: 36
<212> TYPE: DNA
<213> ORGANISM: Artificial Sequence
<220> FEATURE:
<223> OTHER INFORMATION: cDNA Sequence of aMTD848

<400> SEQUENCE: 441
gcggtggcga ttgtggtgct gccggcggtg gcgccg 36

<210> SEQ ID NO 442
<211> LENGTH: 36
<212> TYPE: DNA
<213> ORGANISM: Artificial Sequence
<220> FEATURE:
<223> OTHER INFORMATION: cDNA Sequence of aMTD849

<400> SEQUENCE: 442
gcggtgattc tgctggcgcc gctgattgcg gcgccg 36

<210> SEQ ID NO 443
<211> LENGTH: 36
<212> TYPE: DNA
<213> ORGANISM: Artificial Sequence
<220> FEATURE:
<223> OTHER INFORMATION: cDNA Sequence of aMTD850

<400> SEQUENCE: 443
ctggtgattg cgctggcggc gccggtggcg ctgccg 36

<210> SEQ ID NO 444
<211> LENGTH: 36
<212> TYPE: DNA
<213> ORGANISM: Artificial Sequence
<220> FEATURE:
<223> OTHER INFORMATION: cDNA Sequence of aMTD851

<400> SEQUENCE: 444
gtgctggcgg tggtgctgcc ggcggtggcg ctgccg 36

<210> SEQ ID NO 445
<211> LENGTH: 36
<212> TYPE: DNA
<213> ORGANISM: Artificial Sequence
<220> FEATURE:
<223> OTHER INFORMATION: cDNA Sequence of aMTD852

<400> SEQUENCE: 445
gtgctggcgg tggcggcgcc ggcggtgctg ctgccg 36

<210> SEQ ID NO 446
<211> LENGTH: 36
<212> TYPE: DNA
<213> ORGANISM: Artificial Sequence
<220> FEATURE:
<223> OTHER INFORMATION: cDNA Sequence of aMTD863

<400> SEQUENCE: 446
gcggcggtgg tgctgctgcc gattattgcg gcgccg 36

<210> SEQ ID NO 447
<211> LENGTH: 36
<212> TYPE: DNA
<213> ORGANISM: Artificial Sequence
<220> FEATURE:
<223> OTHER INFORMATION: cDNA Sequence of aMTD864

<400> SEQUENCE: 447
gcgctgctgg tgattgcgcc ggcgattgcg gtgccg 36

<210> SEQ ID NO 448
<211> LENGTH: 36

<212> TYPE: DNA
<213> ORGANISM: Artificial Sequence
<220> FEATURE:
<223> OTHER INFORMATION: cDNA Sequence of aMTD865

<400> SEQUENCE: 448
gcggtgctgg tgattgcggt gccggcgatt gcgccg 36

<210> SEQ ID NO 449
<211> LENGTH: 36
<212> TYPE: DNA
<213> ORGANISM: Artificial Sequence
<220> FEATURE:
<223> OTHER INFORMATION: cDNA Sequence of aMTD867

<400> SEQUENCE: 449
gcgctgctgg tggtgattgc gccgctggcg gcgccg 36

<210> SEQ ID NO 450
<211> LENGTH: 36
<212> TYPE: DNA
<213> ORGANISM: Artificial Sequence
<220> FEATURE:
<223> OTHER INFORMATION: cDNA Sequence of aMTD868

<400> SEQUENCE: 450
gtgctggtgg cggcgattct gccggcggcg attccg 36

<210> SEQ ID NO 451
<211> LENGTH: 36
<212> TYPE: DNA
<213> ORGANISM: Artificial Sequence
<220> FEATURE:
<223> OTHER INFORMATION: cDNA Sequence of aMTD870

<400> SEQUENCE: 451
gtgctggtgg cggcggtgct gccgattgcg gcgccg 36

<210> SEQ ID NO 452
<211> LENGTH: 36
<212> TYPE: DNA
<213> ORGANISM: Artificial Sequence
<220> FEATURE:
<223> OTHER INFORMATION: cDNA Sequence of aMTD872

<400> SEQUENCE: 452
gtgctggcgg cggcggtgct gccgctggtg gtgccg 36

<210> SEQ ID NO 453
<211> LENGTH: 36
<212> TYPE: DNA
<213> ORGANISM: Artificial Sequence
<220> FEATURE:
<223> OTHER INFORMATION: cDNA Sequence of aMTD875

<400> SEQUENCE: 453
gcgattgcga ttgtggtgcc ggcggtggcg gtgccg 36

<210> SEQ ID NO 454
<211> LENGTH: 36
<212> TYPE: DNA
<213> ORGANISM: Artificial Sequence
<220> FEATURE:
<223> OTHER INFORMATION: cDNA Sequence of aMTD877

<400> SEQUENCE: 454
gtggcgatta ttgcggtgcc ggcggtggtg gcgccg 36

<210> SEQ ID NO 455
<211> LENGTH: 36
<212> TYPE: DNA
<213> ORGANISM: Artificial Sequence
<220> FEATURE:
<223> OTHER INFORMATION: cDNA Sequence of aMTD878

<400> SEQUENCE: 455
attgtggcgc tggtggcgcc ggcggcggtg gtgccg 36

<210> SEQ ID NO 456
<211> LENGTH: 36
<212> TYPE: DNA
<213> ORGANISM: Artificial Sequence
<220> FEATURE:
<223> OTHER INFORMATION: cDNA Sequence of aMTD879

<400> SEQUENCE: 456
gcggcgattg tgctgctgcc ggcggtggtg gtgccg 36

<210> SEQ ID NO 457
<211> LENGTH: 36
<212> TYPE: DNA
<213> ORGANISM: Artificial Sequence
<220> FEATURE:
<223> OTHER INFORMATION: cDNA Sequence of aMTD881

<400> SEQUENCE: 457
gcggcgctga ttgtggtgcc ggcggtggcg gtgccg 36

<210> SEQ ID NO 458
<211> LENGTH: 36
<212> TYPE: DNA
<213> ORGANISM: Artificial Sequence
<220> FEATURE:
<223> OTHER INFORMATION: cDNA Sequence of aMTD882

<400> SEQUENCE: 458
gcgattgcgc tggtggtgcc ggcggtggcg gtgccg 36

<210> SEQ ID NO 459
<211> LENGTH: 36
<212> TYPE: DNA
<213> ORGANISM: Artificial Sequence
<220> FEATURE:
<223> OTHER INFORMATION: cDNA Sequence of aMTD883

<400> SEQUENCE: 459
ctggcgattg tgccggcggc gattgcggcg ctgccg 36

<210> SEQ ID NO 460
<211> LENGTH: 36
<212> TYPE: DNA
<213> ORGANISM: Artificial Sequence
<220> FEATURE:
<223> OTHER INFORMATION: cDNA Sequence of aMTD885

<400> SEQUENCE: 460
ctggtggcga ttgcgccggc ggtggcggtg ctgccg 36

<210> SEQ ID NO 461
<211> LENGTH: 36
<212> TYPE: DNA
<213> ORGANISM: Artificial Sequence
<220> FEATURE:
<223> OTHER INFORMATION: cDNA Sequence of aMTD887

<400> SEQUENCE: 461
gtgctggcgg tggcgccggc ggtggcggtg ctgccg 36

<210> SEQ ID NO 462
<211> LENGTH: 36
<212> TYPE: DNA
<213> ORGANISM: Artificial Sequence
<220> FEATURE:
<223> OTHER INFORMATION: cDNA Sequence of aMTD888

<400> SEQUENCE: 462
attctggcgg tggtggcgat tccggcggcg gcgccg 36

<210> SEQ ID NO 463
<211> LENGTH: 36
<212> TYPE: DNA
<213> ORGANISM: Artificial Sequence
<220> FEATURE:
<223> OTHER INFORMATION: cDNA Sequence of aMTD889

<400> SEQUENCE: 463
attctggtgg cggcggcgcc gattgcggcg ctgccg 36

<210> SEQ ID NO 464
<211> LENGTH: 36
<212> TYPE: DNA
<213> ORGANISM: Artificial Sequence
<220> FEATURE:
<223> OTHER INFORMATION: cDNA Sequence of aMTD891

<400> SEQUENCE: 464
attctggcgg tggcggcgat tccggcggcg ctgccg 36

<210> SEQ ID NO 465
<211> LENGTH: 36
<212> TYPE: DNA
<213> ORGANISM: Artificial Sequence
<220> FEATURE:
<223> OTHER INFORMATION: cDNA Sequence of aMTD893

<400> SEQUENCE: 465
gtgattgcga ttccggcgat tctggcggcg gcgccg 36

<210> SEQ ID NO 466
<211> LENGTH: 36
<212> TYPE: DNA
<213> ORGANISM: Artificial Sequence
<220> FEATURE:
<223> OTHER INFORMATION: cDNA Sequence of aMTD895

<400> SEQUENCE: 466
gcgattatta ttgtggtgcc ggcgattgcg gcgccg 36

<210> SEQ ID NO 467
<211> LENGTH: 36
<212> TYPE: DNA
<213> ORGANISM: Artificial Sequence
<220> FEATURE:
<223> OTHER INFORMATION: cDNA Sequence of aMTD896

<400> SEQUENCE: 467
gcgattctga ttgtggtggc gccgattgcg gcgccg 36

<210> SEQ ID NO 468
<211> LENGTH: 36
<212> TYPE: DNA
<213> ORGANISM: Artificial Sequence
<220> FEATURE:
<223> OTHER INFORMATION: cDNA Sequence of aMTD897

<400> SEQUENCE: 468
gcggtgattg tgccggtggc gattattgcg gcgccg 36

<210> SEQ ID NO 469
<211> LENGTH: 36
<212> TYPE: DNA
<213> ORGANISM: Artificial Sequence
<220> FEATURE:
<223> OTHER INFORMATION: cDNA Sequence of aMTD899

<400> SEQUENCE: 469
gcggtggtga ttgcgctgcc ggcggtggtg gcgccg 36

<210> SEQ ID NO 470
<211> LENGTH: 36
<212> TYPE: DNA
<213> ORGANISM: Artificial Sequence
<220> FEATURE:
<223> OTHER INFORMATION: cDNA Sequence of aMTD900

<400> SEQUENCE: 470
gcgctggtgg cggtgattgc gccggtggtg gcgccg 36

<210> SEQ ID NO 471
<211> LENGTH: 36
<212> TYPE: DNA
<213> ORGANISM: Artificial Sequence
<220> FEATURE:
<223> OTHER INFORMATION: cDNA Sequence of aMTD901

<400> SEQUENCE: 471
gcgctggtgg cggtgctgcc ggcggtggcg gtgccg 36

<210> SEQ ID NO 472
<211> LENGTH: 36
<212> TYPE: DNA
<213> ORGANISM: Artificial Sequence
<220> FEATURE:
<223> OTHER INFORMATION: cDNA Sequence of aMTD902

<400> SEQUENCE: 472
gcgctggtgg cgccgctgct ggcggtggcg gtgccg 36

<210> SEQ ID NO 473
<211> LENGTH: 36
<212> TYPE: DNA
<213> ORGANISM: Artificial Sequence
<220> FEATURE:
<223> OTHER INFORMATION: cDNA Sequence of aMTD904

<400> SEQUENCE: 473
gcggtgctgg cggtggtggc gccggtggtg gcgccg 36

<210> SEQ ID NO 474
<211> LENGTH: 36
<212> TYPE: DNA
<213> ORGANISM: Artificial Sequence
<220> FEATURE:
<223> OTHER INFORMATION: cDNA Sequence of aMTD905

<400> SEQUENCE: 474
gcggtgattg cggtggcgcc gctggtggtg gcgccg 36

<210> SEQ ID NO 475
<211> LENGTH: 36
<212> TYPE: DNA
<213> ORGANISM: Artificial Sequence
<220> FEATURE:
<223> OTHER INFORMATION: cDNA Sequence of aMTD906

<400> SEQUENCE: 475
gcggtgattg cgctggcgcc ggtggtggtg gcgccg 36

<210> SEQ ID NO 476
<211> LENGTH: 36
<212> TYPE: DNA
<213> ORGANISM: Artificial Sequence
<220> FEATURE:
<223> OTHER INFORMATION: cDNA Sequence of aMTD907

<400> SEQUENCE: 476
gtggcgattg cgctggcgcc ggtggtggtg gcgccg 36

<210> SEQ ID NO 477
<211> LENGTH: 36
<212> TYPE: DNA
<213> ORGANISM: Artificial Sequence
<220> FEATURE:
<223> OTHER INFORMATION: cDNA Sequence of aMTD908

<400> SEQUENCE: 477
gtggcgctgg cgctggcgcc ggtggtggtg gcgccg 36

<210> SEQ ID NO 478
<211> LENGTH: 36
<212> TYPE: DNA
<213> ORGANISM: Artificial Sequence
<220> FEATURE:
<223> OTHER INFORMATION: cDNA Sequence of aMTD910

<400> SEQUENCE: 478
gtggcggcgc tgctgccggc ggtggtggtg gcgccg 36

<210> SEQ ID NO 479
<211> LENGTH: 36
<212> TYPE: DNA
<213> ORGANISM: Artificial Sequence
<220> FEATURE:
<223> OTHER INFORMATION: cDNA Sequence of aMTD911

<400> SEQUENCE: 479
gtggcgctgg cgctgccggc ggtggtggtg gcgccg 36

<210> SEQ ID NO 480
<211> LENGTH: 36
<212> TYPE: DNA
<213> ORGANISM: Artificial Sequence
<220> FEATURE:
<223> OTHER INFORMATION: cDNA Sequence of aMTD912

<400> SEQUENCE: 480
gtggcgctgc tggcgccggc ggtggtggtg gcgccg 36

<210> SEQ ID NO 481

<211> LENGTH: 69
<212> TYPE: DNA
<213> ORGANISM: Artificial Sequence
<220> FEATURE:
<223> OTHER INFORMATION: cDNA Sequence of aMTD1 5'-primer

<400> SEQUENCE: 481
gggtttcata tggcggcggc gctggcgccg gtggtgctgg cgctgccggc aaatattacc 60
gttttctat 69

<210> SEQ ID NO 482
<211> LENGTH: 69
<212> TYPE: DNA
<213> ORGANISM: Artificial Sequence
<220> FEATURE:
<223> OTHER INFORMATION: cDNA Sequence of aMTD2 5'-primer

<400> SEQUENCE: 482
gggtttcata tggcggcggc ggtgccgctg ctggcggtgg tggtgccggc aaatattacc 60
gttttctat 69

<210> SEQ ID NO 483
<211> LENGTH: 69
<212> TYPE: DNA
<213> ORGANISM: Artificial Sequence
<220> FEATURE:
<223> OTHER INFORMATION: cDNA Sequence of aMTD3 5'-primer

<400> SEQUENCE: 483
gggtttcata tggcggcgct gctggtgccg gcggcggtgc tggcgccggc aaatattacc 60
gttttctat 69

<210> SEQ ID NO 484
<211> LENGTH: 69
<212> TYPE: DNA
<213> ORGANISM: Artificial Sequence
<220> FEATURE:
<223> OTHER INFORMATION: cDNA Sequence of aMTD4 5'-primer

<400> SEQUENCE: 484
gggtttcata tggcgctggc gctgctgccg gtggcggcgc tggcgccggc aaatattacc 60
gttttctat 69

<210> SEQ ID NO 485
<211> LENGTH: 69
<212> TYPE: DNA
<213> ORGANISM: Artificial Sequence
<220> FEATURE:
<223> OTHER INFORMATION: cDNA Sequence of aMTD5 5'-primer

<400> SEQUENCE: 485
gggtttcata tggcggcggc gctgctgccg gtggcgctgg tggcgccggc aaatattacc 60
gttttctat 69

<210> SEQ ID NO 486
<211> LENGTH: 69
<212> TYPE: DNA
<213> ORGANISM: Artificial Sequence
<220> FEATURE:
<223> OTHER INFORMATION: cDNA Sequence of aMTD6 5'-primer

<400> SEQUENCE: 486
gggtttcata tggtgattgc gatgattccg gcggcgtttt gggtggcggc aaatattacc 60
gttttctat 69

<210> SEQ ID NO 487
<211> LENGTH: 69
<212> TYPE: DNA
<213> ORGANISM: Artificial Sequence
<220> FEATURE:
<223> OTHER INFORMATION: cDNA Sequence of aMTD9 5'-primer

<400> SEQUENCE: 487
gggtttcata tggtggcgct ggtgccggcg gcgctgattc tgccgccggc aaatattacc 60
gttttctat 69

<210> SEQ ID NO 488
<211> LENGTH: 69
<212> TYPE: DNA
<213> ORGANISM: Artificial Sequence
<220> FEATURE:
<223> OTHER INFORMATION: cDNA Sequence of aMTD11 5'-primer

<400> SEQUENCE: 488
gggtttcata tggtggtggc gctggcgccg gcgctggcgg cgctgccggc aaatattacc 60
gttttctat 69

<210> SEQ ID NO 489
<211> LENGTH: 69
<212> TYPE: DNA
<213> ORGANISM: Artificial Sequence
<220> FEATURE:
<223> OTHER INFORMATION: cDNA Sequence of aMTD12 5'-primer

<400> SEQUENCE: 489
gggtttcata tgctgctggc ggcggtgccg gcggtgctgc tggcgccggc aaatattacc 60
gttttctat 69

<210> SEQ ID NO 490
<211> LENGTH: 69
<212> TYPE: DNA
<213> ORGANISM: Artificial Sequence
<220> FEATURE:
<223> OTHER INFORMATION: cDNA Sequence of aMTD13 5'-primer

<400> SEQUENCE: 490
gggtttcata tggcggcggc gctggtgccg gtggtggcgc tgctgccggc aaatattacc 60
gttttctat 69

<210> SEQ ID NO 491
<211> LENGTH: 69
<212> TYPE: DNA
<213> ORGANISM: Artificial Sequence
<220> FEATURE:
<223> OTHER INFORMATION: cDNA Sequence of aMTD16 5'-primer

<400> SEQUENCE: 491
gggtttcata tgaacaacag ctgcaccacc tataccaacg gcagccaggc aaatattacc 60
gttttctat 69

<210> SEQ ID NO 492
<211> LENGTH: 69
<212> TYPE: DNA
<213> ORGANISM: Artificial Sequence
<220> FEATURE:

<223> OTHER INFORMATION: cDNA Sequence of aMTD17 5'-primer

<400> SEQUENCE: 492
gggtttcata tgggcggctg cagcgcgccg cagaccacct gcagcaacgc aaatattacc 60
gttttctat 69

<210> SEQ ID NO 493
<211> LENGTH: 69
<212> TYPE: DNA
<213> ORGANISM: Artificial Sequence
<220> FEATURE:
<223> OTHER INFORMATION: cDNA Sequence of aMTD18 5'-primer

<400> SEQUENCE: 493
gggtttcata tgaactattg ctgcaccccg accaccaacg gccagagcgc aaatattacc 60
gttttctat 69

<210> SEQ ID NO 494
<211> LENGTH: 69
<212> TYPE: DNA
<213> ORGANISM: Artificial Sequence
<220> FEATURE:
<223> OTHER INFORMATION: cDNA Sequence of aMTD19 5'-primer

<400> SEQUENCE: 494
gggtttcata tgtatgtgag ctgctgcacc tataccaacg gcagccaggc aaatattacc 60
gttttctat 69

<210> SEQ ID NO 495
<211> LENGTH: 69
<212> TYPE: DNA
<213> ORGANISM: Artificial Sequence
<220> FEATURE:
<223> OTHER INFORMATION: cDNA Sequence of aMTD20 5'-primer

<400> SEQUENCE: 495
gggtttcata tgaactattg caacacctgc ccgacctatg gccagagcgc aaatattacc 60
gttttctat 69

<210> SEQ ID NO 496
<211> LENGTH: 69
<212> TYPE: DNA
<213> ORGANISM: Artificial Sequence
<220> FEATURE:
<223> OTHER INFORMATION: cDNA Sequence of aMTD21 5'-primer

<400> SEQUENCE: 496
gggtttcata tggcggtggc gctgctgccg gcgctgctgg cggtgccggc aaatattacc 60
gttttctat 69

<210> SEQ ID NO 497
<211> LENGTH: 69
<212> TYPE: DNA
<213> ORGANISM: Artificial Sequence
<220> FEATURE:
<223> OTHER INFORMATION: cDNA Sequence of aMTD22 5'-primer

<400> SEQUENCE: 497
gggtttcata tggcggtggt gctggtgccg gtgctggcgg cggcgccggc aaatattacc 60
gttttctat 69

<210> SEQ ID NO 498
<211> LENGTH: 69
<212> TYPE: DNA
<213> ORGANISM: Artificial Sequence
<220> FEATURE:
<223> OTHER INFORMATION: cDNA Sequence of aMTD23 5'-primer

<400> SEQUENCE: 498
gggtttcata tggtggtgct ggtgctgccg gcggcggcgg cggtgccggc aaatattacc 60
gttttctat 69

<210> SEQ ID NO 499
<211> LENGTH: 69
<212> TYPE: DNA
<213> ORGANISM: Artificial Sequence
<220> FEATURE:
<223> OTHER INFORMATION: cDNA Sequence of aMTD24 5'-primer

<400> SEQUENCE: 499
gggtttcata tgattgcgct ggcggcgccg gcgctgattg tggcgccggc aaatattacc 60
gttttctat 69

<210> SEQ ID NO 500
<211> LENGTH: 69
<212> TYPE: DNA
<213> ORGANISM: Artificial Sequence
<220> FEATURE:
<223> OTHER INFORMATION: cDNA Sequence of aMTD25 5'-primer

<400> SEQUENCE: 500
gggtttcata tgattgtggc ggtggcgccg gcgctggtgg cgctgccggc aaatattacc 60
gttttctat 69

<210> SEQ ID NO 501
<211> LENGTH: 69
<212> TYPE: DNA
<213> ORGANISM: Artificial Sequence
<220> FEATURE:
<223> OTHER INFORMATION: cDNA Sequence of aMTD26 5'-primer

<400> SEQUENCE: 501
gggtttcata tggcggcgat tgcgctggcg gcgccgctgg cgattgtggc aaatattacc 60
gttttctat 69

<210> SEQ ID NO 502
<211> LENGTH: 69
<212> TYPE: DNA
<213> ORGANISM: Artificial Sequence
<220> FEATURE:
<223> OTHER INFORMATION: cDNA Sequence of aMTD27 5'-primer

<400> SEQUENCE: 502
gggtttcata tgctggcgat tgtggcggcg gcggcggcgc tggtggcggc aaatattacc 60
gttttctat 69

<210> SEQ ID NO 503
<211> LENGTH: 69
<212> TYPE: DNA
<213> ORGANISM: Artificial Sequence
<220> FEATURE:
<223> OTHER INFORMATION: cDNA Sequence of aMTD28 5'-primer

<400> SEQUENCE: 503
gggtttcata tggcggtgcc gctgctgccg ctggtgccgg cggtgccggc aaatattacc 60
gttttctat 69

<210> SEQ ID NO 504
<211> LENGTH: 69
<212> TYPE: DNA
<213> ORGANISM: Artificial Sequence
<220> FEATURE:
<223> OTHER INFORMATION: cDNA Sequence of aMTD29 5'-primer

<400> SEQUENCE: 504
gggtttcata tggtgctgcc gccgctgccg gtgctgccgg tgctgccggc aaatattacc 60
gttttctat 69

<210> SEQ ID NO 505
<211> LENGTH: 69
<212> TYPE: DNA
<213> ORGANISM: Artificial Sequence
<220> FEATURE:
<223> OTHER INFORMATION: cDNA Sequence of aMTD30 5'-primer

<400> SEQUENCE: 505
gggtttcata tggcgatggc gctgctgccg gcggcggtgg cggtggcggc aaatattacc 60
gttttctat 69

<210> SEQ ID NO 506
<211> LENGTH: 69
<212> TYPE: DNA
<213> ORGANISM: Artificial Sequence
<220> FEATURE:
<223> OTHER INFORMATION: cDNA Sequence of aMTD33 5'-primer

<400> SEQUENCE: 506
gggtttcata tggcggcggc gattctggcg ccggcgtttc tggcggtggc aaatattacc 60
gttttctat 69

<210> SEQ ID NO 507
<211> LENGTH: 69
<212> TYPE: DNA
<213> ORGANISM: Artificial Sequence
<220> FEATURE:
<223> OTHER INFORMATION: cDNA Sequence of aMTD37 5'-primer

<400> SEQUENCE: 507
gggtttcata tgtattataa ccagagcacc tgcggcggcc agtgctatgc aaatattacc 60
gttttctat 69

<210> SEQ ID NO 508
<211> LENGTH: 69
<212> TYPE: DNA
<213> ORGANISM: Artificial Sequence
<220> FEATURE:
<223> OTHER INFORMATION: cDNA Sequence of aMTD38 5'-primer

<400> SEQUENCE: 508
gggtttcata tgaccacctg cagccagcag cagtattgca ccaacggcgc aaatattacc 60
gttttctat 69

<210> SEQ ID NO 509
<211> LENGTH: 69
<212> TYPE: DNA
<213> ORGANISM: Artificial Sequence
<220> FEATURE:
<223> OTHER INFORMATION: cDNA Sequence of aMTD39 5'-primer

<400> SEQUENCE: 509
gggtttcata tgtgctataa caccagcccg tgcaccggct gctgctatgc aaatattacc 60
gttttctat 69

<210> SEQ ID NO 510
<211> LENGTH: 69
<212> TYPE: DNA
<213> ORGANISM: Artificial Sequence
<220> FEATURE:
<223> OTHER INFORMATION: cDNA Sequence of aMTD40 5'-primer

<400> SEQUENCE: 510
gggtttcata tgacctataa caccagctgc accccgggca cctgctatgc aaatattacc 60
gttttctat 69

<210> SEQ ID NO 511
<211> LENGTH: 69
<212> TYPE: DNA
<213> ORGANISM: Artificial Sequence
<220> FEATURE:
<223> OTHER INFORMATION: cDNA Sequence of aMTD42 5'-primer

<400> SEQUENCE: 511
gggtttcata tggtggcggc gctgccggtg gtggcggtgg tggcgccggc aaatattacc 60
gttttctat 69

<210> SEQ ID NO 512
<211> LENGTH: 69
<212> TYPE: DNA
<213> ORGANISM: Artificial Sequence
<220> FEATURE:
<223> OTHER INFORMATION: cDNA Sequence of aMTD43 5'-primer

<400> SEQUENCE: 512
gggtttcata tgctgctggc ggcgccgctg gtggtggcgg cggtgccggc aaatattacc 60
gttttctat 69

<210> SEQ ID NO 513
<211> LENGTH: 69
<212> TYPE: DNA
<213> ORGANISM: Artificial Sequence
<220> FEATURE:
<223> OTHER INFORMATION: cDNA Sequence of aMTD44 5'-primer

<400> SEQUENCE: 513
gggtttcata tggcgctggc ggtgccggtg gcgctgctgg tggcgccggc aaatattacc 60
gttttctat 69

<210> SEQ ID NO 514
<211> LENGTH: 69
<212> TYPE: DNA
<213> ORGANISM: Artificial Sequence
<220> FEATURE:
<223> OTHER INFORMATION: cDNA Sequence of aMTD49 5'-primer

<400> SEQUENCE: 514
gggtttcata tggtggtgcc ggcggcgccg gcggtgccgg tggtgccggc aaatattacc 60
gttttctat 69

<210> SEQ ID NO 515
<211> LENGTH: 69
<212> TYPE: DNA
<213> ORGANISM: Artificial Sequence
<220> FEATURE:
<223> OTHER INFORMATION: cDNA Sequence of aMTD54 5'-primer

<400> SEQUENCE: 515
gggtttcata tgctggcggt ggcggcgccg ccggtggtgg cgctgctggc aaatattacc 60
gttttctat 69

<210> SEQ ID NO 516
<211> LENGTH: 69
<212> TYPE: DNA
<213> ORGANISM: Artificial Sequence
<220> FEATURE:
<223> OTHER INFORMATION: cDNA Sequence of aMTD57 5'-primer

<400> SEQUENCE: 516
gggtttcata tgcagaacaa ctgcaacacc agcagccagg gcggcggcgc aaatattacc 60
gttttctat 69

<210> SEQ ID NO 517
<211> LENGTH: 69
<212> TYPE: DNA
<213> ORGANISM: Artificial Sequence
<220> FEATURE:
<223> OTHER INFORMATION: cDNA Sequence of aMTD59 5'-primer

<400> SEQUENCE: 517
gggtttcata tggcggtgct ggcggcgccg gtggtggcgg cgctggcggc aaatattacc 60
gttttctat 69

<210> SEQ ID NO 518
<211> LENGTH: 69
<212> TYPE: DNA
<213> ORGANISM: Artificial Sequence
<220> FEATURE:
<223> OTHER INFORMATION: cDNA Sequence of aMTD61 5'-primer

<400> SEQUENCE: 518
gggtttcata tggtggcggc gctgccggtg ctgctggcgg cgctgccggc aaatattacc 60
gttttctat 69

<210> SEQ ID NO 519
<211> LENGTH: 69
<212> TYPE: DNA
<213> ORGANISM: Artificial Sequence
<220> FEATURE:
<223> OTHER INFORMATION: cDNA Sequence of aMTD62 5'-primer

<400> SEQUENCE: 519
gggtttcata tggtggcgct gctggcgccg gtggcgctgg cggtgccggc aaatattacc 60
gttttctat 69

<210> SEQ ID NO 520
<211> LENGTH: 69
<212> TYPE: DNA
<213> ORGANISM: Artificial Sequence
<220> FEATURE:
<223> OTHER INFORMATION: cDNA Sequence of aMTD63 5'-primer

<400> SEQUENCE: 520
gggtttcata tggcggcgct gctggtgccg gcgctggtgg cggtgccggc aaatattacc 60
gttttctat 69

<210> SEQ ID NO 521
<211> LENGTH: 69
<212> TYPE: DNA
<213> ORGANISM: Artificial Sequence
<220> FEATURE:
<223> OTHER INFORMATION: cDNA Sequence of aMTD64 5'-primer

<400> SEQUENCE: 521
gggtttcata tggcgattgt ggcgctgccg gtggcggtgc tggcgccggc aaatattacc 60
gttttctat 69

<210> SEQ ID NO 522
<211> LENGTH: 69
<212> TYPE: DNA
<213> ORGANISM: Artificial Sequence
<220> FEATURE:
<223> OTHER INFORMATION: cDNA Sequence of aMTD65 5'-primer

<400> SEQUENCE: 522
gggtttcata tgattgcgat tgtggcgccg gtggtggcgc tggcgccggc aaatattacc 60
gttttctat 69

<210> SEQ ID NO 523
<211> LENGTH: 69
<212> TYPE: DNA
<213> ORGANISM: Artificial Sequence
<220> FEATURE:
<223> OTHER INFORMATION: cDNA Sequence of aMTD66 5'-primer

<400> SEQUENCE: 523
gggtttcata tggcgggcgt gctgggcggc ccgattatgg gcgtgccggc aaatattacc 60
gttttctat 69

<210> SEQ ID NO 524
<211> LENGTH: 69
<212> TYPE: DNA
<213> ORGANISM: Artificial Sequence
<220> FEATURE:
<223> OTHER INFORMATION: cDNA Sequence of aMTD67 5'-primer

<400> SEQUENCE: 524
gggtttcata tgctggatgc ggaagtgccg ctggcggatg atgtgccggc aaatattacc 60
gttttctat 69

<210> SEQ ID NO 525
<211> LENGTH: 69
<212> TYPE: DNA
<213> ORGANISM: Artificial Sequence
<220> FEATURE:
<223> OTHER INFORMATION: cDNA Sequence of aMTD68 5'-primer

<400> SEQUENCE: 525
gggtttcata tggtggcgcc ggtgctgccg gcggcgccgc tggtgccggc aaatattacc 60
gttttctat 69

<210> SEQ ID NO 526
<211> LENGTH: 69
<212> TYPE: DNA

<213> ORGANISM: Artificial Sequence
<220> FEATURE:
<223> OTHER INFORMATION: cDNA Sequence of aMTD69 5'-primer

<400> SEQUENCE: 526
gggtttcata tgccggtggc ggtgctgccg ccggcggcgc tggtgccggc aaatattacc 60
gttttctat 69

<210> SEQ ID NO 527
<211> LENGTH: 69
<212> TYPE: DNA
<213> ORGANISM: Artificial Sequence
<220> FEATURE:
<223> OTHER INFORMATION: cDNA Sequence of aMTD71 5'-primer

<400> SEQUENCE: 527
gggtttcata tgtttatgtg gatgtggttt ccgtttatgt ggtatccggc aaatattacc 60
gttttctat 69

<210> SEQ ID NO 528
<211> LENGTH: 69
<212> TYPE: DNA
<213> ORGANISM: Artificial Sequence
<220> FEATURE:
<223> OTHER INFORMATION: cDNA Sequence of aMTD77 5'-primer

<400> SEQUENCE: 528
gggtttcata tggcgatgct gctgatgccg attgtgctga ttgcgccggc aaatattacc 60
gttttctat 69

<210> SEQ ID NO 529
<211> LENGTH: 69
<212> TYPE: DNA
<213> ORGANISM: Artificial Sequence
<220> FEATURE:
<223> OTHER INFORMATION: cDNA Sequence of aMTD81 5'-primer

<400> SEQUENCE: 529
gggtttcata tggcggcgct gctgccggcg ctggcggcgc tgctgccggc aaatattacc 60
gttttctat 69

<210> SEQ ID NO 530
<211> LENGTH: 69
<212> TYPE: DNA
<213> ORGANISM: Artificial Sequence
<220> FEATURE:
<223> OTHER INFORMATION: cDNA Sequence of aMTD82 5'-primer

<400> SEQUENCE: 530
gggtttcata tggcggtggt gctggcgccg gtggcggcgg tgctgccggc aaatattacc 60
gttttctat 69

<210> SEQ ID NO 531
<211> LENGTH: 69
<212> TYPE: DNA
<213> ORGANISM: Artificial Sequence
<220> FEATURE:
<223> OTHER INFORMATION: cDNA Sequence of aMTD83 5'-primer

<400> SEQUENCE: 531
gggtttcata tgctggcggt ggcggcgccg ctggcgctgg cgctgccggc aaatattacc 60
gttttctat 69

<210> SEQ ID NO 532
<211> LENGTH: 69
<212> TYPE: DNA
<213> ORGANISM: Artificial Sequence
<220> FEATURE:
<223> OTHER INFORMATION: cDNA Sequence of aMTD84 5'-primer

<400> SEQUENCE: 532
gggtttcata tggcggcggt ggcggcgccg ctgctgctgg cgctgccggc aaatattacc 60
gttttctat 69

<210> SEQ ID NO 533
<211> LENGTH: 69
<212> TYPE: DNA
<213> ORGANISM: Artificial Sequence
<220> FEATURE:
<223> OTHER INFORMATION: cDNA Sequence of aMTD85 5'-primer

<400> SEQUENCE: 533
gggtttcata tgctgctggt gctgccggcg gcggcgctgg cggcgccggc aaatattacc 60
gttttctat 69

<210> SEQ ID NO 534
<211> LENGTH: 69
<212> TYPE: DNA
<213> ORGANISM: Artificial Sequence
<220> FEATURE:
<223> OTHER INFORMATION: cDNA Sequence of aMTD97 5'-primer

<400> SEQUENCE: 534
gggtttcata tggcgctgct ggcggcgccg ccggcgctgc tggcgctggc aaatattacc 60
gttttctat 69

<210> SEQ ID NO 535
<211> LENGTH: 69
<212> TYPE: DNA
<213> ORGANISM: Artificial Sequence
<220> FEATURE:
<223> OTHER INFORMATION: cDNA Sequence of aMTD101 5'-primer

<400> SEQUENCE: 535
gggtttcata tgctggtggc ggtggcgccg gtggcggcgg tgctgccggc aaatattacc 60
gttttctat 69

<210> SEQ ID NO 536
<211> LENGTH: 69
<212> TYPE: DNA
<213> ORGANISM: Artificial Sequence
<220> FEATURE:
<223> OTHER INFORMATION: cDNA Sequence of aMTD102 5'-primer

<400> SEQUENCE: 536
gggtttcata tgctggcgct ggcgccggcg gcgctggcgc tgctgccggc aaatattacc 60
gttttctat 69

<210> SEQ ID NO 537
<211> LENGTH: 69
<212> TYPE: DNA
<213> ORGANISM: Artificial Sequence
<220> FEATURE:
<223> OTHER INFORMATION: cDNA Sequence of aMTD103 5'-primer

<400> SEQUENCE: 537
gggtttcata tggcgctgat tgcggcgccg attctggcgc tggcgccggc aaatattacc 60
gttttctat 69

<210> SEQ ID NO 538
<211> LENGTH: 69
<212> TYPE: DNA
<213> ORGANISM: Artificial Sequence
<220> FEATURE:
<223> OTHER INFORMATION: cDNA Sequence of aMTD104 5'-primer

<400> SEQUENCE: 538
gggtttcata tggcggtggt ggcggcgccg ctggtgctgg cgctgccggc aaatattacc 60
gttttctat 69

<210> SEQ ID NO 539
<211> LENGTH: 69
<212> TYPE: DNA
<213> ORGANISM: Artificial Sequence
<220> FEATURE:
<223> OTHER INFORMATION: cDNA Sequence of aMTD105 5'-primer

<400> SEQUENCE: 539
gggtttcata tgctgctggc gctggcgccg gcggcgctgc tggcgccggc aaatattacc 60
gttttctat 69

<210> SEQ ID NO 540
<211> LENGTH: 69
<212> TYPE: DNA
<213> ORGANISM: Artificial Sequence
<220> FEATURE:
<223> OTHER INFORMATION: cDNA Sequence of aMTD113 5'-primer

<400> SEQUENCE: 540
gggtttcata tgccggtggc ggtggcgctg ctgattgcgg tgccgccggc aaatattacc 60
gttttctat 69

<210> SEQ ID NO 541
<211> LENGTH: 69
<212> TYPE: DNA
<213> ORGANISM: Artificial Sequence
<220> FEATURE:
<223> OTHER INFORMATION: cDNA Sequence of aMTD121 5'-primer

<400> SEQUENCE: 541
gggtttcata tggcgattgt ggcgctgccg gcgctggcgc tggcgccggc aaatattacc 60
gttttctat 69

<210> SEQ ID NO 542
<211> LENGTH: 69
<212> TYPE: DNA
<213> ORGANISM: Artificial Sequence
<220> FEATURE:
<223> OTHER INFORMATION: cDNA Sequence of aMTD123 5'-primer

<400> SEQUENCE: 542
gggtttcata tggcggcgat tattgtgccg gcggcgctgc tggcgccggc aaatattacc 60
gttttctat 69

<210> SEQ ID NO 543
<211> LENGTH: 69

<212> TYPE: DNA
<213> ORGANISM: Artificial Sequence
<220> FEATURE:
<223> OTHER INFORMATION: cDNA Sequence of aMTD124 5'-primer

<400> SEQUENCE: 543
gggtttcata tgattgcggt ggcgctgccg gcgctgattg cggcgccggc aaatattacc 60
gttttctat 69

<210> SEQ ID NO 544
<211> LENGTH: 69
<212> TYPE: DNA
<213> ORGANISM: Artificial Sequence
<220> FEATURE:
<223> OTHER INFORMATION: cDNA Sequence of aMTD131 5'-primer

<400> SEQUENCE: 544
gggtttcata tgtggattat tgcgccggtg tggctggcgt ggattgcggc aaatattacc 60
gttttctat 69

<210> SEQ ID NO 545
<211> LENGTH: 69
<212> TYPE: DNA
<213> ORGANISM: Artificial Sequence
<220> FEATURE:
<223> OTHER INFORMATION: cDNA Sequence of aMTD138 5'-primer

<400> SEQUENCE: 545
gggtttcata tgccgccggc ggcgctgctg gcgattctgg cggtggcggc aaatattacc 60
gttttctat 69

<210> SEQ ID NO 546
<211> LENGTH: 69
<212> TYPE: DNA
<213> ORGANISM: Artificial Sequence
<220> FEATURE:
<223> OTHER INFORMATION: cDNA Sequence of aMTD139 5'-primer

<400> SEQUENCE: 546
gggtttcata tgaccggcag caccaacagc ccgacctgca ccagcaccgc aaatattacc 60
gttttctat 69

<210> SEQ ID NO 547
<211> LENGTH: 69
<212> TYPE: DNA
<213> ORGANISM: Artificial Sequence
<220> FEATURE:
<223> OTHER INFORMATION: cDNA Sequence of aMTD141 5'-primer

<400> SEQUENCE: 547
gggtttcata tggcggtgat tgtgctgccg gcgctggcgg tggcgccggc aaatattacc 60
gttttctat 69

<210> SEQ ID NO 548
<211> LENGTH: 69
<212> TYPE: DNA
<213> ORGANISM: Artificial Sequence
<220> FEATURE:
<223> OTHER INFORMATION: cDNA Sequence of aMTD142 5'-primer

<400> SEQUENCE: 548
gggtttcata tgctgctggc ggcggtgccg gtggcgctgg tggcgccggc aaatattacc 60
gttttctat 69

<210> SEQ ID NO 549
<211> LENGTH: 69
<212> TYPE: DNA
<213> ORGANISM: Artificial Sequence
<220> FEATURE:
<223> OTHER INFORMATION: cDNA Sequence of aMTD143 5'-primer

<400> SEQUENCE: 549
gggtttcata tggcggtgct ggcggtgccg gcggtgctgg tggcgccggc aaatattacc 60
gttttctat 69

<210> SEQ ID NO 550
<211> LENGTH: 69
<212> TYPE: DNA
<213> ORGANISM: Artificial Sequence
<220> FEATURE:
<223> OTHER INFORMATION: cDNA Sequence of aMTD144 5'-primer

<400> SEQUENCE: 550
gggtttcata tggcggtgct ggcggtgccg gcggtgctgg tggcgccggc aaatattacc 60
gttttctat 69

<210> SEQ ID NO 551
<211> LENGTH: 69
<212> TYPE: DNA
<213> ORGANISM: Artificial Sequence
<220> FEATURE:
<223> OTHER INFORMATION: cDNA Sequence of aMTD145 5'-primer

<400> SEQUENCE: 551
gggtttcata tgctgctggc ggtggtgccg gcggtggcgc tggcgccggc aaatattacc 60
gttttctat 69

<210> SEQ ID NO 552
<211> LENGTH: 69
<212> TYPE: DNA
<213> ORGANISM: Artificial Sequence
<220> FEATURE:
<223> OTHER INFORMATION: cDNA Sequence of aMTD152 5'-primer

<400> SEQUENCE: 552
gggtttcata tgctggcggc ggcggtggcg gcggtggcgg cgctgctggc aaatattacc 60
gttttctat 69

<210> SEQ ID NO 553
<211> LENGTH: 69
<212> TYPE: DNA
<213> ORGANISM: Artificial Sequence
<220> FEATURE:
<223> OTHER INFORMATION: cDNA Sequence of aMTD159 5'-primer

<400> SEQUENCE: 553
gggtttcata tgtgctatag cggcagcacc agccagaacc agccgccggc aaatattacc 60
gttttctat 69

<210> SEQ ID NO 554
<211> LENGTH: 69
<212> TYPE: DNA
<213> ORGANISM: Artificial Sequence
<220> FEATURE:
<223> OTHER INFORMATION: cDNA Sequence of aMTD161 5'-primer

<400> SEQUENCE: 554
gggtttcata tggcggtgat tgcgctgccg gcgctgattg cggcgccggc aaatattacc 60
gttttctat 69

<210> SEQ ID NO 555
<211> LENGTH: 69
<212> TYPE: DNA
<213> ORGANISM: Artificial Sequence
<220> FEATURE:
<223> OTHER INFORMATION: cDNA Sequence of aMTD162 5'-primer

<400> SEQUENCE: 555
gggtttcata tggcggtggt ggcgctgccg gcggcgctga ttgtgccggc aaatattacc 60
gttttctat 69

<210> SEQ ID NO 556
<211> LENGTH: 69
<212> TYPE: DNA
<213> ORGANISM: Artificial Sequence
<220> FEATURE:
<223> OTHER INFORMATION: cDNA Sequence of aMTD163 5'-primer

<400> SEQUENCE: 556
gggtttcata tgctggcgct ggtgctgccg gcggcgctgg cggcgccggc aaatattacc 60
gttttctat 69

<210> SEQ ID NO 557
<211> LENGTH: 69
<212> TYPE: DNA
<213> ORGANISM: Artificial Sequence
<220> FEATURE:
<223> OTHER INFORMATION: cDNA Sequence of aMTD164 5'-primer

<400> SEQUENCE: 557
gggtttcata tgctggcggc ggtgctgccg gcgctgctgg cggcgccggc aaatattacc 60
gttttctat 69

<210> SEQ ID NO 558
<211> LENGTH: 69
<212> TYPE: DNA
<213> ORGANISM: Artificial Sequence
<220> FEATURE:
<223> OTHER INFORMATION: cDNA Sequence of aMTD165 5'-primer

<400> SEQUENCE: 558
gggtttcata tggcgctggc ggtgccggtg gcgctggcga ttgtgccggc aaatattacc 60
gttttctat 69

<210> SEQ ID NO 559
<211> LENGTH: 69
<212> TYPE: DNA
<213> ORGANISM: Artificial Sequence
<220> FEATURE:
<223> OTHER INFORMATION: cDNA Sequence of aMTD167 5'-primer

<400> SEQUENCE: 559
gggtttcata tggtggcgat tgcgattccg gcggcgctgg cgattccggc aaatattacc 60
gttttctat 69

<210> SEQ ID NO 560

<211> LENGTH: 69
<212> TYPE: DNA
<213> ORGANISM: Artificial Sequence
<220> FEATURE:
<223> OTHER INFORMATION: cDNA Sequence of aMTD169 5'-primer

<400> SEQUENCE: 560
gggtttcata tggtggcgct ggtggcgccg gcgctgattc tggcgccggc aaatattacc 60
gttttctat 69

<210> SEQ ID NO 561
<211> LENGTH: 69
<212> TYPE: DNA
<213> ORGANISM: Artificial Sequence
<220> FEATURE:
<223> OTHER INFORMATION: cDNA Sequence of aMTD182 5'-primer

<400> SEQUENCE: 561
gggtttcata tggcgctgat tgcgccggtg gtggcgctgg tggcgccggc aaatattacc 60
gttttctat 69

<210> SEQ ID NO 562
<211> LENGTH: 69
<212> TYPE: DNA
<213> ORGANISM: Artificial Sequence
<220> FEATURE:
<223> OTHER INFORMATION: cDNA Sequence of aMTD183 5'-primer

<400> SEQUENCE: 562
gggtttcata tgctgctggc ggcgccggtg gtgattgcgc tggcgccggc aaatattacc 60
gttttctat 69

<210> SEQ ID NO 563
<211> LENGTH: 69
<212> TYPE: DNA
<213> ORGANISM: Artificial Sequence
<220> FEATURE:
<223> OTHER INFORMATION: cDNA Sequence of aMTD184 5'-primer

<400> SEQUENCE: 563
gggtttcata tgctggcggc gattgtgccg gcgattattg cggtgccggc aaatattacc 60
gttttctat 69

<210> SEQ ID NO 564
<211> LENGTH: 69
<212> TYPE: DNA
<213> ORGANISM: Artificial Sequence
<220> FEATURE:
<223> OTHER INFORMATION: cDNA Sequence of aMTD185 5'-primer

<400> SEQUENCE: 564
gggtttcata tggcggcgct ggtgctgccg ctgattattg cggcgccggc aaatattacc 60
gttttctat 69

<210> SEQ ID NO 565
<211> LENGTH: 69
<212> TYPE: DNA
<213> ORGANISM: Artificial Sequence
<220> FEATURE:
<223> OTHER INFORMATION: cDNA Sequence of aMTD189 5'-primer

<400> SEQUENCE: 565
gggtttcata tggtgattct ggtggcgccg gcggtgattg cgccgccggc aaatattacc 60
gttttctat 69

<210> SEQ ID NO 566
<211> LENGTH: 69
<212> TYPE: DNA
<213> ORGANISM: Artificial Sequence
<220> FEATURE:
<223> OTHER INFORMATION: cDNA Sequence of aMTD190 5'-primer

<400> SEQUENCE: 566
gggtttcata tggcggcgat tctggcgccg gcggtgattg cgccgccggc aaatattacc 60
gttttctat 69

<210> SEQ ID NO 567
<211> LENGTH: 69
<212> TYPE: DNA
<213> ORGANISM: Artificial Sequence
<220> FEATURE:
<223> OTHER INFORMATION: cDNA Sequence of aMTD201 5'-primer

<400> SEQUENCE: 567
gggtttcata tgctggcgct ggcggtgccg gcgctggcgg cgctgccggc aaatattacc 60
gttttctat 69

<210> SEQ ID NO 568
<211> LENGTH: 69
<212> TYPE: DNA
<213> ORGANISM: Artificial Sequence
<220> FEATURE:
<223> OTHER INFORMATION: cDNA Sequence of aMTD204 5'-primer

<400> SEQUENCE: 568
gggtttcata tgctgattgc ggcgctgccg gcggtggcgg cgctgccggc aaatattacc 60
gttttctat 69

<210> SEQ ID NO 569
<211> LENGTH: 69
<212> TYPE: DNA
<213> ORGANISM: Artificial Sequence
<220> FEATURE:
<223> OTHER INFORMATION: cDNA Sequence of aMTD205 5'-primer

<400> SEQUENCE: 569
gggtttcata tggcgctggc gctggtgccg gcgattgcgg cgctgccggc aaatattacc 60
gttttctat 69

<210> SEQ ID NO 570
<211> LENGTH: 69
<212> TYPE: DNA
<213> ORGANISM: Artificial Sequence
<220> FEATURE:
<223> OTHER INFORMATION: cDNA Sequence of aMTD210 5'-primer

<400> SEQUENCE: 570
gggtttcata tggcgctgat tgcgctgccg gcgctgccgg cgctgccggc aaatattacc 60
gttttctat 69

<210> SEQ ID NO 571
<211> LENGTH: 69
<212> TYPE: DNA
<213> ORGANISM: Artificial Sequence
<220> FEATURE:

<223> OTHER INFORMATION: cDNA Sequence of aMTD214 5'-primer

<400> SEQUENCE: 571
gggtttcata tggcgctgat tgtggcgccg gcgctgatgg cgctgccggc aaatattacc 60
gttttctat 69

<210> SEQ ID NO 572
<211> LENGTH: 69
<212> TYPE: DNA
<213> ORGANISM: Artificial Sequence
<220> FEATURE:
<223> OTHER INFORMATION: cDNA Sequence of aMTD221 5'-primer

<400> SEQUENCE: 572
gggtttcata tggcggcgat tctggcgccg attgtggcgc tggcgccggc aaatattacc 60
gttttctat 69

<210> SEQ ID NO 573
<211> LENGTH: 69
<212> TYPE: DNA
<213> ORGANISM: Artificial Sequence
<220> FEATURE:
<223> OTHER INFORMATION: cDNA Sequence of aMTD222 5'-primer

<400> SEQUENCE: 573
gggtttcata tggcgctgct gattgcgccg gcggcggtga ttgcgccggc aaatattacc 60
gttttctat 69

<210> SEQ ID NO 574
<211> LENGTH: 69
<212> TYPE: DNA
<213> ORGANISM: Artificial Sequence
<220> FEATURE:
<223> OTHER INFORMATION: cDNA Sequence of aMTD223 5'-primer

<400> SEQUENCE: 574
gggtttcata tggcgattct ggcggtgccg attgcggtgg tggcgccggc aaatattacc 60
gttttctat 69

<210> SEQ ID NO 575
<211> LENGTH: 69
<212> TYPE: DNA
<213> ORGANISM: Artificial Sequence
<220> FEATURE:
<223> OTHER INFORMATION: cDNA Sequence of aMTD224 5'-primer

<400> SEQUENCE: 575
gggtttcata tgattctggc ggcggtgccg attgcgctgg cggcgccggc aaatattacc 60
gttttctat 69

<210> SEQ ID NO 576
<211> LENGTH: 69
<212> TYPE: DNA
<213> ORGANISM: Artificial Sequence
<220> FEATURE:
<223> OTHER INFORMATION: cDNA Sequence of aMTD225 5'-primer

<400> SEQUENCE: 576
gggtttcata tggtggcggc gctgctgccg gcggcggcgg tgctgccggc aaatattacc 60
gttttctat 69

<210> SEQ ID NO 577
<211> LENGTH: 69
<212> TYPE: DNA
<213> ORGANISM: Artificial Sequence
<220> FEATURE:
<223> OTHER INFORMATION: cDNA Sequence of aMTD226 5'-primer

<400> SEQUENCE: 577
gggtttcata tggcgctggt ggcggcgatt ccggcgctgg cgattccggc aaatattacc 60
gttttctat 69

<210> SEQ ID NO 578
<211> LENGTH: 69
<212> TYPE: DNA
<213> ORGANISM: Artificial Sequence
<220> FEATURE:
<223> OTHER INFORMATION: cDNA Sequence of aMTD227 5'-primer

<400> SEQUENCE: 578
gggtttcata tgctggcggc gattgtgccg attgcggcgg cggtgccggc aaatattacc 60
gttttctat 69

<210> SEQ ID NO 579
<211> LENGTH: 69
<212> TYPE: DNA
<213> ORGANISM: Artificial Sequence
<220> FEATURE:
<223> OTHER INFORMATION: cDNA Sequence of aMTD241 5'-primer

<400> SEQUENCE: 579
gggtttcata tggcggcggc ggtggtgccg gtgctgctgg tggcgccggc aaatattacc 60
gttttctat 69

<210> SEQ ID NO 580
<211> LENGTH: 69
<212> TYPE: DNA
<213> ORGANISM: Artificial Sequence
<220> FEATURE:
<223> OTHER INFORMATION: cDNA Sequence of aMTD242 5'-primer

<400> SEQUENCE: 580
gggtttcata tggcggcgct gctggtgccg gcgctggtgg cggcgccggc aaatattacc 60
gttttctat 69

<210> SEQ ID NO 581
<211> LENGTH: 69
<212> TYPE: DNA
<213> ORGANISM: Artificial Sequence
<220> FEATURE:
<223> OTHER INFORMATION: cDNA Sequence of aMTD243 5'-primer

<400> SEQUENCE: 581
gggtttcata tggcggcggt gctgctgccg gtggcgctgg cggcgccggc aaatattacc 60
gttttctat 69

<210> SEQ ID NO 582
<211> LENGTH: 69
<212> TYPE: DNA
<213> ORGANISM: Artificial Sequence
<220> FEATURE:
<223> OTHER INFORMATION: cDNA Sequence of aMTD245 5'-primer

<400> SEQUENCE: 582
gggtttcata tggcggcggc gctggcgccg gtgctggcgc tggtgccggc aaatattacc 60
gttttctat 69

<210> SEQ ID NO 583
<211> LENGTH: 69
<212> TYPE: DNA
<213> ORGANISM: Artificial Sequence
<220> FEATURE:
<223> OTHER INFORMATION: cDNA Sequence of aMTD246 5'-primer

<400> SEQUENCE: 583
gggtttcata tggtggtggc ggtgccgctg ctggtggcgt ttgcggcggc aaatattacc 60
gttttctat 69

<210> SEQ ID NO 584
<211> LENGTH: 69
<212> TYPE: DNA
<213> ORGANISM: Artificial Sequence
<220> FEATURE:
<223> OTHER INFORMATION: cDNA Sequence of aMTD248 5'-primer

<400> SEQUENCE: 584
gggtttcata tggtggcggc gattgtgccg attgcggcgc tggtgccggc aaatattacc 60
gttttctat 69

<210> SEQ ID NO 585
<211> LENGTH: 69
<212> TYPE: DNA
<213> ORGANISM: Artificial Sequence
<220> FEATURE:
<223> OTHER INFORMATION: cDNA Sequence of aMTD261 5'-primer

<400> SEQUENCE: 585
gggtttcata tgctggtgct ggtgccgctg ctggcggcgg cggcgccggc aaatattacc 60
gttttctat 69

<210> SEQ ID NO 586
<211> LENGTH: 69
<212> TYPE: DNA
<213> ORGANISM: Artificial Sequence
<220> FEATURE:
<223> OTHER INFORMATION: cDNA Sequence of aMTD262 5'-primer

<400> SEQUENCE: 586
gggtttcata tggcgctgat tgcggtgccg gcgattattg tggcgccggc aaatattacc 60
gttttctat 69

<210> SEQ ID NO 587
<211> LENGTH: 69
<212> TYPE: DNA
<213> ORGANISM: Artificial Sequence
<220> FEATURE:
<223> OTHER INFORMATION: cDNA Sequence of aMTD263 5'-primer

<400> SEQUENCE: 587
gggtttcata tggcgctggc ggtgattccg gcggcggcga ttctgccggc aaatattacc 60
gttttctat 69

<210> SEQ ID NO 588
<211> LENGTH: 69
<212> TYPE: DNA
<213> ORGANISM: Artificial Sequence
<220> FEATURE:
<223> OTHER INFORMATION: cDNA Sequence of aMTD264 5'-primer

<400> SEQUENCE: 588
gggtttcata tgctggcggc ggcgccggtg gtgattgtga ttgcgccggc aaatattacc 60
gttttctat 69

<210> SEQ ID NO 589
<211> LENGTH: 69
<212> TYPE: DNA
<213> ORGANISM: Artificial Sequence
<220> FEATURE:
<223> OTHER INFORMATION: cDNA Sequence of aMTD265 5'-primer

<400> SEQUENCE: 589
gggtttcata tggtgctggc gattgcgccg ctgctggcgg cggtgccggc aaatattacc 60
gttttctat 69

<210> SEQ ID NO 590
<211> LENGTH: 69
<212> TYPE: DNA
<213> ORGANISM: Artificial Sequence
<220> FEATURE:
<223> OTHER INFORMATION: cDNA Sequence of aMTD281 5'-primer

<400> SEQUENCE: 590
gggtttcata tggcgctgat tgtgctgccg gcggcggtgg cggtgccggc aaatattacc 60
gttttctat 69

<210> SEQ ID NO 591
<211> LENGTH: 69
<212> TYPE: DNA
<213> ORGANISM: Artificial Sequence
<220> FEATURE:
<223> OTHER INFORMATION: cDNA Sequence of aMTD282 5'-primer

<400> SEQUENCE: 591
gggtttcata tggtgctggc ggtggcgccg gcgctgattg tggcgccggc aaatattacc 60
gttttctat 69

<210> SEQ ID NO 592
<211> LENGTH: 69
<212> TYPE: DNA
<213> ORGANISM: Artificial Sequence
<220> FEATURE:
<223> OTHER INFORMATION: cDNA Sequence of aMTD283 5'-primer

<400> SEQUENCE: 592
gggtttcata tggcggcgct gctggcgccg gcgctgattg tggcgccggc aaatattacc 60
gttttctat 69

<210> SEQ ID NO 593
<211> LENGTH: 69
<212> TYPE: DNA
<213> ORGANISM: Artificial Sequence
<220> FEATURE:
<223> OTHER INFORMATION: cDNA Sequence of aMTD284 5'-primer

<400> SEQUENCE: 593
gggtttcata tggcgctgat tgcgccggcg gtggcgctga ttgtgccggc aaatattacc 60
gttttctat 69

<210> SEQ ID NO 594
<211> LENGTH: 69
<212> TYPE: DNA
<213> ORGANISM: Artificial Sequence
<220> FEATURE:
<223> OTHER INFORMATION: cDNA Sequence of aMTD285 5'-primer

<400> SEQUENCE: 594
gggtttcata tggcgattgt gctgctgccg gcggcggtgg tggcgccggc aaatattacc 60
gttttctat 69

<210> SEQ ID NO 595
<211> LENGTH: 69
<212> TYPE: DNA
<213> ORGANISM: Artificial Sequence
<220> FEATURE:
<223> OTHER INFORMATION: cDNA Sequence of aMTD301 5'-primer

<400> SEQUENCE: 595
gggtttcata tggtgattgc ggcgccggtg ctggcggtgc tggcgccggc aaatattacc 60
gttttctat 69

<210> SEQ ID NO 596
<211> LENGTH: 69
<212> TYPE: DNA
<213> ORGANISM: Artificial Sequence
<220> FEATURE:
<223> OTHER INFORMATION: cDNA Sequence of aMTD302 5'-primer

<400> SEQUENCE: 596
gggtttcata tgctggcgct ggcgccggcg ctggcgctgc tggcgccggc aaatattacc 60
gttttctat 69

<210> SEQ ID NO 597
<211> LENGTH: 69
<212> TYPE: DNA
<213> ORGANISM: Artificial Sequence
<220> FEATURE:
<223> OTHER INFORMATION: cDNA Sequence of aMTD304 5'-primer

<400> SEQUENCE: 597
gggtttcata tggcgattat tctggcgccg attgcggcga ttgcgccggc aaatattacc 60
gttttctat 69

<210> SEQ ID NO 598
<211> LENGTH: 69
<212> TYPE: DNA
<213> ORGANISM: Artificial Sequence
<220> FEATURE:
<223> OTHER INFORMATION: cDNA Sequence of aMTD305 5'-primer

<400> SEQUENCE: 598
gggtttcata tgattgcgct ggcggcgccg attctgctgg cggcgccggc aaatattacc 60
gttttctat 69

<210> SEQ ID NO 599
<211> LENGTH: 69
<212> TYPE: DNA
<213> ORGANISM: Artificial Sequence
<220> FEATURE:
<223> OTHER INFORMATION: cDNA Sequence of aMTD321 5'-primer

<400> SEQUENCE: 599
gggtttcata tgattgtggc ggtggcgctg ccggcgctgg cggtgccggc aaatattacc 60
gttttctat 69

<210> SEQ ID NO 600
<211> LENGTH: 69
<212> TYPE: DNA
<213> ORGANISM: Artificial Sequence
<220> FEATURE:
<223> OTHER INFORMATION: cDNA Sequence of aMTD322 5'-primer

<400> SEQUENCE: 600
gggtttcata tggtggtggc gattgtgctg ccggcgctgg cggcgccggc aaatattacc 60
gttttctat 69

<210> SEQ ID NO 601
<211> LENGTH: 69
<212> TYPE: DNA
<213> ORGANISM: Artificial Sequence
<220> FEATURE:
<223> OTHER INFORMATION: cDNA Sequence of aMTD323 5'-primer

<400> SEQUENCE: 601
gggtttcata tgattgtggc ggtggcgctg ccggtggcgc tggcgccggc aaatattacc 60
gttttctat 69

<210> SEQ ID NO 602
<211> LENGTH: 69
<212> TYPE: DNA
<213> ORGANISM: Artificial Sequence
<220> FEATURE:
<223> OTHER INFORMATION: cDNA Sequence of aMTD324 5'-primer

<400> SEQUENCE: 602
gggtttcata tgattgtggc ggtggcgctg ccggcggcgc tggtgccggc aaatattacc 60
gttttctat 69

<210> SEQ ID NO 603
<211> LENGTH: 69
<212> TYPE: DNA
<213> ORGANISM: Artificial Sequence
<220> FEATURE:
<223> OTHER INFORMATION: cDNA Sequence of aMTD325 5'-primer

<400> SEQUENCE: 603
gggtttcata tgattgtggc ggtggcgctg ccggcggtgg cgctgccggc aaatattacc 60
gttttctat 69

<210> SEQ ID NO 604
<211> LENGTH: 69
<212> TYPE: DNA
<213> ORGANISM: Artificial Sequence
<220> FEATURE:
<223> OTHER INFORMATION: cDNA Sequence of aMTD329 5'-primer

<400> SEQUENCE: 604
gggtttcata tgctgccggt gctggtgccg gtggtgccgg tggtgccggc aaatattacc 60
gttttctat 69

<210> SEQ ID NO 605
<211> LENGTH: 69
<212> TYPE: DNA

<213> ORGANISM: Artificial Sequence
<220> FEATURE:
<223> OTHER INFORMATION: cDNA Sequence of aMTD331 5'-primer

<400> SEQUENCE: 605
gggtttcata tggtgccggt gctggtgccg ctggtgccgg tggtgccggc aaatattacc 60
gttttctat 69

<210> SEQ ID NO 606
<211> LENGTH: 69
<212> TYPE: DNA
<213> ORGANISM: Artificial Sequence
<220> FEATURE:
<223> OTHER INFORMATION: cDNA Sequence of aMTD341 5'-primer

<400> SEQUENCE: 606
gggtttcata tgattgtggc ggtggcgctg ccggcggtgc tggcgccggc aaatattacc 60
gttttctat 69

<210> SEQ ID NO 607
<211> LENGTH: 69
<212> TYPE: DNA
<213> ORGANISM: Artificial Sequence
<220> FEATURE:
<223> OTHER INFORMATION: cDNA Sequence of aMTD342 5'-primer

<400> SEQUENCE: 607
gggtttcata tggtgattgt ggcgctggcg ccggcggtgc tggcgccggc aaatattacc 60
gttttctat 69

<210> SEQ ID NO 608
<211> LENGTH: 69
<212> TYPE: DNA
<213> ORGANISM: Artificial Sequence
<220> FEATURE:
<223> OTHER INFORMATION: cDNA Sequence of aMTD343 5'-primer

<400> SEQUENCE: 608
gggtttcata tgattgtggc ggtggcgctg ccggcgctgg tggcgccggc aaatattacc 60
gttttctat 69

<210> SEQ ID NO 609
<211> LENGTH: 69
<212> TYPE: DNA
<213> ORGANISM: Artificial Sequence
<220> FEATURE:
<223> OTHER INFORMATION: cDNA Sequence of aMTD345 5'-primer

<400> SEQUENCE: 609
gggtttcata tggcgctgct gattgtggcg ccggtggcgg tggcgccggc aaatattacc 60
gttttctat 69

<210> SEQ ID NO 610
<211> LENGTH: 69
<212> TYPE: DNA
<213> ORGANISM: Artificial Sequence
<220> FEATURE:
<223> OTHER INFORMATION: cDNA Sequence of aMTD349 5'-primer

<400> SEQUENCE: 610
gggtttcata tggtgccggt gctggtgccg gtggtgccgg tggtgccggc aaatattacc 60
gttttctat 69

<210> SEQ ID NO 611
<211> LENGTH: 69
<212> TYPE: DNA
<213> ORGANISM: Artificial Sequence
<220> FEATURE:
<223> OTHER INFORMATION: cDNA Sequence of aMTD350 5'-primer

<400> SEQUENCE: 611
gggtttcata tggtgccgat tctggtgccg gtggtgccgg tggtgccggc aaatattacc 60
gttttctat 69

<210> SEQ ID NO 612
<211> LENGTH: 69
<212> TYPE: DNA
<213> ORGANISM: Artificial Sequence
<220> FEATURE:
<223> OTHER INFORMATION: cDNA Sequence of aMTD361 5'-primer

<400> SEQUENCE: 612
gggtttcata tggcggtggt gattgtggcg ccggcggtga ttgcgccggc aaatattacc 60
gttttctat 69

<210> SEQ ID NO 613
<211> LENGTH: 69
<212> TYPE: DNA
<213> ORGANISM: Artificial Sequence
<220> FEATURE:
<223> OTHER INFORMATION: cDNA Sequence of aMTD363 5'-primer

<400> SEQUENCE: 613
gggtttcata tggcggtgct ggcggtggcg ccggcgctga ttgtgccggc aaatattacc 60
gttttctat 69

<210> SEQ ID NO 614
<211> LENGTH: 69
<212> TYPE: DNA
<213> ORGANISM: Artificial Sequence
<220> FEATURE:
<223> OTHER INFORMATION: cDNA Sequence of aMTD364 5'-primer

<400> SEQUENCE: 614
gggtttcata tgctggtggc ggcggtggcg ccggcgctga ttgtgccggc aaatattacc 60
gttttctat 69

<210> SEQ ID NO 615
<211> LENGTH: 69
<212> TYPE: DNA
<213> ORGANISM: Artificial Sequence
<220> FEATURE:
<223> OTHER INFORMATION: cDNA Sequence of aMTD365 5'-primer

<400> SEQUENCE: 615
gggtttcata tggcggtgat tgtggtggcg ccggcgctgc tggcgccggc aaatattacc 60
gttttctat 69

<210> SEQ ID NO 616
<211> LENGTH: 69
<212> TYPE: DNA
<213> ORGANISM: Artificial Sequence
<220> FEATURE:
<223> OTHER INFORMATION: cDNA Sequence of aMTD381 5'-primer

<400> SEQUENCE: 616
gggtttcata tggtggtggc gattgtgctg ccggcggtgg cggcgccggc aaatattacc 60
gttttctat 69

<210> SEQ ID NO 617
<211> LENGTH: 69
<212> TYPE: DNA
<213> ORGANISM: Artificial Sequence
<220> FEATURE:
<223> OTHER INFORMATION: cDNA Sequence of aMTD382 5'-primer

<400> SEQUENCE: 617
gggtttcata tggcggcggc gctggtgatt ccggcgattc tggcgccggc aaatattacc 60
gttttctat 69

<210> SEQ ID NO 618
<211> LENGTH: 69
<212> TYPE: DNA
<213> ORGANISM: Artificial Sequence
<220> FEATURE:
<223> OTHER INFORMATION: cDNA Sequence of aMTD383 5'-primer

<400> SEQUENCE: 618
gggtttcata tggtgattgt ggcgctggcg ccggcgctgc tggcgccggc aaatattacc 60
gttttctat 69

<210> SEQ ID NO 619
<211> LENGTH: 69
<212> TYPE: DNA
<213> ORGANISM: Artificial Sequence
<220> FEATURE:
<223> OTHER INFORMATION: cDNA Sequence of aMTD384 5'-primer

<400> SEQUENCE: 619
gggtttcata tggtgattgt ggcgattgcg ccggcgctgc tggcgccggc aaatattacc 60
gttttctat 69

<210> SEQ ID NO 620
<211> LENGTH: 69
<212> TYPE: DNA
<213> ORGANISM: Artificial Sequence
<220> FEATURE:
<223> OTHER INFORMATION: cDNA Sequence of aMTD385 5'-primer

<400> SEQUENCE: 620
gggtttcata tgattgtggc gattgcggtg ccggcgctgg tggcgccggc aaatattacc 60
gttttctat 69

<210> SEQ ID NO 621
<211> LENGTH: 69
<212> TYPE: DNA
<213> ORGANISM: Artificial Sequence
<220> FEATURE:
<223> OTHER INFORMATION: cDNA Sequence of aMTD390 5'-primer

<400> SEQUENCE: 621
gggtttcata tggtgccgct gctggtgccg gtggtgccgg tggtgccggc aaatattacc 60
gttttctat 69

<210> SEQ ID NO 622
<211> LENGTH: 69

<212> TYPE: DNA
<213> ORGANISM: Artificial Sequence
<220> FEATURE:
<223> OTHER INFORMATION: cDNA Sequence of aMTD401 5'-primer

<400> SEQUENCE: 622
gggtttcata tggcggcgct ggcggtgatt ccggcggcga ttctgccggc aaatattacc 60
gttttctat 69

<210> SEQ ID NO 623
<211> LENGTH: 69
<212> TYPE: DNA
<213> ORGANISM: Artificial Sequence
<220> FEATURE:
<223> OTHER INFORMATION: cDNA Sequence of aMTD402 5'-primer

<400> SEQUENCE: 623
gggtttcata tggcgctggc ggcggtgatt ccggcggcga ttctgccggc aaatattacc 60
gttttctat 69

<210> SEQ ID NO 624
<211> LENGTH: 69
<212> TYPE: DNA
<213> ORGANISM: Artificial Sequence
<220> FEATURE:
<223> OTHER INFORMATION: cDNA Sequence of aMTD403 5'-primer

<400> SEQUENCE: 624
gggtttcata tggcggcggc gctggtgatt ccggcggcga ttctgccggc aaatattacc 60
gttttctat 69

<210> SEQ ID NO 625
<211> LENGTH: 69
<212> TYPE: DNA
<213> ORGANISM: Artificial Sequence
<220> FEATURE:
<223> OTHER INFORMATION: cDNA Sequence of aMTD404 5'-primer

<400> SEQUENCE: 625
gggtttcata tgctggcggc ggcggtgatt ccggcggcga ttctgccggc aaatattacc 60
gttttctat 69

<210> SEQ ID NO 626
<211> LENGTH: 69
<212> TYPE: DNA
<213> ORGANISM: Artificial Sequence
<220> FEATURE:
<223> OTHER INFORMATION: cDNA Sequence of aMTD405 5'-primer

<400> SEQUENCE: 626
gggtttcata tgctggcggc ggcggtgatt ccggtggcga ttctgccggc aaatattacc 60
gttttctat 69

<210> SEQ ID NO 627
<211> LENGTH: 69
<212> TYPE: DNA
<213> ORGANISM: Artificial Sequence
<220> FEATURE:
<223> OTHER INFORMATION: cDNA Sequence of aMTD421 5'-primer

<400> SEQUENCE: 627
gggtttcata tggcggcgat tctggcggcg ccgctgattg cggtgccggc aaatattacc 60
gttttctat 69

<210> SEQ ID NO 628
<211> LENGTH: 69
<212> TYPE: DNA
<213> ORGANISM: Artificial Sequence
<220> FEATURE:
<223> OTHER INFORMATION: cDNA Sequence of aMTD422 5'-primer

<400> SEQUENCE: 628
gggtttcata tggtggtggc gattctggcg ccgctgctgg cggcgccggc aaatattacc 60
gttttctat 69

<210> SEQ ID NO 629
<211> LENGTH: 69
<212> TYPE: DNA
<213> ORGANISM: Artificial Sequence
<220> FEATURE:
<223> OTHER INFORMATION: cDNA Sequence of aMTD424 5'-primer

<400> SEQUENCE: 629
gggtttcata tggcggtggt ggtggcggcg ccggtgctgg cgctgccggc aaatattacc 60
gttttctat 69

<210> SEQ ID NO 630
<211> LENGTH: 69
<212> TYPE: DNA
<213> ORGANISM: Artificial Sequence
<220> FEATURE:
<223> OTHER INFORMATION: cDNA Sequence of aMTD425 5'-primer

<400> SEQUENCE: 630
gggtttcata tggcggtggt ggcgattgcg ccggtgctgg cgctgccggc aaatattacc 60
gttttctat 69

<210> SEQ ID NO 631
<211> LENGTH: 69
<212> TYPE: DNA
<213> ORGANISM: Artificial Sequence
<220> FEATURE:
<223> OTHER INFORMATION: cDNA Sequence of aMTD426 5'-primer

<400> SEQUENCE: 631
gggtttcata tggcggcggc gctggcgatt ccgctggcga ttattccggc aaatattacc 60
gttttctat 69

<210> SEQ ID NO 632
<211> LENGTH: 69
<212> TYPE: DNA
<213> ORGANISM: Artificial Sequence
<220> FEATURE:
<223> OTHER INFORMATION: cDNA Sequence of aMTD436 5'-primer

<400> SEQUENCE: 632
gggtttcata tggcggtggt gctggtgatt atgccggcgg cgattccggc aaatattacc 60
gttttctat 69

<210> SEQ ID NO 633
<211> LENGTH: 69
<212> TYPE: DNA
<213> ORGANISM: Artificial Sequence
<220> FEATURE:
<223> OTHER INFORMATION: cDNA Sequence of aMTD442 5'-primer

<400> SEQUENCE: 633
gggtttcata tggcgctggc ggcgctggtg ccggcggtgc tggtgccggc aaatattacc 60
gttttctat 69

<210> SEQ ID NO 634
<211> LENGTH: 69
<212> TYPE: DNA
<213> ORGANISM: Artificial Sequence
<220> FEATURE:
<223> OTHER INFORMATION: cDNA Sequence of aMTD443 5'-primer

<400> SEQUENCE: 634
gggtttcata tggcgctggc ggcgctggtg ccggtggcgc tggtgccggc aaatattacc 60
gttttctat 69

<210> SEQ ID NO 635
<211> LENGTH: 69
<212> TYPE: DNA
<213> ORGANISM: Artificial Sequence
<220> FEATURE:
<223> OTHER INFORMATION: cDNA Sequence of aMTD444 5'-primer

<400> SEQUENCE: 635
gggtttcata tgctggcggc ggcgctggtg ccggtggcgc tggtgccggc aaatattacc 60
gttttctat 69

<210> SEQ ID NO 636
<211> LENGTH: 69
<212> TYPE: DNA
<213> ORGANISM: Artificial Sequence
<220> FEATURE:
<223> OTHER INFORMATION: cDNA Sequence of aMTD445 5'-primer

<400> SEQUENCE: 636
gggtttcata tggcgctggc ggcgctggtg ccggcgctgg tggtgccggc aaatattacc 60
gttttctat 69

<210> SEQ ID NO 637
<211> LENGTH: 69
<212> TYPE: DNA
<213> ORGANISM: Artificial Sequence
<220> FEATURE:
<223> OTHER INFORMATION: cDNA Sequence of aMTD461 5'-primer

<400> SEQUENCE: 637
gggtttcata tgattgcggc ggtgattgtg ccggcggtgg cgctgccggc aaatattacc 60
gttttctat 69

<210> SEQ ID NO 638
<211> LENGTH: 69
<212> TYPE: DNA
<213> ORGANISM: Artificial Sequence
<220> FEATURE:
<223> OTHER INFORMATION: cDNA Sequence of aMTD462 5'-primer

<400> SEQUENCE: 638
gggtttcata tgattgcggc ggtgctggtg ccggcggtgg cgctgccggc aaatattacc 60
gttttctat 69

<210> SEQ ID NO 639

<211> LENGTH: 69
<212> TYPE: DNA
<213> ORGANISM: Artificial Sequence
<220> FEATURE:
<223> OTHER INFORMATION: cDNA Sequence of aMTD463 5'-primer

<400> SEQUENCE: 639
gggtttcata tggcggtggc gattctggtg ccgctgctgg cggcgccggc aaatattacc 60
gttttctat 69

<210> SEQ ID NO 640
<211> LENGTH: 69
<212> TYPE: DNA
<213> ORGANISM: Artificial Sequence
<220> FEATURE:
<223> OTHER INFORMATION: cDNA Sequence of aMTD464 5'-primer

<400> SEQUENCE: 640
gggtttcata tggcggtggt gattctggtg ccgctggcgg cggcgccggc aaatattacc 60
gttttctat 69

<210> SEQ ID NO 641
<211> LENGTH: 69
<212> TYPE: DNA
<213> ORGANISM: Artificial Sequence
<220> FEATURE:
<223> OTHER INFORMATION: cDNA Sequence of aMTD465 5'-primer

<400> SEQUENCE: 641
gggtttcata tgattgcggc ggtgattgtg ccggtggcgg cgctgccggc aaatattacc 60
gttttctat 69

<210> SEQ ID NO 642
<211> LENGTH: 69
<212> TYPE: DNA
<213> ORGANISM: Artificial Sequence
<220> FEATURE:
<223> OTHER INFORMATION: cDNA Sequence of aMTD466 5'-primer

<400> SEQUENCE: 642
gggtttcata tgattattgc ggcggcggcg ccgctggcga ttattccggc aaatattacc 60
gttttctat 69

<210> SEQ ID NO 643
<211> LENGTH: 69
<212> TYPE: DNA
<213> ORGANISM: Artificial Sequence
<220> FEATURE:
<223> OTHER INFORMATION: cDNA Sequence of aMTD481 5'-primer

<400> SEQUENCE: 643
gggtttcata tggcgattgc gattgcgatt gtgccggtgg cgctgccggc aaatattacc 60
gttttctat 69

<210> SEQ ID NO 644
<211> LENGTH: 69
<212> TYPE: DNA
<213> ORGANISM: Artificial Sequence
<220> FEATURE:
<223> OTHER INFORMATION: cDNA Sequence of aMTD482 5'-primer

<400> SEQUENCE: 644
gggtttcata tgattctggc ggtggcggcg attccggtgg cggtgccggc aaatattacc 60
gttttctat 69

<210> SEQ ID NO 645
<211> LENGTH: 69
<212> TYPE: DNA
<213> ORGANISM: Artificial Sequence
<220> FEATURE:
<223> OTHER INFORMATION: cDNA Sequence of aMTD483 5'-primer

<400> SEQUENCE: 645
gggtttcata tgattctggc ggcggcgatt attccggcgg cgctgccggc aaatattacc 60
gttttctat 69

<210> SEQ ID NO 646
<211> LENGTH: 69
<212> TYPE: DNA
<213> ORGANISM: Artificial Sequence
<220> FEATURE:
<223> OTHER INFORMATION: cDNA Sequence of aMTD484 5'-primer

<400> SEQUENCE: 646
gggtttcata tgctggcggt ggtgctggcg gcgccggcga ttgtgccggc aaatattacc 60
gttttctat 69

<210> SEQ ID NO 647
<211> LENGTH: 69
<212> TYPE: DNA
<213> ORGANISM: Artificial Sequence
<220> FEATURE:
<223> OTHER INFORMATION: cDNA Sequence of aMTD485 5'-primer

<400> SEQUENCE: 647
gggtttcata tggcgattct ggcggcgatt gtgccgctgg cggtgccggc aaatattacc 60
gttttctat 69

<210> SEQ ID NO 648
<211> LENGTH: 69
<212> TYPE: DNA
<213> ORGANISM: Artificial Sequence
<220> FEATURE:
<223> OTHER INFORMATION: cDNA Sequence of aMTD501 5'-primer

<400> SEQUENCE: 648
gggtttcata tggtgattgt ggcgctggcg gtgccggcgc tggcgccggc aaatattacc 60
gttttctat 69

<210> SEQ ID NO 649
<211> LENGTH: 69
<212> TYPE: DNA
<213> ORGANISM: Artificial Sequence
<220> FEATURE:
<223> OTHER INFORMATION: cDNA Sequence of aMTD502 5'-primer

<400> SEQUENCE: 649
gggtttcata tggcgattgt ggcgctggcg gtgccggtgc tggcgccggc aaatattacc 60
gttttctat 69

<210> SEQ ID NO 650
<211> LENGTH: 69
<212> TYPE: DNA
<213> ORGANISM: Artificial Sequence
<220> FEATURE:

<223> OTHER INFORMATION: cDNA Sequence of aMTD503 5'-primer

<400> SEQUENCE: 650
gggtttcata tggcggcgat tattattgtg ctgccggcgg cgctgccggc aaatattacc 60
gttttctat 69

<210> SEQ ID NO 651
<211> LENGTH: 69
<212> TYPE: DNA
<213> ORGANISM: Artificial Sequence
<220> FEATURE:
<223> OTHER INFORMATION: cDNA Sequence of aMTD504 5'-primer

<400> SEQUENCE: 651
gggtttcata tgctgattgt ggcgctggcg gtgccggcgc tggcgccggc aaatattacc 60
gttttctat 69

<210> SEQ ID NO 652
<211> LENGTH: 69
<212> TYPE: DNA
<213> ORGANISM: Artificial Sequence
<220> FEATURE:
<223> OTHER INFORMATION: cDNA Sequence of aMTD505 5'-primer

<400> SEQUENCE: 652
gggtttcata tggcgattat tattgtgatt gcgccggcgg cggcgccggc aaatattacc 60
gttttctat 69

<210> SEQ ID NO 653
<211> LENGTH: 69
<212> TYPE: DNA
<213> ORGANISM: Artificial Sequence
<220> FEATURE:
<223> OTHER INFORMATION: cDNA Sequence of aMTD521 5'-primer

<400> SEQUENCE: 653
gggtttcata tgctggcggc gctgattgtg gtgccggcgg tggcgccggc aaatattacc 60
gttttctat 69

<210> SEQ ID NO 654
<211> LENGTH: 69
<212> TYPE: DNA
<213> ORGANISM: Artificial Sequence
<220> FEATURE:
<223> OTHER INFORMATION: cDNA Sequence of aMTD522 5'-primer

<400> SEQUENCE: 654
gggtttcata tggcgctgct ggtgattgcg gtgccggcgg tggcgccggc aaatattacc 60
gttttctat 69

<210> SEQ ID NO 655
<211> LENGTH: 69
<212> TYPE: DNA
<213> ORGANISM: Artificial Sequence
<220> FEATURE:
<223> OTHER INFORMATION: cDNA Sequence of aMTD524 5'-primer

<400> SEQUENCE: 655
gggtttcata tggcggtggc gctgattgtg gtgccggcgc tggcgccggc aaatattacc 60
gttttctat 69

<210> SEQ ID NO 656
<211> LENGTH: 69
<212> TYPE: DNA
<213> ORGANISM: Artificial Sequence
<220> FEATURE:
<223> OTHER INFORMATION: cDNA Sequence of aMTD525 5'-primer

<400> SEQUENCE: 656
gggtttcata tggcgctggc gattgtggtg gcgccggtgg cggtgccggc aaatattacc 60
gttttctat 69

<210> SEQ ID NO 657
<211> LENGTH: 69
<212> TYPE: DNA
<213> ORGANISM: Artificial Sequence
<220> FEATURE:
<223> OTHER INFORMATION: cDNA Sequence of aMTD527 5'-primer

<400> SEQUENCE: 657
gggtttcata tgctggtgct ggcggcggtg gcgccgattg cgattccggc aaatattacc 60
gttttctat 69

<210> SEQ ID NO 658
<211> LENGTH: 69
<212> TYPE: DNA
<213> ORGANISM: Artificial Sequence
<220> FEATURE:
<223> OTHER INFORMATION: cDNA Sequence of aMTD541 5'-primer

<400> SEQUENCE: 658
gggtttcata tgctgctggc gctgattatt gcgccggcgg cggcgccggc aaatattacc 60
gttttctat 69

<210> SEQ ID NO 659
<211> LENGTH: 69
<212> TYPE: DNA
<213> ORGANISM: Artificial Sequence
<220> FEATURE:
<223> OTHER INFORMATION: cDNA Sequence of aMTD542 5'-primer

<400> SEQUENCE: 659
gggtttcata tggcgctggc gctgattatt gtgccggcgg tggcgccggc aaatattacc 60
gttttctat 69

<210> SEQ ID NO 660
<211> LENGTH: 69
<212> TYPE: DNA
<213> ORGANISM: Artificial Sequence
<220> FEATURE:
<223> OTHER INFORMATION: cDNA Sequence of aMTD543 5'-primer

<400> SEQUENCE: 660
gggtttcata tgctgctggc ggcgctgatt gcgccggcgg cgctgccggc aaatattacc 60
gttttctat 69

<210> SEQ ID NO 661
<211> LENGTH: 69
<212> TYPE: DNA
<213> ORGANISM: Artificial Sequence
<220> FEATURE:
<223> OTHER INFORMATION: cDNA Sequence of aMTD544 5'-primer

<400> SEQUENCE: 661
gggtttcata tgattgtggc gctgattgtg gcgccggcgg cggtgccggc aaatattacc 60
gttttctat 69

<210> SEQ ID NO 662
<211> LENGTH: 69
<212> TYPE: DNA
<213> ORGANISM: Artificial Sequence
<220> FEATURE:
<223> OTHER INFORMATION: cDNA Sequence of aMTD545 5'-primer

<400> SEQUENCE: 662
gggtttcata tggtggtgct ggtgctggcg gcgccggcgg cggtgccggc aaatattacc 60
gttttctat 69

<210> SEQ ID NO 663
<211> LENGTH: 69
<212> TYPE: DNA
<213> ORGANISM: Artificial Sequence
<220> FEATURE:
<223> OTHER INFORMATION: cDNA Sequence of aMTD561 5'-primer

<400> SEQUENCE: 663
gggtttcata tggcggcggt ggcgattgtg ctgccggcgg tggtgccggc aaatattacc 60
gttttctat 69

<210> SEQ ID NO 664
<211> LENGTH: 69
<212> TYPE: DNA
<213> ORGANISM: Artificial Sequence
<220> FEATURE:
<223> OTHER INFORMATION: cDNA Sequence of aMTD562 5'-primer

<400> SEQUENCE: 664
gggtttcata tggcgctgat tgcggcgatt gtgccggcgc tggtgccggc aaatattacc 60
gttttctat 69

<210> SEQ ID NO 665
<211> LENGTH: 69
<212> TYPE: DNA
<213> ORGANISM: Artificial Sequence
<220> FEATURE:
<223> OTHER INFORMATION: cDNA Sequence of aMTD563 5'-primer

<400> SEQUENCE: 665
gggtttcata tggcgctggc ggtgattgtg gtgccggcgc tggcgccggc aaatattacc 60
gttttctat 69

<210> SEQ ID NO 666
<211> LENGTH: 69
<212> TYPE: DNA
<213> ORGANISM: Artificial Sequence
<220> FEATURE:
<223> OTHER INFORMATION: cDNA Sequence of aMTD564 5'-primer

<400> SEQUENCE: 666
gggtttcata tggtggcgat tgcgctgatt gtgccggcgc tggcgccggc aaatattacc 60
gttttctat 69

<210> SEQ ID NO 667
<211> LENGTH: 69
<212> TYPE: DNA
<213> ORGANISM: Artificial Sequence
<220> FEATURE:
<223> OTHER INFORMATION: cDNA Sequence of aMTD565 5'-primer

<400> SEQUENCE: 667
gggtttcata tggtggcgat tgtgctggtg gcgccggcgg tggcgccggc aaatattacc 60
gttttctat 69

<210> SEQ ID NO 668
<211> LENGTH: 69
<212> TYPE: DNA
<213> ORGANISM: Artificial Sequence
<220> FEATURE:
<223> OTHER INFORMATION: cDNA Sequence of aMTD577 5'-primer

<400> SEQUENCE: 668
gggtttcata tggcggcggt gctgattgtg ccgattatgg tgatgccggc aaatattacc 60
gttttctat 69

<210> SEQ ID NO 669
<211> LENGTH: 69
<212> TYPE: DNA
<213> ORGANISM: Artificial Sequence
<220> FEATURE:
<223> OTHER INFORMATION: cDNA Sequence of aMTD582 5'-primer

<400> SEQUENCE: 669
gggtttcata tggtggcggt ggcgctgatt gtgccggcgc tggcgccggc aaatattacc 60
gttttctat 69

<210> SEQ ID NO 670
<211> LENGTH: 69
<212> TYPE: DNA
<213> ORGANISM: Artificial Sequence
<220> FEATURE:
<223> OTHER INFORMATION: cDNA Sequence of aMTD583 5'-primer

<400> SEQUENCE: 670
gggtttcata tggcggtgat tctggcgctg gcgccgattg tggcgccggc aaatattacc 60
gttttctat 69

<210> SEQ ID NO 671
<211> LENGTH: 69
<212> TYPE: DNA
<213> ORGANISM: Artificial Sequence
<220> FEATURE:
<223> OTHER INFORMATION: cDNA Sequence of aMTD585 5'-primer

<400> SEQUENCE: 671
gggtttcata tggcgctgat tgtggcgatt gcgccggcgc tggtgccggc aaatattacc 60
gttttctat 69

<210> SEQ ID NO 672
<211> LENGTH: 69
<212> TYPE: DNA
<213> ORGANISM: Artificial Sequence
<220> FEATURE:
<223> OTHER INFORMATION: cDNA Sequence of aMTD601 5'-primer

<400> SEQUENCE: 672
gggtttcata tggcggcgat tctgattgcg gtgccgattg cggcgccggc aaatattacc 60
gttttctat 69

<210> SEQ ID NO 673
<211> LENGTH: 69
<212> TYPE: DNA
<213> ORGANISM: Artificial Sequence
<220> FEATURE:
<223> OTHER INFORMATION: cDNA Sequence of aMTD602 5'-primer

<400> SEQUENCE: 673
gggtttcata tggtgattgt ggcgctggcg gcgccggtgc tggcgccggc aaatattacc 60
gttttctat 69

<210> SEQ ID NO 674
<211> LENGTH: 69
<212> TYPE: DNA
<213> ORGANISM: Artificial Sequence
<220> FEATURE:
<223> OTHER INFORMATION: cDNA Sequence of aMTD603 5'-primer

<400> SEQUENCE: 674
gggtttcata tggtgctggt ggcgctggcg gcgccggtga ttgcgccggc aaatattacc 60
gttttctat 69

<210> SEQ ID NO 675
<211> LENGTH: 69
<212> TYPE: DNA
<213> ORGANISM: Artificial Sequence
<220> FEATURE:
<223> OTHER INFORMATION: cDNA Sequence of aMTD604 5'-primer

<400> SEQUENCE: 675
gggtttcata tggtggcgct gattgcggtg gcgccggcgg tggtgccggc aaatattacc 60
gttttctat 69

<210> SEQ ID NO 676
<211> LENGTH: 69
<212> TYPE: DNA
<213> ORGANISM: Artificial Sequence
<220> FEATURE:
<223> OTHER INFORMATION: cDNA Sequence of aMTD605 5'-primer

<400> SEQUENCE: 676
gggtttcata tggtgattgc ggcggtgctg gcgccggtgg cggtgccggc aaatattacc 60
gttttctat 69

<210> SEQ ID NO 677
<211> LENGTH: 69
<212> TYPE: DNA
<213> ORGANISM: Artificial Sequence
<220> FEATURE:
<223> OTHER INFORMATION: cDNA Sequence of aMTD606 5'-primer

<400> SEQUENCE: 677
gggtttcata tggcggcggc gattgcggcg attccgatta ttattccggc aaatattacc 60
gttttctat 69

<210> SEQ ID NO 678
<211> LENGTH: 69
<212> TYPE: DNA
<213> ORGANISM: Artificial Sequence
<220> FEATURE:
<223> OTHER INFORMATION: cDNA Sequence of aMTD622 5'-primer

<400> SEQUENCE: 678
gggtttcata tggcggcggc gattgcggcg attccgatta ttattccggc aaatattacc 60
gttttctat 69

<210> SEQ ID NO 679
<211> LENGTH: 69
<212> TYPE: DNA
<213> ORGANISM: Artificial Sequence
<220> FEATURE:
<223> OTHER INFORMATION: cDNA Sequence of aMTD623 5'-primer

<400> SEQUENCE: 679
gggtttcata tggtggcggc ggcgattgcg ctgccggcga ttgtgccggc aaatattacc 60
gttttctat 69

<210> SEQ ID NO 680
<211> LENGTH: 69
<212> TYPE: DNA
<213> ORGANISM: Artificial Sequence
<220> FEATURE:
<223> OTHER INFORMATION: cDNA Sequence of aMTD625 5'-primer

<400> SEQUENCE: 680
gggtttcata tgattctggc ggcggcggcg gcgccgctga ttgtgccggc aaatattacc 60
gttttctat 69

<210> SEQ ID NO 681
<211> LENGTH: 69
<212> TYPE: DNA
<213> ORGANISM: Artificial Sequence
<220> FEATURE:
<223> OTHER INFORMATION: cDNA Sequence of aMTD635 5'-primer

<400> SEQUENCE: 681
gggtttcata tgggcagcac cggcggcagc cagcagaaca accagtatgc aaatattacc 60
gttttctat 69

<210> SEQ ID NO 682
<211> LENGTH: 69
<212> TYPE: DNA
<213> ORGANISM: Artificial Sequence
<220> FEATURE:
<223> OTHER INFORMATION: cDNA Sequence of aMTD643 5'-primer

<400> SEQUENCE: 682
gggtttcata tgctggcgct ggtgctggcg gcgccggcga ttgtgccggc aaatattacc 60
gttttctat 69

<210> SEQ ID NO 683
<211> LENGTH: 69
<212> TYPE: DNA
<213> ORGANISM: Artificial Sequence
<220> FEATURE:
<223> OTHER INFORMATION: cDNA Sequence of aMTD645 5'-primer

<400> SEQUENCE: 683
gggtttcata tggcgctggc ggtggtggcg ctgccggcga ttgtgccggc aaatattacc 60
gttttctat 69

<210> SEQ ID NO 684
<211> LENGTH: 69
<212> TYPE: DNA

<213> ORGANISM: Artificial Sequence
<220> FEATURE:
<223> OTHER INFORMATION: cDNA Sequence of aMTD661 5'-primer

<400> SEQUENCE: 684
gggtttcata tggcggcgat tctggcgccg attgtggcgg cgctgccggc aaatattacc 60
gttttctat 69

<210> SEQ ID NO 685
<211> LENGTH: 69
<212> TYPE: DNA
<213> ORGANISM: Artificial Sequence
<220> FEATURE:
<223> OTHER INFORMATION: cDNA Sequence of aMTD664 5'-primer

<400> SEQUENCE: 685
gggtttcata tgattctgat tgcgattgcg attccggcgg cggcgccggc aaatattacc 60
gttttctat 69

<210> SEQ ID NO 686
<211> LENGTH: 69
<212> TYPE: DNA
<213> ORGANISM: Artificial Sequence
<220> FEATURE:
<223> OTHER INFORMATION: cDNA Sequence of aMTD665 5'-primer

<400> SEQUENCE: 686
gggtttcata tgctggcgat tgtgctggcg gcgccggtgg cggtgccggc aaatattacc 60
gttttctat 69

<210> SEQ ID NO 687
<211> LENGTH: 69
<212> TYPE: DNA
<213> ORGANISM: Artificial Sequence
<220> FEATURE:
<223> OTHER INFORMATION: cDNA Sequence of aMTD666 5'-primer

<400> SEQUENCE: 687
gggtttcata tggcggcgat tgcgattatt gcgccggcga ttgtgccggc aaatattacc 60
gttttctat 69

<210> SEQ ID NO 688
<211> LENGTH: 69
<212> TYPE: DNA
<213> ORGANISM: Artificial Sequence
<220> FEATURE:
<223> OTHER INFORMATION: cDNA Sequence of aMTD667 5'-primer

<400> SEQUENCE: 688
gggtttcata tgctggcggt ggcgattgtg gcgccggcgc tggtgccggc aaatattacc 60
gttttctat 69

<210> SEQ ID NO 689
<211> LENGTH: 69
<212> TYPE: DNA
<213> ORGANISM: Artificial Sequence
<220> FEATURE:
<223> OTHER INFORMATION: cDNA Sequence of aMTD676 5'-primer

<400> SEQUENCE: 689
gggtttcata tggtgccgct gctggtgccg gtgccggtgg tggtgccggc aaatattacc 60
gttttctat 69

<210> SEQ ID NO 690
<211> LENGTH: 69
<212> TYPE: DNA
<213> ORGANISM: Artificial Sequence
<220> FEATURE:
<223> OTHER INFORMATION: cDNA Sequence of aMTD683 5'-primer

<400> SEQUENCE: 690
gggtttcata tgctggcgat tgtgctggcg gcgccggcgg tgctgccggc aaatattacc 60
gttttctat 69

<210> SEQ ID NO 691
<211> LENGTH: 69
<212> TYPE: DNA
<213> ORGANISM: Artificial Sequence
<220> FEATURE:
<223> OTHER INFORMATION: cDNA Sequence of aMTD684 5'-primer

<400> SEQUENCE: 691
gggtttcata tggcggcgat tgtgctggcg ctgccggcgg tgctgccggc aaatattacc 60
gttttctat 69

<210> SEQ ID NO 692
<211> LENGTH: 69
<212> TYPE: DNA
<213> ORGANISM: Artificial Sequence
<220> FEATURE:
<223> OTHER INFORMATION: cDNA Sequence of aMTD685 5'-primer

<400> SEQUENCE: 692
gggtttcata tggcgctgct ggtggcggtg ctgccggcgg cgctgccggc aaatattacc 60
gttttctat 69

<210> SEQ ID NO 693
<211> LENGTH: 69
<212> TYPE: DNA
<213> ORGANISM: Artificial Sequence
<220> FEATURE:
<223> OTHER INFORMATION: cDNA Sequence of aMTD686 5'-primer

<400> SEQUENCE: 693
gggtttcata tggcggcgct ggtggcggtg ctgccggtgg cgctgccggc aaatattacc 60
gttttctat 69

<210> SEQ ID NO 694
<211> LENGTH: 69
<212> TYPE: DNA
<213> ORGANISM: Artificial Sequence
<220> FEATURE:
<223> OTHER INFORMATION: cDNA Sequence of aMTD687 5'-primer

<400> SEQUENCE: 694
gggtttcata tggcgattct ggcggtggcg ctgccgctgc tggcgccggc aaatattacc 60
gttttctat 69

<210> SEQ ID NO 695
<211> LENGTH: 69
<212> TYPE: DNA
<213> ORGANISM: Artificial Sequence
<220> FEATURE:
<223> OTHER INFORMATION: cDNA Sequence of aMTD692 5'-primer

<400> SEQUENCE: 695
gggtttcata tgccggcgcc gctgccgccg gtggtgattc tggcggtggc aaatattacc 60
gttttctat 69

<210> SEQ ID NO 696
<211> LENGTH: 69
<212> TYPE: DNA
<213> ORGANISM: Artificial Sequence
<220> FEATURE:
<223> OTHER INFORMATION: cDNA Sequence of aMTD693 5'-primer

<400> SEQUENCE: 696
gggtttcata tggcggcgcc ggtgctgccg gtggcggtgc cgattgtggc aaatattacc 60
gttttctat 69

<210> SEQ ID NO 697
<211> LENGTH: 69
<212> TYPE: DNA
<213> ORGANISM: Artificial Sequence
<220> FEATURE:
<223> OTHER INFORMATION: cDNA Sequence of aMTD700 5'-primer

<400> SEQUENCE: 697
gggtttcata tgggcaccag caacacctgc cagagcaacc agaacagcgc aaatattacc 60
gttttctat 69

<210> SEQ ID NO 698
<211> LENGTH: 69
<212> TYPE: DNA
<213> ORGANISM: Artificial Sequence
<220> FEATURE:
<223> OTHER INFORMATION: cDNA Sequence of aMTD703 5'-primer

<400> SEQUENCE: 698
gggtttcata tgattgtggc ggtggcgctg gtgccggcgc tggcgccggc aaatattacc 60
gttttctat 69

<210> SEQ ID NO 699
<211> LENGTH: 68
<212> TYPE: DNA
<213> ORGANISM: Artificial Sequence
<220> FEATURE:
<223> OTHER INFORMATION: cDNA Sequence of aMTD705 5'-primer

<400> SEQUENCE: 699
gggtttcata tattgtggcg gtggcgctgc tgccggcgct ggcgccggca aatattaccg 60
ttttctat 68

<210> SEQ ID NO 700
<211> LENGTH: 69
<212> TYPE: DNA
<213> ORGANISM: Artificial Sequence
<220> FEATURE:
<223> OTHER INFORMATION: cDNA Sequence of aMTD706 5'-primer

<400> SEQUENCE: 700
gggtttcata tgattgtggc ggtggcgctg ctgccggcgg tggcgccggc aaatattacc 60
gttttctat 69

<210> SEQ ID NO 701
<211> LENGTH: 69

-continued

<212> TYPE: DNA
<213> ORGANISM: Artificial Sequence
<220> FEATURE:
<223> OTHER INFORMATION: cDNA Sequence of aMTD707 5'-primer

<400> SEQUENCE: 701
gggtttcata tgattgtggc gctggcggtg ctgccggcgg tggcgccggc aaatattacc 60
gttttctat 69

<210> SEQ ID NO 702
<211> LENGTH: 69
<212> TYPE: DNA
<213> ORGANISM: Artificial Sequence
<220> FEATURE:
<223> OTHER INFORMATION: cDNA Sequence of aMTD724 5'-primer

<400> SEQUENCE: 702
gggtttcata tggtggcggt gctggcggtg ctgccggcgc tggcgccggc aaatattacc 60
gttttctat 69

<210> SEQ ID NO 703
<211> LENGTH: 69
<212> TYPE: DNA
<213> ORGANISM: Artificial Sequence
<220> FEATURE:
<223> OTHER INFORMATION: cDNA Sequence of aMTD725 5'-primer

<400> SEQUENCE: 703
gggtttcata tgattgcggt gctggcggtg gcgccggcgg tgctgccggc aaatattacc 60
gttttctat 69

<210> SEQ ID NO 704
<211> LENGTH: 69
<212> TYPE: DNA
<213> ORGANISM: Artificial Sequence
<220> FEATURE:
<223> OTHER INFORMATION: cDNA Sequence of aMTD726 5'-primer

<400> SEQUENCE: 704
gggtttcata tgctggcggt ggcgattatt gcgccggcgg tggcgccggc aaatattacc 60
gttttctat 69

<210> SEQ ID NO 705
<211> LENGTH: 69
<212> TYPE: DNA
<213> ORGANISM: Artificial Sequence
<220> FEATURE:
<223> OTHER INFORMATION: cDNA Sequence of aMTD727 5'-primer

<400> SEQUENCE: 705
gggtttcata tggtggcgct ggcgattgcg ctgccggcgg tgctgccggc aaatattacc 60
gttttctat 69

<210> SEQ ID NO 706
<211> LENGTH: 69
<212> TYPE: DNA
<213> ORGANISM: Artificial Sequence
<220> FEATURE:
<223> OTHER INFORMATION: cDNA Sequence of aMTD743 5'-primer

<400> SEQUENCE: 706
gggtttcata tggcgattgc gattgcgctg gtgccggtgg cgctgccggc aaatattacc 60
gttttctat 69

<210> SEQ ID NO 707
<211> LENGTH: 69
<212> TYPE: DNA
<213> ORGANISM: Artificial Sequence
<220> FEATURE:
<223> OTHER INFORMATION: cDNA Sequence of aMTD744 5'-primer

<400> SEQUENCE: 707
gggtttcata tggcggcggt ggtgattgtg gcgccggtgg cgctgccggc aaatattacc 60
gttttctat 69

<210> SEQ ID NO 708
<211> LENGTH: 69
<212> TYPE: DNA
<213> ORGANISM: Artificial Sequence
<220> FEATURE:
<223> OTHER INFORMATION: cDNA Sequence of aMTD745 5'-primer

<400> SEQUENCE: 708
gggtttcata tggcggcgat tctggcgatt gtggcgccgc tggcgccggc aaatattacc 60
gttttctat 69

<210> SEQ ID NO 709
<211> LENGTH: 69
<212> TYPE: DNA
<213> ORGANISM: Artificial Sequence
<220> FEATURE:
<223> OTHER INFORMATION: cDNA Sequence of aMTD746 5'-primer

<400> SEQUENCE: 709
gggtttcata tggtggcgat tattgtggtg gcgccggcgc tggcgccggc aaatattacc 60
gttttctat 69

<210> SEQ ID NO 710
<211> LENGTH: 69
<212> TYPE: DNA
<213> ORGANISM: Artificial Sequence
<220> FEATURE:
<223> OTHER INFORMATION: cDNA Sequence of aMTD747 5'-primer

<400> SEQUENCE: 710
gggtttcata tggtggcgct gctggcgatt gcgccggcgc tggcgccggc aaatattacc 60
gttttctat 69

<210> SEQ ID NO 711
<211> LENGTH: 69
<212> TYPE: DNA
<213> ORGANISM: Artificial Sequence
<220> FEATURE:
<223> OTHER INFORMATION: cDNA Sequence of aMTD750 5'-primer

<400> SEQUENCE: 711
gggtttcata tgctggcgat tgcggcgatt gcgccgctgg cgattccggc aaatattacc 60
gttttctat 69

<210> SEQ ID NO 712
<211> LENGTH: 69
<212> TYPE: DNA
<213> ORGANISM: Artificial Sequence
<220> FEATURE:
<223> OTHER INFORMATION: cDNA Sequence of aMTD763 5'-primer

<400> SEQUENCE: 712
gggtttcata tggtggcggt gctgattgcg gtgccggcgc tggcgccggc aaatattacc 60
gttttctat 69

<210> SEQ ID NO 713
<211> LENGTH: 69
<212> TYPE: DNA
<213> ORGANISM: Artificial Sequence
<220> FEATURE:
<223> OTHER INFORMATION: cDNA Sequence of aMTD764 5'-primer

<400> SEQUENCE: 713
gggtttcata tggcggtggc gctggcggtg ctgccggcgg tggtgccggc aaatattacc 60
gttttctat 69

<210> SEQ ID NO 714
<211> LENGTH: 69
<212> TYPE: DNA
<213> ORGANISM: Artificial Sequence
<220> FEATURE:
<223> OTHER INFORMATION: cDNA Sequence of aMTD765 5'-primer

<400> SEQUENCE: 714
gggtttcata tggcggtggc gctggcggtg gtgccggcgg tgctgccggc aaatattacc 60
gttttctat 69

<210> SEQ ID NO 715
<211> LENGTH: 69
<212> TYPE: DNA
<213> ORGANISM: Artificial Sequence
<220> FEATURE:
<223> OTHER INFORMATION: cDNA Sequence of aMTD766 5'-primer

<400> SEQUENCE: 715
gggtttcata tgattgtggt gattgcggtg gcgccggcgg tggcgccggc aaatattacc 60
gttttctat 69

<210> SEQ ID NO 716
<211> LENGTH: 69
<212> TYPE: DNA
<213> ORGANISM: Artificial Sequence
<220> FEATURE:
<223> OTHER INFORMATION: cDNA Sequence of aMTD767 5'-primer

<400> SEQUENCE: 716
gggtttcata tgattgtggt ggcggcggtg gtgccggcgc tggcgccggc aaatattacc 60
gttttctat 69

<210> SEQ ID NO 717
<211> LENGTH: 69
<212> TYPE: DNA
<213> ORGANISM: Artificial Sequence
<220> FEATURE:
<223> OTHER INFORMATION: cDNA Sequence of aMTD772 5'-primer

<400> SEQUENCE: 717
gggtttcata tgctgccggt ggcgccggtg attccgatta ttgtgccggc aaatattacc 60
gttttctat 69

<210> SEQ ID NO 718

<211> LENGTH: 69
<212> TYPE: DNA
<213> ORGANISM: Artificial Sequence
<220> FEATURE:
<223> OTHER INFORMATION: cDNA Sequence of aMTD783 5'-primer

<400> SEQUENCE: 718
gggtttcata tgattgtggc gctggtgccg gcggtggcga ttgcgccggc aaatattacc 60
gttttctat 69

<210> SEQ ID NO 719
<211> LENGTH: 69
<212> TYPE: DNA
<213> ORGANISM: Artificial Sequence
<220> FEATURE:
<223> OTHER INFORMATION: cDNA Sequence of aMTD784 5'-primer

<400> SEQUENCE: 719
gggtttcata tggtggcggc gctgccggcg gtggcgctgg tggtgccggc aaatattacc 60
gttttctat 69

<210> SEQ ID NO 720
<211> LENGTH: 69
<212> TYPE: DNA
<213> ORGANISM: Artificial Sequence
<220> FEATURE:
<223> OTHER INFORMATION: cDNA Sequence of aMTD786 5'-primer

<400> SEQUENCE: 720
gggtttcata tgctggtggc gattgcgccg ctggcggtgc tggcgccggc aaatattacc 60
gttttctat 69

<210> SEQ ID NO 721
<211> LENGTH: 69
<212> TYPE: DNA
<213> ORGANISM: Artificial Sequence
<220> FEATURE:
<223> OTHER INFORMATION: cDNA Sequence of aMTD787 5'-primer

<400> SEQUENCE: 721
gggtttcata tggcggtggc gctggtgccg gtgattgtgg cggcgccggc aaatattacc 60
gttttctat 69

<210> SEQ ID NO 722
<211> LENGTH: 69
<212> TYPE: DNA
<213> ORGANISM: Artificial Sequence
<220> FEATURE:
<223> OTHER INFORMATION: cDNA Sequence of aMTD788 5'-primer

<400> SEQUENCE: 722
gggtttcata tggcgattgc ggtggcgatt gcgccggtgg cgctgccggc aaatattacc 60
gttttctat 69

<210> SEQ ID NO 723
<211> LENGTH: 69
<212> TYPE: DNA
<213> ORGANISM: Artificial Sequence
<220> FEATURE:
<223> OTHER INFORMATION: cDNA Sequence of aMTD803 5'-primer

<400> SEQUENCE: 723
gggtttcata tggcgattgc gctggcggtg ccggtgctgg cgctgccggc aaatattacc 60
gttttctat 69

<210> SEQ ID NO 724
<211> LENGTH: 69
<212> TYPE: DNA
<213> ORGANISM: Artificial Sequence
<220> FEATURE:
<223> OTHER INFORMATION: cDNA Sequence of aMTD805 5'-primer

<400> SEQUENCE: 724
gggtttcata tgctggtgct gattgcggcg gcgccgattg cgctgccggc aaatattacc 60
gttttctat 69

<210> SEQ ID NO 725
<211> LENGTH: 69
<212> TYPE: DNA
<213> ORGANISM: Artificial Sequence
<220> FEATURE:
<223> OTHER INFORMATION: cDNA Sequence of aMTD806 5'-primer

<400> SEQUENCE: 725
gggtttcata tgctggtggc gctggcggtg ccggcggcgg tgctgccggc aaatattacc 60
gttttctat 69

<210> SEQ ID NO 726
<211> LENGTH: 69
<212> TYPE: DNA
<213> ORGANISM: Artificial Sequence
<220> FEATURE:
<223> OTHER INFORMATION: cDNA Sequence of aMTD807 5'-primer

<400> SEQUENCE: 726
gggtttcata tggcggtggc gctggcggtg ccggcgctgg tgctgccggc aaatattacc 60
gttttctat 69

<210> SEQ ID NO 727
<211> LENGTH: 69
<212> TYPE: DNA
<213> ORGANISM: Artificial Sequence
<220> FEATURE:
<223> OTHER INFORMATION: cDNA Sequence of aMTD808 5'-primer

<400> SEQUENCE: 727
gggtttcata tgctggtggt gctggcggcg gcgccgctgg cggtgccggc aaatattacc 60
gttttctat 69

<210> SEQ ID NO 728
<211> LENGTH: 69
<212> TYPE: DNA
<213> ORGANISM: Artificial Sequence
<220> FEATURE:
<223> OTHER INFORMATION: cDNA Sequence of aMTD809 5'-primer

<400> SEQUENCE: 728
gggtttcata tgctgattgt gctggcggcg ccggcgctgg cggcgccggc aaatattacc 60
gttttctat 69

<210> SEQ ID NO 729
<211> LENGTH: 69
<212> TYPE: DNA
<213> ORGANISM: Artificial Sequence
<220> FEATURE:

<223> OTHER INFORMATION: cDNA Sequence of aMTD810 5'-primer

<400> SEQUENCE: 729
gggtttcata tggtgattgt gctggcggcg ccggcgctgg cggcgccggc aaatattacc 60
gttttctat 69

<210> SEQ ID NO 730
<211> LENGTH: 69
<212> TYPE: DNA
<213> ORGANISM: Artificial Sequence
<220> FEATURE:
<223> OTHER INFORMATION: cDNA Sequence of aMTD811 5'-primer

<400> SEQUENCE: 730
gggtttcata tggcggtggt gctggcggtg ccggcgctgg cggtgccggc aaatattacc 60
gttttctat 69

<210> SEQ ID NO 731
<211> LENGTH: 69
<212> TYPE: DNA
<213> ORGANISM: Artificial Sequence
<220> FEATURE:
<223> OTHER INFORMATION: cDNA Sequence of aMTD824 5'-primer

<400> SEQUENCE: 731
gggtttcata tgctgattat tgtggcggcg gcgccggcgg tggcgccggc aaatattacc 60
gttttctat 69

<210> SEQ ID NO 732
<211> LENGTH: 69
<212> TYPE: DNA
<213> ORGANISM: Artificial Sequence
<220> FEATURE:
<223> OTHER INFORMATION: cDNA Sequence of aMTD825 5'-primer

<400> SEQUENCE: 732
gggtttcata tgattgtggc ggtgattgtg gcgccggcgg tggcgccggc aaatattacc 60
gttttctat 69

<210> SEQ ID NO 733
<211> LENGTH: 69
<212> TYPE: DNA
<213> ORGANISM: Artificial Sequence
<220> FEATURE:
<223> OTHER INFORMATION: cDNA Sequence of aMTD826 5'-primer

<400> SEQUENCE: 733
gggtttcata tgctggtggc gctggcggcg ccgattattg cggtgccggc aaatattacc 60
gttttctat 69

<210> SEQ ID NO 734
<211> LENGTH: 69
<212> TYPE: DNA
<213> ORGANISM: Artificial Sequence
<220> FEATURE:
<223> OTHER INFORMATION: cDNA Sequence of aMTD827 5'-primer

<400> SEQUENCE: 734
gggtttcata tgattgcggc ggtgctggcg gcgccggcgc tggtgccggc aaatattacc 60
gttttctat 69

<210> SEQ ID NO 735
<211> LENGTH: 69
<212> TYPE: DNA
<213> ORGANISM: Artificial Sequence
<220> FEATURE:
<223> OTHER INFORMATION: cDNA Sequence of aMTD828 5'-primer

<400> SEQUENCE: 735
gggtttcata tgattgcgct gctggcggcg ccgattattg cggtgccggc aaatattacc 60
gttttctat 69

<210> SEQ ID NO 736
<211> LENGTH: 69
<212> TYPE: DNA
<213> ORGANISM: Artificial Sequence
<220> FEATURE:
<223> OTHER INFORMATION: cDNA Sequence of aMTD829 5'-primer

<400> SEQUENCE: 736
gggtttcata tggcggcgct ggcgctggtg gcgccggtga ttgtgccggc aaatattacc 60
gttttctat 69

<210> SEQ ID NO 737
<211> LENGTH: 69
<212> TYPE: DNA
<213> ORGANISM: Artificial Sequence
<220> FEATURE:
<223> OTHER INFORMATION: cDNA Sequence of aMTD830 5'-primer

<400> SEQUENCE: 737
gggtttcata tgattgcgct ggtggcggcg ccggtggcgc tggtgccggc aaatattacc 60
gttttctat 69

<210> SEQ ID NO 738
<211> LENGTH: 69
<212> TYPE: DNA
<213> ORGANISM: Artificial Sequence
<220> FEATURE:
<223> OTHER INFORMATION: cDNA Sequence of aMTD831 5'-primer

<400> SEQUENCE: 738
gggtttcata tgattattgt ggcggtggcg ccggcggcga ttgtgccggc aaatattacc 60
gttttctat 69

<210> SEQ ID NO 739
<211> LENGTH: 69
<212> TYPE: DNA
<213> ORGANISM: Artificial Sequence
<220> FEATURE:
<223> OTHER INFORMATION: cDNA Sequence of aMTD832 5'-primer

<400> SEQUENCE: 739
gggtttcata tggcggtggc ggcgattgtg ccggtgattg tggcgccggc aaatattacc 60
gttttctat 69

<210> SEQ ID NO 740
<211> LENGTH: 69
<212> TYPE: DNA
<213> ORGANISM: Artificial Sequence
<220> FEATURE:
<223> OTHER INFORMATION: cDNA Sequence of aMTD843 5'-primer

<400> SEQUENCE: 740

```
gggtttcata tggcggtgct ggtgctggtg gcgccggcgg cggcgccggc aaatattacc     60

gttttctat                                                             69


<210> SEQ ID NO 741
<211> LENGTH: 69
<212> TYPE: DNA
<213> ORGANISM: Artificial Sequence
<220> FEATURE:
<223> OTHER INFORMATION: cDNA Sequence of aMTD844 5'-primer

<400> SEQUENCE: 741

gggtttcata tggtggtggc gctgctggcg ccgctgattg cggcgccggc aaatattacc     60

gttttctat                                                             69


<210> SEQ ID NO 742
<211> LENGTH: 69
<212> TYPE: DNA
<213> ORGANISM: Artificial Sequence
<220> FEATURE:
<223> OTHER INFORMATION: cDNA Sequence of aMTD845 5'-primer

<400> SEQUENCE: 742

gggtttcata tggcggcggt ggtgattgcg ccgctgctgg cggtgccggc aaatattacc     60

gttttctat                                                             69


<210> SEQ ID NO 743
<211> LENGTH: 69
<212> TYPE: DNA
<213> ORGANISM: Artificial Sequence
<220> FEATURE:
<223> OTHER INFORMATION: cDNA Sequence of aMTD846 5'-primer

<400> SEQUENCE: 743

gggtttcata tgattgcggt ggcggtggcg gcgccgctgc tggtgccggc aaatattacc     60

gttttctat                                                             69


<210> SEQ ID NO 744
<211> LENGTH: 69
<212> TYPE: DNA
<213> ORGANISM: Artificial Sequence
<220> FEATURE:
<223> OTHER INFORMATION: cDNA Sequence of aMTD847 5'-primer

<400> SEQUENCE: 744

gggtttcata tgctggtggc gattgtggtg ctgccggcgg tggcgccggc aaatattacc     60

gttttctat                                                             69


<210> SEQ ID NO 745
<211> LENGTH: 69
<212> TYPE: DNA
<213> ORGANISM: Artificial Sequence
<220> FEATURE:
<223> OTHER INFORMATION: cDNA Sequence of aMTD848 5'-primer

<400> SEQUENCE: 745

gggtttcata tggcggtggc gattgtggtg ctgccggcgg tggcgccggc aaatattacc     60

gttttctat                                                             69


<210> SEQ ID NO 746
<211> LENGTH: 69
<212> TYPE: DNA
<213> ORGANISM: Artificial Sequence
```

<220> FEATURE:
<223> OTHER INFORMATION: cDNA Sequence of aMTD849 5'-primer

<400> SEQUENCE: 746
gggtttcata tggcggtgat tctgctggcg ccgctgattg cggcgccggc aaatattacc 60
gttttctat 69

<210> SEQ ID NO 747
<211> LENGTH: 69
<212> TYPE: DNA
<213> ORGANISM: Artificial Sequence
<220> FEATURE:
<223> OTHER INFORMATION: cDNA Sequence of aMTD850 5'-primer

<400> SEQUENCE: 747
gggtttcata tgctggtgat tgcgctggcg gcgccggtgg cgctgccggc aaatattacc 60
gttttctat 69

<210> SEQ ID NO 748
<211> LENGTH: 69
<212> TYPE: DNA
<213> ORGANISM: Artificial Sequence
<220> FEATURE:
<223> OTHER INFORMATION: cDNA Sequence of aMTD851 5'-primer

<400> SEQUENCE: 748
gggtttcata tggtgctggc ggtggtgctg ccggcggtgg cgctgccggc aaatattacc 60
gttttctat 69

<210> SEQ ID NO 749
<211> LENGTH: 69
<212> TYPE: DNA
<213> ORGANISM: Artificial Sequence
<220> FEATURE:
<223> OTHER INFORMATION: cDNA Sequence of aMTD852 5'-primer

<400> SEQUENCE: 749
gggtttcata tggtgctggc ggtggcggcg ccggcggtgc tgctgccggc aaatattacc 60
gttttctat 69

<210> SEQ ID NO 750
<211> LENGTH: 69
<212> TYPE: DNA
<213> ORGANISM: Artificial Sequence
<220> FEATURE:
<223> OTHER INFORMATION: cDNA Sequence of aMTD863 5'-primer

<400> SEQUENCE: 750
gggtttcata tggcggcggt ggtgctgctg ccgattattg cggcgccggc aaatattacc 60
gttttctat 69

<210> SEQ ID NO 751
<211> LENGTH: 69
<212> TYPE: DNA
<213> ORGANISM: Artificial Sequence
<220> FEATURE:
<223> OTHER INFORMATION: cDNA Sequence of aMTD864 5'-primer

<400> SEQUENCE: 751
gggtttcata tggcgctgct ggtgattgcg ccggcgattg cggtgccggc aaatattacc 60
gttttctat 69

<210> SEQ ID NO 752
<211> LENGTH: 69
<212> TYPE: DNA
<213> ORGANISM: Artificial Sequence
<220> FEATURE:
<223> OTHER INFORMATION: cDNA Sequence of aMTD865 5'-primer

<400> SEQUENCE: 752
gggtttcata tggcggtgct ggtgattgcg gtgccggcga ttgcgccggc aaatattacc 60
gttttctat 69

<210> SEQ ID NO 753
<211> LENGTH: 69
<212> TYPE: DNA
<213> ORGANISM: Artificial Sequence
<220> FEATURE:
<223> OTHER INFORMATION: cDNA Sequence of aMTD867 5'-primer

<400> SEQUENCE: 753
gggtttcata tggcgctgct ggtggtgatt gcgccgctgg cggcgccggc aaatattacc 60
gttttctat 69

<210> SEQ ID NO 754
<211> LENGTH: 69
<212> TYPE: DNA
<213> ORGANISM: Artificial Sequence
<220> FEATURE:
<223> OTHER INFORMATION: cDNA Sequence of aMTD868 5'-primer

<400> SEQUENCE: 754
gggtttcata tggtgctggt ggcggcgatt ctgccggcgg cgattccggc aaatattacc 60
gttttctat 69

<210> SEQ ID NO 755
<211> LENGTH: 69
<212> TYPE: DNA
<213> ORGANISM: Artificial Sequence
<220> FEATURE:
<223> OTHER INFORMATION: cDNA Sequence of aMTD870 5'-primer

<400> SEQUENCE: 755
gggtttcata tggtgctggt ggcggcggtg ctgccgattg cggcgccggc aaatattacc 60
gttttctat 69

<210> SEQ ID NO 756
<211> LENGTH: 69
<212> TYPE: DNA
<213> ORGANISM: Artificial Sequence
<220> FEATURE:
<223> OTHER INFORMATION: cDNA Sequence of aMTD872 5'-primer

<400> SEQUENCE: 756
gggtttcata tggtgctggc ggcggcggtg ctgccgctgg tggtgccggc aaatattacc 60
gttttctat 69

<210> SEQ ID NO 757
<211> LENGTH: 69
<212> TYPE: DNA
<213> ORGANISM: Artificial Sequence
<220> FEATURE:
<223> OTHER INFORMATION: cDNA Sequence of aMTD875 5'-primer

<400> SEQUENCE: 757
gggtttcata tggcgattgc gattgtggtg ccggcggtgg cggtgccggc aaatattacc 60
gttttctat 69

<210> SEQ ID NO 758
<211> LENGTH: 69
<212> TYPE: DNA
<213> ORGANISM: Artificial Sequence
<220> FEATURE:
<223> OTHER INFORMATION: cDNA Sequence of aMTD877 5'-primer

<400> SEQUENCE: 758
gggtttcata tggtggcgat tattgcggtg ccggcggtgg tggcgccggc aaatattacc 60
gttttctat 69

<210> SEQ ID NO 759
<211> LENGTH: 69
<212> TYPE: DNA
<213> ORGANISM: Artificial Sequence
<220> FEATURE:
<223> OTHER INFORMATION: cDNA Sequence of aMTD878 5'-primer

<400> SEQUENCE: 759
gggtttcata tgattgtggc gctggtggcg ccggcggcgg tggtgccggc aaatattacc 60
gttttctat 69

<210> SEQ ID NO 760
<211> LENGTH: 69
<212> TYPE: DNA
<213> ORGANISM: Artificial Sequence
<220> FEATURE:
<223> OTHER INFORMATION: cDNA Sequence of aMTD879 5'-primer

<400> SEQUENCE: 760
gggtttcata tggcggcgat tgtgctgctg ccggcggtgg tggtgccggc aaatattacc 60
gttttctat 69

<210> SEQ ID NO 761
<211> LENGTH: 69
<212> TYPE: DNA
<213> ORGANISM: Artificial Sequence
<220> FEATURE:
<223> OTHER INFORMATION: cDNA Sequence of aMTD881 5'-primer

<400> SEQUENCE: 761
gggtttcata tggcggcgct gattgtggtg ccggcggtgg cggtgccggc aaatattacc 60
gttttctat 69

<210> SEQ ID NO 762
<211> LENGTH: 69
<212> TYPE: DNA
<213> ORGANISM: Artificial Sequence
<220> FEATURE:
<223> OTHER INFORMATION: cDNA Sequence of aMTD882 5'-primer

<400> SEQUENCE: 762
gggtttcata tggcgattgc gctggtggtg ccggcggtgg cggtgccggc aaatattacc 60
gttttctat 69

<210> SEQ ID NO 763
<211> LENGTH: 69
<212> TYPE: DNA

<213> ORGANISM: Artificial Sequence
<220> FEATURE:
<223> OTHER INFORMATION: cDNA Sequence of aMTD883 5'-primer

<400> SEQUENCE: 763
gggtttcata tgctggcgat tgtgccggcg gcgattgcgg cgctgccggc aaatattacc 60
gttttctat 69

<210> SEQ ID NO 764
<211> LENGTH: 69
<212> TYPE: DNA
<213> ORGANISM: Artificial Sequence
<220> FEATURE:
<223> OTHER INFORMATION: cDNA Sequence of aMTD884 5'-primer

<400> SEQUENCE: 764
gggtttcata tggtgctgat tgtgccggcg gcgattgcgg cgctgccggc aaatattacc 60
gttttctat 69

<210> SEQ ID NO 765
<211> LENGTH: 69
<212> TYPE: DNA
<213> ORGANISM: Artificial Sequence
<220> FEATURE:
<223> OTHER INFORMATION: cDNA Sequence of aMTD885 5'-primer

<400> SEQUENCE: 765
gggtttcata tgctggtggc gattgcgccg gcggtggcgg tgctgccggc aaatattacc 60
gttttctat 69

<210> SEQ ID NO 766
<211> LENGTH: 69
<212> TYPE: DNA
<213> ORGANISM: Artificial Sequence
<220> FEATURE:
<223> OTHER INFORMATION: cDNA Sequence of aMTD886 5'-primer

<400> SEQUENCE: 766
gggtttcata tggtgctggc ggtgccggcg gcgattgcgg cgctgccggc aaatattacc 60
gttttctat 69

<210> SEQ ID NO 767
<211> LENGTH: 69
<212> TYPE: DNA
<213> ORGANISM: Artificial Sequence
<220> FEATURE:
<223> OTHER INFORMATION: cDNA Sequence of aMTD887 5'-primer

<400> SEQUENCE: 767
gggtttcata tggtgctggc ggtggcgccg gcggtggcgg tgctgccggc aaatattacc 60
gttttctat 69

<210> SEQ ID NO 768
<211> LENGTH: 69
<212> TYPE: DNA
<213> ORGANISM: Artificial Sequence
<220> FEATURE:
<223> OTHER INFORMATION: cDNA Sequence of aMTD888 5'-primer

<400> SEQUENCE: 768
gggtttcata tgattctggc ggtggtggcg attccggcgg cggcgccggc aaatattacc 60
gttttctat 69

<210> SEQ ID NO 769
<211> LENGTH: 69
<212> TYPE: DNA
<213> ORGANISM: Artificial Sequence
<220> FEATURE:
<223> OTHER INFORMATION: cDNA Sequence of aMTD889 5'-primer

<400> SEQUENCE: 769
gggtttcata tgattctggt ggcggcggcg ccgattgcgg cgctgccggc aaatattacc 60
gttttctat 69

<210> SEQ ID NO 770
<211> LENGTH: 69
<212> TYPE: DNA
<213> ORGANISM: Artificial Sequence
<220> FEATURE:
<223> OTHER INFORMATION: cDNA Sequence of aMTD891 5'-primer

<400> SEQUENCE: 770
gggtttcata tgattctggc ggtggcggcg attccggcgg cgctgccggc aaatattacc 60
gttttctat 69

<210> SEQ ID NO 771
<211> LENGTH: 69
<212> TYPE: DNA
<213> ORGANISM: Artificial Sequence
<220> FEATURE:
<223> OTHER INFORMATION: cDNA Sequence of aMTD893 5'-primer

<400> SEQUENCE: 771
gggtttcata tggtgattgc gattccggcg attctggcgg cggcgccggc aaatattacc 60
gttttctat 69

<210> SEQ ID NO 772
<211> LENGTH: 69
<212> TYPE: DNA
<213> ORGANISM: Artificial Sequence
<220> FEATURE:
<223> OTHER INFORMATION: cDNA Sequence of aMTD895 5'-primer

<400> SEQUENCE: 772
gggtttcata tggcgattat tattgtggtg ccggcgattg cggcgccggc aaatattacc 60
gttttctat 69

<210> SEQ ID NO 773
<211> LENGTH: 69
<212> TYPE: DNA
<213> ORGANISM: Artificial Sequence
<220> FEATURE:
<223> OTHER INFORMATION: cDNA Sequence of aMTD896 5'-primer

<400> SEQUENCE: 773
gggtttcata tggcgattct gattgtggtg gcgccgattg cggcgccggc aaatattacc 60
gttttctat 69

<210> SEQ ID NO 774
<211> LENGTH: 69
<212> TYPE: DNA
<213> ORGANISM: Artificial Sequence
<220> FEATURE:
<223> OTHER INFORMATION: cDNA Sequence of aMTD897 5'-primer

<400> SEQUENCE: 774
gggtttcata tggcggtgat tgtgccggtg gcgattattg cggcgccggc aaatattacc 60
gttttctat 69

<210> SEQ ID NO 775
<211> LENGTH: 69
<212> TYPE: DNA
<213> ORGANISM: Artificial Sequence
<220> FEATURE:
<223> OTHER INFORMATION: cDNA Sequence of aMTD899 5'-primer

<400> SEQUENCE: 775
gggtttcata tggcggtggt gattgcgctg ccggcggtgg tggcgccggc aaatattacc 60
gttttctat 69

<210> SEQ ID NO 776
<211> LENGTH: 69
<212> TYPE: DNA
<213> ORGANISM: Artificial Sequence
<220> FEATURE:
<223> OTHER INFORMATION: cDNA Sequence of aMTD900 5'-primer

<400> SEQUENCE: 776
gggtttcata tggcgctggt ggcggtgatt gcgccggtgg tggcgccggc aaatattacc 60
gttttctat 69

<210> SEQ ID NO 777
<211> LENGTH: 69
<212> TYPE: DNA
<213> ORGANISM: Artificial Sequence
<220> FEATURE:
<223> OTHER INFORMATION: cDNA Sequence of aMTD901 5'-primer

<400> SEQUENCE: 777
gggtttcata tggcgctggt ggcggtgctg ccggcggtgg cggtgccggc aaatattacc 60
gttttctat 69

<210> SEQ ID NO 778
<211> LENGTH: 69
<212> TYPE: DNA
<213> ORGANISM: Artificial Sequence
<220> FEATURE:
<223> OTHER INFORMATION: cDNA Sequence of aMTD902 5'-primer

<400> SEQUENCE: 778
gggtttcata tggcgctggt ggcgccgctg ctggcggtgg cggtgccggc aaatattacc 60
gttttctat 69

<210> SEQ ID NO 779
<211> LENGTH: 69
<212> TYPE: DNA
<213> ORGANISM: Artificial Sequence
<220> FEATURE:
<223> OTHER INFORMATION: cDNA Sequence of aMTD904 5'-primer

<400> SEQUENCE: 779
gggtttcata tggcggtgct ggcggtggtg gcgccggtgg tggcgccggc aaatattacc 60
gttttctat 69

<210> SEQ ID NO 780
<211> LENGTH: 69

<212> TYPE: DNA
<213> ORGANISM: Artificial Sequence
<220> FEATURE:
<223> OTHER INFORMATION: cDNA Sequence of aMTD905 5'-primer

<400> SEQUENCE: 780
gggtttcata tggcggtgat tgcggtggcg ccgctggtgg tggcgccggc aaatattacc 60
gttttctat 69

<210> SEQ ID NO 781
<211> LENGTH: 69
<212> TYPE: DNA
<213> ORGANISM: Artificial Sequence
<220> FEATURE:
<223> OTHER INFORMATION: cDNA Sequence of aMTD906 5'-primer

<400> SEQUENCE: 781
gggtttcata tggcggtgat tgcgctggcg ccggtggtgg tggcgccggc aaatattacc 60
gttttctat 69

<210> SEQ ID NO 782
<211> LENGTH: 69
<212> TYPE: DNA
<213> ORGANISM: Artificial Sequence
<220> FEATURE:
<223> OTHER INFORMATION: cDNA Sequence of aMTD907 5'-primer

<400> SEQUENCE: 782
gggtttcata tggtggcgat tgcgctggcg ccggtggtgg tggcgccggc aaatattacc 60
gttttctat 69

<210> SEQ ID NO 783
<211> LENGTH: 69
<212> TYPE: DNA
<213> ORGANISM: Artificial Sequence
<220> FEATURE:
<223> OTHER INFORMATION: cDNA Sequence of aMTD908 5'-primer

<400> SEQUENCE: 783
gggtttcata tggtggcgct ggcgctggcg ccggtggtgg tggcgccggc aaatattacc 60
gttttctat 69

<210> SEQ ID NO 784
<211> LENGTH: 69
<212> TYPE: DNA
<213> ORGANISM: Artificial Sequence
<220> FEATURE:
<223> OTHER INFORMATION: cDNA Sequence of aMTD910 5'-primer

<400> SEQUENCE: 784
gggtttcata tggtggcggc gctgctgccg gcggtggtgg tggcgccggc aaatattacc 60
gttttctat 69

<210> SEQ ID NO 785
<211> LENGTH: 69
<212> TYPE: DNA
<213> ORGANISM: Artificial Sequence
<220> FEATURE:
<223> OTHER INFORMATION: cDNA Sequence of aMTD911 5'-primer

<400> SEQUENCE: 785
gggtttcata tggtggcgct ggcgctgccg gcggtggtgg tggcgccggc aaatattacc 60
gttttctat 69

<210> SEQ ID NO 786
<211> LENGTH: 69
<212> TYPE: DNA
<213> ORGANISM: Artificial Sequence
<220> FEATURE:
<223> OTHER INFORMATION: cDNA Sequence of aMTD912 5'-primer

<400> SEQUENCE: 786
gggtttcata tggtggcgct gctggcgccg gcggtggtgg tggcgccggc aaatattacc 60
gttttctat 69

<210> SEQ ID NO 787
<211> LENGTH: 69
<212> TYPE: DNA
<213> ORGANISM: Artificial Sequence
<220> FEATURE:
<223> OTHER INFORMATION: cDNA Sequence of aMTD921 5'-primer

<400> SEQUENCE: 787
gggtttcata tgatttggtg gtttgtggtg ctgccgctgg tggtgccggc aaatattacc 60
gttttctat 69

<210> SEQ ID NO 788
<211> LENGTH: 69
<212> TYPE: DNA
<213> ORGANISM: Artificial Sequence
<220> FEATURE:
<223> OTHER INFORMATION: cDNA Sequence of aMTD922 5'-primer

<400> SEQUENCE: 788
gggtttcata tgtggtatgt gatttttgtg ctgccgctgg tggtgccggc aaatattacc 60
gttttctat 69

<210> SEQ ID NO 789
<211> LENGTH: 69
<212> TYPE: DNA
<213> ORGANISM: Artificial Sequence
<220> FEATURE:
<223> OTHER INFORMATION: cDNA Sequence of aMTD931 5'-primer

<400> SEQUENCE: 789
gggtttcata tggcggtgct gattgcgccg gcgattctgg cggcggcggc aaatattacc 60
gttttctat 69

<210> SEQ ID NO 790
<211> LENGTH: 69
<212> TYPE: DNA
<213> ORGANISM: Artificial Sequence
<220> FEATURE:
<223> OTHER INFORMATION: cDNA Sequence of aMTD934 5'-primer

<400> SEQUENCE: 790
gggtttcata tgctgattct ggcgccggcg gcggtggtgg cggcggcggc aaatattacc 60
gttttctat 69

<210> SEQ ID NO 791
<211> LENGTH: 69
<212> TYPE: DNA
<213> ORGANISM: Artificial Sequence
<220> FEATURE:
<223> OTHER INFORMATION: cDNA Sequence of aMTD935 5'-primer

<400> SEQUENCE: 791
gggtttcata tggcgctgct gattctgccg gcggcggcgg tggcggcggc aaatattacc 60
gttttctat 69

<210> SEQ ID NO 792
<211> LENGTH: 69
<212> TYPE: DNA
<213> ORGANISM: Artificial Sequence
<220> FEATURE:
<223> OTHER INFORMATION: cDNA Sequence of aMTD936 5'-primer

<400> SEQUENCE: 792
gggtttcata tggcgctgct gattctggcg gcggcggtgg cggcgccggc aaatattacc 60
gttttctat 69

<210> SEQ ID NO 793
<211> LENGTH: 69
<212> TYPE: DNA
<213> ORGANISM: Artificial Sequence
<220> FEATURE:
<223> OTHER INFORMATION: cDNA Sequence of aMTD937 5'-primer

<400> SEQUENCE: 793
gggtttcata tggtgccggt gctggtgccg ctgccggtgc cggtggtggc aaatattacc 60
gttttctat 69

<210> SEQ ID NO 794
<211> LENGTH: 69
<212> TYPE: DNA
<213> ORGANISM: Artificial Sequence
<220> FEATURE:
<223> OTHER INFORMATION: cDNA Sequence of aMTD938 5'-primer

<400> SEQUENCE: 794
gggtttcata tggtgccggt gctgctgccg gtggtggtgc cggtgccggc aaatattacc 60
gttttctat 69

<210> SEQ ID NO 795
<211> LENGTH: 69
<212> TYPE: DNA
<213> ORGANISM: Artificial Sequence
<220> FEATURE:
<223> OTHER INFORMATION: cDNA Sequence of aMTD947 5'-primer

<400> SEQUENCE: 795
gggtttcata tgtgctatta taatcagcag tccaataata ataatcaggc aaatattacc 60
gttttctat 69

<210> SEQ ID NO 796
<211> LENGTH: 69
<212> TYPE: DNA
<213> ORGANISM: Artificial Sequence
<220> FEATURE:
<223> OTHER INFORMATION: cDNA Sequence of aMTD949 5'-primer

<400> SEQUENCE: 796
gggtttcata tgtccggcaa ttcctgccag cagtgcggca attcctccgc aaatattacc 60
gttttctat 69

<210> SEQ ID NO 797

<211> LENGTH: 39
<212> TYPE: DNA
<213> ORGANISM: Artificial Sequence
<220> FEATURE:
<223> OTHER INFORMATION: cDNA Sequence of aMTD 3'-primer

<400> SEQUENCE: 797
cgcgtcgact tacctcggct gcaccggcac ggagatgac 39

<210> SEQ ID NO 798
<211> LENGTH: 184
<212> TYPE: PRT
<213> ORGANISM: Artificial Sequence
<220> FEATURE:
<223> OTHER INFORMATION: Amino acid Sequence of SDA

<400> SEQUENCE: 798

Met Ala Asn Ile Thr Val Phe Tyr Asn Glu Asp Phe Gln Gly Lys Gln
1 5 10 15

Val Asp Leu Pro Pro Gly Asn Tyr Thr Arg Ala Gln Leu Ala Ala Leu
20 25 30

Gly Ile Glu Asn Asn Thr Ile Ser Ser Val Lys Val Pro Pro Gly Val
35 40 45

Lys Ala Ile Leu Tyr Gln Asn Asp Gly Phe Ala Gly Asp Gln Ile Glu
50 55 60

Val Val Ala Asn Ala Glu Glu Leu Gly Pro Leu Asn Asn Asn Val Ser
65 70 75 80

Ser Ile Arg Val Ile Ser Val Pro Val Gln Pro Arg Met Ala Asn Ile
85 90 95

Thr Val Phe Tyr Asn Glu Asp Phe Gln Gly Lys Gln Val Asp Leu Pro
100 105 110

Pro Gly Asn Tyr Thr Arg Ala Gln Leu Ala Ala Leu Gly Ile Glu Asn
115 120 125

Asn Thr Ile Ser Ser Val Lys Val Pro Pro Gly Val Lys Ala Ile Leu
130 135 140

Tyr Gln Asn Asp Gly Phe Ala Gly Asp Gln Ile Glu Val Val Ala Asn
145 150 155 160

Ala Glu Glu Leu Gly Pro Leu Asn Asn Asn Val Ser Ser Ile Arg Val
165 170 175

Ile Ser Val Pro Val Gln Pro Arg
180

<210> SEQ ID NO 799
<211> LENGTH: 99
<212> TYPE: PRT
<213> ORGANISM: Artificial Sequence
<220> FEATURE:
<223> OTHER INFORMATION: Amino acid Sequence of SDB

<400> SEQUENCE: 799

Met Ala Glu Gln Ser Asp Lys Asp Val Lys Tyr Tyr Thr Leu Glu Glu
1 5 10 15

Ile Gln Lys His Lys Asp Ser Lys Ser Thr Trp Val Ile Leu His His
20 25 30

Lys Val Tyr Asp Leu Thr Lys Phe Leu Glu Glu His Pro Gly Gly Glu
35 40 45

Glu Val Leu Gly Glu Gln Ala Gly Gly Asp Ala Thr Glu Asn Phe Glu
50 55 60

Asp Val Gly His Ser Thr Asp Ala Arg Glu Leu Ser Lys Thr Tyr Ile

```
65                  70                  75                  80

Ile Gly Glu Leu His Pro Asp Asp Arg Ser Lys Ile Ala Lys Pro Ser
                85                  90                  95

Glu Thr Leu


<210> SEQ ID NO 800
<211> LENGTH: 109
<212> TYPE: PRT
<213> ORGANISM: Artificial Sequence
<220> FEATURE:
<223> OTHER INFORMATION: Amino acid Sequence of SDC

<400> SEQUENCE: 800

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105


<210> SEQ ID NO 801
<211> LENGTH: 208
<212> TYPE: PRT
<213> ORGANISM: Artificial Sequence
<220> FEATURE:
<223> OTHER INFORMATION: Amino acid Sequence of SDD

<400> SEQUENCE: 801

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
        115                 120                 125

Asp Val Phe Ile Asn Ala Gly Ile Lys Gly Glu Glu Tyr Asp Ala Ala
    130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
```

```
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
        195                 200                 205


<210> SEQ ID NO 802
<211> LENGTH: 100
<212> TYPE: PRT
<213> ORGANISM: Artificial Sequence
<220> FEATURE:
<223> OTHER INFORMATION: Amino acid Sequence of SDE

<400> SEQUENCE: 802

Gly Ser Leu Gln Asp Ser Glu Val Asn Gln Glu Ala Lys Pro Glu Val
1               5                   10                  15

Lys Pro Glu Val Lys Pro Glu Thr His Ile Asn Leu Lys Val Ser Asp
            20                  25                  30

Gly Ser Ser Glu Ile Phe Phe Lys Ile Lys Lys Thr Thr Pro Leu Arg
        35                  40                  45

Arg Leu Met Glu Ala Phe Ala Lys Arg Gln Gly Lys Glu Met Asp Ser
    50                  55                  60

Leu Thr Phe Leu Tyr Asp Gly Ile Glu Ile Gln Ala Asp Gln Thr Pro
65                  70                  75                  80

Glu Asp Leu Asp Met Glu Asp Asn Asp Ile Ile Glu Ala His Arg Glu
                85                  90                  95

Gln Ile Gly Gly
            100


<210> SEQ ID NO 803
<211> LENGTH: 297
<212> TYPE: PRT
<213> ORGANISM: Artificial Sequence
<220> FEATURE:
<223> OTHER INFORMATION: Amino acid Sequence of SDF

<400> SEQUENCE: 803

Gly Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160
```

```
Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295


<210> SEQ ID NO 804
<211> LENGTH: 99
<212> TYPE: PRT
<213> ORGANISM: Artificial Sequence
<220> FEATURE:
<223> OTHER INFORMATION: Amino acid Sequence of SDB' for deimunization

<400> SEQUENCE: 804

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Leu Ile Leu His His
            20                  25                  30

Lys Val Tyr Asp Leu Thr Lys Phe Leu Glu Glu His Pro Gly Gly Glu
        35                  40                  45

Glu Val Leu Gly Glu Gln Ala Gly Gly Asp Ala Thr Glu Asn Phe Glu
    50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95

Glu Thr Leu


<210> SEQ ID NO 805
<211> LENGTH: 552
<212> TYPE: DNA
<213> ORGANISM: Artificial Sequence
<220> FEATURE:
<223> OTHER INFORMATION: cDNA Sequence of SDA

<400> SEQUENCE: 805

atggcaaata ttaccgtttt ctataacgaa gacttccagg gtaagcaggt cgatctgccg      60

cctggcaact atacccgcgc ccagttggcg gcgctgggca tcgagaataa taccatcagc     120

tcggtgaagg tgccgcctgg cgtgaaggct atcctgtacc agaacgatgg tttcgccggc     180

gaccagatcg aagtggtggc caatgccgag gagttgggcc cgctgaataa taacgtctcc     240

agcatccgcg tcatctccgt gcccgtgcag ccgcgcatgg caaatattac cgttttctat     300

aacgaagact tccagggtaa gcaggtcgat ctgccgcctg gcaactatac ccgcgcccag     360
```

```
ttggcggcgc tgggcatcga gaataatacc atcagctcgg tgaaggtgcc gcctggcgtg    420

aaggctatcc tctaccagaa cgatggtttc gccggcgacc agatcgaagt ggtggccaat    480

gccgaggagc tgggtccgct gaataataac gtctccagca tccgcgtcat ctccgtgccg    540

gtgcagccga gg                                                        552
```

<210> SEQ ID NO 806
<211> LENGTH: 297
<212> TYPE: DNA
<213> ORGANISM: Artificial Sequence
<220> FEATURE:
<223> OTHER INFORMATION: cDNA Sequence of SDB

<400> SEQUENCE: 806

```
atggcagaac aaagcgacaa ggatgtgaag tactacactc tggaggagat tcagaagcac     60

aaagacagca agagcacctg ggtgatccta catcataagg tgtacgatct gaccaagttt    120

ctcgaagagc atcctggtgg ggaagaagtc ctgggcgagc aagctggggg tgatgctact    180

gagaactttg aggacgtcgg gcactctacg gatgcacgag aactgtccaa aacatacatc    240

atcggggagc tccatccaga tgacagatca aagatagcca agccttcgga aacccctt      297
```

<210> SEQ ID NO 807
<211> LENGTH: 327
<212> TYPE: DNA
<213> ORGANISM: Artificial Sequence
<220> FEATURE:
<223> OTHER INFORMATION: cDNA Sequence of SDC

<400> SEQUENCE: 807

```
atgagcgata aaattattca cctgactgac gacagttttg acacggatgt actcaaagcg     60

gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggcc                                        327
```

<210> SEQ ID NO 808
<211> LENGTH: 624
<212> TYPE: DNA
<213> ORGANISM: Artificial Sequence
<220> FEATURE:
<223> OTHER INFORMATION: cDNA Sequence of SDD

<400> SEQUENCE: 808

```
atgaaaaaga tttggctggc gctggctggt ttagttttag cgtttagcgc atcggcggcg     60

cagtatgaag atggtaaaca gtacactacc ctggaaaaac cggtagctgg cgcgccgcaa    120

gtgctggagt tttctctttt cttctgcccg cactgctatc agtttgaaga agttctgcat    180

atttctgata atgtgaagaa aaaactgccg gaaggcgtga agatgactaa ataccacgtc    240

aacttcatgg gtggtgacct gggcaaagat ctgactcagg catgggctgt ggcgatggcg    300

ctgggcgtgg aagacaaagt gactgttccg ctgtttgaag gcgtacagaa aacccagacc    360

attcgttctg cttctgatat ccgcgatgta tttatcaacg caggtattaa aggtgaagag    420

tacgacgcgg cgtggaacag cttcgtggtg aaatctctgg tcgctcagca ggaaaaagct    480

gcagctgacg tgcaattgcg tggcgttccg gcgatgtttg ttaacggtaa atatcagctg    540

aatccgcagg gtatggatac cagcaatatg gatgtttttg ttcagcagta tgctgataca    600
```

gtgaaatatc tgtccgagaa aaaa 624

<210> SEQ ID NO 809
<211> LENGTH: 300
<212> TYPE: DNA
<213> ORGANISM: Artificial Sequence
<220> FEATURE:
<223> OTHER INFORMATION: cDNA Sequence of SDE

<400> SEQUENCE: 809
gggtccctgc aggactcaga agtcaatcaa gaagctaagc cagaggtcaa gccagaagtc 60
aagcctgaga ctcacatcaa tttaaaggtg tccgatggat cttcagagat cttcttcaag 120
atcaaaaaga ccactccttt aagaaggctg atggaagcgt tcgctaaaag acagggtaag 180
gaaatggact ccttaacgtt cttgtacgac ggtattgaaa ttcaagctga tcagacccct 240
gaagatttgg acatggagga taacgatatt attgaggctc accgcgaaca gattggaggt 300

<210> SEQ ID NO 810
<211> LENGTH: 891
<212> TYPE: DNA
<213> ORGANISM: Artificial Sequence
<220> FEATURE:
<223> OTHER INFORMATION: cDNA Sequence of SDF

<400> SEQUENCE: 810
ggatccgaaa tcggtactgg ctttccattc gacccccatt atgtggaagt cctgggcgag 60
cgcatgcact acgtcgatgt tggtccgcgc gatggcaccc ctgtgctgtt cctgcacggt 120
aacccgacct cctcctacgt gtggcgcaac atcatcccgc atgttgcacc gacccatcgc 180
tgcattgctc cagacctgat cggtatgggc aaatccgaca aaccagacct gggttatttc 240
ttcgacgacc acgtccgctt catggatgcc ttcatcgaag ccctgggtct ggaagaggtc 300
gtcctggtca ttcacgactg gggctccgct ctgggtttcc actgggccaa gcgcaatcca 360
gagcgcgtca aaggtattgc atttatggag ttcatccgcc ctatcccgac ctgggacgaa 420
tggccagaat ttgcccgcga gaccttccag gccttccgca ccaccgacgt cggccgcaag 480
ctgatcatcg atcagaacgt ttttatcgag ggtacgctgc cgatgggtgt cgtccgcccg 540
ctgactgaag tcgagatgga ccattaccgc gagccgttcc tgaatcctgt tgaccgcgag 600
ccactgtggc gcttcccaaa cgagctgcca atcgccggtg agccagcgaa catcgtcgcg 660
ctggtcgaag aatacatgga ctggctgcac cagtcccctg tcccgaagct gctgttctgg 720
ggcaccccag gcgttctgat cccaccggcc gaagccgctc gcctggccaa aagcctgcct 780
aactgcaagg ctgtggacat cggcccgggt ctgaatctgc tgcaagaaga caacccggac 840
ctgatcggca gcgagatcgc gcgctggctg tctactctgg agatttccgg t 891

<210> SEQ ID NO 811
<211> LENGTH: 297
<212> TYPE: DNA
<213> ORGANISM: Artificial Sequence
<220> FEATURE:
<223> OTHER INFORMATION: cDNA Sequence of SDB' for deimunization

<400> SEQUENCE: 811
atggcagaac aaagcgacaa ggatgtgaag tactacactc tggaggagat tcagaagcac 60
aaagacagca agagcacctg gctgatccta catcataagg tgtacgatct gaccaagttt 120
ctcgaagagc atcctggtgg ggaagaagtc ctgggcgagc aagctggggg tgatgctact 180
gagaactttg aggacgtcgg gcactctacg gatgcacgag aactgtccaa aacatacatc 240
atcggggagc tccatccaga tgacagatca aagatagcca agccttcgga aaccctt 297

<210> SEQ ID NO 812
<211> LENGTH: 19
<212> TYPE: PRT
<213> ORGANISM: Artificial Sequence
<220> FEATURE:
<223> OTHER INFORMATION: Amino acid Sequence of Histidine Tag

<400> SEQUENCE: 812

Met Gly Ser Ser His His His His His His Ser Ser Gly Leu Val Pro
1 5 10 15

Arg Gly Ser

<210> SEQ ID NO 813
<211> LENGTH: 57
<212> TYPE: DNA
<213> ORGANISM: Artificial Sequence
<220> FEATURE:
<223> OTHER INFORMATION: cDNA Sequence of Histidine Tag

<400> SEQUENCE: 813
atgggcagca gccatcatca tcatcatcac agcagcggcc tggtgccgcg cggcagc 57

<210> SEQ ID NO 814
<211> LENGTH: 7
<212> TYPE: PRT
<213> ORGANISM: Artificial Sequence
<220> FEATURE:
<223> OTHER INFORMATION: Amino acid Sequence of NLS-1

<400> SEQUENCE: 814

Pro Lys Lys Lys Arg Lys Val
1 5

<210> SEQ ID NO 815
<211> LENGTH: 21
<212> TYPE: DNA
<213> ORGANISM: Artificial Sequence
<220> FEATURE:
<223> OTHER INFORMATION: cDNA Sequence of NLS-1

<400> SEQUENCE: 815
ccgaaaaaga aacgtaaagt g 21

<210> SEQ ID NO 816
<211> LENGTH: 360
<212> TYPE: PRT
<213> ORGANISM: Artificial Sequence
<220> FEATURE:
<223> OTHER INFORMATION: Amino acid Sequence of human OCT4

<400> SEQUENCE: 816

Met Ala Gly His Leu Ala Ser Asp Phe Ala Phe Ser Pro Pro Pro Gly
1 5 10 15

Gly Gly Gly Asp Gly Pro Gly Gly Pro Glu Pro Gly Trp Val Asp Pro
20 25 30

Arg Thr Trp Leu Ser Phe Gln Gly Pro Pro Gly Gly Pro Gly Ile Gly
35 40 45

Pro Gly Val Gly Pro Gly Ser Glu Val Trp Gly Ile Pro Pro Cys Pro
50 55 60

Pro Pro Tyr Glu Phe Cys Gly Gly Met Ala Tyr Cys Gly Pro Gln Val

```
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360


<210> SEQ ID NO 817
<211> LENGTH: 317
<212> TYPE: PRT
<213> ORGANISM: Artificial Sequence
<220> FEATURE:
<223> OTHER INFORMATION: Amino acid Sequence of human SOX2

<400> SEQUENCE: 817

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
```

```
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315


<210> SEQ ID NO 818
<211> LENGTH: 479
<212> TYPE: PRT
<213> ORGANISM: Artificial Sequence
<220> FEATURE:
<223> OTHER INFORMATION: Amino acid Sequence of human KLF4

<400> SEQUENCE: 818

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
```

```
        115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475
```

<210> SEQ ID NO 819
<211> LENGTH: 454
<212> TYPE: PRT
<213> ORGANISM: Artificial Sequence
<220> FEATURE:
<223> OTHER INFORMATION: Amino acid Sequence of human CMYC

<400> SEQUENCE: 819

```
Met Asp Phe Phe Arg Val Val Glu Asn Gln Gln Pro Pro Ala Thr Met
```

-continued

```
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430
```

```
Asp Leu Leu Arg Lys Arg Arg Glu Gln Leu Lys His Lys Leu Glu Gln
        435                 440                 445

Leu Arg Asn Ser Cys Ala
    450
```

<210> SEQ ID NO 820
<211> LENGTH: 305
<212> TYPE: PRT
<213> ORGANISM: Artificial Sequence
<220> FEATURE:
<223> OTHER INFORMATION: Amino acid Sequence of human NANOG

<400> SEQUENCE: 820

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305
```

<210> SEQ ID NO 821

<211> LENGTH: 209
<212> TYPE: PRT
<213> ORGANISM: Artificial Sequence
<220> FEATURE:
<223> OTHER INFORMATION: Amino acid Sequence of human LIN28

<400> SEQUENCE: 821

Met Gly Ser Val Ser Asn Gln Gln Phe Ala Gly Gly Cys Ala Lys Ala
1 5 10 15

Ala Glu Glu Ala Pro Glu Glu Ala Pro Glu Asp Ala Ala Arg Ala Ala
20 25 30

Asp Glu Pro Gln Leu Leu His Gly Ala Gly Ile Cys Lys Trp Phe Asn
35 40 45

Val Arg Met Gly Phe Gly Phe Leu Ser Met Thr Ala Arg Ala Gly Val
50 55 60

Ala Leu Asp Pro Pro Val Asp Val Phe Val His Gln Ser Lys Leu His
65 70 75 80

Met Glu Gly Phe Arg Ser Leu Lys Glu Gly Glu Ala Val Glu Phe Thr
85 90 95

Phe Lys Lys Ser Ala Lys Gly Leu Glu Ser Ile Arg Val Thr Gly Pro
100 105 110

Gly Gly Val Phe Cys Ile Gly Ser Glu Arg Arg Pro Lys Gly Lys Ser
115 120 125

Met Gln Lys Arg Arg Ser Lys Gly Asp Arg Cys Tyr Asn Cys Gly Gly
130 135 140

Leu Asp His His Ala Lys Glu Cys Lys Leu Pro Pro Gln Pro Lys Lys
145 150 155 160

Cys His Phe Cys Gln Ser Ile Ser His Met Val Ala Ser Cys Pro Leu
165 170 175

Lys Ala Gln Gln Gly Pro Ser Ala Gln Gly Lys Pro Thr Tyr Phe Arg
180 185 190

Glu Glu Glu Glu Glu Ile His Ser Pro Thr Leu Leu Pro Glu Ala Gln
195 200 205

Asn

<210> SEQ ID NO 822
<211> LENGTH: 433
<212> TYPE: PRT
<213> ORGANISM: Artificial Sequence
<220> FEATURE:
<223> OTHER INFORMATION: Amino acid Sequence of human ZSCAN4

<400> SEQUENCE: 822

Met Ala Leu Asp Leu Arg Thr Ile Phe Gln Cys Glu Pro Ser Glu Asn
1 5 10 15

Asn Leu Gly Ser Glu Asn Ser Ala Phe Gln Gln Ser Gln Gly Pro Ala
20 25 30

Val Gln Arg Glu Glu Gly Ile Ser Glu Phe Ser Arg Met Val Leu Asn
35 40 45

Ser Phe Gln Asp Ser Asn Asn Ser Tyr Ala Arg Gln Glu Leu Gln Arg
50 55 60

Leu Tyr Arg Ile Phe His Ser Trp Leu Gln Pro Glu Lys His Ser Lys
65 70 75 80

Asp Glu Ile Ile Ser Leu Leu Val Leu Glu Gln Phe Met Ile Gly Gly
85 90 95

His Cys Asn Asp Lys Ala Ser Val Lys Glu Lys Trp Lys Ser Ser Gly
100 105 110

```
Lys Asn Leu Glu Arg Phe Ile Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Ser Lys Thr Thr Arg Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Pro Glu Glu Gly Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

Ser His Gly Val Gln Lys Ser Tyr Lys Cys Glu Glu Cys Pro Lys Val
305                 310                 315                 320

Phe Lys Tyr Leu Cys His Leu Leu Ala His Gln Arg Arg His Arg Asn
                325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
        355                 360                 365

Thr Cys Ser Met Cys Lys Lys Ser Phe Ser His Lys Thr Asn Leu Arg
    370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
            420                 425                 430

Ser
```

<210> SEQ ID NO 823
<211> LENGTH: 1430
<212> TYPE: DNA
<213> ORGANISM: Artificial Sequence
<220> FEATURE:
<223> OTHER INFORMATION: cDNA Sequence of human OCT4

<400> SEQUENCE: 823

```
agagaggggt tgagtagtcc cttcgcaagc cctcatttca ccaggccccc ggcttggggc      60

gccttccttc cccatggcgg gacacctggc ttcggatttc gccttctcgc cccctccagg     120

tggtggaggt gatgggccag gggggccgga gccgggctgg gttgatcctc ggacctggct     180
```

aagcttccaa ggccctcctg gagggccagg aatcgggccg ggggttgggc caggctctga 240
ggtgtggggg attcccccat gcccccgcc gtatgagttc tgtgggggga tggcgtactg 300
tgggccccag gttggagtgg ggctagtgcc ccaaggcggc ttggagacct ctcagcctga 360
gggcgaagca ggagtcgggg tggagagcaa ctccgatggg gcctccccgg agccctgcac 420
cgtcacccct ggtgccgtga agctggagaa ggagaagctg gagcaaaacc cggaggagtc 480
ccaggacatc aaagctctgc agaaagaact cgagcaattt gccaagctcc tgaagcagaa 540
gaggatcacc ctgggatata cacaggccga tgtggggctc accctggggg ttctatttgg 600
gaaggtattc agccaaacga ccatctgccg ctttgaggct ctgcagctta gcttcaagaa 660
catgtgtaag ctgcggccct tgctgcagaa gtgggtggag gaagctgaca acaatgaaaa 720
tcttcaggag atatgcaaag cagaaaccct cgtgcaggcc cgaaagagaa agcgaaccag 780
tatcgagaac cgagtgagag gcaacctgga gaatttgttc ctgcagtgcc cgaaacccac 840
actgcagcag atcagccaca tcgcccagca gcttgggctc gagaaggatg tggtccgagt 900
gtggttctgt aaccggcgcc agaagggcaa gcgatcaagc agcgactatg cacaacgaga 960
ggattttgag gctgctgggt ctcctttctc agggggacca gtgtcctttc ctctggcccc 1020
agggccccat tttggtaccc caggctatgg gagccctcac ttcactgcac tgtactcctc 1080
ggtccctttc cctgaggggg aagcctttcc ccctgtctcc gtcaccactc tgggctctcc 1140
catgcattca aactgaggtg cctgcccttc taggaatggg ggacaggggg aggggaggag 1200
ctagggaaag aaaacctgga gtttgtgcca gggtttttgg gattaagttc ttcattcact 1260
aaggaaggaa ttgggaacac aaagggtggg ggcaggggag tttggggcaa ctggttggag 1320
ggaaggtgaa gttcaatgat gctcttgatt ttaatcccac atcatgtatc actttttttct 1380 taaataaaga agcctgggac acagtagata gacacactta aaaaaaaaaa 1430

<210> SEQ ID NO 824
<211> LENGTH: 2520
<212> TYPE: DNA
<213> ORGANISM: Artificial Sequence
<220> FEATURE:
<223> OTHER INFORMATION: cDNA Sequence of human SOX2

<400> SEQUENCE: 824
ggatggttgt ctattaactt gttcaaaaaa gtatcaggag ttgtcaaggc agagaagaga 60
gtgtttgcaa aagggggaaa gtagtttgct gcctctttaa gactaggact gagagaaaga 120
agaggagaga gaaagaaagg gagagaagtt tgagccccag gcttaagcct ttccaaaaaa 180
taataataac aatcatcggc ggcggcagga tcggccagag gaggagggaa gcgctttttt 240
tgatcctgat tccagtttgc ctctctcttt ttttccccca aattattctt cgcctgattt 300
tcctcgcgga gccctgcgct cccgacaccc ccgcccgcct cccctcctcc tctcccccg 360 cccgcgggcc ccccaaagtc ccggccgggc cgagggtcgg cggccgccgg cgggccgggc 420
ccgcgcacag cgcccgcatg tacaacatga tggagacgga gctgaagccg ccgggcccgc 480
agcaaacttc gggggcggc ggcggcaact ccaccgcggc ggcggccggc ggcaaccaga 540
aaaacagccc ggaccgcgtc aagcggccca tgaatgcctt catggtgtgg tcccgcgggc 600
agcggcgcaa gatggcccag gagaacccca agatgcacaa ctcggagatc agcaagcgcc 660
tgggcgccga gtggaaactt ttgtcggaga cggagaagcg gccgttcatc gacgaggcta 720
agcggctgcg agcgctgcac atgaaggagc acccggatta taaataccgg ccccggcgga 780
aaaccaagac gctcatgaag aaggataagt acacgctgcc cggcgggctg ctggcccccg 840
gcggcaatag catggcgagc ggggtcgggg tgggcgccgg cctgggcgcg ggcgtgaacc 900
agcgcatgga cagttacgcg cacatgaacg gctggagcaa cggcagctac agcatgatgc 960
aggaccagct gggctacccg cagcacccgg gcctcaatgc gcacggcgca gcgcagatgc 1020
agcccatgca ccgctacgac gtgagcgccc tgcagtacaa ctccatgacc agctcgcaga 1080
cctacatgaa cggctcgccc acctacagca tgtcctactc gcagcagggc acccctggca 1140
tggctcttgg ctccatgggt tcggtggtca agtccgaggc cagctccagc ccccctgtgg 1200
ttacctcttc ctcccactcc agggcgccct gccaggccgg ggacctccgg gacatgatca 1260
gcatgtatct ccccggcgcc gaggtgccgg aacccgccgc ccccagcaga cttcacatgt 1320
cccagcacta ccagagcggc ccggtgcccg gcacggccat taacggcaca ctgcccctct 1380
cacacatgtg agggccggac agcgaactgg aggggggaga aattttcaaa gaaaaacgag 1440
ggaaatggga ggggtgcaaa agaggagagt aagaaacagc atggagaaaa cccggtacgc 1500
tcaaaaagaa aaaggaaaaa aaaaaatccc atcacccaca gcaaatgaca gctgcaaaag 1560
agaacaccaa tcccatccac actcacgcaa aaaccgcgat gccgacaaga aaacttttat 1620
gagagagatc ctggacttct tttggggga ctatttttgt acagagaaaa cctggggagg 1680
gtggggaggg cgggggaatg gaccttgtat agatctggag gaaagaaagc tacgaaaaac 1740
tttttaaaag ttctagtggt acggtaggag ctttgcagga agtttgcaaa agtctttacc 1800
aataatattt agagctagtc tccaagcgac gaaaaaaatg ttttaatatt tgcaagcaac 1860
ttttgtacag tatttatcga gataaacatg gcaatcaaaa tgtccattgt ttataagctg 1920
agaatttgcc aatatttttc aaggagaggc ttcttgctga attttgattc tgcagctgaa 1980
atttaggaca gttgcaaacg tgaaaagaag aaaattattc aaatttggac attttaattg 2040
tttaaaaatt gtacaaaagg aaaaaattag aataagtact ggcgaaccat ctctgtggtc 2100
ttgtttaaaa agggcaaaag ttttagactg tactaaattt tataacttac tgttaaaagc 2160
aaaaatggcc atgcaggttg acaccgttgg taatttataa tagcttttgt tcgatcccaa 2220
ctttccattt tgttcagata aaaaaaacca tgaaattact gtgtttgaaa tatttttctta 2280 tggtttgtaa tatttctgta aatttattgt gatattttaa ggttttcccc cctttatttt 2340
ccgtagttgt attttaaaag attcggctct gtattatttg aatcagtctg ccgagaatcc 2400
atgtatatat ttgaactaat atcatcctta taacaggtac attttcaact taagttttta 2460
ctccattatg cacagtttga gataaataaa tttttgaaat atggacactg aaaaaaaaaa 2520

<210> SEQ ID NO 825
<211> LENGTH: 2949
<212> TYPE: DNA
<213> ORGANISM: Artificial Sequence
<220> FEATURE:
<223> OTHER INFORMATION: cDNA Sequence of human KLF4

<400> SEQUENCE: 825
agtttcccga ccagagagaa cgaacgtgtc tgcgggcgcg cggggagcag aggcggtggc 60
gggcggcggc ggcaccggga gccgccgagt gaccctcccc cgcccctctg gcccccacc 120 ctcccacccg cccgtggccc gcgcccatgg ccgcgcgcgc tccacacaac tcaccggagt 180
ccgcgccttg cgccgccgac cagttcgcag ctccgcgcca cggcagccag tctcacctgg 240
cggcaccgcc cgcccaccgc cccggccaca gcccctgcgc ccacggcagc actcgaggcg 300
accgcgacag tggtggggga cgctgctgag tggaagagag cgcagcccgg ccaccggacc 360

-continued

```
tacttactcg ccttgctgat tgtctatttt tgcgtttaca acttttctaa gaacttttgt    420
atacaaagga actttttaaa aaagacgctt ccaagttata tttaatccaa agaagaagga    480
tctcggccaa tttggggttt tggttttgg cttcgtttct tctcttcgtt gactttgggg    540
ttcaggtgcc ccagctgctt cgggctgccg aggaccttct gggcccccac attaatgagg    600
cagccacctg gcgagtctga catggctgtc agcgacgcgc tgctcccatc tttctccacg    660
ttcgcgtctg gcccggcggg aagggagaag acactgcgtc aagcaggtgc cccgaataac    720
cgctggcggg aggagctctc ccacatgaag cgacttcccc cagtgcttcc cggccgcccc    780
tatgacctgg cggcggcgac cgtggccaca gacctggaga gcggcggagc cggtgcggct    840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga agaggcattt ttaaatccca   2040
gacagtggat atgacccaca ctgccagaag agaattcagt atttttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaagggggt gactggaagt tgtggatatc agggtataaa   2340
ttatatccgt gagttggggg agggaagacc agaattccct tgaattgtgt attgatgcaa   2400
tataagcata aaagatcacc ttgtattctc tttaccttct aaaagccatt attatgatgt   2460
tagaagaaga ggaagaaatt caggtacaga aaacatgttt aaatagccta aatgatggtg   2520
cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760
```

```
tgtgtttttc tatatagttc cttgccttaa taaatatgta atataaattt aagcaaacgt   2820

ctattttgta tatttgtaaa ctacaaagta aaatgaacat tttgtggagt ttgtattttg   2880

catactcaag gtgagaatta agttttaaat aaacctataa tattttatct gaaaaaaaaa   2940

aaaaaaaaa                                                           2949
```

```
<210> SEQ ID NO 826
<211> LENGTH: 2379
<212> TYPE: DNA
<213> ORGANISM: Artificial Sequence
<220> FEATURE:
<223> OTHER INFORMATION: cDNA Sequence of human CMYC

<400> SEQUENCE: 826

gacccccgag ctgtgctgct cgcggccgcc accgccgggc cccggccgtc cctggctccc     60

ctcctgcctc gagaagggca gggcttctca gaggcttggc gggaaaaaga acggagggag    120

ggatcgcgct gagtataaaa gccggttttc ggggctttat ctaactcgct gtagtaattc    180

cagcgagagg cagagggagc gagcgggcgg ccggctaggg tggaagagcc gggcgagcag    240

agctgcgctg cgggcgtcct gggaagggag atccggagcg aatagggggc ttcgcctctg    300

gcccagccct cccgctgatc ccccagccag cggtccgcaa cccttgccgc atccacgaaa    360

ctttgcccat agcagcgggc gggcactttg cactggaact tacaacaccc gagcaaggac    420

gcgactctcc cgacgcgggg aggctattct gcccatttgg ggacacttcc ccgccgctgc    480

caggacccgc ttctctgaaa ggctctcctt gcagctgctt agacgctgga tttttttcgg    540

gtagtggaaa accagcagcc tcccgcgacg atgcccctca acgttagctt caccaacagg    600

aactatgacc tcgactacga ctcggtgcag ccgtatttct actgcgacga ggaggagaac    660

ttctaccagc agcagcagca gagcgagctg cagcccccgg cgcccagcga ggatatctgg    720

aagaaattcg agctgctgcc caccccgccc ctgtccccta gccgccgctc cgggctctgc    780

tcgccctcct acgttgcggt cacacccttc tcccttcggg gagacaacga cggcggtggc    840

gggagcttct ccacggccga ccagctggag atggtgaccg agctgctggg aggagacatg    900

gtgaaccaga gtttcatctg cgacccggac gacgagacct tcatcaaaaa catcatcatc    960

caggactgta tgtggagcgg cttctcggcc gccgccaagc tcgtctcaga gaagctggcc   1020

tcctaccagg ctgcgcgcaa agacagcggc agcccgaacc ccgcccgcgg ccacagcgtc   1080

tgctccacct ccagcttgta cctgcaggat ctgagcgccg ccgcctcaga gtgcatcgac   1140

ccctcggtgg tcttccccta ccctctcaac gacagcagct cgcccaagtc ctgcgcctcg   1200

caagactcca gcgccttctc tccgtcctcg gattctctgc tctcctcgac ggagtcctcc   1260

ccgcagggca gccccgagcc cctggtgctc catgaggaga caccgcccac caccagcagc   1320

gactctgagg aggaacaaga agatgaggaa gaaatcgatg ttgtttctgt ggaaaagagg   1380

caggctcctg gcaaaaggtc agagtctgga tcaccttctg ctggaggcca cagcaaacct   1440

cctcacagcc cactggtcct caagaggtgc cacgtctcca cacatcagca caactacgca   1500

gcgcctccct ccactcggaa ggactatcct gctgccaaga gggtcaagtt ggacagtgtc   1560

agagtcctga gacagatcag caacaaccga aaatgcacca gccccaggtc ctcggacacc   1620

gaggagaatg tcaagaggcg aacacacaac gtcttggagc gccagaggag gaacgagcta   1680

aaacggagct ttttgccct gcgtgaccag atcccggagt tggaaaacaa tgaaaaggcc   1740

cccaaggtag ttatccttaa aaaagccaca gcatacatcc tgtccgtcca agcagaggag   1800
```

caaaagctca tttctgaaga ggacttgttg cggaaacgac gagaacagtt gaaacacaaa 1860
cttgaacagc tacggaactc ttgtgcgtaa ggaaaagtaa ggaaaacgat tccttctaac 1920
agaaatgtcc tgagcaatca cctatgaact tgtttcaaat gcatgatcaa atgcaacctc 1980
acaaccttgg ctgagtcttg agactgaaag atttagccat aatgtaaact gcctcaaatt 2040
ggactttggg cataaaagaa ctttttatg cttaccatct tttttttttc tttaacagat 2100
ttgtatttaa gaattgtttt taaaaaattt taagatttac acaatgtttc tctgtaaata 2160
ttgccattaa atgtaaataa ctttaataaa acgtttatag cagttacaca gaatttcaat 2220
cctagtatat agtacctagt attataggta ctataaaccc taattttttt tatttaagta 2280
cattttgctt tttaaagttg atttttttct attgttttta gaaaaaaataa aataactggc 2340 aaatatatca ttgagccaaa tcttaaaaaa aaaaaaaaa 2379

<210> SEQ ID NO 827
<211> LENGTH: 2098
<212> TYPE: DNA
<213> ORGANISM: Artificial Sequence
<220> FEATURE:
<223> OTHER INFORMATION: cDNA Sequence of human NANOG

<400> SEQUENCE: 827
attataaatc tagagactcc aggattttaa cgttctgctg gactgagctg gttgcctcat 60
gttattatgc aggcaactca ctttatccca atttcttgat acttttcctt ctggaggtcc 120
tatttctcta acatcttcca gaaaagtctt aaagctgcct taaccttttt tccagtccac 180
ctcttaaatt ttttcctcct cttcctctat actaacatga gtgtggatcc agcttgtccc 240
caaagcttgc cttgctttga agcatccgac tgtaaagaat cttcacctat gcctgtgatt 300
tgtgggcctg aagaaaacta tccatccttg caaatgtctt ctgctgagat gcctcacacg 360
gagactgtct ctcctcttcc ttcctccatg gatctgctta ttcaggacag ccctgattct 420
tccaccagtc ccaaaggcaa acaacccact tctgcagaga agagtgtcgc aaaaaaggaa 480
gacaaggtcc cggtcaagaa acagaagacc agaactgtgt tctcttccac ccagctgtgt 540
gtactcaatg atagatttca gagacagaaa tacctcagcc tccagcagat gcaagaactc 600
tccaacatcc tgaacctcag ctacaaacag gtgaagacct ggttccagaa ccagagaatg 660
aaatctaaga ggtggcagaa aaacaactgg ccgaagaata gcaatggtgt gacgcagaag 720
gcctcagcac ctacctaccc cagcctttac tcttcctacc accagggatg cctggtgaac 780
ccgactggga accttccaat gtggagcaac cagacctgga acaattcaac ctggagcaac 840
cagacccaga acatccagtc ctggagcaac cactcctgga acactcagac ctggtgcacc 900
caatcctgga acaatcaggc ctggaacagt cccttctata actgtggaga ggaatctctg 960
cagtcctgca tgcagttcca gccaaattct cctgccagtg acttggaggc tgccttggaa 1020
gctgctgggg aaggccttaa tgtaatacag cagaccacta ggtattttag tactccacaa 1080
accatggatt tattcctaaa ctactccatg aacatgcaac ctgaagacgt gtgaagatga 1140
gtgaaactga tattactcaa tttcagtctg gacactggct gaatccttcc tctcccctcc 1200
tcccatccct cataggattt ttcttgtttg gaaaccacgt gttctggttt ccatgatgcc 1260
catccagtca atctcatgga gggtggagta tggttggagc ctaatcagcg aggtttcttt 1320
tttttttttt ttcctattgg atcttcctgg agaaaatact tttttttttt tttttttga 1380 aacggagtct tgctctgtcg cccaggctgg agtgcagtgg cgcggtcttg gctcactgca 1440
agctccgtct cccgggttca cgccattctc ctgcctcagc ctcccgagca gctgggacta 1500
caggcgcccg ccacctcgcc cggctaatat tttgtatttt tagtagagac ggggtttcac 1560
tgtgttagcc aggatggtct cgatctcctg accttgtgat ccacccgcct cggcctccct 1620
aacagctggg atttacaggc gtgagccacc gcgccctgcc tagaaaagac attttaataa 1680
ccttggctgc cgtctctggc tatagataag tagatctaat actagtttgg atatctttag 1740
ggtttagaat ctaacctcaa gaataagaaa tacaagtaca aattggtgat gaagatgtat 1800
tcgtattgtt tgggattggg aggctttgct tattttttaa aaactattga ggtaaagggt 1860
taagctgtaa catacttaat tgatttctta ccgtttttgg ctctgttttg ctatatcccc 1920
taatttgttg gttgtgctaa tctttgtaga aagaggtctc gtatttgctg catcgtaatg 1980
acatgagtac tgctttagtt ggtttaagtt caaatgaatg aaacaactat ttttccttta 2040
gttgatttta ccctgatttc accgagtgtt tcaatgagta aatatacagc ttaaacat 2098

<210> SEQ ID NO 828
<211> LENGTH: 4014
<212> TYPE: DNA
<213> ORGANISM: Artificial Sequence
<220> FEATURE:
<223> OTHER INFORMATION: cDNA Sequence of human LIN28

<400> SEQUENCE: 828
gtgcggggga agatgtagca gcttcttctc cgaaccaacc ctttgccttc ggacttctcc 60
ggggccagca gccgcccgac caggggcccg gggccacggg ctcagccgac gaccatgggc 120
tccgtgtcca accagcagtt tgcaggtggc tgcgccaagg cggcagaaga ggcgcccgag 180
gaggcgccgg aggacgcggc ccgggcggcg gacgagcctc agctgctgca cggtgcgggc 240
atctgtaagt ggttcaacgt gcgcatgggg ttcggcttcc tgtccatgac cgcccgcgcc 300
ggggtcgcgc tcgacccccc agtggatgtc tttgtgcacc agagtaagct gcacatggaa 360
gggttccgga gcttgaagga gggtgaggca gtggagttca cctttaagaa gtcagccaag 420
ggtctggaat ccatccgtgt caccggacct ggtggagtat tctgtattgg gagtgagagg 480
cggccaaaag gaaagagcat gcagaagcgc agatcaaaag gagacaggtg ctacaactgt 540
ggaggtctag atcatcatgc caaggaatgc aagctgccac cccagcccaa gaagtgccac 600
ttctgccaga gcatcagcca tatggtagcc tcatgtccgc tgaaggccca gcagggccct 660
agtgcacagg gaaagccaac ctactttcga gaggaagaag aagaaatcca cagccctacc 720
ctgctcccgg aggcacagaa ttgagccaca atgggtgggg gctattcttt tgctatcagg 780
aagttttgag gagcaggcag agtggagaaa gtgggaatag ggtgcattgg ggctagttgg 840
cactgccatg tatctcaggc ttgggttcac accatcaccc tttcttccct ctaggtgggg 900
ggaaagggtg agtcaaagga actccaacca tgctctgtcc aaatgcaagt gagggttctg 960
ggggcaacca ggagggggga atcaccctac aacctgcata ctttgagtct ccatccccag 1020
aatttccagc ttttgaaagt ggcctggata gggaagttgt tttcctttta aagaaggata 1080
tataataatt cccatgccag agtgaaatga ttaagtataa gaccagattc atggagccaa 1140
gccactacat tctgtggaag gagatctctc aggagtaagc attgtttttt tttcacatct 1200
tgtatcctca tacccacttt tgggataggg tgctggcagc tgtcccaagc aatgggtaat 1260
gatgatggca aaaagggtgt ttgggggaac agctgcagac ctgctgctct atgctcaccc 1320
ccgccccatt ctgggccaat gtgattttat ttatttgctc ccttggatac tgcaccttgg 1380
gtcccacttt ctccaggatg ccaactgcac tagctgtgtg cgaatgacgt atcttgtgca 1440

-continued

```
ttttaacttt ttttccttaa tataaatatt ctggttttgt atttttgtat attttaatct   1500
aaggccctca tttcctgcac tgtgttctca ggtacatgag caatctcagg gatagccagc   1560
agcagctcca ggtctgcgca gcaggaatta ctttttgttg tttttgccac cgtggagagc   1620
aactatttgg agtgcacagc ctattgaact acctcatttt tgccaataag agctggcttt   1680
tctgccatag tgtcctcttg aaaccccctc tgccttgaaa atgttttatg ggagactagg   1740
ttttaactgg gtggccccat gacttgattg ccttctactg gaagattggg aattagtcta   1800
aacaggaaat ggtggtacac agaggctagg agaggctggg cccggtgaaa aggccagaga   1860
gcaagccaag attaggtgag ggttgtctaa tcctatggca caggacgtgc tttacatctc   1920
cagatctgtt cttcaccaga ttaggttagg cctaccatgt gccacagggt gtgtgtgtgt   1980
ttgtaaaact agagttgcta aggataagtt taaagaccaa taccccctgta cttaatcctg   2040
tgctgtcgag ggatggatat atgaagtaag gtgagatcct taacctttca aaattttcgg   2100
gttccaggga gacacacaag cgagggtttt gtggtgcctg gagcctgtgt cctgccctgc   2160
tacagtagtg attaatagtg tcatggtagc taaaggagaa aaagggggtt tcgtttacac   2220
gctgtgagat caccgcaaac ctaccttact gtgttgaaac gggacaaatg caatagaacg   2280
cattgggtgg tgtgtgtctg atcctgggtt cttgtctccc ctaaatgctg ccccccaagt   2340
tactgtattt gtctgggctt tgtaggactt cactacgttg attgctaggt ggcctagttt   2400
gtgtaaatat aatgtattgg tctttctccg tgttctttgg gggttttgtt tacaaacttc   2460
tttttgtatt gagagaaaaa tagccaaagc atctttgaca gaaggttctg caccaggcaa   2520
aaagatctga aacattagtt tggggggccc tcttcttaaa gtggggatct tgaaccatcc   2580
tttcttttgt attccccttc ccctattacc tattagacca gatcttctgt cctaaaaact   2640
tgtcttctac cctgccctct tttctgttca cccccaaaag aaaacttaca cacccacaca   2700
catacacatt tcatgcttgg agtgtctcca caactcttaa atgatgtatg caaaaatact   2760
gaagctagga aaaccctcca tcccttgttc ccaacctcct aagtcaagac cattaccatt   2820
tctttctttc tttttttttt ttttttaaaa tggagtctca ctgtgtcacc caggctggag   2880
tgcagtggca tgatcggctc actgcagcct ctgcctcttg ggttcaagtg attctcctgc   2940
ctcagcctcc tgagtagctg ggatttcagg cacccgccac actcagctaa tttttgtatt   3000
tttagtagag acggggtttc accatgttgt ccaggctggt ctggaactcc tgacctcagg   3060
tgatctgccc accttggctt cccaaagtgc tgggattaca ggcatgagcc accatgctgg   3120
gccaaccatt tcttggtgta ttcatgccaa acacttaaga cactgctgta gcccaggcgc   3180
ggtggctcac acctgtaatc ccagcacttt ggaaggctga ggcgggcgga tcacaaggtc   3240
acgagttcaa aactatcctg gccaacacag tgaaaccccg tctctactaa aatacaaaaa   3300
aattagccgg gtgtggtggt gcatgccttt agtcctagct attcaggagg ctgaggcagg   3360
ggaatcgctt gaacccgaga ggcagaggtt gcagtgagct gagatcgcac cactgcactc   3420
cagcctggtt acagagcaag actctgtctc aaacaaaaca aaacaaaaca aaaacacact   3480
actgtatttt ggatggatca aacctcctta attttaattt ctaatcctaa agtaaagaga   3540
tgcaattggg ggccttccat gtagaaagtg gggtcaggag gccaagaaag ggaatatgaa   3600
tgtatatcca agtcactcag gaacttttat gcaggtgcta gaaactttat gtcaaagtgg   3660
ccacaagatt gtttaatagg agacgaacga atgtaactcc atgtttactg ctaaaaacca   3720
aagctttgtg taaaatcttg aatttatggg gcgggagggt aggaaagcct gtacctgtct   3780
gttttttttcc tgatcctttt ccctcattcc tgaactgcag gagactgagc ccctttgggc   3840
```

tttggtgacc ccatcactgg ggtgtgttta tttgatggtt gattttgctg tactgggtac 3900
ttcctttccc attttctaat catttttttaa cacaagctga ctcttccctt cccttctcct 3960
ttccctggga aaatacaatg aataaataaa gacttattgg tacgcaaact gtca 4014

<210> SEQ ID NO 829
<211> LENGTH: 2260
<212> TYPE: DNA
<213> ORGANISM: Artificial Sequence
<220> FEATURE:
<223> OTHER INFORMATION: cDNA Sequence of human ZSCAN4

<400> SEQUENCE: 829
ccttgtaatt cataaatctc tgaaaactta aaagtttgag caaaagtttg tcatgtttct 60
atgagtaatt tataataaaa cttgatcaga atttgtgaga ctaacgtttg tctttatatt 120
ttcctttttt tttttttttt ttttgagaca cagtctcgct ctgtcgtcca ggctggagtg 180
ccgtggcgta atctcggctc actgcaacct ctgcctcctg gattcaaaca attcttctgc 240
ctcagcctcc tgagtagctg ggattacagg accagtgatg gtatagaaca ctgtattaga 300
gacatggagc tggggctgga tgaagattcc atcagtaatt caatcaacag acaagtgtta 360
tccaatcacg tctttaaatc aatcactgac atggagctgg ggctggatga agattccatc 420
agtaattcaa tcaacagaca agtgttatcc aatcacgtct ttaaatcaat cactgatccc 480
agcccctata aaagggagca gccttaggag gcacatcaga taaacccagt gtggaaagct 540
agtcacacat cagctcagtg ttcggcccgg gattacccag tcaaccaagg agcttgcagt 600
tttaaagaat ccaccaactg ttgaaacaaa tccctagaga cacaaggcaa gagactgaat 660
catcaaagta aagtctctct gagaattatt gctaagaatg gctttagatc taagaaccat 720
atttcagtgt gaaccatccg agaataatct tggatcagaa aattcagcgt ttcaacaaag 780
ccaaggacct gctgttcaga gagaagaagg gatttctgag ttctcaagaa tggtgctcaa 840
ttcatttcaa gacagcaata attcatatgc aaggcaggaa ttgcaaagac tttataggat 900
ctttcactca tggctgcaac cagaaaagca cagcaaggat gaaattattt ctctattagt 960
cctggagcag tttatgattg gtggccactg caatgacaaa gccagtgtga aagagaaatg 1020
gaaatcaagt ggcaaaaact tggagagatt catagaagac ctgactgatg acagcataaa 1080
tccacctgcc ttagtccacg tccacatgca gggacaggaa gctctctttt ctgaggatat 1140
gcccttaaga gatgtcattg ttcatctcac aaaacaagtg aatgcccaaa ccacaagaga 1200
agcaaacatg ggacaccct cccagacttc ccaagatact tccttagaaa caggacaagg 1260
atatgaagat gaacaagatg gctggaacag ttcttcgaaa actactcgag taaatgaaaa 1320
tattactaat caaggcaatc aaatagtttc cctaatcatc atccaggaag agaacggtcc 1380
taggcctgaa gagggaggtg tttcttctga caacccatac aactcaaaaa gagcagagct 1440
agtcactgct agatctcagg aagggtccat aaatggaatc actttccaag gtgtccctat 1500
ggtgatggga gcagggtgta tctctcaacc agagcagtcc tcccctgagt ctgcccttac 1560
ccaccagagc aatgagggaa attccacatg tgaggtacat cagaaaggat cccatggagt 1620
ccaaaaatca tacaaatgtg aagaatgccc caaggtcttt aagtatctct gtcacttatt 1680
agctcaccag agaagacaca ggaatgagag gccatttgtt tgtcccgagt gtcaaaaagg 1740
cttcttccag atatcagacc tacgggtgca tcagataatt cacacaggaa agaagccttt 1800
cacatgcagc atgtgtaaaa agtccttcag ccacaaaacc aacctgcggt ctcatgagag 1860

```
aatccacaca ggagaaaagc cttatacatg tccctttttgt aagacaagct accgccagtc   1920

atccacatac caccgccata tgaggactca tgagaaaatt accctgccaa gtgttccctc   1980

cacaccagaa gcttcctaag ctgctggtct gataatgtgt ataaatatgt atgcaagtat   2040

gtatattcct atagtattta tctacttagg atataagata taatctcctg attatgcttt   2100

caatttattg tcttgcttca ttaaaatgta aggctaagga gagcatggaa tttgtcagtt   2160

ttgttcacta aagtattcca agtggttggg aaagtggaac atttccaaga accaataaat   2220

ttctgttgaa taaatgaatg aatccaaaaa aaaaaaaaaa                          2260


<210> SEQ ID NO 830
<211> LENGTH: 372
<212> TYPE: PRT
<213> ORGANISM: Artificial Sequence
<220> FEATURE:
<223> OTHER INFORMATION: Amino acid Sequence of M5630

<400> SEQUENCE: 830

Ala Leu Ala Val Ile Val Val Pro Ala Leu Ala Pro Met Ala Gly His
1               5                   10                  15

Leu Ala Ser Asp Phe Ala Phe Ser Pro Pro Pro Gly Gly Gly Gly Asp
            20                  25                  30

Gly Pro Gly Gly Pro Glu Pro Gly Trp Val Asp Pro Arg Thr Trp Leu
        35                  40                  45

Ser Phe Gln Gly Pro Pro Gly Gly Pro Gly Ile Gly Pro Gly Val Gly
    50                  55                  60

Pro Gly Ser Glu Val Trp Gly Ile Pro Pro Cys Pro Pro Pro Tyr Glu
65                  70                  75                  80

Phe Cys Gly Gly Met Ala Tyr Cys Gly Pro Gln Val Gly Val Gly Leu
                85                  90                  95

Val Pro Gln Gly Gly Leu Glu Thr Ser Gln Pro Glu Gly Glu Ala Gly
            100                 105                 110

Val Gly Val Glu Ser Asn Ser Asp Gly Ala Ser Pro Glu Pro Cys Thr
        115                 120                 125

Val Thr Pro Gly Ala Val Lys Leu Glu Lys Glu Lys Leu Glu Gln Asn
    130                 135                 140

Pro Glu Glu Ser Gln Asp Ile Lys Ala Leu Gln Lys Glu Leu Glu Gln
145                 150                 155                 160

Phe Ala Lys Leu Leu Lys Gln Lys Arg Ile Thr Leu Gly Tyr Thr Gln
                165                 170                 175

Ala Asp Val Gly Leu Thr Leu Gly Val Leu Phe Gly Lys Val Phe Ser
            180                 185                 190

Gln Thr Thr Ile Cys Arg Phe Glu Ala Leu Gln Leu Ser Phe Lys Asn
        195                 200                 205

Met Cys Lys Leu Arg Pro Leu Leu Gln Lys Trp Val Glu Glu Ala Asp
    210                 215                 220

Asn Asn Glu Asn Leu Gln Glu Ile Cys Lys Ala Glu Thr Leu Val Gln
225                 230                 235                 240

Ala Arg Lys Arg Lys Arg Thr Ser Ile Glu Asn Arg Val Arg Gly Asn
                245                 250                 255

Leu Glu Asn Leu Phe Leu Gln Cys Pro Lys Pro Thr Leu Gln Gln Ile
            260                 265                 270

Ser His Ile Ala Gln Gln Leu Gly Leu Glu Lys Asp Val Val Arg Val
        275                 280                 285

Trp Phe Cys Asn Arg Arg Gln Lys Gly Lys Arg Ser Ser Ser Asp Tyr
```

```
    290                 295                 300

Ala Gln Arg Glu Asp Phe Glu Ala Ala Gly Ser Pro Phe Ser Gly Gly
305                 310                 315                 320

Pro Val Ser Phe Pro Leu Ala Pro Gly Pro His Phe Gly Thr Pro Gly
                325                 330                 335

Tyr Gly Ser Pro His Phe Thr Ala Leu Tyr Ser Ser Val Pro Phe Pro
            340                 345                 350

Glu Gly Glu Ala Phe Pro Pro Val Ser Val Thr Thr Leu Gly Ser Pro
        355                 360                 365

Met His Ser Asn
    370
```

<210> SEQ ID NO 831
<211> LENGTH: 1116
<212> TYPE: DNA
<213> ORGANISM: Artificial Sequence
<220> FEATURE:
<223> OTHER INFORMATION: cDNA Sequence of M563O

<400> SEQUENCE: 831

```
gcgctggcgg tgattgtggt gccggcgctg gcgccgatgg cgggacacct ggcttcggat     60

ttcgccttct cgccccctcc aggtggtgga ggtgatgggc caggggggcc ggagccgggc    120

tgggttgatc ctcggacctg gctaagcttc caaggccctc ctggagggcc aggaatcggg    180

ccgggggttg ggccaggctc tgaggtgtgg gggattcccc catgcccccc gccgtatgag    240

ttctgtgggg ggatggcgta ctgtgggccc caggttggag tggggctagt gccccaaggc    300

ggcttggaga cctctcagcc tgagggcgaa gcaggagtcg ggtggagag caactccgat    360

ggggcctccc cggagccctg caccgtcacc cctggtgccg tgaagctgga gaaggagaag    420

ctggagcaaa acccggagga gtcccaggac atcaaagctc tgcagaaaga actcgagcaa    480

tttgccaagc tcctgaagca gaagaggatc accctgggat atacacaggc cgatgtgggg    540

ctcaccctgg gggttctatt tgggaaggta ttcagccaaa cgaccatctg ccgctttgag    600

gctctgcagc ttagcttcaa gaacatgtgt aagctgcggc ccttgctgca gaagtgggtg    660

gaggaagctg acaacaatga aaatcttcag gagatatgca aagcagaaac cctcgtgcag    720

gcccgaaaga gaaagcgaac cagtatcgag aaccgagtga gaggcaacct ggagaatttg    780

ttcctgcagt gcccgaaacc cacactgcag cagatcagcc acatcgccca gcagcttggg    840

ctcgagaagg atgtggtccg agtgtggttc tgtaaccggc gccagaaggg caagcgatca    900

agcagcgact atgcacaacg agaggatttt gaggctgctg ggtctccttt ctcaggggga    960

ccagtgtcct ttcctctggc cccagggccc cattttggta ccccaggcta tgggagccct   1020

cacttcactg cactgtactc ctcggtccct ttccctgagg gggaagcctt tccccctgtc   1080

tccgtcacca ctctgggctc tcccatgcat tcaaac                             1116
```

<210> SEQ ID NO 832
<211> LENGTH: 473
<212> TYPE: PRT
<213> ORGANISM: Artificial Sequence
<220> FEATURE:
<223> OTHER INFORMATION: Amino acid Sequence of M563OSB

<400> SEQUENCE: 832

```
Ala Leu Ala Val Ile Val Val Pro Ala Leu Ala Pro Met Ala Gly His
1               5                   10                  15

Leu Ala Ser Asp Phe Ala Phe Ser Pro Pro Pro Gly Gly Gly Gly Asp
```

-continued

```
            20                  25                  30

Gly Pro Gly Gly Pro Glu Pro Gly Trp Val Asp Pro Arg Thr Trp Leu
        35                  40                  45

Ser Phe Gln Gly Pro Pro Gly Gly Pro Gly Ile Gly Pro Gly Val Gly
    50                  55                  60

Pro Gly Ser Glu Val Trp Gly Ile Pro Pro Cys Pro Pro Pro Tyr Glu
65                  70                  75                  80

Phe Cys Gly Gly Met Ala Tyr Cys Gly Pro Gln Val Gly Val Gly Leu
                85                  90                  95

Val Pro Gln Gly Gly Leu Glu Thr Ser Gln Pro Glu Gly Glu Ala Gly
            100                 105                 110

Val Gly Val Glu Ser Asn Ser Asp Gly Ala Ser Pro Glu Pro Cys Thr
        115                 120                 125

Val Thr Pro Gly Ala Val Lys Leu Glu Lys Glu Lys Leu Glu Gln Asn
    130                 135                 140

Pro Glu Glu Ser Gln Asp Ile Lys Ala Leu Gln Lys Glu Leu Glu Gln
145                 150                 155                 160

Phe Ala Lys Leu Leu Lys Gln Lys Arg Ile Thr Leu Gly Tyr Thr Gln
                165                 170                 175

Ala Asp Val Gly Leu Thr Leu Gly Val Leu Phe Gly Lys Val Phe Ser
            180                 185                 190

Gln Thr Thr Ile Cys Arg Phe Glu Ala Leu Gln Leu Ser Phe Lys Asn
        195                 200                 205

Met Cys Lys Leu Arg Pro Leu Leu Gln Lys Trp Val Glu Glu Ala Asp
    210                 215                 220

Asn Asn Glu Asn Leu Gln Glu Ile Cys Lys Ala Glu Thr Leu Val Gln
225                 230                 235                 240

Ala Arg Lys Arg Lys Arg Thr Ser Ile Glu Asn Arg Val Arg Gly Asn
                245                 250                 255

Leu Glu Asn Leu Phe Leu Gln Cys Pro Lys Pro Thr Leu Gln Gln Ile
            260                 265                 270

Ser His Ile Ala Gln Gln Leu Gly Leu Glu Lys Asp Val Val Arg Val
        275                 280                 285

Trp Phe Cys Asn Arg Arg Gln Lys Gly Lys Arg Ser Ser Ser Asp Tyr
    290                 295                 300

Ala Gln Arg Glu Asp Phe Glu Ala Ala Gly Ser Pro Phe Ser Gly Gly
305                 310                 315                 320

Pro Val Ser Phe Pro Leu Ala Pro Gly Pro His Phe Gly Thr Pro Gly
                325                 330                 335

Tyr Gly Ser Pro His Phe Thr Ala Leu Tyr Ser Ser Val Pro Phe Pro
            340                 345                 350

Glu Gly Glu Ala Phe Pro Pro Val Ser Val Thr Thr Leu Gly Ser Pro
        355                 360                 365

Met His Ser Asn Gly Ser Met Ala Glu Gln Ser Asp Lys Asp Val Lys
    370                 375                 380

Tyr Tyr Thr Leu Glu Glu Ile Gln Lys His Lys Asp Ser Lys Ser Thr
385                 390                 395                 400

Trp Val Ile Leu His His Lys Val Tyr Asp Leu Thr Lys Phe Leu Glu
                405                 410                 415

Glu His Pro Gly Gly Glu Glu Val Leu Gly Glu Gln Ala Gly Gly Asp
            420                 425                 430

Ala Thr Glu Asn Phe Glu Asp Val Gly His Ser Thr Asp Ala Arg Glu
        435                 440                 445
```

Leu Ser Lys Thr Tyr Ile Ile Gly Glu Leu His Pro Asp Asp Arg Ser
    450                 455                 460

Lys Ile Ala Lys Pro Ser Glu Thr Leu
465                 470

<210> SEQ ID NO 833
<211> LENGTH: 1419
<212> TYPE: DNA
<213> ORGANISM: Artificial Sequence
<220> FEATURE:
<223> OTHER INFORMATION: cDNA Sequence of M563OSB

<400> SEQUENCE: 833
gcgctggcgg tgattgtggt gccggcgctg gcgccgatgg cgggacacct ggcttcggat     60
ttcgccttct cgccccctcc aggtggtgga ggtgatgggc caggggggcc ggagccgggc    120
tgggttgatc ctcggacctg gctaagcttc caaggccctc ctggagggcc aggaatcggg    180
ccgggggttg ggccaggctc tgaggtgtgg gggattcccc catgcccccc gccgtatgag    240
ttctgtgggg ggatggcgta ctgtgggccc caggttggag tggggctagt gccccaaggc    300
ggcttggaga cctctcagcc tgagggcgaa gcaggagtcg ggtggagag caactccgat    360 ggggcctccc cggagccctg caccgtcacc cctggtgccg tgaagctgga gaaggagaag    420
ctggagcaaa acccggagga gtcccaggac atcaaagctc tgcagaaaga actcgagcaa    480
tttgccaagc tcctgaagca gaagaggatc accctgggat atacacaggc cgatgtgggg    540
ctcaccctgg gggttctatt tgggaaggta ttcagccaaa cgaccatctg ccgctttgag    600
gctctgcagc ttagcttcaa gaacatgtgt aagctgcggc ccttgctgca gaagtgggtg    660
gaggaagctg acaacaatga aaatcttcag gagatatgca aagcagaaac cctcgtgcag    720
gcccgaaaga gaaagcgaac cagtatcgag aaccgagtga gaggcaacct ggagaatttg    780
ttcctgcagt gcccgaaacc cacactgcag cagatcagcc acatcgccca gcagcttggg    840
ctcgagaagg atgtggtccg agtgtggttc tgtaaccggc gccagaaggg caagcgatca    900
agcagcgact atgcacaacg agaggatttt gaggctgctg ggtctccttt ctcaggggga    960
ccagtgtcct ttcctctggc cccagggccc cattttggta ccccaggcta tgggagccct   1020
cacttcactg cactgtactc ctcggtccct ttccctgagg gggaagcctt tccccctgtc   1080
tccgtcacca ctctgggctc tcccatgcat tcaaacggat ccatggcaga acaaagcgac   1140
aaggatgtga agtactacac tctggaggag attcagaagc acaaagacag caagagcacc   1200
tgggtgatcc tacatcataa ggtgtacgat ctgaccaagt ttctcgaaga gcatcctggt   1260
ggggaagaag tcctgggcga gcaagctggg ggtgatgcta ctgagaactt tgaggacgtc   1320
gggcactcta cggatgcacg agaactgtcc aaaacataca tcatcgggga gctccatcca   1380
gatgacagat caaagatagc caagccttcg gaaaccctt                          1419

<210> SEQ ID NO 834
<211> LENGTH: 501
<212> TYPE: PRT
<213> ORGANISM: Artificial Sequence
<220> FEATURE:
<223> OTHER INFORMATION: Amino acid Sequence of HNM563OSB

<400> SEQUENCE: 834

Met Gly Ser Ser His His His His His His Ser Ser Gly Leu Val Pro
1               5                   10                  15

Arg Gly Ser His Met Pro Lys Lys Lys Arg Lys Leu Ala Leu Ala Val

-continued

```
            20                  25                  30

Ile Val Val Pro Ala Leu Ala Pro Met Ala Gly His Leu Ala Ser Asp
        35                  40                  45

Phe Ala Phe Ser Pro Pro Pro Gly Gly Gly Gly Asp Gly Pro Gly Gly
    50                  55                  60

Pro Glu Pro Gly Trp Val Asp Pro Arg Thr Trp Leu Ser Phe Gln Gly
65                  70                  75                  80

Pro Pro Gly Gly Pro Gly Ile Gly Pro Gly Val Gly Pro Gly Ser Glu
                85                  90                  95

Val Trp Gly Ile Pro Pro Cys Pro Pro Pro Tyr Glu Phe Cys Gly Gly
            100                 105                 110

Met Ala Tyr Cys Gly Pro Gln Val Gly Val Gly Leu Val Pro Gln Gly
        115                 120                 125

Gly Leu Glu Thr Ser Gln Pro Glu Gly Glu Ala Gly Val Gly Val Glu
    130                 135                 140

Ser Asn Ser Asp Gly Ala Ser Pro Glu Pro Cys Thr Val Thr Pro Gly
145                 150                 155                 160

Ala Val Lys Leu Glu Lys Glu Lys Leu Glu Gln Asn Pro Glu Glu Ser
                165                 170                 175

Gln Asp Ile Lys Ala Leu Gln Lys Glu Leu Glu Gln Phe Ala Lys Leu
            180                 185                 190

Leu Lys Gln Lys Arg Ile Thr Leu Gly Tyr Thr Gln Ala Asp Val Gly
        195                 200                 205

Leu Thr Leu Gly Val Leu Phe Gly Lys Val Phe Ser Gln Thr Thr Ile
    210                 215                 220

Cys Arg Phe Glu Ala Leu Gln Leu Ser Phe Lys Asn Met Cys Lys Leu
225                 230                 235                 240

Arg Pro Leu Leu Gln Lys Trp Val Glu Glu Ala Asp Asn Asn Glu Asn
                245                 250                 255

Leu Gln Glu Ile Cys Lys Ala Glu Thr Leu Val Gln Ala Arg Lys Arg
            260                 265                 270

Lys Arg Thr Ser Ile Glu Asn Arg Val Arg Gly Asn Leu Glu Asn Leu
        275                 280                 285

Phe Leu Gln Cys Pro Lys Pro Thr Leu Gln Gln Ile Ser His Ile Ala
    290                 295                 300

Gln Gln Leu Gly Leu Glu Lys Asp Val Val Arg Val Trp Phe Cys Asn
305                 310                 315                 320

Arg Arg Gln Lys Gly Lys Arg Ser Ser Ser Asp Tyr Ala Gln Arg Glu
                325                 330                 335

Asp Phe Glu Ala Ala Gly Ser Pro Phe Ser Gly Gly Pro Val Ser Phe
            340                 345                 350

Pro Leu Ala Pro Gly Pro His Phe Gly Thr Pro Gly Tyr Gly Ser Pro
        355                 360                 365

His Phe Thr Ala Leu Tyr Ser Ser Val Pro Phe Pro Glu Gly Glu Ala
    370                 375                 380

Phe Pro Pro Val Ser Val Thr Thr Leu Gly Ser Pro Met His Ser Asn
385                 390                 395                 400

Gly Ser Met Ala Glu Gln Ser Asp Lys Asp Val Lys Tyr Tyr Thr Leu
                405                 410                 415

Glu Glu Ile Gln Lys His Lys Asp Ser Lys Ser Thr Trp Val Ile Leu
            420                 425                 430

His His Lys Val Tyr Asp Leu Thr Lys Phe Leu Glu Glu His Pro Gly
        435                 440                 445
```

```
Gly Glu Glu Val Leu Gly Glu Gln Ala Gly Gly Asp Ala Thr Glu Asn
    450                 455                 460

Phe Glu Asp Val Gly His Ser Thr Asp Ala Arg Glu Leu Ser Lys Thr
465                 470                 475                 480

Tyr Ile Ile Gly Glu Leu His Pro Asp Asp Arg Ser Lys Ile Ala Lys
                485                 490                 495

Pro Ser Glu Thr Leu
            500


<210> SEQ ID NO 835
<211> LENGTH: 1503
<212> TYPE: DNA
<213> ORGANISM: Artificial Sequence
<220> FEATURE:
<223> OTHER INFORMATION: cDNA Sequence of HNM563OSB

<400> SEQUENCE: 835

atgggcagca gccatcatca tcatcatcac agcagcggcc tggtgccgcg cggcagccat     60

atgcccaaga agaagaggaa gctggcgctg gcggtgattg tggtgccggc gctggcgccg    120

atggcgggac acctggcttc ggatttcgcc ttctcgcccc ctccaggtgg tggaggtgat    180

gggccagggg ggccggagcc gggctgggtt gatcctcgga cctggctaag cttccaaggc    240

cctcctggag ggccaggaat cgggccgggg gttgggccag gctctgaggt gtgggggatt    300

cccccatgcc ccccgccgta tgagttctgt ggggggatgg cgtactgtgg gccccaggtt    360

ggagtggggc tagtgcccca aggcggcttg gagacctctc agcctgaggg cgaagcagga    420

gtcggggtgg agagcaactc cgatggggcc tccccggagc cctgcaccgt cacccctggt    480

gccgtgaagc tggagaagga gaagctggag caaaacccgg aggagtccca ggacatcaaa    540

gctctgcaga aagaactcga gcaatttgcc aagctcctga agcagaagag gatcaccctg    600

ggatatacac aggccgatgt ggggctcacc ctgggggttc tatttgggaa ggtattcagc    660

caaacgacca tctgccgctt tgaggctctg cagcttagct tcaagaacat gtgtaagctg    720

cggcccttgc tgcagaagtg ggtggaggaa gctgacaaca atgaaaatct tcaggagata    780

tgcaaagcag aaaccctcgt gcaggcccga aagagaaagc gaaccagtat cgagaaccga    840

gtgagaggca acctggagaa tttgttcctg cagtgcccga aacccacact gcagcagatc    900

agccacatcg cccagcagct tgggctcgag aaggatgtgg tccgagtgtg gttctgtaac    960

cggcgccaga agggcaagcg atcaagcagc gactatgcac aacgagagga ttttgaggct   1020

gctgggtctc ctttctcagg gggaccagtg tcctttcctc tggccccagg gccccatttt   1080

ggtaccccag gctatgggag ccctcacttc actgcactgt actcctcggt ccctttccct   1140

gagggggaag cctttccccc tgtctccgtc accactctgg gctctcccat gcattcaaac   1200

ggatccatgg cagaacaaag cgacaaggat gtgaagtact acactctgga ggagattcag   1260

aagcacaaag acagcaagag cacctgggtg atcctacatc ataaggtgta cgatctgacc   1320

aagtttctcg aagagcatcc tggtggggaa gaagtcctgg gcgagcaagc tgggggtgat   1380

gctactgaga actttgagga cgtcgggcac tctacggatg cacgagaact gtccaaaaca   1440

tacatcatcg gggagctcca tccagatgac agatcaaaga tagccaagcc ttcggaaacc   1500

ctt                                                                  1503


<210> SEQ ID NO 836
<211> LENGTH: 329
<212> TYPE: PRT
```

<213> ORGANISM: Artificial Sequence
<220> FEATURE:
<223> OTHER INFORMATION: Amino acid Sequence of M563S

<400> SEQUENCE: 836

Ala Leu Ala Val Ile Val Val Pro Ala Leu Ala Pro Met Tyr Asn Met
1 5 10 15

Met Glu Thr Glu Leu Lys Pro Pro Gly Pro Gln Gln Thr Ser Gly Gly
20 25 30

Gly Gly Gly Asn Ser Thr Ala Ala Ala Ala Gly Gly Asn Gln Lys Asn
35 40 45

Ser Pro Asp Arg Val Lys Arg Pro Met Asn Ala Phe Met Val Trp Ser
50 55 60

Arg Gly Gln Arg Arg Lys Met Ala Gln Glu Asn Pro Lys Met His Asn
65 70 75 80

Ser Glu Ile Ser Lys Arg Leu Gly Ala Glu Trp Lys Leu Leu Ser Glu
85 90 95

Thr Glu Lys Arg Pro Phe Ile Asp Glu Ala Lys Arg Leu Arg Ala Leu
100 105 110

His Met Lys Glu His Pro Asp Tyr Lys Tyr Arg Pro Arg Arg Lys Thr
115 120 125

Lys Thr Leu Met Lys Lys Asp Lys Tyr Thr Leu Pro Gly Gly Leu Leu
130 135 140

Ala Pro Gly Gly Asn Ser Met Ala Ser Gly Val Gly Val Gly Ala Gly
145 150 155 160

Leu Gly Ala Gly Val Asn Gln Arg Met Asp Ser Tyr Ala His Met Asn
165 170 175

Gly Trp Ser Asn Gly Ser Tyr Ser Met Met Gln Asp Gln Leu Gly Tyr
180 185 190

Pro Gln His Pro Gly Leu Asn Ala His Gly Ala Ala Gln Met Gln Pro
195 200 205

Met His Arg Tyr Asp Val Ser Ala Leu Gln Tyr Asn Ser Met Thr Ser
210 215 220

Ser Gln Thr Tyr Met Asn Gly Ser Pro Thr Tyr Ser Met Ser Tyr Ser
225 230 235 240

Gln Gln Gly Thr Pro Gly Met Ala Leu Gly Ser Met Gly Ser Val Val
245 250 255

Lys Ser Glu Ala Ser Ser Ser Pro Pro Val Val Thr Ser Ser Ser His
260 265 270

Ser Arg Ala Pro Cys Gln Ala Gly Asp Leu Arg Asp Met Ile Ser Met
275 280 285

Tyr Leu Pro Gly Ala Glu Val Pro Glu Pro Ala Ala Pro Ser Arg Leu
290 295 300

His Met Ser Gln His Tyr Gln Ser Gly Pro Val Pro Gly Thr Ala Ile
305 310 315 320

Asn Gly Thr Leu Pro Leu Ser His Met
325

<210> SEQ ID NO 837
<211> LENGTH: 987
<212> TYPE: DNA
<213> ORGANISM: Artificial Sequence
<220> FEATURE:
<223> OTHER INFORMATION: cDNA Sequence of M563S

<400> SEQUENCE: 837

```
gcgctggcgg tgattgtggt gccggcgctg gcgccgatgt acaacatgat ggagacggag     60

ctgaagccgc cgggcccgca gcaaacttcg gggggcggcg gcggcaactc caccgcggcg    120

gcggccggcg gcaaccagaa aaacagcccg gaccgcgtca agcggcccat gaatgccttc    180

atggtgtggt cccgcgggca gcggcgcaag atggcccagg agaaccccaa gatgcacaac    240

tcggagatca gcaagcgcct gggcgccgag tggaaacttt tgtcggagac ggagaagcgg    300

ccgttcatcg acgaggctaa gcggctgcga gcgctgcaca tgaaggagca cccggattat    360

aaataccggc cccggcggaa aaccaagacg ctcatgaaga aggataagta cacgctgccc    420

ggcgggctgc tggcccccgg cggcaatagc atggcgagcg gggtcggggt gggcgccggc    480

ctgggcgcgg gcgtgaacca gcgcatggac agttacgcgc acatgaacgg ctggagcaac    540

ggcagctaca gcatgatgca ggaccagctg ggctacccgc agcacccggg cctcaatgcg    600

cacggcgcag cgcagatgca gcccatgcac cgctacgacg tgagcgccct gcagtacaac    660

tccatgacca gctcgcagac ctacatgaac ggctcgccca cctacagcat gtcctactcg    720

cagcagggca cccctggcat ggctcttggc tccatgggtt cggtggtcaa gtccgaggcc    780

agctccagcc cccctgtggt tacctcttcc tcccactcca gggcgccctg ccaggccggg    840

gacctccggg acatgatcag catgtatctc cccggcgccg aggtgccgga acccgccgcc    900

cccagcagac ttcacatgtc ccagcactac cagagcggcc cggtgcccgg cacggccatt    960

aacggcacac tgcccctctc acacatg                                        987
```

```
<210> SEQ ID NO 838
<211> LENGTH: 1089
<212> TYPE: PRT
<213> ORGANISM: Artificial Sequence
<220> FEATURE:
<223> OTHER INFORMATION: Amino acid Sequence of M563SASSASBSASB

<400> SEQUENCE: 838

Ala Leu Ala Val Ile Val Val Pro Ala Leu Ala Pro Met Ala Asn Ile
1               5                   10                  15

Thr Val Phe Tyr Asn Glu Asp Phe Gln Gly Lys Gln Val Asp Leu Pro
            20                  25                  30

Pro Gly Asn Tyr Thr Arg Ala Gln Leu Ala Ala Leu Gly Ile Glu Asn
        35                  40                  45

Asn Thr Ile Ser Ser Val Lys Val Pro Pro Gly Val Lys Ala Ile Leu
    50                  55                  60

Tyr Gln Asn Asp Gly Phe Ala Gly Asp Gln Ile Glu Val Val Ala Asn
65                  70                  75                  80

Ala Glu Glu Leu Gly Pro Leu Asn Asn Asn Val Ser Ser Ile Arg Val
                85                  90                  95

Ile Ser Val Pro Val Gln Pro Arg Met Ala Asn Ile Thr Val Phe Tyr
            100                 105                 110

Asn Glu Asp Phe Gln Gly Lys Gln Val Asp Leu Pro Pro Gly Asn Tyr
        115                 120                 125

Thr Arg Ala Gln Leu Ala Ala Leu Gly Ile Glu Asn Asn Thr Ile Ser
    130                 135                 140

Ser Val Lys Val Pro Pro Gly Val Lys Ala Ile Leu Tyr Gln Asn Asp
145                 150                 155                 160

Gly Phe Ala Gly Asp Gln Ile Glu Val Val Ala Asn Ala Glu Glu Leu
                165                 170                 175

Gly Pro Leu Asn Asn Asn Val Ser Ser Ile Arg Val Ile Ser Val Pro
            180                 185                 190
```

```
Val Gln Pro Arg Gly Ser Met Tyr Asn Met Met Glu Thr Glu Leu Lys
        195                 200                 205

Pro Pro Gly Pro Gln Gln Thr Ser Gly Gly Gly Gly Gly Asn Ser Thr
    210                 215                 220

Ala Ala Ala Ala Gly Gly Asn Gln Lys Asn Ser Pro Asp Arg Val Lys
225                 230                 235                 240

Arg Pro Met Asn Ala Phe Met Val Trp Ser Arg Gly Gln Arg Arg Lys
                245                 250                 255

Met Ala Gln Glu Asn Pro Lys Met His Asn Ser Glu Ile Ser Lys Arg
            260                 265                 270

Leu Gly Ala Glu Trp Lys Leu Leu Ser Glu Thr Glu Lys Arg Pro Phe
        275                 280                 285

Ile Asp Glu Ala Lys Arg Leu Arg Ala Leu His Met Lys Glu His Pro
    290                 295                 300

Asp Tyr Lys Tyr Arg Pro Arg Arg Lys Thr Lys Thr Leu Met Lys Lys
305                 310                 315                 320

Asp Lys Tyr Thr Leu Pro Gly Gly Leu Leu Ala Pro Gly Gly Asn Ser
                325                 330                 335

Met Ala Ser Gly Val Gly Val Gly Ala Gly Leu Gly Ala Gly Val Asn
            340                 345                 350

Gln Arg Met Asp Ser Tyr Ala His Met Asn Gly Trp Ser Asn Gly Ser
        355                 360                 365

Tyr Ser Met Met Gln Asp Gln Leu Gly Tyr Pro Gln His Pro Gly Leu
    370                 375                 380

Asn Ala His Gly Ala Ala Gln Met Gln Pro Met His Arg Tyr Asp Val
385                 390                 395                 400

Ser Ala Leu Gln Tyr Asn Ser Met Thr Ser Ser Gln Thr Tyr Met Asn
                405                 410                 415

Gly Ser Pro Thr Tyr Ser Met Ser Tyr Ser Gln Gln Gly Thr Pro Gly
            420                 425                 430

Met Ala Leu Gly Ser Met Gly Ser Val Val Lys Ser Glu Ala Ser Ser
        435                 440                 445

Ser Pro Pro Val Val Thr Ser Ser Ser His Ser Arg Ala Pro Cys Gln
    450                 455                 460

Ala Gly Asp Leu Arg Asp Met Ile Ser Met Tyr Leu Pro Gly Ala Glu
465                 470                 475                 480

Val Pro Glu Pro Ala Ala Pro Ser Arg Leu His Met Ser Gln His Tyr
                485                 490                 495

Gln Ser Gly Pro Val Pro Gly Thr Ala Ile Asn Gly Thr Leu Pro Leu
            500                 505                 510

Ser His Met Lys Leu Met Ala Asn Ile Thr Val Phe Tyr Asn Glu Asp
        515                 520                 525

Phe Gln Gly Lys Gln Val Asp Leu Pro Pro Gly Asn Tyr Thr Arg Ala
    530                 535                 540

Gln Leu Ala Ala Leu Gly Ile Glu Asn Asn Thr Ile Ser Ser Val Lys
545                 550                 555                 560

Val Pro Pro Gly Val Lys Ala Ile Leu Tyr Gln Asn Asp Gly Phe Ala
                565                 570                 575

Gly Asp Gln Ile Glu Val Val Ala Asn Ala Glu Glu Leu Gly Pro Leu
            580                 585                 590

Asn Asn Asn Val Ser Ser Ile Arg Val Ile Ser Val Pro Val Gln Pro
        595                 600                 605
```

```
Arg Met Ala Asn Ile Thr Val Phe Tyr Asn Glu Asp Phe Gln Gly Lys
    610                 615                 620

Gln Val Asp Leu Pro Pro Gly Asn Tyr Thr Arg Ala Gln Leu Ala Ala
625                 630                 635                 640

Leu Gly Ile Glu Asn Asn Thr Ile Ser Ser Val Lys Val Pro Pro Gly
                645                 650                 655

Val Lys Ala Ile Leu Tyr Gln Asn Asp Gly Phe Ala Gly Asp Gln Ile
            660                 665                 670

Glu Val Val Ala Asn Ala Glu Glu Leu Gly Pro Leu Asn Asn Asn Val
        675                 680                 685

Ser Ser Ile Arg Val Ile Ser Val Pro Val Gln Pro Arg Gly Thr Met
    690                 695                 700

Ala Glu Gln Ser Asp Lys Asp Val Lys Tyr Tyr Thr Leu Glu Glu Ile
705                 710                 715                 720

Gln Lys His Lys Asp Ser Lys Ser Thr Trp Val Ile Leu His His Lys
                725                 730                 735

Val Tyr Asp Leu Thr Lys Phe Leu Glu Glu His Pro Gly Gly Glu Glu
            740                 745                 750

Val Leu Gly Glu Gln Ala Gly Gly Asp Ala Thr Glu Asn Phe Glu Asp
        755                 760                 765

Val Gly His Ser Thr Asp Ala Arg Glu Leu Ser Lys Thr Tyr Ile Ile
    770                 775                 780

Gly Glu Leu His Pro Asp Asp Arg Ser Lys Ile Ala Lys Pro Ser Glu
785                 790                 795                 800

Thr Leu Val Asp Met Ala Asn Ile Thr Val Phe Tyr Asn Glu Asp Phe
                805                 810                 815

Gln Gly Lys Gln Val Asp Leu Pro Pro Gly Asn Tyr Thr Arg Ala Gln
            820                 825                 830

Leu Ala Ala Leu Gly Ile Glu Asn Asn Thr Ile Ser Ser Val Lys Val
        835                 840                 845

Pro Pro Gly Val Lys Ala Ile Leu Tyr Gln Asn Asp Gly Phe Ala Gly
    850                 855                 860

Asp Gln Ile Glu Val Val Ala Asn Ala Glu Glu Leu Gly Pro Leu Asn
865                 870                 875                 880

Asn Asn Val Ser Ser Ile Arg Val Ile Ser Val Pro Val Gln Pro Arg
                885                 890                 895

Met Ala Asn Ile Thr Val Phe Tyr Asn Glu Asp Phe Gln Gly Lys Gln
            900                 905                 910

Val Asp Leu Pro Pro Gly Asn Tyr Thr Arg Ala Gln Leu Ala Ala Leu
        915                 920                 925

Gly Ile Glu Asn Asn Thr Ile Ser Ser Val Lys Val Pro Pro Gly Val
    930                 935                 940

Lys Ala Ile Leu Tyr Gln Asn Asp Gly Phe Ala Gly Asp Gln Ile Glu
945                 950                 955                 960

Val Val Ala Asn Ala Glu Glu Leu Gly Pro Leu Asn Asn Asn Val Ser
                965                 970                 975

Ser Ile Arg Val Ile Ser Val Pro Val Gln Pro Arg Gly Thr Met Ala
            980                 985                 990

Glu Gln Ser Asp Lys Asp Val Lys Tyr Tyr Thr Leu Glu Glu Ile Gln
        995                 1000                1005

Lys His Lys Asp Ser Lys Ser Thr Trp Val Ile Leu His His Lys Val
    1010                1015                1020

Tyr Asp Leu Thr Lys Phe Leu Glu Glu His Pro Gly Gly Glu Glu Val
```

-continued

```
1025                1030                1035                1040

Leu Gly Glu Gln Ala Gly Gly Asp Ala Thr Glu Asn Phe Glu Asp Val
                1045                1050                1055

Gly His Ser Thr Asp Ala Arg Glu Leu Ser Lys Thr Tyr Ile Ile Gly
            1060                1065                1070

Glu Leu His Pro Asp Asp Arg Ser Lys Ile Ala Lys Pro Ser Glu Thr
        1075                1080                1085

Leu


<210> SEQ ID NO 839
<211> LENGTH: 3267
<212> TYPE: DNA
<213> ORGANISM: Artificial Sequence
<220> FEATURE:
<223> OTHER INFORMATION: cDNA Sequence of M563SASSASBSASB

<400> SEQUENCE: 839

gcgctggcgg tgattgtggt gccggcgctg gcgccgatgg caaatattac cgttttctat     60

aacgaagact tccagggtaa gcaggtcgat ctgccgcctg gcaactatac ccgcgcccag    120

ttggcggcgc tgggcatcga gaataatacc atcagctcgg tgaaggtgcc gcctggcgtg    180

aaggctatcc tgtaccagaa cgatggtttc gccggcgacc agatcgaagt ggtggccaat    240

gccgaggagt tgggcccgct gaataataac gtctccagca tccgcgtcat ctccgtgccc    300

gtgcagccgc gcatggcaaa tattaccgtt ttctataacg aagacttcca gggtaagcag    360

gtcgatctgc cgcctggcaa ctatacccgc gcccagttgg cggcgctggg catcgagaat    420

aataccatca gctcggtgaa ggtgccgcct ggcgtgaagg ctatcctcta ccagaacgat    480

ggtttcgccg gcgaccagat cgaagtggtg gccaatgccg aggagctggg tccgctgaat    540

aataacgtct ccagcatccg cgtcatctcc gtgccggtgc agccgagggg atccatgtac    600

aacatgatgg agacggagct gaagccgccg ggcccgcagc aaacttcggg gggcggcggc    660

ggcaactcca ccgcggcggc ggccggcggc aaccagaaaa acagcccgga ccgcgtcaag    720

cggcccatga atgccttcat ggtgtggtcc cgcgggcagc ggcgcaagat ggcccaggag    780

aaccccaaga tgcacaactc ggagatcagc aagcgcctgg gcgccgagtg gaaacttttg    840

tcggagacgg agaagcggcc gttcatcgac gaggctaagc ggctgcgagc gctgcacatg    900

aaggagcacc cggattataa ataccggccc cggcggaaaa ccaagacgct catgaagaag    960

gataagtaca cgctgcccgg cgggctgctg gcccccggcg gcaatagcat ggcgagcggg   1020

gtcggggtgg gcgccggcct gggcgcgggc gtgaaccagc gcatggacag ttacgcgcac   1080

atgaacggct ggagcaacgg cagctacagc atgatgcagg accagctggg ctacccgcag   1140

cacccgggcc tcaatgcgca cggcgcagcg cagatgcagc ccatgcaccg ctacgacgtg   1200

agcgccctgc agtacaactc catgaccagc tcgcagacct acatgaacgg ctcgcccacc   1260

tacagcatgt cctactcgca gcagggcacc cctggcatgg ctcttggctc catgggttcg   1320

gtggtcaagt ccgaggccag ctccagcccc cctgtggtta cctcttcctc ccactccagg   1380

gcgccctgcc aggccgggga cctccgggac atgatcagca tgtatctccc cggcgccgag   1440

gtgccggaac ccgccgcccc cagcagactt cacatgtccc agcactacca gagcggcccg   1500

gtgcccggca cggccattaa cggcacactg cccctctcac acatgaagct tatggcaaat   1560

attaccgttt tctataacga agacttccag ggtaagcagg tcgatctgcc gcctggcaac   1620

tatacccgcg cccagttggc ggcgctgggc atcgagaata ataccatcag ctcggtgaag   1680
```

-continued

```
gtgccgcctg gcgtgaaggc tatcctgtac cagaacgatg gtttcgccgg cgaccagatc   1740
gaagtggtgg ccaatgccga ggagttgggc ccgctgaata ataacgtctc cagcatccgc   1800
gtcatctccg tgcccgtgca gccgcgcatg gcaaatatta ccgttttcta taacgaagac   1860
ttccagggta agcaggtcga tctgccgcct ggcaactata cccgcgccca gttggcggcg   1920
ctgggcatcg agaataatac catcagctcg gtgaaggtgc cgcctggcgt gaaggctatc   1980
ctctaccaga acgatggttt cgccggcgac cagatcgaag tggtggccaa tgccgaggag   2040
ctgggtccgc tgaataataa cgtctccagc atccgcgtca tctccgtgcc ggtgcagccg   2100
aggggtacca tggcagaaca aagcgacaag gatgtgaagt actacactct ggaggagatt   2160
cagaagcaca aagacagcaa gagcacctgg gtgatcctac atcataaggt gtacgatctg   2220
accaagtttc tcgaagagca tcctggtggg gaagaagtcc tgggcgagca agctgggggt   2280
gatgctactg agaactttga ggacgtcggg cactctacgg atgcacgaga actgtccaaa   2340
acatacatca tcggggagct ccatccagat gacagatcaa agatagccaa gccttcggaa   2400
acccttgtcg acatggcaaa tattaccgtt ttctataacg aagacttcca gggtaagcag   2460
gtcgatctgc cgcctggcaa ctatacccgc gcccagttgg cggcgctggg catcgagaat   2520
aataccatca gctcggtgaa ggtgccgcct ggcgtgaagg ctatcctgta ccagaacgat   2580
ggtttcgccg gcgaccagat cgaagtggtg gccaatgccg aggagttggg cccgctgaat   2640
aataacgtct ccagcatccg cgtcatctcc gtgcccgtgc agccgcgcat ggcaaatatt   2700
accgttttct ataacgaaga cttccagggt aagcaggtcg atctgccgcc tggcaactat   2760
acccgcgccc agttggcggc gctgggcatc gagaataata ccatcagctc ggtgaaggtg   2820
ccgcctggcg tgaaggctat cctctaccag aacgatggtt tcgccggcga ccagatcgaa   2880
gtggtggcca atgccgagga gctgggtccg ctgaataata acgtctccag catccgcgtc   2940
atctccgtgc cggtgcagcc gaggggtacc atggcagaac aaagcgacaa ggatgtgaag   3000
tactacactc tggaggagat tcagaagcac aaagacagca agagcacctg ggtgatccta   3060
catcataagg tgtacgatct gaccaagttt ctcgaagagc atcctggtgg ggaagaagtc   3120
ctgggcgagc aagctggggg tgatgctact gagaactttg aggacgtcgg gcactctacg   3180
gatgcacgag aactgtccaa aacatacatc atcggggagc tccatccaga tgacagatca   3240
aagatagcca agccttcgga aacccttgtc                                    3267
```

<210> SEQ ID NO 840
<211> LENGTH: 1117
<212> TYPE: PRT
<213> ORGANISM: Artificial Sequence
<220> FEATURE:
<223> OTHER INFORMATION: Amino acid Sequence of HNM563SASSASBSASB

<400> SEQUENCE: 840

```
Met Gly Ser Ser His His His His His His Ser Ser Gly Leu Val Pro
1               5                   10                  15

Arg Gly Ser His Met Pro Lys Lys Lys Arg Lys Leu Ala Leu Ala Val
            20                  25                  30

Ile Val Val Pro Ala Leu Ala Pro Met Ala Asn Ile Thr Val Phe Tyr
        35                  40                  45

Asn Glu Asp Phe Gln Gly Lys Gln Val Asp Leu Pro Pro Gly Asn Tyr
    50                  55                  60

Thr Arg Ala Gln Leu Ala Ala Leu Gly Ile Glu Asn Asn Thr Ile Ser
65                  70                  75                  80
```

-continued

```
Ser Val Lys Val Pro Pro Gly Val Lys Ala Ile Leu Tyr Gln Asn Asp
                85                  90                  95

Gly Phe Ala Gly Asp Gln Ile Glu Val Val Ala Asn Ala Glu Glu Leu
            100                 105                 110

Gly Pro Leu Asn Asn Asn Val Ser Ser Ile Arg Val Ile Ser Val Pro
        115                 120                 125

Val Gln Pro Arg Met Ala Asn Ile Thr Val Phe Tyr Asn Glu Asp Phe
    130                 135                 140

Gln Gly Lys Gln Val Asp Leu Pro Pro Gly Asn Tyr Thr Arg Ala Gln
145                 150                 155                 160

Leu Ala Ala Leu Gly Ile Glu Asn Asn Thr Ile Ser Ser Val Lys Val
                165                 170                 175

Pro Pro Gly Val Lys Ala Ile Leu Tyr Gln Asn Asp Gly Phe Ala Gly
            180                 185                 190

Asp Gln Ile Glu Val Val Ala Asn Ala Glu Glu Leu Gly Pro Leu Asn
        195                 200                 205

Asn Asn Val Ser Ser Ile Arg Val Ile Ser Val Pro Val Gln Pro Arg
    210                 215                 220

Gly Ser Met Tyr Asn Met Met Glu Thr Glu Leu Lys Pro Pro Gly Pro
225                 230                 235                 240

Gln Gln Thr Ser Gly Gly Gly Gly Gly Asn Ser Thr Ala Ala Ala Ala
                245                 250                 255

Gly Gly Asn Gln Lys Asn Ser Pro Asp Arg Val Lys Arg Pro Met Asn
            260                 265                 270

Ala Phe Met Val Trp Ser Arg Gly Gln Arg Arg Lys Met Ala Gln Glu
        275                 280                 285

Asn Pro Lys Met His Asn Ser Glu Ile Ser Lys Arg Leu Gly Ala Glu
    290                 295                 300

Trp Lys Leu Leu Ser Glu Thr Glu Lys Arg Pro Phe Ile Asp Glu Ala
305                 310                 315                 320

Lys Arg Leu Arg Ala Leu His Met Lys Glu His Pro Asp Tyr Lys Tyr
                325                 330                 335

Arg Pro Arg Arg Lys Thr Lys Thr Leu Met Lys Lys Asp Lys Tyr Thr
            340                 345                 350

Leu Pro Gly Gly Leu Leu Ala Pro Gly Gly Asn Ser Met Ala Ser Gly
        355                 360                 365

Val Gly Val Gly Ala Gly Leu Gly Ala Gly Val Asn Gln Arg Met Asp
    370                 375                 380

Ser Tyr Ala His Met Asn Gly Trp Ser Asn Gly Ser Tyr Ser Met Met
385                 390                 395                 400

Gln Asp Gln Leu Gly Tyr Pro Gln His Pro Gly Leu Asn Ala His Gly
                405                 410                 415

Ala Ala Gln Met Gln Pro Met His Arg Tyr Asp Val Ser Ala Leu Gln
            420                 425                 430

Tyr Asn Ser Met Thr Ser Ser Gln Thr Tyr Met Asn Gly Ser Pro Thr
        435                 440                 445

Tyr Ser Met Ser Tyr Ser Gln Gln Gly Thr Pro Gly Met Ala Leu Gly
    450                 455                 460

Ser Met Gly Ser Val Val Lys Ser Glu Ala Ser Ser Ser Pro Pro Val
465                 470                 475                 480

Val Thr Ser Ser Ser His Ser Arg Ala Pro Cys Gln Ala Gly Asp Leu
                485                 490                 495

Arg Asp Met Ile Ser Met Tyr Leu Pro Gly Ala Glu Val Pro Glu Pro
```

-continued

```
            500                 505                 510

Ala Ala Pro Ser Arg Leu His Met Ser Gln His Tyr Gln Ser Gly Pro
        515                 520                 525

Val Pro Gly Thr Ala Ile Asn Gly Thr Leu Pro Leu Ser His Met Lys
    530                 535                 540

Leu Met Ala Asn Ile Thr Val Phe Tyr Asn Glu Asp Phe Gln Gly Lys
545                 550                 555                 560

Gln Val Asp Leu Pro Pro Gly Asn Tyr Thr Arg Ala Gln Leu Ala Ala
                565                 570                 575

Leu Gly Ile Glu Asn Asn Thr Ile Ser Ser Val Lys Val Pro Pro Gly
            580                 585                 590

Val Lys Ala Ile Leu Tyr Gln Asn Asp Gly Phe Ala Gly Asp Gln Ile
        595                 600                 605

Glu Val Val Ala Asn Ala Glu Glu Leu Gly Pro Leu Asn Asn Asn Val
    610                 615                 620

Ser Ser Ile Arg Val Ile Ser Val Pro Val Gln Pro Arg Met Ala Asn
625                 630                 635                 640

Ile Thr Val Phe Tyr Asn Glu Asp Phe Gln Gly Lys Gln Val Asp Leu
                645                 650                 655

Pro Pro Gly Asn Tyr Thr Arg Ala Gln Leu Ala Ala Leu Gly Ile Glu
            660                 665                 670

Asn Asn Thr Ile Ser Ser Val Lys Val Pro Pro Gly Val Lys Ala Ile
        675                 680                 685

Leu Tyr Gln Asn Asp Gly Phe Ala Gly Asp Gln Ile Glu Val Val Ala
    690                 695                 700

Asn Ala Glu Glu Leu Gly Pro Leu Asn Asn Asn Val Ser Ser Ile Arg
705                 710                 715                 720

Val Ile Ser Val Pro Val Gln Pro Arg Gly Thr Met Ala Glu Gln Ser
                725                 730                 735

Asp Lys Asp Val Lys Tyr Tyr Thr Leu Glu Glu Ile Gln Lys His Lys
            740                 745                 750

Asp Ser Lys Ser Thr Trp Val Ile Leu His His Lys Val Tyr Asp Leu
        755                 760                 765

Thr Lys Phe Leu Glu Glu His Pro Gly Gly Glu Glu Val Leu Gly Glu
    770                 775                 780

Gln Ala Gly Gly Asp Ala Thr Glu Asn Phe Glu Asp Val Gly His Ser
785                 790                 795                 800

Thr Asp Ala Arg Glu Leu Ser Lys Thr Tyr Ile Ile Gly Glu Leu His
                805                 810                 815

Pro Asp Asp Arg Ser Lys Ile Ala Lys Pro Ser Glu Thr Leu Val Asp
            820                 825                 830

Met Ala Asn Ile Thr Val Phe Tyr Asn Glu Asp Phe Gln Gly Lys Gln
        835                 840                 845

Val Asp Leu Pro Pro Gly Asn Tyr Thr Arg Ala Gln Leu Ala Ala Leu
    850                 855                 860

Gly Ile Glu Asn Asn Thr Ile Ser Ser Val Lys Val Pro Pro Gly Val
865                 870                 875                 880

Lys Ala Ile Leu Tyr Gln Asn Asp Gly Phe Ala Gly Asp Gln Ile Glu
                885                 890                 895

Val Val Ala Asn Ala Glu Glu Leu Gly Pro Leu Asn Asn Asn Val Ser
            900                 905                 910

Ser Ile Arg Val Ile Ser Val Pro Val Gln Pro Arg Met Ala Asn Ile
        915                 920                 925
```

```
Thr Val Phe Tyr Asn Glu Asp Phe Gln Gly Lys Gln Val Asp Leu Pro
    930                 935                 940

Pro Gly Asn Tyr Thr Arg Ala Gln Leu Ala Ala Leu Gly Ile Glu Asn
945                 950                 955                 960

Asn Thr Ile Ser Ser Val Lys Val Pro Pro Gly Val Lys Ala Ile Leu
                965                 970                 975

Tyr Gln Asn Asp Gly Phe Ala Gly Asp Gln Ile Glu Val Val Ala Asn
            980                 985                 990

Ala Glu Glu Leu Gly Pro Leu Asn Asn Asn Val Ser Ser Ile Arg Val
        995                 1000                1005

Ile Ser Val Pro Val Gln Pro Arg Gly Thr Met Ala Glu Gln Ser Asp
    1010                1015                1020

Lys Asp Val Lys Tyr Tyr Thr Leu Glu Glu Ile Gln Lys His Lys Asp
1025                1030                1035                1040

Ser Lys Ser Thr Trp Val Ile Leu His His Lys Val Tyr Asp Leu Thr
                1045                1050                1055

Lys Phe Leu Glu Glu His Pro Gly Gly Glu Glu Val Leu Gly Glu Gln
            1060                1065                1070

Ala Gly Gly Asp Ala Thr Glu Asn Phe Glu Asp Val Gly His Ser Thr
        1075                1080                1085

Asp Ala Arg Glu Leu Ser Lys Thr Tyr Ile Ile Gly Glu Leu His Pro
    1090                1095                1100

Asp Asp Arg Ser Lys Ile Ala Lys Pro Ser Glu Thr Leu
1105                1110                1115
```

<210> SEQ ID NO 841
<211> LENGTH: 3351
<212> TYPE: DNA
<213> ORGANISM: Artificial Sequence
<220> FEATURE:
<223> OTHER INFORMATION: cDNA Sequence of HNM563SASSASBSASB

<400> SEQUENCE: 841

```
atgggcagca gccatcatca tcatcatcac agcagcggcc tggtgccgcg cggcagccat      60

atgcccaaga agaagaggaa gctggcgctg gcggtgattg tggtgccggc gctggcgccg     120

atggcaaata ttaccgtttt ctataacgaa gacttccagg gtaagcaggt cgatctgccg     180

cctggcaact atacccgcgc ccagttggcg gcgctgggca tcgagaataa taccatcagc     240

tcggtgaagg tgccgcctgg cgtgaaggct atcctgtacc agaacgatgg tttcgccggc     300

gaccagatcg aagtggtggc caatgccgag gagttgggcc cgctgaataa taacgtctcc     360

agcatccgcg tcatctccgt gcccgtgcag ccgcgcatgg caaatattac cgttttctat     420

aacgaagact tccagggtaa gcaggtcgat ctgccgcctg gcaactatac ccgcgcccag     480

ttggcggcgc tgggcatcga gaataatacc atcagctcgg tgaaggtgcc gcctggcgtg     540

aaggctatcc tctaccagaa cgatggtttc gccggcgacc agatcgaagt ggtggccaat     600

gccgaggagc tgggtccgct gaataataac gtctccagca tccgcgtcat ctccgtgccg     660

gtgcagccga ggggatccat gtacaacatg atggagacgg agctgaagcc gccgggcccg     720

cagcaaactt cgggggggcgg cggcggcaac tccaccgcgg cggcggccgg cggcaaccag     780

aaaaacagcc cggaccgcgt caagcggccc atgaatgcct tcatggtgtg gtcccgcggg     840

cagcggcgca agatggccca ggagaacccc aagatgcaca actcggagat cagcaagcgc     900

ctgggcgccg agtggaaact tttgtcggag acggagaagc ggccgttcat cgacgaggct     960
```

```
aagcggctgc gagcgctgca catgaaggag cacccggatt ataaataccg gccccggcgg   1020
aaaaccaaga cgctcatgaa gaaggataag tacacgctgc ccggcgggct gctggccccc   1080
ggcggcaata gcatggcgag cggggtcggg gtgggcgccg gcctgggcgc gggcgtgaac   1140
cagcgcatgg acagttacgc gcacatgaac ggctggagca acggcagcta cagcatgatg   1200
caggaccagc tgggctaccc gcagcacccg ggcctcaatg cgcacggcgc agcgcagatg   1260
cagcccatgc accgctacga cgtgagcgcc ctgcagtaca actccatgac cagctcgcag   1320
acctacatga acggctcgcc cacctacagc atgtcctact cgcagcaggg cacccctggc   1380
atggctcttg gctccatggg ttcggtggtc aagtccgagg ccagctccag cccccctgtg   1440
gttacctctt cctcccactc cagggcgccc tgccaggccg gggacctccg ggacatgatc   1500
agcatgtatc tccccggcgc cgaggtgccg gaacccgccg cccccagcag acttcacatg   1560
tcccagcact accagagcgg cccggtgccc ggcacggcca ttaacggcac actgcccctc   1620
tcacacatga agcttatggc aaatattacc gttttctata acgaagactt ccagggtaag   1680
caggtcgatc tgccgcctgg caactatacc cgcgcccagt tggcggcgct gggcatcgag   1740
aataatacca tcagctcggt gaaggtgccg cctggcgtga aggctatcct gtaccagaac   1800
gatggtttcg ccggcgacca gatcgaagtg gtggccaatg ccgaggagtt gggcccgctg   1860
aataataacg tctccagcat ccgcgtcatc tccgtgcccg tgcagccgcg catggcaaat   1920
attaccgttt tctataacga agacttccag ggtaagcagg tcgatctgcc gcctggcaac   1980
tatacccgcg cccagttggc ggcgctgggc atcgagaata ataccatcag ctcggtgaag   2040
gtgccgcctg gcgtgaaggc tatcctctac cagaacgatg gtttcgccgg cgaccagatc   2100
gaagtggtgg ccaatgccga ggagctgggt ccgctgaata ataacgtctc cagcatccgc   2160
gtcatctccg tgccggtgca gccgaggggt accatggcag aacaaagcga caaggatgtg   2220
aagtactaca ctctggagga gattcagaag cacaaagaca gcaagagcac ctgggtgatc   2280
ctacatcata aggtgtacga tctgaccaag tttctcgaag agcatcctgg tggggaagaa   2340
gtcctgggcg agcaagctgg gggtgatgct actgagaact ttgaggacgt cgggcactct   2400
acggatgcac gagaactgtc caaaacatac atcatcgggg agctccatcc agatgacaga   2460
tcaaagatag ccaagccttc ggaaaccctt gtcgacatgg caaatattac cgttttctat   2520
aacgaagact tccagggtaa gcaggtcgat ctgccgcctg gcaactatac ccgcgcccag   2580
ttggcggcgc tgggcatcga gaataatacc atcagctcgg tgaaggtgcc gcctggcgtg   2640
aaggctatcc tgtaccagaa cgatggtttc gccggcgacc agatcgaagt ggtggccaat   2700
gccgaggagt tgggcccgct gaataataac gtctccagca tccgcgtcat ctccgtgccc   2760
gtgcagccgc gcatggcaaa tattaccgtt ttctataacg aagacttcca gggtaagcag   2820
gtcgatctgc cgcctggcaa ctatacccgc gcccagttgg cggcgctggg catcgagaat   2880
aataccatca gctcggtgaa ggtgccgcct ggcgtgaagg ctatcctcta ccagaacgat   2940
ggtttcgccg gcgaccagat cgaagtggtg gccaatgccg aggagctggg tccgctgaat   3000
aataacgtct ccagcatccg cgtcatctcc gtgccggtgc agccgagggg taccatggca   3060
gaacaaagcg acaaggatgt gaagtactac actctggagg agattcagaa gcacaaagac   3120
agcaagagca cctgggtgat cctacatcat aaggtgtacg atctgaccaa gtttctcgaa   3180
gagcatcctg gtggggaaga agtcctgggc gagcaagctg ggggtgatgc tactgagaac   3240
tttgaggacg tcgggcactc tacggatgca cgagaactgt ccaaaacata catcatcggg   3300
gagctccatc cagatgacag atcaaagata gccaagcctt cggaaaccct t            3351
```

<210> SEQ ID NO 842
<211> LENGTH: 482
<212> TYPE: PRT
<213> ORGANISM: Artificial Sequence
<220> FEATURE:
<223> OTHER INFORMATION: Amino acid Sequence of M563K

<400> SEQUENCE: 842

```
Ala Leu Ala Val Ile Val Val Pro Ala Leu Ala Pro Met Ala Val Ser
1               5                   10                  15

Asp Ala Leu Leu Pro Ser Phe Ser Thr Phe Ala Ser Gly Pro Ala Gly
            20                  25                  30

Arg Glu Lys Thr Leu Arg Gln Ala Gly Ala Pro Asn Asn Arg Trp Arg
        35                  40                  45

Glu Glu Leu Ser His Met Lys Arg Leu Pro Pro Val Leu Pro Gly Arg
    50                  55                  60

Pro Tyr Asp Leu Ala Ala Ala Thr Val Ala Thr Asp Leu Glu Ser Gly
65                  70                  75                  80

Gly Ala Gly Ala Ala Cys Gly Gly Ser Asn Leu Ala Pro Leu Pro Arg
                85                  90                  95

Arg Glu Thr Glu Glu Phe Asn Asp Leu Leu Asp Leu Asp Phe Ile Leu
            100                 105                 110

Ser Asn Ser Leu Thr His Pro Pro Glu Ser Val Ala Ala Thr Val Ser
        115                 120                 125

Ser Ser Ala Ser Ala Ser Ser Ser Ser Ser Pro Ser Ser Ser Gly Pro
    130                 135                 140

Ala Ser Ala Pro Ser Thr Cys Ser Phe Thr Tyr Pro Ile Arg Ala Gly
145                 150                 155                 160

Asn Asp Pro Gly Val Ala Pro Gly Gly Thr Gly Gly Gly Leu Leu Tyr
                165                 170                 175

Gly Arg Glu Ser Ala Pro Pro Pro Thr Ala Pro Phe Asn Leu Ala Asp
            180                 185                 190

Ile Asn Asp Val Ser Pro Ser Gly Gly Phe Val Ala Glu Leu Leu Arg
        195                 200                 205

Pro Glu Leu Asp Pro Val Tyr Ile Pro Pro Gln Gln Pro Gln Pro Pro
    210                 215                 220

Gly Gly Gly Leu Met Gly Lys Phe Val Leu Lys Ala Ser Leu Ser Ala
225                 230                 235                 240

Pro Gly Ser Glu Tyr Gly Ser Pro Ser Val Ile Ser Val Ser Lys Gly
                245                 250                 255

Ser Pro Asp Gly Ser His Pro Val Val Val Ala Pro Tyr Asn Gly Gly
            260                 265                 270

Pro Pro Arg Thr Cys Pro Lys Ile Lys Gln Glu Ala Val Ser Ser Cys
        275                 280                 285

Thr His Leu Gly Ala Gly Pro Pro Leu Ser Asn Gly His Arg Pro Ala
    290                 295                 300

Ala His Asp Phe Pro Leu Gly Arg Gln Leu Pro Ser Arg Thr Thr Pro
305                 310                 315                 320

Thr Leu Gly Leu Glu Glu Val Leu Ser Ser Arg Asp Cys His Pro Ala
                325                 330                 335

Leu Pro Leu Pro Pro Gly Phe His Pro His Pro Gly Pro Asn Tyr Pro
            340                 345                 350

Ser Phe Leu Pro Asp Gln Met Gln Pro Gln Val Pro Pro Leu His Tyr
        355                 360                 365
```

```
Gln Glu Leu Met Pro Pro Gly Ser Cys Met Pro Glu Glu Pro Lys Pro
    370                 375                 380

Lys Arg Gly Arg Arg Ser Trp Pro Arg Lys Arg Thr Ala Thr His Thr
385                 390                 395                 400

Cys Asp Tyr Ala Gly Cys Gly Lys Thr Tyr Thr Lys Ser Ser His Leu
                405                 410                 415

Lys Ala His Leu Arg Thr His Thr Gly Glu Lys Pro Tyr His Cys Asp
            420                 425                 430

Trp Asp Gly Cys Gly Trp Lys Phe Ala Arg Ser Asp Glu Leu Thr Arg
        435                 440                 445

His Tyr Arg Lys His Thr Gly His Arg Pro Phe Gln Cys Gln Lys Cys
    450                 455                 460

Asp Arg Ala Phe Ser Arg Ser Asp His Leu Ala Leu His Met Lys Arg
465                 470                 475                 480

His Phe


<210> SEQ ID NO 843
<211> LENGTH: 1446
<212> TYPE: DNA
<213> ORGANISM: Artificial Sequence
<220> FEATURE:
<223> OTHER INFORMATION: cDNA Sequence of M563K

<400> SEQUENCE: 843

gcgctggcgg tgattgtggt gccggcgctg gcgccgatgg ctgtcagcga cgcgctgctc     60

ccatctttct ccacgttcgc gtctggcccg gcgggaaggg agaagacact gcgtcaagca    120

ggtgccccga ataaccgctg gcgggaggag ctctcccaca tgaagcgact tcccccagtg    180

cttcccggcc gcccctatga cctggcggcg gcgaccgtgg ccacagacct ggagagcggc    240

ggagccggtg cggcttgcgg cggtagcaac ctggcgcccc tacctcggag agagaccgag    300

gagttcaacg atctcctgga cctggacttt attctctcca attcgctgac ccatcctccg    360

gagtcagtgg ccgccaccgt gtcctcgtca gcgtcagcct cctcttcgtc gtcgccgtcg    420

agcagcggcc ctgccagcgc gccctccacc tgcagcttca cctatccgat ccgggccggg    480

aacgacccgg gcgtggcgcc gggcggcacg ggcggaggcc tcctctatgg cagggagtcc    540

gctccccctc cgacggctcc cttcaacctg gcggacatca acgacgtgag cccctcgggc    600

ggcttcgtgg ccgagctcct gcggccagaa ttggacccgg tgtacattcc gccgcagcag    660

ccgcagccgc caggtggcgg gctgatgggc aagttcgtgc tgaaggcgtc gctgagcgcc    720

cctggcagcg agtacggcag cccgtcggtc atcagcgtca gcaaaggcag ccctgacggc    780

agccacccgg tggtggtggc gccctacaac ggcgggccgc cgcgcacgtg ccccaagatc    840

aagcaggagg cggtctcttc gtgcacccac ttgggcgctg gacccccctct cagcaatggc    900

caccggccgg ctgcacacga cttcccccctg gggcggcagc tccccagcag gactaccccg    960

accctgggtc ttgaggaagt gctgagcagc agggactgtc accctgccct gccgcttcct   1020

cccggcttcc atccccaccc ggggcccaat tacccatcct tcctgcccga tcagatgcag   1080

ccgcaagtcc cgccgctcca ttaccaagag ctcatgccac ccggttcctg catgccagag   1140

gagcccaagc caaagagggg aagacgatcg tggccccgga aaaggaccgc cacccacact   1200

tgtgattacg cgggctgcgg caaaacctac acaaagagtt cccatctcaa ggcacacctg   1260

cgaacccaca caggtgagaa accttaccac tgtgactggg acggctgtgg atggaaattc   1320

gcccgctcag atgaactgac caggcactac cgtaaacaca cggggcaccg cccgttccag   1380
```

```
tgccaaaaat gcgaccgagc attttccagg tcggaccacc tcgccttaca catgaagagg   1440

catttt                                                              1446


<210> SEQ ID NO 844
<211> LENGTH: 1242
<212> TYPE: PRT
<213> ORGANISM: Artificial Sequence
<220> FEATURE:
<223> OTHER INFORMATION: Amino acid Sequence of M563SAKSASBSASB

<400> SEQUENCE: 844

Ala Leu Ala Val Ile Val Val Pro Ala Leu Ala Pro Met Ala Asn Ile
1               5                   10                  15

Thr Val Phe Tyr Asn Glu Asp Phe Gln Gly Lys Gln Val Asp Leu Pro
            20                  25                  30

Pro Gly Asn Tyr Thr Arg Ala Gln Leu Ala Ala Leu Gly Ile Glu Asn
        35                  40                  45

Asn Thr Ile Ser Ser Val Lys Val Pro Pro Gly Val Lys Ala Ile Leu
    50                  55                  60

Tyr Gln Asn Asp Gly Phe Ala Gly Asp Gln Ile Glu Val Val Ala Asn
65                  70                  75                  80

Ala Glu Glu Leu Gly Pro Leu Asn Asn Asn Val Ser Ser Ile Arg Val
                85                  90                  95

Ile Ser Val Pro Val Gln Pro Arg Met Ala Asn Ile Thr Val Phe Tyr
            100                 105                 110

Asn Glu Asp Phe Gln Gly Lys Gln Val Asp Leu Pro Pro Gly Asn Tyr
        115                 120                 125

Thr Arg Ala Gln Leu Ala Ala Leu Gly Ile Glu Asn Asn Thr Ile Ser
    130                 135                 140

Ser Val Lys Val Pro Pro Gly Val Lys Ala Ile Leu Tyr Gln Asn Asp
145                 150                 155                 160

Gly Phe Ala Gly Asp Gln Ile Glu Val Val Ala Asn Ala Glu Glu Leu
                165                 170                 175

Gly Pro Leu Asn Asn Asn Val Ser Ser Ile Arg Val Ile Ser Val Pro
            180                 185                 190

Val Gln Pro Arg Gly Ser Met Ala Val Ser Asp Ala Leu Leu Pro Ser
        195                 200                 205

Phe Ser Thr Phe Ala Ser Gly Pro Ala Gly Arg Glu Lys Thr Leu Arg
    210                 215                 220

Gln Ala Gly Ala Pro Asn Asn Arg Trp Arg Glu Glu Leu Ser His Met
225                 230                 235                 240

Lys Arg Leu Pro Pro Val Leu Pro Gly Arg Pro Tyr Asp Leu Ala Ala
                245                 250                 255

Ala Thr Val Ala Thr Asp Leu Glu Ser Gly Gly Ala Gly Ala Ala Cys
            260                 265                 270

Gly Gly Ser Asn Leu Ala Pro Leu Pro Arg Arg Glu Thr Glu Glu Phe
        275                 280                 285

Asn Asp Leu Leu Asp Leu Asp Phe Ile Leu Ser Asn Ser Leu Thr His
    290                 295                 300

Pro Pro Glu Ser Val Ala Ala Thr Val Ser Ser Ser Ala Ser Ala Ser
305                 310                 315                 320

Ser Ser Ser Ser Pro Ser Ser Ser Gly Pro Ala Ser Ala Pro Ser Thr
                325                 330                 335

Cys Ser Phe Thr Tyr Pro Ile Arg Ala Gly Asn Asp Pro Gly Val Ala
```

```
            340                 345                 350

Pro Gly Gly Thr Gly Gly Gly Leu Leu Tyr Gly Arg Glu Ser Ala Pro
        355                 360                 365

Pro Pro Thr Ala Pro Phe Asn Leu Ala Asp Ile Asn Asp Val Ser Pro
    370                 375                 380

Ser Gly Gly Phe Val Ala Glu Leu Leu Arg Pro Glu Leu Asp Pro Val
385                 390                 395                 400

Tyr Ile Pro Pro Gln Gln Pro Gln Pro Pro Gly Gly Gly Leu Met Gly
                405                 410                 415

Lys Phe Val Leu Lys Ala Ser Leu Ser Ala Pro Gly Ser Glu Tyr Gly
            420                 425                 430

Ser Pro Ser Val Ile Ser Val Ser Lys Gly Ser Pro Asp Gly Ser His
        435                 440                 445

Pro Val Val Val Ala Pro Tyr Asn Gly Gly Pro Pro Arg Thr Cys Pro
    450                 455                 460

Lys Ile Lys Gln Glu Ala Val Ser Ser Cys Thr His Leu Gly Ala Gly
465                 470                 475                 480

Pro Pro Leu Ser Asn Gly His Arg Pro Ala Ala His Asp Phe Pro Leu
                485                 490                 495

Gly Arg Gln Leu Pro Ser Arg Thr Thr Pro Thr Leu Gly Leu Glu Glu
            500                 505                 510

Val Leu Ser Ser Arg Asp Cys His Pro Ala Leu Pro Leu Pro Pro Gly
        515                 520                 525

Phe His Pro His Pro Gly Pro Asn Tyr Pro Ser Phe Leu Pro Asp Gln
    530                 535                 540

Met Gln Pro Gln Val Pro Pro Leu His Tyr Gln Glu Leu Met Pro Pro
545                 550                 555                 560

Gly Ser Cys Met Pro Glu Glu Pro Lys Pro Lys Arg Gly Arg Arg Ser
                565                 570                 575

Trp Pro Arg Lys Arg Thr Ala Thr His Thr Cys Asp Tyr Ala Gly Cys
            580                 585                 590

Gly Lys Thr Tyr Thr Lys Ser Ser His Leu Lys Ala His Leu Arg Thr
        595                 600                 605

His Thr Gly Glu Lys Pro Tyr His Cys Asp Trp Asp Gly Cys Gly Trp
    610                 615                 620

Lys Phe Ala Arg Ser Asp Glu Leu Thr Arg His Tyr Arg Lys His Thr
625                 630                 635                 640

Gly His Arg Pro Phe Gln Cys Gln Lys Cys Asp Arg Ala Phe Ser Arg
                645                 650                 655

Ser Asp His Leu Ala Leu His Met Lys Arg His Phe Lys Leu Met Ala
            660                 665                 670

Asn Ile Thr Val Phe Tyr Asn Glu Asp Phe Gln Gly Lys Gln Val Asp
        675                 680                 685

Leu Pro Pro Gly Asn Tyr Thr Arg Ala Gln Leu Ala Ala Leu Gly Ile
    690                 695                 700

Glu Asn Asn Thr Ile Ser Ser Val Lys Val Pro Pro Gly Val Lys Ala
705                 710                 715                 720

Ile Leu Tyr Gln Asn Asp Gly Phe Ala Gly Asp Gln Ile Glu Val Val
                725                 730                 735

Ala Asn Ala Glu Glu Leu Gly Pro Leu Asn Asn Asn Val Ser Ser Ile
            740                 745                 750

Arg Val Ile Ser Val Pro Val Gln Pro Arg Met Ala Asn Ile Thr Val
        755                 760                 765
```

```
Phe Tyr Asn Glu Asp Phe Gln Gly Lys Gln Val Asp Leu Pro Pro Gly
    770                 775                 780

Asn Tyr Thr Arg Ala Gln Leu Ala Ala Leu Gly Ile Glu Asn Asn Thr
785                 790                 795                 800

Ile Ser Ser Val Lys Val Pro Pro Gly Val Lys Ala Ile Leu Tyr Gln
                805                 810                 815

Asn Asp Gly Phe Ala Gly Asp Gln Ile Glu Val Val Ala Asn Ala Glu
            820                 825                 830

Glu Leu Gly Pro Leu Asn Asn Asn Val Ser Ser Ile Arg Val Ile Ser
        835                 840                 845

Val Pro Val Gln Pro Arg Gly Thr Met Ala Glu Gln Ser Asp Lys Asp
    850                 855                 860

Val Lys Tyr Tyr Thr Leu Glu Glu Ile Gln Lys His Lys Asp Ser Lys
865                 870                 875                 880

Ser Thr Trp Val Ile Leu His His Lys Val Tyr Asp Leu Thr Lys Phe
                885                 890                 895

Leu Glu Glu His Pro Gly Gly Glu Glu Val Leu Gly Glu Gln Ala Gly
            900                 905                 910

Gly Asp Ala Thr Glu Asn Phe Glu Asp Val Gly His Ser Thr Asp Ala
        915                 920                 925

Arg Glu Leu Ser Lys Thr Tyr Ile Ile Gly Glu Leu His Pro Asp Asp
    930                 935                 940

Arg Ser Lys Ile Ala Lys Pro Ser Glu Thr Leu Val Asp Met Ala Asn
945                 950                 955                 960

Ile Thr Val Phe Tyr Asn Glu Asp Phe Gln Gly Lys Gln Val Asp Leu
                965                 970                 975

Pro Pro Gly Asn Tyr Thr Arg Ala Gln Leu Ala Ala Leu Gly Ile Glu
            980                 985                 990

Asn Asn Thr Ile Ser Ser Val Lys Val Pro Pro Gly Val Lys Ala Ile
        995                 1000                1005

Leu Tyr Gln Asn Asp Gly Phe Ala Gly Asp Gln Ile Glu Val Val Ala
    1010                1015                1020

Asn Ala Glu Glu Leu Gly Pro Leu Asn Asn Asn Val Ser Ser Ile Arg
1025                1030                1035                1040

Val Ile Ser Val Pro Val Gln Pro Arg Met Ala Asn Ile Thr Val Phe
                1045                1050                1055

Tyr Asn Glu Asp Phe Gln Gly Lys Gln Val Asp Leu Pro Pro Gly Asn
            1060                1065                1070

Tyr Thr Arg Ala Gln Leu Ala Ala Leu Gly Ile Glu Asn Asn Thr Ile
        1075                1080                1085

Ser Ser Val Lys Val Pro Pro Gly Val Lys Ala Ile Leu Tyr Gln Asn
    1090                1095                1100

Asp Gly Phe Ala Gly Asp Gln Ile Glu Val Val Ala Asn Ala Glu Glu
1105                1110                1115                1120

Leu Gly Pro Leu Asn Asn Asn Val Ser Ser Ile Arg Val Ile Ser Val
                1125                1130                1135

Pro Val Gln Pro Arg Gly Thr Met Ala Glu Gln Ser Asp Lys Asp Val
            1140                1145                1150

Lys Tyr Tyr Thr Leu Glu Glu Ile Gln Lys His Lys Asp Ser Lys Ser
        1155                1160                1165

Thr Trp Val Ile Leu His His Lys Val Tyr Asp Leu Thr Lys Phe Leu
    1170                1175                1180
```

-continued

```
Glu Glu His Pro Gly Gly Glu Glu Val Leu Gly Glu Gln Ala Gly Gly
1185                1190                1195                1200

Asp Ala Thr Glu Asn Phe Glu Asp Val Gly His Ser Thr Asp Ala Arg
                1205                1210                1215

Glu Leu Ser Lys Thr Tyr Ile Ile Gly Glu Leu His Pro Asp Asp Arg
            1220                1225                1230

Ser Lys Ile Ala Lys Pro Ser Glu Thr Leu
        1235                1240
```

<210> SEQ ID NO 845
<211> LENGTH: 3726
<212> TYPE: DNA
<213> ORGANISM: Artificial Sequence
<220> FEATURE:
<223> OTHER INFORMATION: cDNA Sequence of M563SAKSASBSASB

<400> SEQUENCE: 845

```
gcgctggcgg tgattgtggt gccggcgctg gcgccgatgg caaatattac cgttttctat     60

aacgaagact tccagggtaa gcaggtcgat ctgccgcctg gcaactatac ccgcgcccag    120

ttggcggcgc tgggcatcga gaataatacc atcagctcgg tgaaggtgcc gcctggcgtg    180

aaggctatcc tgtaccagaa cgatggtttc gccggcgacc agatcgaagt ggtggccaat    240

gccgaggagt tgggcccgct gaataataac gtctccagca tccgcgtcat ctccgtgccc    300

gtgcagccgc gcatggcaaa tattaccgtt ttctataacg aagacttcca gggtaagcag    360

gtcgatctgc cgcctggcaa ctatacccgc gcccagttgg cggcgctggg catcgagaat    420

aataccatca gctcggtgaa ggtgccgcct ggcgtgaagg ctatcctcta ccagaacgat    480

ggtttcgccg gcgaccagat cgaagtggtg gccaatgccg aggagctggg tccgctgaat    540

aataacgtct ccagcatccg cgtcatctcc gtgccggtgc agccgagggg atccatggct    600

gtcagcgacg cgctgctccc atctttctcc acgttcgcgt ctggcccggc gggaagggag    660

aagacactgc gtcaagcagg tgccccgaat aaccgctggc gggaggagct ctcccacatg    720

aagcgacttc ccccagtgct tcccggccgc ccctatgacc tggcggcggc gaccgtggcc    780

acagacctgg agagcggcgg agccggtgcg gcttgcggcg gtagcaacct ggcgcccta     840

cctcggagag agaccgagga gttcaacgat ctcctggacc tggactttat tctctccaat    900

tcgctgaccc atcctccgga gtcagtggcc gccaccgtgt cctcgtcagc gtcagcctcc    960

tcttcgtcgt cgccgtcgag cagcggccct gccagcgcgc cctccacctg cagcttcacc   1020

tatccgatcc gggccgggaa cgacccgggc gtggcgccgg gcggcacggg cggaggcctc   1080

ctctatggca gggagtccgc tccccctccg acggctccct tcaacctggc ggacatcaac   1140

gacgtgagcc cctcgggcgg cttcgtggcc gagctcctgc ggccagaatt ggacccggtg   1200

tacattccgc cgcagcagcc gcagccgcca ggtggcgggc tgatgggcaa gttcgtgctg   1260

aaggcgtcgc tgagcgcccc tggcagcgag tacggcagcc cgtcggtcat cagcgtcagc   1320

aaaggcagcc ctgacggcag ccacccggtg gtggtggcgc cctacaacgg cgggccgccg   1380

cgcacgtgcc ccaagatcaa gcaggaggcg gtctcttcgt gcacccactt gggcgctgga   1440

ccccctctca gcaatggcca ccggccggct gcacacgact tcccccctggg gcggcagctc  1500

cccagcagga ctaccccgac cctgggtctt gaggaagtgc tgagcagcag ggactgtcac   1560

cctgccctgc cgcttcctcc cggcttccat ccccacccgg ggcccaatta cccatccttc   1620

ctgcccgatc agatgcagcc gcaagtcccg ccgctccatt accaagagct catgccaccc   1680

ggttcctgca tgccagagga gcccaagcca aagaggggaa gacgatcgtg gccccggaaa   1740
```

aggaccgcca cccacacttg tgattacgcg ggctgcggca aaacctacac aaagagttcc 1800
catctcaagg cacacctgcg aacccacaca ggtgagaaac cttaccactg tgactgggac 1860
ggctgtggat ggaaattcgc ccgctcagat gaactgacca ggcactaccg taaacacacg 1920
gggcaccgcc cgttccagtg ccaaaaatgc gaccgagcat tttccaggtc ggaccacctc 1980
gccttacaca tgaagaggca ttttaagctt atggcaaata ttaccgtttt ctataacgaa 2040
gacttccagg gtaagcaggt cgatctgccg cctggcaact atacccgcgc ccagttggcg 2100
gcgctgggca tcgagaataa taccatcagc tcggtgaagg tgccgcctgg cgtgaaggct 2160
atcctgtacc agaacgatgg tttcgccggc gaccagatcg aagtggtggc caatgccgag 2220
gagttgggcc cgctgaataa taacgtctcc agcatccgcg tcatctccgt gcccgtgcag 2280
ccgcgcatgg caaatattac cgttttctat aacgaagact tccagggtaa gcaggtcgat 2340
ctgccgcctg gcaactatac ccgcgcccag ttggcggcgc tgggcatcga gaataatacc 2400
atcagctcgg tgaaggtgcc gcctggcgtg aaggctatcc tctaccagaa cgatggtttc 2460
gccggcgacc agatcgaagt ggtggccaat gccgaggagc tgggtccgct gaataataac 2520
gtctccagca tccgcgtcat ctccgtgccg gtgcagccga ggggtaccat ggcagaacaa 2580
agcgacaagg atgtgaagta ctacactctg gaggagattc agaagcacaa agacagcaag 2640
agcacctggg tgatcctaca tcataaggtg tacgatctga ccaagtttct cgaagagcat 2700
cctggtgggg aagaagtcct gggcgagcaa gctgggggtg atgctactga gaactttgag 2760
gacgtcgggc actctacgga tgcacgagaa ctgtccaaaa catacatcat cggggagctc 2820
catccagatg acagatcaaa gatagccaag ccttcggaaa cccttgtcga catggcaaat 2880
attaccgttt tctataacga agacttccag ggtaagcagg tcgatctgcc gcctggcaac 2940
tatacccgcg cccagttggc ggcgctgggc atcgagaata ataccatcag ctcggtgaag 3000
gtgccgcctg gcgtgaaggc tatcctgtac cagaacgatg gtttcgccgg cgaccagatc 3060
gaagtggtgg ccaatgccga ggagttgggc ccgctgaata ataacgtctc cagcatccgc 3120
gtcatctccg tgcccgtgca gccgcgcatg gcaaatatta ccgttttcta taacgaagac 3180
ttccagggta agcaggtcga tctgccgcct ggcaactata cccgcgccca gttggcggcg 3240
ctgggcatcg agaataatac catcagctcg gtgaaggtgc cgcctggcgt gaaggctatc 3300
ctctaccaga acgatggttt cgccggcgac cagatcgaag tggtggccaa tgccgaggag 3360
ctgggtccgc tgaataataa cgtctccagc atccgcgtca tctccgtgcc ggtgcagccg 3420
aggggtacca tggcagaaca aagcgacaag gatgtgaagt actacactct ggaggagatt 3480
cagaagcaca aagacagcaa gagcacctgg gtgatcctac atcataaggt gtacgatctg 3540
accaagtttc tcgaagagca tcctggtggg gaagaagtcc tgggcgagca agctgggggt 3600
gatgctactg agaactttga ggacgtcggg cactctacgg atgcacgaga actgtccaaa 3660
acatacatca tcggggagct ccatccagat gacagatcaa agatagccaa gccttcggaa 3720
accctt 3726

<210> SEQ ID NO 846
<211> LENGTH: 1270
<212> TYPE: PRT
<213> ORGANISM: Artificial Sequence
<220> FEATURE:
<223> OTHER INFORMATION: Amino acid Sequence of HNM563SAKSASBSASB

<400> SEQUENCE: 846

-continued

```
Met Gly Ser Ser His His His His His His Ser Ser Gly Leu Val Pro
1               5                   10                  15

Arg Gly Ser His Met Pro Lys Lys Lys Arg Lys Leu Ala Leu Ala Val
            20                  25                  30

Ile Val Val Pro Ala Leu Ala Pro Met Ala Asn Ile Thr Val Phe Tyr
        35                  40                  45

Asn Glu Asp Phe Gln Gly Lys Gln Val Asp Leu Pro Pro Gly Asn Tyr
    50                  55                  60

Thr Arg Ala Gln Leu Ala Ala Leu Gly Ile Glu Asn Asn Thr Ile Ser
65                  70                  75                  80

Ser Val Lys Val Pro Pro Gly Val Lys Ala Ile Leu Tyr Gln Asn Asp
                85                  90                  95

Gly Phe Ala Gly Asp Gln Ile Glu Val Val Ala Asn Ala Glu Glu Leu
            100                 105                 110

Gly Pro Leu Asn Asn Asn Val Ser Ser Ile Arg Val Ile Ser Val Pro
        115                 120                 125

Val Gln Pro Arg Met Ala Asn Ile Thr Val Phe Tyr Asn Glu Asp Phe
    130                 135                 140

Gln Gly Lys Gln Val Asp Leu Pro Pro Gly Asn Tyr Thr Arg Ala Gln
145                 150                 155                 160

Leu Ala Ala Leu Gly Ile Glu Asn Asn Thr Ile Ser Ser Val Lys Val
                165                 170                 175

Pro Pro Gly Val Lys Ala Ile Leu Tyr Gln Asn Asp Gly Phe Ala Gly
            180                 185                 190

Asp Gln Ile Glu Val Val Ala Asn Ala Glu Glu Leu Gly Pro Leu Asn
        195                 200                 205

Asn Asn Val Ser Ser Ile Arg Val Ile Ser Val Pro Val Gln Pro Arg
    210                 215                 220

Gly Ser Met Ala Val Ser Asp Ala Leu Leu Pro Ser Phe Ser Thr Phe
225                 230                 235                 240

Ala Ser Gly Pro Ala Gly Arg Glu Lys Thr Leu Arg Gln Ala Gly Ala
                245                 250                 255

Pro Asn Asn Arg Trp Arg Glu Glu Leu Ser His Met Lys Arg Leu Pro
            260                 265                 270

Pro Val Leu Pro Gly Arg Pro Tyr Asp Leu Ala Ala Ala Thr Val Ala
        275                 280                 285

Thr Asp Leu Glu Ser Gly Gly Ala Gly Ala Ala Cys Gly Gly Ser Asn
    290                 295                 300

Leu Ala Pro Leu Pro Arg Arg Glu Thr Glu Glu Phe Asn Asp Leu Leu
305                 310                 315                 320

Asp Leu Asp Phe Ile Leu Ser Asn Ser Leu Thr His Pro Pro Glu Ser
                325                 330                 335

Val Ala Ala Thr Val Ser Ser Ser Ala Ser Ala Ser Ser Ser Ser Ser
            340                 345                 350

Pro Ser Ser Ser Gly Pro Ala Ser Ala Pro Ser Thr Cys Ser Phe Thr
        355                 360                 365

Tyr Pro Ile Arg Ala Gly Asn Asp Pro Gly Val Ala Pro Gly Gly Thr
    370                 375                 380

Gly Gly Gly Leu Leu Tyr Gly Arg Glu Ser Ala Pro Pro Pro Thr Ala
385                 390                 395                 400

Pro Phe Asn Leu Ala Asp Ile Asn Asp Val Ser Pro Ser Gly Gly Phe
                405                 410                 415

Val Ala Glu Leu Leu Arg Pro Glu Leu Asp Pro Val Tyr Ile Pro Pro
```

```
            420                 425                 430

Gln Gln Pro Gln Pro Pro Gly Gly Gly Leu Met Gly Lys Phe Val Leu
        435                 440                 445

Lys Ala Ser Leu Ser Ala Pro Gly Ser Glu Tyr Gly Ser Pro Ser Val
    450                 455                 460

Ile Ser Val Ser Lys Gly Ser Pro Asp Gly Ser His Pro Val Val Val
465                 470                 475                 480

Ala Pro Tyr Asn Gly Gly Pro Pro Arg Thr Cys Pro Lys Ile Lys Gln
                485                 490                 495

Glu Ala Val Ser Ser Cys Thr His Leu Gly Ala Gly Pro Pro Leu Ser
            500                 505                 510

Asn Gly His Arg Pro Ala Ala His Asp Phe Pro Leu Gly Arg Gln Leu
        515                 520                 525

Pro Ser Arg Thr Thr Pro Thr Leu Gly Leu Glu Glu Val Leu Ser Ser
    530                 535                 540

Arg Asp Cys His Pro Ala Leu Pro Leu Pro Pro Gly Phe His Pro His
545                 550                 555                 560

Pro Gly Pro Asn Tyr Pro Ser Phe Leu Pro Asp Gln Met Gln Pro Gln
                565                 570                 575

Val Pro Pro Leu His Tyr Gln Glu Leu Met Pro Pro Gly Ser Cys Met
            580                 585                 590

Pro Glu Glu Pro Lys Pro Lys Arg Gly Arg Arg Ser Trp Pro Arg Lys
        595                 600                 605

Arg Thr Ala Thr His Thr Cys Asp Tyr Ala Gly Cys Gly Lys Thr Tyr
    610                 615                 620

Thr Lys Ser Ser His Leu Lys Ala His Leu Arg Thr His Thr Gly Glu
625                 630                 635                 640

Lys Pro Tyr His Cys Asp Trp Asp Gly Cys Gly Trp Lys Phe Ala Arg
                645                 650                 655

Ser Asp Glu Leu Thr Arg His Tyr Arg Lys His Thr Gly His Arg Pro
            660                 665                 670

Phe Gln Cys Gln Lys Cys Asp Arg Ala Phe Ser Arg Ser Asp His Leu
        675                 680                 685

Ala Leu His Met Lys Arg His Phe Lys Leu Met Ala Asn Ile Thr Val
    690                 695                 700

Phe Tyr Asn Glu Asp Phe Gln Gly Lys Gln Val Asp Leu Pro Pro Gly
705                 710                 715                 720

Asn Tyr Thr Arg Ala Gln Leu Ala Ala Leu Gly Ile Glu Asn Asn Thr
                725                 730                 735

Ile Ser Ser Val Lys Val Pro Pro Gly Val Lys Ala Ile Leu Tyr Gln
            740                 745                 750

Asn Asp Gly Phe Ala Gly Asp Gln Ile Glu Val Val Ala Asn Ala Glu
        755                 760                 765

Glu Leu Gly Pro Leu Asn Asn Asn Val Ser Ser Ile Arg Val Ile Ser
    770                 775                 780

Val Pro Val Gln Pro Arg Met Ala Asn Ile Thr Val Phe Tyr Asn Glu
785                 790                 795                 800

Asp Phe Gln Gly Lys Gln Val Asp Leu Pro Pro Gly Asn Tyr Thr Arg
                805                 810                 815

Ala Gln Leu Ala Ala Leu Gly Ile Glu Asn Asn Thr Ile Ser Ser Val
            820                 825                 830

Lys Val Pro Pro Gly Val Lys Ala Ile Leu Tyr Gln Asn Asp Gly Phe
        835                 840                 845
```

```
Ala Gly Asp Gln Ile Glu Val Val Ala Asn Ala Glu Glu Leu Gly Pro
    850                 855                 860

Leu Asn Asn Asn Val Ser Ser Ile Arg Val Ile Ser Val Pro Val Gln
865                 870                 875                 880

Pro Arg Gly Thr Met Ala Glu Gln Ser Asp Lys Asp Val Lys Tyr Tyr
                885                 890                 895

Thr Leu Glu Glu Ile Gln Lys His Lys Asp Ser Lys Ser Thr Trp Val
            900                 905                 910

Ile Leu His His Lys Val Tyr Asp Leu Thr Lys Phe Leu Glu Glu His
        915                 920                 925

Pro Gly Gly Glu Glu Val Leu Gly Glu Gln Ala Gly Gly Asp Ala Thr
    930                 935                 940

Glu Asn Phe Glu Asp Val Gly His Ser Thr Asp Ala Arg Glu Leu Ser
945                 950                 955                 960

Lys Thr Tyr Ile Ile Gly Glu Leu His Pro Asp Asp Arg Ser Lys Ile
                965                 970                 975

Ala Lys Pro Ser Glu Thr Leu Val Asp Met Ala Asn Ile Thr Val Phe
            980                 985                 990

Tyr Asn Glu Asp Phe Gln Gly Lys Gln Val Asp Leu Pro Pro Gly Asn
        995                 1000                1005

Tyr Thr Arg Ala Gln Leu Ala Ala Leu Gly Ile Glu Asn Asn Thr Ile
    1010                1015                1020

Ser Ser Val Lys Val Pro Pro Gly Val Lys Ala Ile Leu Tyr Gln Asn
1025                1030                1035                1040

Asp Gly Phe Ala Gly Asp Gln Ile Glu Val Val Ala Asn Ala Glu Glu
                1045                1050                1055

Leu Gly Pro Leu Asn Asn Asn Val Ser Ser Ile Arg Val Ile Ser Val
            1060                1065                1070

Pro Val Gln Pro Arg Met Ala Asn Ile Thr Val Phe Tyr Asn Glu Asp
        1075                1080                1085

Phe Gln Gly Lys Gln Val Asp Leu Pro Pro Gly Asn Tyr Thr Arg Ala
    1090                1095                1100

Gln Leu Ala Ala Leu Gly Ile Glu Asn Asn Thr Ile Ser Ser Val Lys
1105                1110                1115                1120

Val Pro Pro Gly Val Lys Ala Ile Leu Tyr Gln Asn Asp Gly Phe Ala
                1125                1130                1135

Gly Asp Gln Ile Glu Val Val Ala Asn Ala Glu Glu Leu Gly Pro Leu
            1140                1145                1150

Asn Asn Asn Val Ser Ser Ile Arg Val Ile Ser Val Pro Val Gln Pro
        1155                1160                1165

Arg Gly Thr Met Ala Glu Gln Ser Asp Lys Asp Val Lys Tyr Tyr Thr
    1170                1175                1180

Leu Glu Glu Ile Gln Lys His Lys Asp Ser Lys Ser Thr Trp Val Ile
1185                1190                1195                1200

Leu His His Lys Val Tyr Asp Leu Thr Lys Phe Leu Glu Glu His Pro
                1205                1210                1215

Gly Gly Glu Glu Val Leu Gly Glu Gln Ala Gly Gly Asp Ala Thr Glu
            1220                1225                1230

Asn Phe Glu Asp Val Gly His Ser Thr Asp Ala Arg Glu Leu Ser Lys
        1235                1240                1245

Thr Tyr Ile Ile Gly Glu Leu His Pro Asp Asp Arg Ser Lys Ile Ala
    1250                1255                1260
```

Lys Pro Ser Glu Thr Leu
1265 1270

<210> SEQ ID NO 847
<211> LENGTH: 3810
<212> TYPE: DNA
<213> ORGANISM: Artificial Sequence
<220> FEATURE:
<223> OTHER INFORMATION: cDNA Sequence of HNM563SAKSASBSASB

<400> SEQUENCE: 847
atgggcagca gccatcatca tcatcatcac agcagcggcc tggtgccgcg cggcagccat 60
atgcccaaga agaagaggaa gctggcgctg gcggtgattg tggtgccggc gctggcgccg 120
atggcaaata ttaccgtttt ctataacgaa gacttccagg gtaagcaggt cgatctgccg 180
cctggcaact atacccgcgc ccagttggcg gcgctgggca tcgagaataa taccatcagc 240
tcggtgaagg tgccgcctgg cgtgaaggct atcctgtacc agaacgatgg tttcgccggc 300
gaccagatcg aagtggtggc caatgccgag gagttgggcc cgctgaataa taacgtctcc 360
agcatccgcg tcatctccgt gcccgtgcag ccgcgcatgg caaatattac cgttttctat 420
aacgaagact tccagggtaa gcaggtcgat ctgccgcctg gcaactatac ccgcgcccag 480
ttggcggcgc tgggcatcga gaataatacc atcagctcgg tgaaggtgcc gcctggcgtg 540
aaggctatcc tctaccagaa cgatggtttc gccggcgacc agatcgaagt ggtggccaat 600
gccgaggagc tgggtccgct gaataataac gtctccagca tccgcgtcat ctccgtgccg 660
gtgcagccga ggggatccat ggctgtcagc gacgcgctgc tcccatcttt ctccacgttc 720
gcgtctggcc cggcgggaag ggagaagaca ctgcgtcaag caggtgcccc gaataaccgc 780
tggcgggagg agctctccca catgaagcga cttcccccag tgcttcccgg ccgcccctat 840
gacctggcgg cggcgaccgt ggccacagac ctggagagcg gcggagccgg tgcggcttgc 900
ggcggtagca acctggcgcc cctacctcgg agagagaccg aggagttcaa cgatctcctg 960
gacctggact ttattctctc caattcgctg acccatcctc cggagtcagt ggccgccacc 1020
gtgtcctcgt cagcgtcagc ctcctcttcg tcgtcgccgt cgagcagcgg ccctgccagc 1080
gcgccctcca cctgcagctt cacctatccg atccgggccg ggaacgaccc gggcgtggcg 1140
ccgggcggca cgggcggagg cctcctctat ggcagggagt ccgctccccc tccgacggct 1200
cccttcaacc tggcggacat caacgacgtg agcccctcgg gcggcttcgt ggccgagctc 1260
ctgcggccag aattggaccc ggtgtacatt ccgccgcagc agccgcagcc gccaggtggc 1320
gggctgatgg gcaagttcgt gctgaaggcg tcgctgagcg cccctggcag cgagtacggc 1380
agcccgtcgg tcatcagcgt cagcaaaggc agccctgacg gcagccaccc ggtggtggtg 1440
gcgccctaca acggcgggcc gccgcgcacg tgccccaaga tcaagcagga ggcggtctct 1500
tcgtgcaccc acttgggcgc tggaccccct ctcagcaatg gccaccggcc ggctgcacac 1560
gacttccccc tggggcggca gctccccagc aggactaccc cgaccctggg tcttgaggaa 1620
gtgctgagca gcagggactg tcaccctgcc ctgccgcttc ctcccggctt ccatccccac 1680
ccggggccca attacccatc cttcctgccc gatcagatgc agccgcaagt cccgccgctc 1740
cattaccaag agctcatgcc acccggttcc tgcatgccag aggagcccaa gccaaagagg 1800
ggaagacgat cgtggccccg gaaaaggacc gccacccaca cttgtgatta cgcgggctgc 1860
ggcaaaacct acacaaagag ttcccatctc aaggcacacc tgcgaaccca cacaggtgag 1920
aaaccttacc actgtgactg ggacggctgt ggatggaaat tcgcccgctc agatgaactg 1980

```
accaggcact accgtaaaca cacggggcac cgcccgttcc agtgccaaaa atgcgaccga   2040

gcattttcca ggtcggacca cctcgcctta cacatgaaga ggcattttaa gcttatggca   2100

aatattaccg ttttctataa cgaagacttc cagggtaagc aggtcgatct gccgcctggc   2160

aactataccc gcgcccagtt ggcggcgctg ggcatcgaga ataataccat cagctcggtg   2220

aaggtgccgc ctggcgtgaa ggctatcctg taccagaacg atggtttcgc cggcgaccag   2280

atcgaagtgg tggccaatgc cgaggagttg ggcccgctga ataataacgt ctccagcatc   2340

cgcgtcatct ccgtgcccgt gcagccgcgc atggcaaata ttaccgtttt ctataacgaa   2400

gacttccagg gtaagcaggt cgatctgccg cctggcaact atacccgcgc ccagttggcg   2460

gcgctgggca tcgagaataa taccatcagc tcggtgaagg tgccgcctgg cgtgaaggct   2520

atcctctacc agaacgatgg tttcgccggc gaccagatcg aagtggtggc caatgccgag   2580

gagctgggtc cgctgaataa taacgtctcc agcatccgcg tcatctccgt gccggtgcag   2640

ccgaggggta ccatggcaga acaaagcgac aaggatgtga agtactacac tctggaggag   2700

attcagaagc acaaagacag caagagcacc tgggtgatcc tacatcataa ggtgtacgat   2760

ctgaccaagt ttctcgaaga gcatcctggt ggggaagaag tcctgggcga gcaagctggg   2820

ggtgatgcta ctgagaactt tgaggacgtc gggcactcta cggatgcacg agaactgtcc   2880

aaaacataca tcatcgggga gctccatcca gatgacagat caaagatagc caagccttcg   2940

gaaacccttg tcgacatggc aaatattacc gttttctata acgaagactt ccagggtaag   3000

caggtcgatc tgccgcctgg caactatacc cgcgcccagt tggcggcgct gggcatcgag   3060

aataatacca tcagctcggt gaaggtgccg cctggcgtga aggctatcct gtaccagaac   3120

gatggtttcg ccggcgacca gatcgaagtg gtggccaatg ccgaggagtt gggcccgctg   3180

aataataacg tctccagcat ccgcgtcatc tccgtgcccg tgcagccgcg catggcaaat   3240

attaccgttt tctataacga agacttccag ggtaagcagg tcgatctgcc gcctggcaac   3300

tatacccgcg cccagttggc ggcgctgggc atcgagaata ataccatcag ctcggtgaag   3360

gtgccgcctg gcgtgaaggc tatcctctac cagaacgatg gtttcgccgg cgaccagatc   3420

gaagtggtgg ccaatgccga ggagctgggt ccgctgaata ataacgtctc cagcatccgc   3480

gtcatctccg tgccggtgca gccgaggggt accatggcag aacaaagcga caaggatgtg   3540

aagtactaca ctctggagga gattcagaag cacaaagaca gcaagagcac ctgggtgatc   3600

ctacatcata aggtgtacga tctgaccaag tttctcgaag agcatcctgg tggggaagaa   3660

gtcctgggcg agcaagctgg gggtgatgct actgagaact ttgaggacgt cgggcactct   3720

acggatgcac gagaactgtc caaaacatac atcatcgggg agctccatcc agatgacaga   3780

tcaaagatag ccaagccttc ggaaaccctt                                  3810
```

<210> SEQ ID NO 848
<211> LENGTH: 451
<212> TYPE: PRT
<213> ORGANISM: Artificial Sequence
<220> FEATURE:
<223> OTHER INFORMATION: Amino acid Sequence of M563M

<400> SEQUENCE: 848

```
Ala Leu Ala Val Ile Val Val Pro Ala Leu Ala Pro Met Pro Leu Asn
1               5                   10                  15

Val Ser Phe Thr Asn Arg Asn Tyr Asp Leu Asp Tyr Asp Ser Val Gln
            20                  25                  30

Pro Tyr Phe Tyr Cys Asp Glu Glu Glu Asn Phe Tyr Gln Gln Gln Gln
```

-continued

```
        35                  40                  45

Gln Ser Glu Leu Gln Pro Pro Ala Pro Ser Glu Asp Ile Trp Lys Lys
    50                  55                  60

Phe Glu Leu Leu Pro Thr Pro Pro Leu Ser Pro Ser Arg Arg Ser Gly
65                  70                  75                  80

Leu Cys Ser Pro Ser Tyr Val Ala Val Thr Pro Phe Ser Leu Arg Gly
                85                  90                  95

Asp Asn Asp Gly Gly Gly Gly Ser Phe Ser Thr Ala Asp Gln Leu Glu
            100                 105                 110

Met Val Thr Glu Leu Leu Gly Gly Asp Met Val Asn Gln Ser Phe Ile
        115                 120                 125

Cys Asp Pro Asp Asp Glu Thr Phe Ile Lys Asn Ile Ile Ile Gln Asp
    130                 135                 140

Cys Met Trp Ser Gly Phe Ser Ala Ala Ala Lys Leu Val Ser Glu Lys
145                 150                 155                 160

Leu Ala Ser Tyr Gln Ala Ala Arg Lys Asp Ser Gly Ser Pro Asn Pro
                165                 170                 175

Ala Arg Gly His Ser Val Cys Ser Thr Ser Ser Leu Tyr Leu Gln Asp
            180                 185                 190

Leu Ser Ala Ala Ala Ser Glu Cys Ile Asp Pro Ser Val Val Phe Pro
        195                 200                 205

Tyr Pro Leu Asn Asp Ser Ser Ser Pro Lys Ser Cys Ala Ser Gln Asp
    210                 215                 220

Ser Ser Ala Phe Ser Pro Ser Ser Asp Ser Leu Leu Ser Ser Thr Glu
225                 230                 235                 240

Ser Ser Pro Gln Gly Ser Pro Glu Pro Leu Val Leu His Glu Glu Thr
                245                 250                 255

Pro Pro Thr Thr Ser Ser Asp Ser Glu Glu Glu Gln Glu Asp Glu Glu
            260                 265                 270

Glu Ile Asp Val Val Ser Val Glu Lys Arg Gln Ala Pro Gly Lys Arg
        275                 280                 285

Ser Glu Ser Gly Ser Pro Ser Ala Gly Gly His Ser Lys Pro Pro His
    290                 295                 300

Ser Pro Leu Val Leu Lys Arg Cys His Val Ser Thr His Gln His Asn
305                 310                 315                 320

Tyr Ala Ala Pro Pro Ser Thr Arg Lys Asp Tyr Pro Ala Ala Lys Arg
                325                 330                 335

Val Lys Leu Asp Ser Val Arg Val Leu Arg Gln Ile Ser Asn Asn Arg
            340                 345                 350

Lys Cys Thr Ser Pro Arg Ser Ser Asp Thr Glu Glu Asn Val Lys Arg
        355                 360                 365

Arg Thr His Asn Val Leu Glu Arg Gln Arg Arg Asn Glu Leu Lys Arg
    370                 375                 380

Ser Phe Phe Ala Leu Arg Asp Gln Ile Pro Glu Leu Glu Asn Asn Glu
385                 390                 395                 400

Lys Ala Pro Lys Val Val Ile Leu Lys Lys Ala Thr Ala Tyr Ile Leu
                405                 410                 415

Ser Val Gln Ala Glu Glu Gln Lys Leu Ile Ser Glu Glu Asp Leu Leu
            420                 425                 430

Arg Lys Arg Arg Glu Gln Leu Lys His Lys Leu Glu Gln Leu Arg Asn
        435                 440                 445

Ser Cys Ala
    450
```

<210> SEQ ID NO 849
<211> LENGTH: 1353
<212> TYPE: DNA
<213> ORGANISM: Artificial Sequence
<220> FEATURE:
<223> OTHER INFORMATION: cDNA Sequence of M563M

<400> SEQUENCE: 849
gcgctggcgg tgattgtggt gccggcgctg gcgccgatgc ccctcaacgt tagcttcacc 60
aacaggaact atgacctcga ctacgactcg gtgcagccgt atttctactg cgacgaggag 120
gagaacttct accagcagca gcagcagagc gagctgcagc cccggcgcc cagcgaggat 180 atctggaaga aattcgagct gctgcccacc ccgcccctgt cccctagccg ccgctccggg 240
ctctgctcgc cctcctacgt tgcggtcaca cccttctccc ttcggggaga caacgacggc 300
ggtggcggga gcttctccac ggccgaccag ctggagatgg tgaccgagct gctgggagga 360
gacatggtga accagagttt catctgcgac ccggacgacg agaccttcat caaaaacatc 420
atcatccagg actgtatgtg gagcggcttc tcggccgccg ccaagctcgt ctcagagaag 480
ctggcctcct accaggctgc gcgcaaagac agcggcagcc cgaaccccgc ccgcggccac 540
agcgtctgct ccacctccag cttgtacctg caggatctga gcgccgccgc ctcagagtgc 600
atcgacccct cggtggtctt cccctaccct ctcaacgaca gcagctcgcc caagtcctgc 660
gcctcgcaag actccagcgc cttctctccg tcctcggatt ctctgctctc ctcgacggag 720
tcctccccgc agggcagccc cgagcccctg gtgctccatg aggagacacc gcccaccacc 780
agcagcgact ctgaggagga acaagaagat gaggaagaaa tcgatgttgt ttctgtggaa 840
aagaggcagg ctcctggcaa aaggtcagag tctggatcac cttctgctgg aggccacagc 900
aaacctcctc acagcccact ggtcctcaag aggtgccacg tctccacaca tcagcacaac 960
tacgcagcgc ctccctccac tcggaaggac tatcctgctg ccaagagggt caagttggac 1020
agtgtcagag tcctgagaca gatcagcaac aaccgaaaat gcaccagccc caggtcctcg 1080
gacaccgagg agaatgtcaa gaggcgaaca cacaacgtct tggagcgcca gaggaggaac 1140
gagctaaaac ggagcttttt tgccctgcgt gaccagatcc cggagttgga aaacaatgaa 1200
aaggccccca aggtagttat ccttaaaaaa gccacagcat acatcctgtc cgtccaagca 1260
gaggagcaaa agctcatttc tgaagaggac ttgttgcgga aacgacgaga acagttgaaa 1320
cacaaacttg aacagctacg gaactcttgt gcg 1353

<210> SEQ ID NO 850
<211> LENGTH: 552
<212> TYPE: PRT
<213> ORGANISM: Artificial Sequence
<220> FEATURE:
<223> OTHER INFORMATION: Amino acid Sequence of M563MSB

<400> SEQUENCE: 850

Ala Leu Ala Val Ile Val Val Pro Ala Leu Ala Pro Met Pro Leu Asn
1 5 10 15

Val Ser Phe Thr Asn Arg Asn Tyr Asp Leu Asp Tyr Asp Ser Val Gln
20 25 30

Pro Tyr Phe Tyr Cys Asp Glu Glu Glu Asn Phe Tyr Gln Gln Gln Gln
35 40 45

Gln Ser Glu Leu Gln Pro Pro Ala Pro Ser Glu Asp Ile Trp Lys Lys
50 55 60

-continued

```
Phe Glu Leu Leu Pro Thr Pro Pro Leu Ser Pro Ser Arg Arg Ser Gly
65                  70                  75                  80

Leu Cys Ser Pro Ser Tyr Val Ala Val Thr Pro Phe Ser Leu Arg Gly
                85                  90                  95

Asp Asn Asp Gly Gly Gly Gly Ser Phe Ser Thr Ala Asp Gln Leu Glu
            100                 105                 110

Met Val Thr Glu Leu Leu Gly Gly Asp Met Val Asn Gln Ser Phe Ile
        115                 120                 125

Cys Asp Pro Asp Asp Glu Thr Phe Ile Lys Asn Ile Ile Ile Gln Asp
    130                 135                 140

Cys Met Trp Ser Gly Phe Ser Ala Ala Ala Lys Leu Val Ser Glu Lys
145                 150                 155                 160

Leu Ala Ser Tyr Gln Ala Ala Arg Lys Asp Ser Gly Ser Pro Asn Pro
                165                 170                 175

Ala Arg Gly His Ser Val Cys Ser Thr Ser Ser Leu Tyr Leu Gln Asp
            180                 185                 190

Leu Ser Ala Ala Ala Ser Glu Cys Ile Asp Pro Ser Val Val Phe Pro
        195                 200                 205

Tyr Pro Leu Asn Asp Ser Ser Ser Pro Lys Ser Cys Ala Ser Gln Asp
    210                 215                 220

Ser Ser Ala Phe Ser Pro Ser Ser Asp Ser Leu Leu Ser Ser Thr Glu
225                 230                 235                 240

Ser Ser Pro Gln Gly Ser Pro Glu Pro Leu Val Leu His Glu Glu Thr
                245                 250                 255

Pro Pro Thr Thr Ser Ser Asp Ser Glu Glu Glu Gln Glu Asp Glu Glu
            260                 265                 270

Glu Ile Asp Val Val Ser Val Glu Lys Arg Gln Ala Pro Gly Lys Arg
        275                 280                 285

Ser Glu Ser Gly Ser Pro Ser Ala Gly Gly His Ser Lys Pro Pro His
    290                 295                 300

Ser Pro Leu Val Leu Lys Arg Cys His Val Ser Thr His Gln His Asn
305                 310                 315                 320

Tyr Ala Ala Pro Pro Ser Thr Arg Lys Asp Tyr Pro Ala Ala Lys Arg
                325                 330                 335

Val Lys Leu Asp Ser Val Arg Val Leu Arg Gln Ile Ser Asn Asn Arg
            340                 345                 350

Lys Cys Thr Ser Pro Arg Ser Ser Asp Thr Glu Glu Asn Val Lys Arg
        355                 360                 365

Arg Thr His Asn Val Leu Glu Arg Gln Arg Arg Asn Glu Leu Lys Arg
    370                 375                 380

Ser Phe Phe Ala Leu Arg Asp Gln Ile Pro Glu Leu Glu Asn Asn Glu
385                 390                 395                 400

Lys Ala Pro Lys Val Val Ile Leu Lys Lys Ala Thr Ala Tyr Ile Leu
                405                 410                 415

Ser Val Gln Ala Glu Glu Gln Lys Leu Ile Ser Glu Glu Asp Leu Leu
            420                 425                 430

Arg Lys Arg Arg Glu Gln Leu Lys His Lys Leu Glu Gln Leu Arg Asn
        435                 440                 445

Ser Cys Ala Gly Ser Met Ala Glu Gln Ser Asp Lys Asp Val Lys Tyr
    450                 455                 460

Tyr Thr Leu Glu Glu Ile Gln Lys His Lys Asp Ser Lys Ser Thr Trp
465                 470                 475                 480

Val Ile Leu His His Lys Val Tyr Asp Leu Thr Lys Phe Leu Glu Glu
```

-continued

```
                485                 490                 495

His Pro Gly Gly Glu Glu Val Leu Gly Glu Gln Ala Gly Gly Asp Ala
            500                 505                 510

Thr Glu Asn Phe Glu Asp Val Gly His Ser Thr Asp Ala Arg Glu Leu
        515                 520                 525

Ser Lys Thr Tyr Ile Ile Gly Glu Leu His Pro Asp Asp Arg Ser Lys
    530                 535                 540

Ile Ala Lys Pro Ser Glu Thr Leu
545                 550
```

<210> SEQ ID NO 851
<211> LENGTH: 1656
<212> TYPE: DNA
<213> ORGANISM: Artificial Sequence
<220> FEATURE:
<223> OTHER INFORMATION: cDNA Sequence of M563MSB

<400> SEQUENCE: 851

```
gcgctggcgg tgattgtggt gccggcgctg gcgccgatgc ccctcaacgt tagcttcacc     60

aacaggaact atgacctcga ctacgactcg gtgcagccgt atttctactg cgacgaggag    120

gagaacttct accagcagca gcagcagagc gagctgcagc ccccggcgcc cagcgaggat    180

atctggaaga aattcgagct gctgcccacc ccgcccctgt cccctagccg ccgctccggg    240

ctctgctcgc cctcctacgt tgcggtcaca cccttctccc ttcggggaga caacgacggc    300

ggtggcggga gcttctccac ggccgaccag ctggagatgg tgaccgagct gctgggagga    360

gacatggtga accagagttt catctgcgac ccggacgacg agaccttcat caaaaacatc    420

atcatccagg actgtatgtg gagcggcttc tcggccgccg ccaagctcgt ctcagagaag    480

ctggcctcct accaggctgc gcgcaaagac agcggcagcc cgaaccccgc ccgcggccac    540

agcgtctgct ccacctccag cttgtacctg caggatctga gcgccgccgc ctcagagtgc    600

atcgacccct cggtggtctt cccctaccct ctcaacgaca gcagctcgcc caagtcctgc    660

gcctcgcaag actccagcgc cttctctccg tcctcggatt ctctgctctc ctcgacggag    720

tcctccccgc agggcagccc cgagcccctg gtgctccatg aggagacacc gcccaccacc    780

agcagcgact ctgaggagga acaagaagat gaggaagaaa tcgatgttgt ttctgtggaa    840

aagaggcagg ctcctggcaa aaggtcagag tctggatcac cttctgctgg aggccacagc    900

aaacctcctc acagcccact ggtcctcaag aggtgccacg tctccacaca tcagcacaac    960

tacgcagcgc ctccctccac tcggaaggac tatcctgctg ccaagagggt caagttggac   1020

agtgtcagag tcctgagaca gatcagcaac aaccgaaaat gcaccagccc caggtcctcg   1080

gacaccgagg agaatgtcaa gaggcgaaca cacaacgtct tggagcgcca gaggaggaac   1140

gagctaaaac ggagcttttt tgccctgcgt gaccagatcc cggagttgga aaacaatgaa   1200

aaggccccca aggtagttat ccttaaaaaa gccacagcat acatcctgtc cgtccaagca   1260

gaggagcaaa agctcatttc tgaagaggac ttgttgcgga aacgacgaga acagttgaaa   1320

cacaaacttg aacagctacg gaactcttgt gcgggatcca tggcagaaca aagcgacaag   1380

gatgtgaagt actacactct ggaggagatt cagaagcaca aagacagcaa gagcacctgg   1440

gtgatcctac atcataaggt gtacgatctg accaagtttc tcgaagagca tcctggtggg   1500

gaagaagtcc tgggcgagca agctgggggt gatgctactg agaactttga ggacgtcggg   1560

cactctacgg atgcacgaga actgtccaaa acatacatca tcggggagct ccatccagat   1620

gacagatcaa agatagccaa gccttcggaa accctt                             1656
```

<210> SEQ ID NO 852
<211> LENGTH: 580
<212> TYPE: PRT
<213> ORGANISM: Artificial Sequence
<220> FEATURE:
<223> OTHER INFORMATION: Amino acid Sequence of HNM563MSB

<400> SEQUENCE: 852

```
Met Gly Ser Ser His His His His His His Ser Ser Gly Leu Val Pro
1               5                   10                  15

Arg Gly Ser His Met Pro Lys Lys Lys Arg Lys Leu Ala Leu Ala Val
            20                  25                  30

Ile Val Val Pro Ala Leu Ala Pro Met Pro Leu Asn Val Ser Phe Thr
        35                  40                  45

Asn Arg Asn Tyr Asp Leu Asp Tyr Asp Ser Val Gln Pro Tyr Phe Tyr
    50                  55                  60

Cys Asp Glu Glu Glu Asn Phe Tyr Gln Gln Gln Gln Gln Ser Glu Leu
65                  70                  75                  80

Gln Pro Pro Ala Pro Ser Glu Asp Ile Trp Lys Lys Phe Glu Leu Leu
                85                  90                  95

Pro Thr Pro Pro Leu Ser Pro Ser Arg Arg Ser Gly Leu Cys Ser Pro
            100                 105                 110

Ser Tyr Val Ala Val Thr Pro Phe Ser Leu Arg Gly Asp Asn Asp Gly
        115                 120                 125

Gly Gly Gly Ser Phe Ser Thr Ala Asp Gln Leu Glu Met Val Thr Glu
    130                 135                 140

Leu Leu Gly Gly Asp Met Val Asn Gln Ser Phe Ile Cys Asp Pro Asp
145                 150                 155                 160

Asp Glu Thr Phe Ile Lys Asn Ile Ile Ile Gln Asp Cys Met Trp Ser
                165                 170                 175

Gly Phe Ser Ala Ala Ala Lys Leu Val Ser Glu Lys Leu Ala Ser Tyr
            180                 185                 190

Gln Ala Ala Arg Lys Asp Ser Gly Ser Pro Asn Pro Ala Arg Gly His
        195                 200                 205

Ser Val Cys Ser Thr Ser Ser Leu Tyr Leu Gln Asp Leu Ser Ala Ala
    210                 215                 220

Ala Ser Glu Cys Ile Asp Pro Ser Val Val Phe Pro Tyr Pro Leu Asn
225                 230                 235                 240

Asp Ser Ser Ser Pro Lys Ser Cys Ala Ser Gln Asp Ser Ser Ala Phe
                245                 250                 255

Ser Pro Ser Ser Asp Ser Leu Leu Ser Ser Thr Glu Ser Ser Pro Gln
            260                 265                 270

Gly Ser Pro Glu Pro Leu Val Leu His Glu Glu Thr Pro Pro Thr Thr
        275                 280                 285

Ser Ser Asp Ser Glu Glu Glu Gln Glu Asp Glu Glu Glu Ile Asp Val
    290                 295                 300

Val Ser Val Glu Lys Arg Gln Ala Pro Gly Lys Arg Ser Glu Ser Gly
305                 310                 315                 320

Ser Pro Ser Ala Gly Gly His Ser Lys Pro Pro His Ser Pro Leu Val
                325                 330                 335

Leu Lys Arg Cys His Val Ser Thr His Gln His Asn Tyr Ala Ala Pro
            340                 345                 350

Pro Ser Thr Arg Lys Asp Tyr Pro Ala Ala Lys Arg Val Lys Leu Asp
        355                 360                 365
```

```
Ser Val Arg Val Leu Arg Gln Ile Ser Asn Asn Arg Lys Cys Thr Ser
    370                 375                 380

Pro Arg Ser Ser Asp Thr Glu Glu Asn Val Lys Arg Arg Thr His Asn
385                 390                 395                 400

Val Leu Glu Arg Gln Arg Arg Asn Glu Leu Lys Arg Ser Phe Phe Ala
                405                 410                 415

Leu Arg Asp Gln Ile Pro Glu Leu Glu Asn Asn Glu Lys Ala Pro Lys
            420                 425                 430

Val Val Ile Leu Lys Lys Ala Thr Ala Tyr Ile Leu Ser Val Gln Ala
        435                 440                 445

Glu Glu Gln Lys Leu Ile Ser Glu Glu Asp Leu Leu Arg Lys Arg Arg
    450                 455                 460

Glu Gln Leu Lys His Lys Leu Glu Gln Leu Arg Asn Ser Cys Ala Gly
465                 470                 475                 480

Ser Met Ala Glu Gln Ser Asp Lys Asp Val Lys Tyr Tyr Thr Leu Glu
                485                 490                 495

Glu Ile Gln Lys His Lys Asp Ser Lys Ser Thr Trp Val Ile Leu His
            500                 505                 510

His Lys Val Tyr Asp Leu Thr Lys Phe Leu Glu Glu His Pro Gly Gly
        515                 520                 525

Glu Glu Val Leu Gly Glu Gln Ala Gly Gly Asp Ala Thr Glu Asn Phe
    530                 535                 540

Glu Asp Val Gly His Ser Thr Asp Ala Arg Glu Leu Ser Lys Thr Tyr
545                 550                 555                 560

Ile Ile Gly Glu Leu His Pro Asp Asp Arg Ser Lys Ile Ala Lys Pro
                565                 570                 575

Ser Glu Thr Leu
            580
```

<210> SEQ ID NO 853
<211> LENGTH: 1740
<212> TYPE: DNA
<213> ORGANISM: Artificial Sequence
<220> FEATURE:
<223> OTHER INFORMATION: cDNA Sequence of HNM563MSB

<400> SEQUENCE: 853

```
atgggcagca gccatcatca tcatcatcac agcagcggcc tggtgccgcg cggcagccat     60

atgcccaaga agaagaggaa gctggcgctg gcggtgattg tggtgccggc gctggcgccg    120

atgcccctca acgttagctt caccaacagg aactatgacc tcgactacga ctcggtgcag    180

ccgtatttct actgcgacga ggaggagaac ttctaccagc agcagcagca gagcgagctg    240

cagcccccgg cgcccagcga ggatatctgg aagaaattcg agctgctgcc caccccgccc    300

ctgtccccta gccgccgctc cgggctctgc tcgccctcct acgttgcggt cacacccttc    360

tcccttcggg gagacaacga cggcggtggc gggagcttct ccacggccga ccagctggag    420

atggtgaccg agctgctggg aggagacatg gtgaaccaga gtttcatctg cgacccggac    480

gacgagacct tcatcaaaaa catcatcatc caggactgta tgtggagcgg cttctcggcc    540

gccgccaagc tcgtctcaga gaagctggcc tcctaccagg ctgcgcgcaa agacagcggc    600

agcccgaacc ccgcccgcgg ccacagcgtc tgctccacct ccagcttgta cctgcaggat    660

ctgagcgccg ccgcctcaga gtgcatcgac ccctcggtgg tcttccccta ccctctcaac    720

gacagcagct cgcccaagtc ctgcgcctcg caagactcca gcgccttctc tccgtcctcg    780
```

```
gattctctgc tctcctcgac ggagtcctcc ccgcagggca gccccgagcc cctggtgctc    840

catgaggaga caccgcccac caccagcagc gactctgagg aggaacaaga agatgaggaa    900

gaaatcgatg ttgtttctgt ggaaaagagg caggctcctg gcaaaaggtc agagtctgga    960

tcaccttctg ctggaggcca cagcaaacct cctcacagcc cactggtcct caagaggtgc   1020

cacgtctcca cacatcagca caactacgca gcgcctccct ccactcggaa ggactatcct   1080

gctgccaaga gggtcaagtt ggacagtgtc agagtcctga gacagatcag caacaaccga   1140

aaatgcacca gccccaggtc ctcggacacc gaggagaatg tcaagaggcg aacacacaac   1200

gtcttggagc gccagaggag gaacgagcta aaacggagct tttttgccct gcgtgaccag   1260

atcccggagt tggaaaacaa tgaaaaggcc cccaaggtag ttatccttaa aaaagccaca   1320

gcatacatcc tgtccgtcca agcagaggag caaaagctca tttctgaaga ggacttgttg   1380

cggaaacgac gagaacagtt gaaacacaaa cttgaacagc tacggaactc ttgtgcggga   1440

tccatggcag aacaaagcga caaggatgtg aagtactaca ctctggagga gattcagaag   1500

cacaaagaca gcaagagcac ctgggtgatc ctacatcata aggtgtacga tctgaccaag   1560

tttctcgaag agcatcctgg tggggaagaa gtcctgggcg agcaagctgg gggtgatgct   1620

actgagaact ttgaggacgt cggccactct acggatgcac gagaactgtc caaaacatac   1680

atcatcgggg agctccatcc agatgacaga tcaaagatag ccaagccttc ggaaaccctt   1740
```

<210> SEQ ID NO 854
<211> LENGTH: 317
<212> TYPE: PRT
<213> ORGANISM: Artificial Sequence
<220> FEATURE:
<223> OTHER INFORMATION: Amino acid Sequence of M161N

<400> SEQUENCE: 854

```
Ala Val Ile Ala Leu Pro Ala Leu Ile Ala Ala Pro Met Ser Val Asp
1               5                   10                  15

Pro Ala Cys Pro Gln Ser Leu Pro Cys Phe Glu Ala Ser Asp Cys Lys
            20                  25                  30

Glu Ser Ser Pro Met Pro Val Ile Cys Gly Pro Glu Glu Asn Tyr Pro
        35                  40                  45

Ser Leu Gln Met Ser Ser Ala Glu Met Pro His Thr Glu Thr Val Ser
    50                  55                  60

Pro Leu Pro Ser Ser Met Asp Leu Leu Ile Gln Asp Ser Pro Asp Ser
65                  70                  75                  80

Ser Thr Ser Pro Lys Gly Lys Gln Pro Thr Ser Ala Glu Asn Ser Val
                85                  90                  95

Ala Lys Lys Glu Asp Lys Val Pro Val Lys Lys Gln Lys Thr Arg Thr
            100                 105                 110

Val Phe Ser Ser Thr Gln Leu Cys Val Leu Asn Asp Arg Phe Gln Arg
        115                 120                 125

Gln Lys Tyr Leu Ser Leu Gln Gln Met Gln Glu Leu Ser Asn Ile Leu
    130                 135                 140

Asn Leu Ser Tyr Lys Gln Val Lys Thr Trp Phe Gln Asn Gln Arg Met
145                 150                 155                 160

Lys Ser Lys Arg Trp Gln Lys Asn Asn Trp Pro Lys Asn Ser Asn Gly
                165                 170                 175

Val Thr Gln Lys Ala Ser Ala Pro Thr Tyr Pro Ser Leu Tyr Ser Ser
            180                 185                 190

Tyr His Gln Gly Cys Leu Val Asn Pro Thr Gly Asn Leu Pro Met Trp
```

```
        195                 200                 205

Ser Asn Gln Thr Trp Asn Asn Ser Thr Trp Ser Asn Gln Thr Gln Asn
    210                 215                 220

Ile Gln Ser Trp Ser Asn His Ser Trp Asn Thr Gln Thr Trp Cys Thr
225                 230                 235                 240

Gln Ser Trp Asn Asn Gln Ala Trp Asn Ser Pro Phe Tyr Asn Cys Gly
                245                 250                 255

Glu Glu Ser Leu Gln Ser Cys Met Gln Phe Gln Pro Asn Ser Pro Ala
            260                 265                 270

Ser Asp Leu Glu Ala Ala Leu Glu Ala Ala Gly Glu Gly Leu Asn Val
        275                 280                 285

Ile Gln Gln Thr Thr Arg Tyr Phe Ser Thr Pro Gln Thr Met Asp Leu
    290                 295                 300

Phe Leu Asn Tyr Ser Met Asn Met Gln Pro Glu Asp Val
305                 310                 315
```

<210> SEQ ID NO 855
<211> LENGTH: 951
<212> TYPE: DNA
<213> ORGANISM: Artificial Sequence
<220> FEATURE:
<223> OTHER INFORMATION: cDNA Sequence of M161N

<400> SEQUENCE: 855

```
gcggtgattg cgctgccggc gctgattgcg gcgccgatga gtgtggatcc agcttgtccc     60

caaagcttgc cttgctttga agcatccgac tgtaaagaat cttcacctat gcctgtgatt    120

tgtgggcctg aagaaaacta tccatccttg caaatgtctt ctgctgagat gcctcacacg    180

gagactgtct ctcctcttcc ctcctccatg gatctgctta ttcaggacag ccctgattct    240

tccaccagtc ccaaaggcaa acaacccact tctgcagaga atagtgtcgc aaaaaaggaa    300

gacaaggtcc cagtcaagaa acagaagacc agaactgtgt tctcttccac ccagctgtgt    360

gtactcaatg atagatttca gagacagaaa tacctcagcc tccagcagat gcaagaactc    420

tccaacatcc tgaacctcag ctacaaacag gtgaagacct ggttccagaa ccagagaatg    480

aaatctaaga ggtggcagaa aaacaactgg ccgaagaata gcaatggtgt gacgcagaag    540

gcctcagcac ctacctaccc cagcctctac tcttcctacc accagggatg cctggtgaac    600

ccgactggga accttccaat gtggagcaac cagacctgga acaattcaac ctggagcaac    660

cagacccaga acatccagtc ctggagcaac cactcctgga acactcagac ctggtgcacc    720

caatcctgga acaatcaggc ctggaacagt cccttctata actgtggaga ggaatctctg    780

cagtcctgca tgcagttcca gccaaattct cctgccagtg acttggaggc tgctttggaa    840

gctgctgggg aaggccttaa tgtaatacag cagaccacta ggtattttag tactccacaa    900

accatggatt tattcctaaa ctactccatg aacatgcaac ctgaagacgt g             951
```

<210> SEQ ID NO 856
<211> LENGTH: 418
<212> TYPE: PRT
<213> ORGANISM: Artificial Sequence
<220> FEATURE:
<223> OTHER INFORMATION: Amino acid Sequence of M161NSB

<400> SEQUENCE: 856

```
Ala Val Ile Ala Leu Pro Ala Leu Ile Ala Ala Pro Met Ser Val Asp
1               5                   10                  15

Pro Ala Cys Pro Gln Ser Leu Pro Cys Phe Glu Ala Ser Asp Cys Lys
```

```
            20                  25                  30

Glu Ser Ser Pro Met Pro Val Ile Cys Gly Pro Glu Glu Asn Tyr Pro
        35                  40                  45

Ser Leu Gln Met Ser Ser Ala Glu Met Pro His Thr Glu Thr Val Ser
    50                  55                  60

Pro Leu Pro Ser Ser Met Asp Leu Leu Ile Gln Asp Ser Pro Asp Ser
65                  70                  75                  80

Ser Thr Ser Pro Lys Gly Lys Gln Pro Thr Ser Ala Glu Asn Ser Val
                85                  90                  95

Ala Lys Lys Glu Asp Lys Val Pro Val Lys Lys Gln Lys Thr Arg Thr
            100                 105                 110

Val Phe Ser Ser Thr Gln Leu Cys Val Leu Asn Asp Arg Phe Gln Arg
        115                 120                 125

Gln Lys Tyr Leu Ser Leu Gln Gln Met Gln Glu Leu Ser Asn Ile Leu
    130                 135                 140

Asn Leu Ser Tyr Lys Gln Val Lys Thr Trp Phe Gln Asn Gln Arg Met
145                 150                 155                 160

Lys Ser Lys Arg Trp Gln Lys Asn Asn Trp Pro Lys Asn Ser Asn Gly
                165                 170                 175

Val Thr Gln Lys Ala Ser Ala Pro Thr Tyr Pro Ser Leu Tyr Ser Ser
            180                 185                 190

Tyr His Gln Gly Cys Leu Val Asn Pro Thr Gly Asn Leu Pro Met Trp
        195                 200                 205

Ser Asn Gln Thr Trp Asn Asn Ser Thr Trp Ser Asn Gln Thr Gln Asn
    210                 215                 220

Ile Gln Ser Trp Ser Asn His Ser Trp Asn Thr Gln Thr Trp Cys Thr
225                 230                 235                 240

Gln Ser Trp Asn Asn Gln Ala Trp Asn Ser Pro Phe Tyr Asn Cys Gly
                245                 250                 255

Glu Glu Ser Leu Gln Ser Cys Met Gln Phe Gln Pro Asn Ser Pro Ala
            260                 265                 270

Ser Asp Leu Glu Ala Ala Leu Glu Ala Ala Gly Glu Gly Leu Asn Val
        275                 280                 285

Ile Gln Gln Thr Thr Arg Tyr Phe Ser Thr Pro Gln Thr Met Asp Leu
    290                 295                 300

Phe Leu Asn Tyr Ser Met Asn Met Gln Pro Glu Asp Val Val Asp Met
305                 310                 315                 320

Ala Glu Gln Ser Asp Lys Asp Val Lys Tyr Tyr Thr Leu Glu Glu Ile
                325                 330                 335

Gln Lys His Lys Asp Ser Lys Ser Thr Trp Val Ile Leu His His Lys
            340                 345                 350

Val Tyr Asp Leu Thr Lys Phe Leu Glu Glu His Pro Gly Gly Glu Glu
        355                 360                 365

Val Leu Gly Glu Gln Ala Gly Gly Asp Ala Thr Glu Asn Phe Glu Asp
    370                 375                 380

Val Gly His Ser Thr Asp Ala Arg Glu Leu Ser Lys Thr Tyr Ile Ile
385                 390                 395                 400

Gly Glu Leu His Pro Asp Asp Arg Ser Lys Ile Ala Lys Pro Ser Glu
                405                 410                 415

Thr Leu

<210> SEQ ID NO 857
<211> LENGTH: 1254
```

<212> TYPE: DNA
<213> ORGANISM: Artificial Sequence
<220> FEATURE:
<223> OTHER INFORMATION: cDNA Sequence of M161NSB

<400> SEQUENCE: 857
gcggtgattg cgctgccggc gctgattgcg gcgccgatga gtgtggatcc agcttgtccc 60
caaagcttgc cttgctttga agcatccgac tgtaaagaat cttcacctat gcctgtgatt 120
tgtgggcctg aagaaaacta tccatccttg caaatgtctt ctgctgagat gcctcacacg 180
gagactgtct ctcctcttcc ctcctccatg gatctgctta ttcaggacag ccctgattct 240
tccaccagtc ccaaaggcaa acaacccact tctgcagaga atagtgtcgc aaaaaaggaa 300
gacaaggtcc cagtcaagaa acagaagacc agaactgtgt tctcttccac ccagctgtgt 360
gtactcaatg atagatttca gagacagaaa tacctcagcc tccagcagat gcaagaactc 420
tccaacatcc tgaacctcag ctacaaacag gtgaagacct ggttccagaa ccagagaatg 480
aaatctaaga ggtggcagaa aaacaactgg ccgaagaata gcaatggtgt gacgcagaag 540
gcctcagcac ctacctaccc cagcctctac tcttcctacc accagggatg cctggtgaac 600
ccgactggga accttccaat gtggagcaac cagacctgga acaattcaac ctggagcaac 660
cagacccaga acatccagtc ctggagcaac cactcctgga acactcagac ctggtgcacc 720
caatcctgga acaatcaggc ctggaacagt ccettctata actgtggaga ggaatctctg 780
cagtcctgca tgcagttcca gccaaattct cctgccagtg acttggaggc tgctttggaa 840
gctgctgggg aaggccttaa tgtaatacag cagaccacta ggtattttag tactccacaa 900
accatggatt tattcctaaa ctactccatg aacatgcaac ctgaagacgt ggtcgacatg 960
gcagaacaaa gcgacaagga tgtgaagtac tacactctgg aggagattca gaagcacaaa 1020
gacagcaaga gcacctgggt gatcctacat cataaggtgt acgatctgac caagtttctc 1080
gaagagcatc ctggtgggga agaagtcctg ggcgagcaag ctgggggtga tgctactgag 1140
aactttgagg acgtcgggca ctctacggat gcacgagaac tgtccaaaac atacatcatc 1200
ggggagctcc atccagatga cagatcaaag atagccaagc cttcggaaac cctt 1254

<210> SEQ ID NO 858
<211> LENGTH: 446
<212> TYPE: PRT
<213> ORGANISM: Artificial Sequence
<220> FEATURE:
<223> OTHER INFORMATION: Amino acid Sequence of HNM161NSB

<400> SEQUENCE: 858

Met Gly Ser Ser His His His His His His Ser Ser Gly Leu Val Pro
1 5 10 15

Arg Gly Ser His Met Pro Lys Lys Lys Arg Lys Leu Ala Val Ile Ala
20 25 30

Leu Pro Ala Leu Ile Ala Ala Pro Met Ser Val Asp Pro Ala Cys Pro
35 40 45

Gln Ser Leu Pro Cys Phe Glu Ala Ser Asp Cys Lys Glu Ser Ser Pro
50 55 60

Met Pro Val Ile Cys Gly Pro Glu Glu Asn Tyr Pro Ser Leu Gln Met
65 70 75 80

Ser Ser Ala Glu Met Pro His Thr Glu Thr Val Ser Pro Leu Pro Ser
85 90 95

Ser Met Asp Leu Leu Ile Gln Asp Ser Pro Asp Ser Ser Thr Ser Pro
100 105 110

```
Lys Gly Lys Gln Pro Thr Ser Ala Glu Asn Ser Val Ala Lys Lys Glu
        115                 120                 125

Asp Lys Val Pro Val Lys Lys Gln Lys Thr Arg Thr Val Phe Ser Ser
    130                 135                 140

Thr Gln Leu Cys Val Leu Asn Asp Arg Phe Gln Arg Gln Lys Tyr Leu
145                 150                 155                 160

Ser Leu Gln Gln Met Gln Glu Leu Ser Asn Ile Leu Asn Leu Ser Tyr
                165                 170                 175

Lys Gln Val Lys Thr Trp Phe Gln Asn Gln Arg Met Lys Ser Lys Arg
            180                 185                 190

Trp Gln Lys Asn Asn Trp Pro Lys Asn Ser Asn Gly Val Thr Gln Lys
        195                 200                 205

Ala Ser Ala Pro Thr Tyr Pro Ser Leu Tyr Ser Ser Tyr His Gln Gly
    210                 215                 220

Cys Leu Val Asn Pro Thr Gly Asn Leu Pro Met Trp Ser Asn Gln Thr
225                 230                 235                 240

Trp Asn Asn Ser Thr Trp Ser Asn Gln Thr Gln Asn Ile Gln Ser Trp
                245                 250                 255

Ser Asn His Ser Trp Asn Thr Gln Thr Trp Cys Thr Gln Ser Trp Asn
            260                 265                 270

Asn Gln Ala Trp Asn Ser Pro Phe Tyr Asn Cys Gly Glu Glu Ser Leu
        275                 280                 285

Gln Ser Cys Met Gln Phe Gln Pro Asn Ser Pro Ala Ser Asp Leu Glu
    290                 295                 300

Ala Ala Leu Glu Ala Ala Gly Glu Gly Leu Asn Val Ile Gln Gln Thr
305                 310                 315                 320

Thr Arg Tyr Phe Ser Thr Pro Gln Thr Met Asp Leu Phe Leu Asn Tyr
                325                 330                 335

Ser Met Asn Met Gln Pro Glu Asp Val Val Asp Met Ala Glu Gln Ser
            340                 345                 350

Asp Lys Asp Val Lys Tyr Tyr Thr Leu Glu Glu Ile Gln Lys His Lys
        355                 360                 365

Asp Ser Lys Ser Thr Trp Val Ile Leu His His Lys Val Tyr Asp Leu
    370                 375                 380

Thr Lys Phe Leu Glu Glu His Pro Gly Gly Glu Glu Val Leu Gly Glu
385                 390                 395                 400

Gln Ala Gly Gly Asp Ala Thr Glu Asn Phe Glu Asp Val Gly His Ser
                405                 410                 415

Thr Asp Ala Arg Glu Leu Ser Lys Thr Tyr Ile Ile Gly Glu Leu His
            420                 425                 430

Pro Asp Asp Arg Ser Lys Ile Ala Lys Pro Ser Glu Thr Leu
        435                 440                 445
```

<210> SEQ ID NO 859
<211> LENGTH: 1338
<212> TYPE: DNA
<213> ORGANISM: Artificial Sequence
<220> FEATURE:
<223> OTHER INFORMATION: cDNA Sequence of HNM161NSB

<400> SEQUENCE: 859

```
atgggcagca gccatcatca tcatcatcac agcagcggcc tggtgccgcg cggcagccat     60

atgcccaaga agaagaggaa gctggcggtg attgcgctgc cggcgctgat tgcggcgccg    120

atgagtgtgg atccagcttg tccccaaagc ttgccttgct ttgaagcatc cgactgtaaa    180
```

```
gaatcttcac ctatgcctgt gatttgtggg cctgaagaaa actatccatc cttgcaaatg    240
tcttctgctg agatgcctca cacggagact gtctctcctc ttccctcctc catggatctg    300
cttattcagg acagccctga ttcttccacc agtcccaaag gcaaacaacc cacttctgca    360
gagaatagtg tcgcaaaaaa ggaagacaag gtcccagtca agaaacagaa gaccagaact    420
gtgttctctt ccacccagct gtgtgtactc aatgatagat ttcagagaca gaaatacctc    480
agcctccagc agatgcaaga actctccaac atcctgaacc tcagctacaa acaggtgaag    540
acctggttcc agaaccagag aatgaaatct aagaggtggc agaaaaacaa ctggccgaag    600
aatagcaatg gtgtgacgca gaaggcctca gcacctacct accccagcct ctactcttcc    660
taccaccagg gatgcctggt gaacccgact gggaaccttc caatgtggag caaccagacc    720
tggaacaatt caacctggag caaccagacc cagaacatcc agtcctggag caaccactcc    780
tggaacactc agacctggtg cacccaatcc tggaacaatc aggcctggaa cagtcccttc    840
tataactgtg gagaggaatc tctgcagtcc tgcatgcagt tccagccaaa ttctcctgcc    900
agtgacttgg aggctgcttt ggaagctgct ggggaaggcc ttaatgtaat acagcagacc    960
actaggtatt ttagtactcc acaaaccatg gatttattcc taaactactc catgaacatg   1020
caacctgaag acgtggtcga catggcagaa caaagcgaca aggatgtgaa gtactacact   1080
ctggaggaga ttcagaagca caaagacagc aagagcacct gggtgatcct acatcataag   1140
gtgtacgatc tgaccaagtt tctcgaagag catcctggtg gggaagaagt cctgggcgag   1200
caagctgggg gtgatgctac tgagaacttt gaggacgtcg ggcactctac ggatgcacga   1260
gaactgtcca aaacatacat catcggggag ctccatccag atgacagatc aaagatagcc   1320
aagccttcgg aaaccctt                                                 1338
```

<210> SEQ ID NO 860
<211> LENGTH: 221
<212> TYPE: PRT
<213> ORGANISM: Artificial Sequence
<220> FEATURE:
<223> OTHER INFORMATION: Amino acid Sequence of M563L

<400> SEQUENCE: 860

```
Ala Leu Ala Val Ile Val Val Pro Ala Leu Ala Pro Met Gly Ser Val
1               5                   10                  15

Ser Asn Gln Gln Phe Ala Gly Gly Cys Ala Lys Ala Ala Glu Glu Ala
            20                  25                  30

Pro Glu Glu Ala Pro Glu Asp Ala Ala Arg Ala Ala Asp Glu Pro Gln
        35                  40                  45

Leu Leu His Gly Ala Gly Ile Cys Lys Trp Phe Asn Val Arg Met Gly
    50                  55                  60

Phe Gly Phe Leu Ser Met Thr Ala Arg Ala Gly Val Ala Leu Asp Pro
65                  70                  75                  80

Pro Val Asp Val Phe Val His Gln Ser Lys Leu His Met Glu Gly Phe
                85                  90                  95

Arg Ser Leu Lys Glu Gly Glu Ala Val Glu Phe Thr Phe Lys Lys Ser
            100                 105                 110

Ala Lys Gly Leu Glu Ser Ile Arg Val Thr Gly Pro Gly Gly Val Phe
        115                 120                 125

Cys Ile Gly Ser Glu Arg Arg Pro Lys Gly Lys Ser Met Gln Lys Arg
    130                 135                 140

Arg Ser Lys Gly Asp Arg Cys Tyr Asn Cys Gly Gly Leu Asp His His
```

```
145                 150                 155                 160

Ala Lys Glu Cys Lys Leu Pro Pro Gln Pro Lys Lys Cys His Phe Cys
                165                 170                 175

Gln Ser Ile Ser His Met Val Ala Ser Cys Pro Leu Lys Ala Gln Gln
            180                 185                 190

Gly Pro Ser Ala Gln Gly Lys Pro Thr Tyr Phe Arg Glu Glu Glu Glu
        195                 200                 205

Glu Ile His Ser Pro Thr Leu Leu Pro Glu Ala Gln Asn
    210                 215                 220


<210> SEQ ID NO 861
<211> LENGTH: 663
<212> TYPE: DNA
<213> ORGANISM: Artificial Sequence
<220> FEATURE:
<223> OTHER INFORMATION: cDNA Sequence of M563L

<400> SEQUENCE: 861

gcgctggcgg tgattgtggt gccggcgctg gcgccgatgg gctccgtgtc caaccagcag     60

tttgcaggtg gctgcgccaa ggcggcagaa gaggcgcccg aggaggcgcc ggaggacgcg    120

gcccgggcgg cggacgagcc tcagctgctg cacggtgcgg gcatctgtaa gtggttcaac    180

gtgcgcatgg ggttcggctt cctgtccatg accgcccgcg ccggggtcgc gctcgacccc    240

ccagtggatg tctttgtgca ccagagtaag ctgcacatgg aagggttccg gagcttgaag    300

gagggtgagg cagtggagtt cacctttaag aagtcagcca agggtctgga atccatccgt    360

gtcaccggac ctggtggagt attctgtatt gggagtgaga ggcggccaaa aggaaagagc    420

atgcagaagc gcagatcaaa aggagacagg tgctacaact gtggaggtct agatcatcat    480

gccaaggaat gcaagctgcc accccagccc aagaagtgcc acttctgcca gagcatcagc    540

catatggtag cctcatgtcc gctgaaggcc cagcagggcc ctagtgcaca gggaaagcca    600

acctactttc gagaggaaga agaagaaatc cacagcccta ccctgctccc ggaggcacag    660

aat                                                                  663


<210> SEQ ID NO 862
<211> LENGTH: 322
<212> TYPE: PRT
<213> ORGANISM: Artificial Sequence
<220> FEATURE:
<223> OTHER INFORMATION: Amino acid Sequence of M563LSB

<400> SEQUENCE: 862

Ala Leu Ala Val Ile Val Val Pro Ala Leu Ala Pro Met Gly Ser Val
1               5                   10                  15

Ser Asn Gln Gln Phe Ala Gly Gly Cys Ala Lys Ala Ala Glu Glu Ala
            20                  25                  30

Pro Glu Glu Ala Pro Glu Asp Ala Ala Arg Ala Ala Asp Glu Pro Gln
        35                  40                  45

Leu Leu His Gly Ala Gly Ile Cys Lys Trp Phe Asn Val Arg Met Gly
    50                  55                  60

Phe Gly Phe Leu Ser Met Thr Ala Arg Ala Gly Val Ala Leu Asp Pro
65                  70                  75                  80

Pro Val Asp Val Phe Val His Gln Ser Lys Leu His Met Glu Gly Phe
                85                  90                  95

Arg Ser Leu Lys Glu Gly Glu Ala Val Glu Phe Thr Phe Lys Lys Ser
            100                 105                 110
```

```
Ala Lys Gly Leu Glu Ser Ile Arg Val Thr Gly Pro Gly Gly Val Phe
        115                 120                 125

Cys Ile Gly Ser Glu Arg Arg Pro Lys Gly Lys Ser Met Gln Lys Arg
    130                 135                 140

Arg Ser Lys Gly Asp Arg Cys Tyr Asn Cys Gly Gly Leu Asp His His
145                 150                 155                 160

Ala Lys Glu Cys Lys Leu Pro Pro Gln Pro Lys Lys Cys His Phe Cys
                165                 170                 175

Gln Ser Ile Ser His Met Val Ala Ser Cys Pro Leu Lys Ala Gln Gln
            180                 185                 190

Gly Pro Ser Ala Gln Gly Lys Pro Thr Tyr Phe Arg Glu Glu Glu Glu
        195                 200                 205

Glu Ile His Ser Pro Thr Leu Leu Pro Glu Ala Gln Asn Val Asp Met
    210                 215                 220

Ala Glu Gln Ser Asp Lys Asp Val Lys Tyr Tyr Thr Leu Glu Glu Ile
225                 230                 235                 240

Gln Lys His Lys Asp Ser Lys Ser Thr Trp Val Ile Leu His His Lys
                245                 250                 255

Val Tyr Asp Leu Thr Lys Phe Leu Glu Glu His Pro Gly Gly Glu Glu
            260                 265                 270

Val Leu Gly Glu Gln Ala Gly Gly Asp Ala Thr Glu Asn Phe Glu Asp
        275                 280                 285

Val Gly His Ser Thr Asp Ala Arg Glu Leu Ser Lys Thr Tyr Ile Ile
    290                 295                 300

Gly Glu Leu His Pro Asp Asp Arg Ser Lys Ile Ala Lys Pro Ser Glu
305                 310                 315                 320

Thr Leu
```

<210> SEQ ID NO 863
<211> LENGTH: 966
<212> TYPE: DNA
<213> ORGANISM: Artificial Sequence
<220> FEATURE:
<223> OTHER INFORMATION: cDNA Sequence of M563LSB

<400> SEQUENCE: 863

```
gcgctggcgg tgattgtggt gccggcgctg gcgccgatgg gctccgtgtc caaccagcag     60

tttgcaggtg gctgcgccaa ggcggcagaa gaggcgcccg aggaggcgcc ggaggacgcg    120

gcccgggcgg cggacgagcc tcagctgctg cacggtgcgg gcatctgtaa gtggttcaac    180

gtgcgcatgg ggttcggctt cctgtccatg accgcccgcg ccggggtcgc gctcgacccc    240

ccagtggatg tctttgtgca ccagagtaag ctgcacatgg aagggttccg gagcttgaag    300

gagggtgagg cagtggagtt cacctttaag aagtcagcca agggtctgga atccatccgt    360

gtcaccggac ctggtggagt attctgtatt gggagtgaga ggcggccaaa aggaaagagc    420

atgcagaagc gcagatcaaa aggagacagg tgctacaact gtggaggtct agatcatcat    480

gccaaggaat gcaagctgcc accccagccc aagaagtgcc acttctgcca gagcatcagc    540

catatggtag cctcatgtcc gctgaaggcc cagcagggcc ctagtgcaca gggaaagcca    600

acctactttc gagaggaaga agaagaaatc cacagcccta ccctgctccc ggaggcacag    660

aatgtcgaca tggcagaaca aagcgacaag gatgtgaagt actacactct ggaggagatt    720

cagaagcaca aagacagcaa gagcacctgg gtgatcctac atcataaggt gtacgatctg    780

accaagtttc tcgaagagca tcctggtggg gaagaagtcc tgggcgagca agctgggggt    840
```

gatgctactg agaactttga ggacgtcggg cactctacgg atgcacgaga actgtccaaa 900
acatacatca tcggggagct ccatccagat gacagatcaa agatagccaa gccttcggaa 960
accctt 966

<210> SEQ ID NO 864
<211> LENGTH: 365
<212> TYPE: PRT
<213> ORGANISM: Artificial Sequence
<220> FEATURE:
<223> OTHER INFORMATION: Amino acid Sequence of HNM563LSB

<400> SEQUENCE: 864

Met Gly Ser Ser His His His His His His Ser Ser Gly Leu Val Pro
1 5 10 15

Arg Gly Ser His Met Ala Ser Met Thr Gly Gly Gln Gln Met Gly Arg
20 25 30

Gly Ser Glu Phe Pro Lys Lys Lys Arg Lys Leu Ala Leu Ala Val Ile
35 40 45

Val Val Pro Ala Leu Ala Pro Met Gly Ser Val Ser Asn Gln Gln Phe
50 55 60

Ala Gly Gly Cys Ala Lys Ala Ala Glu Glu Ala Pro Glu Glu Ala Pro
65 70 75 80

Glu Asp Ala Ala Arg Ala Ala Asp Glu Pro Gln Leu Leu His Gly Ala
85 90 95

Gly Ile Cys Lys Trp Phe Asn Val Arg Met Gly Phe Gly Phe Leu Ser
100 105 110

Met Thr Ala Arg Ala Gly Val Ala Leu Asp Pro Pro Val Asp Val Phe
115 120 125

Val His Gln Ser Lys Leu His Met Glu Gly Phe Arg Ser Leu Lys Glu
130 135 140

Gly Glu Ala Val Glu Phe Thr Phe Lys Lys Ser Ala Lys Gly Leu Glu
145 150 155 160

Ser Ile Arg Val Thr Gly Pro Gly Gly Val Phe Cys Ile Gly Ser Glu
165 170 175

Arg Arg Pro Lys Gly Lys Ser Met Gln Lys Arg Arg Ser Lys Gly Asp
180 185 190

Arg Cys Tyr Asn Cys Gly Gly Leu Asp His His Ala Lys Glu Cys Lys
195 200 205

Leu Pro Pro Gln Pro Lys Lys Cys His Phe Cys Gln Ser Ile Ser His
210 215 220

Met Val Ala Ser Cys Pro Leu Lys Ala Gln Gln Gly Pro Ser Ala Gln
225 230 235 240

Gly Lys Pro Thr Tyr Phe Arg Glu Glu Glu Glu Glu Ile His Ser Pro
245 250 255

Thr Leu Leu Pro Glu Ala Gln Asn Val Asp Met Ala Glu Gln Ser Asp
260 265 270

Lys Asp Val Lys Tyr Tyr Thr Leu Glu Glu Ile Gln Lys His Lys Asp
275 280 285

Ser Lys Ser Thr Trp Val Ile Leu His His Lys Val Tyr Asp Leu Thr
290 295 300

Lys Phe Leu Glu Glu His Pro Gly Gly Glu Glu Val Leu Gly Glu Gln
305 310 315 320

Ala Gly Gly Asp Ala Thr Glu Asn Phe Glu Asp Val Gly His Ser Thr
325 330 335

-continued

```
Asp Ala Arg Glu Leu Ser Lys Thr Tyr Ile Ile Gly Glu Leu His Pro
            340                 345                 350

Asp Asp Arg Ser Lys Ile Ala Lys Pro Ser Glu Thr Leu
        355                 360                 365
```

<210> SEQ ID NO 865
<211> LENGTH: 1095
<212> TYPE: DNA
<213> ORGANISM: Artificial Sequence
<220> FEATURE:
<223> OTHER INFORMATION: cDNA Sequence of HNM563LSB

<400> SEQUENCE: 865

```
atgggcagca gccatcatca tcatcatcac agcagcggcc tggtgccgcg cggcagccat     60

atggctagca tgactggtgg acagcaaatg ggtcgcggat ccgaattccc caagaagaag    120

aggaagctgg cgctggcggt gattgtggtg ccggcgctgg cgccgatggg ctccgtgtcc    180

aaccagcagt ttgcaggtgg ctgcgccaag gcggcagaag aggcgcccga ggaggcgccg    240

gaggacgcgg cccgggcggc ggacgagcct cagctgctgc acggtgcggg catctgtaag    300

tggttcaacg tgcgcatggg gttcggcttc ctgtccatga ccgcccgcgc cggggtcgcg    360

ctcgaccccc cagtggatgt ctttgtgcac cagagtaagc tgcacatgga agggttccgg    420

agcttgaagg agggtgaggc agtggagttc acctttaaga agtcagccaa gggtctggaa    480

tccatccgtg tcaccggacc tggtggagta ttctgtattg ggagtgagag gcggccaaaa    540

ggaaagagca tgcagaagcg cagatcaaaa ggagacaggt gctacaactg tggaggtcta    600

gatcatcatg ccaaggaatg caagctgcca ccccagccca agaagtgcca cttctgccag    660

agcatcagcc atatggtagc ctcatgtccg ctgaaggccc agcagggccc tagtgcacag    720

ggaaagccaa cctactttcg agaggaagaa gaagaaatcc acagccctac cctgctcccg    780

gaggcacaga atgtcgacat ggcagaacaa agcgacaagg atgtgaagta ctacactctg    840

gaggagattc agaagcacaa agacagcaag agcacctggg tgatcctaca tcataaggtg    900

tacgatctga ccaagtttct cgaagagcat cctggtgggg aagaagtcct gggcgagcaa    960

gctgggggtg atgctactga gaactttgag gacgtcgggc actctacgga tgcacgagaa   1020

ctgtccaaaa catacatcat cggggagctc catccagatg acagatcaaa gatagccaag   1080

ccttcggaaa ccctt                                                    1095
```

<210> SEQ ID NO 866
<211> LENGTH: 445
<212> TYPE: PRT
<213> ORGANISM: Artificial Sequence
<220> FEATURE:
<223> OTHER INFORMATION: Amino acid Sequence of M563Z

<400> SEQUENCE: 866

```
Ala Leu Ala Val Ile Val Val Pro Ala Leu Ala Pro Met Ala Leu Asp
1               5                   10                  15

Leu Arg Thr Ile Phe Gln Cys Glu Pro Ser Glu Asn Asn Leu Gly Ser
            20                  25                  30

Glu Asn Ser Ala Phe Gln Gln Ser Gln Gly Pro Ala Val Gln Arg Glu
        35                  40                  45

Glu Gly Ile Ser Glu Phe Ser Arg Met Val Leu Asn Ser Phe Gln Asp
    50                  55                  60

Ser Asn Asn Ser Tyr Ala Arg Gln Glu Leu Gln Arg Leu Tyr Arg Ile
65                  70                  75                  80
```

```
Phe His Ser Trp Leu Gln Pro Glu Lys His Ser Lys Asp Glu Ile Ile
                85                  90                  95

Ser Leu Leu Val Leu Glu Gln Phe Met Ile Gly Gly His Cys Asn Asp
            100                 105                 110

Lys Ala Ser Val Lys Glu Lys Trp Lys Ser Ser Gly Lys Asn Leu Glu
        115                 120                 125

Arg Phe Ile Glu Asp Leu Thr Asp Asp Ser Ile Asn Pro Pro Ala Leu
    130                 135                 140

Val His Val His Met Gln Gly Gln Glu Ala Leu Phe Ser Glu Asp Met
145                 150                 155                 160

Pro Leu Arg Asp Val Ile Val His Leu Thr Lys Gln Val Asn Ala Gln
                165                 170                 175

Thr Thr Arg Glu Ala Asn Met Gly Thr Pro Ser Gln Thr Ser Gln Asp
            180                 185                 190

Thr Ser Leu Glu Thr Gly Gln Gly Tyr Glu Asp Glu Gln Asp Gly Trp
        195                 200                 205

Asn Ser Ser Ser Lys Thr Thr Arg Val Asn Glu Asn Ile Thr Asn Gln
    210                 215                 220

Gly Asn Gln Ile Val Ser Leu Ile Ile Ile Gln Glu Glu Asn Gly Pro
225                 230                 235                 240

Arg Pro Glu Glu Gly Gly Val Ser Ser Asp Asn Pro Tyr Asn Ser Lys
                245                 250                 255

Arg Ala Glu Leu Val Thr Ala Arg Ser Gln Glu Gly Ser Ile Asn Gly
            260                 265                 270

Ile Thr Phe Gln Gly Val Pro Met Val Met Gly Ala Gly Cys Ile Ser
        275                 280                 285

Gln Pro Glu Gln Ser Ser Pro Glu Ser Ala Leu Thr His Gln Ser Asn
    290                 295                 300

Glu Gly Asn Ser Thr Cys Glu Val His Gln Lys Gly Ser His Gly Val
305                 310                 315                 320

Gln Lys Ser Tyr Lys Cys Glu Glu Cys Pro Lys Val Phe Lys Tyr Leu
                325                 330                 335

Cys His Leu Leu Ala His Gln Arg Arg His Arg Asn Glu Arg Pro Phe
            340                 345                 350

Val Cys Pro Glu Cys Gln Lys Gly Phe Phe Gln Ile Ser Asp Leu Arg
        355                 360                 365

Val His Gln Ile Ile His Thr Gly Lys Lys Pro Phe Thr Cys Ser Met
    370                 375                 380

Cys Lys Lys Ser Phe Ser His Lys Thr Asn Leu Arg Ser His Glu Arg
385                 390                 395                 400

Ile His Thr Gly Glu Lys Pro Tyr Thr Cys Pro Phe Cys Lys Thr Ser
                405                 410                 415

Tyr Arg Gln Ser Ser Thr Tyr His Arg His Met Arg Thr His Glu Lys
            420                 425                 430

Ile Thr Leu Pro Ser Val Pro Ser Thr Pro Glu Ala Ser
        435                 440                 445
```

<210> SEQ ID NO 867
<211> LENGTH: 1335
<212> TYPE: DNA
<213> ORGANISM: Artificial Sequence
<220> FEATURE:
<223> OTHER INFORMATION: cDNA Sequence of M563Z

<400> SEQUENCE: 867

-continued

```
gcgctggcgg tgattgtggt gccggcgctg gcgccgatgg ctttagatct aagaaccata     60

tttcagtgtg aaccatccga gaataatctt ggatcagaaa attcagcgtt tcaacaaagc    120

caaggacctg ctgttcagag agaagaaggg atttctgagt tctcaagaat ggtgctcaat    180

tcatttcaag acagcaataa ttcatatgca aggcaggaat tgcaaagact ttataggatc    240

tttcactcat ggctgcaacc agaaaagcac agcaaggatg aaattatttc tctattagtc    300

ctggagcagt ttatgattgg tggccactgc aatgacaaag ccagtgtgaa agagaaatgg    360

aaatcaagtg gcaaaaactt ggagagattc atagaagacc tgactgatga cagcataaat    420

ccacctgcct tagtccacgt ccacatgcag ggacaggaag ctctcttttc tgaggatatg    480

cccttaagag atgtcattgt tcatctcaca aaacaagtga atgcccaaac cacaagagaa    540

gcaaacatgg ggacaccctc ccagacttcc caagatactt ccttagaaac aggacaagga    600

tatgaagatg aacaagatgg ctggaacagt tcttcgaaaa ctactcgagt aaatgaaaat    660

attactaatc aaggcaatca aatagtttcc ctaatcatca tccaggaaga gaacggtcct    720

aggcctgaag agggaggtgt ttcttctgac aacccataca actcaaaaag agcagagcta    780

gtcactgcta gatctcagga agggtccata aatggaatca ctttccaagg tgtccctatg    840

gtgatgggag cagggtgtat ctctcaacca gagcagtcct cccctgagtc tgcccttacc    900

caccagagca atgagggaaa ttccacatgt gaggtacatc agaaaggatc ccatggagtc    960

caaaaatcat acaaatgtga agaatgcccc aaggtcttta agtatctctg tcacttatta   1020

gctcaccaga gaagacacag gaatgagagg ccatttgttt gtcccgagtg tcaaaaaggc   1080

ttcttccaga tatcagacct acgggtgcat cagataattc acacaggaaa gaagcctttc   1140

acatgcagca tgtgtaaaaa gtccttcagc cacaaaacca acctgcggtc tcatgagaga   1200

atccacacag gagaaaagcc ttatacatgt cccttttgta agacaagcta ccgccagtca   1260

tccacatacc accgccatat gaggactcat gagaaaatta ccctgccaag tgttccctcc   1320

acaccagaag cttcc                                                    1335
```

```
<210> SEQ ID NO 868
<211> LENGTH: 546
<212> TYPE: PRT
<213> ORGANISM: Artificial Sequence
<220> FEATURE:
<223> OTHER INFORMATION: Amino acid Sequence of M563ZSB

<400> SEQUENCE: 868

Ala Leu Ala Val Ile Val Val Pro Ala Leu Ala Pro Met Ala Leu Asp
1               5                   10                  15

Leu Arg Thr Ile Phe Gln Cys Glu Pro Ser Glu Asn Asn Leu Gly Ser
            20                  25                  30

Glu Asn Ser Ala Phe Gln Gln Ser Gln Gly Pro Ala Val Gln Arg Glu
        35                  40                  45

Glu Gly Ile Ser Glu Phe Ser Arg Met Val Leu Asn Ser Phe Gln Asp
    50                  55                  60

Ser Asn Asn Ser Tyr Ala Arg Gln Glu Leu Gln Arg Leu Tyr Arg Ile
65                  70                  75                  80

Phe His Ser Trp Leu Gln Pro Glu Lys His Ser Lys Asp Glu Ile Ile
                85                  90                  95

Ser Leu Leu Val Leu Glu Gln Phe Met Ile Gly Gly His Cys Asn Asp
            100                 105                 110

Lys Ala Ser Val Lys Glu Lys Trp Lys Ser Ser Gly Lys Asn Leu Glu
        115                 120                 125
```

```
Arg Phe Ile Glu Asp Leu Thr Asp Asp Ser Ile Asn Pro Pro Ala Leu
    130                 135                 140

Val His Val His Met Gln Gly Gln Glu Ala Leu Phe Ser Glu Asp Met
145                 150                 155                 160

Pro Leu Arg Asp Val Ile Val His Leu Thr Lys Gln Val Asn Ala Gln
                165                 170                 175

Thr Thr Arg Glu Ala Asn Met Gly Thr Pro Ser Gln Thr Ser Gln Asp
            180                 185                 190

Thr Ser Leu Glu Thr Gly Gln Gly Tyr Glu Asp Glu Gln Asp Gly Trp
        195                 200                 205

Asn Ser Ser Ser Lys Thr Thr Arg Val Asn Glu Asn Ile Thr Asn Gln
    210                 215                 220

Gly Asn Gln Ile Val Ser Leu Ile Ile Ile Gln Glu Glu Asn Gly Pro
225                 230                 235                 240

Arg Pro Glu Glu Gly Gly Val Ser Ser Asp Asn Pro Tyr Asn Ser Lys
                245                 250                 255

Arg Ala Glu Leu Val Thr Ala Arg Ser Gln Glu Gly Ser Ile Asn Gly
            260                 265                 270

Ile Thr Phe Gln Gly Val Pro Met Val Met Gly Ala Gly Cys Ile Ser
        275                 280                 285

Gln Pro Glu Gln Ser Ser Pro Glu Ser Ala Leu Thr His Gln Ser Asn
    290                 295                 300

Glu Gly Asn Ser Thr Cys Glu Val His Gln Lys Gly Ser His Gly Val
305                 310                 315                 320

Gln Lys Ser Tyr Lys Cys Glu Glu Cys Pro Lys Val Phe Lys Tyr Leu
                325                 330                 335

Cys His Leu Leu Ala His Gln Arg Arg His Arg Asn Glu Arg Pro Phe
            340                 345                 350

Val Cys Pro Glu Cys Gln Lys Gly Phe Phe Gln Ile Ser Asp Leu Arg
        355                 360                 365

Val His Gln Ile Ile His Thr Gly Lys Lys Pro Phe Thr Cys Ser Met
    370                 375                 380

Cys Lys Lys Ser Phe Ser His Lys Thr Asn Leu Arg Ser His Glu Arg
385                 390                 395                 400

Ile His Thr Gly Glu Lys Pro Tyr Thr Cys Pro Phe Cys Lys Thr Ser
                405                 410                 415

Tyr Arg Gln Ser Ser Thr Tyr His Arg His Met Arg Thr His Glu Lys
            420                 425                 430

Ile Thr Leu Pro Ser Val Pro Ser Thr Pro Glu Ala Ser Val Asp Met
        435                 440                 445

Ala Glu Gln Ser Asp Lys Asp Val Lys Tyr Tyr Thr Leu Glu Glu Ile
    450                 455                 460

Gln Lys His Lys Asp Ser Lys Ser Thr Trp Val Ile Leu His His Lys
465                 470                 475                 480

Val Tyr Asp Leu Thr Lys Phe Leu Glu Glu His Pro Gly Gly Glu Glu
                485                 490                 495

Val Leu Gly Glu Gln Ala Gly Gly Asp Ala Thr Glu Asn Phe Glu Asp
            500                 505                 510

Val Gly His Ser Thr Asp Ala Arg Glu Leu Ser Lys Thr Tyr Ile Ile
        515                 520                 525

Gly Glu Leu His Pro Asp Asp Arg Ser Lys Ile Ala Lys Pro Ser Glu
    530                 535                 540
```

Thr Leu
545

<210> SEQ ID NO 869
<211> LENGTH: 1638
<212> TYPE: DNA
<213> ORGANISM: Artificial Sequence
<220> FEATURE:
<223> OTHER INFORMATION: cDNA Sequence of M563ZSB

<400> SEQUENCE: 869
gcgctggcgg tgattgtggt gccggcgctg gcgccgatgg ctttagatct aagaaccata 60
tttcagtgtg aaccatccga gaataatctt ggatcagaaa attcagcgtt tcaacaaagc 120
caaggacctg ctgttcagag agaagaaggg atttctgagt tctcaagaat ggtgctcaat 180
tcatttcaag acagcaataa ttcatatgca aggcaggaat tgcaaagact ttataggatc 240
tttcactcat ggctgcaacc agaaaagcac agcaaggatg aaattatttc tctattagtc 300
ctggagcagt ttatgattgg tggccactgc aatgacaaag ccagtgtgaa agagaaatgg 360
aaatcaagtg gcaaaaactt ggagagattc atagaagacc tgactgatga cagcataaat 420
ccacctgcct tagtccacgt ccacatgcag ggacaggaag ctctcttttc tgaggatatg 480
cccttaagag atgtcattgt tcatctcaca aaacaagtga atgcccaaac cacaagagaa 540
gcaaacatgg ggacaccctc ccagacttcc caagatactt ccttagaaac aggacaagga 600
tatgaagatg aacaagatgg ctggaacagt tcttcgaaaa ctactcgagt aaatgaaaat 660
attactaatc aaggcaatca aatagtttcc ctaatcatca tccaggaaga gaacggtcct 720
aggcctgaag agggaggtgt ttcttctgac aacccataca actcaaaaag agcagagcta 780
gtcactgcta gatctcagga agggtccata aatggaatca ctttccaagg tgtccctatg 840
gtgatgggag cagggtgtat ctctcaacca gagcagtcct cccctgagtc tgcccttacc 900
caccagagca atgagggaaa ttccacatgt gaggtacatc agaaaggatc ccatggagtc 960
caaaaatcat acaaatgtga agaatgcccc aaggtcttta agtatctctg tcacttatta 1020
gctcaccaga gaagacacag gaatgagagg ccatttgttt gtcccgagtg tcaaaaaggc 1080
ttcttccaga tatcagacct acgggtgcat cagataattc acacaggaaa gaagcctttc 1140
acatgcagca tgtgtaaaaa gtccttcagc cacaaaacca acctgcggtc tcatgagaga 1200
atccacacag gagaaaagcc ttatacatgt cccttttgta agacaagcta ccgccagtca 1260
tccacatacc accgccatat gaggactcat gagaaaatta ccctgccaag tgttccctcc 1320
acaccagaag cttccgtcga catggcagaa caaagcgaca aggatgtgaa gtactacact 1380
ctggaggaga ttcagaagca caaagacagc aagagcacct gggtgatcct acatcataag 1440
gtgtacgatc tgaccaagtt tctcgaagag catcctggtg gggaagaagt cctgggcgag 1500
caagctgggg gtgatgctac tgagaacttt gaggacgtcg ggcactctac ggatgcacga 1560
gaactgtcca aaacatacat catcggggag ctccatccag atgacagatc aaagatagcc 1620
aagccttcgg aaaccctt 1638

<210> SEQ ID NO 870
<211> LENGTH: 589
<212> TYPE: PRT
<213> ORGANISM: Artificial Sequence
<220> FEATURE:
<223> OTHER INFORMATION: Amino acid Sequence of HNM563ZSB

<400> SEQUENCE: 870

-continued

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Pro Lys Lys Lys Arg Lys Leu Ala Leu Ala Val Ile
        35                  40                  45

Val Val Pro Ala Leu Ala Pro Met Ala Leu Asp Leu Arg Thr Ile Phe
    50                  55                  60

Gln Cys Glu Pro Ser Glu Asn Asn Leu Gly Ser Glu Asn Ser Ala Phe
65                  70                  75                  80

Gln Gln Ser Gln Gly Pro Ala Val Gln Arg Glu Glu Gly Ile Ser Glu
                85                  90                  95

Phe Ser Arg Met Val Leu Asn Ser Phe Gln Asp Ser Asn Asn Ser Tyr
            100                 105                 110

Ala Arg Gln Glu Leu Gln Arg Leu Tyr Arg Ile Phe His Ser Trp Leu
        115                 120                 125

Gln Pro Glu Lys His Ser Lys Asp Glu Ile Ile Ser Leu Leu Val Leu
    130                 135                 140

Glu Gln Phe Met Ile Gly Gly His Cys Asn Asp Lys Ala Ser Val Lys
145                 150                 155                 160

Glu Lys Trp Lys Ser Ser Gly Lys Asn Leu Glu Arg Phe Ile Glu Asp
                165                 170                 175

Leu Thr Asp Asp Ser Ile Asn Pro Pro Ala Leu Val His Val His Met
            180                 185                 190

Gln Gly Gln Glu Ala Leu Phe Ser Glu Asp Met Pro Leu Arg Asp Val
        195                 200                 205

Ile Val His Leu Thr Lys Gln Val Asn Ala Gln Thr Thr Arg Glu Ala
    210                 215                 220

Asn Met Gly Thr Pro Ser Gln Thr Ser Gln Asp Thr Ser Leu Glu Thr
225                 230                 235                 240

Gly Gln Gly Tyr Glu Asp Glu Gln Asp Gly Trp Asn Ser Ser Ser Lys
                245                 250                 255

Thr Thr Arg Val Asn Glu Asn Ile Thr Asn Gln Gly Asn Gln Ile Val
            260                 265                 270

Ser Leu Ile Ile Ile Gln Glu Glu Asn Gly Pro Arg Pro Glu Glu Gly
        275                 280                 285

Gly Val Ser Ser Asp Asn Pro Tyr Asn Ser Lys Arg Ala Glu Leu Val
    290                 295                 300

Thr Ala Arg Ser Gln Glu Gly Ser Ile Asn Gly Ile Thr Phe Gln Gly
305                 310                 315                 320

Val Pro Met Val Met Gly Ala Gly Cys Ile Ser Gln Pro Glu Gln Ser
                325                 330                 335

Ser Pro Glu Ser Ala Leu Thr His Gln Ser Asn Glu Gly Asn Ser Thr
            340                 345                 350

Cys Glu Val His Gln Lys Gly Ser His Gly Val Gln Lys Ser Tyr Lys
        355                 360                 365

Cys Glu Glu Cys Pro Lys Val Phe Lys Tyr Leu Cys His Leu Leu Ala
    370                 375                 380

His Gln Arg Arg His Arg Asn Glu Arg Pro Phe Val Cys Pro Glu Cys
385                 390                 395                 400

Gln Lys Gly Phe Phe Gln Ile Ser Asp Leu Arg Val His Gln Ile Ile
                405                 410                 415

His Thr Gly Lys Lys Pro Phe Thr Cys Ser Met Cys Lys Lys Ser Phe
```

-continued

```
            420                 425                 430

Ser His Lys Thr Asn Leu Arg Ser His Glu Arg Ile His Thr Gly Glu
        435                 440                 445

Lys Pro Tyr Thr Cys Pro Phe Cys Lys Thr Ser Tyr Arg Gln Ser Ser
    450                 455                 460

Thr Tyr His Arg His Met Arg Thr His Glu Lys Ile Thr Leu Pro Ser
465                 470                 475                 480

Val Pro Ser Thr Pro Glu Ala Ser Val Asp Met Ala Glu Gln Ser Asp
                485                 490                 495

Lys Asp Val Lys Tyr Tyr Thr Leu Glu Glu Ile Gln Lys His Lys Asp
            500                 505                 510

Ser Lys Ser Thr Trp Val Ile Leu His His Lys Val Tyr Asp Leu Thr
        515                 520                 525

Lys Phe Leu Glu Glu His Pro Gly Gly Glu Glu Val Leu Gly Glu Gln
    530                 535                 540

Ala Gly Gly Asp Ala Thr Glu Asn Phe Glu Asp Val Gly His Ser Thr
545                 550                 555                 560

Asp Ala Arg Glu Leu Ser Lys Thr Tyr Ile Ile Gly Glu Leu His Pro
                565                 570                 575

Asp Asp Arg Ser Lys Ile Ala Lys Pro Ser Glu Thr Leu
            580                 585
```

<210> SEQ ID NO 871
<211> LENGTH: 1767
<212> TYPE: DNA
<213> ORGANISM: Artificial Sequence
<220> FEATURE:
<223> OTHER INFORMATION: cDNA Sequence of HNM563ZSB

<400> SEQUENCE: 871

```
atgggcagca gccatcatca tcatcatcac agcagcggcc tggtgccgcg cggcagccat     60
atggctagca tgactggtgg acagcaaatg ggtcgcggat ccgaattccc caagaagaag    120
aggaagctgg cgctggcggt gattgtggtg ccggcgctgg cgccgatggc tttagatcta    180
agaaccatat ttcagtgtga accatccgag aataatcttg gatcagaaaa ttcagcgttt    240
caacaaagcc aaggacctgc tgttcagaga gaagaaggga tttctgagtt ctcaagaatg    300
gtgctcaatt catttcaaga cagcaataat tcatatgcaa ggcaggaatt gcaaagactt    360
tataggatct ttcactcatg gctgcaacca gaaaagcaca gcaaggatga aattatttct    420
ctattagtcc tggagcagtt tatgattggt ggccactgca atgacaaagc cagtgtgaaa    480
gagaaatgga aatcaagtgg caaaaacttg gagagattca tagaagacct gactgatgac    540
agcataaatc cacctgcctt agtccacgtc cacatgcagg gacaggaagc tctcttttct    600
gaggatatgc ccttaagaga tgtcattgtt catctcacaa aacaagtgaa tgcccaaacc    660
acaagagaag caaacatggg gacaccctcc cagacttccc aagatacttc cttagaaaca    720
ggacaaggat atgaagatga acaagatggc tggaacagtt cttcgaaaac tactcgagta    780
aatgaaaata ttactaatca aggcaatcaa atagtttccc taatcatcat ccaggaagag    840
aacggtccta ggcctgaaga gggaggtgtt tcttctgaca acccatacaa ctcaaaaaga    900
gcagagctag tcactgctag atctcaggaa gggtccataa atggaatcac tttccaaggt    960
gtccctatgg tgatgggagc agggtgtatc tctcaaccag agcagtcctc ccctgagtct   1020
gcccttaccc accagagcaa tgagggaaat tccacatgtg aggtacatca gaaaggatcc   1080
catggagtcc aaaaatcata caaatgtgaa gaatgcccca aggtctttaa gtatctctgt   1140
```

-continued

```
cacttattag ctcaccagag aagacacagg aatgagaggc catttgtttg tcccgagtgt   1200

caaaaaggct tcttccagat atcagaccta cgggtgcatc agataattca cacaggaaag   1260

aagcctttca catgcagcat gtgtaaaaag tccttcagcc acaaaaccaa cctgcggtct   1320

catgagagaa tccacacagg agaaaagcct tatacatgtc ccttttgtaa gacaagctac   1380

cgccagtcat ccacatacca ccgccatatg aggactcatg agaaaattac cctgccaagt   1440

gttccctcca caccagaagc ttccgtcgac atggcagaac aaagcgacaa ggatgtgaag   1500

tactacactc tggaggagat tcagaagcac aaagacagca agagcacctg ggtgatccta   1560

catcataagg tgtacgatct gaccaagttt ctcgaagagc atcctggtgg ggaagaagtc   1620

ctgggcgagc aagctggggg tgatgctact gagaactttg aggacgtcgg gcactctacg   1680

gatgcacgag aactgtccaa aacatacatc atcggggagc tccatccaga tgacagatca   1740

aagatagcca agccttcgga aaccctt                                       1767


<210> SEQ ID NO 872
<211> LENGTH: 7
<212> TYPE: PRT
<213> ORGANISM: Artificial Sequence
<220> FEATURE:
<223> OTHER INFORMATION: Amino acid Sequence of NLS-2

<400> SEQUENCE: 872

Pro Lys Lys Lys Arg Lys Leu
1               5


<210> SEQ ID NO 873
<211> LENGTH: 21
<212> TYPE: DNA
<213> ORGANISM: Artificial Sequence
<220> FEATURE:
<223> OTHER INFORMATION: cDNA Sequence of NLS-2

<400> SEQUENCE: 873

cccaagaaga agaggaagct g                                                21
```

CELL-PERMEABLE REPROGRAMMING FACTOR (ICP-RF) RECOMBINANT PROTEIN AND USE THEREOF

CROSS REFERENCE TO RELATED APPLICATIONS

This application is a Bypass Continuation of International Application No. PCT/KR2016/008757 filed Aug. 9, 2016, claiming benefit of U.S. Provisional Patent Application No. 62/202,987 filed Aug. 10, 2015, the contents of all of which are incorporated herein by reference in their entirety.

TECHNICAL FIELD

The present invention relates to providing improved cell-permeability reprogramming factor (iCP-RF) recombinant protein and uses thereof. The recombinant protein improved cell-permeability and biological activity as a generation of induced pluripotent stem cells (iPSCs) from terminally differentiated somatic cells.

BACKGROUND ART

Stem cells have been emerged as ideal cell sources in cell-based therapies because they possess great ability to differentiate into various lineages and self-renewability. Embryonic stem (ES) cells, which are established from the preimplantation embryos of mouse or human, can be cultures for extended periods while maintaining their pluripotent ability to differentiate into all kind of lineages of cells in the body. Human embryonic stem cells have the potential to be used to understand the mechanisms of disease, screen the efficacy and safety of novel drugs and treat various diseases, including leukemia and Parkinson's disease and to be used as regenerative cell therapy. However, in clinical trials, the embryonic stem cells transplantation caused severe rejection reactions equivalent to organ transplant rejection. Some are ethically opposed to the use of embryonic stem cells obtained by destroying human embryos. To avoid these ethical issues and cell availability, mesenchymal stem cells (MSCs) from adult tissues were suggested as alternatives for embryonic stem cells due to their multi-lineage differentiation potential and ability of unlimited self-renewal (1). MSCs can avoid immune rejection problem since they can be easily obtained from the patients' own various types of tissues, such as bone marrow, adipose tissue and periodontal ligaments. However, MSCs have shown limited differentiation potential into connective tissues including osteogenic, chondrogenic, and adipogenic lineages. Therefore, it was not sufficient to replace embryonic stem cells.

Yamanaka et al. reported that terminally differentiated somatic cells can be reprogrammed to the induced pluripotent stem cells (iPSCs), which possess pluripotency and self-renewability by enforced expression of reprogramming factors (2 and 3). Reprogramming factors (RFs) include transcription factors that require for the maintenance of embryonic stem cells in pluripotent status, OCT4 (Octamer-binding transcription factor 4), SOX2 (Sex determining region Y-box 2) and NANOG (Homeobox protein NANOG), as well as other proteins that facilitate self-renewal and inhibit differentiation of cells, CMYC (c-Myc), KLF4 (Kruppel-like factor 4) and LIN28 (Lin-28 homolog A) (4 and 5). Additionally, ZSCAN4 (Zinc finger and SCAN domain containing 4) plays important role in telomere elongation and genome stabilization which involves in immortalized cell line establishment (6 to 8). These reprogramming factors can be treated as sets: 1) "Yamanaka factor" including OCT4, SOX2, KLF4 and CMYC, and 2) "Thomson factor" including OCT4, SOX2, NANOG and LIN28 (3).

Patient-derived iPSCs are expected to be used for autologous stem cell therapy as an alternative of ES cells without any rejection reaction and the ethical issue of using ES cells. However, the efficiency of retro- or lenti-virus-mediated introduction of reprogramming factor genes into fibroblasts showed only ~0.05% (9 and 10). In addition, it has a potential to cause mutation by the integration of vectors into the genome. Moreover, reprogramming factors that facilitate the formation of iPSCs have shown serious side effects, such as tumorigenesis by CMYC or epithelial dysplasia by enforced expression of OCT4 and KLF4. In terms of practicality, the application of iPSCs in the field of regenerative medicine requires more effective methods to avoid dysregulated RFs activity or vector-induced mutation that may occur during the introduction of reprogramming factors into the somatic cells.

These limitations have led to the development of various different methods to generate transgene free-iPSCs, including: (i) loxP flanked vectors (11), (ii) excisable transposons (12), (iii) adenovirus (13) and Sendai virus (14) vectors, and (iv) non-integrating episomal vectors (15). Adeno virus-mediated reprogramming factor integration shows 10-3 to 10-5 per cells of frequencies (16). Moreover, these methods have displayed problems such as incomplete deletion or continuous existing of exogenous genes. Although the reprogramming factor genes can be introduced into cells by using plasmid transfection, but it shows more than 100-fold lower efficiency than that of retrovirus transduction (9). Other approaches avoid DNA-based vectors to generate iPSCs, such as synthetic modified RNA (17), epigenetic regulation by chemical compounds (18) and direct uptake of RF proteins (19).

Therefore, introducing RF proteins could be considered as the only method to avoid the major obstacles with genetic damage and gene dysregulation caused by gene-based vectors and to provide more quantitatively and timely regulation of stem cell reprogramming. The initial protein-based RFs delivery-mediated by Tat protein transduction domain (PTD) that contains short basic arginine-rich region (aa 48-57) of HIV-1. Although the PTD fused-proteins can be transduced into the cells mediated by lipid raft-dependent micropinocytosis, most of Tat-fused proteins remain trapped in macropinosomes, caused by failure of proteins to escape from macropinosomes. Because of these limitations, Kim and Ding successfully reprogrammed mouse embryonic fibroblast (19) and human newborn fibroblast (20) cells to iPS cells by using poly-arginine (11R or 9R) PTD-fused reprogramming factors (OCT4, SOX2, KLF4, and CMYC), but they shows very low efficiency (0.001% to 0.006%).

REFERENCES

1. Pittenger M F, Mackay A M, Beck S C, Jaiswal R K, Douglas R, Mosca J D et al., Multilineage potential of adult human mesenchymal stem cells, Science 1999; 284(5411):143-7.
2. Yamanaka S. A fresh look at iPS cells. Cell 2009; 137(1):13-7.
3. Yu J, Vodyanik M A, Smuga-Otto K, Antosiewicz-Bourget J, Frane J L, Tian S et al., Induced pluripotent stem cell lines derived from human somatic cells, Science 2007; 318(5858):1917-20.

4. Takahashi K, Yamanaka S. Induction of pluripotent stem cells from mouse embryonic and adult fibroblast cultures by defined factors. Cell 2006; 126(4):663-76.
5. Takahashi K, Tanabe K, Ohnuki M, Narita M, Ichisaka T, Tomoda K et al., Induction of pluripotent stem cells from adult human fibroblasts by defined factors, Cell 2007; 131(5):861-72.
6. Zalzman M, Falco G, Sharova L V, Nishiyama A, Thomas M, Lee S L et al., Zscan4 regulates telomere elongation and genomic stability in E S cells, Nature 2010; 464 (7290):858-63.
7. Hirata T, Amano T, Nakatake Y, Amano M, Piao Y, Hoang H G et al., Zscan4 transiently reactivates early embryonic genes during the generation of induced pluripotent stem cells, Sci Rep 2012; 2:208.
8. Kwon Y W, Paek J S, Cho H J, Lee C S, Lee H J, Park I H et al., Role of Zscan4 in secondary murine iPSC derivation mediated by protein extracts of ESC or iPSC. Biomaterials 2015; 59:102-15.
9. Okita K, Nakagawa M, Hyenjong H, Ichisaka T, Yamanaka S., Generation of mouse induced pluripotent stem cells without viral vectors, Science 2008; 322(5903): 949-53.
10. Yamanaka S. Elite and stochastic models for induced pluripotent stem cell generation. Nature 2009; 460(7251): 49-52.
11. Soldner F, Hockemeyer D, Beard C, Gao Q, Bell G W, Cook E G et al., Parkinson's disease patient-derived induced pluripotent stem cells free of viral reprogramming factors. Cell 2009; 136(5):964-77.
12. Woltjen K, Michael I P, Mohseni P, Desai R, Mileikovsky M, Hamalainen R et al., piggyBac transposition reprograms fibroblasts to induced pluripotent stem cells, Nature 2009; 458(7239):766-70.
13. Stadtfeld M, Nagaya M, Utikal J, Weir G, Hochedlinger K., Induced pluripotent stem cells generated without viral integration, Science 2008; 322(5903):945-9.
14. Ban H, Nishishita N, Fusaki N, Tabata T, Saeki K, Shikamura M et al., Efficient generation of transgene-free human induced pluripotent stem cells (iPSCs) by temperature-sensitive Sendai virus vectors, Proc Natl Acad Sci USA 2011; 108(34):14234-9.
15. Yu J, Hu K, Smuga-Otto K, Tian S, Stewart R, Slukvin, I I et al., Human induced pluripotent stem cells free of vector and transgene sequences, Science 2009; 324 (5928):797-801.
16. Harui A, Suzuki S, Kochanek S, Mitani K., Frequency and stability of chromosomal integration of adenovirus vectors, J Virol 1999; 73(7):6141-6.
17. Warren L, Manos P D, Ahfeldt T, Loh Y H, Li H, Lau F et al., Highly efficient reprogramming to pluripotency and directed differentiation of human cells with synthetic modified mRNA, Cell Stem Cell 2010; 7(5):618-30.
18. Maherali N, Hochedlinger K., Guidelines and techniques for the generation of induced pluripotent stem cells, Cell Stem Cell 2008; 3(6):595-605.
19. Zhou H, Wu S, Joo J Y, Zhu S, Han D W, Lin T et al., Generation of induced pluripotent stem cells using recombinant proteins, Cell Stem Cell 2009; 4(5):381-4.
20. Kim D, Kim C H, Moon J I, Chung Y G, Chang M Y, Han B S et al., Generation of human induced pluripotent stem cells by direct delivery of reprogramming proteins, Cell Stem Cell 2009; 4(6):472-6.
21. Lim J, Kim J, Kang J, Jo D, Partial somatic to stem cell transformations induced by cell-permeable reprogramming factors, Sci Rep 2014; 4:4361.
22. Fischer P M, Cellular uptake mechanisms and potential therapeutic utility of peptidic cell delivery vectors: progress 2001-2006, Med Res Rev 2007; 27(6):755-95.
23. Wadia J S, Stan R V, Dowdy S F, Transducible TAT-H A fusogenic peptide enhances escape of TAT-fusion proteins after lipid raft macropinocytosis, Nat Med 2004; 10(3): 310-5.
24. Lim J, Duong T, Lee G, Seong B L, El-Rifai W, Ruley H E et al., The effect of intracellular protein delivery on the anti-tumor activity of recombinant human endostatin, Biomaterials 2013; 34(26):6261-71.
25. Veach R A, Liu D, Yao S, Chen Y, Liu X Y, Downs S et al., Receptor/transporter-independent targeting of functional peptides across the plasma membrane, J Biol Chem 2004; 279(12): 11425-31.
26. Lim J, Kim J, Duong T, Lee G, Kim J, Yoon J, et al., Antitumor activity of cell-permeable p18(INK4c) with enhanced membrane and tissue penetration, Molecular therapy: the journal of the American Society of Gene Therapy 2012; 20(8):1540-9.
27. Ramamoorthy A, Kandasamy S K, Lee D K, Kidambi S, Larson R G, Structure, topology, and tilt of cell-signaling peptides containing nuclear localization sequences in membrane bilayers determined by solid-state NMR and molecular dynamics simulation studies. Biochemistry 2007; 46(4):965-75.
28. Fischer P M., Cellular uptake mechanisms and potential therapeutic utility of peptidic cell delivery vectors: progress 2001-2006, Med Res Rev. 2007; 27:755-95.
29. Heitz F, Morris M C, Divita G., Twenty years of cell-penetrating peptides: from molecular mechanisms to therapeutics, Br J Pharmacol. 2009; 157:195-206.
30. Lapenna S, Giordano A., Cell cycle kinases as therapeutic targets for cancer, Nat Rev Drug Discov. 2009; 8:547-66.
31. Lim J, Kim J, Duong T, Lee G, Kim J, Yoon J. et al., Antitumor activity of cell-permeable p18(INK4c) with enhanced membrane and tissue penetration, Mol Ther. 2012; 20:1540-9.
32. Jo D, Liu D, Yao S, Collins R D, Hawiger J., Intracellular protein therapy with SOCS3 inhibits inflammation and apoptosis, Nat Med. 2005; 11:892-8.
33. Jo D, Nashabi A, Doxsee C, Lin Q, Unutmaz D, Chen J. et al., Epigenetic regulation of gene structure and function with a cell-permeable Cre recombinase, Nat Biotechnol. 2001; 19:929-33.
34. Liu D, Li C, Chen Y, Burnett C, Liu X Y, Downs S. et al., Nuclear import of proinflammatory transcription factors is required for massive liver apoptosis induced by bacterial lipopolysaccharide, J Biol Chem. 2004; 279: 48434-42.
35. Liu D, Liu X Y, Robinson D, Burnett C, Jackson C, Seele L. et al., Suppression of Staphylococcal Enterotoxin B-induced Toxicity by a Nuclear Import Inhibitor, J Biol Chem. 2004; 279:19239-46.
36. Liu D, Zienkicwicz J, DiGiandomenico A, Hawiger J., Suppression of acute lung inflammation by intracellular peptide delivery of a nuclear import inhibitor, Mol Ther. 2009; 17:796-802.
37. Moore D J, Zienkiewicz J, Kendall P L, Liu D, Liu X, Veach R A. et al., In vivo islet protection by a nuclear import inhibitor in a mouse model of type 1 diabetes, PLoS One. 2010; 5:e13235.
38. Lim J, Jang G, Kang S, Lee G, Nga do T T, Phuong do T L. et al., Cell-permeable NM23 blocks the maintenance and progression of established pulmonary metastasis, Cancer Res. 2011; 71:7216-25.

39. Duong T, Kim J, Ruley H E, Jo D., Cell-permeable parkin proteins suppress Parkinson disease-associated phenotypes in cultured cells and animals, PLoS One. 2014; 9:e102517.
40. Lim J, Duong T, Do N, Do P, Kim J, Kim H. et al., Antitumor activity of cell-permeable RUNX3 protein in gastric cancer cells. Clin Cancer Res. 2013; 19:680-90.
41. Lim J, Duong T, Lee G, Seong B L, El-Rifai W, Ruley H E et al. The effect of intracellular protein delivery on the anti-tumor activity of recombinant human endostatin, Biomaterials. 2013; 34:6261-71.
42. Lim J, Kim J, Kang J, Jo D., Partial somatic to stem cell transformations induced by cell-permeable reprogramming factors, Scientific Reports. 2014; 4:4361.

DISCLOSURE

Technical Problem

A macromolecule, such as reprogramming factors (RFs), cannot be translocated across the cell membrane; furthermore, it cannot be transported into the nucleus of the cell. Therefore, there was a need to develop macromolecule intracellular transduction technology (MITT), which enables the translocation of macromolecules into the cell/tissues.

In the previous studies, MITT-based hydrophobic CPPs named membrane translocating sequence (MTS) and membrane translocating motif (MTM), derived from the hydrophobic signal peptide of fibroblast growth factor 4 (FGF4) have been reported and used to deliver biologically active peptides and proteins, such as reprogramming factors, systemically in animals.

However, they could not effectively deliver reprogramming factor (RF) protein in vitro were also insufficient due to protein aggregation, low solubility/yield and poor cell/tissue-permeability.

Technical Solution

To overcome the limitations and improve CPPs that provide cell-permeability of macromolecules in vitro and in vivo, theoretical critical factors (CFs) to improve the intracellular delivery potential of the CPPs are identified and verified according to one embodiment of the present invention. Based on the CFs determined, hydrophobic CPP sequences are newly created, quantitatively evaluated for cell-permeability and mutually compared to reference CPP sequences in their intracellular delivery potential in live cells. One embodiment of the present invention, newly developed hydrophobic CPPs are presented. The novel peptide sequences termed 'advanced macromolecule transduction domains' (aMTDs) could systematically deliver the aMTD-fused recombinant proteins to live cells and animal tissues.

One aspect of the present invention relates to baseline platform that could be applied to unlimited number of designs, having cell-permeability applicable for biomedical sciences, preclinical and clinical studies that facilitate the traverse of biologically active macromolecules, including proteins, peptides, nucleic acids, chemicals and so on, across the plasma membrane in cells.

The present inventors analyzed, identified, and determined these critical factors that facilitate the cell permeable ability of aMTD sequences. These aMTD sequences are artificially assembled based on the critical factors (CFs) determined from in-depth analysis of previously published hydrophobic CPPs.

One aspect of the present invention relates to novel advanced macromolecule transduction domain (aMTD) sequences.

The aMTD sequences of one aspect of the present invention are the first artificially developed cell permeable polypeptides capable of mediating the transduction of biologically active macromolecules—including peptides, polypeptides, protein domains, or full-length proteins—through the plasma membrane of cells.

Another aspect of the present invention relates to the method of genetically engineering a biologically active molecules having cell-permeability by fusing the aMTD sequences to the biologically active cargo molecules.

One aspect of the present invention also relates to its therapeutic application for the delivery of biologically active molecules to cells, involving cell-permeable recombinant proteins, where aMTDs are attached to the biologically active cargo molecules.

Another aspect of the present invention pertains to a method in which biologically active macromolecules are able to enter into live cells, as constructs of cell-permeable recombinant proteins comprised of aMTD sequences fused to biologically active macromolecules.

Other aspects of the present invention relate to an efficient use of aMTD sequences for molecule delivery, drug delivery, protein therapy, intracellular protein therapy, protein replacement therapy, peptide therapy, gene delivery and so on.

Another aspect of the present invention relates to 240 new hydrophobic CPP sequences—aMTDs, determination of the aMTD-mediated intracellular delivery activity of the recombinant proteins, and comparison of the enhanced protein uptake by live cells at levels greater than or equal to the FGF4-derived MTS/MTM and HRSS-derived MTD sequences. These strengths of newly invented aMTDs could address the setbacks on reference hydrophobic CPPs for clinical development and application.

One aspect of the present invention pertains to advanced macromolecule transduction domain (aMTD) sequences that transduce biologically active macromolecules into the plasma membrane.

Another aspect of the present invention directs to aMTD consisting of amino acid sequences having the following characteristics:

a. Amino acid length: 9 to 13
b. Bending potential: Proline (P) positioned in the middle (5', 6', 7' or 8') and at the end (12') of the sequence.
c. Rigidity/Flexibility: Instability Index (II): 40 to 60
d. Structural Feature: Aliphatic Index (AI): 180 to 220
e. Hydropathy: GRAVY: 2.1 to 2.6
f. Amino acid composition: All of composed amino acids are hydrophobic and aliphatic amino acids (A, V, L, I and P)

According to one embodiment, the amino acid sequences have the general formula composed of 12 amino acid sequences as described below.

[General formula]

X1-X2-X3-X4-U5-U6-U7-U8-X9-X10-X11-P wherein (P) at the end of sequence (12') is proline, one of U5, U6, U7, and U8 is proline, X(s) and U(s) which is not proline are A, V, L and/or I.

According to one embodiment, the amino acid sequences having the general formula are selected from the group consisting of SEQ ID NO: 1 to SEQ ID NO: 240.

According to one embodiment, the secondary structure of the aMTD is α-Helix.

One aspect of the present invention further provides isolated polynucleotides that encode aMTD sequences described above.

According to one embodiment, the isolated polynucleotides are selected from the group consisting of SEQ ID NO: 241 to SEQ ID NO: 480.

Another aspect of the present invention further provides a method of identifying critical factors of aMTDs. The 6 methods comprise selecting superior hydrophobic CPPs from previously published reference hydrophobic CPPs; analyzing physiological and chemical characteristics of the selected hydrophobic CPPs; identifying features that are in association with cell-permeability out of these physiological and chemical characteristics; categorizing previously published reference hydrophobic CPPs into at least 2 groups and determining unique features by in-depth analysis of each groups of CPPs according to their cell-permeability and relative characteristics; configuring critical factors identified through analyzing the determined unique features; confirming the critical factors is valid through experimental studies; and determining critical factors that are based on the confirmed experimental studies.

According to one embodiment, the identified unique features are amino acid length, molecular weight, pI value, bending potential, rigidity, flexibility, structural feature, hydropathy, residue structure, amino acid composition and secondary structure.

According to one embodiment, the determined six critical factors consist of the following characteristics:

a. Amino Acid Length: 9 to 13 b. Bending Potential: Proline (P) positioned in the middle (i.e., U5, U6, U7, or U8) and at the end of the sequence.

c. Rigidity/Flexibility: Instability Index (II): 40 to 60 d. Structural Feature: Aliphatic Index (AI): 180 to 220 e. Hydropathy: GRAVY: 2.1 to 2.6.

f. Amino Acid Composition: All of composed amino acids are hydrophobic and aliphatic amino acids (A, V, L, I and P)

G. Secondary structure: α-Helix

The present disclosure further provides a method of developing the aMTD sequences.

The method comprises designing a platform of aMTDs having the below general formula described below;

[General formula]

X1-X2-X3-X4-U5-U6-U7-U8-X9-X10-X11-P wherein (P) at the end of sequence (12') is proline, one of U sites is proline, X(s) and U(s) which is not proline are A, V, L and/or I; and confirming whether a designed amino acid sequence satisfy six critical factors as follows:

a. Amino Acid Length: 9 to 13 b. Bending Potential: Proline (P) positioned in the middle (i.e., U5, U6, U7, or U8) and at the end of the sequence.

c. Rigidity/Flexibility: Instability Index (II): 40 to 60 d. Structural Feature: Aliphatic Index (AL): 180 to 220 e. Hydropathy: GRAVY: 2.1 to 2.6.

f. Amino Acid Composition: All of composed amino acids are hydrophobic and aliphatic amino acids (A, V, L, I and P)

According to one embodiment, the six critical factors obtained the method of identifying unique features of aMTDs consist of the following factors:

a. Amino Acid Sequence: 12 b. Bending Potential: Proline (P) is positioned in the middle (i.e., U5, U6, U7, or U8) and at the end (12') of the sequence.

c. Rigidity/Flexibility: Instability Index (II): 41.3 to 57.3 d. Structural Feature: Aliphatic Index (AI): 187.5 to 220 e. Hydropathy: GRAVY: 2.2 to 2.6.

f. Amino Acid Composition: All of composed amino acids are hydrophobic and aliphatic amino acids (A, V, L, I and P)

According to one embodiment, the secondary structure of the aMTD is α-Helix.

According to one embodiment, the method further comprises developing the expression vectors of aMTD sequences fused to cargo proteins; selecting proper bacteria strain for inducible expression; purifying and preparing of aMTD-fused to cargo proteins in soluble form; and confirming their cell-permeability.

One aspect of present invention further provides isolated recombinant proteins with a cell-permeability. The isolated recombinant protein comprises an advanced macromolecule transduction domain (aMTD) sequences having amino acid sequences selected from the group consisting of SEQ ID NO: 1 to SEQ ID NO: 240; and a biologically active molecule.

According to one embodiment, the biologically active molecules are any one selected from the group consisting of growth factors, enzymes, transcription factors, toxins, antigenic peptides, antibodies and antibody fragments.

According to one embodiment, the biologically active molecules are any one selected from the group consisting of enzymes, hormones, carriers, immunoglobulins, antibodies, structural proteins, motor functioning peptides, receptors, signaling peptides, storing peptides, membrane peptides, transmembrane peptides, internal peptides, external peptides, secreting peptides, virus peptides, native peptides, glycated proteins, fragmented proteins, disulfide bonded proteins, recombinant proteins, chemically modified proteins and prions.

According to one embodiment, the biologically active molecules are any one selected from the group consisting of nucleic acids, coding nucleic acid sequences, mRNAs, antisense RNA molecules, carbohydrates, lipids and glycolipids.

According to one embodiment, the biologically active molecules are at least one selected from the group consisting of biotherapeutic chemicals and toxic chemicals.

One aspect of the present invention further provides a method of genetically or epigenetically engineering and/or modifying biologically active molecules to have a cell-permeability. The method comprises fusing aMTDs to biologically active molecules under the optimized and effective conditions to generate biologically active molecules that can be cell-permeable, wherein the aMTD consists of any one of amino acid sequences selected from the group consisting of SEQ ID NO: 1 to SEQ ID NO: 240.

One aspect of the present invention also pertains to cell-permeable recombinant protein for generation of induced pluripotent stem cells (iPSCs) based on advanced macromolecule transduction domain (aMTD) sequences capable of mediating the transduction of biologically active macromolecules into live cells.

Other aspect of the present invention relates to cell-permeable protein-based generation of induced pluripotent stem cells (iPSCs) based on an efficient use of aMTD sequences for peptide delivery, protein delivery and intracellular protein delivery.

One aspect of the present invention provides an iCP-RF (improved Cell-Permeable Reprogramming Factor) recombinant protein, which comprises a RF protein selected from the group consisting of OCT4, SOX2, CMYC, KLF4, NANOG, LIN28 and ZSCAN4, and an advanced macromolecule transduction domain (aMTD) being composed of 9 to 13 amino acid sequences and having improved cell or tissue permeability, wherein the aMTD is fused to one end or both ends of the RF protein and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence; and (c) having an instability index of 40 to 60; an aliphatic index of 180 to 220; and a grand average of hydropathy (GRAVY) of 2.1 to 2.6, as measured by Protparam.

According to one embodiment, one or more solubilization domain (SD)(s) are further fused to the end(s) of one or more of the RF protein and the aMTD.

According to another embodiment, the aMTD may have α-Helix structure. According to still another embodiment, the aMTD may be composed of 12 amino acid sequences and represented by the following general formula:

[General formula]

X1-X2-X3-X4-U5-U6-U7-U8-X9-X10-X11-P wherein X(s) refers to Alanine (A), Valine (V), Leucine (L) or Isoleucine (I); one of U refers to proline (P) and the other U(s) refer to A, V, L or I; and P refers to proline.

Another aspect of the present invention provides an iCP-RF recombinant protein which is represented by any one of the following structural formula:

A-B—C and A-C—B—C wherein A is an advanced macromolecule transduction domain (aMTD) having improved cell or tissue permeability, B is a RF protein selected from the group consisting of OCT4, SOX2, CMYC, KLF4, NANOG, LIN28 and ZSCAN4, and C is a solubilization domain (SD); and the aMTD is composed of 9 to 13 amino acid sequences and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence;

(c) having an instability index of 40 to 60; an aliphatic index of 180 to 220; and a grand average of hydropathy (GRAVY) of 2.1 to 2.6, as measured by Protparam; and (d) having α-Helix structure.

According to one embodiment of the present invention, the SD(s) are one or more selected from the group consisting of SDA, SDB, SDB', SDC, SDD, SDE and SDF.

According to one embodiment of the present invention, the RF protein may have an amino acid sequence of SEQ ID NOs: 816 to 822.

According to another embodiment of the present invention, the RF protein may be encoded by a polynucleotide sequence of SEQ ID NOs: 823 to 829.

According to still another embodiment of the present invention, the RF protein may further include a ligand selectively binding to a receptor of a cell, a tissue, or an organ.

According to still another embodiment of the present invention, the aMTD may have an amino acid sequence selected from the group consisting of SEQ ID NOs: 1 to 240.

According to still another embodiment of the present invention, the aMTD may be encoded by a polynucleotide sequence selected from the group consisting of SEQ ID NOs: 241 to 480.

According to still another embodiment of the present invention, the SD(s), independently, may have an amino acid sequence selected from the group consisting of SEQ ID NOs: 798 to 804.

According to still another embodiment of the present invention, the SD(s), independently, may be encoded by a polynucleotide sequence selected from the group consisting of SEQ ID NOs: 805 to 811.

According to still another embodiment of the present invention, the RF recombinant protein may have one or more selected from a histidine-tag affinity domain and a nuclear localization sequence (NLS) additionally fused to one end thereof.

According to still another embodiment of the present invention, the histidine-tag affinity domain may have an amino acid sequence of SEQ ID NO: 812, and the NLS may have an amino acid sequence selected from the group consisting of SEQ ID NOs: 814 and 872.

According to still another embodiment of the present invention, the histidine-tag affinity domain may be encoded by a polynucleotide sequence of SEQ ID NO: 813, and the NLS may be encoded by a polynucleotide sequence selected from the group consisting of SEQ ID NOs: 815 and 873.

According to still another embodiment of the present invention, the fusion may be formed via a peptide bond or a chemical bond.

According to still another embodiment of the present invention, the iCP-RF recombinant protein may be used for generation of induced pluripotent stem cells (iPSCs) from somatic cells.

Still another aspect of the present invention provides a polynucleotide sequence encoding the iCP-RF recombinant protein.

According to one embodiment of the present invention, the polynucleotide sequence may be selected from the group consisting of SEQ ID NOs: 831, 837, 843, 849, 855, 861 and 867.

According to another embodiment of the present invention, the polynucleotide sequence may be selected from the group consisting of SEQ ID NOs: 833, 839, 845, 851, 857, 863 and 869.

Still another aspect of the present invention provides a recombinant expression vector including the polynucleotide sequence.

Still another aspect of the present invention provides a transformant transformed with the recombinant expression vector.

Still another aspect of the present invention provides a preparing method of the iCP-RF recombinant protein including preparing the recombinant expression vector; preparing the transformant using the recombinant expression vector; culturing the transformant; and recovering the recombinant protein expressed by the culturing.

Still another aspect of the present invention provides a composition including the iCP-RF recombinant protein as an active ingredient.

According to one embodiment of the present invention, the composition generates induced pluripotent stem cells (iPSCs) from somatic cells.

Still another aspect of the present invention provides use of the iCP-RF recombinant protein for generating iPSCs from somatic cells.

Still another aspect of the present invention provides a method of generating iPSCs from somatic cells, including preparing somatic cells; and treating the somatic cells with an effective amount of the iCP-RF recombinant protein.

In one embodiment of the present invention, the somatic cells may be derived from a mammal.

Unless defined otherwise, all terms used herein have the same meaning as commonly understood by one of ordinary skill in the art to which the present invention belongs. Although a certain method and a material is described herein, it should not be construed as being limited thereto, any similar or equivalent method and material to those may also be used in the practice or testing of the present invention. All publications mentioned herein are incorporated herein by reference in their entirety to disclose and describe the methods and/or materials in connection with which the publications are cited. It must be noted that as used herein and in the appended claims, the singular forms "a," "an," and "the" include plural referents unless the context clearly dictates otherwise.

A "peptide" refers to a chain-type polymer formed by amino acid residues which are linked to each other via peptide bonds, and used interchangeably with "polypeptide." Further, a "polypeptide" includes a peptide and a protein.

Further, the term "peptide" includes amino acid sequences that are conservative variations of those peptides specifically exemplified herein. The term "conservative variation," as used herein, denotes the replacement of an amino acid residue by another, biologically similar residue. Examples of conservative variations include substitution of one hydrophobic residue, such as isoleucine, valine, leucine, alanine, cysteine, glycine, phenylalanine, proline, tryptophan, tyrosine, norleucine, or methionine for another, or substitution of one polar residue for another, for example, substitution of arginine for lysine, glutamic acid for aspartic acid, or glutamine for asparagine, and the like. Neutral hydrophilic amino acids which may be substituted for one another include asparagine, glutamine, serine, and threonine.

The term "conservative variation" also includes use of a substituted amino acid in place of an unsubstituted parent amino acid, provided that antibodies raised to the substituted polypeptide also immunoreacts with the unsubstituted polypeptide. Such conservative substitutions are within the definition of the classes of the peptides according to one embodiment of the present invention.

A person having ordinary skill in the art may make similar substitutions to obtain peptides having higher cell permeability and a broader host range. For example, one embodiment of the present invention provides peptides corresponding to amino acid sequences (e.g. SEQ ID NOs: 1 to 240) provided herein, as well as analogues, homologs, isomers, derivatives, amidated variations, and conservative variations thereof, as long as the cell permeability of the peptide remains.

Minor modifications to primary amino acid sequence of the peptides according to one embodiment of the present invention may result in peptides which have substantially equivalent or enhanced cell permeability, as compared to the specific peptides described herein. Such modifications may be deliberate, as by site-directed mutagenesis, or may be spontaneous.

All peptides may be synthesized using L-amino acids, but D forms of all of the peptides may be synthetically produced. In addition, C-terminal derivatives, such as C-terminal methyl esters and C-terminal amidates, may be produced in order to increase the cell permeability of the peptide according to one embodiment of the present invention.

All of the peptides produced by these modifications are included herein, as long as in the case of amidated versions of the peptide, the cell permeability of the original peptide is altered or enhanced such that the amidated peptide is therapeutically useful. It is envisioned that such modifications are useful for altering or enhancing cell permeability of a particular peptide.

Furthermore, deletion of one or more amino acids may also result in a modification to the structure of the resultant molecule without any significant change in its cell permeability. This may lead to the development of a smaller active molecule which may also have utility. For example, amino- or carboxyl-terminal amino acids which may not be required for the cell permeability of a particular peptide may be removed.

The term "gene" refers to an arbitrary nucleic acid sequence or a part thereof having a functional role in protein coding or transcription, or regulation of other gene expression. The gene may be composed of all nucleic acids encoding a functional protein or a part of the nucleic acid encoding or expressing the protein. The nucleic acid sequence may include a gene mutation in exon, intron, initiation or termination region, promoter sequence, other regulatory sequence, or a unique sequence adjacent to the gene.

The term "primer" refers to an oligonucleotide sequence that hybridizes to a complementary RNA or DNA target polynucleotide and serves as the starting points for the stepwise synthesis of a polynucleotide from mononucleotides by the action of a nucleotidyltransferase as occurs, for example, in a polymerase chain reaction.

The term "coding region" or "coding sequence" refers to a nucleic acid sequence, a complement thereof, or a part thereof which encodes a particular gene product or a fragment thereof for which expression is desired, according to the normal base pairing and codon usage relationships. Coding sequences include exons in genomic DNA or immature primary RNA transcripts, which are joined together by the cellular biochemical machinery to provide a mature mRNA. The anti-sense strand is the complement of the nucleic acid, and the coding sequence may be deduced therefrom.

One aspect of the present invention provides an iCP-RF recombinant protein, which comprises a RF protein selected from the group consisting of OCT4, SOX2, CMYC, KLF4, NANOG, LIN28 and ZSCAN4, and an advanced macromolecule transduction domain (aMTD) being composed of 9 to 13 amino acid sequences, preferably 10 to 12 amino acid sequences, and having improved cell or tissue permeability, wherein the aMTD is fused to one end or both ends of the RF protein and has the following features of:

(a) being preferably composed of 3 or more amino acids selected from the group consisting of Ala, Val, Ile, Leu, and Pro;

(b) having proline as amino acid sequences corresponding to any one or more of positions 5 to 8, and 12 of its amino acids, and preferably one or more of positions 5 to 8 and position 12 of its amino acid sequence; and (c) having an instability index of preferably 40 to 60 and more preferably 41-58; an aliphatic index of preferably 180 to 220 and more preferably 185 to 225; and a grand average of hydropathy (GRAVY) of preferably 2.1 to 2.6 and more preferably 2.2 to 2.6 as measured by Protparam (see web-.expasy.org).

To determine the GRAVY value of the protein analysed easily, the ProtParam (Gasteiger E. et al., Protein Identification and Analysis Tools on the ExPASy Server, J M Walker ed., The Proteomics Protocols Handbook, Humana Press, 2005, 571-607) program is used. ProtParam program (web.expasy.org) is a computational formula which provides various physicochemical properties of the proteins studied by analysing their sequence; when the said amino-acid sequence is entered, the program calculates the GRAVY value of the protein whose degree of hydrophobicity is to be measured.

According to one embodiment, one or more solubilization domain (SD)(s) are further fused to one or more of the RF protein and the aMTD, preferably one end or both ends of the RF protein, and more preferably the C-terminus or both the C-terminus and the N-terminus of the RF protein.

According to another embodiment, the aMTD may have α-Helix structure.

According to still another embodiment, the aMTD may be preferably composed of 12 amino acid sequences and represented by the following general formula:

[General formula]

X1-X2-X3-X4-U5-U6-U7-U8-X9-X10-X11-P wherein X(s) refers to Alanine (A), Valine (V), Leucine (L) or Isoleucine (I); one of U refers to proline (P) and the other U(s) refer to A, V, L or I; and P refers to proline.

Still another aspect of the present invention provides an iCP-RF recombinant protein which is represented by any one of structural formula A-B—C and/or A-C—B—C, and preferably by A-B—C for iCP-OCT4, iCP-CMYC, iCP-NANOG, iCP-LIN28 or iCP-ZSCAN4 recombinant protein and by A-C—B—C for iCP-SOX2, iCP-KLF4 recombinant protein: wherein A is an advanced macromolecule transduction domain (aMTD) having improved cell or tissue permeability, B is a RF protein selected from the group consisting of OCT4, SOX2, CMYC, KLF4, NANOG, LIN28 and ZSCAN4, and C is a solubilization domain (SD); and the aMTD is composed of 9 to 13, preferably 10 to 12 amino acid sequences and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence, and preferably, one or more of positions 5 to 8 and position 12 of its amino acid sequence;

(c) having an instability index of preferably 40 to 60 and more preferably 41 to 58; an aliphatic index of preferably 180 to 220 and more preferably 185 to 225; and a grand average of hydropathy (GRAVY) of preferably 2.1 to 2.6 and more preferably 2.2 to 2.6, as measured by Protparam (see web.expasy.org); and (d) preferably having α-Helix structure.

Preferably, the iCP-RF recombinant proteins may be iCP-OCT4, iCP-SOX2, iCP-KLF4, iCP-CMYC, iCP-NANOG, iCP-LIN28 or iCP-ZSCAN4.

In one embodiment of the present invention, the SD(s) may has one or more selected from the group consisting of SDA, SDB, SDB', SDC, SDD, SDE and SDF, and preferably one to four selected therefrom. When the SD(s) may be two or more, they may be the same as or different from each other.

In one embodiment of the present invention, the RF protein may have an amino acid sequence selected from the group consisting of SEQ ID NOs: 816 to 822.

In another embodiment of the present invention, the RF protein may be encoded by a polynucleotide sequence selected from the group consisting of SEQ ID NOs: 823 to 829.

When the iCP-RF recombinant protein is intended to be delivered to a particular cell, tissue, or organ, the RF protein may form a fusion product, together with an extracellular domain of a ligand capable of selectively binding to a receptor which is specifically expressed on the particular cell, tissue, or organ, or monoclonal antibody (mAb) capable of specifically binding to the receptor or the ligand and a modified form thereof.

The binding of the peptide and a biologically active substance may be formed either by indirect linkage by a cloning technique using an expression vector at a nucleotide level or by direct linkage via chemical or physical covalent or non-covalent bond of the peptide and the biologically active substance.

In still another embodiment of the present invention, the RF protein may preferably further include a ligand selectively binding to a receptor of a cell, a tissue, or an organ.

In one embodiment of the present invention, the aMTD may have an amino acid sequence selected from the group consisting of SEQ ID NOs: 1 to 240. The aMTD may be preferably $aMTD_{161}$ of SEQ ID NO: 39, $aMTD_{165}$ of SEQ ID NO: 43, $aMTD_{363}$ of SEQ ID NO: 84, $aMTD_{405}$ of SEQ ID NO: 96, $aMTD_{563}$ of SEQ ID NO: 131, $aMTD_{889}$ of SEQ ID NO: 223, $aMTD_{895}$ of SEQ ID NO: 226 or $aMTD_{904}$ of SEQ ID NO: 233, and more preferably $aMTD_{161}$ of SEQ ID NO: 39 or $aMTD_{563}$ of SEQ ID NO: 131.

In still another embodiment of the present invention, the aMTD may be encoded by a polynucleotide sequence selected from the group consisting of SEQ ID NOs: 241 to 480. The aMTD may be preferably $aMTD_{161}$ encoded by a polynucleotide sequence of SEQ ID NO: 279, $aMTD_{165}$ encoded by a polynucleotide sequence of SEQ ID NO: 283, $aMTD_{363}$ encoded by a polynucleotide sequence of SEQ ID NO: 324, $aMTD_{405}$ encoded by a polynucleotide sequence of SEQ ID NO: 336, $aMTD_{563}$ encoded by a polynucleotide sequence of SEQ ID NO: 371, $aMTD_{889}$ encoded by a polynucleotide sequence of SEQ ID NO: 463, $aMTD_{895}$ encoded by a polynucleotide sequence of SEQ ID NO: 466 or $aMTD_{904}$ encoded by a polynucleotide sequence of SEQ ID NO: 473, and more preferably preferably $aMTD_{161}$ encoded by a polynucleotide sequence of SEQ ID NO: 279 or $aMTD_{563}$ encoded by a polynucleotide sequence of SEQ ID NO: 371.

In still another embodiment of the present invention, the SD(s) may have an amino acid sequence independently selected from the group consisting of SEQ ID NOs: 798 to 804. The SD may be preferably SDA of SEQ ID NO: 798 and/or SDB of SEQ ID NO: 799, and more preferably SDB of SEQ ID NO: 799 or both SDA of SEQ ID NO: 798 and SDB of SEQ ID NO: 799 which have superior structural stability.

In still another embodiment of the present invention, the SDs may be encoded by a polynucleotide sequence independently selected from the group consisting of SEQ ID NOs: 805 to 811. The SD may be preferably SDA encoded by a polynucleotide sequence of SEQ ID NO: 805 or SDB encoded by a polynucleotide sequence of SEQ ID NO: 806, and more preferably SDB or both SDA and SDB having superior structural stability, which is encoded by a polynucleotide sequence of SEQ ID NOs: 805 and 806.

In still another embodiment of the present invention, the iCP-RF recombinant protein may be preferably selected from the group consisting of:

1) a recombinant protein, in which RF protein having an amino acid sequence of SEQ ID NOs: 816 to 822 is fused to the N-terminus or the C-terminus of aMTD having any one amino acid sequence selected from the group consisting of SEQ ID NOs: 1 to 240, preferably SEQ ID NOs: 39, 43, 84, 96, 131, 223, 226 and 233, and more preferably SEQ ID NO: 39 and 131;

2) a recombinant protein, in which SD having any one amino acid sequence selected from the group consisting of SEQ ID NOs: 798 to 804, preferably SEQ ID NOs: 798, 799, 801, 802, 803, and 804, and more preferably SEQ ID NO: 798 and 799 is further fused to the N-terminus or the C-terminus of the RF protein in the recombinant protein of 1); and 3) a recombinant protein, in which one or more of a histidine tag having an amino acid sequence of SEQ ID NO: 812 and a NLS may have an amino acid sequence selected from the group consisting of SEQ ID NOs: 814 and 872 are further fused to the N-terminus or the C-terminus of the aMTD in the recombinant protein of 1) or 2).

When the RF protein may be delivered to terminally differentiated somatic cells, it may reprogram the somatic cells to induced pluripotent stem cells (iPSCs). The recombinant expression vector may include a tag sequence which makes it easy to purify the recombinant protein, for example, consecutive histidine codon, maltose binding protein codon, Myc codon, etc., and further include a fusion partner to enhance solubility of the recombinant protein, etc. Further, for the overall structural and functional stability of the recombinant protein or flexibility of the proteins encoded by respective genes, the recombinant expression vector may further include one or more glycine, proline, and spacer amino acid or polynucleotide sequences including AAY amino acids. Furthermore, the recombinant expression vector may include a sequence specifically digested by an enzyme in order to remove an unnecessary region of the recombinant protein, an expression regulatory sequence, and a marker or reporter gene sequence to verify intracellular delivery, but is not limited thereto.

In still another embodiment of the present invention, the iCP-RF recombinant protein may preferably have a one or more of a histidine-tag affinity domain and a nuclear localization sequence (NLS) additionally fused to one end thereof. Preferably, the histidine-tag or the NLS may be fused to the N-terminus of the RF protein, and more preferably, both of the histidine-tag and the NLS may be fused to the N-terminus of the RF protein.

In still another embodiment of the present invention, the histidine-tag affinity domain may have an amino acid sequence of SEQ ID NO: 812, and the NLS may have an amino acid sequence selected from the group consisting of SEQ ID NOs: 814 and 872. The NLS may have one selected from the group consisting of NLS-1 and NLS-2.

In still another embodiment of the present invention, the histidine-tag affinity domain may be encoded by a polynucleotide sequence of SEQ ID NO: 813, and the NLS may be encoded by a polynucleotide sequence selected from the group consisting of SEQ ID NOs: 815 and 873.

In still another embodiment of the present invention, the fusion may be formed via a peptide bond or a chemical bond.

The chemical bond may be preferably selected from the group consisting of disulfide bonds, diamine bonds, sulfide-amine bonds, carboxyl-amine bonds, ester bonds, and covalent bonds.

According to still another embodiment of the present invention, the iCP-RF recombinant protein may be used for generation to induced pluripotent stem cells (iPSCs) from somatic cells.

The induced pluripotent stem cells (iPS cells or iPSCs) are a type of pluripotent stem cell that can be generated directly from adult cells; terminally differentiated somatic cells. The iPSCs are typically derived by introducing products of specific set of pluripotency-associated genes, or "reprogramming factors," into a given cell type. The reprogramming factors include OCT4 (Octamer-binding transcription factor 4), SOX2 (Sex determining region Y-box 2), NANOG (Homeobox protein NANOG), CMYC (c-Myc), KLF4 (Kruppel-like factor 4), LIN28 (Lin-28 homolog A) and ZSCAN4 (Zinc finger and SCAN domain containing 4). The OCT4, SOX2 and NANOG are transcription factors that require for the maintenance of embryonic stem cells in pluripotent status, the CMYC, KLF4 and LIN28 are intranuclear proteins that facilitate self-renewal and inhibit differentiation of cells, and ZSCAN4 is a protein involved in telomere elongation and genome stabilization. The somatic cells form mouse or human can be reprogrammed to the pluripotent state via viral transduction with the sets of reprogramming factors. While this combination is most conventional in producing iPSCs, each of the factors can be functionally replaced by related transcription factors, miRNAs, small molecules, or even non-related genes such as lineage specifiers. The iPSC derivation is typically a slow and inefficient process, taking 1 to 2 weeks/mouse cells and 3 to 4 weeks/human cells, with efficiencies around 0.01% to 0.1%. However, considerable advances have been made in improving the efficiency and the time it takes to obtain iPSCs. Upon introduction of reprogramming factors (RFs), cells begin to form colonies that resemble pluripotent stem cells, which can be isolated based on their morphology, conditions that select for their growth, or through expression of surface markers (alkaline phosphatase, OCT4, TRA-1-60, TRA-1-81, etc.) or reporter genes.

Preferably, the iCP-RF recombinant proteins may be iCP-OCT4, iCP-SOX2, iCP-KLF4, iCP-CMYC, iCP-NANOG, iCP-LIN28 or iCP-ZSCAN4.

Still another aspect of the present invention provides a polynucleotide sequence encoding the iCP-RF recombinant protein.

The polynucleotide sequence according to one embodiment of the present invention may be present in a vector in which the polynucleotide sequence is operably linked to regulatory sequences capable of providing for the expression of the polynucleotide sequence by a suitable host cell.

According to one embodiment of the present invention, the polynucleotide sequence may be selected from the following groups:

1) a polynucleotide sequence, in which any one polynucleotide sequence selected from the group consisting of SEQ ID NOs: 241 to 480, preferably SEQ ID NOs: 279, 283, 324, 336, 371, 463, 466 and 473, and more preferably SEQ ID NOs: 279 and 371, is operably linked with and a polynucleotide sequence selected from the group consisting of SEQ ID NOs: 823 to 829; and 2) a polynucleotide sequence, in which any one polynucleotide sequence selected from the group consisting of SEQ ID NOs: 831, 833, 835, 837, 839, 841, 843, preferably SEQ ID NOs: 805, 806, 808, 809, 810, and 811, and more preferably SEQ ID NOs: 805 and 806 is further operably linked to the polynucleotide sequence of 1).

Within the expression vector, the term "operably linked" is intended to mean that the polynucleotide sequence of interest is linked to the regulatory sequence(s) in a manner which allows for expression of the polynucleotide sequence. The term "regulatory sequence" is intended to include promoters, enhancers, and other expression control elements. Such operable linkage with the expression vector can be achieved by conventional gene recombination techniques known in the art, while site-directed DNA cleavage and linkage are carried out by using conventional enzymes known in the art.

The expression vectors may contain a signal sequence or a leader sequence for membrane targeting or secretion, as well as regulatory sequences such as a promoter, an operator, an initiation codon, a termination codon, a polyadenylation signal, an enhancer and the like. The promoter may be a constitutive or an inducible promoter. Further, the expression vector may include one or more selectable marker genes for selecting the host cell containing the expression vector, and may further include a polynucleotide sequence that enables the vector to replicate in the host cell in question.

The expression vector constructed according to the present invention may be the vector where the polynucleotide encoding the iCP-RF recombinant protein (where an aMTD is fused to the N-terminus or C-terminus of a RF protein) is inserted within the multiple cloning sites (MCS), preferably NdeI/SalI site of a pET-28a(+) vector (Novagen, USA).

In still another embodiment of the present invention, the polynucleotide encoding the SD being additionally fused to the N-terminus or C-terminus of a RF protein may be inserted into a cleavage site of restriction enzyme (NdeI, EcoRI, SalI, XhoI, etc.) within the multiple cloning sites (MCS) of a pET-28a(+) vector (Novagen, USA).

In still another embodiment of the present invention, the polynucleotide is cloned into a pET-28a(+) vector bearing a NLS residues to the N-terminus of the iCP-RF recombinant protein to allow efficient nuclear transport.

In still another embodiment of the present invention, the polynucleotide is cloned into a pET-28a(+) vector bearing a His-tag sequence so as to fuse six histidine residues to the N-terminus of the iCP-RF recombinant protein to allow easy purification.

According to one embodiment of the present invention, the polynucleotide sequence may be a polynucleotide sequence selected from the group consisting of SEQ ID NOs: 831, 837, 843, 849, 855, 861 and 867.

According to another embodiment of the present invention, the polynucleotide sequence may be further fused with SD, and may be a polynucleotide sequence selected from the group consisting of SEQ ID NOs: 833, 839, 845, 851, 857, 863 and 869.

According to still another embodiment of the present invention, the polynucleotide sequence may be fused with a histidine-tag affinity domain and NLS, and may be a polynucleotide sequence selected from the group consisting of SEQ ID NOs: 835, 841, 847, 853, 859, 865 and 871.

Preferably, the iCP-RF recombinant protein of the present invention may be composed of an amino acid sequence selected from the group consisting of SEQ ID NOs: 833, 839, 845, 851, 857, 863 and 869.

Still another aspect of the present invention provides a recombinant expression vector including the polynucleotide sequence.

Preferably, the vector may be inserted in a host cell and recombined with the host cell genome, or refers to any nucleic acid including a nucleotide sequence competent to replicate spontaneously as an episome. Such a vector may include a linear nucleic acid, a plasmid, a phagemid, a cosmid, an RNA vector, a viral vector, etc.

Preferably, the vector may be genetically engineered to incorporate the nucleic acid sequence encoding the recombinant protein in an orientation either N-terminal and/or C-terminal to a nucleic acid sequence encoding a peptide, a polypeptide, a protein domain, or a full-length protein of interest, and in the correct reading frame so that the recombinant protein consisting of aMTD, RF protein, and preferably SD may be expressed. Expression vectors may be selected from those readily available for use in prokaryotic or eukaryotic expression systems.

Standard recombinant nucleic acid methods may be used to express a genetically engineered recombinant protein. The nucleic acid sequence encoding the recombinant protein according to one embodiment of the present invention may be cloned into a nucleic acid expression vector, e.g., with appropriate signal and processing sequences and regulatory sequences for transcription and translation, and the protein may be synthesized using automated organic synthetic methods. Synthetic methods of producing proteins are described in, for example, the literature [Methods in Enzymology, Volume 289: Solid-Phase Peptide Synthesis by Gregg B. Fields (Editor), Sidney P. Colowick, Melvin I. Simon (Editor), Academic Press (1997)].

In order to obtain high level expression of a cloned gene or nucleic acid, for example, a cDNA encoding the recombinant protein according to one embodiment of the present invention, the recombinant protein sequence may be typically subcloned into an expression vector that includes a strong promoter for directing transcription, a transcription/translation terminator, and in the case of a nucleic acid encoding a protein, a ribosome binding site for translational initiation. Suitable bacterial promoters are well known in the art and are described, e.g., in the literature [Sambrook & Russell, Molecular Cloning: A Laboratory Manual, 3d Edition, Cold Spring Harbor Laboratory, N.Y. (2001); and Ausube, et al., Current Protocols in Molecular Biology, Greene Publishing Associates and Wiley Interscience, N.Y. (1989)]. Bacterial expression systems for expression of the recombinant protein according to one embodiment of the present invention are available in, e.g., *E. coli, Bacillus* sp., and *Salmonella* (Palva et al., Gene 22: 229-235 (1983); Mosbach et al., Nature 302: 543-545 (1983)). Kits for such expression systems are commercially available. Eukaryotic expression systems for mammalian cells, yeast, and insect cells are well known in the art and are also commercially available. The eukaryotic expression vector may be preferably an adenoviral vector, an adeno-associated vector, or a retroviral vector.

Generally, the expression vector for expressing the cell permeable recombinant protein according to one embodiment of present invention in which the cargo protein, i.e. RF protein, is attached to the N-terminus, C-terminus, or both termini of aMTD may include regulatory sequences including, for example, a promoter, operably attached to a sequence encoding the advanced macromolecule transduction domain. Non-limiting examples of inducible promoters that may be used include steroid-hormone responsive promoters (e.g., ecdysone-responsive, estrogen-responsive, and glutacorticoid-responsive promoters), tetracycline "Tet-On" and "Tet-Off" systems, and metal-responsive promoters.

The recombinant protein may be introduced into an appropriate host cell, e.g., a bacterial cell, a yeast cell, an insect cell, or a tissue culture cell. The recombinant protein may also be introduced into embryonic stem cells in order to generate a transgenic organism. Large numbers of suitable vectors and promoters are known to those skilled in the art and are commercially available for generating the recombinant protein.

Known methods may be used to construct vectors including the polynucleotide sequence according to one embodiment of the present invention and appropriate transcriptional/translational control signals. These methods include in vitro recombinant DNA techniques, synthetic techniques, and in vivo recombination/genetic recombination. For example, these techniques are described in the literatures [Sambrook & Russell, Molecular Cloning: A Laboratory Manual, 3d Edition, Cold Spring Harbor Laboratory, N. Y. (2001); and Ausubel et al., Current Protocols in Molecular Biology Greene Publishing Associates and Wiley Interscience, N.Y. (1989)].

Still another aspect of the present invention provides a transformant transformed with the recombinant expression vector.

The transformation includes transfection, and refers to a process whereby a foreign (extracellular) DNA, with or without an accompanying material, enters into a host cell. The "transfected cell" refers to a cell into which the foreign DNA is introduced into the cell, and thus the cell harbors the foreign DNA. The DNA may be introduced into the cell so that a nucleic acid thereof may be integrated into the chromosome or replicable as an extrachromosomal element. The cell introduced with the foreign DNA, etc. is called a transformant.

As used herein, 'introducing' of a protein, a peptide, an organic compound into a cell may be used interchangeably with the expression of 'carrying,' 'penetrating,' 'transporting,' 'delivering,' 'permeating' or 'passing.'

It is understood that the host cell refers to a eukaryotic or prokaryotic cell into which one or more DNAs or vectors are introduced, and refers not only to the particular subject cell but also to the progeny or potential progeny thereof. Because certain modifications may occur in succeeding generations due to either mutation or environmental influences, such progeny may not, in fact, be identical to the parent cell, but are still included within the scope of the term as used herein.

The host cells may be preferably bacterial cells, and as the bacterial cells, there are, in principle, no limitations. They may be eubacteria (gram-positive or gram-negative) or archaebacteria, as long as they allow genetic manipulation for insertion of a gene of interest, preferably for site-specific integration, and they may be cultured on a manufacturing scale. Preferably, the host cells may have the property to allow cultivation to high cell densities.

Examples of bacterial host cells that may be used in the preparation of the recombinant protein are *E. coli* (Lee, 1996; Hannig and Makrides, 1998), *Bacillus subtilis, Pseudomonas fluorescens* (Squires et al., 2004; Retallack et al., 2006) as well as various *Corynebacterium* (US 2006/0003404 A1) and *Lactococcus lactis* (Mierau et al., 2005) strains.

Preferably, the host cells are *Escherichia coli* cells.

More preferably, the host cell may include an RNA polymerase capable of binding to a promoter regulating the gene of interest. The RNA polymerase may be endogenous or exogenous to the host cell.

Preferably, host cells with a foreign strong RNA polymerase may be used. For example, *Escherichia coli* strains engineered to carry a foreign RNA polymerase (e.g. like in the case of using a T7 promoter a T7-like RNA polymerase in the so-called "T7 strains") integrated in their genome may be used. Examples of T7 strains, e.g. BL21(DE3), HMS174 (DE3), and their derivatives or relatives (see Novagen, pET System manual, 11$^{th}$ edition), may be widely used and commercially available. Preferably, BL21-CodonPlus (DE3)-RIL or BL21-CodonPlus (DE3)-RIPL (Agilent Technologies) may be used. These strains are DE3 lysogens containing the T7 RNA polymerase gene under control of the lacUV5 promoter. Induction with IPTG allows production of T7 RNA polymerase which then directs the expression of the gene of interest under the control of the T7 promoter.

The host cell strains, *E. coli* BL21(DE3) or HMS174 (DE3), which have received their genome-based T7 RNA polymerase via the phage DE3, are lysogenic. It is preferred that the T7 RNA polymerase contained in the host cell has been integrated by a method which avoids, or preferably excludes, the insertion of residual phage sequences in the host cell genome since lysogenic strains have the disadvantage to potentially exhibit lytic properties, leading to undesirable phage release and cell lysis.

Still another aspect of the present invention provides a preparing method of the iCP-RF recombinant protein including preparing the recombinant expression vector; preparing the transformant using the recombinant expression vector; culturing the transformant; and recovering the recombinant protein expressed by culturing.

Culturing may be preferably in a mode that employs the addition of a feed medium, this mode being selected from the fed-batch mode, semi-continuous mode, or continuous mode. The bacterial expression host cells may include a DNA construct which is integrated in their genome and carrying the DNA sequence encoding the protein of interest under the control of a promoter that enables expression of said protein.

There are no limitations in the type of the culture medium. The culture medium may be semi-defined, i.e. containing complex media compounds (e.g. yeast extract, soy peptone, casamino acids), or it may be chemically defined, without any complex compounds. Preferably, a defined medium may be used. The defined media (also called minimal or synthetic media) are exclusively composed of chemically defined substances, i.e. carbon sources such as glucose or glycerol, salts, vitamins, and, in view of a possible strain auxotrophy, specific amino acids or other substances such as thiamine. Most preferably, glucose may be used as a carbon source. Usually, the carbon source of the feed medium serves as the growth-limiting component which controls the specific growth rate.

Host cells may be disrupted by any convenient method, including freeze-thaw cycling, sonication, mechanical disruption, or the use of cell lysing agents. The literature [Scopes, Protein Purification: Principles and Practice, New York: Springer-Verlag (1994)] describes a number of general methods for purifying recombinant (and non-recombinant) proteins. The methods may include, e.g., ion-exchange chromatography, size-exclusion chromatography, affinity chromatography, selective precipitation, dialysis, and hydrophobic interaction chromatography. These methods may be adapted to devise a purification strategy for the cell permeable recombinant protein. If the cell permeable recombinant protein includes a purification handle, such as an epitope tag or a metal chelating sequence, affinity chromatography may be used to easily purify the protein.

The amount of the protein produced may be evaluated by detecting the advanced macromolecule transduction domain directly (e.g., using Western analysis) or indirectly (e.g., by assaying materials derived from the cells for specific DNA binding activity, such as by electrophoretic mobility shift assay). Proteins may be detected prior to purification, during any stage of purification, or after purification. In some implementations, purification or complete purification may not be necessary.

The genetically engineered recombinant protein prepared by the method according to one embodiment of the present invention may be a cell/tissue-permeable protein. In particular, the recombinant protein may be activating or inhibiting transcription of a target gene in the nucleus to control transcription of the gene.

The cell permeable recombinant proteins according to one embodiment of present invention may be used in vitro to investigate protein function or may be used to maintain cells in a desired state.

Still another aspect of the present invention provides a composition including the iCP-RF Recombinant Protein as an active ingredient.

The composition may be induced dedifferentiation of terminally differentiated somatic cells into iPSCs. The composition may preferably comprise the active ingredient in an amount of 0.1 to 99.9% by weight, based on the total weight of the composition. The composition may comprise one or more recombinant proteins of OCT4, SOX2, CMYC, KLF4, NANOG, LIN28 and ZSCAN4. Preferably, for effective generation of iPSCs from somatic cells, the composition may include OCT4, SOX2, CMYC, KLF4 and LIN28 recombinant proteins, OCT4, SOX2, KLF4, CMYC, LIN28 and ZSCAN4 recombinant proteins, or OCT4, CMYC and NANOG recombinant proteins. In addition to the active ingredient, the composition may include a buffer, an adjuvant, etc. which is physiologically acceptable while stabilizing the recombinant protein.

Still another aspect of the present invention provides an improved cell-permeable reprogramming factor (iCP) RF recombinant protein for generating iPSCs from somatic cells.

Still another aspect of the present invention provides use of the iCP-RF recombinant protein for generating iPSCs from somatic cells.

Still another aspect of the present invention provides a method of generating iPSCs from somatic cells, including preparing terminally differentiated somatic cells; and treating the somatic cells with an effective amount of the iCP-RF recombinant protein.

The somatic cells may be derived from a mammal, and any biological cell forming the body of an organism; that is, in a brain, heart, kidney, bone, etc., any cell other than undifferentiated stem cell. In mammals, the somatic cells make up all the internal organs, skin, bones, blood and connective tissue. The somatic cells already have completed differentiation, can no more be differentiated. The terminally differentiated cells, however, can be "reprogrammed" so that they revert back to an undifferentiated pluripotent state. The reprogrammed cells are "induced pluripotent stem cells" (iPSCs) that are artificially derived from a differentiated cell, which effectively resets the genotype of the cell to that of a pluripotent state. Accordingly, the iPSCs are believed to have many features in common with natural pluripotent stem cells, such as embryonic stem cells, with regard to the expression of certain stem cell genes and proteins, chromatin methylation patterns, doubling time, embryoid body formation, teratoma formation, viable chimera formation, and potency and differentiability. The iPSCs are typically derived by transfection of certain stem cell-associated genes (reprogramming factors; RFs) into non-pluripotent cells, such as adult fibroblasts.

The methods that generating iPSCs from somatic cells may be used to conveniently and efficiently establish iPSCs having pluripotency and growth ability similar to that of ES cells. The iCP-RF recombinant proteins can effectively increase the ability of reprogramming in a somatic cell, and thus can be useful in the establishment of iPSCs.

Advantageous Effects

One aspect of the present invention provides artificially constructed aMTD sequences based on the critical factors (CFs) that overcome the limitations of prior arts (MTM/MTS/MTD), such as limited diversity and unpredictable cell-permeability. Based on the CFs that assure the cell-permeability, the aMTD displays these sequences shows up to 109.9 relative fold enhanced ability compared to prior arts thereof to deliver biologically active macromolecules into live cells. Therefore, according to one aspect of the present invention, the aMTD is fused to an RF protein to provide an iCP-RF recombinant protein showing improved cell-permeability and intranuclear delivery and enhanced protein solubility and yield.

The iCP-RF recombinant proteins directly penetrate into cell membrane and transduces into nucleus with high efficiency, which can be useful to establish iPSCs from terminally differentiated somatic cells. In addition, the use of iCP-RF recombinant proteins would be safe and ethical solution to previous exogenous gene integration and provide opportunities to use patient derived-iPSCs in clinical applications.

However, the effects are not limited to the above-mentioned effects, and another effects not mentioned will be clearly understood by those skilled in the art from the following description.

DESCRIPTION OF DRAWINGS

FIG. 1 shows Structure of aMTD- or rPeptide-Fused Recombinant Proteins. A schematic diagram of the His-tagged CRA recombinant proteins is illustrated and constructed according to the present invention. The his-tag for affinity purification (white), aMTD or rPeptide (gray) and cargo A (CRA, black) are shown.

FIGS. 2*a* to 2*c* show Construction of Expression Vectors for aMTDs- or rPeptide-Fused Recombinant Proteins. These FIGs. show the agarose gel electrophoresis analysis showing plasmid DNA fragments at 645 bp insert encoding aMTDs or rPeptide-fused CRA cloned into the pET28a(+) vector according to the present invention.

FIGS. 3*a* to 3*d* show Inducible Expression of aMTD- or rPeptide-Fused Recombinant Proteins. Expressed recombinant aMTD- or random peptide-fused CRA recombinant proteins were transformed in *E. coli* BL21 (DE3) strain. Expression of recombinant proteins in *E. coli* before (−) and after (+) induction with IPTG was monitored by SDS-PAGE, and stained with Coomassie blue.

FIGS. 4*a* and 4*b* show Purification of aMTD- or rPeptide-Fused Recombinant Proteins. Expressed recombinant proteins were purified by $Ni^2$+ affinity chromatography under the natural condition. Purification of recombinant proteins displayed through SDS-PAGE analysis.

FIGS. 5*a* to 5*u* show Determination of aMTD-Mediated Cell-Permeability. Cell-permeability of a negative control (A: rP38) and reference hydrophobic CPPs (MTM12 and MTD85) are shown. The cell-permeability of each aMTD and/or rPeptide is visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins (HMCA) fused to negative control (rP38), reference CPP (MTM12 or MTD85) or new hydrophobic CPP (aMTD) are shown with light thick line and indicated by arrows.

FIGS. 6*a* to 6*c* show Determination of rPeptide-Mediated Cell-Permeability. The cell-permeability of each aMTD and/or rPeptide was visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins fused to rPeptides are shown with light thick line and indicated by arrows.

FIGS. 7*a* to 7*k* shows Visualized Cell-Permeability of aMTD-Fused Recombinant Proteins. NIH3T3 cells were treated with FITC-labeled protein (10 uM) fused to aMTD for 1 hour at 37° C. Cell-permeability of the proteins was visualized by laser scanning confocal microscopy (LSM700 version).

FIG. 8 shows Visualized Cell-Permeability of rPeptide-Fused Recombinant Proteins. Cell-permeability of rPeptide-fused recombinant proteins was visualized by laser scanning confocal microscopy (LSM700 version).

FIGS. 9*a* to 9*c* show Relative Cell-Permeability of aMTD-Fused Recombinant Proteins Compared to Negative Control (rP38). The FIG. shows graphs comparing the cell-permeability of the recombinant proteins fused to aMTDs and a negative control (A: rP38).

FIGS. 10*a* to 10*c* show Relative Cell-Permeability of aMTD-Fused Recombinant Proteins Compared to Reference CPP (MTM12). The FIG. shows graphs comparing the cell-permeability of the recombinant proteins fused to aMTDs and a reference CPP (MTM12).

FIGS. 11*a* to 11*c* show Relative Cell-Permeability of aMTD-Fused Recombinant Proteins Compared to Reference CPP (MTD85). The FIG. shows graphs comparing the cell-permeability of the recombinant proteins fused to aMTDs and a reference CPP (MTD85).

FIG. 12 shows Relative Cell-Permeability of rPeptide-Mediated Recombinant Proteins Compared to Average that of aMTDs. The FIG. shows graphs comparing the cell-permeability of the recombinant proteins fused to rPeptides and that (average value: aMTD AVE) of aMTDs.

FIGS. 13*a* to 13*d* show Association of Cell-Permeability with Amino Acid Composition in aMTD Sequences. These graphs display delivery potential (Geometric Mean) of aMTDs influenced with amino acid composition (A, I, V and L).

FIGS. 14*a* to 14*d* show Association of Cell-Permeability with Critical Factors in aMTDs. These graphs show the association of cell-permeability with critical factors [bending potential: proline position (PP), rigidity/flexibility: instability index (II), structural feature: aliphatic index (AI) and hydropathy: grand average of hydropathy (GRAVY)].

FIGS. 15*a* to 15*d* show Relative Relevance of aMTD-Mediated Cell-Permeability with Critical Factors. Cell-permeability of 10 high and 10 low ranked aMTDs in their delivery potential were examined for their association with the critical factors [bending potential: proline position (PP), rigidity/flexibility: instability index (II), structural feature: aliphatic index (AI) and hydropathy: grand average of hydropathy (GRAVY)].

FIG. 16 shows Relative Relevance of rPeptide-Mediated Cell-Permeability with Hydropathy Range (GRAVY). This graph and a chart illustrate relative relevance of rPeptide-mediated cell-permeability with its hydropathy range (GRAVY).

FIG. 17*a* to 17*g* show agarose gel electrophoresis analysis showing plasmid DNA fragments insert encoding aMTD/SD-fused RF cloned into the pET28a (+) vector according to Example <6-1>.

FIG. 18 shows structure of OCT4 recombinant proteins.

FIG. 19 shows expression, purification and the solubility/yield of OCT4 recombinant protein according to Example <7-1>.

FIG. 20 shows structure of SOX2 recombinant proteins.

FIG. 21 shows expression, purification and the solubility/yield of SOX2 recombinant protein according to Example <7-2>.

FIG. 22 shows structure of KLF4 recombinant proteins.

FIG. 23 shows expression, purification and the solubility/yield of KLF4 recombinant protein according to Example <7-3>.

FIG. 24 shows structure of CMYC recombinant proteins.

FIG. 25 shows expression, purification and the solubility/yield of CMYC recombinant protein according to Example <7-4>.

FIG. 26 shows structure of NANOG recombinant proteins.

FIG. 27 shows expression, purification and the solubility/yield of NANOG recombinant protein according to Example <7-5>.

FIG. 28 shows structure of LIN28 recombinant proteins.

FIG. 29 shows expression, purification and the solubility/yield of LIN28 recombinant protein according to Example <7-6>.

FIG. 30 shows structure of ZSCAN4 recombinant proteins.

FIG. 31 shows expression, purification and the solubility/yield of ZSCAN4 recombinant protein according to Example <7-7>.

FIG. 32 shows structure of SOX2 recombinant proteins fused to 7 different aMTDs.

FIG. 33 shows expression, purification and the solubility/yield of SOX2 Recombinant Proteins Fused to 7 Different aMTDs according to Example <8-1>.

FIG. 34 shows structure of NANOG recombinant proteins fused to 5 different aMTDs.

FIG. 35 shows expression, purification and the solubility/yield of NANOG recombinant proteins fused to 5 different aMTDs according to Example <8-2>.

FIG. 36 shows structure of OCT4 recombinant proteins fused to 7 different aMTDs.

FIG. 37 shows structure of CMYC recombinant proteins fused to 8 different aMTDs.

FIG. 38 shows structure of LIN28 recombinant proteins fused to 4 different aMTDs.

FIG. 39 shows aMTD-mediated cell-permeability of RF recombinant proteins

FIG. 40 shows aMTD-mediated intracellular delivery and localization of RF recombinant proteins.

FIG. 41*a* shows structure of a luciferase vector having promoters of OCT4, SOX2, CMYC, KLF4, NANOG and LIN28.

FIG. 41*b* shows induction of transactivation with iCP-OCT4 recombinant protein in luciferase reporter cells according to Example <10-1>.

FIG. 42 shows induction of transactivation with iCP-SOX2 recombinant protein in luciferase reporter cells according to Example <10-2>.

FIG. 43 shows induction of transactivation with iCP-KLF4 recombinant protein in luciferase reporter cells according to Example <10-3>.

FIG. 44 shows induction of transactivation with iCP-CMYC recombinant protein in luciferase reporter cells according to Example <10-3>.

FIG. 45 shows induction of transactivation with iCP-NANOG recombinant protein in luciferase reporter cells according to Example <10-4>.

FIG. 46 shows induction of transactivation with iCP-LIN28 recombinant protein in luciferase reporter cells according to Example <10-5>.

FIG. 47 shows induction of formation of iPSC-like colonies with iCP-RFs recombinant protein: Protocol 1 according to Example <11-1>.

FIG. 48 shows induction of formation of iPSC-like colonies with iCP-RFs recombinant protein: Protocol 2 according to Example <11-2>.

FIG. 49 shows induction of formation of iPSC-like colonies with iCP-RFs recombinant protein: Protocol 3 according to Example <11-3>.

FIG. 50 shows induction of formation of iPSC-like colonies with iCP-RFs recombinant protein: Protocol 4 according to Example <11-4>.

FIG. 51 shows induction of formation of iPSC-like colonies with iCP-RFs recombinant protein: Protocol 5 according to Example <11-5>.

FIG. 52 shows expression of stem cell specific biomarkers of iPSC-like colonies according to Example 12.

MODE FOR INVENTION

1. Analysis of Reference Hydrophobic CPPs to Identify 'Critical Factors' for Development of Advanced MTDs Previously reported MTDs were selected from a screen of more than 1,500 signal peptide sequences. Although the MTDs that have been developed did not have a common sequence or sequence motif, they were all derived from the hydrophobic (H) regions of signal sequences (HOURSS) that also lack common sequences or motifs except their hydrophobicity and the tendency to adopt alpha-helical conformations. The wide variation in H-region sequences may reflect prior evolution for proteins with membrane translocating activity and subsequent adaptation to the SRP/Sec61 machinery, which utilizes a methionine-rich signal peptide binding pocket in SRP to accommodate a wide-variety of signal peptide sequences.

Previously described hydrophobic CPPs (e.g. MTS/MTM and MTD) were derived from the hydrophobic regions present in the signal peptides of secreted and cell surface proteins. The prior art consists first, of ad hoc use of H-region sequences (MTS/MTM), and second, of H-region sequences (with and without modification) with highest CPP activity selected from a screen of 1,500 signal sequences (MTM). Second prior art, the modified H-region derived hydrophobic CPP sequences had advanced in diversity with multiple number of available sequences apart from MTS/MTM derived from fibroblast growth factor (FGF) 4. However, the number of MTDs that could be modified from naturally occurring secreted proteins are somewhat limited. Because there is no set of rules in determining their cell-permeability, no prediction for the cell-permeability of modified MTD sequences can be made before testing them.

The hydrophobic CPPs, like the signal peptides from which they originated, did not conform to a consensus sequence, and they had adverse effects on protein solubility when incorporated into protein cargo. We therefore set out to identify optimal sequence and structural determinants, namely critical factors (CFs), to design new hydrophobic CPPs with enhanced ability to deliver macromolecule cargoes including proteins into the cells and tissues while maintaining protein solubility. These newly developed CPPs, advanced macromolecule transduction domains (aMTDs) allowed almost infinite number of possible designs that could be designed and developed based on the critical factors. Also, their cell-permeability could be predicted by their character analysis before conducting any in vitro and/or in vivo experiments. These critical factors below have been developed by analyzing all published reference hydrophobic CPPs.

1-1. Analysis of Hydrophobic CPPs

Seventeen different hydrophobic CPPs (Table 1) published from 1995 to 2014 (Table 2) were selected. After physiological and chemical properties of selected hydrophobic CPPs were analyzed, 11 different characteristics that may be associated with cell-permeability have been chosen for further analysis. These 11 characteristics are as follows: sequence, amino acid length, molecular weight, pI value, bending potential, rigidity/flexibility, structural feature, hydropathy, residue structure, amino acid composition and secondary structure of the sequences (Table 3).

Table 1 shows the Summary of Published Hydrophobic Cell-Penetrating Peptides which were Chosen.

TABLE 1

| # | Pepides | Origin | Protein | Ref. |
|---|---|---|---|---|
| 1 | MTM | *Homo sapiens* | NP_001998 Kaposi fibroblast growth factor (K-FGF) | 1 |
| 2 | MTS | *Homo sapiens* | NP_001998 Kaposi fibroblastgrowth factor (K-FGF) | 2 |
| 3 | MTD10 | *Streptomyces coelicolor* | NP_625021 Glycosyl hydrolase | 8 |
| 4 | MTD13 | *Streptarnyces coelicolor* | NP_639877 Putative secreted protein | 3 |
| 5 | MTD47 | *Streptomyces coelicolor* | NP_627512 Secreted protein | 4 |
| 6 | MTD56 | *Homo sapiens* | P23274 Peptodyl-prolyl cis-trans isomerase B precursor | 5 |
| 7 | MTD73 | *Drosophila melanogaster* | AAA17887 Spatzle (spz) protein | 5 |
| 8 | MTD77 | *Homo sapiens* | NP_003231 Kaposi fibroblast growth factor (K-FGF) | 6 |
| 9 | MTD84 | *Phytophthora cactorum* | AAK63068 Phytotoxic protein PcF precusor | 4 |
| 10 | MTD85 | *Streptomyces coelicolor* | NP_629842 Peptide transport system peptide binding protein | 7 |
| 11 | MTD86 | *Streptomyces coelicolor* | NP_99842 Peptide transport system secreted peptide binding protein | |
| 12 | MTD103 | *Homo sapiens* | TMBV19 domain Family member B | 8 |
| 13 | MTD132 | *Streptomyces coelicolor* | NP_628377 P60-family secreted protein | 4 |
| 14 | MTD151 | *Streptomyces coelicolor* | NP_630126 Secreted chitinase | a |
| 15 | MTD173 | *Streptomyces coelicolor* | NP_624384 Secreted protein | 4 |
| 16 | MTD174 | *Streptomyces coelicolor* | NP_733505 Large, multifunctional secreted protein | 8 |
| 17 | MTD181 | *Neisseria meningitidis* Z2491 | CAB84257.1 Putative secreted protein | 4 |

Table 2 shows the Summarizes Reference Information.

TABLE 2

| # | Title | Journal | Year | Vol | Issue | Page |
|---|---|---|---|---|---|---|
| | References | | | | | |
| 1 | Inhibition of Nuclear Translocation of Transcription Factor NF-kB by a Synthetic peptide Containing a Cell Membrane-permeable Motif and Nuclear Localization Sequence | JOURNALOF BIOLOGICAL CHEMISTRY | 1995 | 270 | 24 | 14255 |
| 2 | Epigenetic Regulation of Gene Structure and Function with a Cell-Permeable Cre Recombinase | NATURE BIOTECHNOLOGY | 2001 | 19 | 10 | 929 |
| 3 | Cell-Permeable NM23 Blocks the Maintenance and Progression of Established Pulmonary Metastasis | CANCER RESEARCH | 2011 | 71 | 23 | 7216 |
| 4 | Antitumor Activity of Cell-Permeable p18INK4c With Enhanced Membrane and Tissue Penetration | MOLECULAR THERAPY | 2012 | 20 | 8 | 1540 |
| 5 | Antitumor Activity of Cell-Permeable RUNX3 Protein in Gastric Cancer Cells | CLINICAL CANCER RESEARCH | 2012 | 19 | 3 | 680 |
| 6 | The Effect of Intracellular Protein Delivery on the Anti-Tumor Activity of Recombinant Human Endostatin | BIOMATERIALS | 2013 | 34 | 26 | 6261 |
| 7 | Partial Somatic to Stem Cell Transformations Induced By Cell-Permeable Reprogramming Factors | SCIENTIFIC REPORTS | 2014 | 4 | 10 | 4361 |
| 8 | Cell-Permeable Parkin Proteins Suppress Parkinson Disease-Associated Phenotypes in Cultured Cells and Animals | PLOS ONE | 2014 | 9 | 7 | 17 |

Table 3 shows the Characteristics of Published Hydrophobic Cell-Penetrating Peptides (A) which were Analyzed.

TABLE 3

| # | Peptide | Sequence | Length | Molecular Weight | pI | Bending Potential | Rigidity/Flexibility (Instability Index: II) | Structural Feature (Aliphatic Index: AI) | Hydropathy (GRAVY) | Residue Structure | A/a Composition A | V | L | I | P | G | Secondary Structure | Cargo | Ref. |
|---|---|---|---|---|---|---|---|---|---|---|---|---|---|---|---|---|---|---|---|
| 1 | MTM | AAVALLPAVLLALLAP | 16 | 1,515.9 | 5.6 | Bending | 45.5 | 220.0 | 2.4 | Aliphatic Ring | 6 | 2 | 6 | 0 | 2 | 0 | Helix | p50 | 1 |
| 2 | MTS | AAVLLPVLLAAP | 12 | 1,147.4 | 5.6 | Bending | 57.3 | 211.7 | 2.3 | Aliphatic Ring | 4 | 2 | 4 | 0 | 2 | 0 | No-Helix | CRE | 2 |
| 3 | MTD10 | LGGAVVAAPVAAAVAP | 16 | 1,333.5 | 5.5 | Bending | 47.9 | 140.6 | 1.8 | Aliphatic Ring | 7 | 4 | 1 | 0 | 2 | 2 | Helix | Parkin | 8 |
| 4 | MTD13 | LAAAALAVLPL | 11 | 1,022.3 | 5.5 | Bending | 26.6 | 213.6 | 2.4 | Aliphatic Ring | 5 | 1 | 4 | 0 | 1 | 0 | No-Helix | RUNX3 | 3 |
| 5 | MTD47 | AAAVPVLVAA | 10 | 881.0 | 5.6 | Bending | 47.5 | 176.0 | 2.4 | Aliphatic Ring | 5 | 3 | 1 | 0 | 1 | 0 | No-Helix | CMYC | 4 |
| 6 | MTD56 | VLLAAALIA | 9 | 854.1 | 5.5 | No-Bending | 8.9 | 250.0 | 3.0 | Aliphatic Ring | 4 | 1 | 3 | 1 | 0 | 0 | Helix | ES | 5 |
| 7 | MTD73 | PVLLLLA | 7 | 737.9 | 6.0 | No-Bending | 36.1 | 278.6 | 2.8 | Aliphatic Ring | 1 | 1 | 4 | 0 | 1 | 0 | Helix | ES | 5 |
| 8 | MTD77 | AVALLILAV | 9 | 882.1 | 5.6 | No-Bending | 30.3 | 271.1 | 3.3 | Aliphatic Ring | 3 | 2 | 3 | 1 | 0 | 0 | Helix | NM23 | 6 |

TABLE 3-continued

| # | Peptides | Sequence | Length | Molecular Weight | pI | Bending Potential | Rigidity/ Flexibility (Instability Index: II) | Structural Feature (Aliphatic Index: AI) | Hydropathy (GRAVY) | Residue Structure | A/a Composition A V L I P G | Secondary Structure | Cargo | Ref. |
|---|---|---|---|---|---|---|---|---|---|---|---|---|---|---|
| 9 | MTD84 | AVALVA VVAVA | 11 | 982.2 | 5.6 | No-Bending | 9.1 | 212.7 | 3.1 | Aliphatic Ring | 5 5 1 0 0 0 | Helix | OCT4 | 4 |
| 10 | MTD85 | LLAAAA ALLLA | 11 | 1,010.2 | 5.5 | No-Bending | 9.1 | 231.8 | 2.7 | Aliphatic Ring | 6 0 5 0 0 0 | No-Helix | RUNX 3 | 7 |
| 11 | MTD86 | LLAAAA ALLLA | 11 | 1,010.2 | 5.5 | No-Bending | 9.1 | 231.8 | 2.7 | Aliphatic Ring | 6 0 5 0 0 0 | No-Helix | SOX2 | 7 |
| 12 | MTD 103 | LALPVL LLA | 9 | 922.2 | 5.5 | Bending | 51.7 | 271.1 | 2.8 | Aliphatic Ring | 2 1 5 0 1 0 | Helix | p18 | 8 |
| 13 | MTD 132 | AVVVPA LIVAAP | 12 | 1,1194 | 5.6 | Bending | 50.3 | 195.0 | 2.4 | Aliphatic Ring | 4 4 1 1 2 0 | No-Helix | LIN 28 | 4 |
| 14 | MTD 151 | AAAPVA AVP | 9 | 1,031.4 | 5.5 | Bending | 73.1 | 120.0 | 1.6 | Aliphatic Ring | | No-Helix | Parkin | 8 |
| 15 | MTD 173 | AVIPIL AVP | 9 | 892.1 | 5.6 | Bending | 48.5 | 216.7 | 2.4 | Aliphatic Ring | 2 2 1 2 2 0 | Helix | KLF4 | 4 |
| 16 | MTD 174 | LILLLP AVALP | 12 | 1,011.8 | 5.5 | Bending | 79.1 | 257.3 | 2.6 | Aliphatic Ring | | Helix | Parkin | 8 |
| 17 | MTD 181 | AVLLLP AAA | 9 | 838.0 | 5.6 | Bending | 51.7 | 206.7 | 2.4 | Aliphatic | 4 1 3 0 1 0 | No-Helix | SOX2 | 4 |
| | | AVE | 10.8 ± 2.4 | 1,011 ± 189.6 | 5.6 ± 0.1 | Proline Presence | 40.1 ± 21.9 | 217.9 ± 43.6 | 2.5 ± 0.4 | | | | | |

Two peptide/protein analysis programs were used (ExPasy: SoSui: harrier.nagahama-i-bio.ac.jp) to determine various indexes and structural features of the peptide sequences and to design new sequence. Followings are important factors analyzed.

1-2. Characteristics of Analyzed Peptides: Length, Molecular Weight and pl Value Average length, molecular weight and pl value of the peptides analyzed were 10.8±2.4, 1,011±189.6 and 5.6±0.1, respectively (Table 4)

Table 4 shows the Summarizes Critical Factors (CFs) of Published Hydrophobic Cell-Penetrating Peptides (A) which were Analyzed.

TABLE 4

Length: 10.8 ± 2.4
Molecular Weight: 1,011 ± 189.6
pl: 5.6 ± 0.1
Bending Potential (BP): Proline presences in the middle and/or the end of peptides, or No Proline.
Instability Index (II): 40.1 ± 21.9

TABLE 4-continued

Residue Structure & Aliphatic Index (AI): 217.9 ± 43.6
Hydropathy (GRAVY): 2.5 ± 0.4
Aliphatic Ring: Non polar hydrophobic & aliphatic amino acid (A, V, L, I).
Secondary Structure: α-Helix is favored but not required.

1-3. Characteristics of Analyzed Peptides: Bending Potential—Proline Position (PP)

Bending potential (bending or no-bending) was determined based on the fact whether proline (P) exists and/or where the amino acid(s) providing bending potential to the peptide in recombinant protein is/are located. Proline differs from the other common amino acids in that its side chain is bonded to the backbone nitrogen atom as well as the alpha-carbon atom. The resulting cyclic structure markedly influences protein architecture which is often found in the bends of folded peptide/protein chain.

Eleven out of 17 were determined as 'Bending' peptide which means that proline is present in the middle of sequence for peptide bending and/or located at the end of the peptide for protein bending. As indicated above, peptide sequences could penetrate the plasma membrane in a "bent" configuration. Therefore, bending or no-bending potential is considered as one of the critical factors for the improvement of current hydrophobic CPPs.

1-4. Characteristics of Analyzed Peptides: Rigidity/Flexibility—Instability Index (II)

Since one of the crucial structural features of any peptide is based on the fact whether the motif is rigid or flexible, which is an intact physicochemical characteristic of the peptide sequence, instability index (II) of the sequence was determined. The index value representing rigidity/flexibility of the peptide was extremely varied (8.9 to 79.1), but average value was 40.1±21.9 which suggested that the peptide should be somehow flexible, but not too much rigid or flexible (Table 3).

1-5. Characteristics of Analyzed Peptides: Structural Features—Structural Feature (Aliphatic Index: AI) and Hydropathy (Grand Average of Hydropathy: GRAVY)

Alanine (V), valine (V), leucine (L) and isoleucine (I) contain aliphatic side chain and are hydrophobic—that is, they have an aversion to water and like to cluster. These amino acids having hydrophobicity and aliphatic residue enable them to pack together to form compact structure with few holes. Analyzed peptide sequence showed that all composing amino acids were hydrophobic (A, V, L and I) except glycine (G) in only one out of 17 (MTD10—Table 3) and aliphatic (A, V, L, I, and P). Their hydropathic index (Grand Average of Hydropathy: GRAVY) and aliphatic index (AI) were 2.5±0.4 and 217.9±43.6, respectively. Their amino acid composition is also indicated in the Table 3.

1-6. Characteristics of Analyzed Peptides: Secondary Structure (Helicity)

As explained above, the CPP sequences may be supposed to penetrate the plasma membrane directly after inserting into the membranes in a "bent" configuration with hydrophobic sequences having α-helical conformation. In addition, our analysis strongly indicated that bending potential was crucial for membrane penetration. Therefore, structural analysis of the peptides was conducted to determine whether the sequences were to form helix or not. Nine peptides were helix and eight were not (Table 3). It seems to suggest that helix structure may not be required.

1-7. Determination of Critical Factors (CFs)

In the 11 characteristics analyzed, the following 6 are selected namely "Critical Factors" for the development of new hydrophobic CPPs—advanced MTDs: amino acid length, bending potential (proline presence and location), rigidity/flexibility (instability index: I), structural feature (aliphatic index: AI), hydropathy (GRAVY) and amino acid composition/residue structure (hydrophobic and aliphatic A/a) (Tables 3 and Table 4).

2. Analysis of Selected Hydrophobic CPPs to Optimize 'Critical Factors'

Since the analyzed data of the 17 different hydrophobic CPPs (analysis A, Tables 3 and 4) previously developed during the past 2 decades showed high variation and were hard to make common- or consensus-features, analysis B (Tables 5 and 6) and C (Tables 7 and 8) were also conducted to optimize the critical factors for better design of improved CPPs-aMTDs. Therefore, 17 hydrophobic CPPs have been grouped into two groups and analyzed the groups for their characteristics in relation to the cell permeable property. The critical factors have been optimized by comparing and contrasting the analytical data of the groups and determining the common homologous features that may be critical for the cell permeable property.

2-1. Selective Analysis (B) of Peptides Used to Biologically Active Cargo Protein for In Vivo In analysis B, eight CPPs were used with each biologically active cargo in vivo. Length was 11±3.2, but 3 out of 8 CPPs possessed little bending potential. Rigidity/Flexibility (instability index: II) was 41±15, but removing one [MTD85: rigid, with minimal II (9.1)] of the peptides increased the overall instability index to 45.6±9.3. This suggested that higher flexibility (40 or higher II) is potentially be better. All other characteristics of the 8 CPPs were similar to the analysis A, including structural feature and hydropathy (Tables 5 and 6).

Table 5 shows the Characteristics of Published Hydrophobic Cell-Penetrating Peptides (B): Selected CPPs That were Used to Each Cargo In Vivo.

TABLE 5

| # | Peptides | Sequence | Length | Molecular Weight | pI | Bending Potential | Rigidity/Flexibility (Instability Index: II) | Structural Feature (Aliphatic Index: AI) | Hydropathy (GRAVY) | Residue Structure | A/a Composition A V L I P G | Secondary Structure | Cargo | Ref. |
|---|---|---|---|---|---|---|---|---|---|---|---|---|---|---|
| 1 | MTM | AAVALLPAVLLALLAP | 16 | 1,515.9 | 5.6 | Bending | 45.5 | 220.0 | 2.4 | Aliphatic Ring | 6 2 6 0 2 0 | Helix | p50 | 1 |
| 2 | MTS | AAVLLPVLLAAP | 12 | 1,147.4 | 5.6 | Bending | 57.3 | 211.7 | 2.3 | Aliphatic Ring | 4 2 4 0 2 0 | No-Helix | CRE | 2 |
| 3 | MTD10 | LGGAVVAAPVAAAVAP | 16 | 1,333.5 | 5.5 | Bending | 47.9 | 140.6 | 1.8 | Aliphatic Ring | 7 4 1 0 2 2 | Helix | Parkin | 8 |
| 4 | MTD73 | PVLLLLA | 7 | 737.9 | 6.0 | No-Bending | 36.1 | 278.6 | 2.8 | Aliphatic Ring | 1 1 4 0 1 0 | Helix | ES | 6 |

TABLE 5-continued

| # | Peptides | Sequence | Length | Molecular Weight | pI | Bending Potential | Rigidity/Flexibility (Instability Index: II) | Structural Feature (Aliphatic Index: AI) | Hydropathy (GRAVY) | Residue Structure | A/a Composition A V L I P G | Secondary Structure | Cargo | Ref. |
|---|---|---|---|---|---|---|---|---|---|---|---|---|---|---|
| 5 | MTD77 | AVALLILAV | 9 | 882.1 | 5.6 | No-Bending | 30.3 | 271.1 | 3.3 | Aliphatic Ring | 3 2 3 1 0 0 | Helix | NM23 | 3 |
| 6 | MTD85 | LLAAAAALLA | 11 | 1,010.2 | 5.5 | No-Bending | 9.1* | 231.8 | 2.7 | Aliphatic Ring | 6 0 5 0 0 0 | No-Helix | RUNX 3 | 5 |
| 7 | MTD 103 | LALPVLLLA | 9 | 922.2 | 5.5 | Bending | 51.7 | 271.1 | 2.8 | Aliphatic Ring | 2 1 5 0 1 0 | Helix | p18 | 4 |
| 8 | MTD 132 | AVVVPAIVLAAP | 12 | 1,119.4 | 5.6 | Bending | 50.3 | 195.0 | 2.4 | Aliphatic Ring | 4 4 1 1 2 0 | No-Helix | LIN 28 | 7 |
| | | AVE | 11 ± 3.2 | 1,083 ± 252 | 5.6 ± 0.1 | Proline Presence | 41 ± 15 | 227 ± 47 | 2.5 ± 0.4 | | | | | |

*Removing the MTD85 increases II to 45.6 ± 9.3

Table 6 shows the Summarized Critical Factors of Published Hydrophobic Cell-Penetrating Peptides (B).

TABLE 6

Length: 11 ± 3.2
Molecular Weight: 1,083 ± 252
pI: 5.6 ± 0.1
Bending Potential (BP): Proline presences in the middle and/or the end of peptides, or No Proline.
Instability Index (II): 41.0 ± 15 (* Removing the MTD85 increases II to 45.6 ± 9.3)
Residue Structure & Aliphatic Index (AI): 227 ± 47
Hydropathy (GRAVY): 2.5 ± 0.4
Aliphatic Ring: Non-polar hydrophobic & aliphatic amino acid (A, V, L, I).
Secondary Structure: α-Helix is favored but not required.

2-2. Selective Analysis (C) of Peptides that Provided Bending Potential and Higher Flexibility To optimize the 'Common Range and/or Consensus Feature of Critical Factor' for the practical design of aMTDs and the random peptides (rPs or rPeptides), which were to prove that the 'Critical Factors' determined in the analysis A, B and C were correct to improve the current problems of hydrophobic CPPs—protein aggregation, low solubility/yield, and poor cell-/tissue-permeability of the recombinant proteins fused to the MTS/MTM or MTD, and non-common sequence and non-homologous structure of the peptides, empirically selected peptides were analyzed for their structural features and physicochemical factor indexes.

Hydrophobic CPPs which did noTo optimize the 'Common Range and/or Consensus Feature of Critical Factor' for the practical design of aMTDs and the random peptides (rPs or rPeptides), which were to prove that the 'Critical Factors' determined in the analysis A, B and C were correct to improve the current problems of hydrophobic CPPs—protein aggregation, low solubility/yield, and poor cell-/tissue-permeability of the recombinant proteins fused to the MTS/MTM or MTD, and non-common sequence and non-homologous structure of the peptides, empirically selected peptides were analyzed for their structural features and physicochemical factor indexes.

Hydrophobic CPPs which did not have a bending potential, rigid or too much flexible sequences (too much low or too much high Instability Index), or too low or too high hydrophobic CPPs were unselected, but secondary structure was not considered because helix structure of sequence was not required.

In analysis C, eight selected CPP sequences that could provide a bending potential and higher flexibility were finally analyzed (Table 7 and 8). Common amino acid length is 12 (11.6±3.0). Proline is presence in the middle of and/or the end of sequence. Rigidity/Flexibility (II) is 45.5 to 57.3 (Avg: 50.1±3.6). AI and GRAVY representing structural feature and hydrophobicity of the peptide are 204.7±37.5 and 2.4±0.3, respectively. All peptides are consisted with hydrophobic and aliphatic amino acids (A, V, L, I, and P). Therefore, analysis C was chosen as a standard for the new design of new hydrophobic CPPs—aMTDs.

Table 7 shows the Characteristics of Published Hydrophobic Cell-Penetrating Peptides (C): Selected CPPs that Provided Bending Potential and Higher Flexibility.

TABLE 7

| # | Pep tides | Se- quence | Length | Molecu- lar Weight | pI | Bend- ing Po- ten- tial | Rigid- ity/ Flexi- bility (In- sta- bility Index: II) | Struc- tural Fea- ture (Ali- phatic Index: AI) | Hydro- pathy (GRA- VY) | Resi- due Struc- ture | A/a Compo- sition A V L I P G | Secon- dary Struc- ture | Car- go | Ref. |
|---|---|---|---|---|---|---|---|---|---|---|---|---|---|---|
| 1 | MTM | AAVALL PAVLLA LLAP | 16 | 1515.9 | 5.6 | Bend- ing | 45.5 | 220.0 | 2.4 | Ali- phatic Ring | 6 2 6 0 2 0 | Helix | p50 | 1 |
| 2 | MTS | AAVLLP VLLAAP | 12 | 1147.4 | 5.6 | Bend- ing | 57.3 | 211.7 | 2.3 | Ali- phatic Ring | 4 2 4 0 2 0 | No- Helix | CRE | 2 |
| 3 | MTD10 | LGGAVV AAPVAA AVAP | 16 | 1333.5 | 5.5 | Bend- ing | 47.9 | 140.6 | 1.8 | Ali- phatic Ring | 7 4 1 0 2 2 | Helix | Par- kin | 8 |
| 4 | MTD47 | AAAVPV LVAA | 10 | 881.0 | 5.6 | Bend- ing | 47.5 | 176.0 | 2.4 | Ali- phatic Ring | 5 3 1 0 1 0 | No- Helix | CMYC | 4 |
| 5 | MTD 103 | LALPVL LLA | 9 | 922.2 | 5.5 | Bend- ing | 51.7 | 271.1 | 2.8 | Ali- phatic Ring | 2 1 5 0 1 0 | Helix | p18 | 8 |
| 6 | MTD 132 | AVVVPA IVLAAP | 12 | 1119.4 | 5.6 | Bend- ing | 50.3 | 195.0 | 2.4 | Ali- phatic Ring | 4 4 1 1 2 0 | No- Helix | LIN 28 | 4 |
| 7 | MTD 173 | AVIPIL AVP | 9 | 892.1 | 5.6 | Bend- ing | 48.5 | 216.7 | 2.4 | Ali- phatic Ring | 2 2 1 2 2 0 | Helix | KLF4 | 4 |
| 8 | MTD 181 | AVLLLP AAA | 9 | 838.0 | 5.6 | Bend- ing | 51.7 | 206.7 | 2.4 | Ali- phatic Ring | 4 1 3 0 1 0 | No- Helix | SOX2 | 4 |
| | | AVE | 11.6 ± 3.0 | 1081.2 ± 244.6 | 5.6 ± 0.1 | Pro- line Pres- ence | 50.1 ± 3.6 | 204.7 ± 37.5 | 2.4 ± 0.3 | | | | | |

Table 8 shows the Summarized Critical Factors of Published Hydrophobic Cell-Penetrating Peptides (C).

TABLE 8

| |
|---|
| Length: 11.6 ± 3.0 |
| Molecular Weight: 1,081.2 ± 224.6 |
| pI: 5.6 t 0.1 |
| Bending Potential (BP): Proline presences in the middle and/or the end of peptides. |
| Instability index (II): 50.1 ± 3.6 |
| Residue Structure & Aliphatic Index (AI): 204.7 ± 37.5 |
| Hydropathy (GRAVY): 2.4 ± 0.3 |
| Aliphatic Ring: Non-polar hydrophobic & aliphatic amino acid (A, V, L, I). |
| Secondary Structure: α-Helix is favored but not required. |

3. New Design of Improved Hydrophobic CPPs—aMTDs Based on the Optimized Critical Factors 3-1. Determination of Common Sequence and/or Common Homologous Structure As mentioned above, H-regions of signal sequence (HOURSS)-derived CPPs (MTS/MTM and MTD) do not have a common sequence, sequence motif, and/or common-structural homologous feature. According to one embodiment of the present invention, the aim is to develop improved hydrophobic CPPs formatted in the common sequence- and structural-motif which satisfy newly determined 'Critical Factors' to have 'Common Function,' namely, to facilitate protein translocation across the membrane with similar mechanism to the analyzed reference CPPs. Based on the analysis A, B and C, the common homologous features have been analyzed to determine the critical factors that influence the cell-permeability. The range value of each critical factor has been determined to include the analyzed index of each critical factor from analysis A, B and C to design novel aMTDs (Table 9). These features have been confirmed experimentally with newly designed aMTDs in their cell-permeability.

Table 9 shows the Comparison The Range/Feature of Each Critical Factor Between The Value of Analyzed CPPs and The Value Determined for New Design of Novel aMTDs Sequences.

TABLE 9

| Summarized Critical Factors of aMTD | | |
|---|---|---|
| Critical Factor | Selected CPPs Range | Newly Designed CPPs Range |
| Bending Potential (Proline Position: PP) | Proline presences in the middle and/or at the end of peptides | Proline presences in the middle (5', 6', 7' or 8' and at the end of peptides |
| Rigidity/Flexibility (Instability Index: II) | 45.5-57.3 (50.1 ± 3.6) | 40-60 |
| Structural Feature (Aliphatic Index: AI) | 140.6-220.0 (204.7 ± 37.5) | 180-220 |
| Hydropathy (Grand Average of Hydropathy GRAVY) | 1.8-2.8 (2.4 ± 0.3) | 2.1-2.6 |
| Length (Number of Amino Acid) | 11.6 ± 3.0 | 9-13 |
| Amino acid Composition | A, V, I, L, P | A, V, I, L, P |

In Table 9, universal common features and sequence/structural motif are provided. Length is 9 to 13 amino acids, and bending potential is provided with the presence of proline in the middle of sequence (at 5', 6', 7' or 8' amino acid) for peptide bending and at the end of peptide for recombinant protein bending and Rigidity/Flexibility of aMTDs is II >40 are described in Table 9.

3-2. Critical Factors for Development of Advanced MTDs

Recombinant cell-permeable proteins fused to the hydrophobic CPPs to deliver therapeutically active cargo molecules including proteins into live cells had previously been reported, but the fusion proteins expressed in bacteria system were hard to be purified as a soluble form due to their low solubility and yield. To address the crucial weakness for further clinical development of the cell-permeable proteins as protein-based biotherapeutics, greatly improved form of the hydrophobic CPP, named as advanced MTD (aMTD) has newly been developed through critical factors-based peptide analysis. The critical factors used for the current invention of the aMTDs are herein (Table 9).

1. Amino Acid Length: 9 to 13
2. Bending Potential (Proline Position: PP)

: Proline presences in the middle (from 5' to 8' amino acid) and at the end of sequence 3. Rigidity/Flexibility (Instability Index: II): 40 to 60
4. Structural Feature (Aliphatic Index: AI): 180 to 220
5. Hydropathy (GRAVY): 2.1 to 2.6
6. Amino Acid Composition: Hydrophobic and Aliphatic amino acids to A, V, L, I and P 3-3. Design of Potentially Best aMTDs that all Critical Factors are Considered and Satisfied After careful consideration of six critical factors derived from analysis of unique features of hydrophobic CPPs, advanced macromolecule transduction domains (aMTDs) have been designed and developed based on the common 12 amino acid platform which satisfies the critical factors including amino acid length (9 to 13) determined from the analysis.

[General formula]

X1-X2-X3-X4-U5-U6-U7-U8-X9-X10-X11-P

Unlike previously published hydrophobic CPPs that require numerous experiments to determine their cell-permeability, newly developed aMTD sequences could be designed by performing just few steps as follows using above mentioned platform to follow the determined range value/feature of each critical factor.

First, prepare the 12 amino acid sequence platform for aMTD. Second, place proline (P) in the end (12') of sequence and determine where to place proline in one of four U(s) in 5', 6', 7', and 8. Third, alanine (A), valine (V), leucine (L) or isoleucine (I) is placed in either X(s) and/or U(s), where proline is not placed. Lastly, determine whether the amino acid sequences designed based on the platform, satisfy the value or feature of six critical factors to assure the cell permeable property of aMTD sequences. Through these processes, numerous novel aMTD sequences have been constructed. The expression vectors for preparing non-functional cargo recombinant proteins fused to each aMTD, expression vectors have been constructed and forcedly expressed in bacterial cells. These aMTD-fused recombinant proteins have been purified in soluble form and determined their cell-permeability quantitatively. aMTD sequences have been newly designed, numbered from 1 to 240, as shown in Tables 10 to 15. In Tables 10 to 15, sequence ID Number is a sequence listings for reference, and aMTD numbers refer to amino acid listing numbers that actually have been used at the experiments. For further experiments, aMTD numbers have been used. In addition, polynucleotide sequences shown in the sequence lists have been numbered from SEQ ID NO: 241 to SEQ ID NO: 480.

Tables 10 to 15 show the 240 new hydrophobic aMTD sequences that were developed to satisfy all critical factors.

TABLE 10

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 1 | 1 | AAALAPVVLALP | 12 | 57.3 | 187.5 | 2.1 | Aliphatic |
| 2 | 2 | AAAVPLLAVVVP | 12 | 41.3 | 195.0 | 2.4 | Aliphatic |
| 3 | 3 | AALLVPAAVLAP | 12 | 57.3 | 187.5 | 2.1 | Aliphatic |
| 4 | 4 | ALALLPVAALAP | 12 | 57.3 | 195.8 | 2.1 | Aliphatic |
| 5 | 5 | AAALLPVALVAP | 12 | 57.3 | 187.5 | 2.1 | Aliphatic |
| 6 | 11 | VVALAPALAALP | 12 | 57.3 | 187.5 | 2.1 | Aliphatic |
| 7 | 12 | LLAAVPAVLLAP | 12 | 57.3 | 211.7 | 2.3 | Aliphatic |
| 8 | 13 | AAALVPVVALLP | 12 | 57.3 | 203.3 | 2.3 | Aliphatic |
| 9 | 21 | AVALLPALLAVP | 12 | 57.3 | 211.7 | 2.3 | Aliphatic |

TABLE 10-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 10 | 22 | AVVLVPVLAAAP | 12 | 57.3 | 195.0 | 2.4 | Aliphatic |
| 11 | 23 | VVLVLPAAAAVP | 12 | 57.3 | 195.0 | 2.4 | Aliphatic |
| 12 | 24 | IALAAPALIVAP | 12 | 50.2 | 195.8 | 2.2 | Aliphatic |
| 13 | 25 | IVAVAPALVALP | 12 | 50.2 | 203.3 | 2.4 | Aliphatic |
| 14 | 42 | VAALPVVAVVAP | 12 | 57.3 | 186.7 | 2.4 | Aliphatic |
| 15 | 43 | LLAAPLVVAAVP | 12 | 41.3 | 187.5 | 2.1 | Aliphatic |
| 16 | 44 | ALAVPVALLVAP | 12 | 57.3 | 203.3 | 2.3 | Aliphatic |
| 17 | 61 | VAALPVLLAALP | 12 | 57.3 | 211.7 | 2.3 | Aliphatic |
| 18 | 62 | VALLAPVALAVP | 12 | 57.3 | 203.3 | 2.3 | Aliphatic |
| 19 | 63 | AALLVPALVAVP | 12 | 57.3 | 203.3 | 2.3 | Aliphatic |

TABLE 11

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 20 | 64 | AIVALPVAVLAP | 12 | 50.2 | 203.3 | 2.4 | Aliphatic |
| 21 | 65 | IAIVAPVVALAP | 12 | 50.2 | 203.2 | 2.4 | Aliphatic |
| 22 | 81 | AALLPALAALLP | 12 | 57.2 | 204.2 | 2.1 | Aliphatic |
| 23 | 82 | AVVLAPVAAVLP | 12 | 57.3 | 195.0 | 2.4 | Aliphatic |
| 24 | 83 | LAVAAPLALALP | 12 | 41.2 | 195.8 | 2.1 | Aliphatic |
| 25 | 84 | AAVAAPLLLALP | 12 | 41.3 | 195.2 | 2.1 | Aliphatic |
| 26 | 85 | LLVLPAAALAAP | 12 | 57.3 | 195.2 | 2.1 | Aliphatic |
| 27 | 101 | LVALAPVAAVLP | 12 | 57.2 | 203.3 | 2.3 | Aliphatic |
| 20 | 102 | LALAPAALALLP | 12 | 57.2 | 204.2 | 2.1 | Aliphatic |
| 29 | 103 | ALIAAPILALAP | 12 | 57.2 | 204.2 | 2.2 | Aliphatic |
| 30 | 104 | AVVAAPLVLALP | 12 | 41.3 | 203.3 | 2.3 | Aliphatic |
| 31 | 105 | LLALAPAALLAP | 12 | 57.3 | 204.1 | 2.1 | Aliphatic |
| 32 | 121 | AIVALPALALAP | 12 | 50.2 | 195.8 | 2.2 | Aliphatic |
| 33 | 123 | AAIIVPAALLAP | 12 | 50.2 | 195.8 | 2.2 | Aliphatic |
| 34 | 124 | IAVALPALIAAP | 12 | 50.3 | 195.2 | 2.2 | Aliphatic |
| 35 | 141 | AVIVLPALAVAP | 12 | 50.2 | 203.3 | 2.4 | Aliphatic |
| 36 | 143 | AVLAVPAVLVAP | 12 | 57.3 | 195.0 | 2.4 | Aliphatic |
| 37 | 144 | VLAIVPAVALAP | 12 | 50.2 | 203.3 | 2.4 | Aliphatic |
| 38 | 14$ | LLAVVPAVALAP | 12 | 57.2 | 203.3 | 2.3 | Aliphatic |
| 39 | 161 | AVIALPALIAAP | 12 | 57.3 | 195.2 | 2.2 | Aliphatic |
| 40 | 162 | AVVALPAALIVP | 12 | 50.2 | 203.2 | 2.4 | Aliphatic |
| 41 | 163 | LALVLPAALAAP | 12 | 57.3 | 195.2 | 2.1 | Aliphatic |
| 42 | 164 | LAAVLPALLAAP | 12 | 57.3 | 195.2 | 2.1 | Aliphatic |

TABLE 11-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 43 | 165 | ALAVPVALAIVP | 12 | 50.2 | 203.3 | 2.4 | Aliphatic |
| 44 | 182 | ALIAPVVALVAP | 12 | 57.2 | 203.3 | 2.4 | Aliphatic |
| 45 | 183 | LLAAPVVIALAP | 12 | 57.3 | 211.6 | 2.4 | Aliphatic |
| 46 | 184 | LAAIVPAIIAVP | 12 | 50.2 | 211.6 | 2.4 | Aliphatic |
| 47 | 185 | AALVLPLIIAAP | 12 | 41.3 | 220.0 | 2.4 | Aliphatic |
| 48 | 201 | LALAVPALAALP | 12 | 57.2 | 195.2 | 2.1 | Aliphatic |
| 49 | 204 | LIAALPAVAALP | 12 | 57.2 | 195.2 | 2.2 | Aliphatic |
| 50 | 205 | ALALVPAIAALP | 12 | 57.2 | 195.2 | 2.2 | Aliphatic |
| 51 | 221 | AAILAPIVALAP | 12 | 50.2 | 195.2 | 2.2 | Aliphatic |
| 52 | 222 | ALLIAPAAVIAP | 12 | 57.2 | 195.2 | 2.2 | Aliphatic |
| 53 | 223 | AILAVPIAVVAP | 12 | 57.3 | 203.2 | 2.4 | Aliphatic |
| 54 | 224 | ILAAVPIALAAP | 12 | 57.2 | 195.2 | 2.2 | Aliphatic |
| 55 | 225 | VAALLPAAAVLP | 12 | 57.3 | 187.5 | 2.1 | Aliphatic |
| 56 | 241 | AAAVVPVLLVAP | 12 | 57.3 | 195.0 | 2.4 | Aliphatic |
| 57 | 242 | AALLVPALVAAP | 12 | 57.2 | 187.5 | 2.1 | Aliphatic |
| 58 | 243 | AAVLLPVALAAP | 12 | 57.3 | 187.5 | 2.1 | Aliphatic |
| 59 | 245 | AAALAPVLALVP | 12 | 57.2 | 187.5 | 2.1 | Aliphatic |
| 60 | 261 | LVLVPLLAAAAP | 12 | 41.3 | 211.6 | 2.3 | Aliphatic |
| 61 | 262 | ALIAVPAIIVAP | 12 | 50.2 | 211.6 | 2.4 | Aliphatic |
| 62 | 263 | ALAVIPAAAILP | 12 | 54.2 | 195.2 | 2.2 | Aliphatic |
| 63 | 264 | LAAAPVVIVIAP | 12 | 50.2 | 203.3 | 2.4 | Aliphatic |
| 64 | 265 | VLAIAPLLAAVP | 12 | 41.3 | 211.6 | 2.2 | Aliphatic |
| 65 | 281 | ALIVLPAAVAVP | 12 | 50.2 | 203.2 | 2.4 | Aliphatic |
| 66 | 282 | VLAVAPALIVAP | 12 | 50.2 | 203.3 | 2.4 | Aliphatic |
| 67 | 283 | AALLAPALIVAP | 12 | 50.2 | 195.2 | 2.2 | Aliphatic |
| 68 | 284 | ALIAPAVALIVP | 12 | 50.2 | 211.7 | 2.4 | Aliphatic |
| 69 | 285 | AIVLLPAAVVAP | 12 | 50.2 | 203.3 | 2.4 | Aliphatic |

TABLE 12

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 70 | 301 | VIAAPVLAVLAP | 12 | 57.3 | 203.3 | 2.4 | Aliphatic |
| 71 | 302 | LALAPALALLAP | 12 | 57.3 | 204.2 | 2.1 | Aliphatic |
| 72 | 304 | AIILAPIAAIAP | 12 | 57.3 | 204.2 | 2.3 | Aliphatic |
| 73 | 305 | IALAAPILLAAP | 12 | 57.3 | 204.2 | 2.2 | Aliphatic |
| 74 | 321 | IVAVALPALAVP | 12 | 50.2 | 203.3 | 2.2 | Aliphatic |
| 75 | 322 | VVAIVLPALAAP | 12 | 50.2 | 203.3 | 2.3 | Aliphatic |
| 76 | 323 | IVAVALPVALAP | 12 | 50.2 | 203.3 | 2.2 | Aliphatic |

TABLE 12-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 77 | 324 | IVAVALPAALVP | 12 | 50.2 | 203.3 | 2.2 | Aliphatic |
| 78 | 325 | IVAVALPAVALP | 12 | 50.2 | 203.3 | 2.3 | Aliphatic |
| 79 | 341 | IVAVALPAVLAP | 12 | 50.2 | 203.3 | 2.3 | Aliphatic |
| 80 | 342 | VIVALAPAVLAP | 12 | 50.2 | 203.3 | 2.2 | Aliphatic |
| 81 | 343 | IVAVALPALVAP | 12 | 50.2 | 203.3 | 2.2 | Aliphatic |
| 82 | 345 | ALLIVAPVAVAP | 12 | 50.2 | 203.3 | 2.3 | Aliphatic |
| 83 | 361 | AVVIVAPAVIAP | 12 | 50.2 | 195.0 | 2.4 | Aliphatic |
| 84 | 363 | AVLAVAPALIVP | 12 | 50.2 | 203.3 | 2.3 | Aliphatic |
| 85 | 364 | LVAAVAPALIVP | 12 | 50.2 | 203.3 | 2.3 | Aliphatic |
| 86 | 365 | AVIVVAPALLAP | 12 | 50.2 | 203.3 | 2.3 | Aliphatic |
| 87 | 381 | VVAIVLPAVAAP | 12 | 50.2 | 195.0 | 2.4 | Aliphatic |
| 88 | 382 | AAALVIPAILAP | 12 | 54.9 | 195.8 | 2.2 | Aliphatic |
| 89 | 383 | VIVALAPALLAP | 12 | 50.2 | 211.6 | 2.3 | Aliphatic |
| 90 | 384 | VIVAIAPALLAP | 12 | 50.2 | 211.6 | 2.4 | Aliphatic |
| 91 | 385 | IVAIAVPALVAP | 12 | 50.2 | 203.3 | 2.4 | Aliphatuc |
| 92 | 401 | AALAVIPAAILP | 12 | 54,9 | 195.8 | 2.2 | Aliphatic |
| 93 | 402 | ALAAVIPAAILP | 12 | 54.9 | 196.2 | 2.2 | Aliphatic |
| 94 | 403 | AAALVIPAAILP | 12 | 54.9 | 195.8 | 2.2 | Aliphatic |
| 95 | 404 | LAAAVIPAAILP | 12 | 54.9 | 195.2 | 2.2 | Aliphatic |
| 96 | 405 | LAAAVIPVAILP | 12 | 54.9 | 211.7 | 2.4 | Aliphatic |
| 97 | 421 | AAILAAPLIAVP | 12 | 57.3 | 195.8 | 2.2 | Aliphatic |
| 98 | 422 | VVAILAPLLAAP | 12 | 57.3 | 211.7 | 2.4 | Aliphatic |
| 99 | 424 | AVVVAAPVLALP | 12 | 57.3 | 195.0 | 2.4 | Aliphatic |
| 100 | 425 | AVVAIAPVLALP | 12 | 57.3 | 200.3 | 2.4 | Aliphatic |
| 101 | 442 | ALAALVPAVLVP | 12 | 57.3 | 203.3 | 2.3 | Aliphatic |
| 102 | 443 | ALAALVPVALVP | 12 | 57.3 | 203.3 | 2.3 | Aliphatic |
| 103 | 444 | LAAALVPVALVP | 12 | 57.3 | 203.3 | 2.2 | Aliphatic |
| 104 | 445 | ALAALVPALVVP | 12 | 57.3 | 203.3 | 2.3 | Aliphatic |
| 105 | 461 | IAAVIVPAVALP | 12 | 60.2 | 203.3 | 2.4 | Aliphatic |
| 106 | 482 | IAAVLVPAVALP | 12 | 57.3 | 203.3 | 2.4 | Aliphatic |
| 107 | 463 | AVAILVPLLAAP | 12 | 57.3 | 211.7 | 2.4 | Aliphatic |
| 108 | 464 | AVVILVPLAAAP | 12 | 57.3 | 203.3 | 2.4 | Aliphatic |
| 109 | 485 | IAAVIVPVAALP | 12 | 50.2 | 203.3 | 2.4 | Aliphatic |
| 110 | 481 | AIAIAIVPVALP | 12 | 50.2 | 211.6 | 2.4 | Aliphatic |
| 111 | 482 | ILAVAAIPVAVP | 12 | 54.9 | 203.3 | 2.4 | Aliphatic |
| 112 | 483 | ILAAAIIPAALP | 12 | 54.9 | 204.1 | 2.2 | Aliphatic |
| 113 | 484 | LAVVLAAPAIVP | 12 | 50.2 | 203.3 | 2.4 | Aliphatic |
| 114 | 485 | AILAAIVPLAVP | 12 | 50.2 | 211.2 | 2.4 | Aliphatic |

TABLE 12-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 115 | 501 | VIVALAVPALAP | 12 | 50.2 | 203.3 | 2.4 | Aliphatic |
| 116 | 502 | AIVALAVPVLAP | 12 | 50.2 | 203.3 | 2.4 | Aliphatic |
| 117 | 503 | AAIIIVLPAALP | 12 | 50.2 | 220.0 | 2.4 | Aliphatic |
| 118 | 504 | LIVALAVPALAP | 12 | 50.2 | 211.7 | 2.4 | Aliphatic |
| 119 | 505 | AIIIVIAPAAAP | 12 | 50.2 | 195.8 | 2.3 | Aliphatic |

TABLE 13

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 120 | 521 | LAALIVVPAVAP | 12 | 60.2 | 203.3 | 2.4 | Aliphatic |
| 121 | 522 | ALLVIAVPAVAP | 12 | 57.3 | 203.3 | 2.4 | Aliphatic |
| 122 | 524 | AVALIVVPALAP | 12 | 50.2 | 203.3 | 2.4 | Aliphatic |
| 123 | 625 | ALAIVVAPVAVP | 12 | 50.2 | 195.0 | 2.4 | Aliphatic |
| 124 | 541 | LLALIIAPAAAP | 12 | 57.3 | 204.1 | 2.1 | Aliphatic |
| 125 | 542 | ALALIIVPAVAP | 12 | 50.2 | 211.6 | 2.4 | Aliphatic |
| 126 | 543 | LLAALIAPAALP | 12 | 57.3 | 204.1 | 2.1 | Aliphatic |
| 127 | 544 | IVALIVAPAAVP | 12 | 43.1 | 203.3 | 2.4 | Aliphatic |
| 128 | 645 | VVLVLAAPAAVP | 12 | 57.3 | 195.0 | 2.3 | Aliphatic |
| 129 | 561 | AAVAIVLPAVVP | 12 | 50.2 | 195.0 | 2.4 | Aliphatic |
| 130 | 562 | ALIAAIVPALVP | 12 | 50.2 | 211.7 | 2.4 | Aliphatic |
| 131 | 563 | ALAVIVVPALAP | 12 | 50.2 | 203.3 | 2.4 | Aliphatic |
| 132 | 664 | VAIALIVPALAP | 12 | 60.2 | 211.7 | 2.4 | Aliphatic |
| 133 | 565 | VAIVLVAPAVAP | 12 | 50.2 | 195.2 | 2.4 | Aliphatic |
| 134 | 582 | VAVALIVPALAP | 12 | 50.2 | 203.3 | 2.4 | Aliphatic |
| 135 | 583 | AVILALAPIVAP | 12 | 50.2 | 211.6 | 2.4 | Aliphatic |
| 136 | 585 | ALIVAIAPALVP | 12 | 50.2 | 211.6 | 2.4 | Aliphatic |
| 137 | 601 | AAILIAVPIAAP | 12 | 57.3 | 195.2 | 2.3 | Aliphatic |
| 138 | 602 | VIVALAAPVLAP | 12 | 50.2 | 203.3 | 2.4 | Aliphatic |
| 139 | 603 | VLVALAAPVIAP | 12 | 57.3 | 203.3 | 2.4 | Aliphatic |
| 140 | 604 | VALIAVAPAVVP | 12 | 57.3 | 195.0 | 2.4 | Aliphatic |
| 141 | 605 | VIAAVLAPVAVP | 12 | 57.3 | 195.0 | 2.4 | Aliphatic |
| 142 | 622 | ALIVLAAPVAVP | 12 | 50.2 | 203.3 | 2.4 | Aliphatic |
| 143 | 623 | VAAAIALPAIVP | 12 | 50.2 | 187.5 | 2.3 | Aliphatic |
| 144 | 625 | ILAAAAAPLIVP | 12 | 50.2 | 195.8 | 2.2 | Aliphatic |
| 145 | 643 | LALVLAAPAIVP | 12 | 50.2 | 211.6 | 2.4 | Aliphatic |
| 146 | 645 | ALAVVALPAIVP | 12 | 50.2 | 203.3 | 2.4 | Aliphatic |
| 147 | 661 | AAILAPIVAALP | 12 | 50.2 | 195.8 | 2.2 | Aliphatic |

TABLE 13-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 148 | 664 | ILIAIAIPAAAP | 12 | 54.9 | 204.1 | 2.3 | Aliphatic |
| 149 | 665 | LAIVLAAPVAVP | 12 | 50.2 | 203.3 | 2.3 | Aliphatic |
| 150 | 666 | AAIAIIAPAIVP | 12 | 50.2 | 195.2 | 2.3 | Aliphatic |
| 151 | 667 | LAVAIVAPALVP | 12 | 50.2 | 203.3 | 2.3 | Aliphatic |
| 152 | 683 | LAIVLAAPAVLP | 12 | 50.2 | 211.7 | 2.4 | Aliphatic |
| 153 | 684 | AAIVLALPAVLP | 12 | 50.2 | 211.7 | 2.4 | Aliphatic |
| 154 | 685 | ALLVAVLPAALP | 12 | 57.3 | 211.7 | 2.3 | Aliphatic |
| 155 | 686 | AALVAVLPVALP | 12 | 57.3 | 203.3 | 2.3 | Aliphatic |
| 156 | 687 | AILAVALPLLAP | 12 | 57.3 | 220.0 | 2.3 | Aliphatic |
| 157 | 703 | IVAVALVPALAP | 12 | 50.2 | 203.3 | 2.4 | Aliphatic |
| 158 | 705 | IVAVALLPALAP | 12 | 50.2 | 211.7 | 2.4 | Aliphatic |
| 159 | 706 | IVAVALLPAVAP | 12 | 50.2 | 203.3 | 2.4 | Aliphatic |
| 160 | 707 | IVALAVLPAVAP | 12 | 50.2 | 203.3 | 2.4 | Aliphatic |
| 161 | 724 | VAVLAVLPALAP | 12 | 57.3 | 203.3 | 2.3 | Aliphatic |
| 162 | 725 | IAVLAVAPAVLP | 12 | 57.3 | 203.3 | 2.3 | Aliphatic |
| 163 | 725 | LAVAIIAPAVAP | 12 | 57.3 | 187.5 | 2.2 | Aliphatic |
| 164 | 727 | VALAIALPAVLP | 12 | 57.3 | 211.6 | 2.3 | Aliphatic |
| 165 | 743 | AIAIALVPVALP | 12 | 57.3 | 211.6 | 2.4 | Aliphatic |
| 166 | 744 | AAVVIVAPVALP | 12 | 50.2 | 195.0 | 2.4 | Aliphatic |
| 167 | 746 | VAIIVVAPALAP | 12 | 50.2 | 203.3 | 2.4 | Aliphatic |
| 168 | 747 | VALLAIAPALAP | 12 | 57.3 | 195.8 | 2.2 | Aliphatic |
| 169 | 763 | VAVLIAVPALAP | 12 | 67.3 | 203.3 | 2.3 | Aliphatic |

TABLE 14

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 170 | 764 | AVALAVLPAVVP | 12 | 57.3 | 196.0 | 2.3 | Aliphatic |
| 171 | 765 | AVALAVVPAVLP | 12 | 57.3 | 196.0 | 2.3 | Aliphatic |
| 172 | 766 | IVVIAVAPAVAP | 12 | 50.2 | 195.0 | 2.4 | Aliphatic |
| 173 | 767 | IVVAAVVPALAP | 12 | 50.2 | 195.0 | 2.4 | Aliphatic |
| 174 | 783 | IVALVPAVAIAP | 12 | 50.2 | 203.3 | 2.5 | Aliphatic |
| 175 | 784 | VAALPAVALVVP | 12 | 57.3 | 195.0 | 2.4 | Aliphatic |
| 176 | 786 | LVAIAPLAVLAP | 12 | 41.3 | 211.7 | 2.4 | Aliphatic |
| 177 | 787 | AVALVPVIVAAP | 12 | 50.2 | 195.0 | 2.4 | Aliphatic |
| 178 | 788 | AIAVAIAPVALP | 12 | 57.3 | 187.5 | 2.3 | Aliphatic |
| 179 | 803 | AIALAVPVLALP | 12 | 57.3 | 211.7 | 2.4 | Aliphatic |
| 180 | 805 | LVLIAAAPIALP | 12 | 41.3 | 220.0 | 2.4 | Aliphatic |
| 181 | 806 | LVALAVPAAVLP | 12 | 57.3 | 203.3 | 2.3 | Aliphatic |

TABLE 14-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 182 | 807 | AVALAVPALVLP | 12 | 57.3 | 203.3 | 2.3 | Aliphatic |
| 183 | 808 | LVVLAAAPLAVP | 12 | 41.3 | 203.3 | 2.3 | Aliphatic |
| 184 | 809 | LIVLAAPALAAP | 12 | 50.2 | 195.3 | 2.2 | Aliphatic |
| 185 | 810 | VIVLAAPALAAP | 12 | 50.2 | 187.5 | 2.2 | Aliphatic |
| 186 | 811 | AVVLAVPALAVP | 12 | 57.3 | 195.0 | 2.3 | Aliphatic |
| 187 | 824 | LIIVAAAPAVAP | 12 | 50.2 | 187.5 | 2.3 | Aliphatic |
| 188 | 825 | IVAVIVAPAVAP | 12 | 43.2 | 195.0 | 2.5 | Aliphatic |
| 189 | 826 | LVALAAPIIAVP | 12 | 41.3 | 211.7 | 2.4 | Aliphatic |
| 190 | 827 | IAAVLAAPALVP | 12 | 57.3 | 187.5 | 2.2 | Aliphatic |
| 191 | 828 | IALLAAPIIAVP | 12 | 41.3 | 220.0 | 2.4 | Aliphatic |
| 192 | 828 | AALALVAPVIVP | 12 | 50.2 | 203.3 | 2.4 | Aliphatic |
| 193 | 830 | IALVAAPVALVP | 12 | 57.3 | 203.3 | 2.4 | Aliphatic |
| 194 | 831 | IIVAVAPAAIVP | 12 | 43.2 | 203.3 | 2.5 | Aliphatic |
| 195 | 832 | AVAAIVPVIVAP | 12 | 43.2 | 195.0 | 2.5 | Aliphatic |
| 196 | 843 | AVLVLVAPAAAP | 12 | 41.3 | 219.2 | 2.5 | Aliphatic |
| 197 | 844 | VVALLAPLIAAP | 12 | 41.3 | 211.8 | 2.4 | Aliphatic |
| 198 | 845 | AAVVIAPLLAVP | 12 | 41.3 | 203.3 | 2.4 | Aliphatic |
| 199 | 846 | IAVAVAAPLLVP | 12 | 41.3 | 203.3 | 2.4 | Aliphatic |
| 200 | 847 | LVAIVVLPAVAP | 12 | 50.2 | 219.2 | 2.6 | Aliphatic |
| 201 | 848 | AVAIVVLPAVAP | 12 | 50.2 | 195.0 | 2.4 | Aliphatic |
| 202 | 849 | AVILLAPLIAAP | 12 | 57.3 | 220.0 | 2.4 | Aliphatic |
| 203 | 850 | LVIALAAPVALP | 12 | 57.3 | 211.7 | 2.4 | Aliphatic |
| 204 | 851 | VLAVVLPAVALP | 12 | 57.3 | 219.2 | 2.5 | Aliphatic |
| 205 | 852 | VLAVAAPAVLLP | 12 | 57.3 | 203.3 | 2.3 | Aliphatic |
| 206 | 863 | AAVVLLPIIAAP | 12 | 41.3 | 211.7 | 2.4 | Aliphatic |
| 207 | 864 | ALLVIAPAIAVP | 12 | 57.3 | 211.7 | 2.4 | Aliphatic |
| 208 | 865 | AVLVIAVPAIAP | 12 | 57.3 | 203.3 | 2.5 | Aliphatic |
| 209 | 867 | ALLVVIAPLAAP | 12 | 41.3 | 211.7 | 2.4 | Aliphatic |
| 210 | 868 | VLVAAILPAAIP | 12 | 54.9 | 211.7 | 2.4 | Aliphatic |
| 211 | 870 | VLVAAVLPIAAP | 12 | 41.3 | 203.3 | 2.4 | Aliphatic |
| 212 | 872 | VLAAAVLPLVVP | 12 | 41.3 | 219.2 | 2.5 | Aliphatic |
| 213 | 875 | AIAIVVPAVAVP | 12 | 50.2 | 196.0 | 2.4 | Aliphatic |
| 214 | 877 | VAIIAVPAVVAP | 12 | 57.3 | 195.0 | 2.4 | Aliphatic |
| 215 | 878 | IVALVAPAAVVP | 12 | 50.2 | 196.0 | 2.4 | Aliphatic |
| 216 | 879 | AAIVLLPAVVVP | 12 | 50.2 | 219.1 | 2.5 | Aliphatic |
| 217 | 881 | AALIVVPAVAVP | 12 | 50.2 | 195.0 | 2.4 | Aliphatic |

TABLE 14-continued

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 218 | 882 | AIALVVPAVAVP | 12 | 57.3 | 196.0 | 2.4 | Aliphatic |
| 219 | 883 | LAIVPAAIAALP | 12 | 50.2 | 195.8 | 2.2 | Aliphatic |

TABLE 15

| Sequence ID Number | aMTD | Sequences | Length | Rigidity/ Flexibility (II) | Sturctural Feature (AI) | Hydropathy (GRAVY) | Residue Structure |
|---|---|---|---|---|---|---|---|
| 220 | 885 | LVAIAPAVAVLP | 12 | 57.3 | 203.3 | 2.4 | Aliphatic |
| 221 | 887 | VLAVAPAVAVLP | 12 | 57.3 | 185.0 | 2.4 | Aliphatic |
| 222 | 888 | ILAVVAIPAAAP | 12 | 54.9 | 187.5 | 2.3 | Aliphatic |
| 223 | 889 | ILVAAAPIAALP | 12 | 57.3 | 195.8 | 2.2 | Aliphatic |
| 224 | 891 | ILAVAAIPAALP | 12 | 54.9 | 195.8 | 2.2 | Aliphatic |
| 225 | 893 | VIAIPAILAAAP | 12 | 54.9 | 195.8 | 2.3 | Aliphatic |
| 226 | 895 | AIIIVVPAIAAP | 12 | 50.2 | 211.3 | 2.5 | Aliphatic |
| 227 | 896 | AILIVVAPIAAP | 12 | 50.2 | 211.7 | 2.5 | Aliphatic |
| 228 | 897 | AVIVPVAIIAAP | 12 | 50.2 | 203.3 | 2.5 | Aliphatic |
| 229 | 899 | AVVIALPAVVAP | 12 | 57.3 | 195.0 | 2.4 | Aliphatic |
| 230 | 900 | ALVAVIAPVVAP | 12 | 57.3 | 195.0 | 2.4 | Aliphatic |
| 231 | 901 | ALVAVLPAVAVP | 12 | 57.3 | 195.0 | 2.4 | Aliphatic |
| 232 | 902 | ALVAPLLAVAVP | 12 | 41.3 | 203.3 | 2.3 | Aliphatic |
| 233 | 904 | AVLAVVAPVVAP | 12 | 57.3 | 186.7 | 2.4 | Aliphatic |
| 234 | 905 | AVIAVAPLVVAP | 12 | 41.3 | 195.0 | 2.4 | Aliphatic |
| 235 | 906 | AVIALAPVVVAP | 12 | 57.3 | 195.0 | 2.4 | Aliphatic |
| 236 | 907 | VAIALAPVVVAP | 12 | 57.3 | 195.0 | 2.4 | Aliphatic |
| 237 | 908 | VALALAPVVVAP | 12 | 57.3 | 195.0 | 2.3 | Aliphatic |
| 238 | 910 | VAALLPAVVVAP | 12 | 57.3 | 195.0 | 2.3 | Aliphatic |
| 239 | 911 | VALALPAVVVAP | 12 | 57.3 | 195.0 | 2.3 | Aliphatic |
| 240 | 912 | VALLAPAVVVAP | 12 | 57.3 | 195.0 | 2.3 | Aliphatic |
| | | | | 52.6 ± 5.1 | 201.7 ± 7.8 | 2.3 ± 0.1 | |

3-4. Design of the Peptides that Did not Satisfy at Least One Critical Factor

To demonstrate that one embodiment of the present invention of new hydrophobic CPPs—aMTDs, which satisfy all critical factors described above, are correct and rationally designed, the peptides which do not satisfy at least one critical factor have also been designed. Total of 31 rPeptides (rPs) are designed, developed and categorized as follows: no bending peptides, either no proline in the middle as well at the end and/or no central proline; rigid peptides (II<40); too much flexible peptides; aromatic peptides (aromatic ring presences); hydrophobic, with non-aromatic peptides but have amino acids other than A, V, L, I, P or additional proline residues; hydrophilic, but non-aliphatic peptides.

3-4-1. Peptides that do not Satisfy the Bending Potential

Table 16 shows the peptides that do not have any proline in the middle (at 5', 6', 7' or 8') and at the end of the sequences. In addition, Table 16 describes the peptides that do not have proline in the middle of the sequences. All these peptides are supposed to have no-bending potential.

TABLE 16

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| No Bending Peptides (No Praline at 5, 6, 7 or 8 and/or 12) | 931 | AVLIAPAILAAA | 12 | 6 | 57.3 | 204.2 | 2.5 |
| | 936 | ALLILAAAVAAP | 12 | 12 | 41.3 | 204.2 | 2.4 |
| | 152 | LAAAVAAVAALL | 12 | None | 9.2 | 204.2 | 2.7 |
| | 27 | LAIVAAAAALVA | 12 | None | 2.1 | 204.2 | 2.8 |
| | 935 | ALLILPAAAVAA | 12 | 6 | 57.3 | 204.2 | 2.4 |
| | 670 | ALLILAAAVAAL | 12 | None | 25.2 | 236.6 | 2.3 |
| | 934 | LILAPAAVVAAA | 12 | 5 | 57.3 | 195.8 | 2.5 |
| | 37 | TTCSQQQVCTNG | 12 | None | 53.1 | 0.0 | -1.1 |
| | 16 | NNSCTTYTNGSQ | 12 | None | 47.4 | 0.0 | -1.4 |
| | 113 | PVAVALLIAVPP | 12 | 1, 11, 12 | 57.3 | 195.0 | 2.1 |

3-4-2. Peptides that do not Satisfy the Rigidity/Flexibility

To prove that rigidity/flexibility of the sequence is a crucial critical factor, rigid (Avg. II: 21.8±6.6) and too high flexible sequences (Avg. II: 82.3±21.0) were also designed. Rigid peptides that instability index is much lower than that of new aMTDs (II: 41.3 to 57.3, Avg. II: 53.3±5.7) are shown in Table 17. Bending, but too high flexible peptides that II is much higher than that of new aMTDs are also provided in Table 18.

TABLE 17

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Rigid Peptides (II < 50) | 226 | ALVAAIPALAIP | 12 | 6 | 20.4 | 195.8 | 2.2 |
| | 6 | VIAMIPAAFWVA | 12 | 6 | 15.7 | 146.7 | 2.2 |
| | 750 | LAIAAIAPLAIP | 12 | 8, 12 | 22.8 | 204.2 | 2.2 |
| | 26 | AAIALAAPLAIV | 12 | 8 | 18.1 | 204.2 | 2.5 |
| | 527 | LVLAAVAPIAIP | 12 | 8, 12 | 22.8 | 211.7 | 2.4 |
| | 466 | IIAAAAPLAIIP | 12 | 7, 12 | 22.8 | 204.2 | 2.3 |
| | 167 | VAIAIPAALAIP | 12 | 6, 12 | 20.4 | 195.8 | 2.3 |
| | 246 | VVAVPLLVAFAA | 12 | 5 | 25.2 | 195.0 | 2.7 |
| | 426 | AAALAIPLAIIP | 12 | 7, 12 | 4.37 | 204.2 | 2.2 |
| | 606 | AAAIAAIPIIIP | 12 | 8, 12 | 4.4 | 204.2 | 2.4 |
| | 66 | AGVLGGPIMGVP | 12 | 7, 12 | 35.5 | 121.7 | 1.3 |
| | 248 | VAAIVPIAALVP | 12 | 6, 12 | 34.2 | 203.3 | 2.5 |
| | 227 | LAAIVPIAAAVP | 12 | 6, 12 | 34.2 | 187.5 | 2.2 |
| | 17 | GGCSAPQTTCSN | 12 | 6 | 51.6 | 8.3 | -0.5 |
| | 67 | LDAEVPLADDVP | 12 | 6, 12 | 34.2 | 130.0 | 0.3 |

TABLE 18

| Group | rPeptide ID | Sequences | Length | Proline Position (PP) | Rigidity/ Flexibility (II) | Sturctural Feature (AI) | Hydropathy (GARVY) |
|---|---|---|---|---|---|---|---|
| Bending Peptides but Too High Flexibility | 692 | PAPLPPVVILAV | 12 | 1, 3, 5, 6 | 105.5 | 186.7 | 1.8 |
| | 69 | PVAVLPPAALVP | 12 | 1, 6, 7, 12 | 89.4 | 162.5 | 1.6 |
| | 390 | VPLLVPVVPVVP | 12 | 2, 6, 9, 12 | 105.4 | 210.0 | 2.2 |
| | 350 | VPILVPVVPVVP | 12 | 2, 6, 9, 12 | 121.5 | 210 0 | 2.2 |
| | 331 | VPVLVPLVPVVR | 12 | 2, 6, 9, 12 | 105.4 | 210.0 | 2.2 |
| | 9 | VALVPAALILPP | 12 | 5, 11, 12 | 89.4 | 203.3 | 2.1 |
| | 68 | VAPVLPPAPLVP | 12 | 3, 6, 9, 12 | 105.5 | 162 5 | 1.6 |
| | 349 | VPVLVPVVPVVP | 12 | 2, 6, 9, 12 | 121.5 | 201.6 | 2.2 |
| | 937 | VPVLVPLPVPVV | 12 | 2, 6, 8, 10 | 121.5 | 210.0 | 2.2 |
| | 938 | VPVLLPVVVPVP | 12 | 2, 6, 10, 12 | 121.5 | 210.0 | 2.2 |
| | 329 | LPVLVPVVPVVP | 12 | 2, 6, 9, 12 | 121.5 | 210.0 | 2.2 |
| | 49 | VVPAAPAVPVVP | 12 | 3, 6, 9, 12 | 121.5 | 145.8 | 1.7 |
| | 772 | LPVAPVIPIIVP | 12 | 2, 5, 8, 12 | 79.9 | 210.8 | 2.1 |
| | 210 | ALIALPALPALP | 12 | 6, 9, 12 | 89.4 | 195.8 | 1.8 |
| | 28 | AVPLLPLVPAVP | 12 | 3, 6, 9, 12 | 89.4 | 186.8 | 1.8 |
| | 693 | AAPVLPVAVPIV | 12 | 3, 6, 10 | 82.3 | 186.7 | 2.1 |
| | 169 | VALVAPALILAP | 12 | 6, 12 | 73.4 | 211.7 | 2.4 |
| | 29 | VLPPLPVLPVLP | 12 | 3, 4, 6, 9, 12 | 121.5 | 202.5 | 1.7 |
| | 190 | AAILAPAVIAPP | 12 | 6, 11, 12 | 89.4 | 163.3 | 1.8 |

3-4-3. Peptides that do not Satisfy the Structural Features

New hydrophobic CPPs—aMTDs are consisted with only hydrophobic and aliphatic amino acids (A, V, L, I and P) with average ranges of the indexes—AI: 180 to 220 and GRAVY: 2.1 to 2.6 (Table 9). Based on the structural indexes, the peptides which contain an aromatic residue (W, F or Y) are shown in Table 19 and the peptides which are hydrophobic with non-aromatic sequences but have amino acids residue other than A, V, L, I, P or additional proline residues are designed (Table 20). Finally, hydrophilic and/or bending peptides which are consisted with non-aliphatic amino acids are shown in Table 21.

flexible peptides are 24; aromatic peptides (aromatic ring presences) are 27; hydrophobic, but non-aromatic peptides are 23; and hydrophilic, but non-aliphatic peptides are 18.

4. Preparation of Recombinant Report Proteins Fused to aMTDs and rPeptides

Recombinant proteins fused to aMTDs and others [rPeptides, reference hydrophobic CPP sequences (MTM and MTD)] were expressed in a bacterial system, purified with single-step affinity chromatography and prepared as soluble proteins in physiological condition. These recombinant proteins have been tested for the ability of their cell-permeability by utilizing flow cytometry and laser scanning confocal microscopy.

TABLE 19

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Aromatic Peptides (Aromatic Ring Presences) | 30 | WFFAGPIMLIWP | 12 | 6, 12 | 9.2 | 105.1 | 1.4 |
| | 33 | AAAILAPAFLAV | 12 | 7 | 57.3 | 171.7 | 2.4 |
| | 131 | WIIAPVWLAWIA | 12 | 5 | 51.6 | 179.2 | 1.9 |
| | 922 | WYVIFVLPLVVP | 12 | 8, 12 | 41.3 | 194.2 | 2.2 |
| | 71 | FMWMWFPFMWYP | 12 | 7, 12 | 71.3 | 0.0 | 0.6 |
| | 921 | IWWPVVLPLVVP | 12 | 8, 12 | 41.3 | 194.2 | 2.2 |

TABLE 20

| Group | rPeptide ID | Sequences | Length | Proline Position (PP) | Rigidity/ Flexibility (II) | Sturctural Feature (AI) | Hydropathy (GARVY) |
|---|---|---|---|---|---|---|---|
| Hydrophobic but Non Aromatic Peptides | 436 | VVMLVVPAVMLP | 12 | 7, 12 | 57.3 | 194.2 | 2.6 |
| | 138 | PPAALLAILAVA | 12 | 1, 2 | 57.3 | 195.8 | 2.2 |
| | 77 | PVALVLVALVAP | 12 | 1, 12 | 41.3 | 219.2 | 2.5 |
| | 577 | MLMIALVPMIAV | 12 | 8 | 18.9 | 195.0 | 2.7 |
| | 97 | ALLAAPPALLAL | 12 | 6, 7 | 57.3 | 204.2 | 2.1 |
| | 214 | ALIVAPALMALP | 12 | 6, 12 | 60.5 | 187.5 | 2.2 |
| | 59 | AVLAAPVVAALA | 12 | 6 | 41.3 | 187.5 | 2.5 |
| | 54 | LAVAAPPVVALL | 12 | 6, 7 | 57.3 | 203.3 | 2.3 |

TABLE 21

| Group | rPeptide ID | Sequences | Length | Proline Position (PP) | Rigidity Flexibility (II) | Structural Feature (AI) | Hydropathy (GRAVY) |
|---|---|---|---|---|---|---|---|
| Hydrophilic Peptides but Non Aliphatic | 949 | SGNSCOOCGNSS | 12 | None | 41.7 | 0.0 | -1.1 |
| | 39 | CYNTSPCTGCCY | 12 | 6 | 52.5 | 0.0 | 0.0 |
| | 19 | YVSCCTYTNGSO | 12 | None | 47.7 | 0.0 | -1.0 |
| | 947 | CYYNOOSNNNNO | 12 | None | 59.6 | 0.0 | -2.4 |
| | 139 | TGSTNSPTCTST | 12 | 7 | 53.4 | 0.0 | -0.7 |
| | 18 | NYCCTPTTNGOS | 12 | 6 | 47.9 | 0.0 | -0.9 |
| | 20 | NYCNTCPTYGOS | 12 | 7 | 47.4 | 0.0 | -0.9 |
| | 635 | GSTGGSOONNOY | 12 | None | 31.9 | 0.0 | -1.9 |
| | 40 | TYNTSCTPGTCY | 12 | 8 | 49.4 | 0.0 | -0.6 |
| | 57 | ONNCNTSSOGGG | 12 | None | 52.4 | 0.0 | -1.6 |
| | 159 | CYSGSTSONOPP | 12 | 11, 12 | 51.0 | 0.0 | -1.3 |
| | 700 | GTSNTCOSNONS | 12 | None | 19.1 | 0.0 | -1.6 |
| | 38 | YYNOSTCGGOCY | 12 | None | 53.3 | 0.0 | -1.0 |

3-5. Summary of Newly Designed Peptides

Total of 457 sequences have been designed based on the critical factors. Designed potentially best aMTDs (hydrophobic, flexible, bending, aliphatic and 12-A/a length peptides) that do satisfy all range/feature of critical factors are 316. Designed rPeptides that do not satisfy at least one of the critical factors are 141 that no bending peptide sequences are 26; rigid peptide (II<40) sequences are 23; too much 4-1. Selection of Cargo Protein for Recombinant Proteins Fused to Peptide Sequences For clinical/non-clinical application, aMTD-fused cargo materials would be biologically active molecules that could be one of the following: enzymes, transcription factors, toxic, antigenic peptides, antibodies and antibody fragments. Furthermore, biologically active molecules could be one of these following macromolecules: enzymes, hormones, carriers, immunoglobulin, membrane-bound proteins, transmembrane proteins, internal proteins, external proteins, secreted proteins, virus proteins, native proteins, glycoproteins, fragmented proteins, disulfide bonded proteins, recombinant proteins, chemically modified proteins and prions. In addition, these biologically active molecules could be one of the following: nucleic acid, coding nucleic acid sequence, mRNAs, antisense RNA molecule, carbohydrate, lipids and glycolipids.

According to these pre-required conditions, a non-functional cargo to evaluate aMTD-mediated protein uptake has been selected and called as Cargo A (CRA) that should be soluble and non-functional. The domain (A/a 289 to 840; 184 A/a length) is derived from protein S (Genbank ID: CP000113.1).

4-2. Construction of Expression Vector and Preparation of Recombinant Proteins

Coding sequences for recombinant proteins fused to each aMTD are cloned NdeI (5') and SalI (3') in pET-28a(+) (Novagen, Darmstadt, Germany) from PCR-amplified DNA segments. PCR primers for the recombinant proteins fused to aMTD and rPeptides are represented by SEQ ID NOs: 481 to 797. Structure of the recombinant proteins is displayed in FIG. 1.

The recombinant proteins were forcedly expressed in *E. coli* BL21 (DE3) cells grown to an $OD_{600}$ of 0.6 and induced for 2 hours with 0.7 mM isopropyl-β-D-thiogalactopyranoside (IPTG). The proteins were purified by $Ni^{2}+$ affinity chromatography as directed by the supplier (Qiagen, Hilden, Germany) in natural condition. After the purification, purified proteins were dissolved in a physiological buffer such as DMEM medium.

| | |
|---|---|
| ►Potentially Best aMTDs (Hydrophobic, Flexible, Bending, Aliphatic & Helical) | 240 |
| ►Random Peptides | 31 |
| No Bending Peptides (No Proline at 5 or 6 and/or 12) | 02 |
| No Bending Peptides (No Central Proline) | 01 |
| Rigid Peptides (II < 50) | 09 |
| Too Much Flexible Peptides | 09 |
| Aromatic Peptides (Aromatic Ring Presences) | 01 |
| Hydrophobic, But Non-Aromatic Peptides | 02 |
| Hydrophilic, But Non-Aliphatic Peptides | 07 |

4-3. Expression of aMTD- or Random Peptide (rP)-Fused Recombinant Proteins

One embodiment of the present invention also relates to the development method of aMTD sequences having cell-permeability. Using the standardized six critical factors, 316 aMTD sequences have been designed. In addition, 141 rPeptides are also developed that lack one of these critical factors: no bending peptides: i) absence of proline both in the middle and at the end of sequence or ii) absence of proline either in the middle or at the end of sequence, rigid peptides, too much flexible peptides, aromatic peptides (aromatic ring presence), hydrophobic but non-aromatic peptides, and hydrophilic but non-aliphatic peptides (Table 22).

These rPeptides are devised to be compared and contrasted with aMTDs in order to analyze structure/sequence activity relationship (SAR) of each critical factor with regard to the peptides' intracellular delivery potential. All peptide (aMTD or rPeptide)-containing recombinant proteins have been fused to the CRA to enhance the solubility of the recombinant proteins to be expressed, purified, prepared and analyzed.

These designed 316 aMTDs and 141 rPeptides fused to CRA were all cloned (FIG. 2) and tested for inducible expression in *E. coli* (FIG. 3). Out of these peptides, 240 aMTDs were inducibly expressed, purified and prepared in soluble form (FIG. 4). In addition, 31 rPeptides were also prepared as soluble form (FIG. 4).

To prepare the proteins fused to rPeptides, 60 proteins were expressed that were 10 out of 26 rPeptides in the category of no bending peptides (Table 16); 15 out of 23 in the category of rigid peptides [instability index (II)<40] (Table 17); 19 out of 24 in the category of too much flexible peptides (Table 18); 6 out of 27 in the category of aromatic peptides (Table 19); 8 out of 23 in the category of hydrophobic but non-aromatic peptides (Table 20); and 12 out of 18 in the category of hydrophilic but non-aliphatic peptides (Table 21).

4-4. Quantitative Cell-Permeability of aMTD-Fused Recombinant Proteins

The aMTDs and rPeptides were fluorescently labeled and compared based on the critical factors for cell-permeability by using flow cytometry and confocal laser scanning microscopy (FIGS. 5 to 8). The cellular uptake of the peptide-fused non-functional cargo recombinant proteins could quantitatively be evaluated in flow cytometry, while confocal laser scanning microscopy allows intracellular uptake to be assessed visually. The analysis included recombinant proteins fused to a negative control [rP38] that has opposite characteristics (hydrophilic and aromatic sequence: YYNQSTCGGQCY) to the aMTDs (hydrophobic and aliphatic sequences). Relative cell-permeability (relative fold) of aMTDs to the negative control was also analyzed (Table 23 and FIG. 9).

Table 23 shows the Comparison Analysis of Cell-Permeability of aMTDs with a Negative Control (A: rP38).

TABLE 23

| | Negative Control rP38 |
|---|---|
| aMTD<br>The Average of 240 aMTDs | 19.6 ± 1.6*<br>(Best: 164.2) |

*Relative Fold (aMTD in Geo Mean in its comparison to rP38)

Relative cell-permeability (relative fold) of aMTDs to the reference CPPs [B: MTM12 (AAVLLPVLLAAP), C: MTD85 (AVALLILAV)] was also analyzed (Tables 40 and 41)

Table 24 shows Comparison Analysis of Cell-Permeability of aMTDs with a Reference CPP (B: MTM12).

TABLE 24

| | MTM12 |
|---|---|
| aMTD<br>The Average of 240 aMTDs | 13.1 ± 1.1*<br>(Best: 109.9) |

*Relative Fold (aMTD in Geo Mean in its comparison to MTM12)

Table 25 shows the Comparison Analysis of Cell-Permeability of aMTDs with a Reference CPP (C: MTD85).

TABLE 25

| | MTD85 |
|---|---|
| aMTD<br>The Average of 240 aMTDs | 6.6 ± 5*<br>(Best: 55.5) |

*Relative Fold (aMTD in Geo Mean in its comparison to MTD85)

Geometric means of negative control (histidine-tagged rP38-fused CRA recombinant protein) subtracted by that of naked protein (histidine-tagged CRA protein) lacking any peptide (rP38 or aMTD) was standardized as relative fold of 1. Relative cell-permeability of 240 aMTDs to the negative control (A type) was significantly increased by up to 164 fold, with average increase of 19.6±1.6 (Tables 26 to 31).

TABLE 26

| Sequence ID Number | aMTD | Sequences | Length | Proline Position (PP) | Rigidity/ Flexibility (II) | Sturctural Feature (AI) | Hydropathy (GRAVY) | Relative Ratio (Fold) A | B | C |
|---|---|---|---|---|---|---|---|---|---|---|
| 1 | 899 | AVVIALPAVVAP | 12 | 7 | 57.3 | 195.0 | 2.4 | 164.2 | 109.9 | 55.5 |
| 2 | 908 | VALALAPVVVAP | 12 | 7 | 57.3 | 195.0 | 2.3 | 150.6 | 100.8 | 50.9 |
| 3 | 910 | VAALLPAVVVAP | 12 | 6 | 57.3 | 195.0 | 2.3 | 148.5 | 99.4 | 50.2 |
| 4 | 810 | VIVLAAPALAAP | 12 | 7 | 50.2 | 187.5 | 2.2 | 120.0 | 80.3 | 40.6 |
| 5 | 804 | AVLAVVAPVVAP | 12 | 8 | 57.3 | 186.7 | 2.4 | 105.7 | 70.2 | 35.8 |
| 6 | 321 | IVAVALPALAVP | 12 | 7 | 50.2 | 203.3 | 2.3 | 97.8 | 65.2 | 32.9 |
| 7 | 851 | VLAVVLPAVALP | 12 | 7 | 57.3 | 219.2 | 2.5 | 96.6 | 64.7 | 32.7 |
| 8 | 911 | VALALPAVVVAP | 12 | 6 | 57.3 | 195.2 | 2.3 | 84.8 | 56.2 | 28.7 |
| 9 | 852 | VLAVAAPAVLLP | 12 | 7 | 57.3 | 203.3 | 2.3 | 84.6 | 56.6 | 28.6 |
| 10 | 803 | AIALAVPVLALP | 12 | 7 | 57.3 | 211.7 | 2.4 | 74.7 | 50.0 | 25.3 |
| 11 | 888 | ILAVVAIPAAAP | 12 | 8 | 54.9 | 187.5 | 2.3 | 71.0 | 47.5 | 24.0 |
| 12 | 825 | IVAVIVAPAVAP | 12 | 8 | 43.2 | 195.0 | 2.6 | 69.7 | 46.6 | 23.6 |
| 13 | 895 | AIIIVVPAIAAP | 12 | 7 | 50.2 | 211.7 | 2.2 | 60.2 | 40.7 | 20.6 |
| 14 | 896 | AILIVVAPIAAP | 12 | 8 | 50.2 | 211.7 | 2.5 | 57.5 | 38.5 | 19.4 |
| 15 | 727 | VALA1ALPAVLP | 12 | 8 | 57.3 | 211.6 | 2.3 | 54.7 | 36.1 | 18.5 |
| 16 | 603 | VLVALAAPVIAP | 12 | 8 | 57.3 | 203.3 | 2.4 | 54.1 | 36.1 | 18.2 |
| 17 | 847 | LVAIVVLPAVAP | 12 | 8 | 50.2 | 219.2 | 2.6 | 50.2 | 33.4 | 12.9 |
| 18 | 826 | LVALAAPIIAVP | 12 | 7 | 41.2 | 211.7 | 2.4 | 49.2 | 32.2 | 16.6 |
| 19 | 724 | VAVLAVLPALAP | 12 | 8 | 57.3 | 203.2 | 2.3 | 47.5 | 31.8 | 16.1 |
| 20 | 563 | ALAVIVVPALAP | 12 | 8 | 50.2 | 203.3 | 2.4 | 47.1 | 31.4 | 15.9 |
| 21 | 811 | AVVLAVPALAVP | 12 | 7 | 57.3 | 195.0 | 2.3 | 46.5 | 31.1 | 15.7 |
| 22 | 831 | IIVAVAPAAIVP | 12 | 7 | 43.2 | 203.3 | 2.5 | 46.3 | 31.0 | 15.7 |
| 23 | 829 | AALALVAPVIVP | 12 | 8 | 50.2 | 203.3 | 2.4 | 44.8 | 30.0 | 15.2 |
| 24 | 891 | ILAVAAIPAALP | 12 | 8 | 54.9 | 195.2 | 2.2 | 44.7 | 29.9 | 15.1 |
| 25 | 905 | AVIAVAPLVVAP | 12 | 7 | 41.3 | 195.0 | 2.4 | 44.0 | 29.5 | 14.9 |
| 26 | 664 | VAIALIVPALAP | 12 | 8 | 50.2 | 211.7 | 2.4 | 43.6 | 29.1 | 14.7 |
| 27 | 124 | IAVALPALIAAP | 12 | 6 | 50.3 | 195.2 | 2.2 | 43.6 | 29.0 | 14.7 |
| 28 | 827 | IAAVLAAPALVP | 12 | 8 | 57.3 | 187.5 | 2.2 | 43.0 | 28.2 | 14.6 |
| 29 | 2 | AAAVPLLAVVVP | 12 | 5 | 41.2 | 195.0 | 2.4 | 40.9 | 27.2 | 13.8 |
| 30 | 385 | IVAIAVPALVAP | 12 | 7 | 50.2 | 203.3 | 2.4 | 38.8 | 25.9 | 13.1 |
| 31 | 828 | IALLAAPIIAVP | 12 | 7 | 41.3 | 220.0 | 2.4 | 36.8 | 24.6 | 12.4 |
| 32 | 806 | LVALAVPAAVLP | 12 | 7 | 57.3 | 203.3 | 2.3 | 36.7 | 24.2 | 12.4 |

TABLE 26-continued

| Sequence ID Number | aMTD | Sequences | Length | Proline Position (PP) | Rigidity/ Flexibility (II) | Sturctural Feature (AI) | Hydropathy (GRAVY) | Relative Ratio (Fold) A | B | C |
|---|---|---|---|---|---|---|---|---|---|---|
| 33 | 845 | AAVVIAPLLAVP | 12 | 7 | 41.3 | 203.3 | 2.4 | 35.8 | 24.0 | 12.1 |
| 34 | 882 | AIALVVPAVAVP | 12 | 7 | 57.3 | 195.0 | 2.4 | 35.0 | 23.4 | 11.8 |
| 35 | 545 | VVLVLAAPAAVP | 12 | 8 | 57.2 | 195.0 | 2.3 | 34.6 | 23.1 | 11.7 |
| 36 | 161 | AVIALPALIAAP | 12 | 6 | 57.3 | 195.8 | 2.2 | 34.5 | 23.0 | 11.6 |
| 37 | 481 | AIAIAIVPVALP | 12 | 8 | 50.2 | 211.6 | 2.4 | 34.3 | 23.0 | 11.6 |
| 38 | 900 | ALVAVIAPVVAP | 12 | 8 | 57.3 | 195.0 | 2.4 | 34.3 | 22.9 | 11.6 |
| 39 | 223 | AILAVPIAVVAP | 12 | 6 | 57.3 | 203.2 | 2.4 | 33.0 | 22.1 | 11.2 |
| 40 | 824 | LIIVAAAPAVAP | 12 | 8 | 50.2 | 187.5 | 2.3 | 32.8 | 21.9 | 11.1 |
| 41 | 562 | ALIAAIVPALVP | 12 | 8 | 50.2 | 211.7 | 2.4 | 32.7 | 21.2 | 11.0 |
| 42 | 222 | ALLIARAAVIAP | 12 | 6 | 57.3 | 195.2 | 2.2 | 32.6 | 21.7 | 11.0 |
| 43 | 61 | VAALPVLLAALP | 12 | 5 | 57.3 | 211.7 | 2.3 | 31.2 | 20.2 | 10.5 |
| 44 | 582 | VAVALIVPALAP | 12 | 8 | 50.2 | 203.3 | 2.4 | 30.2 | 20.4 | 10.3 |
| 45 | 889 | ILVAAAPIAALP | 12 | 7 | 57.3 | 195.8 | 2.2 | 30.3 | 20.3 | 10.3 |
| 46 | 787 | AVALVPVIVAAP | 12 | 6 | 50.2 | 195.0 | 2.4 | 29.3 | 19.6 | 9.9 |
| 47 | 703 | IVAVALVPALAP | 12 | 8 | 50.2 | 203.3 | 2.4 | 29.2 | 19.5 | 9.9 |
| 48 | 705 | IVAVALLPALAP | 12 | 8 | 50.2 | 211.7 | 2.4 | 28.6 | 19.1 | 9.7 |
| 49 | 885 | LVAIAPAVAVLP | 12 | 6 | 57.3 | 203.3 | 2.4 | 28.3 | 19.0 | 9.6 |
| 50 | 3 | AALLVPAAVLAP | 12 | 6 | 57.3 | 187.5 | 2.1 | 27.0 | 18.0 | 9.1 |
| 51 | 601 | AAILIAVPIAAP | 12 | 8 | 57.3 | 195.8 | 2.3 | 26.8 | 17.9 | 9.0 |
| 52 | 843 | AVLVLVAPAAAP | 12 | 8 | 41.3 | 219.2 | 2.5 | 26.4 | 17.7 | 8.9 |
| 53 | 403 | AAALVIPAAILP | 12 | 7 | 54.9 | 195.8 | 2.2 | 25.2 | 16.8 | 8.5 |
| 54 | 544 | IVALIVAPAAVP | 12 | 8 | 43.1 | 203.3 | 2.4 | 23.4 | 15.6 | 7.9 |
| 55 | 522 | ALLVIAVPAVAP | 12 | 8 | 57.3 | 203.3 | 2.4 | 22.7 | 15.2 | 7.7 |

TABLE 27

| Sequence ID Number | aMTD | Sequences | Length | Proline Position (PP) | Rigidity/ Flexibility (II) | Sturctural Feature (AI) | Hydropathy (GRAVY) | Relative Ration (Fold) A | B | C |
|---|---|---|---|---|---|---|---|---|---|---|
| 56 | 805 | LVLIAAAPIALP | 12 | 8 | 41.3 | 220.0 | 2.4 | 22.3 | 14.9 | 7.6 |
| 57 | 464 | AVVILVPLAAAP | 12 | 7 | 57.3 | 203.3 | 2.4 | 22.3 | 14.9 | 7.5 |
| 58 | 405 | LAAAVIPVAILP | 12 | 7 | 54.9 | 211.7 | 2.4 | 22.2 | 14.8 | 7.5 |
| 59 | 747 | VALLAIAPALAP | 12 | 8 | 57.3 | 195.8 | 2.2 | 22.0 | 14.8 | 7.5 |
| 60 | 501 | VIVALAVPALAP | 12 | 8 | 50.2 | 203.3 | 2.4 | 21.5 | 14.4 | 7.3 |
| 61 | 661 | AAILAPIVAALP | 12 | 6 | 50.2 | 195.8 | 2.2 | 21.4 | 14.3 | 7.2 |
| 62 | 786 | LVAIAPLAVLAP | 12 | 6 | 41.3 | 211.7 | 2.4 | 21.2 | 14.2 | 7.2 |
| 63 | 625 | ILAAAAAPLIVP | 12 | 8 | 50.2 | 195.8 | 2.2 | 20.9 | 13.9 | 7.0 |
| 64 | 442 | ALAALVPAVLVP | 12 | 7 | 57.3 | 203.3 | 2.3 | 20.4 | 13.6 | 6.9 |
| 65 | 912 | VALLAPAVVVAP | 12 | 6 | 57.3 | 195.0 | 2.3 | 19.9 | 13.3 | 6.7 |

TABLE 27-continued

| Sequence ID Number | aMTD | Sequences | Length | Proline Position (PP) | Rigidity/ Flexibility (II) | Sturctural Feature (AI) | Hydropathy (GRAVY) | Relative Ration (Fold) A | B | C |
|---|---|---|---|---|---|---|---|---|---|---|
| 66 | 165 | ALAVPVALAIVP | 12 | 5 | 50.2 | 203.3 | 2.4 | 19.8 | 13.2 | 6.7 |
| 67 | 422 | VVAILAPLLAAP | 12 | 7 | 57.3 | 211.7 | 2.4 | 19.6 | 13.1 | 6.6 |
| 68 | 686 | AALVAVLPVALP | 12 | 8 | 57.3 | 203.3 | 2.3 | 19.5 | 13.1 | 6.6 |
| 69 | 343 | IVAVALPALVAP | 12 | 7 | 50.2 | 203.3 | 2.3 | 19.4 | 12.9 | 6.5 |
| 70 | 323 | IVAVALPVALAP | 12 | 7 | 50.2 | 203.3 | 2.3 | 19.1 | 12.8 | 6.4 |
| 71 | 461 | IAAVIVPAVALP | 12 | 7 | 50.2 | 203.3 | 2.4 | 19.0 | 12.7 | 6.4 |
| 72 | 21 | AVALLPALLAVP | 12 | 6 | 57.3 | 211.7 | 2.3 | 18.9 | 12.6 | 6.4 |
| 73 | 404 | LAAAVIPAAILP | 12 | 7 | 54.9 | 195.8 | 2.2 | 18.9 | 12.6 | 6.4 |
| 74 | 261 | LVLVPLLAAAAP | 12 | 5 | 41.3 | 211.6 | 2.3 | 18.5 | 12.3 | 6.2 |
| 75 | 524 | AVALIVVPALAP | 12 | 8 | 50.2 | 203.3 | 2.4 | 18.3 | 12.2 | 6.2 |
| 76 | 225 | VAALLPAAAVLP | 12 | 6 | 57.2 | 187.5 | 2.1 | 18.3 | 12.2 | 6.2 |
| 77 | 264 | LAAAPVVIVIAP | 12 | 5 | 50.2 | 203.3 | 2.4 | 18.2 | 12.1 | 6.1 |
| 78 | 1 | AAALAPVVLALP | 12 | 6 | 57.3 | 187.5 | 2.1 | 17.7 | 11.8 | 6.0 |
| 79 | 382 | AAALVIPAILAP | 12 | 7 | 54.9 | 195.8 | 2.2 | 17.7 | 11.8 | 6.0 |
| 80 | 463 | AVAILVPLLAAP | 12 | 7 | 57.3 | 211.7 | 2.4 | 17.6 | 11.7 | 5.9 |
| 81 | 322 | VVAIVLPALAAP | 12 | 7 | 50.2 | 203.3 | 2.3 | 17.6 | 11.7 | 5.9 |
| 82 | 503 | AAIIIVLPAALP | 12 | 8 | 50.2 | 220.0 | 2.4 | 17.6 | 11.8 | 5.9 |
| 83 | 870 | VLVAAVLPIAAP | 12 | 8 | 41.3 | 203.3 | 2.4 | 16.6 | 11.1 | 5.6 |
| 84 | 241 | AAAVVPVLLVAP | 12 | 6 | 57.3 | 195.0 | 2.4 | 16.6 | 11.0 | 5.6 |
| 85 | 726 | LAVAIIAPAVAP | 12 | 8 | 57.3 | 187.5 | 2.2 | 16.5 | 11.0 | 5.6 |
| 86 | 341 | IVAVALPAVLAP | 12 | 7 | 50.2 | 203.3 | 2.3 | 16.4 | 10.9 | 5.5 |
| 87 | 542 | ALALIIVPAVAP | 12 | 8 | 50.2 | 211.6 | 2.4 | 16.2 | 10.8 | 5.5 |
| 88 | 361 | AVVIVAPAVIAP | 12 | 7 | 50.2 | 195.0 | 2.4 | 16.0 | 10.7 | 5.4 |
| 89 | 224 | ILAAVPIALAAP | 12 | 6 | 57.3 | 195.8 | 2.2 | 15.8 | 10.6 | 5.3 |
| 90 | 482 | ILAVAAIPVAVP | 12 | 8 | 54.9 | 203.3 | 2.4 | 15.8 | 10.6 | 5.3 |
| 91 | 64 | AIVALPVAVLAP | 12 | 6 | 50.2 | 203.3 | 2.4 | 15.8 | 10.6 | 5.3 |
| 92 | 484 | LAVVLAAPAIVP | 12 | 8 | 50.2 | 203.3 | 2.4 | 15.6 | 10.4 | 5.3 |
| 93 | 868 | VLVAAILPAAIP | 12 | 8 | 54.9 | 211.7 | 2.4 | 14.9 | 10.0 | 5.0 |
| 94 | 541 | LLALIIAPAAAP | 12 | 8 | 57.3 | 204.1 | 2.1 | 14.8 | 9.9 | 5.0 |
| 95 | 666 | AAIAIIAPAIVP | 12 | 8 | 50.2 | 195.8 | 2.3 | 14.7 | 9.9 | 5.0 |
| 96 | 665 | LAIVLAAPVAVP | 12 | 8 | 50.2 | 203.3 | 2.3 | 14.7 | 9.9 | 5.0 |
| 97 | 363 | AVLAVAPALIVP | 12 | 7 | 50.2 | 203.3 | 2.3 | 14.7 | 9.8 | 4.9 |
| 98 | 242 | AALLVPALVAAP | 12 | 6 | 57.3 | 187.5 | 2.1 | 14.6 | 9.7 | 4.9 |
| 99 | 384 | VIVAIAPALLAP | 12 | 7 | 50.2 | 211.6 | 2.4 | 14.0 | 9.4 | 4.7 |
| 100 | 877 | VAIIAVPAVVAP | 12 | 7 | 57.3 | 195.0 | 2.4 | 14.0 | 9.4 | 4.7 |
| 101 | 863 | AAVVLLPIIAAP | 12 | 7 | 41.3 | 211.7 | 2.4 | 13.8 | 9.3 | 4.7 |
| 102 | 525 | ALAIVVAPVAVP | 12 | 8 | 50.2 | 195.0 | 2.4 | 13.8 | 9.2 | 4.7 |

TABLE 27-continued

| Sequence ID Number | aMTD | Sequences | Length | Proline Position (PP) | Rigidity/ Flexibility (II) | Sturctural Feature (AI) | Hydropathy (GRAVY) | Relative Ration (Fold) A | B | C |
|---|---|---|---|---|---|---|---|---|---|---|
| 103 | 875 | AIAIVVPAVAVP | 12 | 7 | 50.2 | 195.0 | 2.4 | 13.8 | 9.2 | 4.7 |
| 104 | 285 | AIVLLPAAVVAP | 12 | 6 | 50.2 | 203.3 | 2.4 | 13.3 | 8.9 | 4.5 |
| 105 | 281 | ALIVLPAAVAVP | 12 | 6 | 50.2 | 203.3 | 2.4 | 13.3 | 8.9 | 4.5 |
| 106 | 867 | ALLVVIAPLAAP | 12 | 8 | 41.3 | 211.7 | 2.4 | 13.2 | 8.8 | 4.4 |
| 107 | 766 | IVVIAVAPAVAP | 12 | 8 | 50.2 | 195.0 | 2.4 | 12.9 | 8.6 | 4.4 |
| 108 | 342 | VIVALAPAVLAP | 12 | 7 | 50.2 | 203.3 | 2.3 | 12.7 | 8.5 | 4.3 |
| 109 | 881 | AALIVVPAVAVP | 12 | 7 | 50.2 | 195.0 | 2.4 | 12.7 | 8.5 | 4.3 |
| 110 | 505 | AIIIVIAPAAAP | 12 | 8 | 50.2 | 195.8 | 2.3 | 12.4 | 8.3 | 4.2 |

TABLE 28

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 111 | 763 | VAVLIAVPALAP | 12 | 8 | 57.3 | 203.3 | 2.3 | 12.3 | 7.2 | 4.2 |
| 112 | 706 | IVAVALLPAVAP | 12 | 8 | 50.2 | 203.3 | 2.4 | 12.0 | 7.0 | 4.1 |
| 113 | 687 | AILAVALPLLAP | 12 | 8 | 57.3 | 220.0 | 2.3 | 12.0 | 7.0 | 4.1 |
| 114 | 643 | LALVLAAPAIVP | 12 | 8 | 50.2 | 211.6 | 2.4 | 11.8 | 7.9 | 4.0 |
| 115 | 282 | VLAVAPALIVAP | 12 | 6 | 50.2 | 203.3 | 2.4 | 11.8 | 7.9 | 4.0 |
| 116 | 543 | LLAALIAPAALP | 12 | 8 | 57.3 | 204.1 | 2.1 | 11.7 | 7.8 | 4.0 |
| 117 | 325 | IVAVALPAVALP | 12 | 7 | 50.2 | 203.3 | 2.3 | 11.7 | 7.8 | 4.0 |
| 118 | 846 | IAVAVAAPLLVP | 12 | 8 | 41.3 | 203.3 | 2.4 | 11.7 | 6.8 | 4.0 |
| 119 | 383 | VIVALAPALLAP | 12 | 7 | 50.2 | 211.6 | 2.3 | 11.6 | 7.7 | 3.9 |
| 120 | 381 | VVAIVLPAVAAP | 12 | 7 | 50.2 | 195.0 | 2.4 | 11.5 | 7.7 | 3.9 |
| 121 | 808 | LVVLAAAPLAVP | 12 | 8 | 41.3 | 203.3 | 2.3 | 11.5 | 7.6 | 3.9 |
| 122 | 865 | AVLVIAVPAIAP | 12 | 8 | 57.3 | 203.3 | 2.5 | 11.3 | 7.5 | 3.8 |
| 123 | 725 | IAVLAVAPAVLP | 12 | 8 | 57.3 | 203.3 | 2.3 | 11.2 | 7.5 | 3.8 |
| 124 | 844 | VVALLAPLIAAP | 12 | 7 | 41.3 | 211.8 | 2.4 | 11.2 | 7.5 | 3.8 |
| 125 | 897 | AVIVPVAIIAAP | 12 | 5 | 50.2 | 203.3 | 2.5 | 11.2 | 7.5 | 3.8 |
| 126 | 605 | VIAAVLAPVAVP | 12 | 8 | 57.3 | 195.0 | 2.4 | 11.0 | 7.4 | 3.7 |
| 127 | 744 | AAVVIVAPVALP | 12 | 8 | 50.2 | 195.0 | 2.4 | 11.0 | 7.3 | 3.7 |
| 128 | 221 | AAILAPIVALAP | 12 | 6 | 50.2 | 195.8 | 2.2 | 10.9 | 7.3 | 3.7 |
| 129 | 622 | ALIVLAAPVAVP | 12 | 8 | 50.2 | 203.3 | 2.4 | 10.6 | 7.1 | 3.6 |
| 130 | 401 | AALAVIPAAILP | 12 | 7 | 54.9 | 195.8 | 2.2 | 10.6 | 7.1 | 3.6 |
| 131 | 324 | IVAVALPAALVP | 12 | 7 | 50.2 | 203.3 | 2.3 | 10.3 | 6.9 | 3.5 |
| 132 | 878 | IVALVAPAAVVP | 12 | 7 | 50.2 | 195.0 | 2.4 | 10.3 | 6.9 | 3.5 |
| 133 | 302 | LALAPALALLAP | 12 | 5 | 57.3 | 204.2 | 2.1 | 10.2 | 6.8 | 3.4 |
| 134 | 685 | ALLVAVLPAALP | 12 | 8 | 57.3 | 211.7 | 2.3 | 10.2 | 5.9 | 3.4 |

TABLE 28-continued

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 135 | 848 | AVAIVVLPAVAP | 12 | 8 | 50.2 | 195.0 | 2.4 | 10.0 | 6.7 | 3.4 |
| 136 | 602 | VIVALAAPVLAP | 12 | 8 | 50.2 | 203.3 | 2.4 | 9.9 | 5.8 | 3.4 |
| 137 | 788 | AIAVAIAPVALP | 12 | 8 | 57.3 | 187.5 | 2.3 | 9.8 | 6.6 | 3.3 |
| 138 | 145 | LLAVVPAVALAP | 12 | 6 | 57.3 | 203.3 | 2.3 | 9.5 | 6.3 | 3.2 |
| 139 | 11 | VVALAPALAALP | 12 | 6 | 57.3 | 187.5 | 2.1 | 9.5 | 6.3 | 3.2 |
| 140 | 141 | AVIVLPALAVAP | 12 | 6 | 50.2 | 203.3 | 2.4 | 9.4 | 6.3 | 3.2 |
| 141 | 521 | LAALIVVPAVAP | 12 | 8 | 50.2 | 203.3 | 2.4 | 9.4 | 6.3 | 3.2 |
| 142 | 425 | AVVAIAPVLALP | 12 | 7 | 57.3 | 203.3 | 2.4 | 9.4 | 6.3 | 3.2 |
| 143 | 365 | AVIVVAPALLAP | 12 | 7 | 50.2 | 203.3 | 2.3 | 9.3 | 6.2 | 3.1 |
| 144 | 263 | ALAVIPAAAILP | 12 | 6 | 54.9 | 195.8 | 2.2 | 9.0 | 6.0 | 3.0 |
| 145 | 345 | ALLIVAPVAVAP | 12 | 7 | 50.2 | 203.3 | 2.3 | 8.9 | 5.9 | 3.0 |
| 146 | 850 | LVIALAAPVALP | 12 | 8 | 57.3 | 211.7 | 2.4 | 8.8 | 5.9 | 3.0 |
| 147 | 144 | VLAIVPAVALAP | 12 | 6 | 50.2 | 203.3 | 2.4 | 8.8 | 5.9 | 3.0 |
| 148 | 767 | IVVAAVVPALAP | 12 | 8 | 50.2 | 195.0 | 2.4 | 8.5 | 5.0 | 2.9 |
| 149 | 185 | AALVLPLIIAAP | 12 | 6 | 41.3 | 220.0 | 2.4 | 8.5 | 5.7 | 2.9 |
| 150 | 849 | AVILLAPLIAAP | 12 | 7 | 57.3 | 220.0 | 2.4 | 8.3 | 4.8 | 2.8 |
| 151 | 864 | ALLVIAPAIAVP | 12 | 7 | 57.3 | 211.7 | 2.4 | 8.2 | 4.8 | 2.8 |
| 152 | 162 | AVVALPAALIVP | 12 | 6 | 50.2 | 203.3 | 2.4 | 8.2 | 5.5 | 2.8 |
| 153 | 164 | LAAVLPALLAAP | 12 | 6 | 57.3 | 195.8 | 2.1 | 8.2 | 5.5 | 2.8 |
| 154 | 907 | VAIALAPVVVAP | 12 | 7 | 57.3 | 195.0 | 2.4 | 8.1 | 5.4 | 2.8 |
| 155 | 444 | LAAALVPVALVP | 12 | 7 | 57.3 | 203.3 | 2.3 | 8.1 | 5.4 | 2.7 |
| 156 | 443 | ALAALVPVALVP | 12 | 7 | 57.3 | 203.3 | 2.3 | 8.0 | 5.3 | 2.7 |
| 157 | 901 | ALVAVLPAVAVP | 12 | 7 | 57.3 | 195.0 | 2.4 | 7.7 | 5.1 | 2.6 |
| 158 | 887 | VLAVAPAVAVLP | 12 | 6 | 57.3 | 195.0 | 2.4 | 7.7 | 5.1 | 2.6 |
| 159 | 746 | VAIIVVAPALAP | 12 | 8 | 50.2 | 203.3 | 2.4 | 7.6 | 4.4 | 2.6 |
| 160 | 902 | ALVAPLLAVAVP | 12 | 5 | 41.3 | 203.3 | 2.3 | 7.6 | 5.1 | 2.6 |
| 161 | 565 | VAIVLVAPAVAP | 12 | 8 | 50.2 | 195.0 | 2.4 | 7.5 | 5.0 | 2.5 |
| 162 | 245 | AAALAPVLALVP | 12 | 6 | 57.3 | 187.5 | 2.1 | 7.5 | 5.0 | 2.5 |
| 163 | 743 | AIAIALVPVALP | 12 | 8 | 57.3 | 211.6 | 2.4 | 7.4 | 4.9 | 2.5 |
| 164 | 465 | AVVILVPLAAAP | 12 | 7 | 57.3 | 203.3 | 2.4 | 7.4 | 4.9 | 2.5 |
| 165 | 104 | AVVAAPLVLALP | 12 | 6 | 41.3 | 203.3 | 2.3 | 7.3 | 4.9 | 2.5 |

TABLE 29

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 166 | 707 | IVALAVLPAVAP | 12 | 8 | 50.2 | 203.3 | 2.4 | 7.3 | 4.9 | 2.5 |
| 167 | 872 | VLAAAVLPLVVP | 12 | 8 | 41.3 | 219.2 | 2.5 | 7.3 | 4.9 | 2.5 |
| 168 | 583 | AVILALAPIVAP | 12 | 8 | 50.2 | 211.6 | 2.4 | 7.3 | 4.8 | 2.4 |
| 169 | 879 | AAIVLLPAVVVP | 12 | 7 | 50.2 | 219.1 | 2.5 | 7.2 | 4.8 | 2.4 |
| 170 | 784 | VAALPAVALVVP | 12 | 5 | 57.3 | 195.0 | 2.4 | 7.1 | 4.7 | 2.4 |
| 171 | 893 | VIAIPAILAAAP | 12 | 5 | 54.9 | 195.8 | 2.3 | 7.0 | 4.7 | 2.4 |
| 172 | 13 | AAALVPVVALLP | 12 | 6 | 57.3 | 203.3 | 2.3 | 7.0 | 4.7 | 2.4 |
| 173 | 809 | LIVLAAPALAAP | 12 | 7 | 50.2 | 195.8 | 2.2 | 7.0 | 4.7 | 2.4 |
| 174 | 445 | ALAALVPALVVP | 12 | 7 | 57.3 | 203.3 | 2.3 | 6.9 | 4.6 | 2.3 |
| 175 | 81 | AALLPALAALLP | 12 | 5 | 57.3 | 204.2 | 2.1 | 6.9 | 4.6 | 2.3 |
| 176 | 667 | LAVAIVAPALVP | 12 | 8 | 50.2 | 203.3 | 2.3 | 6.9 | 4.6 | 2.3 |
| 177 | 906 | AVIALAPVVVAP | 12 | 7 | 57.3 | 195.0 | 2.4 | 6.8 | 4.6 | 2.3 |
| 178 | 483 | ILAAAIIPAALP | 12 | 8 | 54.9 | 204.1 | 2.2 | 6.8 | 4.5 | 2.3 |
| 179 | 485 | AILAAIVPLAVP | 12 | 8 | 50.2 | 211.6 | 2.4 | 6.8 | 4.5 | 2.3 |
| 180 | 421 | AAILAAPLIAVP | 12 | 7 | 57.3 | 195.8 | 2.2 | 6.7 | 4.5 | 2.3 |
| 181 | 585 | ALIVAIAPALVP | 12 | 8 | 50.2 | 211.6 | 2.4 | 6.6 | 4.4 | 2.2 |
| 182 | 424 | AVVVAAPVLALP | 12 | 7 | 57.3 | 195.0 | 2.4 | 6.6 | 4.4 | 2.2 |
| 183 | 364 | LVAAVAPALIVP | 12 | 7 | 50.2 | 203.3 | 2.3 | 6.5 | 4.3 | 2.2 |
| 184 | 402 | ALAAVIPAAILP | 12 | 7 | 54.9 | 195.8 | 2.2 | 6.4 | 4.3 | 2.2 |
| 185 | 462 | IAAVLVPAVALP | 12 | 7 | 57.3 | 203.3 | 2.4 | 6.3 | 4.2 | 2.1 |
| 186 | 265 | VLAIAPLLAAVP | 12 | 6 | 41.3 | 211.6 | 2.3 | 6.0 | 4.0 | 2.0 |
| 187 | 301 | VIAAPVLAVLAP | 12 | 6 | 57.3 | 203.3 | 2.4 | 6.0 | 4.0 | 2.0 |
| 188 | 183 | LLAAPVVIALAP | 12 | 6 | 57.3 | 211.6 | 2.4 | 6.0 | 4.0 | 2.0 |
| 189 | 243 | AAVLLPVALAAP | 12 | 6 | 57.3 | 187.5 | 2.1 | 5.9 | 3.9 | 2.0 |
| 190 | 664 | ILIAIAIPAAAP | 12 | 8 | 54.9 | 204.1 | 2.3 | 5.7 | 3.8 | 1.9 |
| 191 | 783 | IVALVPAVAIAP | 12 | 6 | 50.2 | 203.3 | 2.5 | 5.7 | 3.8 | 1.9 |
| 192 | 502 | AIVALAVPVLAP | 12 | 8 | 50.2 | 203.3 | 2.4 | 5.6 | 3.7 | 1.9 |
| 193 | 262 | ALIAVPAIIVAP | 12 | 6 | 50.2 | 211.6 | 2.4 | 5.5 | 3.7 | 1.9 |
| 194 | 683 | LAIVLAAPAVLP | 12 | 8 | 50.2 | 211.7 | 2.4 | 5.5 | 3.2 | 1.9 |
| 195 | 830 | IALVAAPVALVP | 12 | 7 | 57.3 | 203.3 | 2.4 | 5.3 | 3.5 | 1.8 |
| 196 | 764 | AVALAVLPAVVP | 12 | 8 | 57.3 | 195.0 | 2.3 | 5.0 | 3.4 | 1.7 |
| 197 | 807 | AVALAVPALVLP | 12 | 7 | 57.3 | 203.3 | 2.3 | 5.0 | 3.3 | 1.7 |
| 198 | 184 | LAAIVPAIIAVP | 12 | 6 | 50.2 | 211.6 | 2.4 | 4.8 | 3.2 | 1.6 |
| 199 | 305 | IALAAPILLAAP | 12 | 6 | 57.3 | 204.2 | 2.2 | 4.8 | 3.2 | 1.6 |
| 200 | 101 | LVALAPVAAVLP | 12 | 6 | 57.3 | 203.3 | 2.3 | 4.5 | 3.0 | 1.5 |
| 201 | 304 | AIILAPIAAIAP | 12 | 6 | 57.3 | 204.2 | 2.3 | 4.4 | 3.0 | 1.5 |
| 202 | 604 | VALIAVAPAVVP | 12 | 8 | 57.3 | 195.0 | 2.4 | 4.3 | 2.5 | 1.5 |

TABLE 29-continued

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 203 | 645 | ALAVVALPAIVP | 12 | 8 | 50.2 | 203.3 | 2.4 | 4.3 | 2.9 | 1.5 |
| 204 | 201 | LALAVPALAALP | 12 | 6 | 57.3 | 195.8 | 2.1 | 4.2 | 2.8 | 1.4 |
| 205 | 163 | LALVLPAALAAP | 12 | 6 | 57.3 | 195.8 | 2.1 | 4.1 | 2.4 | 1.4 |
| 206 | 832 | AVAAIVPVIVAP | 12 | 7 | 43.2 | 195.0 | 2.5 | 4.1 | 2.7 | 1.4 |
| 207 | 182 | ALIAPVVALVAP | 12 | 6 | 57.3 | 203.3 | 2.4 | 4.0 | 2.7 | 1.4 |
| 208 | 23 | VVLVLPAAAAVP | 12 | 6 | 57.3 | 195.0 | 2.4 | 4.0 | 2.6 | 1.3 |
| 209 | 105 | LLALAPAALLAP | 12 | 6 | 57.3 | 204.1 | 2.1 | 4.0 | 2.6 | 1.3 |
| 210 | 561 | AAVAIVLPAVVP | 12 | 8 | 50.2 | 195.0 | 2.4 | 3.9 | 2.6 | 1.3 |
| 211 | 765 | AVALAVVPAVLP | 12 | 8 | 57.3 | 195.0 | 2.3 | 3.8 | 2.2 | 1.3 |
| 212 | 684 | AAIVLALPAVLP | 12 | 8 | 50.2 | 211.7 | 2.4 | 3.5 | 2.1 | 1.2 |
| 213 | 143 | AVLAVPAVLVAP | 12 | 6 | 57.3 | 195.0 | 2.4 | 3.3 | 2.2 | 1.1 |
| 214 | 504 | LIVALAVPALAP | 12 | 8 | 50.2 | 211.7 | 2.4 | 3.3 | 2.2 | 1.1 |
| 215 | 22 | AVVLVPVLAAAP | 12 | 6 | 57.3 | 195.0 | 2.4 | 3.1 | 2.1 | 1.1 |
| 216 | 5 | AAALLPVALVAP | 12 | 6 | 57.3 | 187.5 | 2.1 | 3.1 | 2.1 | 1.0 |
| 217 | 283 | AALLAPALIVAP | 12 | 6 | 50.2 | 195.8 | 2.2 | 3.1 | 2.0 | 1.0 |
| 218 | 65 | IAIVAPVVALAP | 12 | 6 | 50.2 | 203.3 | 2.4 | 3.0 | 2.0 | 1.0 |
| 219 | 883 | LAIVPAAIAALP | 12 | 6 | 50.2 | 195.8 | 2.2 | 3.0 | 2.0 | 1.0 |
| 220 | 123 | AAIIVPAALLAP | 12 | 6 | 50.2 | 195.8 | 2.2 | 2.9 | 2.0 | 1.0 |

TABLE 30

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 221 | 284 | ALIAPAVALIVP | 12 | 5 | 50.2 | 211.7 | 2.4 | 2.8 | 1.8 | 0.9 |
| 222 | 205 | ALALVPAIAALP | 12 | 6 | 57.3 | 195.8 | 2.2 | 2.6 | 1.7 | 0.9 |
| 223 | 42 | VAALPVVAVVAP | 12 | 5 | 57.3 | 186.7 | 2.4 | 2.5 | 1.7 | 0.8 |
| 224 | 121 | AIVALPALALAP | 12 | 6 | 50.2 | 195.8 | 2.2 | 2.5 | 1.7 | 0.8 |
| 225 | 25 | IVAVAPALVALP | 12 | 6 | 50.2 | 203.3 | 2.4 | 2.4 | 1.6 | 0.8 |
| 226 | 24 | IALAAPALIVAP | 12 | 6 | 50.2 | 195.8 | 2.2 | 2.3 | 1.6 | 0.8 |
| 227 | 204 | LIAALPAVAALP | 12 | 6 | 57.3 | 195.8 | 2.2 | 2.2 | 1.5 | 0.8 |
| 228 | 12 | LLAAVPAVLLAP | 12 | 6 | 57.3 | 211.7 | 2.3 | 2.2 | 1.5 | 0.7 |
| 229 | 43 | LLAAPLVVAAVP | 12 | 5 | 41.3 | 187.5 | 2.1 | 2.1 | 1.4 | 0.7 |
| 230 | 103 | ALIAAPILALAP | 12 | 6 | 57.3 | 204.2 | 2.2 | 2.1 | 1.4 | 0.7 |
| 231 | 82 | AVVLAPVAAVLP | 12 | 6 | 57.3 | 195.0 | 2.4 | 2.1 | 1.4 | 0.7 |
| 232 | 4 | ALALLPVAALAP | 12 | 6 | 57.3 | 195.8 | 2.1 | 2.0 | 1.3 | 0.7 |
| 233 | 85 | LLVLPAAALAAP | 12 | 5 | 57.3 | 195.8 | 2.1 | 1.9 | 1.3 | 0.7 |

TABLE 30-continued

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 234 | 63 | AALLVPALVAVP | 12 | 6 | 57.3 | 203.3 | 2.3 | 1.9 | 1.3 | 0.7 |
| 235 | 44 | ALAVPVALLVAP | 12 | 5 | 57.3 | 203.3 | 2.3 | 1.6 | 1.1 | 0.5 |
| 236 | 84 | AAVAAPLLLALP | 12 | 6 | 41.3 | 195.8 | 2.1 | 1.5 | 1.0 | 0.5 |
| 237 | 62 | VALLAPVALAVP | 12 | 6 | 57.3 | 203.3 | 2.3 | 1.4 | 0.9 | 0.5 |
| 238 | 83 | LAVAAPLALALP | 12 | 6 | 41.3 | 195.8 | 2.1 | 1.4 | 0.9 | 0.5 |
| 239 | 102 | LALAPAALALLP | 12 | 5 | 57.3 | 204.2 | 2.1 | 1.4 | 0.9 | 0.5 |
| 240 | 623 | VAAAIALPAIVP | 12 | 8 | 50.2 | 187.5 | 2.3 | 0.8 | 0.6 | 0.3 |
| | | | | | | | | 19.6 ± 1.6 | 13.1 ± 1.1 | 6.6 ± 0.5 |

Moreover, compared to reference CPPs (B type: MTM12 and C type: MTD85), novel 240 aMTDs averaged of 13±1.1 (maximum 109.9) and 6.6-0.5 (maximum 55.5) fold higher cell-permeability, respectively (Tables 26 to 31).

TABLE 31

| | Negative Control rP38 | MTM12 | MTD85 |
|---|---|---|---|
| aMTD<br>The Average of 240 aMTDs | 19.6 ± 1.6*<br>(Best: 164.2) | 13.1 ± 1.1*<br>(Best: 109.9) | 6.6 ± 0.5*<br>(Best: 55.5) |

*Relative Fold (aMTD in Geo Mean in its comparison to rP38, MTM12 or MTD85)

In addition, cell-permeabilities of 31 rPeptides have been compared with that of 240 aMTDs (0.3±0.04; Tables 32 and 33).

TABLE 32

| Number | ID | Sequence | Length | Proline Position (PP) | Rigidity/ Flexibility (II) | Structural Feature (AI) | Hydropathy (GRAVY) | Relative Ratio to aMTD AVE |
|---|---|---|---|---|---|---|---|---|
| 1 | 692 | PAPLPPVVILAV | 12 | 1, 3, 5, 6 | 105.5 | 186.7 | 1.8 | 0.74 |
| 2 | 26 | AAIALAAPLAIV | 12 | 8 | 18.1 | 204.2 | 2.5 | 0.65 |
| 3 | 113 | PVAVALLIAVPP | 12 | 1, 11, 12 | 57.3 | 195.0 | 2.1 | 0.61 |
| 4 | 466 | IIAAAAPLAIIP | 12 | 7, 12 | 22.8 | 204.2 | 2.3 | 0.52 |
| 5 | 167 | VAIAIPAALAIP | 12 | 6, 12 | 20.4 | 195.8 | 2.3 | 0.50 |
| 6 | 97 | ALLAAPPALLAL | 12 | 6, 7 | 57.3 | 204.2 | 2.1 | 0.41 |
| 7 | 390 | VPLLVPVVPVVP | 12 | 2, 6, 9, 12 | 105.4 | 210.0 | 2.2 | 0.41 |

TABLE 32-continued

| Number | ID | Sequence | Length | Proline Position (PP) | Rigidity/Flexibility (II) | Structural Feature (AI) | Hydropathy (GRAVY) | Relative Ratio to aMTD AVE |
|---|---|---|---|---|---|---|---|---|
| 8 | 426 | AAALAIPLAIIP | 12 | 7, 12 | 4.37 | 204.2 | 2.2 | 0.40 |
| 9 | 214 | ALIVAPALMALP | 12 | 6, 12 | 60.5 | 187.5 | 2.2 | 0.33 |
| 10 | 68 | VAPVLPAAPLVP | 12 | 3, 6, 9, 12 | 105.5 | 162.5 | 1.6 | 0.32 |
| 11 | 39 | CYNTSPCTGCCY | 12 | 6 | 52.5 | 0.0 | 0.0 | 0.29 |
| 12 | 934 | LLLAPAAVVAAA | 12 | 5 | 57.3 | 195.8 | 2.5 | 0.28 |
| 13 | 938 | VPVLLPVVVPVP | 12 | 2, 6, 10, 12 | 121.5 | 210.0 | 2.2 | 0.28 |
| 14 | 329 | LPVLVPVVPVVP | 12 | 2, 6, 9, 12 | 121.5 | 210.0 | 2.2 | 0.23 |
| 15 | 606 | AAAIAAIPIIIP | 12 | 8, 12 | 4.4 | 204.2 | 2.4 | 0.20 |
| 16 | 49 | VVPAAPAVPVVP | 12 | 3, 6, 9, 12 | 121.5 | 145.8 | 1.7 | 0.18 |
| 17 | 139 | TGSTNSPTCTST | 12 | 7 | 53.4 | 0.0 | -0.7 | 0.17 |
| 18 | 772 | LPVAPVIPIIVP | 12 | 2, 5, 8, 12 | 79.9 | 210.8 | 2.1 | 0.16 |
| 19 | 921 | IWWFVVLPLVVP | 12 | 8, 12 | 41.3 | 194.2 | 2.2 | 0.14 |
| 20 | 66 | AGVLGGPIMGVP | 12 | 7, 12 | 35.5 | 121.7 | 1.3 | 0.13 |
| 21 | 693 | AAPVLPVAVPIV | 12 | 3, 6, 10 | 82.3 | 186.7 | 2.1 | 0.13 |
| 22 | 18 | NYCCTPTTNGQS | 12 | 6 | 47.9 | 0.0 | -0.9 | 0.10 |
| 23 | 16 | NNSCTTYTNGSQ | 12 | None | 47.4 | 0.0 | -1.4 | 0.08 |
| 24 | 227 | LAAIVPIAAAVP | 12 | 6, 12 | 34.2 | 187.5 | 2.2 | 0.08 |
| 25 | 17 | GGCSAPQTTCSN | 12 | 6 | 51.6 | 8.3 | -0.5 | 0.08 |
| 26 | 67 | LDAEVPLADDVP | 12 | 6, 12 | 34.2 | 130.0 | 0.3 | 0.08 |
| 27 | 635 | GSTGGSQQNNQY | 12 | None | 31.9 | 0.0 | -1.9 | 0.07 |
| 28 | 29 | VLPPLPVLPVLP | 12 | 3, 4, 6, 9, 12 | 121.5 | 202.5 | 1.7 | 0.07 |
| 29 | 57 | QNNCNTSSQGGG | 12 | None | 52.4 | 0.0 | -1.6 | 0.06 |

TABLE 32-continued

| Number | ID | Sequence | Length | Proline Position (PP) | Rigidity/ Flexibility (II) | Structural Feature (AI) | Hydropathy (GRAVY) | Relative Ratio to aMTD AVE |
|---|---|---|---|---|---|---|---|---|
| 30 | 700 | GTSNTCQSNQNS | 12 | None | 19.1 | 0.0 | −1.6 | 0.05 |
| 31 | 38 | YYNQSTCGGQCY | 12 | ND | 53.8 | 0.0 | −1.0 | 0.05 |
| | | | | | | | AVE | 0.3 ± 0.04 |

TABLE 33

| | Relative Ratio to aMTD AVE* |
|---|---|
| rPeptide<br>The Average of 31 aMTDs | 0.3 ± 0.04 |

*Out of 240 aMTDs, average relative fold of aMTD had been 19.6 fold compared to type A (rP38).

In summary, relatively cell-permeability of aMTDs has shown maximum of 164.0, 109.9 and 55.5 fold higher to rP38, MTM12 and MTD85, respectively. In average of total 240 aMTD sequences, 19.6±1.6, 13.1±1.1 and 6.6±0.5 fold higher cell-permeability are shown to the rP38, MTM12 and MTD85, respectively (Tables 26 to 31). Relative cell-permeability of negative control (rP38) to the 240 aMTDs is only 0.3±0.04 fold.

4-5. Intracellular Delivery and Localization of aMTD-Fused Recombinant Proteins

Recombinant proteins fused to the aMTDs were tested to determine their intracellular delivery and localization by laser scanning confocal microscopy with a negative control (rP38) and previous published CPPs (MTM12 and MTD85) as the positive control references. NIH3T3 cells were exposed to 10 uM of FITC-labeled protein for 1 hour at 37° C., and nuclei were counterstained with DAPI. Then, cells were examined by confocal laser scanning microscopy (FIG. 7). Recombinant proteins fused to aMTDs clearly display intracellular delivery and cytoplasmic localization (FIG. 7) that are typically higher than the reference CPPs (MTM12 and MTD85). The rP38-fused recombinant protein did not show internalized fluorescence signal (FIG. 7*a*). In addition, as seen in FIG. 8, rPeptides (his-tagged CRA recombinant proteins fused to each rPeptide) display lower- or non-cell-permeability.

4-6. Summary of Quantitative and Visual Cell-Permeability of Newly Developed aMTDs Histidine-tagged aMTD-fused cargo recombinant proteins have been greatly enhanced in their solubility and yield. Thus, FITC-conjugated recombinant proteins have also been tested to quantitate and visualize intracellular localization of the proteins and demonstrated higher cell-permeability compared to the reference CPPs.

In the previous studies using the hydrophobic signal-sequence-derived CPPs-MTS/MTM or MTDs, 17 published sequences have been identified and analyzed in various characteristics such as length, molecular weight, pI value, bending potential, rigidity, flexibility, structural feature, hydropathy, amino acid residue and composition, and secondary structure of the peptides. Based on these analytical data of the sequences, novel artificial and non-natural peptide sequences designated as advanced MTDs (aMTDs) have been invented and determined their functional activity in intracellular delivery potential with aMTD-fused recombinant proteins.

aMTD-fused recombinant proteins have promoted the ability of protein transduction into the cells compared to the recombinant proteins containing rPeptides and/or reference hydrophobic CPPs (MTM12 and MTD85). According to the results, it has been demonstrated that critical factors of cell-penetrating peptide sequences play a major role to determine peptide-mediated intracellular delivery by penetrating plasma membrane. In addition, cell-permeability can considerably be improved by following the rational that all satisfy the critical factors.

5. Structure/Sequence Activity Relationship (SAR) of aMTDs on Delivery Potential After determining the cell-permeability of novel aMTDs, structure/sequence activity relationship (SAR) has been analyzed for each critical factor in selected some of and all of novel aMTDs (FIGS. 13*a* to 16 and Table 34).

TABLE 34

| Rank of Delivery Potential | Rigidity/ Flexibility (II) | Structural Feature (AI) | Hydropathy (GRAVY) | Relative Ratio (Fold) A | B | C | Amino Acid Composition A | V | I | L |
|---|---|---|---|---|---|---|---|---|---|---|
| 1~10 | 55.9 | 199.2 | 2.3 | 112.7 | 75.5 | 38.1 | 4.0 | 3.5 | 0.4 | 2.1 |
| 11~20 | 51.2 | 205.8 | 2.4 | 56.2 | 37.6 | 19.0 | 4.0 | 2.7 | 1.7 | 1.6 |
| 21~30 | 49.1 | 199.2 | 2.3 | 43.6 | 28.9 | 14.6 | 4.3 | 2.7 | 1.4 | 1.6 |
| 31~40 | 52.7 | 201.0 | 2.4 | 34.8 | 23.3 | 11.8 | 4.2 | 2.7 | 1.5 | 1.6 |
| 41~50 | 53.8 | 201.9 | 2.3 | 30.0 | 20.0 | 10.1 | 4.3 | 2.3 | 1.1 | 2.3 |
| 51~60 | 51.5 | 205.2 | 2.4 | 23.5 | 15.7 | 7.9 | 4.4 | 2.1 | 1.5 | 2.0 |
| 222~231 | 52.2 | 197.2 | 2.3 | 2.2 | 1.5 | 0.8 | 4.5 | 2.1 | 1.0 | 2.4 |
| 232~241 | 54.1 | 199.7 | 2.2 | 1.7 | 1.2 | 0.6 | 4.6 | 1.7 | 0.2 | 3.5 |

5-1. Proline Position:

In regards to the bending potential (proline position: PP), aMTDs with its proline at 7' or 8' amino acid in their sequences have much higher cell-permeability compared to the sequences in which their proline position is at 5' or 6' (FIGS. 14*a* and *b* and FIGS. 15*a* and *b*).

5-2. Hydropathy:

In addition, when the aMTDs have GRAVY (Grand Average of Hydropathy) ranging in 2.1 to 2.2, these sequences display relatively lower cell-permeability, while the aMTDs with 2.3 to 2.6 GRAVY are shown significantly higher one (FIGS. 14*c* and *d* and FIGS. 15*c* and *d*).

5-3. rPeptide SAR:

To the SAR of aMTDs, rPeptides have shown similar SAR correlations in the cell-permeability, pertaining to their proline position (PP) and hydropathy (GRAVY). These results confirm that rPeptides with high GRAVY (2.4 to 2.6) have better cell-permeability (FIG. 16).

5-4. Analysis of Amino Acid Composition:

In addition to proline position and hydropathy, the difference of amino acid composition is also analyzed. Since aMTDs are designed based on critical factors, each aMTD-fused recombinant protein has equally two proline sequences in the composition. Other hydrophobic and aliphatic amino acids—alanine, isoleucine, leucine and valine—are combined to form the rest of aMTD peptide sequences.

Alanine:

In the composition of amino acids, the result does not show a significant difference by the number of alanine in terms of the aMTD's delivery potential because all of the aMTDs have three to five alanines. However, in the sequences, four alanine compositions show the most effective delivery potential (geometric mean) (FIGS. 13*a* and *b*).

Leucine and Isoleucine:

Also, the compositions of isoleucine and leucine in the aMTD sequences show inverse relationship between the number of amino acid (I and L) and delivery potential of aMTDs. Lower number of isoleucine and leucine in the sequences tends to have higher delivery potential (geometric mean) (FIGS. 13*a* to 13*d*).

Valine:

Conversely, the composition of valine of aMTD sequences shows positive correlation with their cell-permeability. When the number of valine in the sequence is low, the delivery potential of aMTD is also relatively low (FIGS. 13*c* and *d*).

Ten aMTDs having the highest cell-permeability are selected (average geometric mean: 2584±126). Their average number of valine in the sequences is 3.5; 10 aMTDs having relatively low cell-permeability (average geometric mean: 80±4) had average of 1.9 valine amino acids. The average number of valine in the sequences is lowered as their cell-permeability is also lowered as shown in FIGS. 13*c* and 13*d*. Compared to higher cell-permeable aMTDs group, lower sequences had average of 1.9 in their valine composition. Therefore, to obtain high cell-permeable sequence, an average of 2-4 valines should be composed in the sequence.

5-5. Conclusion of SAR Analysis:

As seen in FIG. 15, all 240 aMTDs have been examined for these associations of the cell-permeability and the critical factors: bending potential (PP), rigidity/flexibility (II), structure feature (AI), and hydropathy (GRAVY), amino acid length and composition. Through this analysis, cell-permeability of aMTDs tends to be lower when their central proline position is at 5' or 6' and GRAVY is 2.1 or lower (FIG. 15). Moreover, after investigating 10 higher and 10 lower cell-permeable aMTDs, these trends are clearly shown to confirm the association of cell-permeability with the central proline position and hydropathy.

6. Experimental Confirmation of Index Range/Feature of Critical Factors

The range and feature of five out of six critical factors have been empirically and experimentally determined that are also included in the index range and feature of the critical factors initially proposed before conducting the experiments and SAR analysis. In terms of index range and feature of critical factors of newly developed 240 aMTDs, the bending potential (proline position: PP), rigidity/flexibility (Instability Index: II), structural feature (Aliphatic Index: AI), hydropathy (GRAVY), amino acid length and composition are all within the characteristics of the critical factors derived from analysis of reference hydrophobic CPPs.

Therefore, our hypothesis to design and develop new hydrophobic CPP sequences as advanced MTDs is empirically and experimentally proved and demonstrated that critical factor-based new aMTD rational design is correct.

TABLE 35

Summarized Critical Factors of aMTD

| Critical Factor | Newly Designed CPPs Range | Analysis of Experimental Results Range |
|---|---|---|
| Bending Potential (Proline Position: PP) | Proline presences in the middle (5', 6', 7' or 8') and at the end of peptides | Proline presences in the middle (5', 6', 7' or 8') and at the end of peptides |
| Rigidity/Flexibility (Instability Index: II) | 40-60 | 41.3-57.3 |
| Structural Feature (Aliphatic Index: AI) | 180-220 | 187.5-220.0 |
| Hydropathy (Grand Average of Hydropathy GRAVY) | 2.1-2.6 | 2.2-2.6 |
| Length (Number of Amino Acid) | 9-13 | 12 |
| Amino acid Composition | A, V, I, L, P | A, V, I, L, P |

7. Discovery and Development of Protein-Based New Biotherapeutics with MITT Enabled by aMTDs for Protein Therapy 240 aMTD sequences have been designed and developed based on the critical factors. Quantitative and visual cell-permeability of 240 aMTDs (hydrophobic, flexible, bending, aliphatic and 12 ala-length peptides) are all practically determined.

To measure the cell-permeability of aMTDs, rPeptides have also been designed and tested. As seen in FIGS. 13*a* through 15*d*, there are vivid association of cell-permeability and the critical factors of the peptides. Out of these critical factors, we are able to configure that the most effective cell-permeable aMTDs have the amino acid length of 12; composition of A, V, L, I and P; multiple proline located at either 7' or 8' and at the end (12'); instability index ranged of 41.3 to 57.3; aliphatic index ranged of 187.5 to 220.0; and hydropathy (GRAVY) ranged of 2.2 to 2.6.

These examined critical factors are within the range that we have set for our critical factors; therefore, we are able to confirm that the aMTDs that satisfy these critical factors have relatively high cell-permeability and much higher intracellular delivery potential compared to reference hydrophobic CPPs reported during the past two decades.

It has been widely evident that many human diseases are caused by proteins with deficiency or over-expression that causes mutations such as gain-of-function or loss-of-function. If biologically active proteins could be delivered for replacing abnormal proteins within a short time frame, possibly within an hour or two, in a quantitative manner, the dosage may be regulated depending on when and how proteins may be needed. By significantly improving the solubility and yield of novel aMTD according to one embodiment of the present invention (Table 31), one could expect its practical potential as an agent to effectively deliver therapeutic macromolecules such as proteins, peptides, nucleic acids, and other chemical compounds into live cells as well as live mammals including human. Therefore, newly developed MITT utilizing the pool (240) of novel aMTDs can be used as a platform technology for discovery and development of protein-based biotherapeutics to apprehend intracellular protein therapy after determining the optimal cargo-aMTD relationship.

8. Novel Hydrophobic CPPs—aMTDs for Development of iCP-RF Recombinant Proteins 8-1. Selection of aMTD for Cell-Permeability From 240 aMTDs, 8 aMTDs were selected and used for the construction of iCP-RF recombinant proteins. 8 aMTDs used are shown in the following Table 36.

Various hydrophobic CPP have been used to enhance the delivery of protein cargoes to mammalian cells and tissues.

TABLE 36

| SEQ ID NO | aMTD ID | Amino Acid Sequences |
|---|---|---|
| 39 | 161 | AVIALPALIAAP |
| 43 | 165 | ALAVPVALAIVP |
| 84 | 363 | AVLAVAPALIVP |
| 96 | 405 | LAAAVIPVAILP |
| 131 | 563 | ALAVIVVPALAP |
| 223 | 889 | ILVAAAPIAALP |
| 226 | 895 | AIIIVVPAIAAP |
| 233 | 904 | AVLAVVAPVVAP |

8-2. Selection of Solubilization Domain (SD) for Structural Stability

Recombinant cargo (OCT4, SOX2, CMYC, KLF4, NANOG, LIN28 and ZSCAN4) proteins fused to hydrophobic CPP could be expressed in bacteria system, purified with single-step affinity chromatography, but protein dissolved in physiological buffers (e.q. PBS, DMEM or RPMI1640 etc.) was highly insoluble and had extremely low yield as a soluble form. Therefore, an additional non-functional protein domain (solubilization domain: SD) has been applied to fuse with the recombinant protein for improving the solubility, yield and eventually cell and tissue permeability.

According to the specific aim, the selected domains are SDA to SDF (Table 37). The aMTD/SD-fused RF recombinant proteins have been determined for their stability.

The solubilization domains (SDs) and aMTDs have greatly influenced in increasing solubility/yield and cell-/tissue-permeability of the protein. Therefore, we have developed highly soluble and highly stable RF recombinant protein fused with SD (SDA and/or SDB) and aMTDs.

Table 37 shows the Characteristics of Solubilization Domains.

TABLE 37

| SD | Genbank ID | Origin | Protein (kDa) | pI | Instability Index (II) | GRAVY |
|---|---|---|---|---|---|---|
| A | CP000113.1 | Bacteria | 23 | 4.6 | 48.1 | −0.1 |
| B | BC086945.1 | Rat | 11 | 4.9 | 43.2 | −0.9 |
| C | CP012127.1 | Human | 12 | 5.8 | 30.7 | −0.1 |
| D | CP012127.1 | Bacteria | 23 | 5.9 | 26.3 | −0.1 |
| E | CP011550.1 | Human | 11 | 5.3 | 44.4 | −0.9 |
| F | NG_034970 | Human | 34 | 7.1 | 56.1 | −0.2 |

8-3. Construction of Expression Vector 5 different types of recombinant proteins with or without the aMTD and solubilization domains (SDs) for reprogramming factor (RF) protein were designed. Protein structures were labeled as follows: (1) a RF protein fused with His-tag, (2) a RF protein fused with His-tag, NLS and aMTD, (3) a RF protein fused with His-tag, NLS, aMTD and solubilization domain B (SDB), (4) a RF protein fused with His-tag, NLS, aMTD, solubilization domain A (SDA) and two solubilization domain B (SDB), and (5) a RF protein fused with His-tag, NLS, three solubilization domain A (SDA) and two solubilization domain B (SDB), (FIGS. 18, 20, 22, 24, 26, 28 and 30). Among them, (3) to (5) structures were used as candidate proteins having the biological efficacy of iCP-RF recombinant protein, and (1) and (2) were used as control groups (Non-CP RF) with respect to (3) to (5).

8-4. Preparation of RF Recombinant Proteins

The RF recombinant proteins (OCT4, SOX2, CMYC, KLF4, NANOG, LIN28 and ZSCAN4) were successfully induced by adding IPTG and purified (FIGS. 19, 21, 23, 25, 27, 29 and 31, top). The solubility and yield of the RF recombinant proteins were determined.

Solubility will be scored on a 5-point scale ranging from highly soluble proteins with little tendency to precipitate (*****) to largely insoluble proteins (*) by measuring their turbidity (A450). Yield (mg/L) in physiological buffer condition of each recombinant protein will also be determined.

We observed a significant increase of solubility of RF protein fused with SDB on C-terminus ($HNM_{563}OSB$, $HNM_{563}MSB$, $HNM_{161}NSB$, $HNM_{563}LSB$ and $HNM_{563}ZSB$) and RF protein fused with both SDAs and SDBs on C-/N-terminus ($HNM_{563}SASSASBSASB$ and $HNM_{563}SAKSASBSASB$), which were compared to a RF protein only or RF protein fused with aMTD on N-terminus (FIGS. 19, 21, 23, 25, 27, 29 and 31, bottom). And, we observed that yield and solubility of RF protein fused with SDB or both SDA and SDB on N-/C-terminus were greatly improved. The results suggested that the RF recombinant proteins fused with SD displayed a significant improvement of solubility and yields.

Further, solubility and yield of the RF recombinant proteins fused with different aMTDs (FIGS. 32, 34, 36 and 38, bottom) were measured. We observed that increase of both yield and solubility of SOX2 protein fused with $aMTD_{563}$, which were compared to a SOX2 protein fused with $aMTD_{161}$, $aMTD_{165}$, $aMTD_{363}$, $aMTD_{405}$, $aMTD_{889}$ and $aMTD_{904}$ (FIG. 33, bottom), and increase of both yield and solubility of NANOG protein fused with $aMTD_{161}$, which were compared to a NANOG protein fused with $aMTD_{405}$, $aMTD_{889}$, $aMTD_{895}$ and $aMTD_{904}$ (FIG. 35, bottom).

As a result, iCP-RF (OCT4, SOX2, CMYC, KLF4, NANOG, LIN28 and ZSCAN4) recombinant proteins were selected by comparing the solubility and yield between the RF recombinant proteins.

9. Determination of Cell-Permeability of iCP-RF Recombinant Proteins

In the cell-permeability of iCP-RF recombinant proteins (OCT4, SOX2, CMYC, KLF4 and LIN28) was investigated.

RF recombinant proteins were labeled fluorescence dye, FITC (fluorescein isothiocyanate), then cell permeability of the RF recombinant proteins was evaluated in RAW 264.7 cells and NIH3T3 cells. The RAW 264.7 cells and NIH3T3 cells were cultured in DMEM media containing 10% fetal bovine serum (FBS) and 500 mg/ml of 5% penicillin/streptomycin (P/S). After the culture, the cells were treated with Trypsin/EDTA for removal of the remained FITC on the cell membranes of the RAW 264.7 cells and the NIH3T3 cells, and washed with cold PBS three times.

The RAW 264.7 cells analyzed by FACS (fluorescence-activated cell sorting) showed a gain in fluorescence, indicative of the presence of FITC-labeled proteins as compared with control that only FITC or diluent. For FACS analysis, the cells ($1\times10^4$) were analyzed using the CellQues Pro cytometric analysis software (FACS Calibur, Beckton-Dickinson, San Diego Calif., USA). Cell permeability of each iCP-RF recombinant protein fused with aMTD/SD was examined (FIG. 39).

In the NIH3T3 cells, DNAs were stained with DAPI (4',6-diamidino-2-phenylindole) to distinguish intracellular localization of the RF recombinant proteins, and intranuclear delivery and cell-permeability of the RF recombinant proteins were examined by confocal laser microscopy (FIG. 40). The original shape of the cells and both FITC and DAPI staining of the cells were observed by means of a confocal laser microscope using a Nomarski filter.

As a result, aMTD/SD-fused iCP-RF recombinant proteins have cell-permeability and are delivered to the nucleus.

10. Determination of Biological Activity of iCP-RF Recombinant Proteins

Reprogramming factors (RFs) (OCT4, SOX2, CMYC, KLF4, NANOG and LIN28) are transcription factors which bind to target genes to activate or inhibit transcription of the genes. Biological activity of the iCP-RF recombinant proteins was determined by measuring activities of the target genes which occur upon binding of the RF proteins and the genes. A luciferase vector that expresses luciferase when the iCP-RF recombinant protein binds to the target gene was constructed (FIG. 41*a*). The luciferase vector was constructed, based on a pGL3 basic vector (Genscript, USA). Promoters containing 4 repeats of the binding sites of OCT4, SOX2, KLF4, CMYC, NANOG and LIN28 were synthesized. The vector and the promoter were digested using KpnI/HindIII restriction enzymes, and followed by ligation using T4 ligase.

As a result, the iCP-RF recombinant proteins delivered into the cells or nucleus exhibit a biological activity by binding to the DNA binding site of the luciferase promoter to express luciferase.

11. Determination of Formation of iPSC-Like Colony by iCP-RF Recombinant Proteins Generation of iPSCs by treatment from somatic cells with the iCP-RF recombinant proteins was confirmed. An effective preparation method of iPSCs was determined by controlling combination, concentration, treatment duration, and treatment time of the iCP-RF recombinant proteins (OCT4, SOX2, KLF4, CMYC, LIN28, NANOG and ZSCAN4) (FIGS. 47 to 51, top). Since iPSCs express alkaline phosphatase (AP) on their surface, AP staining was performed. Further, stem cell-specific biomarkers, OCT4 and TRA-1-81 in iPSCs were examined by immunofluorescence staining analysis (FIG. 52, top).

As a result, the iCP-RF recombinant proteins have reprogramming activity for a somatic cell, and therefore, they are able to induce dedifferentiation of terminally differentiated somatic cells to iPSCs.

12. Summary

According to one embodiment of the present invention, cell-permeable RF recombinant proteins have been designed and developed with the aMTD and SDs. All RF recombinant proteins fused with aMTD/SD and control recombinant proteins lacking both aMTD and SD have been confirmed for their quantitative, visual cell-permeability and biological activity in vitro. Consequently, the RF recombinant proteins fused with aMTD/SD has relatively high solubility and yield, and the optimized structure of the RF recombinant proteins was determined. The optimal aMTD was also determined for the high yield and solubility of the RF recombinant proteins. The RF proteins fused with optimal aMTD and SD were improved cell-permeable RF (iCP-RF) recombinant proteins. It was confirmed that these iCP-RF recombinant proteins induce reprogramming of terminally differentiated somatic cells into iPSCs in a combination of iCP-OCT4, iCP-SOX2, iCP-KLF4, iCP-CMYC, iCP-LIN28, iCP-NANOG and iCP-ZSCAN4.

The following examples are presented to aid practitioners of the invention, to provide experimental support for the invention, and to provide model protocols. In no way are these examples to be understood to limit the embodiment.

Example 1. Development of Novel Advanced Macromolecule Transduction Domain (aMTD)

H-regions of signal sequences (HOURSP)-derived CPPs (MTS/MTM and MTD) do not have a common sequence, a sequence motif, and/or a common structural homologous feature. According to one embodiment of the present invention, the aim is to develop improved hydrophobic CPPs formatted in the common sequence and structural motif that satisfy newly determined 'critical factors' to have a 'common function,' to facilitate protein translocation across the plasma membrane with similar mechanism to the analyzed CPPs.

The structural motif as follows:

X1-X2-X3-X4-U5-U6-U7-U8-X9-X10-X11-P

X: A, V, L or I

P: Proline

U: Proline at any one or X

In Table 9, universal common sequence/structural motif is provided as follows. The amino acid length of the peptides according to one embodiment of the present invention ranges from 9 to 13 amino acids, mostly 12 amino acids, and their bending potentials are dependent with the presence and location of proline in the middle of sequence (i.e., U5, U6, U7, or U8) and at the end of peptide (at 12') for recombinant protein bending. Instability index (II) for rigidity/flexibility of aMTDs is 11<40, grand average of hydropathy (GRAVY) for hydropathy is around 2.2, and aliphatic index (AI) for structural features is around 200 (Table 9). Based on these standardized critical factors, new hydrophobic peptide sequences, namely advanced macromolecule transduction domain peptides (aMTDs), according to one embodiment of the present invention have been developed and summarized in Tables 10 to 15.

Example 2. Construction of Expression Vectors for Recombinant Proteins Fused to aMTDs Our newly developed technology has enabled us to expand the method for making cell-permeable recombinant proteins. The expression vectors were designed for histidine-tagged CRA proteins fused with aMTDs or rPeptides. To construct expression vectors for recombinant proteins, polymerase chain reaction (PCR) had been devised to amplify each designed aMTD or rPeptide fused to CRA.

The PCR reactions (100 ng genomic DNA, 10 pmol each primer, each 0.2 mM dNTP mixture, 1× reaction buffer and 2.5 U Pfu(+) DNA polymerase (Doctor protein, Korea) was digested on the restriction enzyme site between Nde 1(5') and Sal I (3') involving 35 cycles of denaturation (95° C.), annealing (62° C.), and extension (72° C.) for 30 seconds each. For the last extension cycle, the PCR reactions remained for 5 minutes at 72° C. Then, they were cloned into the site of pET-28a(+) vectors (Novagen, Madison, Wis., USA). DNA ligation was performed using T4 DNA ligase at 4° C. overnight. These plasmids were mixed with competent cells of *E. coli* DH5-alpha strain on the ice for 10 minutes. This mixture was placed on the ice for 2 minutes after it was heat shocked in the water bath at 42° C. for 90 seconds. Then, the mixture added with LB broth media was recovered in 37° C. shaking incubator for 1 hour. Transformant was plated on LB broth agar plate with kanamycin (50 ug/mL) (Biopure, Johnson City, Tenn., USA) before incubating at 37° C. overnight. From a single colony, plasmid DNA was extracted, and after the digestion of Nde I and Sal I restriction enzymes, digested DNA was confirmed at 645 bp by using 1.2% agarose gels electrophoresis (FIG. 2). PCR primers for the CRA recombinant proteins fused to aMTD and random peptides (rPeptide) are summarized in Tables 23 to 30. Amino acid sequences of aMTD and rPeptide primers are shown in Tables 31 to 38.

Example 3. Inducible Expression, Purification and Preparation of Recombinant Proteins Fused to aMTDs and rPeptides To express recombinant proteins, pET-28a(+) vectors for the expression of CRA proteins fused to a negative control [rPeptide 38 (rP38)], reference hydrophobic CPPs ($MTM_{12}$ and $MTD_{85}$) and aMTDs were transformed in *E. coli* BL21 (DE3) strains. Cells were grown at 37° C. in LB medium containing kanamycin (50 ug/ml) with a vigorous shaking and induced at $OD_{600}$=0.6 by adding 0.7 mM IPTG (Biopure) for 2 hours at 37° C. Induced recombinant proteins were loaded on 15% SDS-PAGE gel and stained with Coomassie Brilliant Blue (InstantBlue, Expedeon, Novexin, UK) (FIG. 3).

The *E. coli* cultures were harvested by centrifugation at 5,000×rpm for 10 minutes, and the supernatant was discarded. The pellet was re-suspended in the lysis buffer (50 mM $NaH_2PO_4$, 10 mM Imidazol, 300 mM NaCl, pH 8.0). The cell lysates were sonicated on ice using a sonicator (Sonics and Materials, Inc., Newtown, Conn., USA) equipped with a probe.

After centrifuging the cell lysates at 5,000×rpm for 10 minutes to pellet the cellular debris, the supernatant was incubated with lysis buffer-equilibrated Ni-NTA resin (Qiagen, Hilden, Germany) gently by open-column system (Bio-rad, Hercules, Calif., USA). After washing protein-bound resin with 200 ml wash buffer (50 mM $NaH_2PO_4$, 20 mM Imidazol, 300 mM NaCl, pH 8.0), the bounded proteins were eluted with elution buffer (50 mM $NaH_2PO_4$, 250 mM Imidazol, 300 mM NaCl, pH 8.0).

Recombinant proteins purified under natural condition were analyzed on 15% SDS-PAGE gel and stained with Coomassie Brilliant Blue (FIG. 4). All of the recombinant proteins were dialyzed for 8 hours and overnight against physiological buffer, a 1:1 mixture of cell culture medium (Dulbecco's Modified Eagle's Medium: DMEM, Hyclone, Logan, Utah, USA) and Dulbecco's phosphate buffered saline (DPBS, Gibco, Grand Island, N.Y., USA). From 316 aMTDs and 141 rPeptides cloned, 240 aMTD- and 31 rPeptide-fused recombinant proteins were induced, purified, prepared and analyzed for their cell-permeability.

Example 4. Determination of Quantitative Cell-Permeability of Recombinant Proteins For quantitative cell-permeability, the aMTD- or rPeptide-fused recombinant proteins were conjugated to fluorescein isothiocyanate (FITC) according to the manufacturer's instructions (Sigma-Aldrich, St. Louis, Mo., USA). RAW 264.7 cells were treated with 10 uM FITC-labeled recombinant proteins for 1 hour at 37° C.° C., washed three times with cold PBS, treated with 0.25% tripsin/EDTA (Sigma-Aldrich, St. Louis, Mo.) for 20 minutes at 37° C.° C. to remove cell-surface bound proteins. Cell-permeability of these recombinant proteins were analyzed by flow cytometry (Guava, Millipore, Darmstadt, Germany) using the FlowJo cytometric analysis software (FIGS. 5 to 6). The relative cell-permeability of aMTDs were measured and compared with the negative control (rP38) and reference hydrophobic CPPs (MTM12 and MTD85) (Table 31).

Example 5. Determination of Cell-Permeability and Intracellular Localization of Recombinant Proteins For a visual reference of cell-permeability, NIH3T3 cells were cultured for 24 hours on coverslip in 24-wells chamber slides, treated with 10 uM FITC-conjugated recombinant proteins for 1 hour at 37° C., and washed three times with cold PBS. Treated cells were fixed in 4% paraformaldehyde (PFA, Junsei, Tokyo, JP) for 10 minutes at room temperature, washed three times with PBS, and mounted with VECTASHIELD Mounting Medium (Vector laboratories, Burlingame, Calif., USA), and counter stained with DAPI (4',6-diamidino-2-phenylindole). The intracellular localization of the fluorescent signal was determined by confocal laser scanning microscopy (LSM700, Zeiss, Germany; FIGS. 7 and 8).

Example 6. Expression RF Recombinant Proteins

<6-1> Construction of Expression Vectors for Recombinant Proteins

Our newly developed technology, aMTD-based MITT, has enabled us to improve the method for developing cell-permeable recombinant proteins. The expression vectors were designed for RF proteins (OCT4, SOX2, CMYC, KLF4, NANOG, LIN28 and ZSCAN4) fused with aMTD/SDs (HNM#SB, HNMSA#SBSB and HNMSA#SASBSASB) and control proteins without aMTD and/or SD (H# and HNM#). To acquire expression vectors for RF recombinant proteins, polymerase chain reaction (PCR) had been devised to amplify these recombinant proteins.

The PCR reactions (100 ng genomic DNA, 10 pmol each primer, each 0.2 mM dNTP mixture, 1× reaction buffer and 2.5 U Pfu(+) DNA polymerase (Doctor Protein, Korea)) was digested on the different restriction enzyme site involving 40 cycles of denaturation (95° C.), annealing (58° C.), and extension (72° C.) for 30 seconds each. For the last extension cycle, the PCR reactions remained for 10 minutes at 72° C.

Histidine-tagged human RF proteins were separately constructed by amplifying the original gene cDNA for each proteins, including OCT4 (360 aa), SOX2 (317 aa), CMYC (439 aa), KLF4 (470 aa), NANOG (305 aa), LIN28 (209 aa) and ZSCAN4 (433 aa), using their specific primers (Tables 28 to 44), for aMTD/SD fused to RF proteins. The PCR products are cleaved with NdeI and SalI, then ligated into 6×His expression vector, pET-28a(+) (Novagen, USA). The amino acid sequences and cDNA of human RFs, independently, were shown in SEQ ID NOs: 816 to 822 and SEQ ID NOs: 823 to 829. For OCT4 or CMYC recombinant protein, NLS/aMTD-OCT4 or NLS/aMTD-CMYC was ligated into the NdeI and BamHI sites in pET-28(a) vector where SDB was located between the BamHI and SalI sites. For SOX2 or KLF4 recombinant protein, NLS/aMTD-SDA was ligated into the NdeI and BamHI sites in pET-28(a) vector where SOX2 or KLF4 was located between the BamHI and HindIII sites. SA/SB/SA/SB was located between the HindIII and XhoI sites. For NANOG recombinant protein, NLS/aMTD-NANOG was ligated into the NdeI and Sail sites in pET-28(a) vector where SDB was located between the Sail and XhoI sites. For LIN28 recombinant protein, NLS/aMTD-LIN28 was ligated into the EcoRI and SalI sites in pET-28(a) vector where SDB was located between the Sail and XhoI sites. For ZSCAN4 recombinant protein, NLS/aMTD-ZSCAN4 was ligated into the EcoRI and Sal sites in pET-28(a) vector where SDB was located between the SalI and NotI sites. DNA ligations, independently, were performed using T4 DNA ligase (NEB, USA) at 4° C. overnight.

These plasmids were mixed with competent cells of *E. coli*(BL21(DE3) codon plus RIL) strain (Agilent, USA) on the ice for 10 minutes. This mixture was placed on the ice for 2 minutes after it was heat shocked in the water bath at 42° C. for 90 seconds. Then, the mixture added with LB broth media (ELPIS, Korea) was recovered in 37° C. shaking incubator for 1 hour. Transformant was plated on LB broth agar plate with kanamycin (50 ug/mL) with a vigorous shaking and induced with 0.7 mM IPTG (Biopure, Johnson, Tenn.) at $OD_{600}$=0.6 before incubating at 37° C. overnight. From a single colony, plasmid DNA was extracted, and after the digestion of BamHI and HindIII restriction enzymes (NEB, USA), digested DNA was confirmed by using 1.2% agarose gels electrophoresis (FIGS. 17*a* to 17*g*).

As shown in FIGS. 17*a* to 17*g*, it was confirmed that the RF recombinant proteins (OCT4, SOX2, KLF4, CMYC, NANOG, LIN28 and ZSCAN4) were expressed from the respective recombinant expression vectors.

TABLE 38

| Cargo Protein | aMTD ID | Amino Acid Sequence | 5' Primer (5'→3') | 3' Primer (5'→3') |
|---|---|---|---|---|
| RF-01 OCT4 | 165 | ALAVPVALAIVP | GGAATTC CATATG CCC AAG AAG AAG AGG AAG CTG GCG CTG GCG GTG CCG GTG GCG CTG GCG ATT GTG CCG GCGGGACACCTGGCTTCGGATTTC | CG GGATCC GTT TGA ATG CAT GGG AGA GCC |
| | 363 | AVLAVAPALIVP | GGAATTC CATATG CCC AAG AAG AAG AGG AAG CTG GCG GTG CTG GCG GTG GCG CCG GCG CTG ATT GTG CCG GCGGGACACCTGGCTTCGGATTTC | |
| | 405 | LAAAVIPVAILP | GGAATTC CATATG CCC AAG AAG AAG AGG AAG CTG CTG GCG GCG GCG GTG ATT CCG GTG GCG ATT CTG CCG GCGGGACACCTGGCTTCGGATTTC | |
| | 563 | ALAVIVVPALAP | GGAATTC CATATG CCC AAG AAG AAG AGG AAG CTG GCG CTG GCG GTG ATT GTG GTG CCG GCG CTG GCG CCG GCGGGACACCTGGCTTCGGATTTC | |
| | 889 | ILVAAAPIAALP | GGAATTC CATATG CCC AAG AAG AAG AGG AAG CTG ATT CTG GTG GCG GCG GCG CCG ATT GCG GCG CTG CCG GCGGGACACCTGGCTTCGGATTTC | |
| | 895 | AIIIVVPAIAAP | GGAATTC CATATG CCC AAG AAG AAG AGG AAG CTG GCG ATT ATT ATT GTG GTG CCG GCG ATT GCG GCG CCG GCGGGACACCTGGCTTCGGATTTC | |
| | 904 | AVLAVVAPVVAP | GGAATTC CATATG CCC AAG AAG AAG AGG AAG CTG GCG GTG CTG GCG GTG GTG GCG CCG GTG GTG GCG CCG GCGGGACACCTGGCTTCGGATTTC | |

TABLE 39

| Cargo Protein | aMTD ID | Amino Acid Sequence | 5' Primer (5'→3') | 3' Primer (5'→3') |
|---|---|---|---|---|
| RF-02 SOX2 | 161 | AVIALPALIAAP | GGAATTC CATATG CCC AAG AAG AAG AGG AAG CTG GCG GTG ATT GCG CTG CCG GCG CTG ATT GCG GCG CCG GCAAATATTACCGTTTTCTAT | CG GGATCC CCT CGG CTG CAC CGG CAC GGA |
| | 165 | ALAVPVALAIVP | GGAATTC CATATG CCC AAG AAG AAG AGG AAG CTG GCG CTG GCG GTG CCG GTG GCG CTG GCG ATT GTG CCG GCAAATATTACCGTTTTCTAT | |
| | 363 | AVLAVAPALIVP | GGAATTC CATATG CCC AAG AAG AAG AGG AAG CTG GCG GTG CTG GCG GTG GCG CCG GCG CTG ATT GTG CCG GCAAATATTACCGTTTTGTAT | |
| | 405 | LAAAVIPVAILP | GGAATTC CATATG CCC AAG AAG AAG AGG AAG CTG CTG GCG GCG GCG GTG ATT CCG GTG GCG ATT CTG CCG GCAAATATTACCGTTTTCTAT | |
| | 563 | ALAVIVVPALAP | GGAATTC CATATG CCC AAG AAG AAG AGG AAG CTG GCG CTG GCG GTG ATT GTG GTG CCG GCG CTG GCG CCG GCAAATATTACCGTTTTCTAT | |
| | 889 | ILVAAAPIAALP | GGAATTC CATATG CCC AAG AAG AAG AGG AAG CTG ATT CTG GTG GCG GCG GCG CCG ATT GCG GCG CTG CCG GCAAATATTACCGTTTTCTAT | |
| | 904 | AVLAVVAPVVAP | GGAATTC CATATG CCC AAG AAG AAG AGG AAG CTG GCG GTG CTG GCG GTG GTG GCG CCG GTG GTG GCG CCG GCAAATATTACCGTTTTCTAT | |

TABLE 40

| Cargo Protein | aMTD ID | Amino Acid Sequence | 5' Primer (5'→3') | 3' Primer (5'→3') |
|---|---|---|---|---|
| RF-03 KLF4 | 563 | ALAVIVVPALAP | GGAATTC CATATG CCC AAG AAG AAG AGG AAG CTG GCG CTG GCG GTG ATT GTG GTG CCG GCG CTG GCG CCG GCAAATATTACCGTTTTCTAT | CG GGATCC CCT CGG CTG CAC CGG CAC GGA |

TABLE 41

| Cargo Protein | aMTD ID | Amino Acid Sequence | 5' Primer (5'→3') | 3' Primer (5'→3') |
|---|---|---|---|---|
| RF-04 CMYC | 161 | AVIALPALIAAP | GGAATTC CATATG CCC AAG AAG AAG AGG AAG CTG GCG GTG ATT GCG CTG CCG GCG CTG ATT GCG GCG CCG CCCCTCAACGTTAGCTTCACCAAC | CG GGATCC CCT CGG CTG CAC CGG CAC GGA |
| | 165 | ALAVPVALAIVP | GGAATTC CATATG CCC AAG AAG AAG AGG AAG CTG GCG CTG GCG GTG CCG GTG GCG | |

TABLE 41-continued

| Cargo Protein | aMTD ID | Amino Acid Sequence | 5' Primer (5'→3') | 3' Primer (5'→3') |
|---|---|---|---|---|
| | | | CTG GCG ATT GTG CCG CCCCTCAACGTTAGCTTCACCAAC | |
| | 363 | AVLAVAPALIVP | GGAATTC CATATG CCC AAG AAG AAG AGG AAG CTG GCG GTG CTG GCG GTG GCG CCG GCG CTG ATT GTG CCG CCCCTCAACGTTAGCTTCACCAAC | |
| | 405 | LAAAVIPVAILP | GGAATTC CATATG CCC AAG AAG AAG AGG AAG CTG CTG GCG GCG GCG GTG ATT CCG GTG GCG ATT CTG CCG CCCCTCAACGTTAGCTTCACCAAC | |
| | 563 | ALAVIVVPALAP | GGAATTC CATATG CCC AAG AAG AAG AGG AAG CTG GCG CTG GCG GTG ATT GTG GTG CCG GCG CTG GCG CCG CCCCTCAACGTTAGCTTCACCAAC | |
| | 889 | ILVAAAPIAALP | GGAATTC CATATG CCC AAG AAG AAG AGG AAG CTG ATT CTG GTG GCG GCG GCG CCG ATT GCG GCG CTG CCG CCCCTCAACGTTAGCTTCACCAAC | |
| | 895 | AIIIVVPAIAAP | GGAATTC CATATG CCC AAG AAG AAG AGG AAG CTG GCG ATT ATT ATT GTG GTG CCG GCG ATT GCG GCG CCG CCCCTCAACGTTAGCTTCACCAAC | |
| | 904 | AVLAVVAPVVAP | GGAATTC CATATG CCC AAG AAG AAG AGG AAG CTG GCG GTG CTG GCG GTG GTG GCG CCG GTG GTG GCG CCG CCCCTCAACGTTAGCTTCACCAAC | |

TABLE 42

| Cargo Protein | aMTD ID | Amino Acid Sequence | 5' Primer (5'→3') | 3' Primer (5'→3') |
|---|---|---|---|---|
| RF-05 NANOG | 161 | AVIALPALIAAP | GGAATTC CATATG CCC AAG AAG AAG AGG AAG CTG GCG GTG ATT GCG CTG CCG GCG CTG ATT GCG GCG CCG AGTGTGGATCCAGCTTGTCCCCAA | ACGC GTCGAC CAC GTC TTC AGG TTG CAT GTT |
| | 405 | LAAAVIPVAILP | GGAATTC CATATG CCC AAG AAG AAG AGG AAG CTG CTG GCG GCG GCG GTG ATT CCG GTG GCG ATT CTG CCG AGTGTGGATCCAGCTTGTCCCCAA | |
| | 889 | ILVAAAPIAALP | GGAATTC CATATG CCC AAG AAG AAG AGG AAG CTG ATT CTG GTG GCG GCG GCG CCG ATT GCG GCG CTG CCG AGTGTGGATCCAGCTTGTCCCCAA | |
| | 895 | AIIIVVPAIAAP | GGAATTC CATATG CCC AAG AAG AAG AGG AAG CTG GCG ATT ATT ATT GTG GTG CCG GCG ATT GCG GCG CCG AGTGTGGATCCAGCTTGTCCCCAA | |
| | 904 | AVLAVVAPVVAP | GGAATTC CATATG CCC AAG AAG AAG AGG AAG CTG GCG GTG CTG GCG GTG GTG GCG CCG GTG GTG GCG CCG AGTGTGGATCCAGCTTGTCCCCAA | |

TABLE 43

| Cargo Protein | aMTD ID | Amino Acid Sequence | 5' Primer (5'→3') | 3' Primer (5'→3') |
|---|---|---|---|---|
| RF-06 LIN28 | 161 | AVIALPALIAAP | CCG GAATTC CCC AAG AAG AAG AGG AAG CTG GCG GTG ATT GCG CTG CCG GCG CTG ATT GCG GCG CCG GGCTCCGTGTCCAACCAGCAGTTT | ACGC GTCGAC ATT CTG TGC CTC CGG GAG CAG |
| | 165 | ALAVPVALAIVP | CCG GAATTC CCC AAG AAG AAG AGG AAG CTG GCG CTG GCG GTG CCG GTG GCG CTG GCG ATT GTG CCG GGCTCCGTGTCCAACCAGCAGTTT | |
| | 563 | ALAVIVVPALAP | CCG GAATTC CCC AAG AAG AAG AGG AAG CTG GCG CTG GCG GTG ATT GTG GTG CCG GCG CTG GCG CCG GGCTCCGTGTCCAACCAGCAGTTT | |
| | 895 | AIIIVVPAIAAP | CCG GAATTC CCC AAG AAG AAG AGG AAG CTG GCG ATT ATT ATT GTG GTG CCG GCG ATT GCG GCG CCG GGCTCCGTGTCCAACCAGCAGTTT | |

TABLE 44

| Cargo Protein | aMTD ID | Amino Acid Sequence | 5' Primer (5'→3') | 3' Primer (5'→3') |
|---|---|---|---|---|
| RF-07 ZSCAN4 | 563 | ALAVIVVPALAP | CCG GAATTC CCC AAG AAG AAG AGG AAG CTG GCG CTG GCG GTG ATT GTG GTG CCG GCG CTG GCG CCG GCTTTAGATCTAAGAACCATATTT | ACGC GTCGAC GGA AGC TTC TGG TGT GGA GGG |

<6-2> Expression and Purification of Histidine-Tagged RF Recombinant Proteins

The transformant was cultured in LB medium containing 50 ug/ml of kanamycin, and the transformant was inoculated in 7 ml of LB medium at 37° C. overnight. The incubated transformant was inoculated in 700 ml of LB medium at 37° C. until $OD_{600}$ reached 0.5. The medium was added with 0.7 mM isopropyl-β-D-thiogalactoside (IPTG) as a protein expression inducer, and further incubated at 37° C. for 3 hours. The medium was centrifuged at 4° C. and 8,000×g for 10 minutes, and a supernatant was discarded to recover a cell pellet. The pellet was loaded on SDS-PAGE to analyze expression levels. The pellet was re-suspended in the lysis buffer (50 mM $NaH_2PO_4$, 10 mM Imidazol, 300 mM NaCl, pH 8.0). This suspension was disrupted with sonication to the cells. The disrupted cells were centrifuged at 4° C. and 15,000×g for 30 minutes to obtain a soluble fraction and an insoluble fraction. Recombinant proteins are supposed to be purified by $Ni^2$+ affinity chromatography as directed by the supplier (Qiagen, Germany) in the natural condition. After purification, they will be changed to a Dulbecco's Modified Eagle's Medium (DMEM), (Hyclone, USA).

Example 7. Determination of Solubility/Yield of RF Recombinant Proteins

The aMTD-fused RF proteins (OCT4, SOX2, CMYC, KLF4, NANOG, LIN28 and ZSCAN4) containing SDs (SA and SB) were individually cloned, expressed, purified and prepared in a soluble form. The solubility and yield of each recombinant protein fused to the aMTD with the SD were determined.

Each RF recombinant protein was determined for their size (number of amino acids), yield (mg/L) and solubility on 10% SDS-PAGE gel and stained with Coomassie Brilliant Blue.

Consequently, the SD was confirmed to influence improvement of solubility and yield of the RF recombinant proteins.

<7-1> OCT4 Recombinant Proteins

Each recombinant protein; HO, $HNM_{563}0$ and $HNM_{563}OSB$ (FIG. 18) was determined for their size (number of amino acids), yield (mg/L) and solubility.

As shown in FIG. 19 (top), the proteins were observed as a single band.

As shown in FIG. 19 (bottom), it was confirmed that $HNM_{563}OSB$ showed improved yield and solubility, compared to HO and $HNM_{563}0$, and $HNM_{563}OSB$ was determined as a basic structure of the OCT4 recombinant protein.

<7-2> SOX2 Recombinant Proteins

Each recombinant protein; HS, $HNM_{563}S$, $HNM_{563}SSB$, $HNM_{563}SASSBSB$ and $HNM_{563}SASSASBSASB$ (FIG. 20) was determined for their size (number of amino acids), yield (mg/L) and solubility.

As shown in FIG. 21 (top), the proteins were observed as a single band.

As shown in FIG. 21 (bottom), it was confirmed that $HNM_{563}SSB$, $HNM_{563}SASSBSB$ and $HNM_{563}$SASSASBSASB showed improved yield and solubility, compared to HS and $HNM_{563}$S, and $HNM_{563}$SASSASBSASB was determined as a basic structure of the SOX2 recombinant protein.

<7-3> KLF4 Recombinant Proteins

Each recombinant protein; HK, $HNM_{563}$K, $HNM_{563}$KSB, $HNM_{563}$SAKSBSB and $HNM_{563}$SAKSASBSASB (FIG. 22) was determined for their size (number of amino acids), yield (mg/L) and solubility.

As shown in FIG. 23 (top), the proteins were observed as a single band.

As shown in FIG. 23 (bottom), it was confirmed that $HNM_{563}$KSB, $HNM_{563}$SAKSBSB and $HNM_{563}$SAKSASBSASB showed improved yield and solubility, compared to HK and $HNM_{563}$K, and $HNM_{563}$SAKSASBSASB was determined as a basic structure of the KLF4 recombinant protein.

<7-4> CMYC Recombinant Proteins

Each recombinant protein; HM, $HNM_{563}$M and $HNM_{563}$MSB (FIG. 24) was determined for their size (number of amino acids), yield (mg/L) and solubility.

As shown in FIG. 25 (top), the proteins were observed as a single band.

As shown in FIG. 25 (bottom), it was confirmed that $HNM_{563}$MSB showed improved yield and solubility, compared to HM and $HNM_{563}$M, and $HNM_{563}$MSB was determined as a basic structure of the CMYC recombinant protein.

<7-5> NANOG Recombinant Proteins

Each recombinant protein; HN, $HNM_{161}$N and $HNM_{161}$NSB (FIG. 26) was determined for their size (number of amino acids), yield (mg/L) and solubility.

As shown in FIG. 27 (top), the proteins were observed as a single band.

As shown in FIG. 27 (bottom), it was confirmed that $HNM_{161}$NSB showed improved yield and solubility, compared to HN and $HNM_{161}$N, and $HNM_{161}$NSB was determined as a basic structure of the NANOG recombinant protein.

<7-6> LIN28 Recombinant Proteins

Each recombinant protein; HL, $HNM_{563}$L and $HNM_{563}$LSB (FIG. 28) was determined for their size (number of amino acids), yield (mg/L) and solubility.

As shown in FIG. 29 (top), the proteins were observed as a single band.

As shown in FIG. 29 (bottom), it was confirmed that $HNM_{563}$LSB showed improved yield and solubility, compared to HL and $HNM_{563}$L, and $HNM_{563}$LSB was determined as a basic structure of the LIN28 recombinant protein.

<7-7> ZSCAN4 Recombinant Proteins

Each recombinant protein; HZ, $HNM_{563}$Z and $HNM_{563}$ZSB (FIG. 30) was determined for their size (number of amino acids), yield (mg/L) and solubility.

As shown in FIG. 31 (top), the proteins were observed as a single band.

As shown in FIG. 31 (bottom), it was confirmed that $HNM_{563}$ZSB showed improved yield and solubility, compared to HZ and $HNM_{563}$Z, and $HNM_{563}$ZSB was determined as a basic structure of the ZSCAN4 recombinant protein.

Example 8. Determination of Optimal aMTD for iCP-RF Recombinant Proteins

To increase the cell-permeability of the RF recombinant proteins, aMTD fused to RF protein was replaced various aMTDs. The yield and solubility of each RF recombinant protein fused various aMTDs were measured. Consequently, it was confirmed that both aMTD and SD improved solubility and yield of the RF proteins, and optimal aMTD for each RF recombinant protein was determined.

<8-1> SOX2 Recombinant Proteins

In the same manner as in Example 6, $aMTD_{161}$, $aMTD_{165}$, $aMTD_{363}$, $aMTD_4$05, $aMTD_{563}$, $aMTD_{889}$, and $aMTD_{904}$-fused SOX2 recombinant proteins were prepared (FIG. 32). Yield and solubility of the SOX2 recombinant proteins were measured in the same manner as in Example 7. Primers used are as given in Table 39.

As shown in FIG. 33 (top), the proteins were observed as a single band.

As shown in FIG. 33 (bottom), all the SOX2 recombinant proteins fused with aMTDs showed high solubility. The $aMTD_{563}$-fused SOX2 recombinant protein was found to have the highest yield and solubility. Consequently, the $aMTD_{563}$-fused SOX2 recombinant protein was determined as iCP-SOX2 recombinant protein.

<8-2> NANOG Recombinant Proteins

In the same manner as in Example 6, $aMTD_{161}$, $aMTD_{405}$, $aMTD_{889}$, $aMTD_{895}$, and $aMTD_{904}$-fused NANOG recombinant proteins were prepared (FIG. 34). Yield and solubility of the NANOG recombinant proteins were measured in the same manner as in Example 7. Primers used are as given in Table 42.

As shown in FIG. 35 (top), the proteins were observed as a single band.

As shown in FIG. 35 (bottom), all the NANOG recombinant proteins fused with aMTDs showed high solubility. The $aMTD_{161}$-fused NANOG recombinant protein was found to have the highest yield and solubility. Consequently, the $aMTD_{161}$-fused NANOG recombinant protein was determined as iCP-NANOG recombinant protein.

<8-3> OCT4 Recombinant Proteins

In the same manner as in Example 6, $aMTD_{165}$, $aMTD_{363}$, $aMTD_{405}$, $aMTD_{563}$, $aMTD_{889}$, $aMTD_{895}$, and $aMTD_9$04-fused OCT4 recombinant proteins were prepared (FIG. 36). Yield and solubility of the OCT4 recombinant proteins were measured in the same manner as in Example 7. Primers used are as given in Table 38.

All the OCT4 recombinant proteins fused with aMTDs showed high solubility. The $aMTD_{563}$-fused OCT4 recombinant protein was found to have the highest yield and solubility. Consequently, the $aMTD_{563}$-fused OCT4 recombinant protein was determined as iCP-OCT4 recombinant protein.

<8-4> CMYC Recombinant Proteins

In the same manner as in Example 6, $aMTD_{161}$, $aMTD_{165}$, $aMTD_{363}$, $aMTD_{405}$, $aMTD_{563}$, $aMTD_{889}$, $aMTD_{895}$, and $aMTD_{904}$-fused CMYC recombinant proteins were prepared (FIG. 37). Yield and solubility of the CMYC recombinant proteins were measured in the same manner as in Example 7. Primers used are as given in Table 41.

All the CMYC recombinant proteins fused with aMTDs showed high solubility. The $aMTD_{563}$-fused CMYC recombinant protein was found to have the highest yield and solubility. Consequently, the $aMTD_{563}$-fused CMYC recombinant protein was determined as iCP-CMYC recombinant protein.

<8-5> LIN28 Recombinant Proteins

In the same manner as in Example 6, $aMTD_{161}$, $aMTD_{165}$, $aMTD_{563}$, and $aMTD_{595}$-fused LIN28 recombinant proteins were prepared (FIG. 38). Yield and solubility of the LIN28 recombinant proteins were measured in the same manner as in Example 7. Primers used are as given in Table 43.

All the LIN28 recombinant proteins fused with aMTDs showed high solubility. The $aMTD_{563}$-fused LIN28 recombinant protein was found to have the highest yield and solubility. Consequently, the $aMTD_{563}$-fused LIN28 recombinant protein was determined as iCP-LIN28 recombinant protein.

<8-6> KLF4 Recombinant Proteins and ZSCAN4 Recombinant Proteins $aMTD_{563}$-fused KLF4 recombinant protein was determined as iCP-KLF4 recombinant protein, and $aMTD_{563}$-fused ZSCAN4 recombinant protein was determined as iCP-ZSCAN4 recombinant protein.

9. Determination of Cell-Permeability of iCP-RF Recombinant Proteins

Cell-permeability and intranuclear delivery of the iCP-RF recombinant proteins; iCP-OCT4, iCP-SOX2, iCP-CMYC, iCP-KLF4 and iCP-LIN28 were examined by flow cytometry and confocal laser microscopy. Overall, it was confirmed that the aMTD-fused RF proteins had improved cell-permeability and they were efficiently delivered into the nuclei of the cells.

<9-1> Flow Cytometry

For cell permeability, the iCP-RF recombinant proteins were conjugated to FITC according to the manufacturer's instructions (Pierce Chemical, Rockford, Ill.). RAW 264.7 cells (ATCC, USA) were treated with 10 uM FITC-labeled RF proteins for 1 hour at 37° C., washed three times with cold PBS, treated with proteinase K (10 ug/ml) for 20 min at 37° C. to remove cell-surface bound proteins and subjected to fluorescence-activated cell sorting (FACS) analysis (FACSCalibur; BD, Franklin Lakes, N.J.).

As shown in FIG. 39, aMTD-fused OCT4/SOX2/KLF4/LIN28/CMYC recombinant proteins (aMTD-RF-SD) showed improved cell-permeability, compared to the RF recombinant protein without aMTD (RF). Consequently, it was confirmed that the iCP-RF recombinant proteins are provided with excellent cell permeability by aMTD.

<9-2> Confocal Laser Microscope

NIH3T3 cells were seeded in 8-well chamber, $2\times10^4$ cells/well. After day, the NIH3T3 cells were treated with 10 uM FITC-labeled iCP-RF recombinant proteins for 2 hours, and then fixed in 2% paraformaldehyde for 10 minutes. Then, 1 or 2 drops of a DAPI-containing mounting solution (Vector Laboratories, Inc., VECTASHIELD® MOUNTING MEDIUM with DAPI, Catalog Number H-1200), the cells were observed under a confocal laser scanning microscope.

As shown in FIG. 40, it was found that the iCP-RF recombinant proteins showed cell-permeability and intranuclear delivery. These results suggest that the iCP-RF recombinant proteins have excellent cell permeability and induce delivery of RF proteins into the nucleus to show the biological activity (generation of iPSCs).

Example 10. Determination of Biological Activity of iCP-RF Recombinant Proteins in Reporter Cells To measure the biological activity of the RF recombinant proteins in the nucleus, the constructed luciferase vector regulating luciferase expression was used (FIG. 41*a*).

Human HeLa cells were transfected with 300 ng of the luciferase expression vector. After 24 hours, the cells were treated with 0.1, 0.5, 1, and 2 uM of each iCP-RF recombinant protein for 6 hours. Each of the cells treated with the iCP-RF recombinant proteins was lysed using a 1× passive lysis buffer (Promega) and incubated at room temperature for 15 minutes. Luciferase activity was measured using a Dual-luciferase reporter assay (Promega) and a LUMIstar omega luminometer (BMG LABTECH) according to the manufacturer's instructions.

<10-1> iCP-OCT4 Recombinant Proteins

As shown in FIG. 41*b*, it was confirmed that the iCP-OCT4 recombinant protein bound with luciferase promoter in the nucleus, and expressed luciferase.

Further, when 0.5 uM of the iCP-OCT4 recombinant protein was treated, the activity was 38-fold higher than that of the control (only vector).

<10-2> iCP-SOX2 Recombinant Proteins

As shown in FIG. 42, it was confirmed that the iCP-SOX2 recombinant protein bound with luciferase promoter in the nucleus, and expressed luciferase.

Further, when 0.1 uM of the iCP-SOX2 recombinant protein was treated, the activity was 27-fold higher than that of the control (only vector).

<10-3> iCP-KLF4 Recombinant Proteins

As shown in FIG. 43, it was confirmed that the iCP-KLF4 recombinant protein bound with luciferase promoter in the nucleus, and expressed luciferase.

Further, when 0.1 uM of the iCP-KLF4 recombinant protein was treated, the activity was 22-fold higher than that of the control (only vector).

<10-4> iCP-CMYC Recombinant Proteins

As shown in FIG. 44, it was confirmed that the iCP-CMYC recombinant protein bound with luciferase promoter in the nucleus, and expressed luciferase.

Further, when 0.5 uM of the iCP-CMYC recombinant protein was treated, the activity was 34-fold higher than that of the control (only vector).

<10-5> iCP-NANOG Recombinant Proteins

As shown in FIG. 45, it was confirmed that the iCP-NANOG recombinant protein bound with luciferase promoter in the nucleus, and expressed luciferase.

Further, when 0.5 uM of the iCP-NANOG recombinant protein was treated, the activity was 27-fold higher than that of the control (only vector).

<10-6> iCP-LIN28 Recombinant Proteins

As shown in FIG. 46, it was confirmed that the iCP-LIN28 recombinant protein bound with luciferase promoter in the nucleus, and expressed luciferase.

Further, when 0.1 uM of the iCP-LIN28 recombinant protein was treated, the activity was 30-fold higher than that of the control (only vector).

Example 11. Protocol for iPSC-Like Colony Formation by iCP-RF Recombinant Proteins To generate iPSCs with high efficiency, treatment conditions of the iCP-RF recombinant proteins (iCP-OCT4, iCP-SOX2, iCP-KLF4, iCP-CMYC, iCP-LIN28, iCP-NANOG and iCP-ZSCAN4) were controlled to carry out Protocol 1 to Protocol 5.

<11-1> Protocol 1

Human umbilical vein endothelial cells (HUVEC) were treated with each 0.1 uM of the RF recombinant proteins (iCP-OCT4, iCP-SOX2, iCP-KLF4, iCP-CMYC and iCP-LIN28) for 6 hours a day for total 5 days. After 3 days, the cells began to form colonies (FIG. 47, top). To examine whether the colonies were iPSC-like colonies, alkaline phosphatase (AP) staining (Life Technologies) was performed according to the manufacturer's instructions.

As shown in FIG. 47 (bottom), the colonies formed at 3 days exhibited AP positive fluorescence, indicating iPSC-like colonies. As a result, when somatic cells were treated with 0.1 uM of the RF recombinant proteins (iCP-OCT4, iCP-SOX2, iCP-KLF4, iCP-CMYC and iCP-LIN28), iPSCs generation was observed at 3 days.

<11-2> Protocol 2

Human umbilical vein endothelial cells (HUVEC) were treated with each 0.5 uM of the RF recombinant proteins (iCP-OCT4, iCP-SOX2, iCP-KLF4, iCP-CMYC and iCP-LIN28) for 6 hours a day for total 5 days. After 3 days, the cells began to form colonies (FIG. 48, top). To examine whether the colonies were iPSC-like colonies, alkaline phosphatase (AP) staining (Life Technologies) was performed according to the manufacturer's instructions.

As shown in FIG. 48 (bottom), the colonies formed at 3 days exhibited AP positive fluorescence, indicating iPSC-like colonies. As a result, when somatic cells were treated with 0.5 uM of the RF recombinant proteins (iCP-OCT4, iCP-SOX2, iCP-KLF4, iCP-CMYC and iCP-LIN28), iPSCs generation was observed at 3 days.

<11-3> Protocol 3

BJ cells (Human fibroblast) were treated with each 0.5 uM of the RF recombinant proteins (iCP-OCT4, iCP-SOX2, iCP-KLF4, iCP-CMYC, iCP-LIN28 and iCP-ZSCAN4) for 6 hours a day for total 10 days. After 3 days, the cells began to form colonies (FIG. 49, top). In order to examine whether the colonies were iPSC-like colonies, alkaline phosphatase (AP) staining (Life Technologies) was performed according to the manufacturer's instructions.

As shown in FIG. 49 (bottom), the colonies formed at 3 days exhibited AP positive fluorescence, indicating iPSC-like colonies, and the colonies maintained for 7 days. As a result, when somatic cells were treated with 0.5 uM of the RF recombinant proteins (iCP-OCT4, iCP-SOX2, iCP-KLF4, iCP-CMYC, iCP-LIN28 and iCP-ZSCAN4), iPSCs generation was observed at 3 days.

<11-4> Protocol 4

BJ cells (Human fibroblast) were treated with each 0.5 uM of the RF recombinant proteins (iCP-OCT4, iCP-CMYC and iCP-NANOG) for 6 hours a day for total 10 days. After 6 days, the cells began to form colonies (FIG. 50, top). To examine whether the colonies were iPSC-like colonies, alkaline phosphatase (AP) staining (Life Technologies) was performed according to the manufacturer's instructions.

As shown in FIG. 50 (bottom), the colonies formed at 6 days exhibited AP positive fluorescence, indicating iPSC-like colonies. As a result, when somatic cells were treated with 0.5 uM of the RF recombinant proteins (iCP-OCT4, iCP-CMYC and iCP-NANOG), iPSCs generation was observed at 6 days.

<11-5> Protocol 5

4 groups of Detroit 573 cells (Human fibroblast) were treated with each 0.00025, 0.0005, 0.00125 or 0.0025 uM of the RF recombinant proteins (iCP-OCT4, iCP-SOX2, iCP-KLF4, iCP-CMYC, iCP-NANOG, iCP-LIN28 and iCP-ZSCAN4) for 6 hours a day for total 7 days. After 7 days, the cells began to form colonies (FIG. 51, top). To examine whether the colonies were iPSC-like colonies, alkaline phosphatase (AP) staining (Life Technologies) and immunocytochemistry were performed according to the manufacturer's instructions.

As shown in FIG. 51 (bottom), the colonies formed at 7 days were observed under a microscope. As a result, when all 4 groups of somatic cells were treated with each 0.00025, 0.0005, 0.00125 or 0.0025 uM of the RF recombinant proteins (iCP-OCT4, iCP-SOX2, iCP-KLF4, iCP-CMYC, iCP-NANOG, iCP-LIN28 and iCP-ZSCAN4), iPSCs generation was observed at 7 days.

In conclusion, terminally differentiated somatic cells can be reprogrammed and dedifferentiated to iPSC by the combination of the RF recombinant proteins (iCP-OCT4, iCP-SOX2, iCP-CMYC, iCP-KLF4, iCP-NANOG, iCP-LIN28 and iCP-ZSCAN4).

Example 12. Determination of Activity of iPSC-Like Colony Formed by iCP-RF Recombinant Proteins To determinate the activity of dedifferentiated iPSCs, OCT4 and TRA-1-81 expressed in iPSCs were examined.

The iPSC-like colonies formed in the same manner as in Example <11-4> were expanded and the iPSC-like colonies were maintained for 30 days (FIG. 52, top). The colonies were transferred to 8-well chamber slide (NUNC, Waltham, Mass.) using a capillary glass tube. After day, the chamber slide was washed with PBS twice. The colonies were fixed in 2% paraformaldehyde for 20 minutes, and washed with PBS twice. The colonies treated with 0.1% Triton X-100 for 5 minutes, and washed with PBS twice. The colonies incubated with 2% BSA at room temperature for 1 hr, and incubated with a goat polyclonal anti-OCT4 or anti-Tra-1-81 antibody (1:1000 dilution in 2% BSA/PBS) at 4° C. o/n. The colonies were washed with PBS twice and incubated with an Alexa Fluor 488 rabbit anti-goat IgG secondary antibody (1:1000 dilution in 2% BSA/PBS) at room temperature for 1 hr. The nucleus were stained with 300 nM DAPI (4, 6-diamidino-2-phenylindele) in the dark at room temperature for 5 minutes, and then washed with PBS three times. The cells were treated with a mounting medium (Vector Laboratories, Inc., VECTASHIELD® MOUNTING MEDIUM with DAPI, Catalog Number H-1200) and covered with a coverslip. After 15 minutes, the cells were observed under a confocal microscope.

As shown in FIG. 52 (bottom), overall colonies showed OCT4 and TRA-1-81 expressions. As a result, it was confirmed that iPSCs were generated by treatment of somatic cells with the iCP-RF recombinant proteins, and the iPSCs were maintained for 30 days. These results suggest that the RF recombinant proteins provide the reprogramming activity for dedifferentiation of somatic cells.

Example 13. Statistical Analysis

All experimental data using cultured cells are expressed as means S.D. for at least three independent experiments. Statistical significance is evaluated using a two-tailed Student's t-test or ANOVA method. Experimental differences between groups are assessed using paired Student's t-tests. For animal experiments, ANOVA is used for comparing between and within groups to determine the significance. Differences with $p<0.05$ are considered to be statistically significant.

Those skilled in the art to which the present invention pertains will appreciate that the present invention may be implemented in different forms without departing from the essential characteristics thereof. Therefore, it should be understood that the disclosed embodiments are not limitative, but illustrative in all aspects. The scope of the present invention is made to the appended claims rather than to the foregoing description, and all variations which come within the range of equivalency of the claims are therefore intended to be embraced therein.

The invention claimed is:

1. A recombinant protein, which comprises a RF protein selected from the group consisting of OCT4, SOX2, CMYC, KLF4, NANOG, LIN28 and ZSCAN4, and an advanced macromolecule transduction domain (aMTD) being composed of 12 amino acid residues and having improved cell or tissue permeability, wherein the aMTD has an amino acid sequence selected from the group consisting of SEQ ID NOs: 39, 43, 84, 96, 131, 223, 226, and 233, or the aMTD is encoded by a polynucleotide sequence selected from the group consisting of SEQ ID NOs: 279, 283, 324, 336 371, 463, 466, and 473.

2. The recombinant protein according to claim 1, wherein one or more solubilization domain (SD)(s) are further fused to the end(s) of one or more of the RF protein and the aMTD, wherein the one or more SD(s) independently have an amino acid sequence selected from the group consisting of SEQ ID NOs: 798-804.

3. The recombinant protein according to claim 2, wherein the recombinant protein is represented by any one of the following structural formula:

A-B—C and A-C—B—C wherein A is an advanced macromolecule transduction domain (aMTD) having improved cell or tissue permeability, B is a RF protein selected from the group consisting of OCT4, SOX2, CMYC, KLF4, NANOG, LIN28 and ZSCAN4, and C is a solubilization domain (SD); and wherein one or more SD(s) independently have an amino acid sequence selected from the group consisting of SEQ ID NOs: 798-804.

4. The recombinant protein according to claim 1, wherein the RF protein has an amino acid sequence selected from the group consisting of SEQ ID NOs: 816 to 822.

5. The recombinant protein according to claim 4, wherein the RF protein is encoded by a polynucleotide sequence selected from the group consisting of SEQ ID NOs: 823 to 829.

6. The recombinant protein of claim 2, wherein the SD(s), independently, are encoded by a polynucleotide sequence selected from the group consisting of SEQ ID NOs: 805 to 811.

7. The recombinant protein according to claim 1, wherein the fusion is formed via a peptide bond or a chemical bond.

8. The recombinant protein according to claim 1, wherein the recombinant protein is used for the generation of induced pluripotent stem cells (iPSCs) from somatic cells.

9. A preparing method of the recombinant protein of claim 1 comprising:

culturing a transformant comprising an exogenous polynucleotide encoding the recombinant protein of claim 1 in a culture medium to produce the recombinant protein; and recovering the recombinant protein expressed by the culturing.

10. A method of inducing generation of iPSCs from somatic cells comprising:

treating the somatic cells with an effective amount of the recombinant protein according to claim 1.

11. The recombinant protein of claim 3, wherein the SD(s), independently, are encoded by a polynucleotide sequence selected from the group consisting of SEQ ID NOs: 805 to 811.

12. A preparing method of the recombinant protein comprising:

culturing a transformant comprising a n exogenous polynucleotide encoding the recombinant protein of claim 3 in a culture medium to produce the recombinant protein; and recovering the recombinant protein expressed by the culturing.

13. The method according to claim 9, wherein the polynucleotide sequence is selected from the group consisting of SEQ ID NOs: 831, 837, 843, 849, 855, 861, and 867.

14. The method according to claim 12, wherein the polynucleotide sequence is selected from the group consisting of SEQ ID NOs: 833, 839, 845, 851, 857, 863, and 869.

* * * * *